US012491264B2

(12) United States Patent
Kay et al.

(10) Patent No.: US 12,491,264 B2
(45) Date of Patent: Dec. 9, 2025

(54) COMPOSITIONS AND METHODS FOR THE DIAGNOSIS AND TREATMENT OF RETINOPATHIES

(71) Applicant: Duke University, Durham, NC (US)

(72) Inventors: Jeremy Kay, Durham, NC (US); Thomas Ray, Durham, NC (US)

(73) Assignee: Duke University, Durham, NC (US)

( * ) Notice: Subject to any disclaimer, the term of this patent is extended or adjusted under 35 U.S.C. 154(b) by 955 days.

(21) Appl. No.: 17/436,419

(22) PCT Filed: Mar. 4, 2020

(86) PCT No.: PCT/US2020/020977

§ 371 (c)(1),
(2) Date: Sep. 3, 2021

(87) PCT Pub. No.: WO2020/180981

PCT Pub. Date: Sep. 10, 2020

(65) Prior Publication Data

US 2022/0125948 A1 Apr. 28, 2022

Related U.S. Application Data

(60) Provisional application No. 62/813,272, filed on Mar. 4, 2019.

(51) Int. Cl.
*A61K 48/00* (2006.01)
*C07K 14/47* (2006.01)
*C12N 15/86* (2006.01)

(52) U.S. Cl.
CPC ........ *A61K 48/005* (2013.01); *C07K 14/4702* (2013.01); *C12N 15/86* (2013.01); *C12N 2750/14143* (2013.01)

(58) Field of Classification Search
None
See application file for complete search history.

(56) References Cited

U.S. PATENT DOCUMENTS

| | | | |
|---|---|---|---|
| 5,902,598 | A | 5/1999 | Chen et al. |
| 6,331,313 | B1 | 12/2001 | Wong et al. |
| 6,375,972 | B1 | 4/2002 | Guo et al. |
| 6,566,118 | B1 | 5/2003 | Atkinson et al. |
| 6,723,551 | B2 | 4/2004 | Kotin et al. |
| 6,989,264 | B2 | 1/2006 | Atkinson et al. |
| 6,995,006 | B2 | 2/2006 | Atkinson et al. |
| 8,147,823 | B2 | 4/2012 | Acland et al. |
| 2003/0100005 | A1 | 5/2003 | Karim et al. |
| 2007/0082337 | A1 | 4/2007 | Sorek et al. |
| 2009/0011040 | A1 | 1/2009 | Naash et al. |
| 2014/0335054 | A1 | 11/2014 | Gao et al. |
| 2016/0022836 | A1 | 1/2016 | Banfi et al. |
| 2016/0194374 | A1 | 7/2016 | Wijnholds et al. |
| 2018/0161405 | A1 | 6/2018 | Le Meur et al. |

FOREIGN PATENT DOCUMENTS

| | | | |
|---|---|---|---|
| WO | 1998010088 | A1 | 3/1998 |
| WO | 2005071059 | A2 | 8/2005 |
| WO | 2009105690 | A2 | 8/2009 |
| WO | 2015020522 | A1 | 2/2015 |
| WO | 2015168666 | A2 | 11/2015 |

OTHER PUBLICATIONS

Richard et al. "Towards understanding CRUMBS function in retinal dystrophies." Human Molecular Genetics 15.suppl_2 (2006): R235-R243. (Year: 2006).*
Shiraki, T. et al. Cap analysis gene expression for high-throughput analysis of transcriptional starting point and identification of promoter usage. Proc. Natl. Acad. Sci. 100, 15776-15781 (2003).
Smolders, K. et al. An effective plasma membrane proteomics approach for small tissue samples. Sci. Rep. 5, 10917 (2015).
Sokolov, M. et al. Massive light-driven translocation of transducin between the two major compartments of rod cells: a novel mechanism of light adaptation. Neuron 34, 95-106 (2002).
Sperry, R.W. Chemoaffinity in the orderly growth of nerve fiber patterns and connections. Proc. Natl. Acad. Sci. U. S. A. 50, 703-10 (1963).
Südhof, T C. Neuroligins and neurexins link synaptic function to cognitive disease. Nature 455, 903-11 (2008).
Takahashi, H. & Craig, A.M. Protein tyrosine phosphatases PTPδ, PTPσ, and LAR: presynaptic hubs for synapse organization. Trends Neurosci. 36, 522-34 (2013).
Taliaferro, J.M. et al. Distal Alternative Last Exons Localize mRNAs to Neural Projections. Mol. Cell 61, 821-33 (2016).
Tardaguila, M. et al. SQANTI: extensive characterization of long-read transcript sequences for quality control in full-length transcriptome identification and quantification. Genome Res. 28, 396-411 (2018).
Taylor, J.P. et al. Decoding ALS: from genes to mechanism. Nature 539, 197-206 (2016).
Thompson, B.J. et al. Sticking together the Crumbs—an unexpected function for an old friend. Nat. Rev. Mol. Cell Biol. 14, 307-14 (2013).
Trapnell, C. et al. The dynamics and regulators of cell fate decisions are revealed by pseudotemporal ordering of single cells. Nat. Biotechnol. 32, 381-386 (2014).
Treutlein, B. et al. Cartography of neurexin alternative splicing mapped by single-molecule long-read mRNA sequencing. Proc. Natl. Acad. Sci. U. S. A. 111, E1291-9 (2014).
Tushev, G. et al. Alternative 3' UTRs Modify the Localization, Regulatory Potential, Stability, and Plasticity of mRNAs in Neuronal Compartments. Neuron 98, 495-511.e6 (2018).
Van De Pavert, S. a et al. Crumbs homologue 1 is required for maintenance of photoreceptor cell polarization and adhesion during light exposure. J. Cell Sci. 117, 4169-77 (2004).

(Continued)

*Primary Examiner* — Emily A Cordas
(74) *Attorney, Agent, or Firm* — Quarles & Brady, LLP

(57) ABSTRACT

The present invention provides compositions and methods related to the cell surface protein CRB1 for the treatment of retinopathies in a subject, as well as systems and kits employing such compositions.

10 Claims, 44 Drawing Sheets
(14 of 44 Drawing Sheet(s) Filed in Color)

Specification includes a Sequence Listing.

(56) References Cited

OTHER PUBLICATIONS

Van De Pavert, S. A. et al. A Single Amino Acid Substitution (Cys249Trp) in Crb1 Causes Retinal Degeneration and Deregulates Expression of Pituitary Tumor Transforming Gene Pttg1. J. Neurosci. 27, 564-573 (2007).
Van Den Hurk, J.A.J.M. et al. Characterization of the Crumbs homolog 2 (CRB2) gene and analysis of its role in retinitis pigmentosa and Leber congenital amaurosis. Mol Vis. Apr. 15, 2005:11:263-73.
Van Rossum, A.G.S.H. et al. Pals1/Mpp5 is required for correct localization of Crb1 at the subapical region in polarized Muller glia cells. Hum. Mol. Genet. 15, 2659-72 (2006).
Vecino, E. et al. Glia-neuron interactions in the mammalian retina. Prog. Retin. Eye Res. 51, 1-40 (2016).
Veldwijk Mr, Topaly J, Laufs S, Hengge UR, Wenz F, Zeller WJ, Fruehauf S. Development and optimization of a real-time quantitative PCR-based method for the titration of AAV-2 vector stocks. Mol Ther 6(2):272-8 (2002).
Wang Y, DeMayo FJ, Tsai SY, O'Malley BW. Ligand-inducible and liver-specific target gene expression in transgenic mice. Nat Biotechnol 15(3):239-43 (1997).
Wang Y, Xu J, Pierson T, O'Malley BW, Tsai SY. Positive and negative regulation of gene expression in eukaryotic cells with an inducible transcriptional regulator. Gene Ther 4(5):432-41 (1997).
Wang, J. et al. ATAC-Seq analysis reveals a widespread decrease of chromatin accessibility in age-related macular degeneration. Nat. Commun. 9, 1364 (2018).
Wojtowicz, W.M. et al. A vast repertoire of Dscam binding specificities arises from modular interactions of variable Ig domains. Cell 130, 1134-45 (2007).
Yasuda, M. et al. Retinal transcriptome profiling at transcription start sites: a cap analysis of gene expression early after axonal injury. BMC Genomics 15, 982 (2014).
Yin, Y. et al. Laminets: laminin- and netrin-related genes expressed in distinct neuronal subsets. Mol. Cell. Neurosci. 19, 344-58 (2002).
Young Je, Vogt T, Gross KW, Khani Sc. A short, highly active photoreceptor-specific enhancer/promoter region upstream of the human rhodopsin kinase gene. Invest Ophthalmol Vis Sci 44(9):4076-85 (2003).
Zipursky, S.L. & Grueber, W.B. The molecular basis of self-avoidance. Annu. Rev. Neurosci. 36, 547-68 (2013).
Zipursky, S.L. & Sanes, J.R. Chemoaffinity revisited: dscams, protocadherins, and neural circuit assembly. Cell 143, 343-53 (2010).
Aldiri, I. et al. The Dynamic Epigenetic Landscape of the Retina During Development, Reprogramming, and Tumorigenesis. Neuron 94, 550-568.e10 (2017).
Alves, C.H. et al. Loss of CRB2 in the mouse retina mimics human retinitis pigmentosa due to mutations in the CRB1 gene. Hum Mol Genet. Jan. 1, 2013;22(1):35-50. doi: 10.1093/hmg/dds398. Epub Sep. 21, 2012.
Alves, CH, Wijnholds J. AAV Gene Augmentation Therapy for CRB1-Associated Retinitis Pigmentosa. Methods Mol Biol 1715:135-151 (2018).
Ambati J Adamis AP. Transscleral drug delivery to the retina and choroid. Prog Retin Eye Res 21(2):145-51 (2002).
Andersen JK, Frim DM, Isacson O, Breakefield XO. Herpesvirus-mediated gene delivery into the rat brain: specificity and efficiency of the neuron-specific enolase promoter. Cell Mol Neurobiol 13(5):503-15 (1993).
Au, K.F. et al. Characterization of the human ESC transcriptome by hybrid sequencing. Proc. Natl. Acad. Sci. U. S. A. 110, E4821-30 (2013).
Baker, A.-M et al. Robust RNA-based in situ mutation detection delineates colorectal cancer subclonal evolution. Nat. Commun. 8, 1998 (2017).
Bennett J, Pakola S, Zeng Y, Maguire A. Humoral response after administration of E1-deleted adenoviruses: immune privilege of the subretinal space. Hum Gene Ther 7(14):1763-9 (1996).
Boshart M, Weber F, Jahn G, Dorsch-Häsler K, Fleckenstein B, Schaffner W. A very strong enhancer is located upstream of an immediate early gene of human cytomegalovirus. Cell 41(2):521-30 (1985).
Bossis I, Chiorini JA. Cloning of an avian adeno-associated virus (AAAV) and generation of recombinant AAAV particles. J Virol 77(12):6799-810 (2003).
Bujakowska K, Audo I, Mohand-Saïd S, Lancelot ME, Antonio A, Germain A, Léveillard T, Letexier M, Saraiva JP, Lonjou C, Carpentier W, Sahel JA, Bhattacharya SS, Zeitz C. CRB1 mutations in inherited retinal dystrophies. Hum Mutat 33(2):306-15 (2012).
Bussotti, G. et al. Improved definition of the mouse transcriptome via targeted RNA sequencing. Genome Res. 26, 705-716 (2016).
Byrne, A. et al. Nanopore long-read RNAseq reveals widespread transcriptional variation among the surface receptors of individual B cells. Nat. Commun. 8, 16027 (2017).
Chen, W. V. & Maniatis, T. Clustered protocadherins. Development 140, 3297-3302 (2013).
Clark KR, Liu X, McGrath JP, Johnson PR. Highly purified recombinant adeno-associated virus vectors are biologically active and free of detectable helper and wild-type viruses. Hum Gene Ther 10(6): 1031-9 (1999).
Clark, B. et al. Comprehensive analysis of retinal development at single cell resolution identifies NFI factors as essential for mitotic exit and specification of late-born cells. bioRxiv (2018).
Clark, B.S. et al. Single-Cell RNA-Seq Analysis of Retinal Development Identifies NFI Factors as Regulating Mitotic Exit and Late-Born Cell Specification. Neuron 102, 1111-1126.e5 (2019).
Clark, M.B. et al. Quantitative gene profiling of long noncoding RNAs with targeted RNA sequencing. Nat. Methods 12, 339-42 (2015).
Conway Je, Zolotukhin S, Muzyczka N, Hayward GS, Byrne BJ. Recombinant adeno-associated virus type 2 replication and packaging is entirely supported by a herpes simplex virus type 1 amplicon expressing Rep and Cap. J Virol 71(11):8780-9 (1997).
Davidson BL, Stein CS, Heth JA, Martins I, Kotin RM, Derksen TA, Zabner J, Ghodsi A, Chiorini JA. Recombinant adeno-associated virus type 2, 4, and 5 vectors: transduction of variant cell types and regions in the mammalian central nervous system. Proc Natl Acad Sci U S A. 97(7):3428-32 (2000).
Davis, C. A. et al. The Encyclopedia of DNA elements (ENCODE): data portal update. Nucleic Acids Res. 46, D794-D801 (2018).
Day T, et al. 121. Expanding the Potential of AAV Vectors for the Treatment of Intractable Inherited Retinal Degenerations. Sensory (Ophthalmic and Auditory) Diseases vol. 22, Supplement 1, S45-S46 (2014).
De Hoon, M., Shin, J. W. & Carninci, P. Paradigm shifts in genomics through the FANTOM projects. Mamm. Genome 26, 391-402 (2015).
Den Hollander, A.I. et al. CRB1 has a cytoplasmic domain that is functionally conserved between human and Drosophila. Hum. Mol. Genet. 10, 2767-2773 (2001).
Den Hollander, A.I. et al. Leber Congenital Amaurosis and Retinitis Pigmentosa with Coats-like Exudative Vasculopathy Are Associated with Mutations in the Crumbs Homologue 1 (CRB1) Gene. Am. J. Hum. Genet. 69, 198-203 (2001).
Den Hollander, A.I. et al. Mutations in a human homologue of Drosophila crumbs cause retinitis pigmentosa (RP12). Nat. Genet. 23, 217-21 (1999).
Ehrenberg, M. et al. CRB1: one gene, many phenotypes. Semin. Ophthalmol. 28, 397-405 (2013).
Erben, L. et al. A Novel Ultrasensitive In Situ Hybridization Approach to Detect Short Sequences and Splice Variants with Cellular Resolution. Mol. Neurobiol. 55, 6169-6181 (2018).
Fagan XJ, Al-Qureshi S. Intravitreal injections: a review of the evidence for best practice. Clin Exp Ophthalmol 41 (5):500-7 (2013).
Furlanis, E. & Scheiffele, P. Regulation of Neuronal Differentiation, Function, and Plasticity by Alternative Splicing. Annu. Rev. Cell Dev. Biol. 34, 451-469 (2018).
Furlanis, E. et al. Landscape of ribosome-engaged transcript isoforms reveals extensive neuronal-cell-class-specific alternative splicing programs. Nat. Neurosci. 22, 1709-1717 (2019).6.

(56) References Cited

OTHER PUBLICATIONS

Gandal, M.J. et al. Transcriptome-wide isoform-level dysregulation in ASD, schizophrenia, and bipolar disorder. Science (80-. ). 362, eaat8127 (2018).
Gao G, Alvira MR, Somanathan S, Lu Y, Vandenberghe LH, Rux JJ, Calcedo R, Sanmiguel J, Abbas Z, Wilson JM. Adeno-associated viruses undergo substantial evolution in primates during natural infections. Proc Natl Acad Sci U S A 100(10):6081-6 (2003).
Gao GP, Alvira MR, Wang L, Calcedo R, Johnston J, Wilson JM. Novel adeno-associated viruses from rhesus monkeys as vectors for human gene therapy. Proc Natl Acad Sci U S A 99(18):11854-9 (2002).
Gossen M, Bujard H. Tight control of gene expression in mammalian cells by tetracycline-responsive promoters. Proc Natl Acad Sci U S A 89(12):5547-51 (1992).
Gossen M, Freundlieb S, Bender G, Müller G, Hillen W, Bujard H. Transcriptional activation by tetracyclines in mammalian cells. Science 268(5218):1766-9 (1995).
Guo ZS, Wang LH, Eisensmith RC, Woo SL. Evaluation of promoter strength for hepatic gene expression in vivo following adenovirus-mediated gene transfer. Gene Ther 3(9):802-10 (1996).
Gupta, I. et al. Single-cell isoform RNA sequencing characterizes isoforms in thousands of cerebellar cells. Nat. Biotechnol. 36, (2018).
Hammond, T.R. et al. Immune Signaling in Neurodegeneration. Immunity 50, 955-974 (2019).
Harvey DM, Caskey CT. Inducible control of gene expression: prospects for gene therapy. Curr Opin Chem Biol 2 (4):512-8 (1998).
Hassan, B.A. & Hiesinger, P.R. Beyond Molecular Codes: Simple Rules to Wire Complex Brains. Cell 163, 285-291 (2015).
Hollingworth, P. et al. Common variants at ABCA7, MS4A6A/MS4A4E, EPHA1, CD33 and CD2AP are associated with Alzheimer's disease. Nat. Genet. 43, 429-35 (2011).
Hoshino, A. et al. Molecular Anatomy of the Developing Human Retina. Dev. Cell 43, 763-779.e4 (2017).
Huang, Y. et al. Identification of a novel homozygous nonsense mutation in EYS in a Chinese family with autosomal recessive retinitis pigmentosa. BMC Med Genet. Aug. 10, 2010:11:121. doi: 10.1186/1471-2350-11-121.
Hughes, A.E.O. et al. Cell Type-Specific Epigenomic Analysis Reveals a Uniquely Closed Chromatin Architecture in Mouse Rod Photoreceptors. Sci. Rep. 7, 43184 (2017).
International Search Report and Written Opinion for International Patent Application No. PCT/US2020/020977, dated Jun. 17, 2020.
Jiang, L. et al. Synthetic spike-in standards for RNA-seq experiments. Genome Res. 21, 1543-51 (2011).
Juttner J, Szabo A, Gross-Scherf B, Morikawa RK, Rompani SB, Hantz P, Szikra T, Esposti F, Cowan CS, Bharioke A, Patino-Alvarez CP, Keles Ö, Kusnyerik A, Azoulay T, Hartl D, Krebs AR, Schübeler D, Hajdu RI, Lukats A, Nemeth J, Nagy ZZ, Wu KC, Wu RH, Xiang L, Fang XL, Jin ZB, Goldblum D, Hasler PW, Scholl HPN, Krol J, Roska B. Targeting neuronal and glial cell types with synthetic promoter AAVs in mice, non-human primates and humans. Nat Neurosci 22(8):1345-1356 (2019).
Karlsson, K. & Linnarsson, S. Single-cell mRNA isoform diversity in the mouse brain. BMC Genomics 18, 126 (2017).
Kay, J.N. et al. MEGF10 and MEGF11 mediate homotypic interactions required for mosaic spacing of retinal neurons. Nature 483, 465-9 (2012).
Khan, K.N. et al. A clinical and molecular characterisation of CRB1-associated maculopathy. Eur. J. Hum. Genet. 26, 687-694 (2018).
Khani SC, Pawlyk BS, Bulgakov OV, Kasperek E, Young JE, Adamian M, Sun X, Smith AJ, Ali RR, Li T. Aav- mediated expression targeting of rod and cone photoreceptors with a human rhodopsin kinase promoter. Invest Ophthalmol Vis Sci 48(9):3954-61 (2007).
Kim DW, Uetsuki T, Kaziro Y, Yamaguchi N, Sugano S. Use of the human elongation factor 1 alpha promoter as a versatile and efficient expression system. Gene 91(2):217-23 (1990).
Kim, J.-W et al. Recruitment of Rod Photoreceptors from Short-Wavelength-Sensitive Cones during the Evolution of Nocturnal Vision in Mammals. Dev. Cell 37, 520-32 (2016).
Kotin RM. Prospects for the use of adeno-associated virus as a vector for human gene therapy. Hum Gene Ther 5 (7):793-801 (1994).
Lagarde, J. et al. High-throughput annotation of full-length long noncoding RNAs with capture long-read sequencing. Nat. Genet. 49, 1731-1740 (2017).
Lefebvre, J.L. et al. Development of dendritic form and function. Annu. Rev. Cell Dev. Biol. 31, 741-77 (2015).
Li, M. et al. Comprehensive analysis of gene expression in human retina and supporting tissues. Hum. Mol. Genet. 23, 4001-4014 (2014).
Li, Y. et al. Splicing-Dependent Trans-synaptic SALM3-LAR-RPTP Interactions Regulate Excitatory Synapse Development and Locomotion. Cell Rep. 12, 1618-1630 (2015).
Li, Y.I. et al. RNA splicing is a primary link between genetic variation and disease. Science 352, 600-4 (2016).
Lipscombe, D. & Lopez Soto, E.J. Alternative splicing of neuronal genes: new mechanisms and new therapies. Curr. Opin. Neurobiol. 57, 26-31 (2019).
Lobanova, E.S. et al. Transducin gamma-subunit sets expression levels of alpha- and beta-subunits and is crucial for rod viability. J. Neurosci. 28, 3510-20 (2008).
Logan, M. et al. Negative regulation of glial engulfment activity by Draper terminates glial responses to axon injury. Nat. Neurosci. 15, 722-30 (2012).
Luhmann, U.F.O. et al. The severity of retinal pathology in homozygous Crb1rd8/rd8 mice is dependent on additional genetic factors. Hum. Mol. Genet. 24, 128-141 (2015).
Magari SR, Rivera VM, luliucci JD, Gilman M, Cerasoli F Jr. Pharmacologic control of a humanized gene therapy system implanted into nude mice. J Clin Invest 100(11):2865-72 (1997).
Magurran, A. Measuring Biological Diversity. (Wiley-Blackwell, 2004).
Mah C, Byrne BJ, Flotte TR. Virus-based gene delivery systems. Clin Pharmacokinet 41(12):901-11 (2002).
Martin J, Frederick A, Luo Y, Jackson R, Joubert M, Sol B, Poulin F, Pastor E, Armentano D, Wadsworth S, Vincent K. Generation and characterization of adeno-associated virus producer cell lines for research and preclinical vector production. Hum Gene Ther Methods 24(4):253-69 (2013).
Mehalow, A.K. et al. CRB1 is essential for external limiting membrane integrity and photoreceptor morphogenesis in the mammalian retina. Hum. Mol. Genet. 12, 2179-89 (2003).
Mercer, T.R. et al. Targeted RNA sequencing reveals the deep complexity of the human transcriptome. Nat. Biotechnol. 30, 99-104 (2012).
Miyazaki J, Takaki S, Araki K, Tashiro F, Tominaga A, Takatsu K, Yamamura K. Expression vector system based on the chicken beta-actin promoter directs efficient production of interleukin-5. Gene 79(2):269-77 (1989).
Moore, B.A. et al. A Population Study of Common Ocular Abnormalities in C57BL/6N rd8 Mice. Investig. Opthalmology Vis. Sci. 59, 2252 (2018).
Morillon, A. & Gautheret, D. Bridging the gap between reference and real transcriptomes. Genome Biol. 20, 112 (2019).
Mulley, J.C. et al. Channelopathies as a genetic cause of epilepsy. Curr. Opin. Neurol. 16, 171-6 (2003).
Naj, A.C. et al. Common variants at MS4A4/MS4A6E, CD2AP, CD33 and EPHA1 are associated with late-onset Alzheimer's disease. Nat. Genet. 43, 436-441 (2011).
Nicklin SA, Baker AH. Tropism-modified adenoviral and adeno-associated viral vectors for gene therapy. Curr Gene Ther 2(3):273-93 (2002).
Niwa H, Yamamura K, Miyazaki J. Efficient selection for high-expression transfectants with a novel eukaryotic vector. Gene 108(2):193-9 (1991).

(56) References Cited

OTHER PUBLICATIONS

No D, Yao TP, Evans RM. Ecdysone-inducible gene expression in mammalian cells and transgenic mice. Proc Natl Acad Sci U S A 93(8):3346-51 (1996).

Omori, Y. & Malicki, J. oko meduzy and related crumbs genes are determinants of apical cell features in the vertebrate embryo. Curr. Biol. 16, 945-57 (2006).

Passini MA, Watson DJ, Vite CH, Landsburg DJ, Feigenbaum AL, Wolfe JH. Intraventricular brain injection of adeno-associated virus type 1 (AAV1) in neonatal mice results in complementary patterns of neuronal transduction to AAV2 and total long-term correction of storage lesions in the brains of beta-glucuronidase-deficient mice. J Virol 77 (12):7034-40 (2003).

Pawlyk BS, Smith AJ, Buch PK, Adamian M, Hong DH, Sandberg MA, Ali RR, Li T. Gene replacement therapy rescues photoreceptor degeneration in a murine model of Leber congenital amaurosis lacking RPGRIP. Invest Ophthalmol Vis Sci 46(9):3039-45 (2005).

Pechan P, Rubin H, Lukason M, Ardinger J, DuFresne E, Hauswirth WW, Wadsworth SC, Scaria A. Novel anti-VEGF chimeric molecules delivered by AAV vectors for inhibition of retinal neovascularization. Gene Ther 16(1):10-6 (2009).

Pederick, D.T. et al. Abnormal Cell Sorting Underlies the Unique X-Linked Inheritance of PCDH19 Epilepsy. Neuron 97, 59-66.e5 (2018).

Pellissier LP, Hoek RM, Vos RM, Aartsen WM, Klimczak RR, Hoyng SA, Flannery JG, Wijnholds J. Specific tools for targeting and expression in Müller glial cells. Mol Ther Methods Clin Dev 1:14009 (2014).

Pellissier LP, Quinn PM, Alves CH, Vos RM, Klooster J, Flannery JG, Heimel JA, Wijnholds J. Gene therapy into photoreceptors and Müller glial cells restores retinal structure and function in CRB1 retinitis pigmentosa mouse models. Hum Mol Genet 24(11):3104-18 (2015).

Peng, J. et al. High-Throughput Sequencing and Co-Expression Network Analysis of lncRNAs and mRNAs in Early Brain Injury Following Experimental Subarachnoid Haemorrhage. Sci. Rep. 7, 46577 (2017).

Peyman GA, Lad EM, Moshfeghi DM. Intravitreal injection of therapeutic agents. Retina 29(7):875-912 (2009).

Piccioli P, Di Luzio A, Amann R, Schuligoi R, Surani MA, Donnerer J, Cattaneo A. Neuroantibodies: ectopic expression of a recombinant anti-substance P antibody in the central nervous system of transgenic mice. Neuron 15 (2):373-84 (1995).

Piccioli P, Ruberti F, Biocca S, Di Luzio A, Werge TM, Bradbury A, Cattaneo A. Neuroantibodies: molecular cloning of a monoclonal antibody against substance P for expression in the central nervous system. Proc Natl Acad Sci U S A 88(13):5611-5 (1991).

Puñal, V.M. et al. Large-scale death of retinal astrocytes during normal development mediated by microglia. bioRxiv 593731 (2019). doi: 10.1101/593731.

Qiu, X. et al. Single-cell mRNA quantification and differential analysis with Census. Nat. Methods 14, 309-315 (2017).

Quinn, P.M. et al. The CRB1 Complex: Following the Trail of Crumbs to a Feasible Gene Therapy Strategy. Front. Neurosci. 11, 175 (2017).

Raj, B. & Blencowe, B.J. Alternative Splicing in the Mammalian Nervous System: Recent Insights into Mechanisms and Functional Roles. Neuron 87, 14-27 (2015).

Ray T, Cochran K, and Kay J. Single molecule sequencing elucidates retinal mRNA isoform diversity—implications for CRB1 retinopathies. ARVO Annual Meeting Abstract. Investigative Ophthalmology & Visual Science vol. 5 9, 2351 (2018).

Reyes, A. & Huber, W. Alternative start and termination sites of transcription drive most transcript isoform differences across human tissues. Nucleic Acids Res. 46, 582-592 (2018).

Rubinstein, R. et al. Molecular Logic of Neuronal Self-Recognition through Protocadherin Domain Interactions. Cell 163, 629-642 (2015).

Sando, R. et al. Latrophilin GPCRs direct synapse specificity by coincident binding of FLRTs and teneurins. Science 363, eaav7969 (2019).

Schindelin, J. et al. Fiji: an open-source platform for biological-image analysis. Nat. Methods 9, 676-82 (2012).

Schmucker, D. et al. Drosophila Dscam is an axon guidance receptor exhibiting extraordinary molecular diversity. Cell 101, 671-84 (2000).

Schreiner, D. et al. Targeted Combinatorial Alternative Splicing Generates Brain Region-Specific Repertoires of Neurexins. Neuron 1-13 (2014). doi: 10.1016/j.neuron.2014.09.011.

* cited by examiner

C

D

E

F

G

C
Megf11 exon inclusion
Pearson Correlation
−1.0 −0.5 0.0 0.5 1.0
Exons
01 02 03 04 05 06 07 08 08b 09 10 11 12 13 14 15 16 16b 17 18 19 20 21 22 23 23l 23b 24 24l 25
*
*

A

B

C

| Sequencing Profiles | | | | | | |
|---|---|---|---|---|---|---|
| | P1 Retina | P6 Retina | P10 Retina | Adult Retina | Adult Cortex | Combined |
| Number of SMRT Cells | 9 | 8 | 8 | 1 Sequel | 2 Sequel | 25 SMRT/3 Sequel |
| Reads of Insert | 255,930 | 362,892 | 397,192 | 236,025 | 71,116 | 1,323,155 |
| Number of 5 Prime Reads | 130,167 | 191,980 | 225,931 | 198,831 | 62,689 | 809,598 |
| Number of Poly-A Reads | 153,200 | 206,252 | 246,590 | 209,625 | 66,797 | 882,464 |
| Number of Non-Full-Length Reads | 153,214 | 179,274 | 207,406 | 59,504 | 9,941 | 609,339 |
| Number of Full-Length Non-Chimeric Reads | 89,675 | 157,898 | 179,414 | 176,457 | 61,159 | 664,603 |
| Average Full-Length Non-Chimerc Read Length (bp) | 5,515 | 4,427 | 5,063 | 4,576 | 4,937 | 4,832 |

A
Total isoforms
Cufflinks
Stringtie
PacBio
4000
2000
0
Isoform Intersections
4000
3000
2000
1000
0
3814
791
298
132
116
54
B
Read Counts
10000
1000
100
10
Partial
Full
RNAseq Junction Coverage
C
Number of isoforms
8000
6000
4000
2000
0
70
80
90
100
Gene Percentile Cutoff
all isoforms
isoforms with a non canonical junction
D
Number of isoforms contributing to specified level of gene expression:
Top 50%
20
10
0
Top 75%
150
100
50
0

C

*Vldlr* locus

D *Cntn4* locus

Fig. 16

CRB1-B sequence (SEQ ID NO:1) with annotated protein domains

```
MFGARTHGFH ILMAMLIGIH CEEDVNECSS NPCQNGGTCE NLPGNYTCHC PFDNLSRTFY     60
GGRDCSDILL GCTHQQCLNN GTCIPHFQDG QHGFSCLCPS GYTGSLCEIA TTLSFEGDGF    120
LWVKSGSVTT KGSVCNIALR PQTFQPMALL LFRSNRDVFV KLEFLSGYIH LSIQVNNQSK    180
VLLFISHNTS DGEWHFVEVI FAEAVTLTLI DDSCKEKCIA KAPTPLESDQ SICAFQNSFL    240
GGLPVGMTSN GVALLNFYNM PSTPSFVGCL QDIKIDWNHI TLENISSGSS LNVKAGCVRK    300
DWCESQPCQS RGRCINLWLS YQCDCHRPYE GPNCLREYVA GRFGQDDSTG YVIFTLDESY    360
GDTISLSMFV KTLQPSGLLL ALSRSTYQYI RVALERGRLA MLTPNSPKLV VKFVLNDGNV    420
HLISLKIKPY KIELYQSSQN LGFISASTWK IEKGDVIYIG GLPDKQETEL NGGFFKGCIQ    480
DVRLNNQNLE FFPNPTNNAS LNPVLVNVTQ GCAGDNSCKS NPCHNGGVCH SRWDDFSCSC    540
PALTSGKACE EVQWCGFSPC PHGAQCQPVL QGFECIANAV FNGQSGQILF RSNGNITREL    600
TNITFGKRTR DANVIIHAEK PPPFLNISIQ QSRLFPQLQS GNSKYMFLLT KQEKNNGGWH    660
WHEVTLSMTD PLSQTSRWQM EVDNETPFVT STIATGSLNF LKDNTDIYVG DRAIDNIKGL    720
QGCLSTIEIG GIYLSYFENV HGFINKPQEE QFLKISTNSV VTGCLQLNVC NSNPCLHGGN    780
CEDIYSSYHC SCPLGWSGKH CELNIDECFS NPCIHGNCSD RVAAYHCTCE PGYTGVNCEV    840
DIDNCQSHQC ANGATCISHT NGYSCLCFGN FTGKFCRQSR LPSTVCGNEK TNLTCYNGGN    900
CTEFQTELKC MCRPGFTGEW CEKDIDECAS DPCVNGGLCQ DLLNKFQCLC DVAFAGERCE    960
VDVSSLSFYV SLLFWQNLFQ LLSYLILRMN DEPVVEWGEQ EDY                     1003
```

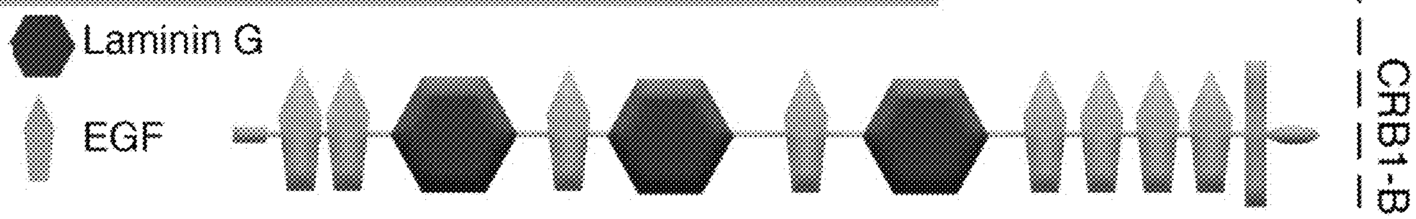

COMPOSITIONS AND METHODS FOR THE DIAGNOSIS AND TREATMENT OF RETINOPATHIES

CROSS REFERENCE TO RELATED APPLICATIONS

This application is a national stage filing under 35 U.S.C. § 371 of International Application No. PCT/US2020/020977, filed Mar. 4, 2020, which claims the benefit of priority of U.S. Provisional Application No. 62/813,272, filed on Mar. 4, 2019, the contents of which are incorporated herein by reference in their entireties.

STATEMENT REGARDING FEDERALLY SPONSORED RESEARCH

This invention was made with Government support under Federal Grant number F32EY026344 awarded by the National Institutes of Health. The Government has certain rights to this invention.

SEQUENCE LISTING

A Sequence Listing accompanies this application and is submitted as an ASCII text file of the sequence listing named "2020-03-04_155554.00531_ST25.txt" which is 342 KB in size and was created on Mar. 4, 2020. The sequence listing is electronically submitted via EFS-Web with the application and is incorporated herein by reference in its entirety.

BACKGROUND

Loss-of-function mutations in the CRB1 gene cause a wide spectrum of retinal degenerative diseases. Recent advances in gene therapy have opened new possibilities for halting progressive vision loss in single-gene blinding diseases. If CRB1 disease is to become a strong candidate for such therapy, it is essential to understand the normal and pathobiological functions of CRB1 protein in the retina in vivo. The prevailing model of CRB1 function posits that it is required for structural integrity of the outer limiting membrane (OLM). CRB1 protein—a cell surface molecule with a large extracellular domain—has been localized to OLM cell-cell adhesions linking photoreceptors and Müller glia. Loss of CRB1 function is thought to weaken OLM adhesion, leading to structural deficits that ultimately cause photoreceptor death. According to this model, replacement of the CRB1 gene is a promising therapeutic strategy: Restoring adhesion would be expected to improve OLM integrity, thereby slowing or even halting photoreceptor death. To design an effective gene replacement strategy, it is important to know two critical pieces of information that are currently unclear. First, in which cell type should CRB1 be replaced? Is it needed on the glial or photoreceptor side of the OLM junction—or both? Second, which splice variant of the CRB molecule should be used for replacement? CRB1 is known to encode several alternative mRNA isoforms; moreover, since the true complexity of the human transcriptome remains surprisingly murky, there may still be additional isoforms that are not described. Because only one cDNA species can be chosen for inclusion in a gene therapy vector, it is critical to establish which isoform is most effective at halting degeneration when reintroduced into the mature retina.

SUMMARY

In one aspect, the present disclosure provides an isolated polynucleotide comprising a polynucleotide sequence encoding a Crumbs 1-B (CRB1-B) isoform comprising SEQ ID NO:1 operably linked to a heterologous promoter capable of expressing the isoform in a retinal cell. In another aspect, the disclosure provides a vector comprising the isolated polynucleotide.

In another aspect, the disclosure provides a recombinant vector comprising a polynucleotide encoding a Crumbs 1-B (CRB1-B) isoform, wherein the CRB1-B isoform comprises an N-terminal signal peptide linked to an extracellular polypeptide comprising, from N-terminus-to-C-terminus: two EGF domains, a lamG domain, an EGF domain, a lamG domain, an EGF domain, a lamG domain, and four EGF domains; wherein the C terminus of the extracellular polypeptide is linked to a C-terminal domain comprising a transmembrane domain and intracellular domain.

In a further aspect, the present disclosure provides an isolated polypeptide made from the isolated polynucleotide or recombinant vector described herein.

In another aspect, the disclosure provides a pharmaceutical composition comprising the isolated polynucleotide or the recombinant vector described herein and a pharmaceutically acceptable carrier.

In another aspect, the present disclosure provides a method of treating an ocular disorder in a subject, the method comprising administering to the subject a therapeutically effective amount of the polynucleotide, the recombinant vector, the isolated polypeptide, or the pharmaceutical composition described herein such that the ocular disorder is treated in the subject.

In yet another aspect, the disclosure provides a method of reducing progression of loss of vision or maintaining vision function in a subject in need thereof, the method comprising administering to the subject a therapeutically effective amount of the polynucleotide, the recombinant vector, the isolated polypeptide, or the pharmaceutical composition described herein such that loss of vision is reduced.

In yet another embodiment, the disclosure provides a kit for treating an ocular disorder in a subject, the kit comprising the isolated polynucleotide, the recombinant vector, the isolated polypeptide, or the pharmaceutical composition described herein, a device for delivery of the isolated polynucleotide, recombinant vector, isolated polypeptide or pharmaceutical composition to the subject, and instructions for use.

In a further aspect, the disclosure provides a kit for reducing progression or reducing loss of vision or maintaining vision function in a subject, the kit comprising the isolated polynucleotide, the recombinant vector, the isolated polypeptide, or the pharmaceutical composition described herein and a device for delivery of the isolated polynucleotide, recombinant vector, isolated polypeptide, or pharmaceutical composition to the subject, and instructions for use.

In another aspect, the disclosure provides a system for the delivery of the isolated polynucleotide, the recombinant vector, the isolated polypeptide or the pharmaceutical composition to an eye of a subject, the system comprising a therapeutically effective amount of the isolated polynucleotide, the recombinant vector, the isolated polypeptide, or the pharmaceutical composition described herein, and a device for delivery to the subject.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 16 shows the polypeptide sequence of the CRB1-B isoform (SEQ ID NO:1) with the EGF domains highlighted in gray (residues 24-65, 68-109, 303-334, 516-550, 773-802, 804-839, 841-876 and 924-960) and the laminin G domains highlighted in red (residues 141-276, 370-487, and 607-732). A schematic depiction of the protein domains is shown below the sequence.

DETAILED DESCRIPTION

Figure 1:
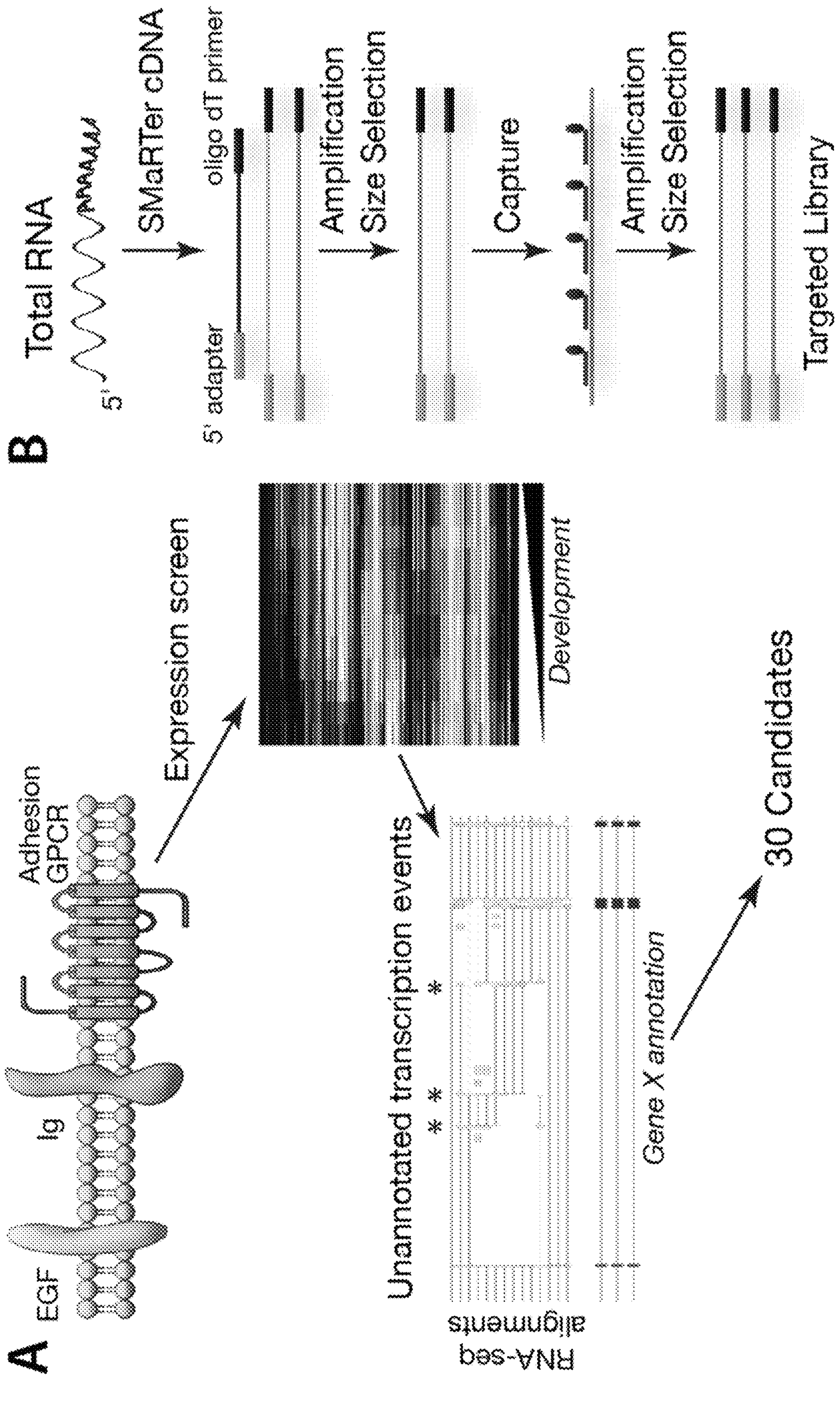
FIG. 1 depicts the strategy used herein for identifying cell surface receptors that exhibit high isoform diversity. (A) Screening strategy for selecting genes for lrCaptureSeq. Members of EGF, Ig, and adhesion GPCR families were tested for 1) expression during neural development, using RNA-seq data from retina and cortex; and 2) unannotated transcript diversity, based on RNA-seq read alignments compared to UCSC Genes public database. Thirty genes showing strong evidence for unannotated events such as alternative splicing, novel exons, and novel transcriptional start sites (asterisks) were selected for targeted sequencing of full length transcripts (B,C). (B) lrCaptureSeq workflow. cDNAs are 5' tagged to enable identification of full-length reads. Biotinylated capture probes tiling known exons. To obtain sequencing libraries enriched for intact cDNAs, two rounds of amplification and size selection were used. (C) Size distribution of full-length reads for each lrCaptureSeq experiment. Mouse retinal transcripts were analyzed at P1, P6, P10 and adult; cortex data is from adult mice. The vast majority of reads are within expected size range for cDNAs of targeted genes. Dashed lines, quartiles of read length distribution.
Figure 1:
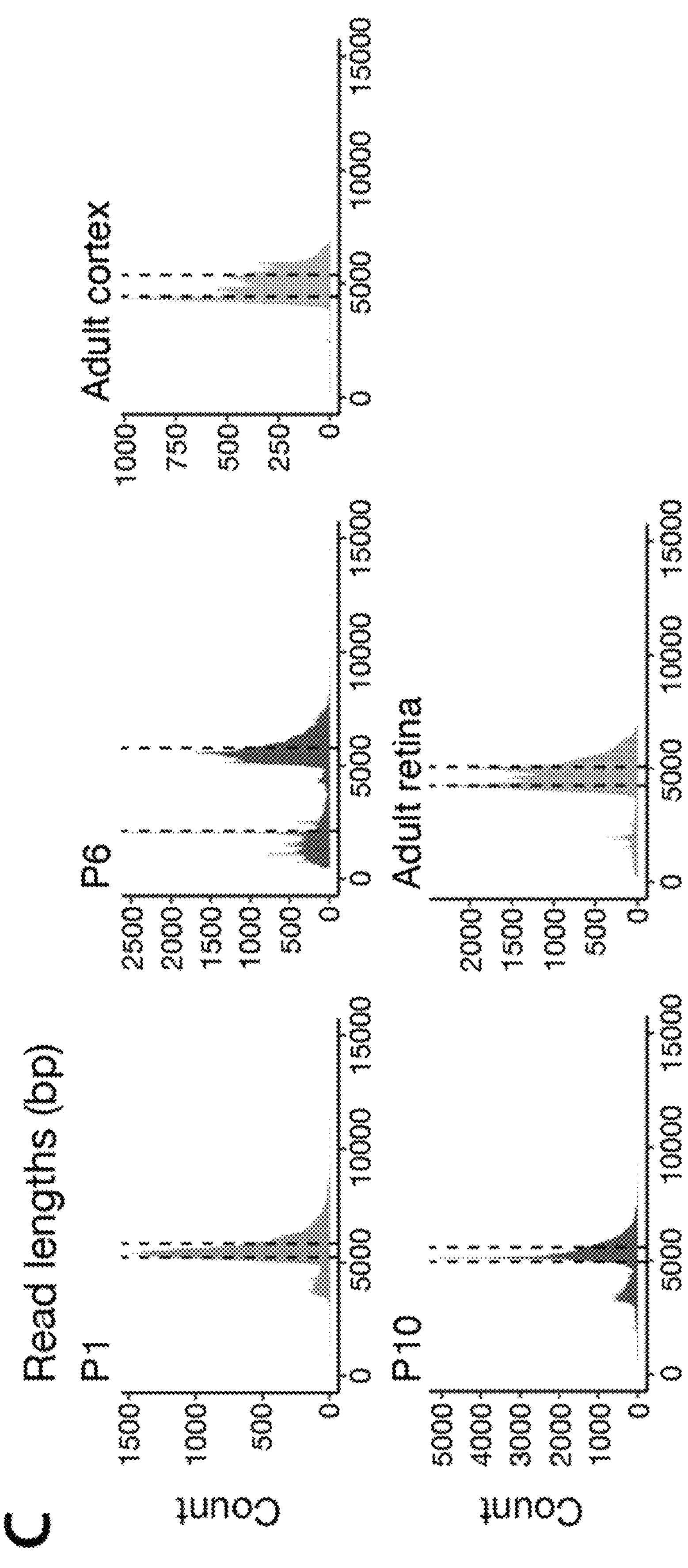

Gene replacement is a promising therapeutic strategy for the wide spectrum of retinal degenerative diseases caused by loss-of-function mutations in the Crb1 gene. However, to design an effective gene replacement strategy, both the cell type in which this gene needs to be replaced and the proper Crb1 isoform to provide must be identified.

Crb1 is a member of the evolutionarily conserved Crumbs gene family, which encode cell-surface proteins that mediate apico-basal epithelial polarity[33]. Notably, it is considered standard practice to refer to the mouse version of the gene as Crb1 and refer to human version of the gene as CRB1. However, in the present application, the nomenclatures Crb1 and CRB1 are used interchangeably to refer to the gene and are not necessarily used to indicate the species from which the gene is derived.

In the retina, CRB1 localizes to the outer limiting membrane (OLM), a set of structurally important junctions between photoreceptors and neighboring glial cells known as Müller glia[26]. OLM junctions form at precise subcellular domains within each cell type, suggesting a high degree of molecular specificity in the establishment of these intercellular contacts[34]. There is great interest in understanding the function of CRB1 at OLM junctions, because loss-of-function mutations in human CRB1 cause a spectrum of retinal degenerative disorders[35]. It has been proposed that loss of OLM integrity might play a role in disease pathogenesis[26, 36]. Yet, studies in mice have yet to provide convincing support for this model. For example, in mice, deletion of the known Crb1 isoform neither disrupts the OLM nor causes significant photoreceptor degeneration[37].

In the present application, the inventors identify a new Crb1 isoform that is far more abundant—in both mouse and human retina—than the canonical isoform. Using a mouse model, they show that this new isoform is required for OLM integrity and that its removal is required to adequately phenocopy the human degenerative disease. These results call for a major revision to prevailing models of CRB1 disease genetics and pathobiology. Remarkably, the present inventors discover that the major isoform of the retinal degeneration gene Crb1 was previously overlooked. This isoform, Crb1-B, is the only one expressed by photoreceptors, the affected cells in CRB1 disease. Using a mouse model, the inventors identify a function for this isoform at photoreceptor-glial junctions and demonstrate that loss of this isoform accelerates photoreceptor death.

The present invention demonstrates that the major isoform Crb1-B, when presented in trans, is sufficient to retain photoreceptor function, allowing for its use to maintain vision and reduce vision loss. Specifically, introduction of the Crb1-B isoform into retinal photoreceptor cells is sufficient to maintain photoreceptor function and reduce loss of photoreceptor function.

Isoform Annotation:

Most genes generate multiple mRNA isoforms. As used herein the term "isoform" is used to describe mRNAs that are produced from the same locus but are different in their transcription start sites (TSSs), protein coding DNA sequences (CDSs) and/or untranslated regions (UTRs). Alternative isoforms are produced by mechanisms such as alternative splicing, intron retention, and alternative transcription start/stop sites. Alternative isoforms often differ in their protein-coding capacity[1-4], which sometimes results in altered gene function. These mechanisms are especially common in the central nervous system (CNS), where the use of alternative isoforms is particularly prevalent[1,5]. Moreover, dysregulation of isoform expression is implicated in several neurological disorders[9-11].

Despite the clear importance of isoform diversity, information about the number and the identity of CNS mRNA isoforms remains surprisingly scarce—even within the major transcriptome annotation databases[12]. RNA-sequencing (RNA-seq) has generated an explosion of new information about alternative splicing However, because typical RNA-seq read lengths are less than 200 bp, this method is not able to resolve the full-length sequence of multi-kilobase transcripts. Therefore, by relying on RNA-seq alone, it is impossible to determine the number of isoforms produced by any given gene, or their full-length sequences. In the absence of reliable full-length transcript annotations, the design and interpretation of genetic experiments becomes exceedingly difficult. For example, unless transcript sequences are known, it is difficult to be certain that a "knockout" mouse allele has been properly designed such that it fully eliminates expression of all isoforms. Unannotated isoforms can also be problematic for understanding how mutations lead to pathology in human genetic disease. Hidden isoforms may possess uncharacterized protein-coding sequences or novel expression patterns, which could cause the molecular and cellular consequences of disease-linked mutations to be misinterpreted. Thus, a lack of comprehensive isoform sequence information remains a major impediment to our understanding of both normal gene function and the phenotypic consequences of gene dysfunction[12].

In the present application, the inventors devised a strategy that leverages Pacific Biosciences (PacBio) long-read sequencing technology to generate comprehensive catalogs of CNS cell-surface molecules. Long-read sequencing is ideal for full-length transcript identification; however, the available sequencing depth is not sufficient to reveal the full scope of isoform diversity[27-30]. To overcome this limitation, the inventors adapted a strategy from short-read sequencing, in which targeted cDNAs are pulled down with biotinylated probes against known exons[31,32]. This approach yielded major improvements in long-read coverage, revealing an unexpectedly rich diversity of isoforms encoded by the targeted genes. To make sense of these complex datasets, the inventors developed bioinformatics tools for the classification and comparison of isoforms, and for determining their expression patterns using short-read RNA-seq data. Using these methods, the inventors were able to identify a novel Crb1 isoform that offers great potential for the treatment of retinopathies.

Compositions:

i. Polynucleotide Sequences, Vectors and Isolated Proteins

Gene therapy protocols for disorders of the eye require the localized delivery of the polynucleotide or vector to the cells in the eye (e.g., cells of the retina) for local expression. The cells that will be the treatment target in these diseases may include, inter alia, one or more cells of the eye (e.g., photoreceptors, ocular neurons, etc.). The polynucleotides, vectors, polypeptides, compositions, methods, systems and kits of the present disclosure are based, at least in part, on the discovery that a certain unknown isoform of the gene Crb1, termed Crb11 B is, exclusively expressed in retinal photoreceptors. The Crb1-B isoform has been found by the inventors to be an attractive candidate for Crb1 gene replacement therapy for numerous reasons, including for example: (i) size; (ii) their localized expression in retinal photoreceptors—the cell type that degenerates in retinal dystrophies; (iii) the presence of a unique promoter as well as unique first and last coding exons making them functionally distinct from other isoforms; and (iv) increased expression (e.g., Crb1-B is expressed ~10 fold higher) than other Crb1 isoforms in the retina, suggesting their function may be the most important to replace to rescue vision. As demonstrated in the examples, CRB1-B is the majority isoform expressed in retinal photoreceptors, while the other isoforms are expressed in other retinal cell types (e.g. CRB1-A is found expressed in Müller cells). As such, in trans expression of CRB1-B protein within photoreceptors in a subject is sufficient by itself to retain photoreceptor function and maintain vision in the subject.

In one embodiment, the present technology provides an isolated polynucleotide comprising a polynucleotide sequence encoding a Crumbs 1-B (CRB1-B) isoform comprising SEQ ID NO:1 (the human CRB1-B protein) operably linked to a heterologous promoter capable of expressing the isoform in a retinal cell. CRB1-B isoform is specifically expressed in photoreceptor cells, predominantly within the inner and outer segments. This localization is in marked contrast to CRB1-A which has been localized to the apical tips of Müller cells, within the OLM (See FIG. 6E). In one embodiment, the polynucleotide sequence encoding the CRB1-B isoform is SEQ ID NO:2.

In other embodiments, the present technology provides isolated polynucleotides encoding other isoforms of the human Crumbs 1 gene. In one embodiment, the polynucleotide sequence (SEQ ID NO:4) encodes a Crumbs 1-A (CRB1-A) isoform comprising SEQ ID NO:5 (human CRB1-A protein). In another embodiment, the polynucleotide sequence (SEQ ID NO:6) encodes a Crumbs 1-C (CRB1-C) isoform comprising SEQ ID NO:7 (human CRB1-C protein).

In further embodiments, the isolated polynucleotides encode isoforms of the mouse Crumbs 1 gene. In one embodiment, the polynucleotide sequence (SEQ ID NO:8) encodes a Crumbs 1-A (CRB1-A) isoform comprising SEQ ID NO:9 (mouse CRB1-A protein). In another embodiment, the polynucleotide sequence (SEQ ID NO:10) encodes a Crumbs 1-B (CRB1-B) isoform comprising SEQ ID NO:11 (mouse CRB1-B protein). In yet another embodiment, the polynucleotide sequence (SEQ ID NO:12) encodes a Crumbs 1-C(CRB1-C) isoform comprising SEQ ID NO:13 (mouse CRB1-C protein). In yet a further embodiment, the polynucleotide sequence encodes a Crumbs 1-A2 (CRB1-A2) protein.

The terms "polynucleotide" or "nucleic acid" are used interchangeably herein and refer to a polymeric form of nucleotides of any length, either ribonucleotides or deoxyribonucleotides. Thus, this term includes, but is not limited to, single-, double- or multi-stranded DNA or RNA, genomic DNA, cDNA, DNA-RNA hybrids, or a polymer comprising purine and pyrimidine bases, or other natural, chemically or biochemically modified, non-natural, or derivatized nucleotide bases. The backbone of the polynucleotide can comprise sugars and phosphate groups (as may typically be found in RNA or DNA), or modified or substituted sugar or phosphate groups. Alternatively, the backbone of the polynucleotide can comprise a polymer of synthetic subunits such as phosphoramidates and thus can be an oligodeoxynucleoside phosphoramidate ($P—NH_2$) or a mixed phosphoramidate-phosphodiester oligomer. In addition, a double-stranded polynucleotide can be obtained from the single stranded polynucleotide product of chemical synthesis either by synthesizing the complementary strand and annealing the strands under appropriate conditions, or by synthesizing the complementary strand de novo using a DNA polymerase with an appropriate primer. Polynucleotide sequences provided herein are provided as the cDNA encoding for the CRB1 isoform of interest.

As used herein, a "therapeutic" agent (e.g., a therapeutic polypeptide, nucleic acid, or transgene) is one that provides a beneficial or desired clinical result, such as the exemplary clinical results described above. As such, a therapeutic agent may be used in a treatment as described herein. In some embodiments, the polynucleotide comprises a Crb1 isoform. In a preferred embodiment, the Crb1 isoform is Crb1-B. In another embodiment, the isoform is selected from the group consisting of Crb1-A, Crb1-A2, Crb1-B, Crb1-C and combinations thereof.

"Heterologous" means derived from a genotypically distinct entity from that of the rest of the entity to which it is compared or into which it is introduced or incorporated. For example, a polynucleotide introduced by genetic engineering techniques into a different cell type is a heterologous polynucleotide (and, when expressed, can encode a heterologous polypeptide). Similarly, a cellular sequence (e.g., a gene or portion thereof) that is incorporated into a viral vector is a heterologous nucleotide sequence with respect to the vector. The term "transgene" refers to a polynucleotide that is introduced into a cell and is capable of being transcribed into RNA and optionally, translated and/or expressed under appropriate conditions. In aspects, it confers a desired property to a cell into which it was introduced, or otherwise leads to a desired therapeutic or diagnostic outcome. In another aspect, it may be transcribed into a molecule that mediates RNA interference, such as miRNA, siRNA, or shRNA. The transgene for use in the present invention is an isoform of Crb1, preferably Crb1-B.

As used herein, the term "isolated" means that the material is removed from its original environment (e.g., the natural environment if it is naturally occurring). For example, a naturally occurring polynucleotide or polypeptide present in a living microorganism is not isolated, but the same polynucleotide or polypeptide, separated from some or all of the coexisting materials in the natural system, is isolated. Such polynucleotides could be part of a vector and/or such polynucleotides or polypeptides could be part of a composition and still be isolated in that such vector or composition is not part of its natural environment.

Accordingly, in another aspect of the present disclosure provides a recombinant vector comprising, consisting of, or consisting essentially of a polynucleotide comprising a Crb1 isoform and encoding the CRB1-B protein.

The terms "vector" or "recombinant vector" are used interchangeably herein and refer to a recombinant plasmid or virus that comprises a nucleic acid to be delivered into a host cell, either in vitro or in vivo. The vector can be a nucleic acid molecule capable of propagating another nucleic acid to which it is linked, and include the term "expression vectors." Vectors also include any pharmaceutical compositions thereof (e.g., a recombinant vector and a pharmaceutically acceptable carrier/excipient as provide herein). The term vector includes the vector as a self-replicating nucleic acid structure as well as the vector incorporated into the genome of a host cell into which it has been introduced. Vectors, including expression vectors, comprise the nucleotide sequence encoding the CRB1-B isoform described herein and a heterogeneous sequence necessary for proper propagation of the vector and expression of the encoded polypeptide. The heterogeneous sequence (i.e., sequence from a difference species than the polypeptide) can comprise a heterologous promoter or heterologous transcriptional regulatory region that allows for expression of the polypeptide. As used herein, the terms "heterologous promoter," "promoter," "promoter region," or "promoter sequence" refer generally to transcriptional regulatory regions of a gene, which may be found at the 5' or 3' side of the polynucleotides described herein, or within the coding region of the polynucleotides, or within introns in the polynucleotides. Typically, a promoter is a DNA regulatory region capable of binding RNA polymerase in a cell and initiating transcription of a downstream (3' direction) coding sequence. The typical 5' promoter sequence is bounded at its 3' terminus by the transcription initiation site and extends upstream (5' direction) to include the minimum number of bases or elements necessary to initiate transcription at levels detectable above background. Within the promoter sequence is a transcription initiation site, as well as protein binding domains (consensus sequences) responsible for the binding of RNA polymerase. Any promoter capable of expressing CRB1-B in a retinal cell are contempated to be used in the practice of the present invention.

In some embodiments, the recombinant vector comprises a polynucleotide encoding a Crumbs 1-B (CRB1-B) isoform, wherein the CRB1-B isoform comprises an N-terminal signal peptide linked to an extracellular polypeptide comprising or consisting of, from N-terminus-to-C-terminus: two EGF domains, a lamG domain, an EGF domain, a lamG domain, an EGF domain, a lamG domain, and four EGF domains (see FIG. 16 for the CRB1-B protein sequence with these domains annotated); wherein the C terminus of the extracellular polypeptide is linked to a C-terminal domain comprising a transmembrane domain and intracellular domain. In a preferred embodiment, the polynucleotide is operably linked to a heterologous promoter capable of expressing the isoform in a retinal cell. In some embodiments, the extracellular polypeptide extends from the N-terminus of the ninth EGF domain of a CRB1-A isoform to the C-terminus of the sixteenth EGF domain of the CRB1-A isoform. In some embodiments, the C-terminal domain comprises the amino acid sequence of VSSLSFYVSLLFWQNLFQLLSYLILRMNDEPVVEWGEQEDY (SEQ ID NO: 3).

As used herein, the term "EGF domain" (also referred to as an "EGF-like domain") is an evolutionary conserved protein domain, which derives its name from the epidermal growth factor where it was first described. Most occurrences of the EGF-like domain are found in the extracellular domain of membrane-bound proteins or in proteins known to be secreted. The main structure of EGF-like domains is a two-stranded 3-sheet followed by a loop to a short C-terminal, two-stranded β-sheet. EGF-like domains frequently occur in numerous tandem copies within proteins, which typically fold together to form a single, linear solenoid domain block. Suitable EGF domains include, without limitation, SEQ ID NO:14-20 and SEQ ID NO:52 which are the EGF domains found within the human CRB1-B isoform.

As used herein, the terms "laminin globular (G) domain" and "lamG domain" are used interchangeably to refer to a domain found in various members of the laminin protein family as well as in a large number of other extracellular proteins. Suitable lamG domains include, without limitation, SEQ ID NO:21-23, which are the lamG domains found within the human CRB1-B isoform.

The term "N-terminal signal peptide" (also commonly referred to as a "signal peptide", "signal sequence", or "leader peptide") refers to a short peptide present at the N-terminus of a protein that directs the cellular localization of a protein by targeting it within the cell's secretory pathway. The term "extracellular polypeptide" refers to a polypeptide or portion thereof that localizes outside of the cell in the extracellular space (i.e., outside of the plasma membrane).

Accordingly, another aspect of the present disclosure provides a recombinant vector comprising, consisting of, or consisting essentially of a polynucleotide comprising a Crb1 isoform selected from the group consisting of Crb1-A, Crb1-A2, Crb1-B, Crb1-C and combinations thereof. In one embodiment, the Crb1 isoform comprises Crb1-A. In another embodiment, the Crb1 isoform comprises Crb1-A2. In another embodiment, the Crb1 isoform comprises Crb1-B. In yet another embodiment, the Crb1 isoform comprises Crb1-C.

In some embodiments, the vector comprises a viral vector. The term viral vector as used herein also include the virus particles containing the viral vector produced by expression of viral vectors within a cell (e.g. a cell line), wherein the cell produces the viral vector containing viral particles (i.e. virions). The virus particles comprise a viral DNA or RNA that encodes and is capable of expression of the isoform of interest in a cell to which it is introduced. Thus, the term "viral vector" includes the mature viral particles containing the viral vector that are capable of expressing the isoform of interest in a host cell, preferably a retinal cell. Introduction or transduction of the viral vector into a host cell, preferably a retinal cell, allows for the expression of the encoded CRB1-B isoform within the host cell. Methods of packaging the viral vector into virions (i.e. particles) are known in the art. In a preferred embodiment, the viral vector is an adeno-associated virus (AAV). It is understood that other gene delivery vectors, including retroviruses, lentiviruses, HSV vectors, or Semliki-Forrest-Virus vectors and adenoviruses may also be used and are contemplated to be part of the present invention. The advantage of AAV vectors is that they can generally be concentrated to titers of about $10^{14}$ viral particles per ml, a level of vector that has the potential to transduce a greater number of target cells, e.g., retinal cells, in a patient. Moreover, AAV-based vectors have a well-established record of safety and do not integrate at significant levels into the target cell genome, thus avoiding the potential for insertional activation of deleterious genes or deactivation of necessary genes. Accordingly, in certain embodiments the viral vector comprises an AAV vector.

In some embodiments, the polynucleotide is under the control of a promoter sequence that is expressed in the retina. In other embodiments, the polynucleotide is operably linked to a promoter suitable for expression of the polynucleotide in one or more retina cell types. In some embodiments, the retina cell is selected from the group consisting of a photoreceptor cells, a retinal pigmented epithelial cell, a bipolar cell, a horizontal cell, an amacrine cell, a Müller cell, and/or a ganglion cell. In certain embodiments, the retinal cell comprises a photoreceptor cell. In some embodiments, the promoter is selected from the group consisting of a rhodopsin kinase (RK) promoter, an opsin promoter, a Cytomegalovirus (CMV) promoter, and a chicken β-actin (CBA promoter), among others.

For example, in one embodiment, the target cell of the isolated polynucleotide or recombinant vector encoding CRB1-B is a photoreceptor cell in the retina. In another example, the isolated polynucleotide or recombinant vector encodes CRB1-A and the target cell is a Mueller cell. In some embodiments, one or more vectors may be used in combination, wherein one vector encodes the CRB1-B isoform, and the one or more other vectors encodes one of the other Crb isoforms, for example, CRB1-A, CRB1-A2, or CRB-C.

A "recombinant viral vector" refers to a recombinant polynucleotide vector comprising one or more heterologous sequences (i.e., nucleic acid sequence not of viral origin). In the case of recombinant AAV vectors, the recombinant nucleic acid is flanked by at least one inverted terminal repeat sequence (ITR). In some embodiments, the recombinant nucleic acid is flanked by two ITRs.

A "recombinant AAV vector (rAAV vector)" refers to a polynucleotide vector comprising one or more heterologous sequences (i.e., nucleic acid sequence not of AAV origin) that are flanked by at least one AAV inverted terminal repeat sequence (ITR). Such rAAV vectors can be replicated and packaged into infectious viral particles when present in a host cell that has been infected with a suitable helper virus (or that is expressing suitable helper functions) and that is expressing AAV rep and cap gene products (i.e. AAV Rep and Cap proteins). When a rAAV vector is incorporated into a larger polynucleotide (e.g., in a chromosome or in another vector such as a plasmid used for cloning or transfection), then the rAAV vector may be referred to as a "pro-vector" which can be "rescued" by replication and encapsidation in the presence of AAV packaging functions and suitable helper functions. A rAAV vector can be in any of a number of forms, including, but not limited to, plasmids, linear artificial chromosomes, complexed with lipids, encapsulated within liposomes, and encapsidated in a viral particle, e.g., an AAV particle. A rAAV vector can be packaged into an AAV virus capsid to generate a "recombinant adeno-associated viral particle (rAAV particle)". Methods and kits for making AAV are known in the art, for example, but not limited to, AdEasy® cloning system (e.g., available from QBiogene GmbH, Heidelberg, Germany). Corresponding vectors and helper vectors are extensively known in the art (Nicklin S A, Baker A H, Curr Gene Ther., 2002, 2: 273-93; Mah et al., Clin Pharmacokinet., 2002, 41: 901-11).

An "rAAV virus" or "rAAV viral particle" refers to a viral particle composed of at least one AAV capsid protein and an encapsidated rAAV vector genome.

In some embodiments, the vector comprises a recombinant AAV (rAAV) vector. In some embodiments, the vector comprises a transgene flanked by one or two AAV inverted terminal repeats (ITRs). The nucleic acid is encapsidated in the AAV particle. The AAV vector may also comprise capsid proteins. In some embodiments, the nucleic acid comprises the coding sequence(s) of interest (e.g., Crb1-A, Crb1-A2, Crb1-B, Crb1-C, preferably Crb1-B) operatively linked components in the direction of transcription, control sequences including transcription initiation and termination sequences, thereby forming an expression cassette.

In some embodiments, the expression cassette is flanked on the 5' and 3' end by at least one functional AAV ITR sequences. By "functional AAV ITR sequences" it is meant that the ITR sequences function as intended for the rescue, replication and packaging of the AAV virion. See Davidson et al., PNAS, 2000, 97(7)3428-32; Passini et al., J. Virol., 2003, 77(12):7034-40; and Pechan i., Gene Ther., 2009, 16:10-16, all of which are incorporated herein in their entirety by reference. For practicing some aspects of the present disclosure, the recombinant vectors comprise at least all of the sequences of AAV essential for encapsidation and the physical structures for infection by the rAAV. AAV ITRs for use in the vectors of the present disclosure need not have a wild-type nucleotide sequence (e.g., as described in Kotin, Hum. Gene Ther., 1994, 5:793-801), and may be altered by the insertion, deletion or substitution of nucleotides or the AAV ITRs may be derived from any of several AAV serotypes. More than 40 serotypes of AAV are currently known, and new serotypes and variants of existing serotypes continue to be identified. See Gao et al., PNAS, 2002, 99(18): 11854-6; Gao et al., PNAS, 2003, 100(10):6081-6; and Bossis et al., J. Virol., 2003, 77(12):6799-810.

Use of any AAV serotype is considered within the scope of the present disclosure. In some embodiments, a rAAV vector is a vector derived from an AAV serotype, including without limitation, AAV ITRs are AAV1, AAV2, AAV3, AAV4, AAV5, AAV6, AAV7, AAV8, AAVrh8, AAVrh8R, AAV9, AAV10, AAVrh10, AAV11, AAV12, AAV2R471A, AAV DJ, a goat AAV, bovine AAV, or mouse AAV ITRs or the like. In some embodiments, the nucleic acid in the AAV comprises an ITR of AAV ITRs are AAV1, AAV2, AAV3, AAV4, AAV5, AAV6, AAV7, AAV8, AAVrh8, AAVrh8R, AAV9 (Aschauer et al., 2013), AAV10, AAVrh10, AAV 11, AAV12, AAV2R471A, AAV DJ, a goat AAV, bovine AAV, or mouse AAV or the like. In certain embodiments, the nucleic acid in the AAV comprises an AAV2 ITR. In some embodiments, a vector may include a stuffer nucleic acid. In some embodiments, the stuffer nucleic acid may encode a green fluorescent protein. In some embodiments, the stuffer nucleic acid may be located between the promoter and the nucleic acid encoding the CRB1-B isoform.

Numerous methods are known in the art for production of viral vectors, including rAAV vectors, including transfection, stable cell line production, and infectious hybrid virus production systems. Some of those systems include, but are not limited to, for example, adenovirus-AAV hybrids, herpesvirus-AAV hybrids (Conway, J E et al., (1997) J. Virology 71(11):8780-8789) and baculovirus-AAV hybrids. rAAV production cultures for the production of rAAV virus particles all require; 1) suitable host cells, including, for example, human-derived cell lines such as HeLa, A549, or 293 cells, or insect-derived cell lines such as SF-9, in the case of baculovirus production systems; 2) suitable helper virus function, provided by wild-type or mutant adenovirus (such as temperature sensitive adenovirus), herpes virus, baculovirus, or a plasmid construct providing helper functions; 3) AAV rep and cap genes and gene products; 4) a transgene (such as a therapeutic transgene) flanked by at least one AAV ITR sequences; and 5) suitable media and media components to support rAAV production. Suitable media known in the art may be used for the production of rAAV vectors. These media include, without limitation, media produced by Hyclone Laboratories and JRH including Modified Eagle Medium (MEM), Dulbecco's Modified Eagle Medium (DMEM), custom formulations such as those described in U.S. Pat. No. 6,566,118, and Sf-900 II SFM media as described in U.S. Pat. No. 6,723,551, each of which is incorporated herein by reference in its entirety, particularly with respect to custom media formulations for use in production of recombinant AAV vectors.

The vectors according to the present disclosure can be produced using methods known in the art. See, e.g., U.S. Pat. Nos. 6,566,118; 6,989,264; and 6,995,006. In practicing the invention, host cells for producing rAAV particles include mammalian cells, insect cells, plant cells, microorganisms and yeast. Host cells can also be packaging cells in which the AAV rep and cap genes are stably maintained in the host cell or producer cells in which the AAV vector genome is stably maintained. Exemplary packaging and producer cells are derived from 293, A549 or HeLa cells. AAV vectors are purified and formulated using standard techniques known in the art.

In some embodiments, vectors according to the present disclosure may be produced by a triple transfection method, such as the exemplary triple transfection method provided infra. Briefly, a plasmid containing a rep gene and a capsid gene, along with a helper adenoviral plasmid, may be transfected (e.g., using the calcium phosphate method) into a cell line (e.g., HEK-293 cells), and virus may be collected and optionally purified.

In some embodiments, the vectors may be produced by a producer cell line method, such as the exemplary producer cell line method provided infra (see also (referenced in Martin et al., (2013)) Human Gene Therapy Methods 24:253-269). Briefly, a cell line (e.g., a HeLa cell line) may be stably transfected with a plasmid containing a rep gene, a capsid gene, and a promoter-transgene sequence. Cell lines may be screened to select a lead clone for vector production, which may then be expanded to a production bioreactor and infected with an adenovirus (e.g., a wild-type adenovirus) as helper to initiate vector production. Virus may subsequently be harvested, adenovirus may be inactivated (e.g., by heat) and/or removed, and the vectors may be purified.

The terms "genome particles (gp)," "genome equivalents," or "genome copies" as used in reference to a viral titer, refer to the number of virions containing the recombinant AAV DNA genome, regardless of infectivity or functionality. The number of genome particles in a particular vector preparation can be measured by procedures such as described in, for example, Clark et al. (1999) *Hum. Gene Ther.,* 10:1031-1039; Veldwijk et al. (2002) *Mol. Ther.,* 6:272-278. The term "vector genome (vg)" as used herein may refer to one or more polynucleotides comprising a set of the polynucleotide sequences of a vector, e.g., a viral vector. A vector genome may be encapsidated in a viral particle. Depending on the particular viral vector, a vector genome may comprise single-stranded DNA, double-stranded DNA, or single-stranded RNA, or double-stranded RNA. A vector genome may include endogenous sequences associated with a particular viral vector and/or any heterologous sequences inserted into a particular viral vector through recombinant techniques. For example, a recombinant AAV vector genome may include at least one ITR sequence flanking a promoter, a stuffer, a sequence of interest (e.g., an RNAi), and a polyadenylation sequence. A complete vector genome may include a complete set of the polynucleotide sequences of a vector. In some embodiments, the nucleic acid titer of a viral vector may be measured in terms of vg/mL. In another embodiment, for example in the use of AAV vectors, the viral titer may be measured in terms of DNase resistant particles (DRP) as mature, enveloped AAV particles are counted from not fully formed AAV particles. Methods suitable for measuring this titer are known in the art (e.g., quantitative PCR).

Promoters:

In some embodiments, the nucleic acids (polynucleotides) of the present disclosure (e.g., Crb1 isoform B, and in other embodiments, Crb1 isoforms A, A2 and/or C) are operably linked to a promoter. The promoter can be a constitutive, inducible, or repressible promoter. Preferably, the promoter is capable of expression of the isoform encoded in the polynucleotide in the target cell. Exemplary promoters include, but are not limited to, the cytomegalovirus (CMV) immediate early promoter, the RSV LTR, the MoMLV LTR, the phosphoglycerate kinase-1 (PGK) promoter, a simian virus 40 (SV40) promoter and a CK6 promoter, a transthyretin promoter (TTR), a TK promoter, a tetracycline responsive promoter (TRE), an HBV promoter, an hAAT promoter, a LSP promoter, chimeric liver-specific promoters (LSPs), the E2F promoter, the telomerase (hTERT) promoter; the cytomegalovirus enhancer/chicken β-actin/Rabbit β-globin promoter (CAG promoter; Niwa et al., Gene, 1991, 108(2): 193-9) and the elongation factor 1-α promoter (EF1-α) promoter (Kim et al., Gene, 1990, 91(2):217-23 and Guo et al., Gene Ther., 1996, 3(9):802-10).

As used herein, a promoter is "operably connected to" or "operably linked to" when it is placed into a functional relationship with a second polynucleotide sequence. For instance, a promoter is operably connected to a polynucleotide if the promoter is connected to the polynucleotide such that it may effect transcription of the polynucleotide coding sequence. In various embodiments, the polynucleotides may be operably linked to at least 1, at least 2, at least 3, at least 4, at least 5, or at least 10 promoters.

Advantageously, the promoter is a tissue-specific promoter that drives gene expression in retinal cells. Numerous retinal-specific promoters are known in the art. For example, the rhodopsin kinase (RK) promoter (SEQ ID NO:24), which is derived from the human rhodopsin kinase gene (GenBank Entrez Gene ID 6011), has been shown to drive expression specifically in rod and cone photoreceptor cells, as well as retinal cell lines such as WERI Rb-1 (Khani, S. C., et al. (2007) *Invest. Ophthalmol. Vis. Sci.* 48(9):3954-61). As used herein, "rhodopsin kinase promoter" may refer to an entire promoter sequence or a fragment of the promoter sequence sufficient to drive photoreceptor-specific expression, such as the sequences described in Khani, S. C., et al. (2007) *Invest. Ophthalmol. Vis. Sci.* 48(9):3954-61 and Young, J. E., et al. (2003) *Invest. Ophthalmol. Vis. Sci.* 44(9):4076-85. In some embodiments, the RK promoter spans from −112 to +180 relative to the transcription start site.

Opsin promoters and derivatives thereof are also commonly used to drive retinal-specific gene expression. For example, a minimal promoter has been derived from the mouse opsin gene (SEQ ID NO:25) has been shown to drive robust expression in photoreceptors (Pawlyk, B. S., et al. (2005) Invest Ophthalmol Vis Sci, 46 (9), 3039-45). Thus, in some embodiments, the promoter is a rhodopsin kinase (RK) promoter or an opsin promoter.

Alternatively, the promoter may be a constitutive promoter that is not tissue-specific. Use of such promoters may be advantageous when a high-level of gene expression is desirable. For example, the cytomegalovirus (CMV) promoter (SEQ ID NO:26) is commonly included in vectors used to genetically engineering mammalian cells, as it is well-characterized as a strong constitutive promoter (Boshart et al., Cell, 41:521-530 (1985)). Another example of a commonly used constitutive promoter is the chicken β-actin promoter (SEQ ID NO:27), which is also known as the "CAG promoter" (see Definitions; Miyazaki, J., et al. (1989) *Gene* 79(2):269-77)). The CAG promoter is a strong synthetic promoter that was formed by combining the cytomegalovirus (CMV) early enhancer element, the promoter, first exon and the first intron of chicken beta-actin gene, and the splice acceptor of the rabbit beta-globin gene. Thus, in some embodiments, the promoter is a cytomegalovirus (CMV) promoter or a chicken β-actin (CAG promoter). 69502412As used herein, the term "CAG promoter" may be used interchangeably with "CBA promoter."

In some embodiments, the promoter comprises a human β-glucuronidase promoter or a cytomegalovirus enhancer linked to a chicken β-actin (CBA) promoter. In some embodiments, the invention provides a recombinant vector comprising nucleic acid encoding a heterologous transgene of the present disclosure operably linked to a CBA promoter. Exemplary promoters and descriptions may be found, e.g., in U.S. PG Pub. 20140335054.

Examples of constitutive promoters include, without limitation, the retroviral Rous sarcoma virus (RSV) LTR promoter (optionally with the RSV enhancer), the cytomegalovirus (CMV) promoter (optionally with the CMV enhancer) [see, e.g., Boshart et al., Cell, 41:521-530 (1985)], the SV40 promoter, the dihydrofolate reductase promoter, the 13-actin promoter, the phosphoglycerol kinase (PGK) promoter, and the EF1α promoter [Invitrogen].

Inducible promoters allow regulation of gene expression and can be regulated by exogenously supplied compounds, environmental factors such as temperature, or the presence of a specific physiological state, e.g., acute phase, a particular differentiation state of the cell, or in replicating cells only. Inducible promoters and inducible systems are available from a variety of commercial sources, including, without limitation, Invitrogen, Clontech and Ariad. Many other systems have been described and can be readily selected by one of skill in the art. Examples of inducible promoters regulated by exogenously supplied promoters include the zinc-inducible sheep metallothionine (MT) promoter, the dexamethasone (Dex)-inducible mouse mammary tumor virus (MMTV) promoter, the T7 polymerase promoter system (WO 98/10088); the ecdysone insect promoter (No et al., Proc. Natl. Acad. Sci. USA, 93:3346-3351 (1996)), the tetracycline-repressible system (Gossen et al., Proc. Natl. Acad. Sci. USA, 89:5547-5551 (1992)), the tetracycline-inducible system (Gossen et al., Science, 268:1766-1769 (1995), see also Harvey et al., Curr. Opin. Chem. Biol., 2:512-518 (1998)), the RU486-inducible system (Wang et al., Nat. Biotech., 15:239-243 (1997) and Wang et al., Gene Ther., 4:432-441 (1997)) and the rapamycin-inducible system (Magari et al., J. Clin. Invest., 100:2865-2872 (1997)). Still other types of inducible promoters which may be useful in this context are those which are regulated by a specific physiological state, e.g., temperature, acute phase, a particular differentiation state of the cell, or in replicating cells only.

Suitable promoters for use in AAV vectors capable of expression in retinal cells are known in the art, for example, as found in "Targeting neuronal and glial cell types with synthetic promoter AAVs in mice, non-human primates, and humans" see, Table S1 in Jüttner et. al, bioRxiv 434720; doi: doi.org/10.1101/434720 (October 2018), Now published in *Nature Neuroscience* doi: 10.1038/s41593-019-0431-2, incorporated by reference in its entirety.

In another embodiment, the native promoter, or fragment thereof, for the transgene will be used. The native promoter can be used when it is desired that expression of the transgene should mimic the native expression. The native promoter may be used when expression of the transgene must be regulated temporally or developmentally, or in a tissue-specific manner, or in response to specific transcriptional stimuli. In a further embodiment, other native expression control elements, such as enhancer elements, polyadenylation sites or Kozak consensus sequences may also be used to mimic the native expression.

In some aspects, the present disclosure provides an isolated polypeptide comprising or consisting of the CRB1-B isoform (e.g., SEQ ID NO:1). Suitably, the isolated polypeptide may be expressed from the polynucleotide or vector described herein. The terms "polypeptide" and "protein" are used interchangeably to refer to a polymer of amino acid residues, and are not limited to a minimum length. Such polymers of amino acid residues may contain natural or non-natural amino acid residues, and include, but are not limited to, peptides, oligopeptides, dimers, trimers, and multimers of amino acid residues. Both full-length proteins and fragments thereof are encompassed by the definition. The terms also include post-expression modifications of the polypeptide, for example, glycosylation, sialylation, acetylation, phosphorylation, and the like. Furthermore, for purposes of the present invention, a "polypeptide" refers to a protein which includes modifications, such as deletions, additions, and substitutions (generally conservative in nature), to the native sequence, as long as the protein maintains the desired activity. These modifications may be deliberate, as through site-directed mutagenesis, or may be accidental, such as through mutations of hosts which produce the proteins or errors due to PCR amplification.

The term "substantial identity" of polynucleotide sequences means that a polynucleotide comprises a sequence that has at least 95% sequence identity to the polynucleotide encoding the polypeptide of interest described herein. Alternatively, percent identity can be any integer from 95% to 100%. In one embodiment, the sequence identity is at least 95%, alternatively at least 99%. More preferred embodiments include at least: 96%, 97%, 98%, 99% or 100% compared to a reference sequence using the programs described herein; preferably BLAST using standard parameters, as described. These values can be appropriately adjusted to determine corresponding identity of proteins encoded by two nucleotide sequences by taking into account codon degeneracy, amino acid similarity, reading frame positioning and the like.

In some preferred embodiments, the term "substantial identity" of amino acid sequences for purposes of this invention means polypeptide sequence identity of at least 95%, preferably 98%, most preferably 99% or 100%. Preferred percent identity of polypeptides can be any integer from 95% to 100%. More preferred embodiments include at least 96%, 97%, 98%, 99%, or 100%.

iii. Pharmaceutical Compositions

The present disclosure further provides a pharmaceutical composition. The pharmaceutical composition may comprise or consists of the isolated polynucleotide encoding the CRB1 isoform, the recombinant vector encoding the CRB1 isoform, preferably the CRB1-B isoform described herein and a pharmaceutically acceptable carrier. In one example, the pharmaceutical composition may comprise viral vectors encoding the CRB1-B isoform. The pharmaceutical composition can comprise viral vectors, for example rAAV viral vectors, at a concentration of about $1\times10^6$ DNase-resistant particles (DRP)/ml to about $1\times10^{14}$ DRP/ml. The pharmaceutical composition may further comprise a second vector encoding CRB1-A, CRB1-A2, CRB1-C, or combinations thereof.

The vectors according to the present disclosure may further be in the form of a pharmaceutical composition. Accordingly, in some embodiments, the vectors provided herein may further contain buffers and/or pharmaceutically acceptable excipients and/or pharmaceutically acceptable carriers. As is well known in the art, pharmaceutically acceptable excipients and/or carriers are relatively inert substances that facilitate administration of a pharmacologically effective substance and can be supplied as liquid solutions or suspensions, as emulsions, or as solid forms suitable for dissolution or suspension in liquid prior to use. The pharmaceutically acceptable carrier may be selected based upon the route of administration desired. For example, an excipient can give form or consistency, or act as a diluent. Suitable excipients include but are not limited to stabilizing agents, wetting and emulsifying agents, salts for varying osmolarity, encapsulating agents, pH buffering substances, and buffers. Such excipients include any pharmaceutical agent suitable for direct delivery to the eye which may be administered without undue toxicity. Suitably the pharmaceutically acceptable carrier helps maintain the viral particle integrity of the viral vector prior to administration, e.g., provide a suitable pH balanced solution. Pharmaceutically acceptable excipients include, but are not limited to, sorbitol, any of the various TWEEN® (surfactant/detergent) compounds, and liquids such as water, saline, glycerol and ethanol. Pharmaceutically acceptable salts can be included therein, for example, mineral acid salts such as hydrochlorides, hydrobromides, phosphates, sulfates, and the like; and the salts of organic acids such as acetates, propionates, malonates, benzoates, and the like. A thorough discussion of pharmaceutically acceptable excipients is available in REMINGTON'S PHARMACEUTICAL SCIENCES (Mack Pub. Co., N.J. 1991). The compositions can be sterilized by conventional, well known sterilization techniques prior to administration (e.g., filtration, addition of sterilizing agent, etc.). The compositions may contain pharmaceutically acceptable additional substances as required to approximate physiological conditions such as a pH adjusting and buffering agent, toxicity adjusting agents, such as, sodium acetate, sodium chloride, potassium chloride, calcium chloride, sodium lactate, and the like.

In some embodiments related to ocular delivery, pharmaceutically acceptable carriers include, for example, sterile liquids, such as water and oil, including those of petroleum, animal, vegetable or synthetic origin, such as peanut oil, soybean oil, mineral oil, and the like. Saline solutions and aqueous dextrose, polyethylene glycol (PEG) and glycerol solutions can also be employed as liquid carriers, particularly for injectable solutions. Additional ingredients may also be used, for example preservatives, buffers, tonicity agents, antioxidants and stabilizers, nonionic wetting or clarifying agents, viscosity-increasing agents, and the like.

In some embodiments, the pharmaceutical compositions of the present disclosure are formulated for administration by subretinal injection. Accordingly, these compositions can be combined with pharmaceutically acceptable vehicles such as saline, Ringer's balanced salt solution (pH 7.4), and the like. Although not required, the compositions may optionally be supplied in unit dosage form suitable for administration of a precise amount.

In other embodiments, the pharmaceutical compositions of the present disclosure are formulated for topical administration to the eye. In such embodiments, conventional intraocular delivery reagents can be used. For example, pharmaceutical compositions of the present disclosure for topical intraocular delivery can comprise saline solutions as described above, corneal penetration enhancers, insoluble particles, petrolatum or other gel-based ointments, polymers which undergo a viscosity increase upon instillation in the eye, or mucoadhesive polymers.

Preferably, the intraocular delivery reagent increases corneal penetration, or prolongs preocular retention of the siRNA through viscosity effects or by establishing physicochemical interactions with the mucin layer covering the corneal epithelium.

Methods of Treatment:

The present disclosure further provides methods of treating and/or preventing ocular disorders in a subject using the polynucleotides, vectors and pharmaceutical compositions according to the present disclosure. In some embodiments, the method of treating is a gene therapy protocol for such ocular disorders and requires the localized delivery of the polynucleotide or vectors according to the present disclosure to the cells in the retina. The cells that will be the treatment target in such embodiments are either the photoreceptor cells in the retina or the cells of the RPE underlying the neurosensory retina. Hence, in one embodiment, the delivery of the polynucleotides and vectors according to the present disclosure are achieved by injection into the subretinal space between the retina and the RPE. Accordingly, one aspect of the present disclosure provides a method of treating and/or preventing an ocular disorder in a subject, the method comprising, consisting of, or consisting essentially of administering the subject a therapeutically effective amount of a polynucleotide, recombinant vector or pharmaceutical composition according to the present disclosure such that the ocular disorder is treated in the subject. Preferably, the polynucleotide or recombinant vector or pharmaceutical composition comprising the same encodes the CRB1-B isoform described herein.

The present disclosure provides a method of reducing progression of loss of vision or maintaining vision function in a subject in need thereof. The method comprises administering the subject a therapeutically effective amount of the isolated polynucleotide, the recombinant vector, the isolated polypeptide, or pharmaceutical composition described herein such that progression of loss of vision or is reduced. In some embodiments, the loss of vision is maintained at a level similar to the vision level when treatment was started, for example, vision is maintained within about 10% of the vision at the start of treatment. Not to be bound by any theory, but maintenance of the level of CRB1-B expression in trans in photoreceptor cells within the retina of subject in need of treatment may allow for the reduction in the death of photoreceptor cells and the maintenance of the photoreceptor-glial junctions, maintain the vision in the subject. In some embodiments, the isolated polynucleotide, recombinant vector or pharmaceutical composition is administered intravitreally, subretinally, or topically.

In some embodiments, the method described herein can further comprise monitoring the visual function of the subject, wherein the vision function in the subject is maintained and not reduced after administration. Methods of monitoring visual function are known in the art (described further below) and include, for example, monitoring visual acuity of the subject.

In some examples, the function for this isoform at photoreceptor-glial junctions is maintained after treatment with the isolated polynucleotide, the recombinant vector, the isolated polypeptide, or pharmaceutical composition described herein. The term "administering" encompasses methods of delivering the isolated polypeptide, vector or pharmaceutical composition to one or more cells within the retina of the subject. In a preferred embodiment, the isoform is CRB1-B and the one or more cells are photoreceptor cells within the retina. Suitable techniques for delivering the isolated polynucleotide, vector or pharmaceutical composition according to the present disclosure to a subject may include numerous methods known in the art, such as by gene gun, electroporation, nanoparticles, transduction by viral particles, micro-encapsulation, gene editing, and the like, or by parenteral and enteral administration routes. Suitable parenteral administration routes include, for example, peri- and intra-tissue administration (e.g., intra-retinal injection or subretinal injection); direct (e.g., topical) application to the area at or near the site of neovascularization, for example by a catheter or other placement device (e.g., a corneal pellet or a suppository, eyedropper, or an implant comprising a porous, non-porous, or gelatinous material). Suitable placement devices include the ocular implants described in U.S. Pat. Nos. 5,902,598 and 6,375,972, and the biodegradable ocular implants described in U.S. Pat. No. 6,331,313, the entire disclosures of which are herein incorporated by reference. Such ocular implants are available from Control Delivery Systems, Inc. (Watertown, Mass.) and Oculex Pharmaceuticals, Inc. (Sunnyvale, Calif.). In certain embodiments, the parenteral administration route comprises intraocular administration. It is understood that intraocular administration of the isolated polynucleotides, vectors and pharmaceutical compositions according to the present disclosure can be accomplished by injection or direct (e.g., topical) administration to the eye, as long as the administration route allows the isolated polynucleotides, vectors or pharmaceutical compositions to enter the eye. In addition to the topical routes of administration to the eye described above, suitable intraocular routes of administration include intravitreal, intraretinal, subretinal, subtenon, peri- and retro-orbital, trans-corneal and trans-scleral administration. Such intraocular administration routes are within the skill in the art; see, e.g., and Acheampong A A et al, 2002, supra; and Bennett et al. (1996), Hum. Gene Ther. 7: 1763-1769 and Ambati J et al., 2002, Progress in Retinal and Eye Res. 21: 145-151, the entire disclosures of which are herein incorporated by reference.

As used herein, the term "topically" means application to the surface of the eye.

In some embodiments, the isolated polynucleotides, vectors or pharmaceutical compositions according to the present disclosure are administered to a subject via subretinal delivery. Methods of subretinal delivery are known in the art. For example, see WO 2009/105690, incorporated herein by reference. Briefly, the general method for delivering a vector according to the present disclosure to the subretina of the macula and fovea may be illustrated by the following brief outline. This example is merely meant to illustrate certain features of the method, and is in no way meant to be limiting.

Generally, they can be delivered in the form of a composition injected intraocularly (subretinally) under direct observation using an operating microscope. This procedure may involve vitrectomy followed by injection of the vector suspension using a fine cannula through one or more small retinotomies into the subretinal space.

Briefly, an infusion cannula can be sutured in place to maintain a normal globe volume by infusion (of e.g., saline) throughout the operation. A vitrectomy is performed using a cannula of appropriate bore size (for example 20 to 27 gauge), wherein the volume of vitreous gel that is removed is replaced by infusion of saline or other isotonic solution from the infusion cannula. The vitrectomy is advantageously performed because (1) the removal of its cortex (the posterior hyaloid membrane) facilitates penetration of the retina by the cannula; (2) its removal and replacement with fluid (e.g., saline) creates space to accommodate the intraocular injection of vector, and (3) its controlled removal reduces the possibility of retinal tears and unplanned retinal detachment.

In some embodiments, the isolated polynucleotide, vector or pharmaceutical composition according to the present disclosure is directly injected into the subretinal space outside the central retina, by utilizing a cannula of the appropriate bore size (e.g., 27-45 gauge), thus creating a bleb in the subretinal space. In other embodiments, the subretinal injection of the isolated polynucleotide, vector or pharmaceutical composition according to the present disclosure is preceded by subretinal injection of a small volume (e.g., about 0.1 to about 0.5 ml) of an appropriate fluid (such as saline or Ringer's solution) into the subretinal space outside the central retina. This initial injection into the subretinal space establishes an initial fluid bleb within the subretinal space, causing localized retinal detachment at the location of the initial bleb. This initial fluid bleb can facilitate targeted delivery of the isolated polynucleotide, vector and/or pharmaceutical composition to the subretinal space (by defining the plane of injection prior to vector and/or pharmaceutical composition delivery), and minimize possible isolated polynucleotide, vector and/or pharmaceutical composition administration into the choroid and the possibility of isolated polynucleotide, vector and/or pharmaceutical composition injection or reflux into the vitreous cavity. In some embodiments, this initial fluid bleb can be further injected with fluids comprising one or more isolated polynucleotidevector and/or pharmaceutical compositions and/or one or more additional therapeutic agents by administration of these fluids directly to the initial fluid bleb with either the same or additional fine bore cannulas.

Intraocular administration of the isolated polynucleotide, vector or pharmaceutical composition according to the present disclosure and/or the initial small volume of fluid can be performed using a fine bore cannula (e.g., 27-45 gauge) attached to a syringe. In some embodiments, the plunger of this syringe may be driven by a mechanized device, such as by depression of a foot pedal. The fine bore cannula is advanced through the sclerotomy, across the vitreous cavity and into the retina at a site pre-determined in each subject according to the area of retina to be targeted (but outside the central retina). Under direct visualization the isolated polynucleotide, vector or pharmaceutical composition suspension is injected mechanically under the neurosensory retina causing a localized retinal detachment with a self-sealing non-expanding retinotomy. As noted above, the isolated polynucleotide, vector or pharmaceutical composition can be either directly injected into the subretinal space creating a bleb outside the central retina or the isolated polynucleotide, vector or pharmaceutical composition can be injected into an initial bleb outside the central retina, causing it to expand (and expanding the area of retinal detachment). In some embodiments, the injection of the isolated polynucleotide, vector or pharmaceutical composition according to the present disclosure is followed by injection of another fluid into the bleb.

Without wishing to be bound by theory, the rate and location of the subretinal injection(s) can result in localized shear forces that can damage the macula, fovea and/or underlying RPE cells. The subretinal injections may be performed at a rate that minimizes or avoids shear forces. In some embodiments, the isolated polynucleotide, vector or pharmaceutical composition according to the present disclosure is injected over about 15-17 minutes. In some embodiments, the vector is injected over about 17-20 minutes. In some embodiments, the isolated polynucleotide, vector and/or pharmaceutical composition is injected over about 20-22 minutes. In some embodiments, the isolated polynucleotide-vector and/or pharmaceutical composition is injected at a rate of about 35 to about 65 μl/min. In some embodiments, the isolated polynucleotide, vector and/or pharmaceutical composition is injected at a rate of about 35 μl/min. In some embodiments, the isolated polynucleotide, vector and/or pharmaceutical composition is injected at a rate of about 40 μl/min. In some embodiments, the isolated polynucleotide, vector and/or pharmaceutical composition is injected at a rate of about 45 μl/min. In some embodiments, the isolated polynucleotide, vector and/or pharmaceutical composition is injected at a rate of about 500 min. In some embodiments, the isolated polynucleotide, vector and/or pharmaceutical composition is injected at a rate of about 55 μl/min. In some embodiments, the isolated polynucleotide, vector and/or pharmaceutical composition is injected at a rate of about 60 μl/min. In some embodiments, the isolated polynucleotide, vector and/or pharmaceutical composition is injected at a rate of about 65 μl/min. One of ordinary skill in the art would recognize that the rate and time of injection of the bleb may be directed by, for example, the volume of the vector and/or pharmaceutical composition or size of the bleb necessary to create sufficient retinal detachment to access the cells of central retina, the size of the cannula used to deliver the isolated polynucleotide, vector and/or pharmaceutical composition, and the ability to safely maintain the position of the cannula of the invention.

In some embodiments of the present disclosure, the volume of the isolated polynucleotide or vector (in solution or in a pharmaceutical composition as provided herein) injected to the subretinal space of the retina is more than about any one of 1 μl, 2 μl, 3 μl, 4 μl, 5 μl, 6 μl, 7 μl, 8 μl, 9 μl, 10 μl, 15 μl, 20 μl, 25 μl, 50 μl, 75 μl, 100 μl, 200 μl, 300 μl, 400 μl, 500 μl, 600 μl, 700 μl, 800 μl, 900 μl, or 1 mL, or any amount therebetween.

In some embodiments, the methods comprise administration to the eye (e.g., by subretinal and/or intravitreal administration) an effective amount of an isolated polynucleotide, vector or pharmaceutical composition according to the present disclosure. In some embodiments, a viral vector is used in a pharmaceutical composition, and the viral titer of the composition is at least about any of $5\times10^{12}$, $6\times10^{12}$, $7\times10^{12}$, $8\times10^{12}$, $9\times10^{12}$, $10\times10^{12}$, $11\times10^{12}$, $15\times10^{12}$, $20\times10^{12}$, $25\times10^{12}$, $30\times10^{12}$, or $50\times10^{12}$ genome copies/mL. In some embodiments, the viral titer of the composition is about any of $5\times10^{12}$ to $6\times10^{12}$, $6\times10^{12}$ to $7\times10^{12}$, $7\times10^{12}$ to $8\times10^{12}$, $8\times10^{12}$ to $9\times10^{12}$, $9\times10^{12}$ to $10\times10^{12}$, $10\times10^{12}$ to $11\times10^{12}$, $11\times10^{12}$ to $15\times10^{12}$, $15\times10^{12}$ to $20\times10^{12}$, 20 $25\times10^{12}$ to $25\times10^{12}$, $25\times10^{12}$ to $30\times10^{12}$, $30\times10^{12}$ to $50\times10^{12}$, or $50\times10^{12}$ to $100\times10^{12}$ genome copies/mL In some embodiments, the viral titer of the composition is about any of $5\times10^{12}$ to $10\times10^{12}$, $10\times10^{12}$ to $25\times10^{12}$, or $25\times10^{12}$ to $50\times10^{12}$ genome copies/mL In some embodiments, the viral titer of the composition is at least about any of $5\times10^{9}$, $6\times10^{9}$, $7\times10^{9}$, $8\times10^{9}$, $9\times10^{9}$, $10\times10^{9}$, $11\times10^{9}$, $15\times10^{9}$, $20\times10^{9}$, $25\times10^{9}$, $30\times10^{9}$, or $50\times10^{9}$ transducing units/mL. In some embodiments, the viral titer of the composition is about any of $5\times10^{9}$ to $6\times10^{9}$, $6\times10^{9}$ to $7\times10^{9}$, $7\times10^{9}$ to $8\times10^{9}$, $8\times10^{9}$ to $9\times10^{9}$, $9\times10^{9}$ to $10\times10^{9}$, $10\times10^{9}$ to $11\times10^{9}$, $11\times10^{9}$ to $15\times10^{9}$, $15\times10^{9}$ to $20\times10^{9}$, $20\times10^{9}$ to $25\times10^{9}$, $25\times10^{9}$ to $30\times10^{9}$, $30\times10^{9}$ to $50\times10^{9}$ or $50\times10^{9}$ to $100\times10^{9}$ transducing units/mL. In some embodiments, the viral titer of the composition is about any of $5\times10^{9}$ to $10\times10^{9}$, $10\times10^{9}$ to $15\times10^{9}$, $15\times10^{9}$ to $25\times10^{9}$, or $25\times10^{9}$ to $50\times10^{9}$ transducing units/mL In some embodiments, the viral titer of the composition is at least any of about $5\times10^{10}$, $6\times10^{10}$, $7\times10^{10}$, $8\times10^{10}$, $9\times10^{10}$, $10\times10^{10}$, $11\times10^{10}$, $15\times10^{10}$, $20\times10^{10}$, $25\times10^{10}$, $30\times10^{10}$, $40\times10^{10}$, or $50\times10^{10}$ infectious units/mL In some embodiments, the viral titer of the composition is at least any of about $5\times10^{10}$ to $6\times10^{10}$, $6\times10^{10}$ to $7\times10^{10}$, $7\times10^{10}$ to $8\times10^{10}$, $8\times10^{10}$ to $9\times10^{10}$, $9\times10^{1}$ to $10\times10^{10}$, $10\times10^{10}$ to $11\times10^{10}$, $11\times10^{10}$ to $15\times10^{10}$, $15\times10^{10}$ to $20\times10^{10}$, $20\times10^{10}$ to $25\times10^{10}$, $25\times10^{10}$ to $30\times10^{10}$, $30\times10^{10}$ to $40\times10^{10}$, $40\times10^{10}$ to $50\times10^{10}$, or $50\times10^{10}$ to $100\times10^{10}$ infectious units/mL In some embodiments, the viral titer of the composition is at least any of about $5\times10^{10}$ to $10\times10^{10}$, $10\times10^{10}$ to $15\times10^{10}$, $15\times10^{10}$ to $25\times10^{10}$, or $25\times10^{10}$ to $50\times10^{10}$ infectious units/mL One or multiple (e.g., 2, 3, or more) blebs can be created. Generally, the total volume of bleb or blebs created by the methods and systems of the invention cannot exceed the fluid volume of the eye, for example about 4 ml in a typical human subject. The total volume of each individual bleb can be at least about 0.3 ml, or at least about 0.5 ml in order to facilitate a retinal detachment of sufficient size to expose the cell types of the central retina and create a bleb of sufficient dependency for optimal manipulation. One of ordinary skill in the art will appreciate that in creating the bleb according to the methods and systems of the invention that the appropriate intraocular pressure must be maintained in order to avoid damage to the ocular structures. The size of each individual bleb may be, for example, about 0.5 to about 1.2 ml, about 0.8 to about 1.2 ml, about 0.9 to about 1.2 ml, about 0.9 to about 1.0 ml, about 1.0 to about 2.0 ml, about 1.0 to about 3.0 ml. Thus, in one example, to inject a total of 3 ml of isolated polynucleotide, vector and/or pharmaceutical composition suspension, 3 blebs of about 1 ml each can be established. The total volume of all blebs in combination may be, for example, about 0.5 to about 3.0 ml, about 0.8 to about 3.0 ml, about 0.9 to about 3.0 ml, about 1.0 to about 3.0 ml, about 0.5 to about 1.5 ml, about 0.5 to about 1.2 ml, about 0.9 to about 3.0 ml, about 0.9 to about 2.0 ml, about 0.9 to about 1.0 ml.

In order to safely and efficiently transduce areas of target retina (e.g., the central retina) outside the edge of the original location of the bleb, the bleb may be manipulated to reposition the bleb to the target area for transduction. Manipulation of the bleb can occur by the dependency of the bleb that is created by the volume of the bleb, repositioning of the eye containing the bleb, repositioning of the head of the human with an eye or eyes containing one or more blebs, and/or by means of a fluid-air exchange. This is particularly relevant to the central retina since this area typically resists detachment by subretinal injection. In some embodiments fluid-air exchange is utilized to reposition the bleb; fluid from the infusion cannula is temporarily replaced by air, e.g., from blowing air onto the surface of the retina. As the volume of the air displaces vitreous cavity fluid from the surface of the retina, the fluid in the vitreous cavity may flow out of a cannula. The temporary lack of pressure from the vitreous cavity fluid causes the bleb to move and gravitate to a dependent part of the eye. By positioning the eye globe appropriately, the bleb of subretinal vector and/or pharmaceutical composition position is manipulated to involve adjacent areas (e.g., the macula and/or fovea). In some cases, the mass of the bleb is sufficient to cause it to gravitate, even without use of the fluid-air exchange. Movement of the bleb to the desired location may further be facilitated by altering the position of the subject's head, so as to allow the bleb to gravitate to the desired location in the eye. Once the desired configuration of the bleb is achieved, fluid is returned to the vitreous cavity. The fluid is an appropriate fluid, e.g., fresh saline. Generally, the subretinal vector and/or pharmaceutical composition may be left in situ without retinopexy to the retinotomy and without intraocular tamponade, and the retina will spontaneously reattach within about 48 hours.

The term "bleb" as used herein refers to a fluid space within the subretinal space of an eye. A bleb of the invention may be created by a single injection of fluid into a single space, by multiple injections of one or more fluids into the same space, or by multiple injections into multiple spaces, which when repositioned create a total fluid space useful for achieving a therapeutic effect over the desired portion of the subretinal space.

By safely and effectively transducing ocular cells (e.g., RPE and/or photoreceptor cells of e.g., the macula and/or fovea) with a vector comprising a therapeutic polypeptide (e.g., CRB1-B), the methods of the invention may be used to treat an individual; e.g., a human, having an ocular disorder, wherein the transduced cells produce the therapeutic polypeptide CRB1-B or RNA sequence in an amount sufficient to treat the ocular disorder.

An effective amount of an isolated polynucleotide, vector or pharmaceutical composition according to the present disclosure is administered, depending on the objectives of treatment. For example, in use of a viral vector where a low percentage of transduction can achieve the desired therapeutic effect, then the objective of treatment is generally to meet or exceed this level of transduction. In some instances, this level of transduction can be achieved by transduction of only about 1 to 5% of the target cells, in some embodiments at least about 20% of the cells of the desired tissue type, in some embodiments at least about 50%, in some embodiments at least about 80%, in some embodiments at least about 95%, in some embodiments at least about 99% of the cells of the desired tissue type. The isolated polynucleotide, vector and/or pharmaceutical compositions may be administered by one or more subretinal injections, either during the same procedure or spaced apart by days, weeks, months, or years. In some embodiments, multiple vectors may be used to treat the human. For example, in one embodiment, multiple vectors, each encoding a different CRB1 isoform or other retinal therapeutic agent can be used. For example, a vector encoding for CRB1-B can be used and targeted to photoreceptor cells within the retina alone or in combination with a second vector encoding a CRB1 isoform selected from CRB1-A and CRB1-A2 which can be targeted to Müller cells within the retina.

In some embodiments, the administration to the retina of an effective amount of an isolated polynucleotide, vector or pharmaceutical composition according to the present disclosure transduces photoreceptor cells at or near the site of administration. In some embodiments, when a viral vector is used, more than about any of 5%, 10%, 15%, 20%, 25%, 30%, 35%, 40%, 45%, 50%, 55%, 60%, 65%, 70%, 75% or 100% of photoreceptor cells incorporate the isolated polynucleotide or vector and express the CRB1 isoform. In some embodiments, when a viral vector is used, more than about any of 5%, 10%, 15%, 20%, 25%, 30%, 35%, 40%, 45%, 50%, 55%, 60%, 65%, 70%, 75% or 100% of photoreceptor cells incorporate the isolated polynucleotide or vector and express the CRB1 isoform, are transduced. In some embodiments, about 5% to about 100%, about 10% to about 50%, about 10% to about 30%, about 25% to about 75%, about 25% to about 50%, or about 30% to about 50% of the photoreceptor cells are targeted (e.g. transduced with a viral vector). Methods to identify photoreceptor cells transduced by AAV viral particles comprising a vector or targeted with the pharmaceutical composition are known it the art and include, for example, immunohistochemistry or the use of a marker within the polynucleotide or vector such as enhanced green fluorescent protein can be used to detect incorporation or transduction of the vectors or pharmaceutical compositions.

In some embodiments of the present disclosure, the methods comprise administration to the subretina (e.g., the subretinal space) of a mammal an effective amount of an isolated polynucleotide, vector or pharmaceutical composition according to the present disclosure for treating an individual with an ocular disorder; e.g., a human with an ocular disorder. In some embodiments, the isolated polynucleotide, vector or pharmaceutical composition is injected to one or more locations in the subretina to allow expression of the polynucleotide in photoreceptor cells. In some embodiments, the isolated polynucleotide, vector or pharmaceutical composition is injected into any one of one, two, three, four, five, six, seven, eight, nine, ten or more than ten locations in the subretina.

In some embodiments the isolated polynucleotide, vector or pharmaceutical composition according to the present disclosure are administered to more than one location simultaneously or sequentially. In some embodiments, multiple injections of isolated polynucleotide, vector or pharmaceutical composition are no more than one hour, two hours, three hours, four hours, five hours, six hours, nine hours, twelve hours or 24 hours apart.

In other embodiments, the isolated polynucleotide, vector or pharmaceutical composition according to the present disclosure may be administered to the subject intravitreally. The general method for intravitreal injection may be illustrated by the following brief outline. This example is merely meant to illustrate certain features of the method, and is in no way meant to be limiting. Procedures for intravitreal injection are known in the art (see, e.g., Peyman, G. A., et al. (2009) Retina 29(7):875-912 and Fagan, X. J. and Al-Qureshi, S. (2013) Clin. Experiment. Ophthalmol. 41(5): 500-7).

Briefly, a subject for intravitreal injection may be prepared for the procedure by pupillary dilation, sterilization of the eye, and administration of anesthetic. Any suitable mydriatic agent known in the art may be used for pupillary dilation. Adequate pupillary dilation may be confirmed before treatment. Sterilization may be achieved by applying a sterilizing eye treatment, e.g., an iodide-containing solution such as Povidone-Iodine (BETADINE™). A similar solution may also be used to clean the eyelid, eyelashes, and any other nearby tissues (e.g., skin). Any suitable anesthetic may be used, such as lidocaine or proparacaine, at any suitable concentration. Anesthetic may be administered by any method known in the art, including without limitation topical drops, gels or jellies, and subconjuctival application of anesthetic.

Prior to injection, a sterilized eyelid speculum may be used to clear the eyelashes from the area. The site of the injection may be marked with a syringe. The site of the injection may be chosen based on the lens of the patient. For example, the injection site may be 3-3.5 mm from the limus in pseudophakic or aphakic patients, and 3.5-4 mm from the limbus in phakic patients. The patient may look in a direction opposite the injection site.

In some embodiments, the methods comprise administration to the eye (e.g., by subretinal and/or intravitreal administration) an effective amount of an isolated polynucleotide, vector or pharmaceutical composition according to the present disclosure. In some embodiments, a viral vector is administered in a pharmaceutical composition, the viral titer of the composition is at least about any of $5\times10^{12}$, $6\times10^{12}$, $7\times10^{12}$, $8\times10^{12}$, $9\times10^{12}$, $10\times10^{12}$, $11\times10^{12}$, $15\times10^{12}$, $20\times10^{12}$, $25\times10^{12}$, $30\times10^{12}$, or $50\times10^{12}$ genome copies/mL In some embodiments, the viral titer of the vector and/or pharmaceutical composition is about any of $5\times10^{12}$ to $6\times10^{12}$, $6\times10^{12}$ to $7\times10^{12}$, $7\times10^{12}$ to $8\times10^{12}$, $8\times10^{12}$ to $9\times10^{12}$, $9\times10^{12}$ to $10\times10^{12}$, $10\times10^{12}$ to $11\times10^{12}$, $11\times10^{12}$ to $15\times10^{12}$, $15\times10^{12}$ to $20\times10^{12}$, $20\times10^{12}$ to $25\times10^{12}$, $25\times10^{12}$ to $30\times10^{12}$, $30\times10^{12}$ to $50\times10^{12}$, or $50\times10^{12}$ to $100\times10^{12}$ genome copies/mL. In some embodiments, the viral titer of the composition is about any of $5\times10^{9}$ to $10\times10^{9}$, $10\times10^{9}$ to $15\times10^{9}$, $15\times10^{9}$ to $25\times10^{9}$, or $25\times10^{9}$ to $50\times10^{9}$ transducing units/mL In some embodiments, the viral titer of the composition is at least any of about $5\times10^{10}$, $6\times10^{10}$, $7\times10^{10}$, $8\times10^{10}$, $9\times10^{10}$, $10\times10^{10}$, $11\times10^{10}$, $15\times10^{10}$, $20\times10^{10}$, $25\times10^{10}$, $30\times10^{10}$, $40\times10^{10}$, or $50\times10^{10}$ infectious units/mL In some embodiments, the viral titer of the composition is at least any of about $5\times^{10}$ to $6\times^{10}$, $6\times10^{10}$ to $7\times10^{10}$, $7\times10^{10}$ to $8\times10^{10}$, $8\times10^{10}$ to $9\times10^{10}$, $9\times10^{10}$ to $10\times10^{10}$, $10\times10^{10}$ to $11\times10^{10}$, $11\times10^{10}$ to $15\times10^{10}$, $15\times10^{10}$ to $20\times10^{10}$, $20\times10^{10}$ to $25\times10^{10}$, $25\times10^{10}$ to $30\times10^{10}$, $30\times10^{10}$ to $40\times10^{10}$, $40\times10^{10}$ to $50\times10^{10}$, or $50\times10^{10}$ to $100\times10^{10}$ infectious units/mL In some embodiments, the viral titer of the composition is at least any of about $5\times10^{10}$ to $10\times10^{10}$, $10\times10^{10}$ to $15\times10^{10}$, $15\times10^{10}$ to $25\times10^{10}$, or $25\times10^{10}$ to $50\times10^{10}$ infectious units/mL of $5\times10^{12}$ to $10\times10^{12}$, $10\times10^{12}$ to $25\times10^{12}$, or $25\times10^{12}$ to $50\times10^{12}$ genome copies/mL In some embodiments, the methods comprise administration to the eye (e.g., by subretinal and/or intravitreal administration) of an individual (e.g., a human) an effective amount of a vector according to the present disclosure. In some embodiments, the dose of vectors and/or pharmaceutical compositions administered to the individual is at least about any of $1\times10^{8}$ to about $1\times10^{13}$ genome copies/kg of body weight. In some embodiments, the dose of vectors and/or pharmaceutical compositions administered to the individual is about any of $1\times10^{8}$ to about $1\times10^{13}$ genome copies/kg of body weight.

During injection, the needle may be inserted perpendicular to the sclera and pointed to the center of the eye. The needle may be inserted such that the tip ends in the vitreous, rather than the subretinal space. Any suitable volume known in the art for injection may be used. After injection, the eye may be treated with a sterilizing agent such as an antibiotic. The eye may also be rinsed to remove excess sterilizing agent.

Other embodiments of the present disclosure provides a means to determine the effectiveness of delivery of a vector or pharmaceutical composition according to the present disclosure. The effectiveness of delivery by subretinal or intravitreal injection of a vector or pharmaceutical composition according to the present disclosure can be monitored by several criteria as described herein. For example, after treatment in a subject using methods of the present invention, the subject may be assessed for e.g., an improvement and/or stabilization and/or delay in the progression of one or more signs or symptoms of the disease state by one or more clinical parameters including those described herein. Examples of such tests are known in the art, and include objective as well as subjective (e.g., subject reported) measures. For example, to measure the effectiveness of a treatment on a subject's visual function, one or more of the following may be evaluated: the subject's subjective quality of vision or improved central vision function (e.g., an improvement in the subject's ability to read fluently and recognize faces), the subject's visual mobility (e.g., a decrease in time needed to navigate a maze), visual acuity (e.g., an improvement in the subject's Log MAR score), microperimetry (e.g., an improvement in the subject's dB score), dark-adapted perimetry (e.g., an improvement in the subject's dB score), fine matrix mapping (e.g., an improvement in the subject's dB score), Goldmann perimetry (e.g., a reduced size of scotomatous area (i.e. areas of blindness) and improvement of the ability to resolve smaller targets), flicker sensitivities (e.g., an improvement in Hertz), autofluorescence, and electrophysiology measurements (e.g., improvement in ERG). In some embodiments, the visual function is measured by the subject's visual mobility. In some embodiments, the visual function is measured by the subject's visual acuity. In some embodiments, the visual function is measured by microperimetry. In some embodiments, the visual function is measured by dark-adapted perimetry. In some embodiments, the visual function is measured by ERG. In some embodiments, the visual function is measured by the subject's subjective quality of vision.

In the case of diseases resulting in progressive degenerative visual function, treating the subject at an early age may not only result in a slowing or halting of the progression of the disease, it may also ameliorate or prevent visual function loss due to acquired amblyopia. Amblyopia may be of two types. In studies in nonhuman primates and kittens that are kept in total darkness from birth until even a few months of age, the animals even when subsequently exposed to light are functionally irreversibly blind despite having functional signals sent by the retina. This blindness occurs because the neural connections and "education" of the cortex is developmentally is arrested from birth due to stimulus arrest. It is unknown if this function could ever be restored. In the case of diseases of retinal degeneration, normal visual cortex circuitry was initially "learned" or developmentally appropriate until the point at which the degeneration created significant dysfunction. The loss of visual stimulus in terms of signaling in the dysfunctional eye creates "acquired" or "learned" dysfunction ("acquired amblyopia"), resulting in the brain's inability to interpret signals, or to "use" that eye. It is unknown in these cases of "acquired amblyopia" whether with improved signaling from the retina as a result of gene therapy of the amblyopic eye could ever result in a gain of more normal function in addition to a slowing of the progression or a stabilization of the disease state. In some embodiments, the human treated is less than 30 years of age. In some embodiments, the human treated is less than 20 years of age. In some embodiments, the human treated is less than 18 years of age. In some embodiments, the human treated is less than 15 years of age. In some embodiments, the human treated is less than 14 years of age. In some embodiments, the human treated is less than 13 years of age. In some embodiments, the human treated is less than 12 years of age. In some embodiments, the human treated is less than 10 years of age. In some embodiments, the human treated is less than 8 years of age. In some embodiments, the human treated is less than 6 years of age.

In some ocular disorders, there is a "nurse cell" phenomena, in which improving the function of one type of cell improves the function of another. For example, transduction of the etinal pigment epithelium (RPE) of the central retina by an isolated polynucleotide, vector and/or pharmaceutical composition of the present disclosure may then improve the function of the rods, and in turn, improved rod function results in improved cone function. Accordingly, treatment of one type of cell may result in improved function in another.

The selection of a particular isolated polynucleotide, vector or pharmaceutical composition according to the present disclosure depend on a number of different factors, including, but not limited to, the individual human's medical history and features of the condition and the individual being treated. The assessment of such features and the design of an appropriate therapeutic regimen is ultimately the responsibility of the prescribing physician.

As used herein, the term "individual," "subject," and "patient" are used interchangeably herein and refer to both human and nonhuman animals. The term "nonhuman animals" of the disclosure includes all vertebrates, e.g., mammals and non-mammals, such as, domesticated animals (e.g., cows, sheep, cats, dogs, and horses), primates (e.g., humans and non-human primates such as monkeys), rabbits, and rodents (e.g., mice and rats), amphibians, reptiles, and the like. In some embodiments, the individual or subject comprises a human. In certain embodiments, the subject comprises a human suffering from, or is at risk of suffering from, an ocular disorder.

In some embodiments, the subject to be treated has a genetic ocular disorder, but has not yet manifested clinical signs or symptoms. In some embodiments, the human to be treated has an ocular disorder. In some embodiments, the human to be treated has manifested one or more signs or symptoms of an ocular disorder. In some embodiments, the subject to be treated has a mutation in one or both alleles of the crb1 gene.

An "allele" refers to one of several alternative forms of a gene occupying a given locus on a chromosome. The length of an allele can be as small as one nucleotide, but is often larger. As used herein, a "mutation" refers to an alteration in the DNA sequence of a gene, such that the sequence differs from what is found in most people. A mutation may comprise a substitution of one or more nucleotides, an insertion of one or more nucleotides, or a deletion of one or more nucleotides.

In some embodiments, the ocular disorder comprises a retinopathy. As used herein, the term "retinopathy" refers to any damage to the retina of the eyes. This term often refers to retinal vascular disease, or damage to the retina caused by abnormal blood flow. Non-limiting examples of ocular disorder or retinopathies which may be treated by the systems and methods of the invention include: autosomal recessive severe early-onset retinal degeneration (Leber's Congenital Amaurosis), congenital achromatopsia, Stargardt's disease, Best's disease, Doyne's disease, cone dystrophy, retinitis pigmentosa, X-linked retinoschisis, Usher's syndrome, age related macular degeneration, atrophic age related macular degeneration, neovascular AMD, diabetic maculopathy, proliferative diabetic retinopathy (PDR), cystoid macular oedema, central serous retinopathy, retinal detachment, intra-ocular inflammation, glaucoma, posterior uveitis, choroideremia, and Leber hereditary optic neuropathy.

The isolated polynucleotide, vector, or pharmaceutical composition according to the present disclosure can be used either alone or in combination with one or more additional therapeutic agents for treating ocular disorders. The interval between sequential administration can be in terms of at least (or, alternatively, less than) minutes, hours, or days.

In some embodiments, one or more additional therapeutic agents may be administered to the subretina or vitreous (e.g., through intravitreal administration). Non-limiting examples of the additional therapeutic agent include polypeptide neurotrophic factors (e.g., GDNF, CNTF, BDNF, FGF2, PEDF, EPO), polypeptide anti-angiogenic factors (e.g., sFlt, angiostatin, endostatin), anti-angiogenic nucleic acids (e.g., siRNA, miRNA, ribozyme), for example anti-angiogenic nucleic acids against VEGF, anti-angiogenic morpholinos, for example anti-angiogenic morpholinos against VEGF, anti-angiogenic antibodies and/or antibody fragments (e.g., Fab fragments), for example anti-angiogenic antibodies and/or antibody fragments against VEGF.

In another embodiment, the therapeutic agent used may be the use of stem cell therapy to be used in the retina of the eye in order to restore cell loss. Suitable stem cells for use in combination may be known in the art, and include administering progenitor stem cells that are capable of differentiating into retinal photoreceptor cells.

In some embodiments of the above aspects and embodiments, the isolated polynucleotide, the recombinant vector, the isolated polypeptide, or pharmaceutical composition described herein according to the present disclosure is delivered by stereotactic delivery. In some embodiments, the isolated polynucleotide, isolated polypeptide, vector and/or pharmaceutical compositions according to the present disclosure is delivered by convection enhanced delivery. In some embodiments, the isolated polynucleotide, isolated polypeptide, vector and/or pharmaceutical compositions according to the present disclosure is administered using a CED delivery system. In some embodiments, the cannula is a reflux-resistant cannula or a stepped cannula. In some embodiments, the CED delivery system comprises a cannula and/or a pump. In some embodiments, the isolated polynucleotide, isolated polypeptide, vector and/or pharmaceutical compositions according to the present disclosure is administered using a CED delivery system. In some embodiments, the pump is a manual pump. In some embodiments, the pump is an osmotic pump. In some embodiments, the pump is an infusion pump.

An "effective amount" or "therapeutically effective amount" is an amount sufficient to effect beneficial or desired results, including clinical results (e.g., amelioration of symptoms, achievement of clinical endpoints, and the like). An effective amount can be administered in one or more administrations. In terms of a disease state, an effective amount is an amount sufficient to ameliorate, stabilize, or delay development of a disease.

As used herein, "treatment," "treating," "therapy," and/or "therapy regimen" are used interchangeably and refer to an approach for obtaining beneficial or desired clinical results. For purposes of the present disclosure, beneficial or desired clinical results include, but are not limited to, alleviation of symptoms, diminishment of extent of disease, stabilized (e.g., not worsening) state of disease, preventing spread (e.g., additional loss of photoreceptors and vision) of disease, delay or slowing of disease progression, amelioration or palliation of the disease state, and remission (whether partial or total), whether detectable or undetectable. "Treatment" can also mean prolonging vision as compared to expected loss of vision if not receiving treatment.

As used herein, the term "prophylactic treatment" or "preventative treatment" refers to treatment, wherein an individual is known or suspected to have or be at risk for having a disorder but has displayed no symptoms or minimal symptoms of the disorder. An individual undergoing prophylactic treatment may be treated prior to onset of symptoms. In some embodiments, a subject having an inheritable genetic ocular disease may be treated prior to showing signs and/or symptoms of the ocular disease.

The term "central retina" as used herein refers to the outer macula and/or inner macula and/or the fovea. The term "central retina cell types" as used herein refers to cell types of the central retina, such as, for example, RPE and photoreceptor cells.

The term "macula" refers to a region of the central retina in primates that contains a higher relative concentration of photoreceptor cells, specifically rods and cones, compared to the peripheral retina. The term "outer macula" as used herein may also be referred to as the "peripheral macula". The term "inner macula" as used herein may also be referred to as the "central macula".

The term "fovea" refers to a small region in the central retina of primates of approximately equal to or less than 0.5 mm in diameter that contains a higher relative concentration of photoreceptor cells, specifically cones, when compared to the peripheral retina and the macula.

The term "subretinal space" as used herein refers to the location in the retina between the photoreceptor cells and the retinal pigment epithelium cells. The subretinal space may be a potential space, such as prior to any subretinal injection of fluid. The subretinal space may also contain a fluid that is injected into the potential space. In this case, the fluid is "in contact with the subretinal space." Cells that are "in contact with the subretinal space" include the cells that border the subretinal space, such as RPE and photoreceptor cells.

Systems and Kits:

The isolated polynucleotide(s), vector(s) or pharmaceutical composition(s) according to the present disclosure may be contained within a system designed for use in one of the methods of the present disclosure as provided herein. In such aspects, the system comprises, consists of, or consists essentially of a therapeutically effective amount of a vector as provided herein, and a device for delivery of the vector to the subject.

In some embodiments, the system is designed for subretinal delivery of a vector according to the present disclosure to an eye of an individual. In other embodiments, the system is designed for intravitreal delivery of a vector according to the present disclosure to the eye of an individual. In yet other embodiments, the system is designed for topical delivery of a vector according to the present disclosure to the eye of an individual.

In general, for the intravitreal or subretinal delivery of a vector according to the present disclosure, the system comprises a fine-bore cannula, wherein the cannula is 27 to 45 gauge, one or more syringes (e.g., 1, 2, 3, 4 or more), and one or more fluids (e.g., 1, 2, 3, 4 or more) suitable for use in the methods of the present disclosure. The fine bore cannula is suitable for subretinal injection of the vector and/or other fluids to be injected into the subretinal space. In some embodiments, the cannula is 27 to 45 gauge. In some embodiments, the fine-bore cannula is 35-41 gauge. In some embodiments, the fine-bore cannula is 40 or 41 gauge. In some embodiments, the fine-bore cannula is 41-gauge. The cannula may be any suitable type of cannula, for example, a de-Juan™ cannula or an Eagle™ cannula.

The syringe may be any suitable syringe, provided it is capable of being connected to the cannula for delivery of a fluid. In some embodiments, the syringe is an Accurus™ system syringe. In some embodiments, the system has one syringe. In some embodiments, the system has two syringes. In some embodiments, the system has three syringes. In some embodiments, the system has four or more syringes.

The system may further comprise an automated injection pump, which may be activated by, e.g., a foot pedal.

The fluids suitable for use in the methods of the present disclosure include those described herein, for example, one or more fluids each comprising an effective amount of one or more vectors as described herein, one or more fluids for creating an initial bleb (e.g., saline or other appropriate fluid), and one or more fluids comprising one or more therapeutic agents.

The fluids suitable for use in the methods of the present disclosure include those described herein, for example, one or more fluids each comprising an effective amount of one or more vectors as described herein, one or more fluids for creating an initial bleb (e.g., saline or other appropriate fluid), and one or more fluids comprising one or more therapeutic agents.

In some embodiments, the volume of the fluid comprising an effective amount of the vector is greater than about 0.8 ml. In some embodiments, the volume of the fluid comprising an effective amount of the vector is at least about 0.9 ml. In some embodiments, the volume of the fluid comprising an effective amount of the vector is at least about 1.0 ml. In some embodiments, the volume of the fluid comprising an effective amount of the vector is at least about 1.5 ml. In some embodiments, the volume of the fluid comprising an effective amount of the vector is at least about 2.0 ml. In some embodiments, the volume of the fluid comprising an effective amount of the vector is greater than about 0.8 to about 3.0 ml. In some embodiments, the volume of the fluid comprising an effective amount of the vector is greater than about 0.8 to about 2.5 ml. In some embodiments, the volume of the fluid comprising an effective amount of the vector is greater than about 0.8 to about 2.0 ml. In some embodiments, the volume of the fluid comprising an effective amount of the vector is greater than about 0.8 to about 1.5 ml. In some embodiments, the volume of the fluid comprising an effective amount of the vector is greater than about 0.8 to about 1.0 ml. In some embodiments, the volume of the fluid comprising an effective amount of the vector is about 0.9 to about 3.0 ml. In some embodiments, the volume of the fluid comprising an effective amount of the vector is about 0.9 to about 2.5 ml. In some embodiments, the volume of the fluid comprising an effective amount of the vector is about 0.9 to about 2.0 ml. In some embodiments, the volume of the fluid comprising an effective amount of the vector is about 0.9 to about 1.5 ml. In some embodiments, the volume of the fluid comprising an effective amount of the vector is about 0.9 to about 1.0 ml. In some embodiments, the volume of the fluid comprising an effective amount of the vector is about 1.0 to about 3.0 ml. In some embodiments, the volume of the fluid comprising an effective amount of the vector is about 1.0 to about 2.0 ml.

The fluid for creating the initial bleb may be, for example, about 0.1 to about 0.5 ml. In some embodiments, the total volume of all fluids in the system is about 0.5 to about 3.0 ml.

In some embodiments, the system comprises a single fluid (e.g., a fluid comprising an effective amount of the vector). In some embodiments, the system comprises 2 fluids. In some embodiments, the system comprises 3 fluids. In some embodiments, the system comprises 4 or more fluids.

The systems of the present disclosure may further be packaged into kits, wherein the kits may further comprise instructions for use. In some embodiments, the kits further comprise a device for delivery of a vector according to the present disclosure. In some embodiments, the delivery comprises subretinal delivery. In other embodiments, the delivery comprises topical delivery. In yet other embodiments, the delivery comprises intravitreal delivery. In some embodiments, the instructions for use include instructions according to one of the methods described herein. In some embodiments, the instructions for use include instructions for subretinal, intravitreal and/or topical delivery of a vector according to the present disclosure.

In another embodiment, the present disclosure provides a kit for treating an ocular disorder in a subject, the kit comprising a the isolated polynucleotide, the recombinant vector, the isolated polypeptide, or pharmaceutical composition described herein and a device for delivery of the isolated polynucleotide, recombinant vector, or isolated polypeptide or pharmaceutical composition to the subject, and instructions for use. In some embodiments, the device for delivery is designed for subretinal delivery. In another embodiment, the device for delivery is designed for intravitreal delivery. In a further embodiment, the device for delivery is designed for topical delivery.

In another aspect, the disclosure provides a kit for reducing progression or reducing loss of vision or maintaining vision function in a subject, the kit comprising the isolated polynucleotide, the recombinant vector, the isolated polypeptide, or pharmaceutical composition and a device for delivery of the isolated polynucleotide, recombinant vector isolated polypeptide, or pharmaceutical composition to the subject, and instructions for use. In a preferred embodiment, the kit comprises a first vector encoding CRB1-B and a second vector encoding a CRB1-A, CRB1-A2, or CRB1-C, and instructions for use.

The kits described herein can be packaged in single unit dosages or in multidosage forms. The contents of the kits are generally formulated as sterile and substantially isotonic solution.

Yet another aspect of the present disclosure provides all that is disclosed and illustrated herein.

For the purposes of promoting an understanding of the principles of the present disclosure, reference will now be made to preferred embodiments and specific language will be used to describe the same. It will nevertheless be understood that no limitation of the scope of the disclosure is thereby intended, such alteration and further modifications of the disclosure as illustrated herein, being contemplated as would normally occur to one skilled in the art to which the disclosure relates.

Articles "a" and "an" are used herein to refer to one or to more than one (i.e. at least one) of the grammatical object of the article. By way of example, "an element" means at least one element and can include more than one element.

"About" is used to provide flexibility to a numerical range endpoint by providing that a given value may be "slightly above" or "slightly below" the endpoint without affecting the desired result.

The use herein of the terms "including," "comprising," or "having," and variations thereof, is meant to encompass the elements listed thereafter and equivalents thereof as well as additional elements. Embodiments recited as "including," "comprising," or "having" certain elements are also contemplated as "consisting essentially of and "consisting of those certain elements. As used herein, "and/or" refers to and encompasses any and all possible combinations of one or more of the associated listed items, as well as the lack of combinations where interpreted in the alternative ("or").

As used herein, the transitional phrase "consisting essentially of" (and grammatical variants) is to be interpreted as encompassing the recited materials or steps "and those that do not materially affect the basic and novel characteristic(s)" of the claimed invention. See, In re Herz, 537 F.2d 549, 551-52, 190 U.S.P.Q. 461, 463 (CCPA 1976) (emphasis in the original); see also MPEP § 2111.03. Thus, the term "consisting essentially of" as used herein should not be interpreted as equivalent to "comprising."

Moreover, the present disclosure also contemplates that in some embodiments, any feature or combination of features set forth herein can be excluded or omitted. To illustrate, if the specification states that a complex comprises components A, B and C, it is specifically intended that any of A, B or C, or a combination thereof, can be omitted and disclaimed singularly or in any combination.

Recitation of ranges of values herein are merely intended to serve as a shorthand method of referring individually to each separate value falling within the range, unless otherwise-Indicated herein, and each separate value is incorporated into the specification as if it were individually recited herein. For example, if a concentration range is stated as 1% to 50%, it is intended that values such as 2% to 40%, 10% to 30%, or 1% to 3%, etc., are expressly enumerated in this specification. These are only examples of what is specifically intended, and all possible combinations of numerical values between and including the lowest value and the highest value enumerated are to be considered to be expressly stated in this disclosure.

Unless otherwise defined, all technical terms used herein have the same meaning as commonly understood by one of ordinary skill in the art to which this disclosure belong.

It should be apparent to those skilled in the art that many additional modifications beside those already described are possible without departing from the inventive concepts. In interpreting this disclosure, all terms should be interpreted in the broadest possible manner consistent with the context. Variations of the term "comprising" should be interpreted as referring to elements, components, or steps in a non-exclusive manner, so the referenced elements, components, or steps may be combined with other elements, components, or steps that are not expressly referenced. Embodiments referenced as "comprising" certain elements are also contemplated as "consisting essentially of" and "consisting of" those elements. The term "consisting essentially of" and "consisting of" should be interpreted in line with the MPEP and relevant Federal Circuit interpretation. The transitional phrase "consisting essentially of" limits the scope of a claim to the specified materials or steps "and those that do not materially affect the basic and novel characteristic(s)" of the claimed invention. "Consisting of" is a closed term that excludes any element, step or ingredient not specified in the claim. For example, with regard to sequences "consisting of" refers to the sequence listed in the SEQ ID NO. and does refer to larger sequences that may contain the SEQ ID as a portion thereof.

All publications, patent applications, patents, and other references mentioned herein are incorporated by reference in their entirety. In the case of conflict, the present specification, including definitions, will control.

Other features and advantages of the invention will be apparent from the description of the preferred embodiments thereof, and from the claims. Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. In addition, the materials, methods, and examples are illustrative only and not intended to be limiting.

EXAMPLES

Genes encoding cell surface proteins control nervous system development and are implicated in neurological disorders. These genes produce alternative mRNA isoforms, which remain poorly characterized, impeding our understanding of how disease-associated mutations cause pathology. Here we introduce a strategy to reveal complete full-length isoform portfolios encoded by individual genes. We use this strategy to catalog a diversity of neural cell-surface molecules, identifying thousands of unannotated isoforms expressed in the retina and brain. By mass spectrometry, we confirm expression of newly discovered proteins on the cell surface in vivo. Remarkably, we discover that the major isoform of the retinal degeneration gene CRB1 was previously overlooked. This isoform is the only one expressed by photoreceptors, the affected cells in CRB1 disease. Using a mouse model, we identify a function for this isoform at photoreceptor-glial junctions and we demonstrate that loss of this isoform accelerates photoreceptor death.

Materials and Methods

Resources and Reagents

All key reagents used in this study, including antibodies, primers, datasets, and animal strains, are listed in a table of key resources (Table 1).

TABLE 1

Key resources. Provides the name and source of key reagents and resources used in this study, such as antibodies, mouse strains, datasets, primers, and chemicals.

| Reagent Type | Reagent | Source or reference | Identifier | Additional information |
|---|---|---|---|---|
| Antibody | Alexa Fluor 488 AffiniPure Donkey Anti-rabbit: 1:1000 | Jackson ImmunoResearch | 711-545-152 | |
| Antibody | Calbindin | Swant | CB-38 | |
| Antibody | CRB1 B: 1:500 WB | this study | | |

TABLE 1-continued

Key resources. Provides the name and source of key reagents and resources used in this study, such as antibodies, mouse strains, datasets, primers, and chemicals.

| Reagent Type | Reagent | Source or reference | Identifier | Additional information |
|---|---|---|---|---|
| Antibody | ABCA4 | Santa Cruz | SC21460 | |
| Antibody | rhodopsin | Abcam | ab5417 | |
| Antibody | Sheep anti-phosducin | Sokolov et al., 2004 | | |
| Antibody | IRDye 800CW Donkey anti-Rabbit IgG (H + L): 1:1000 | Li-Cor Biosciences | 925-32213 | |
| Antibody | IRDye 680RD Donkey anti-Mouse IgG (H + L): 1:1000 | Li-Cor Biosciences | 925-68072 | |
| biological reagent | KAPA HiFi DNA Polymerase | Kapa Biosystems | KK2602 | |
| biological reagent | Takara LA Taq | Takara Bio | RR002A | |
| biological reagent | Nimblegen's SeqCap EZ Developer (≤200 Mb) custom baits | Nimblegen | | Capture probes |
| biological reagent | Twist Bioscience NGS Taret Enrichment | Twist Bioscience | | Capture probes |
| biological reagent | Phusion High-Fidelity DNA Polymerase | New England Biolabs | M05305 | |
| biological reagent | Ttypsin/Lys-C Mix, Mass Spec Grade | Promega | v072 | |
| Chemical compound | 16% Paraformaldehyde | Electron Microscopy Sciences | 15710 | |
| Chemical compound | 50% Glutaraldehyde | Electron Microscopy Sciences | G5882 | |
| Chemical compound | Normal Donkey Serum | Jackson ImmunoResearch | 017-000-121 | |
| Chemical compound | TriReagent | Thermo Fisher Scientific | AM9738 | |
| Chemical compound | Hank's balanced salt solution (HBSS) | Sgma Aldrich | H8264 | |
| Chemical compound | Fetal Bovine Serum | Life Technologies | 16250-078 | |
| Chemical compound | Opti-MEM I Reduced Serum Medium | Thermo Fisher Scientific | 31985070 | |
| Chemical compound | Vecta-Mount | Vector Laboraories | H-5000 | |
| Chemical compound | ammonium bicarbonate | Sigma-Aldrich | J1213 | |
| Chemical compound | Iodoacetamide (IAA) | Sigma-Aldrich | J1149 | |
| Chemical compound | Dithiothreitol (DTT) | Sigma-Aldrich | 43815 | |
| Chemical compound | Pierce ™ Streptavidin Magnetic Beads | Thermo Fischer Scientific | 88816 | |
| Chemical compound | EZLink ™ Sulfo-NHS-SS-Biotin | Thermo Fischer Scientific | 21328 | |

TABLE 1-continued

Key resources. Provides the name and source of key reagents and resources used in this study, such as antibodies, mouse strains, datasets, primers, and chemicals.

| Reagent Type | Reagent | Source or reference | Identifier | Additional information |
|---|---|---|---|---|
| Chemical compound | Hoechst 33258 | Invitrogen | H21491 | |
| Chemical compound | Isothesia: Isoflurane | Henry Schein | 11695-6776 | |
| Chemical compound | Tissue Freezing Medium | VWR | 15148-031 | |
| Chemical compound | 4x Laemmli Sample Buffer | Bio-Rad | 1610747 | |
| Chemical compound | Odyssey Blocking Buffer | Li-Cor Biosciences | 927-40000 | |
| Chemical compound | cOmplete, Mini, EDTA-free Protease Inhibitor Cocktail Tablets | Roche | 4693159001 | |
| Other | Immun-Blot Low Fluorescence PVDF membrane | Bio-Rad | 1620264 | |
| commercial assay or kit | Bio-Rad DC Protein Assay Kit | Bio-Rad | 5000112 | |
| recombinant DNA | CAG-Crb1-B-YFP | this study | | |
| recombinant DNA | CAG-Crb1-A-YFP | this study | | |
| recombinant DNA | CAG-YFP | Addgene | 11180 | |
| Cell line | K562 | ATCC | CCL-243 | |
| model organism | Mouse: C57B16/J | Jackson Labs | 000664 | |
| model organism | Mouse: Cd1 | Charles River | 022 | |
| model organism | Mouse: Crb1null | this study | | |
| model organism | Mouse: Crb1delB | this study | | |
| model organism | Mouse: B6SJLF1/J | Jackson Labs | 100012 | |
| model organism | Mouse: C57B16/N | Charles River | 027 | |
| Software | Fiji/ImageJ | Schindelin et al. (2012) | | |
| Software | Cufflinks | Trapnell et al., 2012 | | |
| Software | CummeRbund | Trapnell et al., 2012 | | |
| Software | StringTie | Perteaet al., 2016 | | |
| Software | Hisat2 | Kim et al., 2015 | | |
| Software | SQANTI | Tardaguila et al., 2018 | | |
| Software | NIS Elements | Nikon Instruments | | |
| Software | Image StudioTM | LI-COR Biosciences | | |
| Software | Photoshop | Adobe | | |
| Software | IGV | Robinson et al., 2011 | | |
| Software | STAR | Dobin et al., 2013 | | |
| Software | Gviz | hahne et al., 2016 | | |

TABLE 1-continued

Key resources. Provides the name and source of key reagents and resources used in this study, such as antibodies, mouse strains, datasets, primers, and chemicals.

| Reagent Type | Reagent | Source or reference | Identifier | Additional information |
|---|---|---|---|---|
| Software | Iso-Seq | Pacific Biosciences | | |
| Software | SMART embl | smartembl-heidelberg.de/ | | |
| Software | text2vec | http://text2vec.org/ | | |
| Software | treemapify | https://github.com/wilkox/treemapify | | |
| Software | UpSetR | https://github.com/hms-dbmi/UpSetR | | |
| Software | GMAP | research-pub.gene.corn/gmap/ | | |
| Software | R v3.3.3 | https://statethz.ch/pipermail/r-help/2008-May/161481.html | | |
| Software | Tidyverse R packages ggp10t2, dplyr, stringr, magrittr | https://tidyverse.org/ | | |
| Software | reshape2 R package | https://CRAN.R-project.org/package=reshape2 | | used in making correlation heatmaps |
| Software | plotly R package | https://plot.ly/r/ | | used for 3D plots |
| Software | dendextend R package | https://github.com/gtalalili/dendextend | | used in clustering dendrogram tree plots |
| Software | Rtsne R package | https://github.com/jkrijthe/Rtsne | | used for t-SNE |
| Software | vegan R package | https://github.com/vegandevs/vegan | | used to calculate Shannon Index |
| Software | text2vec | http://text2vec.org/ | | used for k-mer counting |
| Software | IsoPops | https://github.com/kellycochran/IsoPops | | Analysis and visualization of long-read data. Introduced in this study |
| GEO dataset GSE74660 | P2_rep1 | PMID: 27326930 | SRR2936836 | mouse photoreceptor bulk RNA-seq (FIG. 14B) |
| GEO dataset GSE74660 | P2_rep2 | PMID: 27326930 | SRR2936837 | mouse photoreceptor bulk RNA-seq (FIG. 14B) |
| GEO dataset GSE74660 | P4_rep1 | PMID: 27326930 | SRR2936838 | mouse photoreceptor bulk RNA-seq (FIG. 14B) |
| GEO dataset GSE74660 | P4_rep2 | PMID: 27326930 | SRR2936839 | mouse photoreceptor bulk RNA-seq (FIG. 14B) |
| GEO dataset GSE74660 | P6_rep1 | PMID: 27326930 | SRR2936840 | mouse photoreceptor bulk RNA-seq (FIG. 14B) |
| GEO dataset GSE74660 | P6_rep2 | PMID: 27326930 | SRR2936841 | mouse photoreceptor bulk RNA-seq (FIG. 14B) |
| GEO dataset GSE74660 | P6_rep3 | PMID: 27326930 | SRR2936842 | mouse photoreceptor bulk RNA-seq (FIG. 14B) |
| GEO dataset GSE74660 | P10_rep1 | PMID: 27326930 | SRR2936843 | mouse photoreceptor bulk RNA-seq (FIG. 14B) |
| GEO dataset GSE74660 | P10_rep2 | PMID: 27326930 | SRR2936844 | mouse photoreceptor bulk RNA-seq (FIG. 14B) |
| GEO dataset GSE74660 | P10_rep3 | PMID: 27326930 | SRR2936845 | mouse photoreceptor bulk RNA-seq (FIG. 14B) |

TABLE 1-continued

Key resources. Provides the name and source of key reagents and resources used in this study, such as antibodies, mouse strains, datasets, primers, and chemicals.

| Reagent Type | Reagent | Source or reference | Identifier | Additional information |
|---|---|---|---|---|
| GEO dataset GSE74660 | P14_rep1 | PMID: 27326930 | SRR2936846 | mouse photoreceptor bulk RNA-seq (FIG. 14B) |
| GEO dataset GSE74660 | P14_rep2 | PMID: 27326930 | SRR2936847 | mouse photoreceptor bulk RNA-seq (FIG. 14B) |
| GEO dataset GSE74660 | P28_rep1 | PMID: 27326930 | SRR2936848 | mouse photoreceptor bulk RNA-seq (FIG. 14B) |
| GEO dataset GSE74660 | P28_rep2 | PMID: 27326930 | SRR2936849 | mouse photoreceptor bulk RNA-seq (FIG. 14B) |
| GEO dataset GSE74660 | P28_rep3 | PMID: 27326930 | SRR2936850 | mouse photoreceptor bulk RNA-seq (FIG. 14B) |
| GEO dataset GSE74660 | P28_rep4 | PMID: 27326930 | SRR2936851 | mouse photoreceptor bulk RNA-seq (FIG. 14B) |
| GEO dataset GSE74660 | P2_KO_rep1 | PMID: 27326930 | SRR2936852 | mouse photoreceptor bulk RNA-seq (FIG. 14B) |
| GEO dataset GSE74660 | P2_KO_rep2 | PMID: 27326930 | SRR2936853 | mouse photoreceptor bulk RNA-seq (FIG. 14B) |
| GEO dataset GSE74660 | P4_KO_rep1 | PMID: 27326930 | SRR2936854 | mouse photoreceptor bulk RNA-seq (FIG. 14B) |
| GEO dataset GSE74660 | P4_KO_rep2 | PMID: 27326930 | SRR2936855 | mouse photoreceptor bulk RNA-seq (FIG. 14B) |
| GEO dataset GSE74660 | P6_KO_rep1 | PMID: 27326930 | SRR2936856 | mouse photoreceptor bulk RNA-seq (FIG. 14B) |
| GEO dataset GSE74660 | P6_KO_rep2 | PMID: 27326930 | SRR2936857 | mouse photoreceptor bulk RNA-seq (FIG. 14B) |
| GEO dataset GSE74660 | P6_KO_rep3 | PMID: 27326930 | SRR2936858 | mouse photoreceptor bulk RNA-seq (FIG. 14B) |
| GEO dataset GSE74660 | P10_KO_rep1 | PMID: 27326930 | SRR2936859 | mouse photoreceptor bulk RNA-seq (FIG. 14B) |
| GEO dataset GSE74660 | P10_KO_rep2 | PMID: 27326930 | SRR2936860 | mouse photoreceptor bulk RNA-seq (FIG. 14B) |
| GEO dataset GSE74660 | P10_KO_rep3 | PMID: 27326930 | SRR2936861 | mouse photoreceptor bulk RNA-seq (FIG. 14B) |
| GEO dataset GSE74660 | P14_KO_rep1 | PMID: 27326930 | SRR2936862 | mouse photoreceptor bulk RNA-seq (FIG. 14B) |
| GEO dataset GSE74660 | P14_KO_rep2 | PMID: 27326930 | SRR2936863 | mouse photoreceptor bulk RNA-seq (FIG. 14B) |
| GEO dataset GSE74660 | P28_KO_rep1 | PMID: 27326930 | SRR2936864 | mouse photoreceptor bulk RNA-seq (FIG. 14B) |
| GEO dataset GSE74660 | P28_KO_rep2 | PMID: 27326930 | SRR2936865 | mouse photoreceptor bulk RNA-seq (FIG. 14B) |
| GEO dataset GSE102092 | E14.5 | Ref [68] | SRR5884802 | ATAC-seq (FIG. 5C) |
| GEO dataset GSE102092 | E17.5 | Ref [68] | SRR5884803 | ATAC-seq (FIG. 5C) |
| GEO dataset GSE102092 | P0 | Ref [68] | SRR5884804 | ATAC-seq (FIG. 5C) |
| GEO dataset GSE102092 | p3 | Ref [68] | SRR5884805 | ATAC-seq (FIG. 5C) |
| GEO dataset GSE102092 | p7 | Ref [68] | SRR5884807 | ATAC-seq (FIG. 5C) |

TABLE 1-continued

Key resources. Provides the name and source of key reagents and resources used in this study, such as antibodies, mouse strains, datasets, primers, and chemicals.

| Reagent Type | Reagent | Source or reference | Identifier | Additional information |
|---|---|---|---|---|
| GEO dataset GSE102092 | P10 | Ref [68] | SRR5884808 | ATAC-seq (FIG. 5C) |
| GEO dataset GSE102092 | P14 | Ref [68] | SRR5884810 | ATAC-seq (FIG. 5C) |
| GEO dataset GSE102092 | P21 | Ref [68] | SRR5884811 | ATAC-seq (FIG. 5C) |
| GEO dataset GSE83312 | Rod | Ref [69] | SRR3662499 | ATAC-seq (FIG. 5C) |
| GEO dataset GSE83313 | Green Cone | Ref [69] | SRR3662503 | ATAC-seq (FIG. 5C) |
| GEO dataset GSE83314 | Blue Cone | Ref [69] | SRR3662509 | ATAC-seq (FIG. 5C) |
| ENCODE dataset | Frontal Cortex | Ref [71] | ENCFF018VSA.bam | DNAse footprinting (FIG. 5C) |
| GEO dataset GSE99287 | Retina-Macula 1 | Ref [70] | SRR5601846 | Human ATAC-seq (FIG. 5F) |
| GEO dataset GSE99287 | Retina-Macula 2 | Ref [70] | SRR5601851 | Human ATAC-seq (FIG. 5F) |
| GEO dataset GSE99287 | Retina-Peripheiy 1 | Ref [70] | SRR5601847 | Human ATAC-seq (FIG. 5F) |
| GEO dataset GSE99287 | Retina-Peripheiy 2 | Ref [70] | SRR5601850 | Human ATAC-seq (FIG. 5F) |
| GEO dataset GSE101986 | E12.1 | Ref [38] | SRR5877174 | Mouse whole retina RNA-seq (FIG. 5H) |
| GEO dataset GSE101986 | E12.2 | Ref [38] | SRR5877175 | Mouse whole retina RNA-seq (FIG. 5H) |
| GEO dataset GSE101986 | E14.1 | Ref [38] | SRR5877176 | Mouse whole retina RNA-seq (FIG. 5H) |
| GEO dataset GSE101986 | E14.2 | Ref [38] | SRR5877177 | Mouse whole retina RNA-seq (FIG. 5H) |
| GEO dataset GSE101986 | E16.1 | Ref [38] | SRR5877178 | Mouse whole retina RNA-seq (FIG. 5H) |
| GEO dataset GSE101986 | E16.2 | Ref [38] | SRR5877179 | Mouse whole retina RNA-seq (FIG. 5H) |
| GEO dataset GSE101986 | P0.1 | Ref [38] | SRR5877180 | Mouse whole retina RNA-seq (FIG. 5H) |
| GEO dataset GSE101986 | P0.2 | Ref [38] | SRR5877181 | Mouse whole retina RNA-seq (FIG. 5H) |
| GEO dataset GSE101986 | P2.1 | Ref [38] | SRR5877182 | Mouse whole retina RNA-seq (FIG. 5H) |
| GEO dataset GSE101986 | P2.2 | Ref [38] | SRR5877183 | Mouse whole retina RNA-seq (FIG. 5H) |
| GEO dataset GSE101986 | P4.1 | Ref [38] | SRR5877184 | Mouse whole retina RNA-seq (FIG. 5H) |
| GEO dataset GSE101986 | P4.2 | Ref [38] | SRR5877185 | Mouse whole retina RNA-seq (FIG. 5H) |
| GEO dataset GSE101986 | P6.1 | Ref [38] | SRR5877186 | Mouse whole retina RNA-seq (FIG. 5H) |
| GEO dataset GSE101986 | P6.2 | Ref [38] | SRR5877187 | Mouse whole retina RNA-seq (FIG. 5H) |

TABLE 1-continued

Key resources. Provides the name and source of key reagents and resources used in this study, such as antibodies, mouse strains, datasets, primers, and chemicals.

| Reagent Type | Reagent | Source or reference | Identifier | Additional information |
|---|---|---|---|---|
| GEO dataset GSE101986 | P10.1 | Ref [38] | SRR5877188 | Mouse whole retina RNA-seq (FIG. 5H) |
| GEO dataset GSE101986 | P10.2 | Ref [38] | SRR5877189 | Mouse whole retina RNA-seq (FIG. 5H) |
| GEO dataset GSE101986 | P14.1 | Ref [38] | SRR5877190 | Mouse whole retina RNA-seq (FIG. 5H) |
| GEO dataset GSE101986 | P14.2 | Ref [38] | SRR5877191 | Mouse whole retina RNA-seq (FIG. 5H) |
| GEO dataset GSE101986 | P21.1 | Ref [38] | SRR5877192 | Mouse whole retina RNA-seq (FIG. 5H) |
| GEO dataset GSE101986 | P21.2 | Ref [38] | SRR5877193 | Mouse whole retina RNA-seq (FIG. 5H) |
| GEO dataset GSE101986 | P28.1 | Ref [38] | SRR5877194 | Mouse whole retina RNA-seq (FIG. 5H) |
| GEO dataset GSE101986 | P28.2 | Ref [38] | SRR5877195 | Mouse whole retina RNA-seq (FIG. 5H) |
| GEO dataset GSE94437 | 11-1516 Peripheral Retina | PMID: 4634144 | SRR5225761 | Human retina RNA-seq (FIG. 5I) |
| GEO dataset GSE94437 | 11-1556 Peripheral Retina | PMID: 4634144 | SRR5225765 | Human retina RNA-seq (FIG. 5I) |
| GEO dataset GSE94437 | 11-1614 Peripheral Retina | PMID: 4634144 | SRR5225769 | Human retina RNA-seq (FIG. 5I) |
| GEO dataset GSE94437 | 11-1624 Peripheral Retina | PMID: 4634144 | SRR5225773 | Human retina RNA-seq (FIG. 5I) |
| GEO dataset GSE94437 | 11-1648 Peripheral Retina | PMID: 4634144 | SRR5225777 | Human retina RNA-seq (FIG. 5I) |
| GEO dataset GSE94437 | 11-1833 Peripheral Retina | PMID: 4634144 | SRR5225781 | Human retina RNA-seq (FIG. 5I) |
| GEO dataset GSE94437 | 11-1875 Peripheral Retina | PMID: 4634144 | SRR5225785 | Human retina RNA-seq (FIG. 5I) |
| GEO dataset GSE94437 | 11-2043 Peripheral Retina | PMID: 4634144 | SRR5225789 | Human retina RNA-seq (FIG. 5I) |
| GEO dataset GSE94437 | 11-1516 Macular Retina | PMID: 4634144 | SRR5225763 | Human retina RNA-seq (FIG. 5I) |
| GEO dataset GSE94437 | 11-1556 Macular Retina | PMID: 4634144 | SRR5225767 | Human retina RNA-seq (FIG. 5I) |
| GEO dataset GSE94437 | 11-1614 Macular Retina | PMID: 4634144 | SRR5225771 | Human retina RNA-seq (FIG. 5I) |
| GEO dataset GSE94437 | 11-1624 Macular Retina | PMID: 4634144 | SRR5225775 | Human retina RNA-seq (FIG. 5I) |
| GEO dataset GSE94437 | 11-1648 Macular Retina | PMID: 4634144 | SRR5225779 | Human retina RNA-seq (FIG. 5I) |
| GEO dataset GSE94437 | 11-1833 Macular Retina | PMID: 4634144 | SRR5225783 | Human retina RNA-seq (FIG. 5I) |
| GEO dataset GSE94437 | 11-1875 Macular Retina | PMID: 4634144 | SRR5225787 | Human retina RNA-seq (FIG. 5I) |
| GEO dataset GSE94437 | 11-2043 Macular Retina | PMID: 4634144 | SRR5225791 | Human retina RNA-seq (FIG. 5I) |
| GEO dataset GSE79416 | Cortex_CC1 | Ref [39] | SRR3269772 | Bulk RNA-seq |

TABLE 1-continued

Key resources. Provides the name and source of key reagents and resources used in this study, such as antibodies, mouse strains, datasets, primers, and chemicals.

| Reagent Type | Reagent | Source or reference | Identifier | Additional information |
|---|---|---|---|---|
| GEO dataset GSE79416 | Cortex_CC2 | Ref [39] | SRR3269773 | Bulk RNA-seq |
| GEO dataset GSE79416 | Cortex_CC3 | Ref [39] | SRR3269774 | Bulk RNA-seq |
| GEO dataset GSE101544 | zf_retina_1 | | SRR5833542 | Bulk RNA-seq |
| GEO dataset GSE101544 | zf_retina_2 | | SRR5833543 | Bulk RNA-seq |
| GEO dataset GES59911 | Bovine_rep1 | | SRR1532566 | Bulk RNA-seq |
| GEO dataset GES59911 | Bovine_rep2 | | SRR1532567 | Bulk RNA-seq |
| GEO dataset GES59911 | Bovine_rep3 | | SRR1532568 | Bulk RNA-seq |
| GEO dataset GSE84932 | rat_rep1 | | SRR3957262 | Bulk RNA-seq |
| GEO dataset GSE84932 | rat_rep2 | | SRR3957263 | Bulk RNA-seq |
| DDBJ SRA dataset DRA002410 | Sham1 | Ref [42] | DRR021692 | Adult mouse retina CAGE RNA-seq |
| DDBJ SRA dataset DRA002410 | Sham2 | Ref [42] | DRR021693 | Adult mouse retina CAGE RNA-seq |
| DDBJ SRA dataset DRA002410 | Sham3 | Ref [42] | DRR021694 | Adult mouse retina CAGE RNA-seq |
| CRISPR gRNA | Crb1 guide 5′4 | | GAATAAGTACCC GTTCCTTG (SEQ ID NO: 28) | 5' guide for making Crb1 AB and B mouse |
| CRISPR gRNA | Crb1 guide 3′2 | | AAAGCGATTAGG TGATGCCC (SEQ ID NO: 29) | 3' guide for making Crb1 B mouse |
| CRISPR gRNA | Crb1 guide 3′4 | | TGTCCGAACACG TCAACCCC (SEQ ID NO: 30) | 3' guide for making Crb1 AB mouse |
| Primer | MegF11_1.1F | IDT | GCTTGCTCACTCG TTCTCAGT (SEQ ID NO: 31) | RT-PCR primer |
| Primer | Megf11_2.1R | IDT | AGCTCTCTCCTTC CAAACCC (SEQ ID NO: 32) | RT-PCR primer |
| Primer | Megf11_alt23_R | IDT | ACCCACAAGCGT TTGCTAAG (SEQ ID NO: 33) | RT-PCR primer |
| Primer | Crb1 delB F1 | IDT | CAGTATCCCAGG AGCATTCC (SEQ ID NO: 34) | genotyping primer |
| Primer | Crb1 delB F2 | IDT | TTTTTCAGTGTGC CAGGAAGT (SEQ ID NO: 35) | genotyping primer |
| Primer | Crb1 delB R | IDT | AAGACTTTCCGA AGCCATGA (SEQ ID NO: 36) | genotyping primer |

TABLE 1-continued

Key resources. Provides the name and source of key reagents and resources used in this study, such as antibodies, mouse strains, datasets, primers, and chemicals.

| Reagent Type | Reagent | Source or reference | Identifier | Additional information |
|---|---|---|---|---|
| Primer | Crb1 delAB F | IDT | CAAGACACCCAG GACCAAGT (SEQ ID NO: 37) | genotyping primer |
| Primer | Crb1 delAB F2 | IDT | CTTCCCTCTTTGG ACATTGC (SEQ ID NO: 38) | genotyping primer |
| Primer | Crb1 delAB R | IDT | AACTTGGGAGAG CCTGGAGT (SEQ ID NO: 39) | genotyping primer |
| Primer | Crb1_5Fq.seq | IDT | GCCTCGGGCTAT GTGTGTAT (SEQ ID NO: 40) | qPCR primer |
| Primer | Crb1_5cFq.seq | IDT | AAACGGTTCCTG TCGACCTA (SEQ ID NO: 41) | qPCR primer |
| Primer | Crb1_6Rq.seq | IDT | Ggcaagggtgcag taaacat (SEQ ID NO: 42) | qPCR primer |
| Primer | Crb1_11Fq.seq | IDT | Tgcatcaatggagg actgtg (SEQ ID NO: 43) | qPCR primer |
| Primer | Crb1_11UTRRq.seq | IDT | Tcatgcgcagtacg aggtag (SEQ ID NO: 44) | qPCR primer |
| Primer | Crb1_12Rq.seq | IDT | TGAAGAACAGGG CCAAAGTT (SEQ ID NO: 45) | qPCR primer |
| Primer | Crb1_6Fq.seq | IDT | AGAGGACGCTGC ATCAACTT (SEQ ID NO: 46) | qPCR primer |
| Primer | Crb1_7Rq.seq | IDT | TCATCTTGGCCAA ATCTTCC (SEQ ID NO: 47) | qPCR primer |
| Primer | Crb1_8Fq.seq | IDT | GCTCCCTCAAGG GTTTGAAT (SEQ ID NO: 48) | qPCR primer |
| Primer | Crb1_9Rq.seq | IDT | CCATCAGGTGCA GCGTATAA (SEQ ID NO: 49) | qPCR primer |
| Base Scope Probe | BA-Mm-Megf11-E14E17 | Advanced Cell Diagnostics | 720881 | 1999-2304 |
| Base Scope Probe | BA-Mm-Megf11-E16bE17 | Advanced Cell Diagnostics | 720891 | 2210-2247 |
| Base Scope Probe | BA-Mm-Megf11-E16E17 | Advanced Cell Diagnostics | 720901 | 2264-2302 |
| Base Scope Probe | BA-Mm-Megf11-E19E23 | Advanced Cell Diagnostics | 720911 | 2699-2744 |
| Base Scope Probe | BA-Mm-Megf11-E20E23 | Advanced Cell Diagnostics | 720921 | 2822-2864 |
| Base Scope Probe | BA-Mm-Megf11-E22E23 | Advanced Cell Diagnostics | 720931 | 3050-3086 |
| Base Scope Probe | BA-Mm-Megf11-E23E23alt | Advanced Cell Diagnostics | 720941 | 3030-3070 |

TABLE 1-continued

Key resources. Provides the name and source of key reagents and resources used in this study, such as antibodies, mouse strains, datasets, primers, and chemicals.

| Reagent Type | Reagent | Source or reference | Identifier | Additional information |
|---|---|---|---|---|
| Base Scope Probe | BA-Mm-Megf11-E23123 | Advanced Cell Diagnostics | 720951 | 64700141-64700189 |
| Base Scope Probe | BA-Mm-Megf11-E24E25 | Advanced Cell Diagnostics | 720961 | 3329-3370 |
| Base Scope Probe | BA-Mm-Megf11-E24124 | Advanced Cell Diagnostics | 720971 | 3024-3072 |
| Base Scope Probe | BA-Mm-Megf11-E2E3 | Advanced Cell Diagnostics | 720981 | 273-314 |
| Base Scope Probe | BA-Mm-Crb1-004-E5CE6 | Advanced Cell Diagnostics | 704351 | CACAAGGTTTTCACATTTT AATGGCAGTGCTCATAGG AATTCACTGTG (SEQ ID NO: 50) |
| Base Scope Probe | BA-Mm-Crb1-E1E2 | Advanced Cell Diagnostics | 704341 | ACCTCAGCTCCTCACTGCT CATCTGCATAAAGAATTC ATTTTGCA (SEQ ID NO: 51) |

Animals

The use of mice in this study was approved by the Duke University Institutional Animal Care and Use Committee. All experimental procedures followed the guidelines outlined in the National Institute of Health Guide for the Care and Use of Laboratory Animals. The mice were housed under a 12 hr light-dark cycle with ad lib access to food and water.

Knockout Mouse Generation

For the generation of Crb1$^{delB}$, CRISPR guides were designed to target genomic coordinates chr1:139,256,486 and 139,254,837 and validated in vitro on genomic DNA prior to injection. A C57B16J/SJL F1 hybrid mouse line was used for injection; both strains are wild-type at the Crb1 locus (i.e. they do not carry rd8). Founders were genotyped using PCR primers to distinguish the alleles (see Table 1 for primer sequences). Two founder lines with genomic deletions were maintained. One carrying the deletion 139,254,836-139,256,488 (Δ1,652 bp) plus two additional cytosines, and the other 139,254,836-139,256,488 (Δ1,652 bp). Both alleles effectively delete the entire first exon of Crb1-B and the promoter region and are currently phenotypically indistinguishable. For the generation of Crb1$^{null}$, CRISPR guides were designed to target genomic coordinates chr1:139,256,486-139,243,407 and validated in vitro on genomic DNA prior to injection. A C57B16J/SJL F1 hybrid mouse line was used for injection and founders were genotyped using PCR primers (Table 1) to distinguish the alleles. Two founder lines with genomic deletions were maintained. One carrying the deletion chr1: 139,256,844-139,243,411 (Δ13,433 bp) and the other 139,257,194-139,243,411 (Δ13,783 bp). Both alleles effectively delete the entire first exon of Crb1-B and the promoter region in addition to exon 6 and part of exon 7 of Crb1-A. This deletion would eliminate the exon 7 splice acceptor and is predicted to exclude exon 7 altogether. Splicing from exons 5 to 8 (as in Crb1-A) and 4 to 8 (as in Crb1-A2) would result in frameshifts. The Crb1-C-specific retained intron after exon 6 is also entirely deleted. Founder animals were backcrossed with C57B16J mice for at least two generations before analysis and genotyped to ensure they were not carrying rd1 mutation from the SJL background. Animals generated in this study will be made available to the research community for non-commercial use.

Human Retina Tissue

Human donor eyes were obtained from Miracles in Sight® (eye bank; Winston Salem, NC), which were distributed by BioSight (Duke University Shared Resource) under the Institutional Review Board protocol #PRO-00050810. Postmortem human donor eyes were enucleated and stored on ice in PBS until dissection. Retinas were dissected from posterior poles and proceeded to RNA isolation. Donors with a history of retinal disease were excluded from the study.

CRB1-B Antibody

We used Pierce Custom antibody service (Thermo Fisher Scientific) to generate a CRB1-B specific antibody. The antigen was the last 16 amino acids (RMNDEPVVEWGAQENY; SEQ ID NO:53) of CRB1-B, which are predicted to be exclusive to this isoform at the protein level. Antibodies were made in rabbit according to their 90-day protocol with initial inoculation followed by 3 boosts. The antibody was affinity purified and validated by western blot with a Crb1$^{delB}$ knockout control. CRB1-B produces a band of approximately 150 kDa, larger than the predicted size of 110 kDa. This discrepancy in experimental vs predicted size is likely due to post translational modifications such as glycosylation, since addition of PNGase F lowered the band size (not shown). Antibodies generated in this study will be made available to the research community for non-commercial use.

RNA Extraction

For PacBio sequencing experiments and qRT-PCR, C57B16/J mice were used. Mice were anesthetized with isoflurane or cryoanesthesia (neonates only) followed by decapitation. Eyes were enucleated and retinas were dissected out, or brain was dissected from the skull and the cerebral cortex was removed. Total RNA was isolated using TRI Reagent® (lysis reagent; ThermoFisher Scientific AM9738) according to the manufacturer's protocol. Tissue was mechanically homogenized in TRI Reagent® followed by phase separation with chloroform and isopropanol precipitation. RNA samples were stored at −80° C. RIN number was calculated using a Bioanalyzer. Only RIN values above 9 were used for sequencing.

PacBio Library Preparation for Mouse Samples

Reverse transcription was carried out using the Clontech SMARTer™ cDNA kit according to the manufacturer's protocol. cDNA was amplified with KAPA HiFi™ DNA Polymerase for 12 cycles followed by size selection (4.5 to 10 Kb). For capture, 1 ug of cDNA was denatured and blocked with DTT primer and Clontech primer then mixed with Nimblegen's SeqCap EZ Developer (≤200 Mb) custom baits at 47° C. for 20 hrs. Biotynaylated cDNAs were pulled down with streptavidin beads and washed with Nimblegen hybridization buffers to minimize non-specific binding. Targeted cDNA library was amplified 11 cycles with Takara LA Taq™ (polymerase mixture). SMRT bell library was constructed then additional size selection was performed (4.5 to 10Kb) followed by binding of Polymerase with P6-C4 chemistry (RSII). Library was loaded onto SMRT cell using MagBead loading at 80 pM (RSII). For PacBio Sequel library, sequencing primer version 2.1 was annealed and bound using polymerase version 2.0. The bound complex was cleaned with PB Ampure beads and loaded by diffusion at 6 pM with 120 min pre-extension.

PacBio Library Prep for Human Retina

Reverse transcription was carried out using Clontech SMARTer cDNA kit according to the manufacturer's protocol. cDNA was amplified with PrimeSTAR® GXL DNA Polymerase for 14 cycles followed by Blue Pippin size selection (4.5 to 10 Kb). For capture, 1 ug denatured cDNA was used then incubated with Twist Custom Probes at 70° C. for 20 hrs. Biotynaylated cDNAs were pulled down with streptavidin beads and washed with Twist hybridization buffers to reduce non-specific binding. Targeted cDNA library was amplified 11 cycles with Takara LA Taq™ (polymerase mixture) yielding 650 ng of enriched cDNA for library prep. SMRTbell® Template Prep Kit 1.0 post exonuclease was used for library prep followed by a Blue Pippin size selection (4Kb to 50 KB). Post size selection yielded 120 ng of DNA. Sequencing primer version 3.0 was annealed and bound using polymerase version 2.0. The bound complex was cleaned with PB Ampure beads and loaded onto PacBio Sequel instrument by diffusion at 6 pM.

Processing of PacBio Raw Data

Iso-Seq software was used for initial post-processing of raw PacBio data. For lrCaptureSeq experiments, reads of insert were generated from PacBio raw reads using ConsensusTools.sh with the parameters--minFullPasses 1--minPredictedAccuracy 80--parameters/smrtanalysis/current/analysis/etc/algorithm_parameters/2014-09/. From the reads of insert full-length, non-chimeric reads (FLNC reads) were generated using pbtranscript.py classify with the parameters-min_seq_len 500 and presence of 5' and 3' Clontech primers in addition to a polyA tail preceding the 3' primer. For Megf11 PCR product sequencing, parameters were the same except that full length reads were distinguished by the presence of Megf11-specific primer sequences (5' GGCTCCGGGGTATAGGA (SEQ ID NO:54); 3' sequence CTGGCTGCATTGCATTGG (SEQ ID NO:55) for Megf11 long or GGTGTCCAATAAAGTC (SEQ ID NO:56) for Megf11 short).

Isoform Level Clustering

Clustering of FLNC reads into isoforms was performed using ToFU, which consists of two parts: 1) Isoform-level clustering algorithm ICE (Iterative Clustering for Error Correction), used to generate consensus isoforms; and 2) Quiver, used to polish consensus isoforms. Transcript isoforms were generated using the ToFU_wrap script with the parameters--bin_manual "(0,4,6,9,30)"--quiver--hq_quiver_min_accuracy 0.99 (0.98 for Megf11 PCR data). This generated high-quality full-length transcripts with ≥99% post correction accuracy (≥98% for Megf11 PCR data). Isoforms were aligned to the mouse genome mm10 using GMAP (version 1.3.3b) with default values of alignment accuracy (0.85) and coverage (0.99). To prevent over clustering based on 5' end lengths, redundant clusters were removed by collapsing all transcripts that share exactly the same exon structure. To minimize the impact truncated mRNAs may have on inflating isoform numbers, we set a threshold of ≥2 independent full-length reads that must cluster together in order to define an isoform.

To generate the entire isoform catalog, the complete dataset (all timepoints, retina and cortex) was analyzed using the cluster function of Iso-Seq (version 3), with default parameters. Only the highest-quality full-length reads (≥99% accuracy or QV≥20) from each experiment were passed to this analysis. At the conclusion of Iso-Seq 8,287 isoforms of our 30 genes were identified. HQ reads were mapped to the genome (mm10 for mouse, hg19 for human) Cupcake ToFU (github.com/Magdoll/cDNA_Cupcake) in order to further reduce overclustering of isoform subdivisions.

Figure 10:
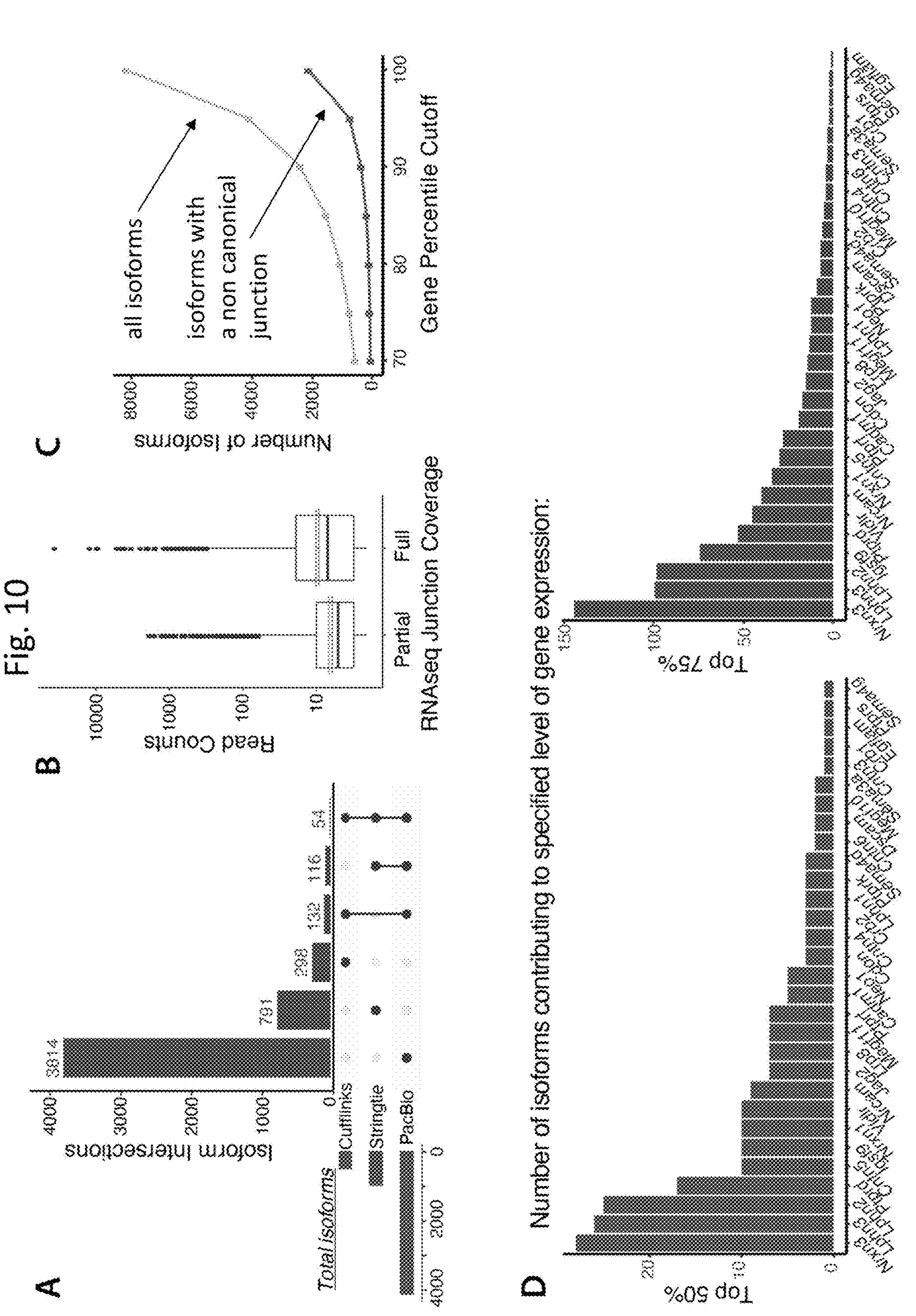
FIG. 10 shows the isoform length and abundance in the lrCaptureSeq catalog. (A) UpSet plot comparing number of "ground-truth" isoforms in the lrCaptureSeq dataset with ones computationally predicted from retina and cortex RNA-seq datasets by Cufflinks or Stringtie. Many more isoforms were detected by lrCaptureSeq than were assembled by these two programs. Nevertheless, only a minority of predicted isoforms were validated by long-read sequencing: 186 isoforms predicted by Cufflinks ($3^{rd}$+$5^{th}$ columns) were detected in the PacBio dataset (or 38% of Cufflinks isoforms), and 170 isoforms predicted by Stringtie ($4^{th}$+$5^{th}$ columns) were detected (or 17.7% of Stringtie isoforms). (B) Box and whisker plot showing number of RNA-seq reads that mapped to lrCaptureSeq isoforms. Two classes of isoforms are compared: those for which all exon junctions were validated in RNA-seq data (Full), and those that were not 100% validated (Partial). Read counts were lower for the latter group, suggesting that failure to validate all junctions may have resulted at least in part from low expression levels and/or insufficient RNA-seq read coverage of those particular isoforms. Box represents IQR, horizontal line represents median, whiskers equal to 1.5*IQR. Split bar indicates 95% confidence interval of the mean. (C) Contribution of isoforms containing non-canonical splice junctions to overall isoform count. Curves show abundance rank ordering of all isoforms and the same rank ordering for only those isoforms that contain a non-canonical splice junction. Non-canonical junctions account for a small fraction of total isoforms. Successively removing the least abundant isoforms from each gene (i.e. moving along the X axis) yields a similar fraction of isoforms that use a non-canonical junction, suggesting some of these are abundantly expressed. (D) Plots depicting the number of isoforms that account for the top 50% (D) or 75% (E) of each gene's total read count (see FIG. 2C). These plots show that, even with strict abundance cutoffs, many isoforms exist and contribute to overall gene expression. (E,F) Isoforms vary substantially in their length. This is shown by a dotplot depicting the lengths of isoforms for each gene (F) and by a box and whiskers plot depicting the number of exons used across isoforms of each gene. Box represents IQR, horizontal line represents median, whiskers equal to 1.5*IQR. (G) t-SNE plot of all isoforms. Most isoforms segregate into their respective gene families, validating efficacy of clustering algorithms for comparing isoform similarity. Isoforms in center of plot that do not segregate well generally contain large genomic elements (i.e. retained introns) which impede clustering with other isoforms of the same gene. The spread of isoforms suggests significant variations in sequence composition. Plot was generated with 1,000 iterations and perplexity=35.
Figure 10:
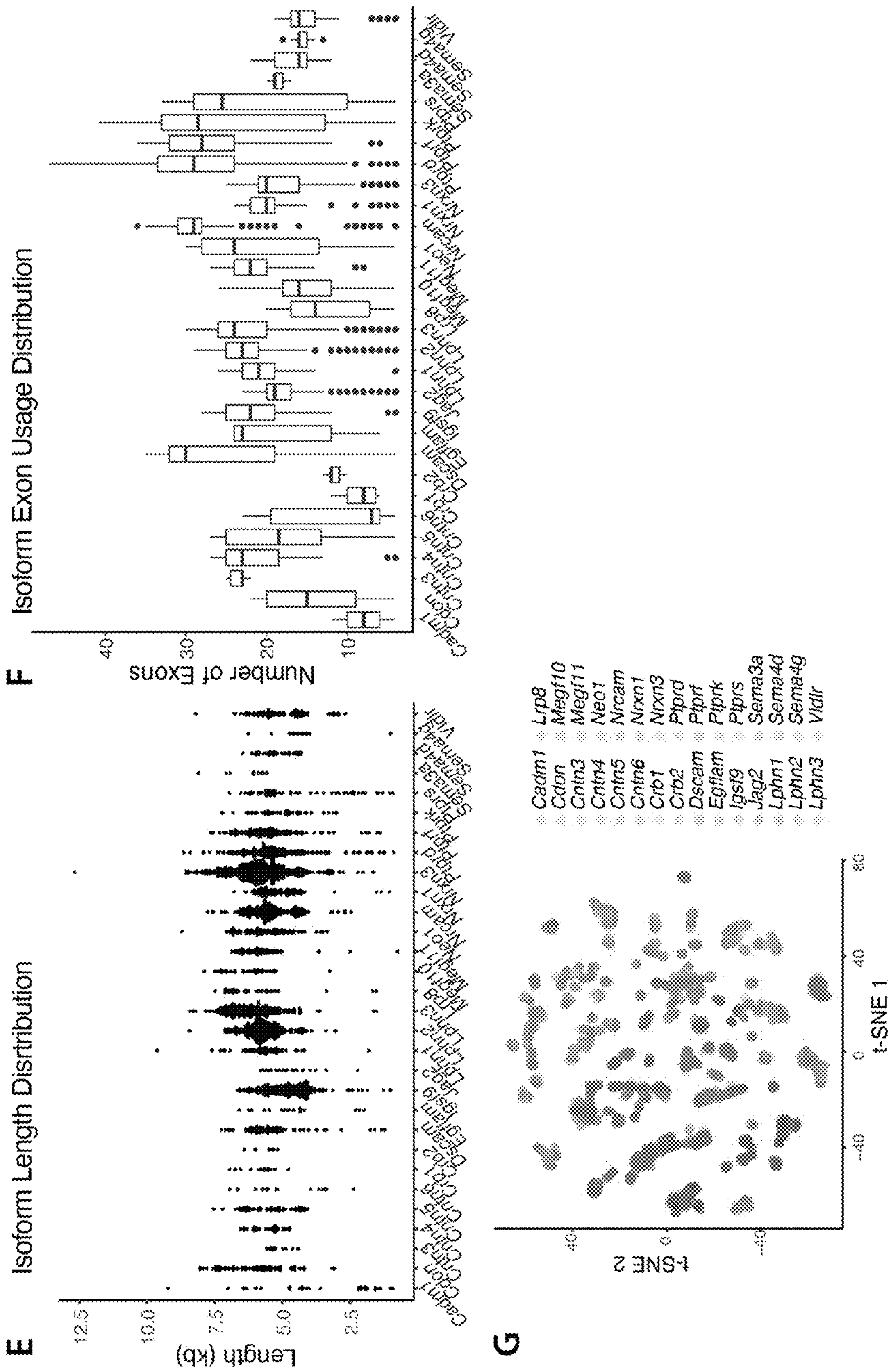

Finally, additional filtering of putative spurious isoforms was performed with our IsoPops software. The goal of this filtering was to remove artifacts arising from cDNA truncations or poly-A mispriming within genomic DNA. Details of the filtering methodology are provided below in the section describing the software package. Applying these filters yielded the final catalog of 4,116 isoforms. We did not exclude isoforms that contained non-canonical junctions, because many such isoforms were highly abundant; however, even if they were excluded, overall isoform counts would be only slightly reduced (FIG. 10C).

Figure 2:
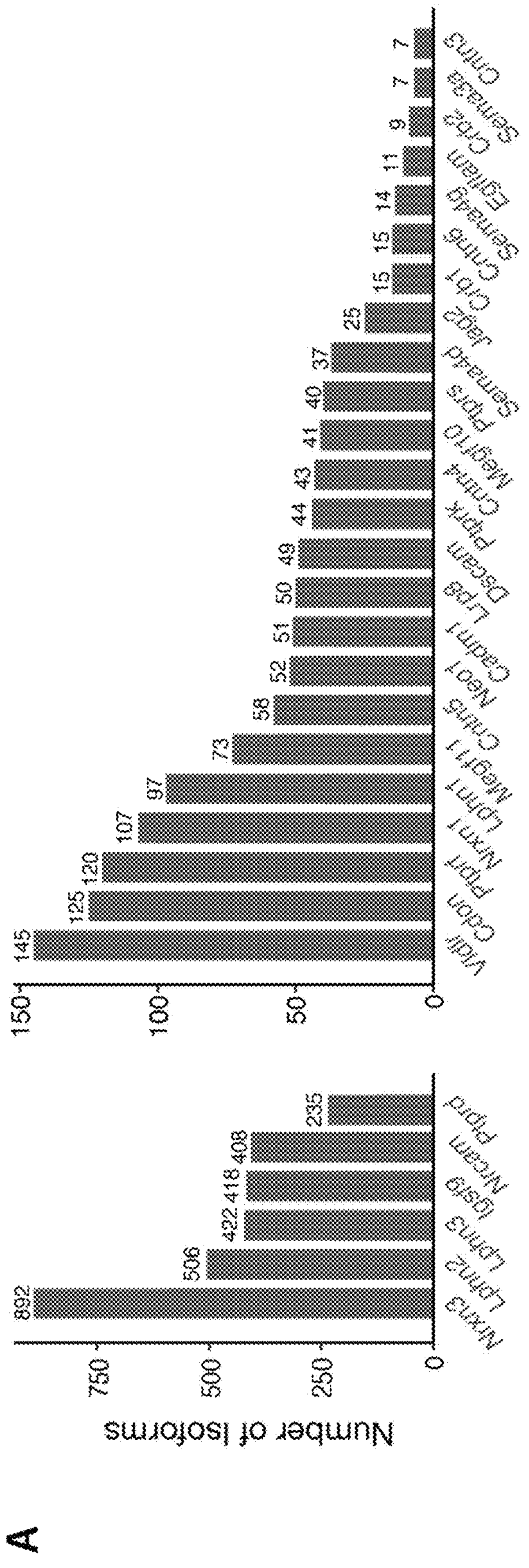
FIG. 2 illustrates the mRNA isoform diversity revealed by lrCaptureSeq. (A) Total number of isoforms catalogued for each gene after completion of lrCaptureSeq bioinformatic pipeline. (B) UpSet plot comparing isoform numbers in the PacBio lrCaptureSeq dataset with public databases (RefSeq, UCSC Genes). Intersections show that 53.9% of NCBI RefSeq isoforms were detected in the PacBio dataset (255 RefSeq isoforms, $4^{rd}+6^{th}$ columns from left). For UCSC genes, 72.3% of isoforms annotated in this database were detected in the PacBio dataset (102 UCSC isoforms, $5^{th}+6^{th}$ columns). (C) Lorenz plots depicting total number of isoforms cataloged for each gene (right Y intercepts), and fraction of each gene's total reads represented by each of its isoforms (dots). Curves are cumulative functions, with isoforms displayed in order from highest (left) to lowest (right) fraction of total gene reads. Also see FIG. 10D. (D) Shannon diversity index was used to compare the relative diversity of each gene. Higher Shannon index reflects both higher isoform number and parity of isoform expression. (E) Treeplot depicting relative abundance of genes and isoforms (nested rectangles) within the entire dataset. Rectangle size is proportional to total read number. The most abundant isoform belonged to Crb1; the most abundant gene was Nrcam. (F,G) Unsupervised clustering applied at single gene level identifies families of related isoforms that share specific sequence elements. Ptprd gene is shown as an example. A subset of Ptprd isoforms cluster into 5 groups (F, bottom). These differ based upon 3 variables: length of 5' UTR; length of 3' UTR; and splicing of a variable exon cluster (F, top). The same groups segregate within principal components plot (G).
Figure 2:
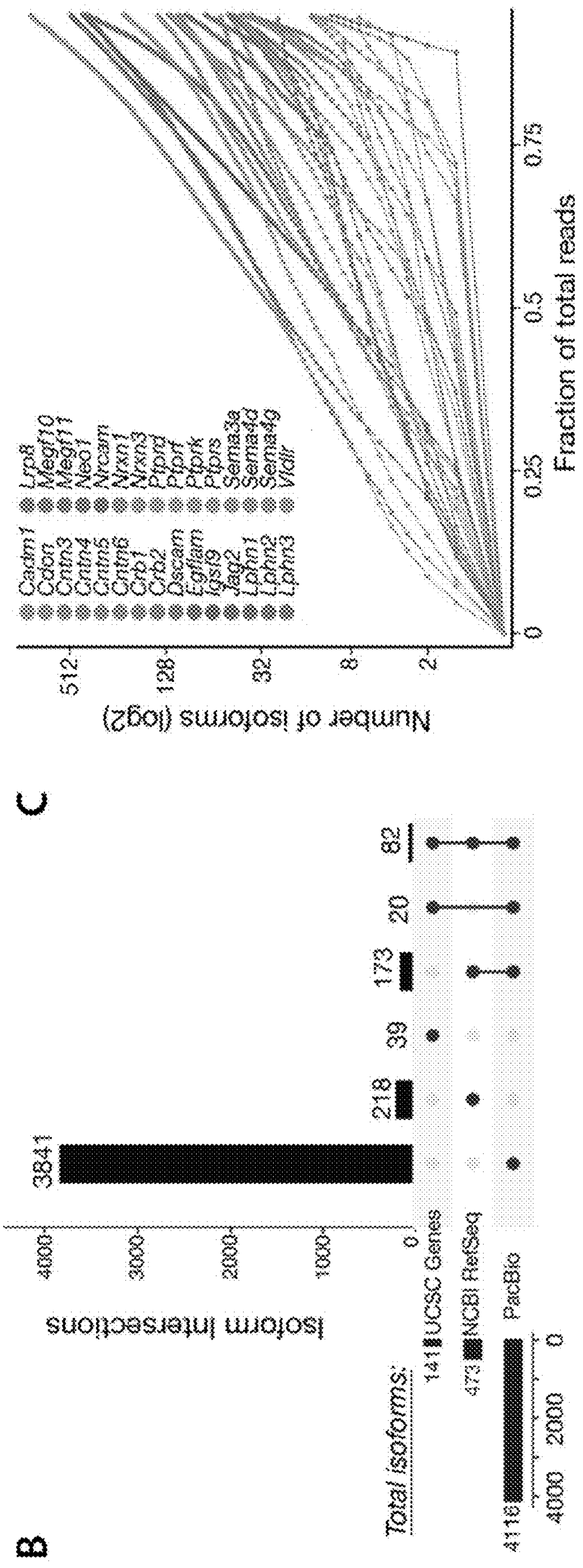
Figure 2:
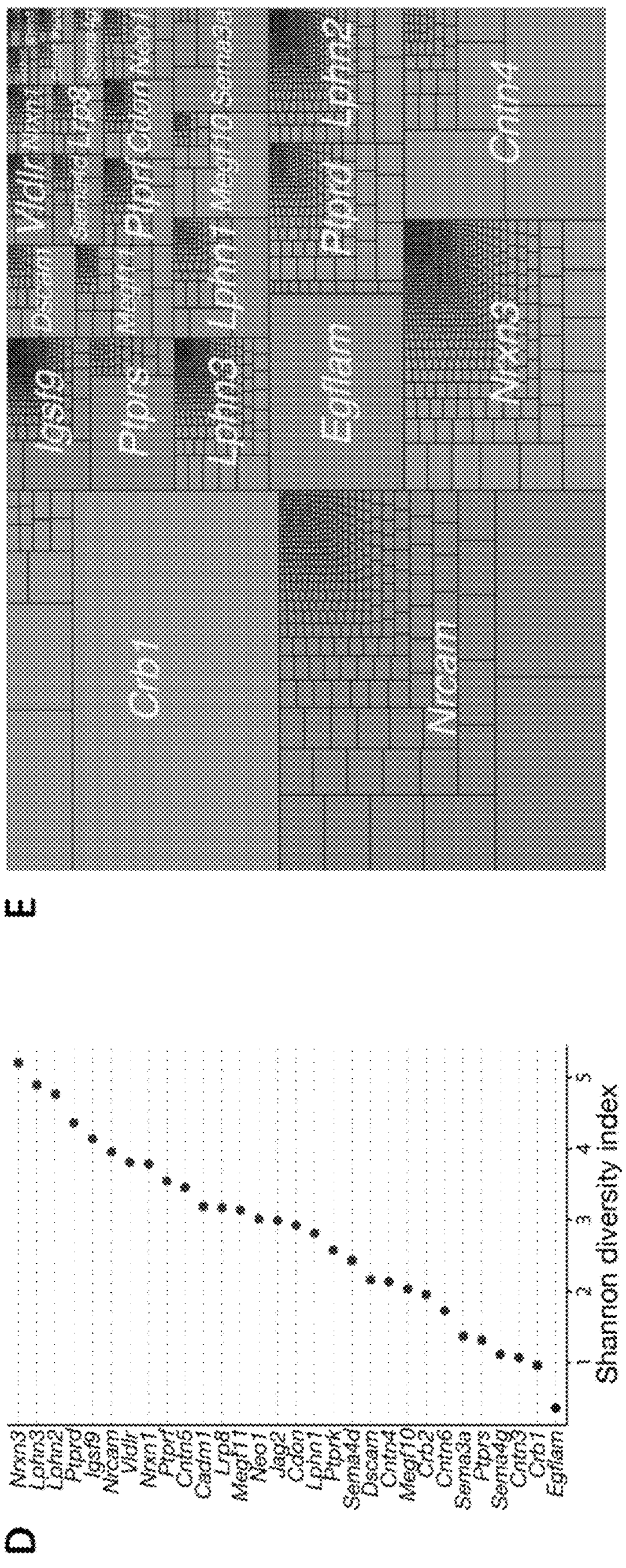
Figure 2:
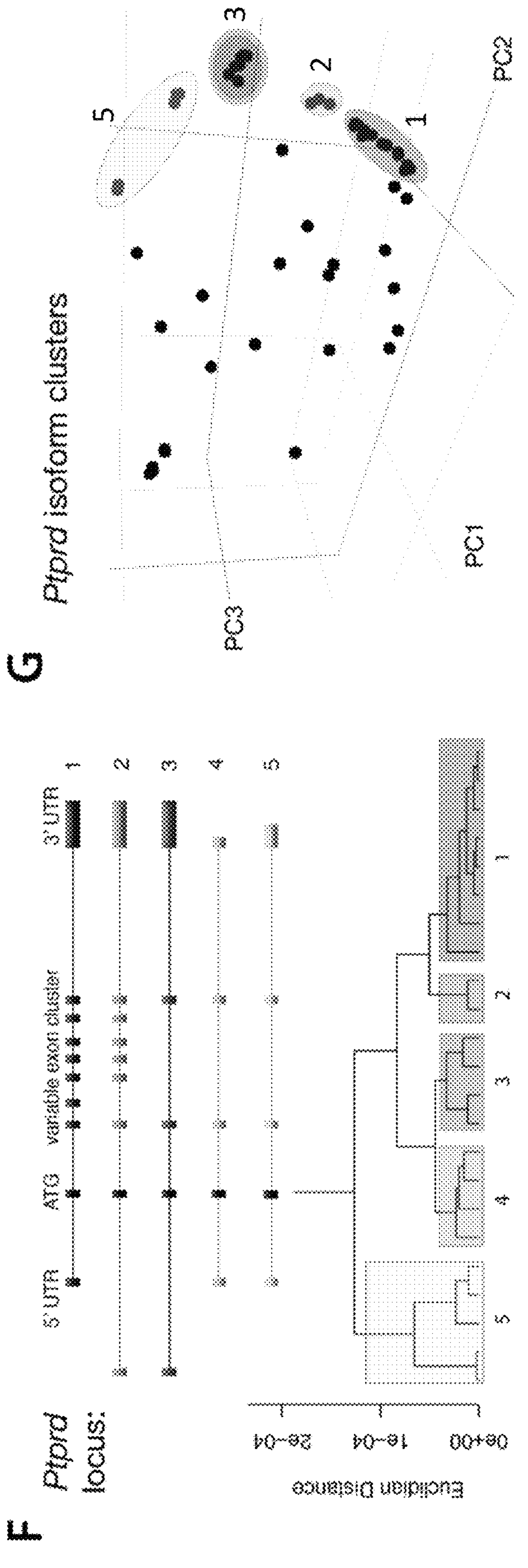
Figure 3:
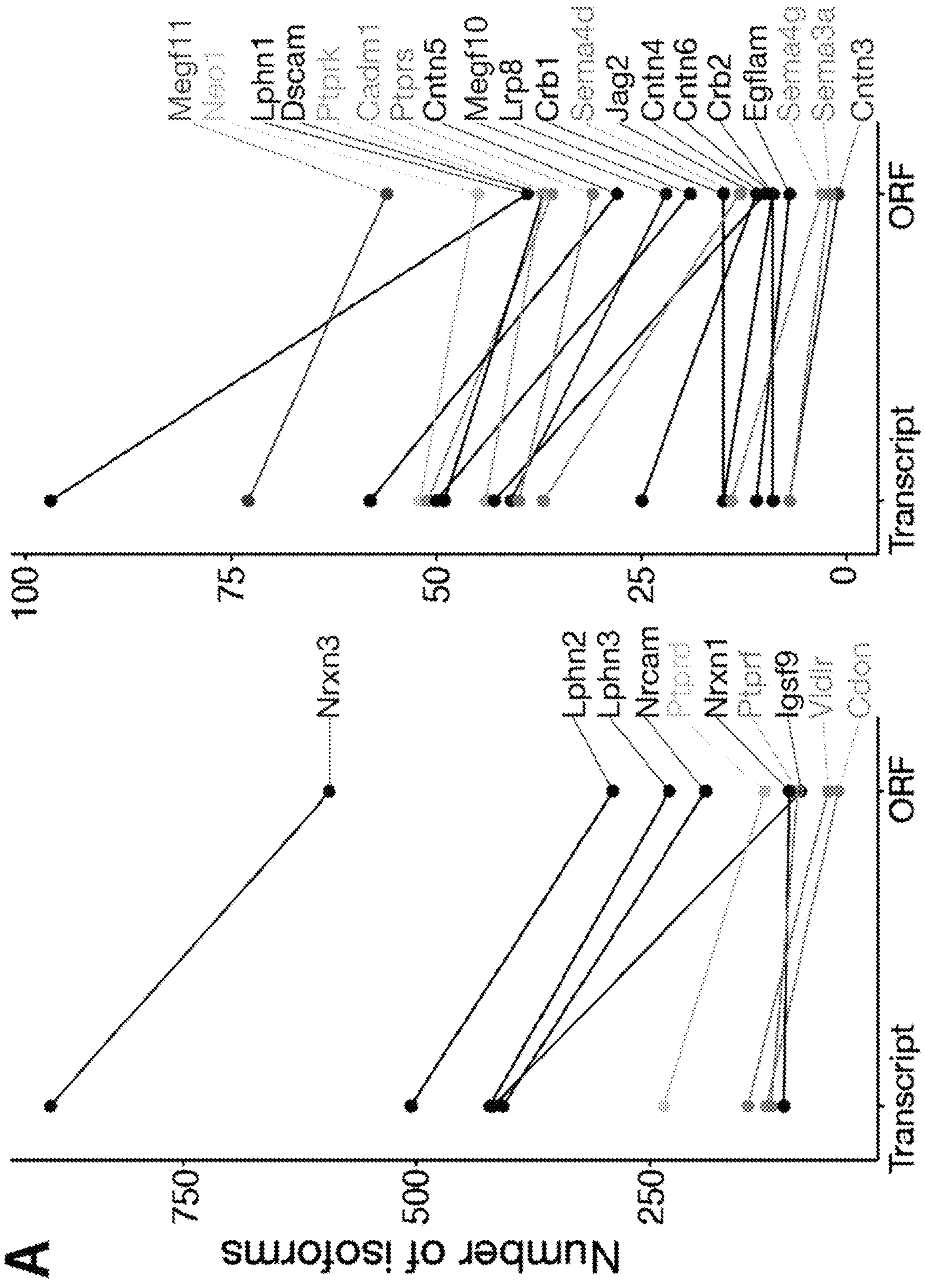
FIG. 3 demonstrates that transcript diversity contributes to a wealth of protein diversity. (A) Total number of transcripts and ORFs for each gene in the lrCaptureSeq dataset. ORF number typically scales with transcript number, as shown by similar line slopes across most genes. A minority of genes exhibit far fewer ORFs than transcript isoforms (steep slopes). (B) Lorenz plots of isoform ORF distributions, similar to FIG. 2C. Many predicted protein isoforms (dots) are expected to contribute to overall gene expression. (Also see FIG. 11A,B). (C) Shannon diversity index for unique predicted ORFs for each gene. Genes that encode trans-synaptic binding proteins are highlighted using gray text. (D) Treeplot depicting relative abundance of predicted ORFs within the dataset. For most genes, overall expression is distributed across many ORF isoforms. Genes with steep slopes in A (e.g. Cntn4) show differences here compared to transcript treeplot (FIG. 2E). (E) Schematic of proteomic techniques used to enrich for cell surface proteins. (F) Coomasie stained protein gel from biotin labeled and streptavidin-enriched cell surface proteins. Elution lane (E) shows enrichment of higher molecular weight proteins compared to total lysate input (I). Bands from 75 kDa-250 kDa were excised for mass spectrometry. (G) Plot depicting number of unannotated peptides discovered by mass spectrometry that do not exist in the UniProtKB database. Such peptides would have gone undetected if they had not been predicted to exist by lrCaptureSeq.
Figure 3:
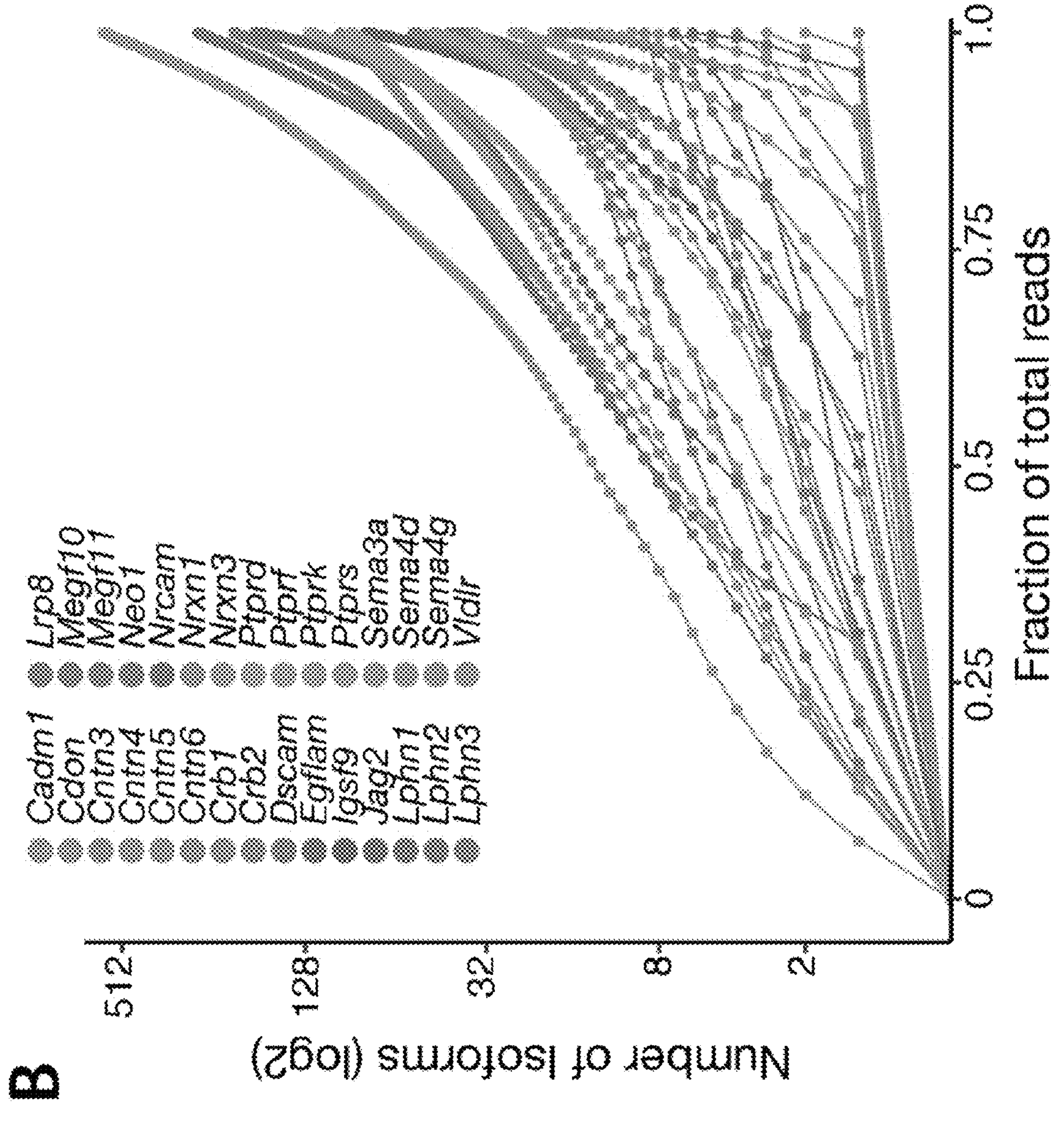
Figure 3:
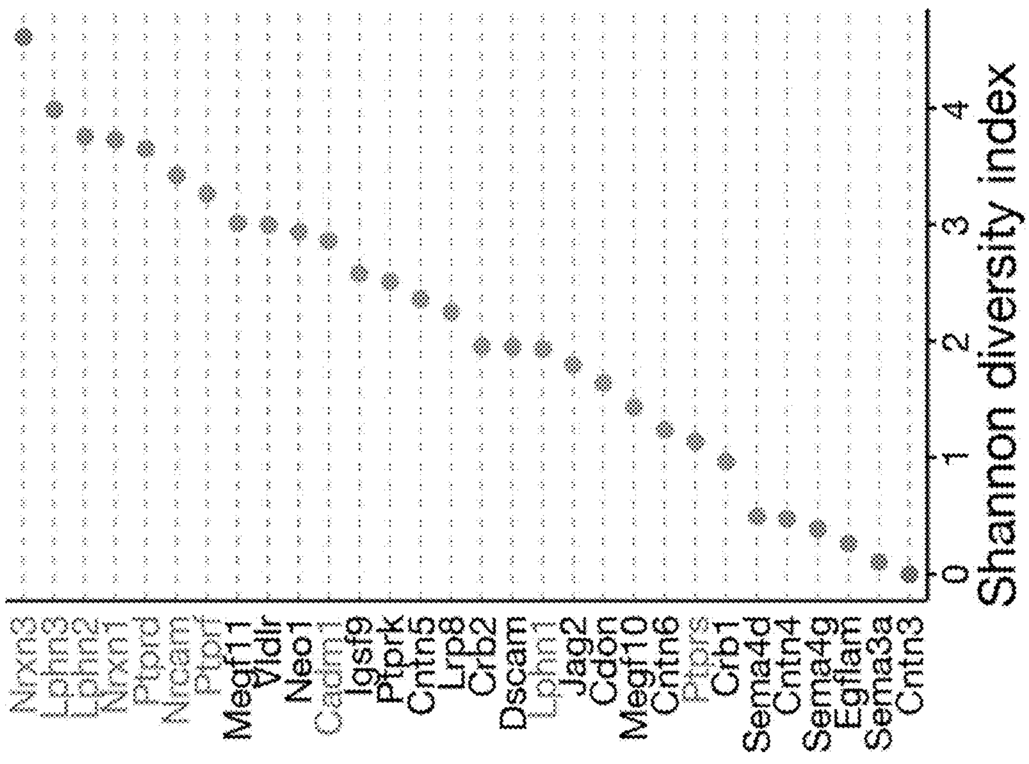
Figure 3:
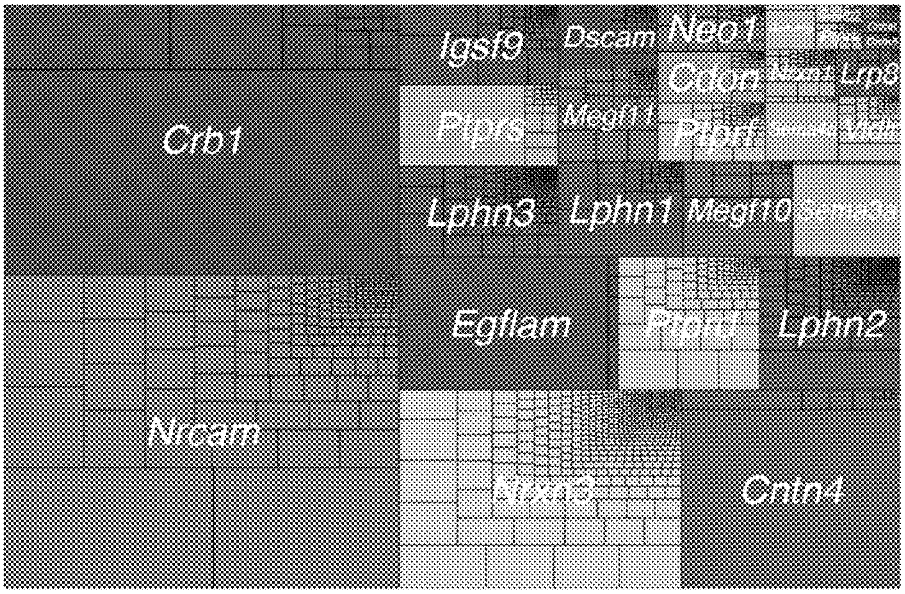
Figure 3:
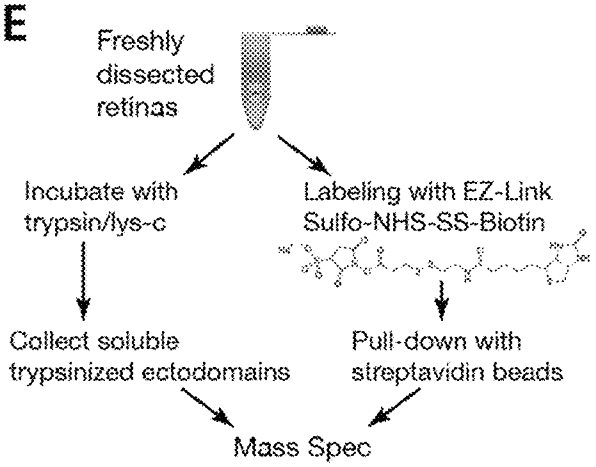
Figure 3:
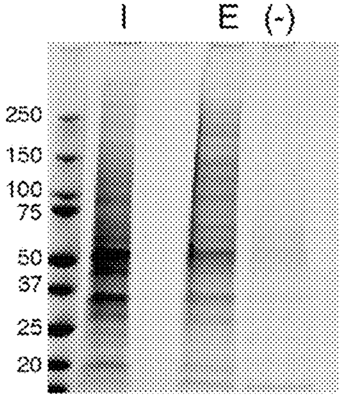
Figure 3:
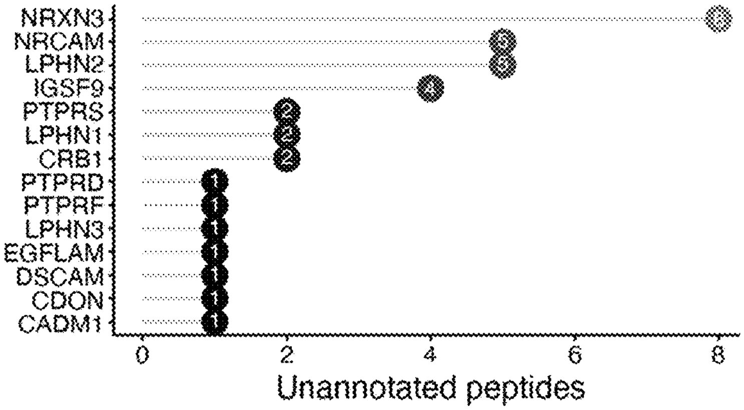

The final isoform catalog specified not only the number of isoforms, but also the number of full-length reads obtained for each isoform. We have reported these read counts for some of our analyses (e.g. FIG. 2C,E; FIG. 3B,D). These data aid in understanding how the overall expression of a particular gene is distributed across its isoform portfolio. We have avoided making conclusions about the expression level of particular isoforms, unless the PacBio data are supported by independent short-read RNA-seq data (e.g. FIG. 5D,G,H,I).

IsoPops R Package

We developed a package of R software for convenient analysis and viewing of PacBio transcriptome sequence output. The IsoPops R package allows users to perform many of the analyses described in this study on their own long-read data.

The package offers the following features. First, it permits filtering of truncated and spurious isoforms to facilitate downstream analysis. Second, it displays maps of exon usage enabling the user to visually compare how isoforms differ. Third, it generates plots summarizing expression levels of isoforms within an individual gene and across a dataset. These include tree plots (FIG. 2E) and a variant on the Lorenz plot that we have termed a jellyfish plot (FIG. 2C). Fourth, it clusters similar isoforms and displays the data in various dimension-reducing plots such as dendrograms and 3-dimensional PCA plots. Fifth, it provides summary statistics such as the length distribution of a gene's isoforms or the number of exons used in each isoform. Finally, it performs cross-correlations, enabling the user to ask if certain exons tend to appear together in the same transcripts. Methods relevant to these features are described below.

Filtering

The IsoPops isoform filtering process consists of 3 steps: First, transcripts containing fewer than n exons are removed. For our study, n was set to 4, because we did not expect any such short isoforms for the genes in our dataset. To quantify exon number, we did not reference exon annotations, but instead defined the number of non-contiguous genomic segments (or the number of junctions plus one) as the exon count for each isoform. This filtering step removed most spurious transcripts arising from genomic poly-A mispriming, as these sequences typically mapped to a single "exon."

Second, we filtered out truncation artifacts. To identify truncated isoforms, we developed an algorithm designed to filter as thoroughly as possible without discarding potentially valuable unique transcripts. In particular, we wanted to preserve all unique splicing events and tolerate unique transcription start sites (TSS) and transcription termination sites (TTS) modestly. The algorithm compares the set of exon boundaries (coordinates of acceptor and donor splice sites) for an isoform pair A and B and applies the following two rules. Rule 1: If all the exon boundaries in B form a contiguous subset of the exon boundaries in A, then B is a truncation of A. We required the subset to be contiguous to avoid filtering transcripts with retained introns. Rule 2: If all 3 of the following conditions are met, B is a truncation of A. 1) The TSS of B falls within an exon in A; 2) the TTS of B is either found in A or within/beyond the 3'-most exon of the gene; 3) internal exon boundaries of B (i.e. excluding the 5'- and 3'-most exon boundaries of B) are a contiguous subset of A.

Third, the least abundant 5% of isoforms for each gene were filtered out, on the assumption that these extremely low-abundance isoforms might constitute experimental or biological noise.

Pearson Correlation

This function enables analysis of exon co-occurrence across isoforms. Each isoform in a given gene was labeled with a series of binary values representing the exons called within its cDNA sequence. Exon calls were determined by searching for exact matches of either the first 30 bp or last 30 bp of each exon within the transcript. Exon definitions were derived from PacBio isofom GFF file. Isoforms were weighted by their full-length read counts before pairwise Pearson correlations between exon calls were calculated.

K-Mer Vectorization

IsoPops enables quantification of sequence differences between isoforms. To quantify relative differences between isoforms, we calculated the Euclidean distances between vectorizations of each isoform's cDNA sequence (or their predicted ORF amino acid sequence). We used the text2vec R package to generate a vector for each isoform, where each element in the vector equals the number of times a certain k-mer (sequence fragment) appears within the isoform. We counted all possible 6-mers within isoforms, choosing k=6 to maximize k-mer count uniqueness between isoforms without requiring excessive computational resources. Each isoform's vector of k-mer counts was then normalized to sum to 1, so that isoform distances calculated from these vectors would not be dominated by differences in length between transcripts.

Isoform Clustering

To cluster isoforms, we calculated pairwise euclidean distances between isoforms' k-mer count vectorizations. We then performed hierarchical agglomerative clustering using the R base algorithm hclust using default settings and the "complete" agglomeration method. Dendrogram plots of clusterings were generated by the dendextend R package.

Dimension Reduction

PCA and t-SNE were performed directly on the k-mer count vectorizations. We used the R base algorithm prcomp for PCA with default settings. For t-SNE, we ran the Rtsne package's algorithm for exact t-SNE (theta=0, maximum iterations=1000, perplexity=35), which includes a round of PCA for data pre-processing. t-SNE results are plotted in the same number of dimensions as output by the algorithm (i.e. 3D t-SNE plots were generated with ndim=3).

Lorenz (Jellyfish) Plot

Cumulative percent abundance was calculated independently for the isoforms of each gene. First, full-length read counts were normalized across the gene and labeled "percent abundance." Next, isoforms for a given gene were rank ordered by percent abundance in descending order. Finally, a cumulative percent abundance was calculated for each isoform, via partial summation of percent abundances in descending order. Isoforms were then plotted in this order along the y-axis and positioned according to cumulative percent abundance along the x-axis.

ORF Prediction

Sqanti[67] was used for ORF prediction and genomic correction of PacBio isoforms.

RNA-seq Analysis

RNA-seq fastq files were downloaded from NCBI GEO and the data was mapped with Hisat2 (version 2.1.0) to reference build mm10 (for mouse), hg19 (for human), bosTau8 (bovine), danRer11 (zebrafish), and rn6 (rat). Dataset GSE101986 and GSE74660 were quantified with Cufflinks (version 2.2.1). Datasets GSE94437, GSE101544, GES49911, and GSE84932 were quantified with StringTie (version 1.3.3b). All reference annotations for isoform quantification analysis were generated from corresponding reference GTF files merged with the Iso-Seq GFF output using the top 3 most abundant isoforms for each of the 30 genes.

Isoform Predictions from RNA-Seq Data

Computational prediction of isoforms was performed on the RNA-seq data set GSE101986 and GSE79416 using Cufflinks (version 2.2.1) or Stringtie (version 1.3.3b) without a reference assembly. Resulting assemblies were merged using Cuffmerge to create the final reference assembly. Isoform matching between datasets was performed using Sqanti. Isoforms were considered a match if they were identified as "full-splice match" by Sqanti. All other isoforms were considered non-matching.

Matching of lrCaptureSeq Isoforms to Other Databases

Sqanti was used for validation of isoforms in public databases, as well as Cufflinks/Stringtie predicted isoform databases. Validation was performed using the reference GTF (either from computational assembly, NCBI RefSeq, or UCSC Genes) as input. Isoforms were validated if they were "full-splice match" to the reference. All other isoforms were considered distinct.

Validation of Splice Junctions and 5' Ends of lrCaptureSeq Isoforms

Junction coverage of PacBio isoforms by RNA-seq data was assessed using Sqanti software. The junction input file for Sqanti was generated using STAR (STAR_2.6.0a) by mapping mouse retina and cortex RNA-seq data (GSE101986 and GSE79416) to the mm10 genome with a custom index made using the PacBio GFF output. Junctions were classified as either canonical (GT-AG, GC-AG, and AT-AC) or noncanonical (all other combinations).

CAGE RNA-seq data from adult mouse retina (DRA002410; samples Sham1, Sham2, and Sham3) were aligned to the genome (mm10) using Hisat2. Read coverage at exon 1 of the lrCaptureSeq isoforms was determined using BedTools (version 2.29.2). CAGE data coverage across normalized isoform lengths was performed using Qualimap (version 2.2.1).

Chromatin Accessibility

Publicly available ATAC-seq data was used to assess chromatin accessibility (i.e. putative promoter sites) in mouse and human retina[68-71]. DNAse I hypersensitivity data from the ENCODE project was used for assessment of mouse cortex[71]. All raw fastq files were downloaded from SRA or aligned bam files from ENCODE data portal. Reads were trimmed using fastqc (version 0.11.3) and trim galore (version 0.4.1) and mapped to either the mm9 or hg19 genomes using bowtie2 (version 2.2.5). Aligned bam files were filtered for quality (>Q30) and mitochondrial and blacklisted regions were removed. Files were converted to bigwigs using deeptools (version 3.1.0) and visualized in IGV (version 2.4.16). All tracks from the same experiment are group scaled.

Shannon Diversity Index

The Shannon index was calculated with the R package Vegan (github.com/vegandevs/vegan) according to the following equation $$H'=-\Sigma p_i \ln p_i$$

where $p_i$ is the proportion of isoforms found in a gene ($p_i=n_i/N$) and $n_i$ is the number of reads for isoform i and N is the total number of reads for a gene.

Sashimi Plots

Sashimi plots were generated using Gviz (version 1.24.0) with the PacBio generated GFF file. The reads for the plot were generated by mapping the PacBio FLNC.fastq (≥85% accuracy) file to the genome (mm10, hg19) with GMAP (version 2014Sep. 30). Because the FLNC reads had relatively high error rates that had not been filtered out like in our final datasets, and because expression varied by gene, minimum junction coverage was variable for each plot. Minimum junction coverage was set to 60 for Crb1 mouse retina, 4 for Crb1 Cortex, 11 for human CRB1, and 4 for Megf11.

scRNA-seq

Raw scRNAseq data profiling mouse retinal development[48] were aligned to a custom mm10 mouse genome/transcriptome using CellRanger (v3.0, 10× Genomics). mm10 reference genome and transcriptomes were downloaded from 10× Genomics and the GTF file was modified to identify the dominant Crb1 isoforms (Crb1-A and Crb1-B) as independent genes. As the CellRanger count function only considers alignments that uniquely map to a single gene, output files only report reads that map within the independent 3' exons or splice into these from the most distal last shared exon.

Data was subsequently analyzed exactly as previously reported[48]. Each cell barcode of this new analysis was assigned to a cell type based on the classifications in the original manuscript. Monocle (v3.0)[72,73] and custom R scripts were used for data visualization and plotting.

BaseScope In Situ Hybridization

Eyes were enucleated and retinas were dissected from the eyecup, washed in PBS, and fixed at RT for 24 hours in PBS supplemented with 4% formaldehyde. Retinas were cryoprotected by osmotic equilibrium overnight at 4 degrees in PBS supplemented with 30% sucrose. Retinas were imbedded in Tissue Freezing Medium and flash frozen in 2-methyl butane chilled by dry ice. Retina tangential sections were cut to 18 μm on a Thermo Scientific Microm HM 550 Cryostat and adhered to Superfrost® Plus slides.

Probes were designed against splice junctions to detect various splicing events (see Table 1 for sequences). Probe detection was performed using the Red detection kit. BaseScope in situ hybridization was performed according to the manufacturers protocol with slight modifications. Fixed frozen retinas were baked in an oven at 60° C. for 1 hr then proceeded with standard fixed frozen pretreatment conditions with the following exceptions: Incubation in Pretreatment 2 was reduced to 2 minutes and Pretreatment 3 was reduced to 13 minutes at RT. BaseScope probes were added to the tissue and hybridized for 2 hours at 40° C. Slides were washed with wash buffer and probes were detected using the Red Singleplex detection kit. Immunostaining was performed after probe detection by incubation with primary antibodies overnight. For Megf11 BaseScope, α-Calbindin antibodies were used to label starburst amacrine cells and horizontal cells. Tissue was washed 3 times with PBS and secondary antibodies were applied and incubated for 1 hour at RT. Slides were washed once again and coverslips mounted.

Expression of CRB1 Isoforms in K562 Cells

Tagged CRB1 constructs were built by cloning YFP in-frame at the C-terminus of CRB1-A and CRB1-B. The tagged constructs were cloned into the pCAG-YFP plasmid (Addgene #11180).

K562 cells (ATCC® CCL-243™) were obtained from, validated by, and *mycoplasma* tested by ATCC. The cells were cultured in Dulbecco's Modified Eagle's Medium (DMEM) with 10% bovine growth serum, 4.5 g/L D-glucose, 2.0 mM L-glutamine, 1% Penicillin/Streptomycin in 10 cm cell culture dishes. Cells were passaged every 2-3 days before reaching 2 million cells/ml. Cells were transfected using the Amaxa® Cell Line Nucleofector® Kit V following instructions in the K562 nucleofection manual. Specifically, aliquots of 1 million cells were pelleted through centrifuging at 200× g for 5 minutes at room temperature in Eppendorf® tubes. Supernatant was completely and cell pellets were suspend in 100 ul Nucleofector® solution per sample. 2 ug of plasmid DNA (pCAG:Crb1A-YFP, pCAG:Crb1B-YFP, or pCAG:YFP) were added and gently mixed with the suspended cells. Cell and DNA mixture were transfected into cuvettes, inserted into the Nucleofector® Cuvette Holder, and transfected with program T-016. Cuvettes were taken out of the holder after program is completed and immediately added with 500 ul of pre-equilibrated cultured medium. These transfected cells were then divided and transferred into two wells of the 24-well glass bottom dish (MatTek Corporation). Cells were imaged 24-hour post transfection with an inverted confocal microscope (Nikon).

Retina Thin Sectioning and Electron Microscopy

Mice were anesthetized with isoflurane followed by decapitation. Superior retina was marked with a low temperature cautery to track orientation. Eyes were enucleated and fixed overnight at RT in Glut Buffer (40 mM MOPS, 0.005% $CaCl_2$), 2% formaldehyde, 2% glutaraldehyde in $H_2O$). The dorsal-ventral axis was marked at the time of dissection so that superior and inferior retina could subsequently be identified in thin sections. Eyes were transferred to a fresh tube containing PBS for storage 4° C. until prepped for embedding.

For thin sections, the cornea was removed from the eyecup and the eyecup was immersed in 2% osmium tetroxide in 0.1% cacodylate buffer. The eyecup was then dehydrated and embedded in Epon 812 resin. Semi-thin sections of 0.5 μm were cut through the optic nervehead from superior to inferior retina. The sections were counterstained with 1% methylene blue and imaged on an Olympus IX81 bright-filed microscope.

For electron microscopy, tissue was processed and imaged as described[74]. Briefly, far peripheral retina was trimmed and 65-75 μm sections were prepared on a Leica ultramicrotome. Sections were prepared separately from superior and inferior hemisections of each retina, and counterstained with a solution of 2% uranyl acetate+3.5% lead citrate. Imaging was performed on a JEM-1400 electron microscope equipped with an Orius® 1000 camera.

Retina Nuclei Counting

Retina semi-thin sections were tile scanned on an Olympus IX81 bright-filed microscope with a 60× oil objective and stitched together with cellSens software. Using Fiji software[75], a segmented line was drawn from the optic nerve head to the periphery for both superior and inferior retina. At intervals of 500 μm, four boxes of 100 μm were drawn encapsulating the outer nuclear layer so that the center of the box was a factor of 500 μm from the optic nerve head. For each hemisphere of the retina, four boxes were made. Using the count function in ImageJ, the total number of nuclei encapsulated by each box were counted at each position. Counts were averaged across each position and plotted as well as total counts for all 8 measurements for each retina.

Assessment of OLM Junctions by Electron Microscopy

Each section, comprising ~90% of one retinal hemisection (far peripheral retina was trimmed during sectioning), was evaluated on the electron microscope for OLM gaps. Each potential gap was imaged and gaps were subsequently confirmed offline by evaluating the presence of electron-dense OLM junctions on the inner segments of imaged photoreceptors. The number of gaps per section was quantified, along with the size of each gap, using Fiji software. For quantification and statistics, wild-type and null/+ heterozygous controls were grouped together, since neither genotype showed any OLM gaps.

Retina Serial Sectioning with Western Blotting

Serial sectioning was performed as described[51,51]. Briefly, mice were anesthetized with isoflurane followed by decapitation. Eyes were enucleated and dissected in ice-cold Ringer's solution. A retina punch (2 mm diameter) was cut from the eyecup with a surgical trephine positioned adjacent next to the optic disc, transferred onto PVDF membrane with the photoreceptor layer facing up, flat mounted between two glass slides separated by plastic spacers (ca. 240 μm) and frozen on dry ice. The retina surface was aligned with the cutting plane of a cryostat and uneven edges were trimmed away. Progressive 10-μm or 20-μm tangential sections were collected—depending upon endpoint of sectioning (photoreceptors or inner retina, respectively).

Proteomics

Retina Trypsin Ectodomain Extraction

Juvenile P14 Mice were anesthetized with isoflurane followed by decapitation. Eyes were enucleated and dissected out of the eyecup in Ringers solution (154 mM NaCl, 5.6 mM KCl, 1 mM $MgCl_2$, 2.2 mM $CaCl_2$), 10 mM glucose, 20 mM HEPES). Retinas were placed in 100 μl Ringers solution containing 5 μg trypsin/lys-c. Solution with retina was incubated at RT for 10 minutes with periodic gentle mixing. Contents were then centrifuged at 300×G for 1.5 minutes and the supernatant was transferred to new tube. Urea was added to protein mixture to 8M then incubated at 50° C. After 1 hr incubation, DTT was added to a final concentration of 10 mM and incubated for 15 min at 50° C. Peptides were alkylated by adding 3.25 μl of 20 mM Iodoacetamide and incubated for 30 min at room temperature in the dark. Reaction was quenched by adding DTT to 50 mM final concentration. Mixture was diluted 1:3 with ~270 μl of ammonium bicarbonate. Mixture was further digested overnight by adding 1 μg of trypsin/lys-c at 37° C.

Cell Surface Protein Labeling and Pulldown

Cell surface labeling of membrane proteins was performed based on a described protocol[76]. Mice were anesthetized with isoflurane followed by decapitation. Eyes were enucleated and retinas were dissected out of the eyecup into ice cold HBSS. Retinas were washed with HBSS followed by incubation in HBSS supplemented with EZ-Link™ Sulfo_NHS-SS-Biotin (biotinylation reagent; 0.5 mg/ml in HBSS) for 45 min on ice. Retinas were then washed 3× with HBSS+100 μM lysine to quench remaining reactive esters. Retinas were then collected in 400 μl (200 μl/retina) lysis buffer (1% Triton® X-100 (detergent), 20 mM Tris, 50 mM NaCl, 0.1% SDS, 1 mM EDTA). Retinas were homogenized using short pulses on a sonicator. The lysate centrifuged at 21,000×G for 20 min at 4° C. and the soluble fraction was collected. For immunoprecipitation, 75 μg of protein lysate was mixed with 100 μl of Streptavidin Magnetic Beads (Pierce™) and incubated at room temperature while rotating. Streptavidin/biotin complex was sequestered using a magnet and washed with lysis buffer. Proteins were eluted from the beads by incubation with elution buffer (PBS with 0.1% SDS 100 mM DTT) at 50° C. for 30 min. Experimental samples (input, biotin enriched, and non-biotin labeled negative control) were mixed with 4×SDS-PAGE sample buffer and incubated on a heat block at 90° C. for 10 min. Samples were then loaded on a 4-15% Mini-PROTEAN® TGX™ Stain-Free protein gel. Electrophoresis was carried out at 65 V through the stacking gel then adjusted to 100 V until the dye front reached the end of the gel.

In-Gel Tryptic Digestion

After electrophoresis, the gel was washed twice with $H_2O$, fixed with 50% methanol, 7% acetic acid for 20 min and stained with colloidal Coomassie based GelCode™ Blue Stain reagent (Thermo Fischer Scientific, cat #24590) for 30 min. The gel was destained with distilled water at 4° C. for 2 h while rocking. Protein bands were imaged on a Bio-Rad® ChemiDoc™ Touch imager. Using a clean razor blade, bands between 75-250 kDa were excised, cut into ~1×1 mm pieces and collected in 0.5 ml siliconized (low retention) centrifuge tube. Gel pieces were destained with 200 μl of Destaining Solution (50 mM ammonium bicarbonate, $NH_4HCO_3$ in 50:50 acetonitrile:water) at 37° C. for 30 min with shaking. Solution was removed and replaced with 200 μl of Destaining Solution and incubated again at 37° C. for 30 min with shaking. Solution was removed from the gel pieces and peptides were reduced with 20 μl of 20 mM DTT in 50 mM ammonium bicarbonate buffer (pH 7.8) at 60° C. for 15 min. Cysteines were alkylated by adding 50 μl of the alkylation buffer (ammonium bicarbonate buffer with 50 mM Iodoacetamide) and incubated in the dark at room temperature for 1 h. Alkylation buffer was removed from tubes and replaced with 200 μl destaining buffer. Samples were incubated for 30 min at 37° C. with shaking, buffer removed, and washed again with destaining buffer. Gel pieces were dehydrated with 75 μl of acetonitrile and incubated at room temperature for 15 min. Acetonitrile was removed from tubes and shrunken gel pieces were left to dry for 15 min. Trypsin/lys-c (5 ng/μl in 25 μl of ammonium bicarbonate buffer) was added to gel pieces and incubated for 1 h at room temperature. An additional 25 μl of ammonium bicarbonate buffer was added to the tubes and incubated overnight at 37° C. Sample volume was brought to 125

μl with distilled water, and liquid containing trypsinized peptides was placed in a clean siliconized 0.5 ml tube.

Generating lrCaptureSeq Peptide Library for Mass Spec

Sqanti software was used on the Iso-seq output from retina samples to predict ORFs and amino acid sequences of isoforms. Amino acid sequences were trypsinized in silico using the python program trypsin with default settings. The proline rule was followed which did not cut lysine or arginine if it immediately preceded a proline.

Mass Spectrometry Analysis of Retinal Samples

2 μl aliquots of tryptic digests were analyzed by LC-MS/MS using a nanoAcquity UPLC system coupled to a Synapt® G2 HDMS™ mass spectrometer (Waters Corp, Milford, MA). Peptides were initially trapped on a 180 μm×20 mm Symmetry C18 column (at the 5 μl/min flow rate for 3 min in 99.9% water, 0.1% formic acid). Peptide separation was then performed on a 75 μm×150 mm column filled with the 1.7 μm C18 BEH resin (Waters) using the 6 to 30% acetonitrile gradient with 0.1% formic acid for 90 min at the flow rate of 0.3 μl/min at 35° C. Eluted peptides were sprayed into the ion source of Synapt® G2 using the 10 μm PicoTip® emitter (Waters) at the voltage of 3.0 kV.

Each sample was subjected to a data-independent analysis (HDMSE) using ion mobility workflow for simultaneous peptide quantitation and identification. For robust peak detection and alignment of individual peptides across all HDMSE runs we performed automatic alignment of ion chromatography peaks representing the same mass/retention time features using Progenesis QI software. To perform peptide assignment to the ion features, PLGS 2.5.1 (Waters) was used to generate searchable files that were submitted to the IdentityE search engine incorporated into Progenesis QI for Proteomics. For peptide identification we searched against the Iso-Seq custom database described above. To identify novel peptides, all peptides identified were cross-referenced with UniProtKb mouse database. Protein and peptide false discovery rates were determined using Protein and Peptide Prophet software (Scaffold 4.4) with a decoy database—reversed mouse UniProt 2016 database. Protein and peptide FDRs were less than 1% and 5%, respectively. To distinguish newly discovered peptides from known peptides containing posttranslational modifications, we conducted an additional database search using the most common protein modifications, including phosphorylation at S,T and Y; glutamylation at E; acetylation at K; methylation at D and E. No potential false identifications were found.

Western Blotting

Retinas from littermate WT and Crb1 mutant mice were briefly sonicated and vortexed in 400 μl of the lysis buffer containing 2% SDS in PBS plus protease inhibitor cocktail (cOmplete™; Roche). The lysates were spun at 20,000×g for 10 min at 22° C., supernatants collected and total protein concentration determined by the DC protein assay kit (Bio-Rad®). Using lysis buffer, the volumes were adjusted to normalize the lysates by total protein concentration before adding 4×SDS-PAGE buffer containing 400 mM DTT and heating the lysates for 10 min at 90° C. Equal volumes of the lysates, each containing 15 μg total protein, were subjected to SDS-PAGE and proteins were transferred to polyvinylidene fluoride membranes (Bio-Rad®). The membranes were blocked in the Odyssey™ blocking buffer (LiCor Bioscience) and incubated with the appropriate primary antibodies and Alexa® Fluor 680 or 800 (fluorescent dye) conjugated secondary antibodies (Invitrogen). Protein bands were imaged by the Odyssey™ CLx infrared imaging system (LiCor Bioscience).

To separate soluble and insoluble proteins, mouse retinas were briefly sonicated and hypotonically shocked in 300 μl of water on ice. The lysed retinal suspensions were spun at 20,000×g at 4° C. for 20 min, the resulting supernatant was collected and the pellet was rinsed once with water. The pellet and supernatant were reconstituted in a final volume of 400 μL lysis buffer, containing 2% SDS, 1×PBS, and protease inhibitor cocktail (cOmplete™; Roche) Equal volume aliquots of these lysates were used as described above for Western blotting.

Data Availability

Long-read sequencing data is available in the NCBI BioProject repository (accession number PRJNA547800). Table 2 specifies the sequence, genomic location, and read number for all isoforms of Crb1 within the lrCaptureSeq dataset.

Mass spectrometry proteomics data have been deposited at the ProteomeXchange Consortium via the PRIDE partner repository with the dataset identifier PXD017290 (DOI: 10.6019/PXD017290).

Code Availability

IsoPops code is available at kellycochran.github.io/IsoPops/index.html, licensed under the GNU General Public License v3.0.

TABLE 2 mRNA and ORF isoforms of Crb1 identified in this study.

| PBID | Transcript | Length | Prefix | FL_reads | Protein | ORFLength | ExonCount | Chr | % Abund |
|---|---|---|---|---|---|---|---|---|---|
| PB.338.150 | SEQ ID NO: 57 | 5764 | PB.338 | 36872 | SEQ ID NO:58 | 1003 | 7 | chr1 | 0.7217916 |
| PB.338.8 | SEQ ID NO: 59 | 6170 | PB.338 | 4869 | SEQ ID NO:60 | 1405 | 12 | chr1 | 0.0953136 |
| PB.338.10 | SEQ ID NO: 61 | 5894 | PB.338 | 3303 | SEQ ID NO:62 | 1344 | 11 | chr1 | 0.0646582 |
| PB.338.154 | SEQ ID NO: 63 | 5554 | PB.338 | 1093 | SEQ ID NO:64 | 574 | 7 | chr1 | 0.0213961 |
| PB.338.17 | SEQ ID NO: 65 | 4783 | PB.338 | 506 | SEQ ID NO:66 | 1033 | 8 | chr1 | 0.0099053 |
| PB.338.165 | SEQ ID NO: 67 | 6739 | PB.338 | 329 | SEQ ID NO:68 | 1314 | 10 | chr1 | 0.0064404 |
| PB.338.162 | SEQ ID NO: 69 | 5481 | PB.338 | 286 | SEQ ID NO:70 | 528 | 6 | chr1 | 0.0055986 |
| PB.338.174 | SEQ ID NO: 71 | 6950 | PB.338 | 255 | SEQ ID NO:72 | 1375 | 11 | chr1 | 0.0049918 |
| PB.338.156 | SEQ ID NO: 73 | 5434 | PB.338 | 234 | SEQ ID NO:74 | 844 | 6 | chr1 | 0.0045807 |
| PB.338.12 | SEQ ID NO: 75 | 5678 | PB.338 | 162 | SEQ ID NO:76 | 874 | 10 | chr1 | 0.0031712 |
| PB.338.194 | SEQ ID NO: 77 | 5277 | PB.338 | 158 | SEQ ID NO:78 | 520 | 8 | chr1 | 0.0030929 |
| PB.338.151 | SEQ ID NO: 79 | 5530 | PB.338 | 121 | SEQ ID NO:80 | 960 | 6 | chr1 | 0.0023686 |
| PB.338.160 | SEQ ID NO: 81 | 5692 | PB.338 | 101 | SEQ ID NO:82 | 576 | 7 | chr1 | 0.0019771 |

TABLE 2-continued mRNA and ORF isoforms of Crb1 identified in this study.

| PBID | Transcript | Length | Prefix | FL_reads | Protein | ORFLength | ExonCount | Chr | % Abund |
|---|---|---|---|---|---|---|---|---|---|
| PB.338.339 | SEQ ID NO: 83 | 5801 | PB.338 | 95 | SEQ ID NO:84 | 761 | 6 | chr1 | 0.0018597 |
| PB.338.163 | SEQ ID NO: 85 | 5547 | PB.338 | 95 | SEQ ID NO:86 | 420 | 8 | chr1 | 0.0018597 |

PBID: Iso-Seq isoform identifier.
Transcript: full sequence of isoform as determined by PacBio sequencing.
Lenth: length of sequence in base pairs.
Prefix: Iso-Seq gene identifier.
FL_reads: number of reads across all of our mouse experiments.
Protein: ORF predicted within transcript.
ORFLength: length of predicted protein in amino acids.
ExonCount: number of exons comprising transcript.
Chr: mouse chromosome location of gene.
% Abund: fraction of total gene reads for this isoform.

Results

Workflow for Cataloguing Isoforms Via Long-Read Capture Sequencing

To catalog the isoform diversity of CNS cell surface molecules, we first manually screened RNA-seq data from mouse retina and brain[38,39] to identify genes that showed substantial unannotated mRNA diversity. We focused on cell surface receptors of the epidermal growth factor (EGF), Immunoglobulin (Ig), and adhesion G-protein coupled receptor superfamilies, as these genes have many known roles in cell-cell recognition. For each gene screened (n=402), we assessed whether it was expressed during CNS development, and if so, whether the RNA-seq reads supported existence of unannotated exons or splice junctions (FIG. 1A). We found that ~15% of genes (60/402) showed strong evidence of multiple unannotated features. These genes were selected as candidates for long-read sequencing.

To comprehensively identify these genes' transcripts, we developed a method to improve PacBio sequencing depth for large (>4 kb) and moderately expressed cDNAs, such as the ones on our candidate gene list. We term this strategy long-read capture sequencing (lrCaptureSeq), because we adapted prior CaptureSeq approaches[31,32,40] to enable characterization of protein-coding cDNAs with the long-read PacBio platform. In lrCaptureSeq (FIG. 1B,C), biotinylated probes are designed to tile known exons without crossing splice junctions, so as to avoid biasing the pool of captured transcripts towards particular isoforms. These probes are used to pull down cDNAs from libraries that have been size-selected to filter truncated cDNAs. In pilot experiments we found that size selection was essential to obtaining full-length reads (FIG. 9A), because shorter fragments tend to dominate the sequencing output[15].

Figure 9:
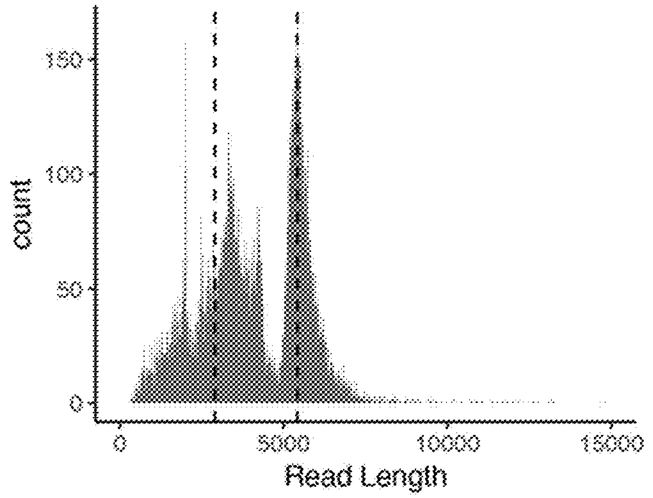
FIG. 9 illustrates PacBio sequencing of captured cDNAs. (A) Histogram of PacBio read size distribution for a pilot lrCaptureSeq experiment, in which the second size selection after PCR amplification was not performed (see workflow, FIG. 1B. Profile demonstrates that this size selection is necessary for enrichment of long transcripts. Dotted line represents interquartile range. FLNC, full-length non-chimeric reads called by Iso-Seq software. (B) Percentage of on target reads per experiment, calculated as the number of high quality (HQ) reads corresponding to our targeted genes vs. all other reads. HQ reads called by Iso-Seq software. (C) Sequencing statistics from each individual lrCaptureSeq experiment and the combined dataset. (D,E) Validation of lrCaptureSeq isoform 5' ends by CAGE. Three independent CAGE-seq replicates from adult mouse retina were mapped to the adult mouse retina lrCaptureSeq isoforms. D: Box and whiskers plot showing CAGE read coverage at the first exon of lrCaptureSeq isoforms. Coverage is extensive, supporting the accuracy of lrCaptureSeq 5' ends. Box represents IQR, horizontal line represents median, whiskers equal to 1.5*IQR. E: Position along 5'-3' axis of CAGE reads that mapped to lrCaptureSeq isoforms. CAGE coverage was exclusive to the 5' end of transcripts.
Figure 9:
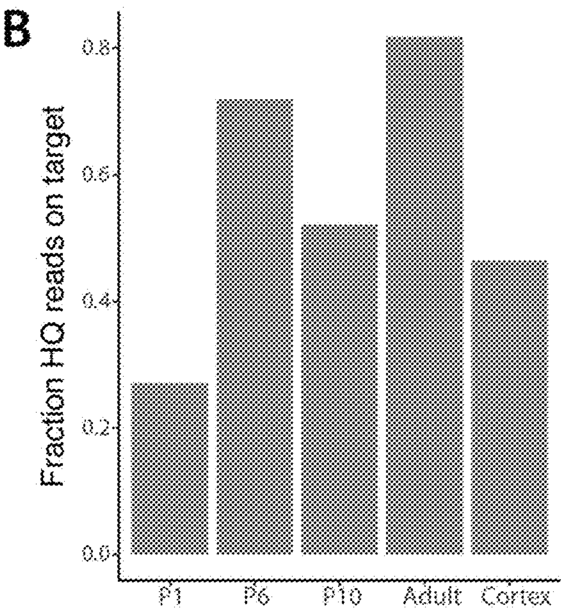
Figure 9:
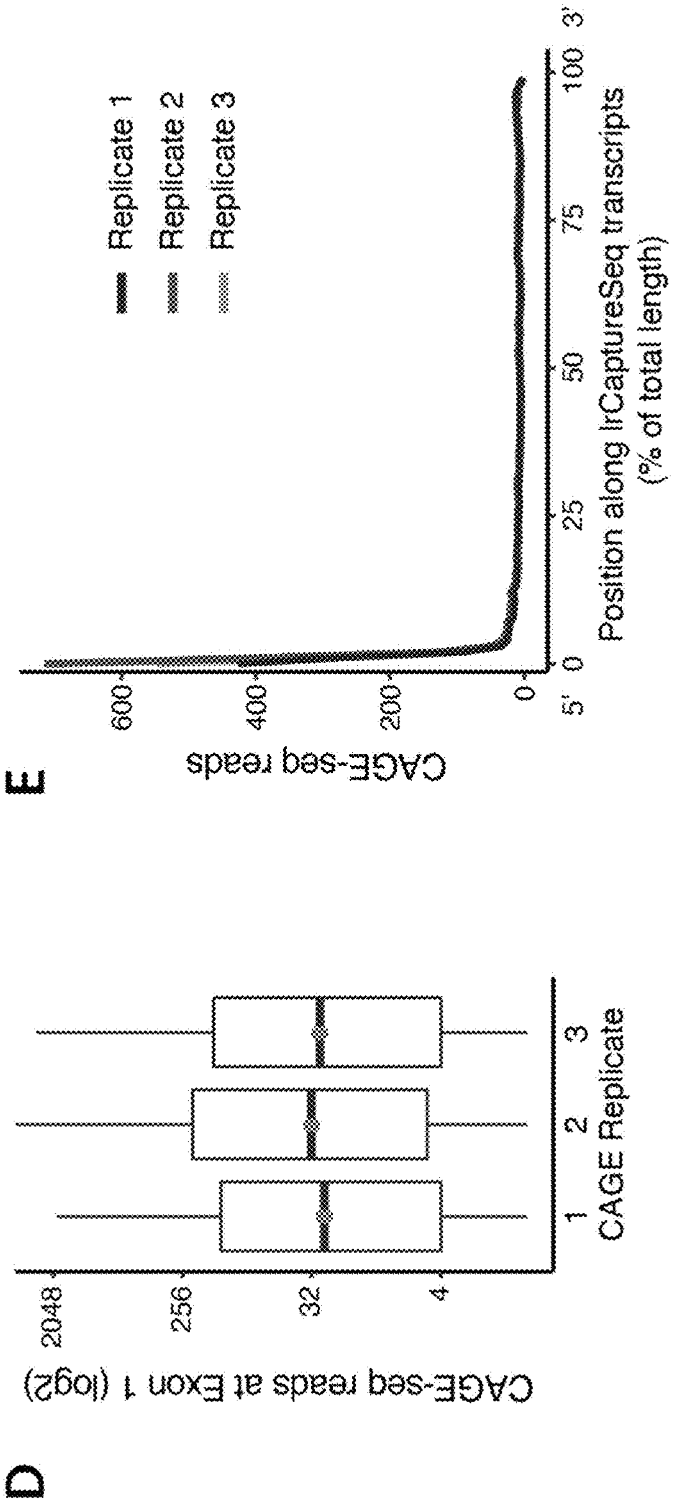

To implement lrCaptureSeq, we first filtered the initial list of 60 candidates down to 30 that were predicted to encode cDNAs of similar length (4-8 kb). The final target list included genes involved in axon guidance, synaptogenesis, and neuron-glial interactions; it also included the retinal disease gene Crb1, which is implicated in inherited photoreceptor degeneration. Some of the target genes were known to generate many isoforms (Nrxn1, Nrxn3), but in most cases isoform diversity had not previously been characterized. When captured cDNAs were sequenced on the PacBio platform, ~132,000 full-length reads were generated per experiment (FIG. 9C). These reads were strongly enriched for the targeted genes (FIG. 9B), and the vast majority of reads were within the targeted length range (FIG. 1C). Thus, lrCaptureSeq can achieve deep full-length coverage of larger cDNAs that are underrepresented in other long-read datasets.

A Comprehensive Isoform Catalog Generated by lrCaptureSeq

To catalog isoforms for all 30 genes across development and across CNS regions, we performed lrCaptureSeq at a variety of timepoints in mouse retina and brain (FIG. 1C; FIG. 9C). The number of isoforms, and reads comprising each, were determined using PacBio Iso-Seq software, together with custom software we developed for the analysis of isoform populations (IsoPops; github.com/kellycochran/IsoPops). After this processing pipeline, the lrCaptureSeq catalog contained 4,116 isoforms of the 30 targeted genes (FIG. 2A,B; Table 2;)—approximately one order of magnitude greater than the number of isoforms currently annotated for this gene set in public databases (FIG. 2B). It was also far higher than the number of isoforms predicted by popular short-read transcriptome assembly software (FIG. 10A). Only 9% of lrCaptureSeq isoforms appeared in any of the databases we examined, suggesting most of them are novel.

To ensure that these novel isoforms are real, we used independent datasets to validate their transcription start sites and exon junctions. Start sites were identified using cap analysis of gene expression (CAGE), a short-read method for identifying sequences associated with the 5' cap[41]. CAGE-seq reads from adult mouse retina[42] corroborated 97.5% of transcription start sites identified by lrCaptureSeq (1051/1078 adult retina isoforms had CAGE-seq coverage at their 5' end; FIG. 9D). Moreover, CAGE-seq reads mapped selectively to 5' ends of lrCaptureSeq isoforms (FIG. 9D,E), further supporting the accuracy of our transcription start site annotations. To validate splice junctions we first verified that the vast majority (98.9%) of lrCaptureSeq exon junctions occurred at canonical splice sites (n=80,590 junctions). Next, we tested for the existence of lrCaptureSeq exon junctions in short-read datasets from retina and brain[38,39]. The vast majority (98.1%) of lrCaptureSeq junctions (n 79,020) were corroborated by these short-read datasets, providing independent confirmation of their validity. This included complete junction coverage for 71% of lrCaptureSeq isoforms (n=2,925). The unconfirmed junctions were likely absent from the RNA-seq data due to low expression levels, since the isoforms that did not show complete coverage were significantly less abundant (FIG. 10B). Consistent with this interpretation, unconfirmed junctions could be detected by sequencing of RT-PCR products, suggesting that they were simply below RNA-seq detection threshold (n 9/12 absent RNA-seq junctions in Megf11 gene were detected by RT-PCR). Together, these analyses strongly support the validity of our lrCaptureSeq isoform catalog.

Efficient Isoform Detection by lrCaptureSeq

To probe the accuracy and sensitivity of isoform detection, we compared our lrCaptureSeq data to previous long-read sequencing studies cataloguing isoform diversity of the Nrxn1 and Nrxn3 genes. In these studies, PCR was used to generate isoform libraries of the α and β classes of Nrxn transcripts, which were then characterized using PacBio sequencing[15,16]. The total number of Nrxn1 and Nrxn3 isoforms we identified was similar in scale to the previous studies (FIG. 2A), despite radically different library preparation methods and bioinformatic workflows. Patterns of exon usage in alternative splice sites (AS)1-AS4 were also similar (data not shown). For example, a deterministic AS4 splicing event identified in the previous work, wherein Nrxn3 exon 24 always splices to exon 25a, was confirmed in our data (n=76 exon 24-containing isoforms, all spliced to exon 25). These findings suggest that our Nrxn 1 and 3 isoform catalog largely matches those generated by past studies. Nevertheless, we were able to find new features of the neurexin genes not noted in the previous catalogs. Because our method was not biased by PCR primer placement, we found isoforms that did not contain canonical α or β transcript start/termination sites. For example, 64% of our Nrxn3α reads contained a distinct first exon, upstream of the annotated a transcriptional start site that lengthens the 5' UTR. Further, we identified 7 novel transcription termination sites, used by 16 different Nrxn3α isoforms, that truncate the mRNA upstream of the transmembrane domain (data not shown). All 7 of these new sites were corroborated with junction coverage from RNA-seq data. Together, these findings demonstrate the utility of lrCaptureSeq in recovering isoform diversity with high efficiency.

Many Isoforms Contribute to Overall Gene Expression

Given the large number of isoforms identified in our lrCaptureSeq dataset, we next sought to learn the extent to which isoform diversity is positioned to impact gene function. For diversity to be functionally significant, two conditions must be met: 1) multiple isoforms of individual genes should be expressed at meaningful levels; and 2) the sequences of the isoforms must differ enough to encode functional differences. To investigate isoform expression levels, we assessed how each gene's overall expression was distributed across its isoform portfolio (FIG. 2C,E; FIG. 10D). Some genes—for example, Egflam and Crb1—were dominated by a small number of isoforms. However, for the genes with the largest number of isoforms, expression levels were distributed far more equitably across isoforms (FIG. 2C,E). Using the Shannon diversity index[43], we rank-ordered genes based on the diversity of their expressed mRNA species. Nrnx3, which is known to generate extensive diversity, was the top-ranked gene. However, several other genes of the latrophilin and protein tyrosine phosphatase receptor (PTPR) families scored nearly as high (FIG. 2D). Thus, Nrxn3 is far from unique in expressing a large number of isoforms. We conclude that, for the genes in our dataset, much of the isoform diversity is expressed at appreciable levels.

Predicted Functional Diversity of lrCaptureSeq Isoforms

We next investigated the extent of sequence differences across the isoforms of each gene in our dataset. Most of the 30 genes encoded isoforms that varied widely in length and number of exons (FIG. 10E,F), suggesting the potential for great functional diversity. To identify isoforms that are most likely to diverge functionally, unsupervised clustering methods were used to group isoforms based on their sequence similarity (FIG. 2F,G; FIG. 10G). For most genes, isoforms clustered into distinct groups of related isoforms that made similar choices among alternative mRNA elements (FIG. 2F,G). Thus, major sequence differences exist within the isoform portfolio of individual genes, which can be traced to the inclusion of specific exon sequences by families of related isoforms.

Figure 11:
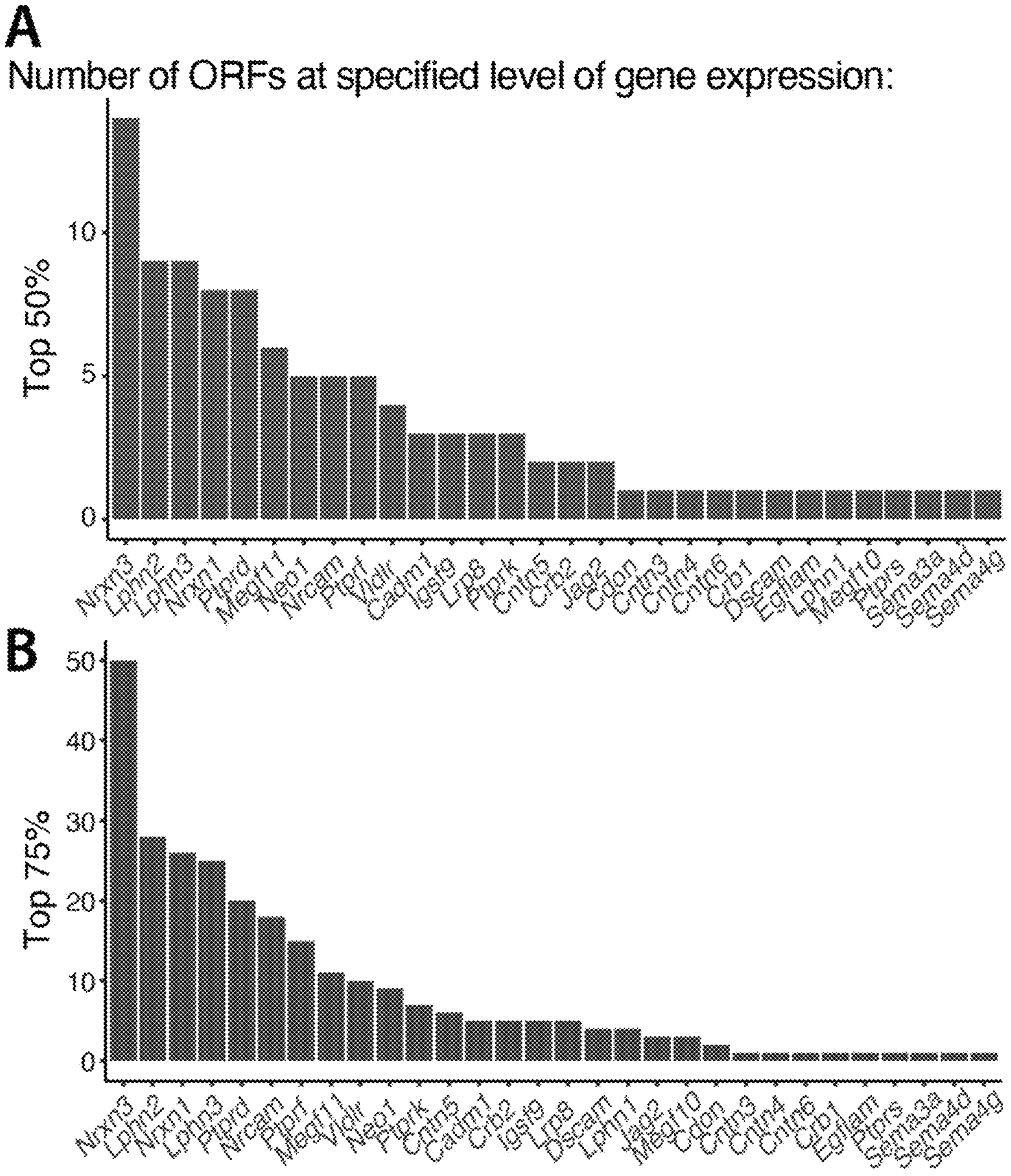
FIG. 11 shows coding and non-coding isoform variations. (A,B) Plots depicting the number of unique predicted ORFs that account for the top 50% (A) or 75% (B) of each gene's total read count (see FIG. 3B). (C) Intron retention is a major source of non-protein-coding isoform diversity, as exemplified here by Vldlr gene. The top 20 most abundant Vldlr isoforms are illustrated. Thick black bars, exons. Note extensive, combinatorial intron retention. Asterisks, introns that were detected in lrCaptureSeq isoforms (i.e. within polyadenylated transcripts). Intron retention creates a high degree of transcript diversity that does not translate to high ORF diversity. All of the retained introns introduce premature stop codons. (D) Non-coding transcript diversity can arise from variations in the 5' UTR region of the gene, as exemplified here by Cntn4. Figure shows 5' end of top 20 most abundant Cntn4 isoforms. Note alternative transcriptional start sites and differential exon usage within 5' UTR. (E) The number of unique trypsin peptide products encoded by our 30 genes in the UniProtKb database (right bar), compared to the number of predicted trypsin peptide products that exist within the lrCaptureSeq dataset (left bar).
Figure 11:
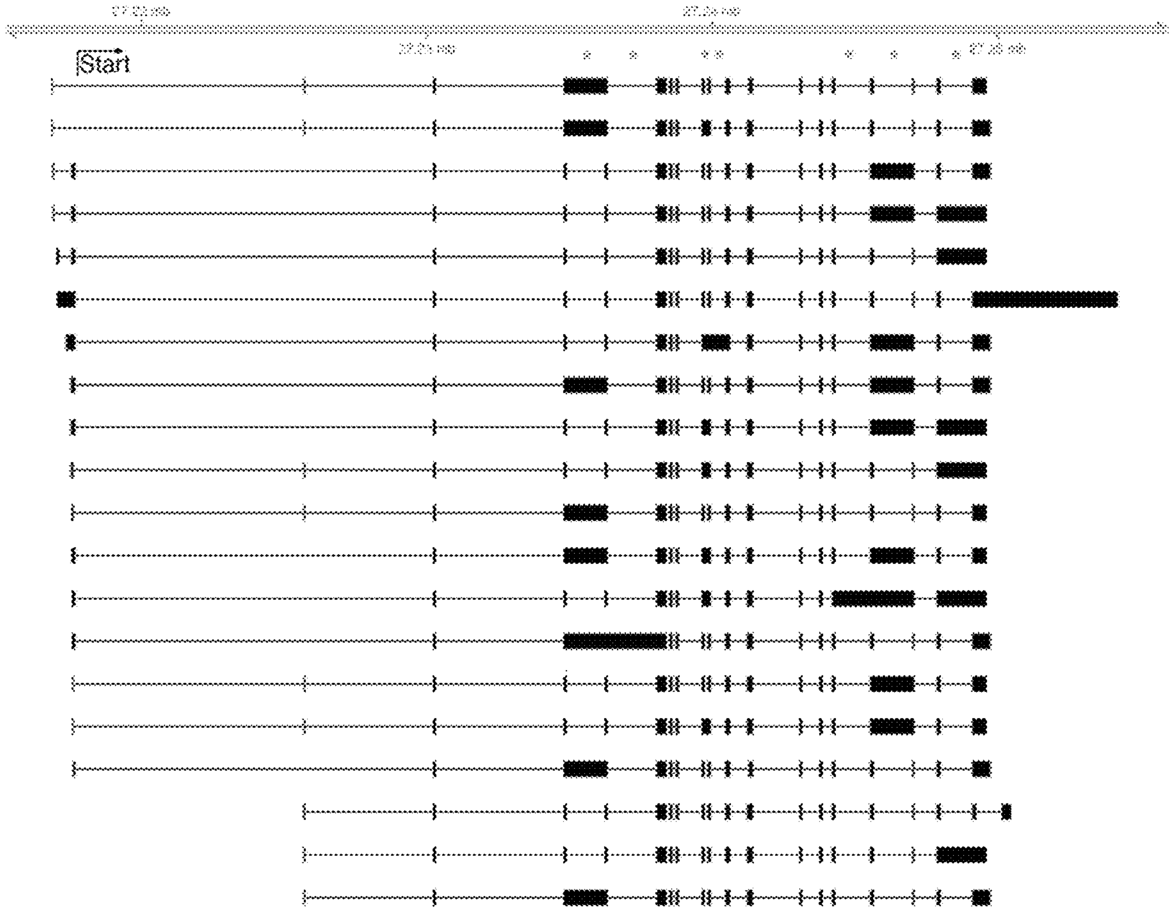
Figure 11:
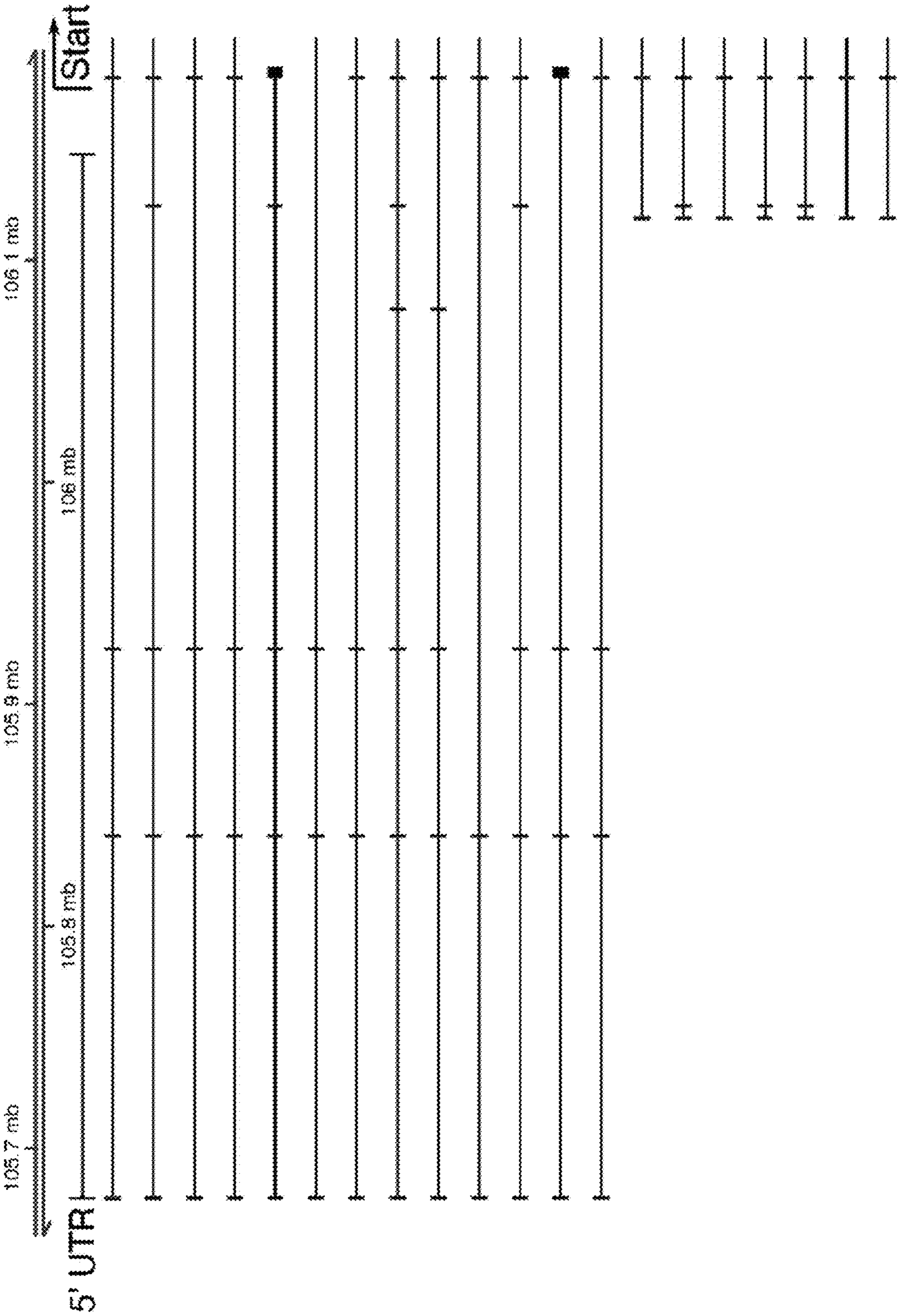
Figure 11:
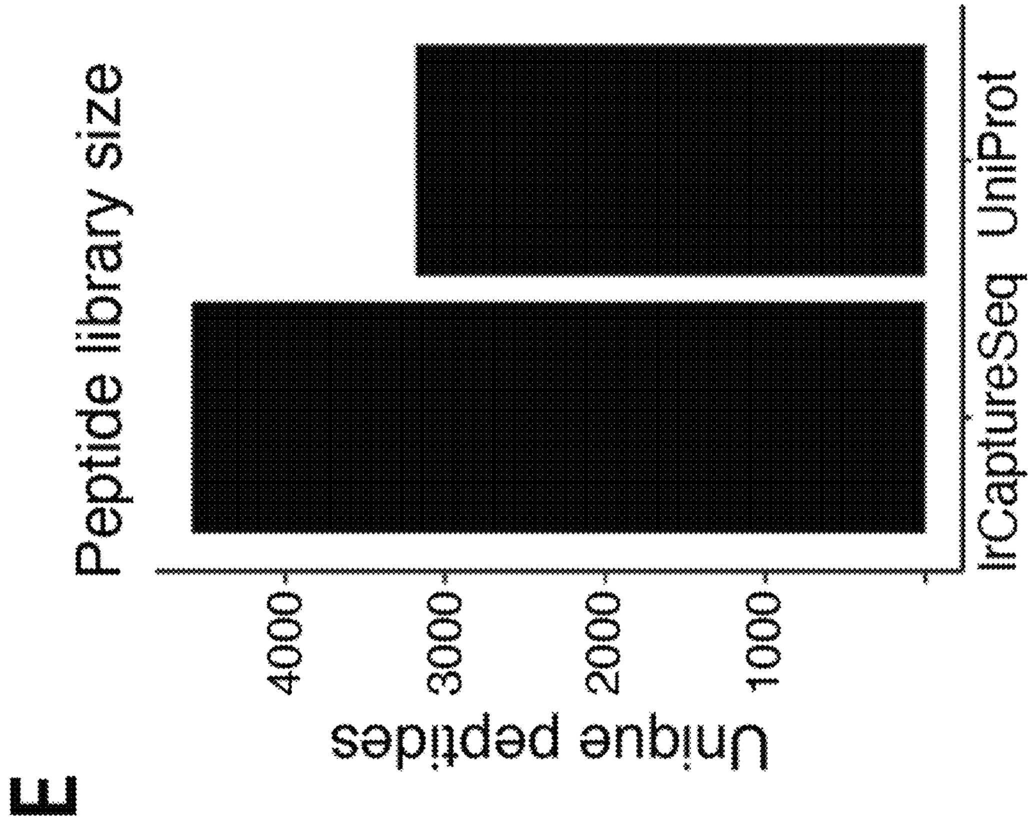

To learn whether these sequence differences might diversify protein output, we analyzed predicted open reading frames (ORFs; Table 2). Over half of the 4,116 isoforms in our dataset were found to contain unique ORFs (2,247; 54.6%). A small subset of genes expressed great mRNA diversity but no equivalent ORF diversity (FIG. 3A); this was largely due to variations in 5' UTRs or systematic intron retention (FIG. 11C,D). Overall, however, there was a strong correlation between the number of isoforms and the number of predicted ORFs (FIG. 3A). The amount of expressed ORF diversity varied by gene; but similar to mRNAs, a large amount of this predicted protein diversity was expressed at appreciable levels (FIG. 3B-D; FIG. 11A,B). Remarkably, the genes with the most ORF diversity tended to encode a specific type of cell-surface protein: The top genes by Shannon diversity index all encode trans-synaptic adhesion molecules (FIG. 3C). This result indicates that a major function of mRNA diversity is the generation of protein variants that are positioned to influence formation or stability of synaptic connections.

Figure 4:
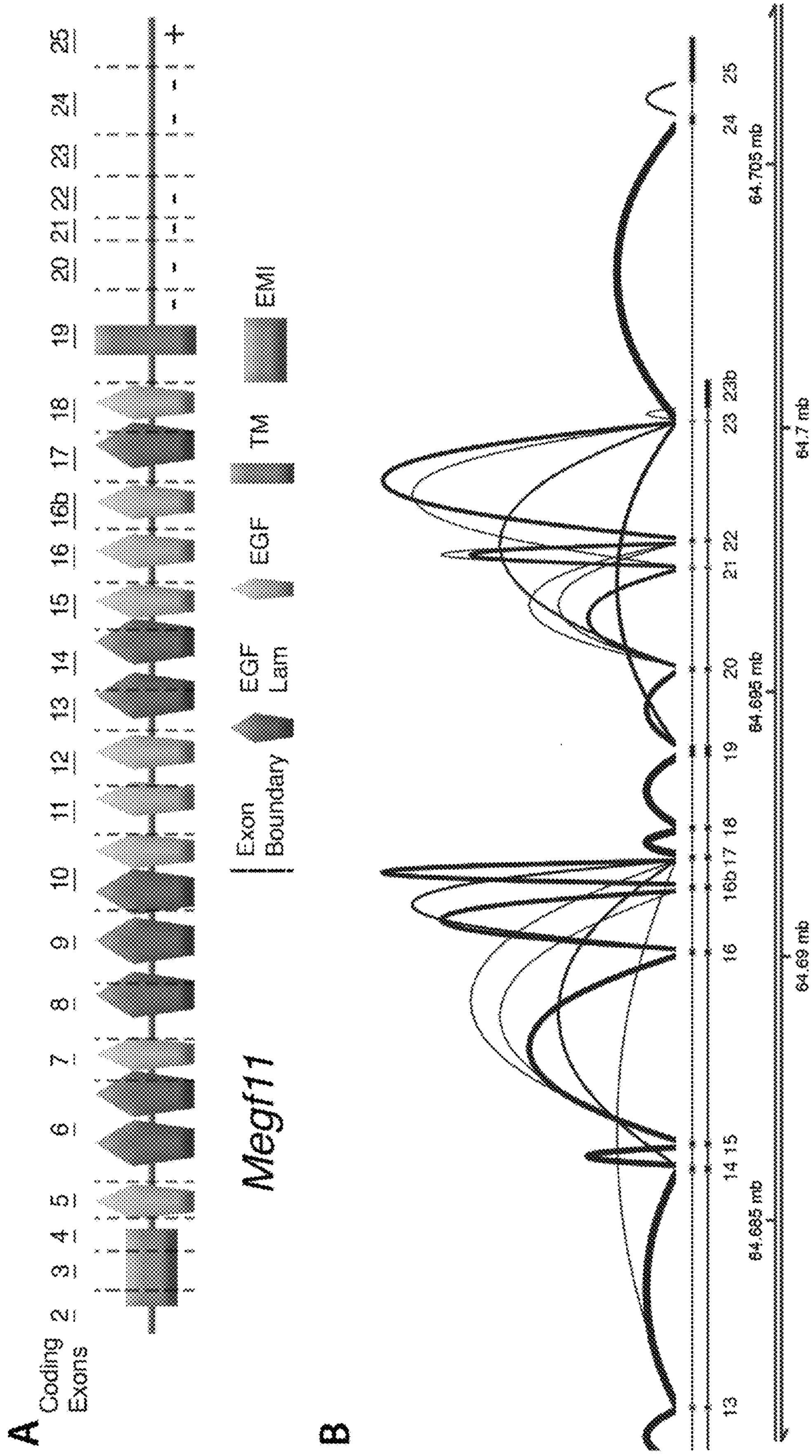
FIG. 4 demonstrates that the isoform diversity of Megf11 driven by modular alternative splicing. (A) Schematic of MEGF11 protein, showing how domain features correspond to exon boundaries. Most extracellular domain exons encode individual EGF or EGF-Laminin (Lam) repeats. Splicing that truncates EGF-Lam domains (e.g. skipping of exon 14) is predicted to leave behind an intact EGF domain, preserving modularity. Intracellular domain exons encoding canonical signaling motifs are noted: +, immunoreceptor tyrosine-based activation motif ($YxxL/Ix_{(6-8)}YxxL/I$); –, immunoreceptor tyrosine-based inhibitory motif (S/I/V/LxYxxI/V/L). TM, transmembrane domain; EMI, Emilin-homology domain. (B) Megf11 sashimi plot generated from combined PacBio dataset. The most variable exon clusters (13-17 and 19-23) are shown. Exons in these clusters can splice with any downstream exon within the cluster. Width of line corresponds to frequency of splicing event in isoform database. (C) Exon usage correlations across Megf11 isoforms. High Pearson correlation values (red) are seen at short range among exons that show minimal splicing, e.g. 1-8 and 17-19. Long range correlations are largely absent, suggesting that most splicing is stochastic. Strong long-range negative correlations are only observed in the trivial case of exons downstream from an alternative transcription stop site (asterisks). (D) Predicted protein structures of the 10 most abundant Megf11 isoforms. Alternative splicing varies number and identity of EGF and EGF-Lam domains on the extracellular portion of the protein, and produces 5 distinct cytoplasmic domains. Isoform 8 is the result of an alternative transcriptional stop site (C, exon 8b) and is predicted to encode a secreted isoform. *splicing from exon 19 to 20 results in a frameshift and early stop codon. ** Retention of intron 24 results in a frameshift and early stop codon. (E) BaseScope in situ hybridization of P10 mouse retinal cross sections, using probes targeting indicated splice junctions (red). A constitutive junction (2-3, top left) shows full Megf11 expression pattern, in four cell types: ON and OFF starburst amacrine cells (blue arrows), horizontal cells (red arrow), and an unidentified amacrine cell (black arrow). Calbindin (green) marks starburst and horizontal cells. Staining intensity for each junctional probe is consistent with junction frequency in sequencing data (see Sashimi plot, B). All junctions are expressed by all individual cells of the starburst and horizontal populations. Scale bar=10 μm.
Figure 4:
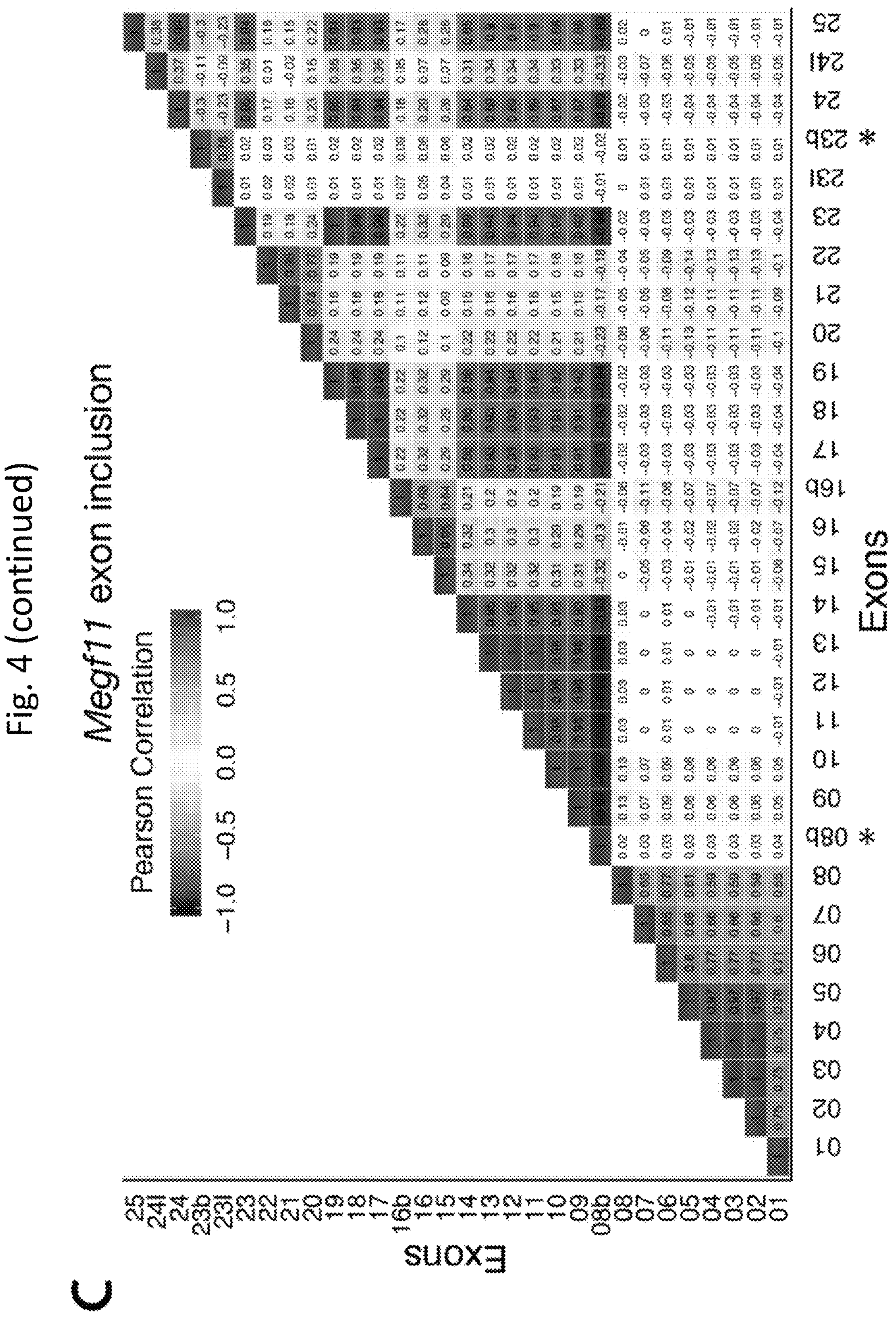
Figure 4:
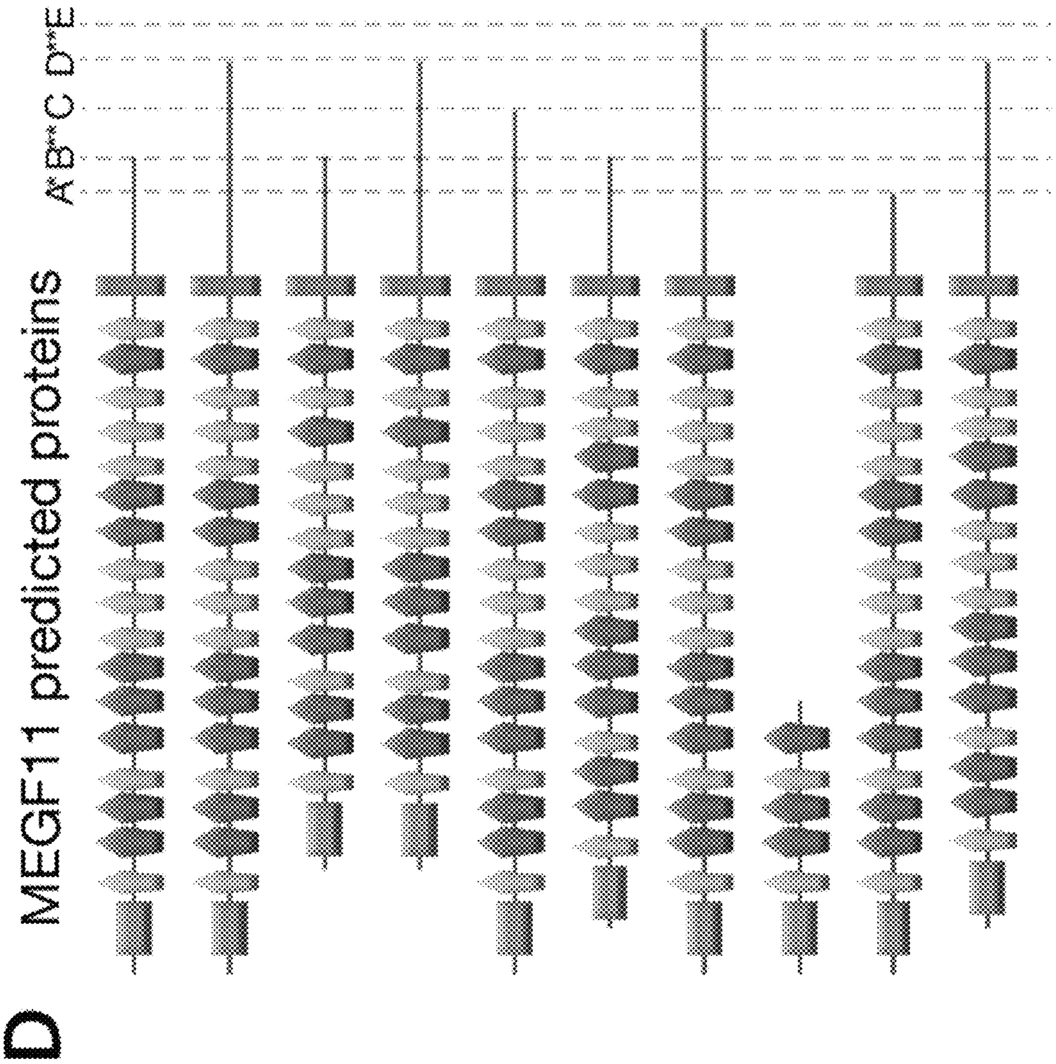
Figure 4:
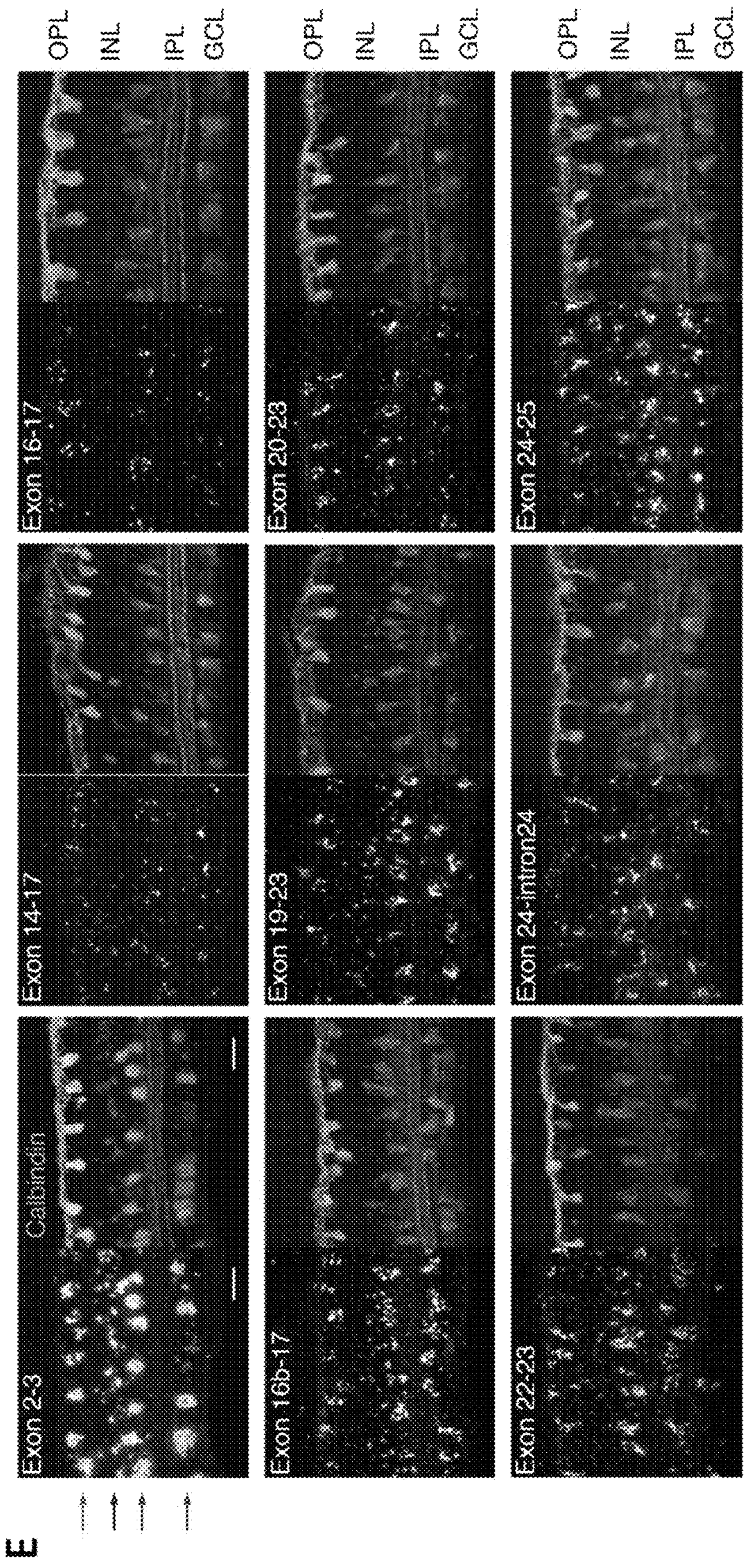
Figure 12:
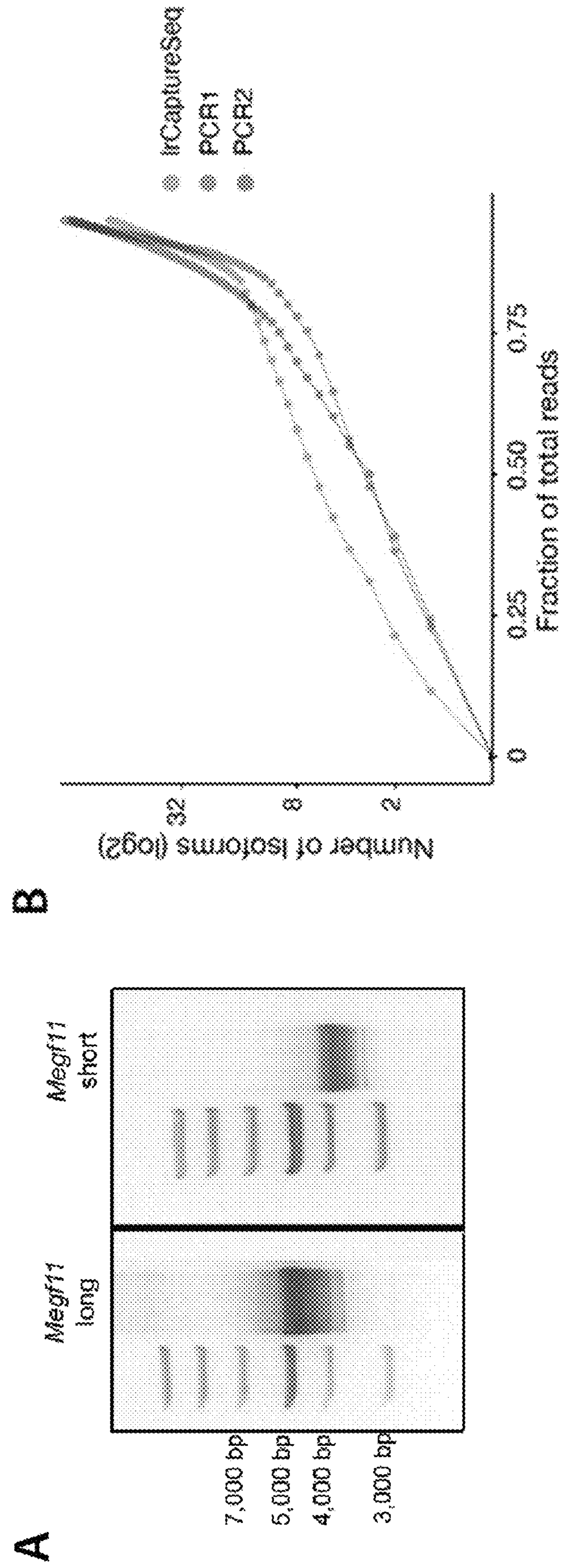
FIG. 12 shows the Megf11 isoform diversity uncovered by PacBio sequencing. (A) DNA electrophoresis gel image of Megl1 RT-PCR products. Primers were designed to amplify two different Megf11 variants (denoted long and short) by placing primers in exon 25 or alternative exon 23, respectively. PCR was performed on retinal (long) or cortex (short) cDNA. The size spread of RT-PCR products indicates that numerous Megf11 isoforms of different sizes can be readily amplified. (B) Lorenz plot profiles of Megf11 isoform abundance from lrCaptureSeq and PCR datasets. All datasets suggest that many isoforms contribute to overall Megf11 expression. The rightward shift of the PCR dataset curves suggests overrepresentation of the most abundant isoforms, likely due to PCR-induced bias. (C) Transcript maps depicting the long and short forms of Megf11 (top) and corresponding exon coverage and sashimi plots from 3 different PacBio sequencing datasets. PCR1 dataset was generated by sequencing Megf11 long form PCR products, while PCR2 dataset was generated by sequencing short form PCR products. These are compared to the Megf11 reads from the 30-gene lrCaptureSeq experiment. All three experiments reveal extensive alternative splicing of Megf11 transcripts. Sashimi plots show remarkable similarity between the different datasets.
Figure 12:
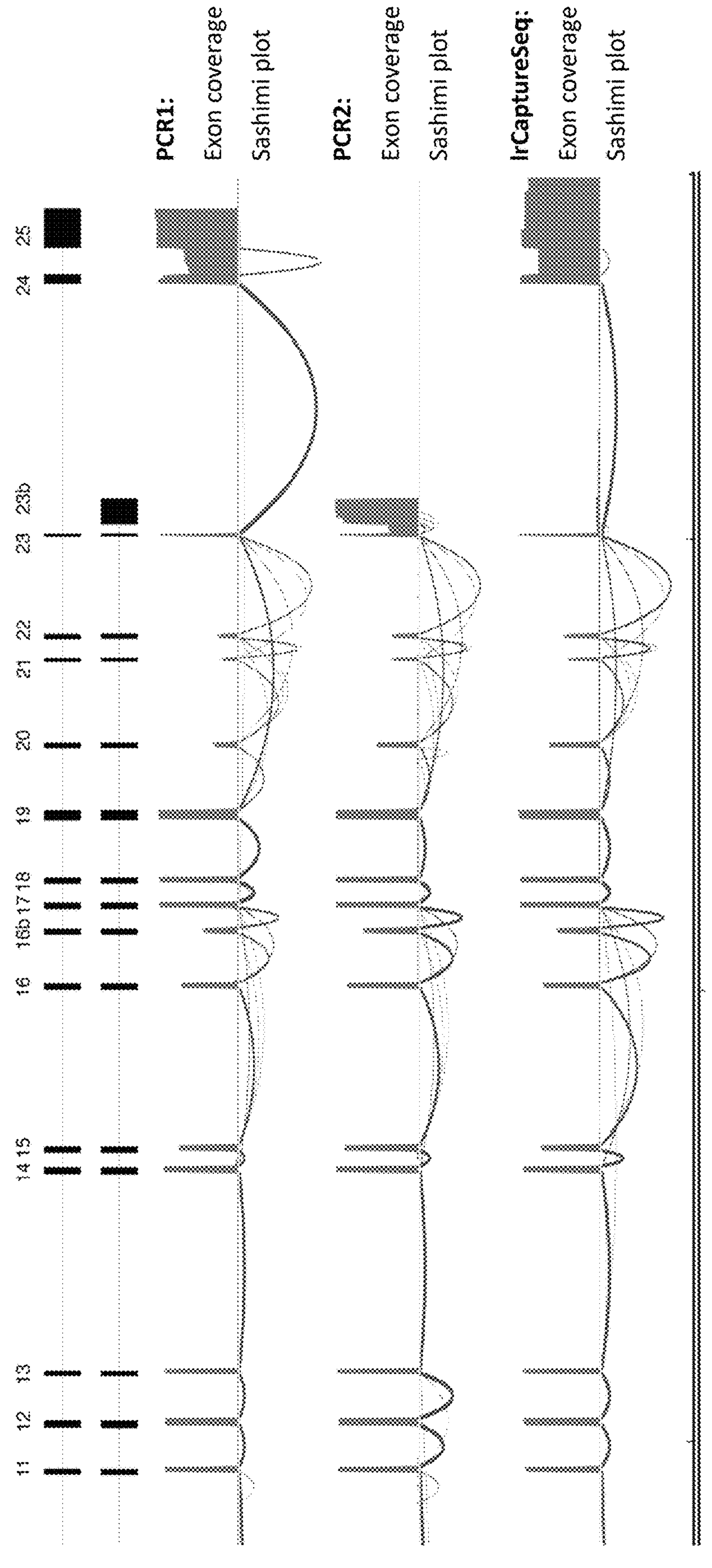

To determine whether mRNA diversity has a significant impact on protein sequences, we studied the predicted protein output of individual genes. In many cases, predicted proteins varied substantially in their inclusion of well-characterized features or functional domains. This phenomenon is exemplified by the Megf11 gene, which encodes a transmembrane EGF repeat protein implicated in cell-cell recognition during retinal development[44]. Megf11 is subject to extensive alternative splicing: Out of 26 protein-coding exons, 21 are alternatively spliced (81%). In fact, we documented only 10 constitutive splice junctions within the 234 Megf11 isoforms identified in three independent long-read sequencing experiments (FIG. 4A,B; FIG. 12). Examination of predicted proteins revealed a potential reason for such extensive splicing: Most of the EGF repeats comprising the extracellular domain are encoded by individual exons, such that alternative splicing causes them to be deployed in a modular fashion (FIG. 4A-D). Intracellular domain exons also showed potential for modularity in the use of ITAM or ITIM signaling motifs (FIG. 4A-D), similar to the situation in its *Drosophila* homolog Draper[45]. As a result of this modular organization, predicted MEGF11 proteins showed substantial variability in the number and/or identity of included EGF repeats (FIG. 4D). The most variable EGF repeats were encoded by exons 14-16b (FIG. 4B); however, most of the EGF repeats were subject to alternative usage. Using BaseScope™ in situ hybridization[46,47], we confirmed that each of the most variable exon junctions are expressed by retinal neurons in vivo (FIG. 4E). Remarkably, individual Megf11-expressing cells were found to use all of the exon junctions we tested, suggesting that extensive Megf11 isoform diversity is present even within individual neurons (FIG. 4E). Therefore, similar to insect Dscam1, Megf11 uses alternative splicing of modular extracellular domain features to create a large family of isoforms encoding distinct cell-surface molecules. Together with our analysis of the full lrCaptureSeq dataset, these findings strongly suggest that isoform diversity serves to diversify the neuronal cell-surface proteome in vivo.

Cell-Surface Proteins Predicted by lrCaptureSeq are Expressed in Developing Retina To determine whether novel lrCaptureSeq isoforms are translated into proteins, we performed mass spectrometry on cell-surface protein samples obtained from developing retina. Cell-surface proteins were captured using cell-impermeant reagents that either cleaved or biotinylated extracellular epitopes (FIG. 3E,F). To learn whether any of the captured peptides came from novel protein isoforms, we generated a database of possible trypsin peptide products derived from the isoforms within the lrCaptureSeq catalog. This was essential because protein identification requires comparison of raw mass spectrometry data to a reference peptide database. On generation of this new predicted peptide database, we found that it contained ~25% more putative peptides for our 30 genes than the UniProt Mouse Reference Database typically used in most proteomics experiments (FIG. 11E). The extra putative peptides represent novel protein regions predicted by lrCaptureSeq.

Using this new database as a reference, we found 686 total peptides corresponding to 28 of the genes. 35 of these peptides were absent from the UniProt standard reference, and were present only in our new reference database (FIG. 3G). This fraction represents novel peptides, predicted from our lrCaptureSeq isoform catalog, that would have gone undetected in a typical mass spectrometry experiment. Novel peptides were found for 14 of our 30 genes, validating novel exonic sequences, splice junctions, and splice acceptor sites (data not shown). These findings demonstrate that at least some of the predicted proteins are expressed on the surface of retinal cells in vivo. Thus, the mRNA diversity we describe here contributes to the diversity of the retinal cell surface proteome.

The Most Abundant Transcript in the lrCaptureSeq Database is a Novel Isoform of Crb1

Figure 5:
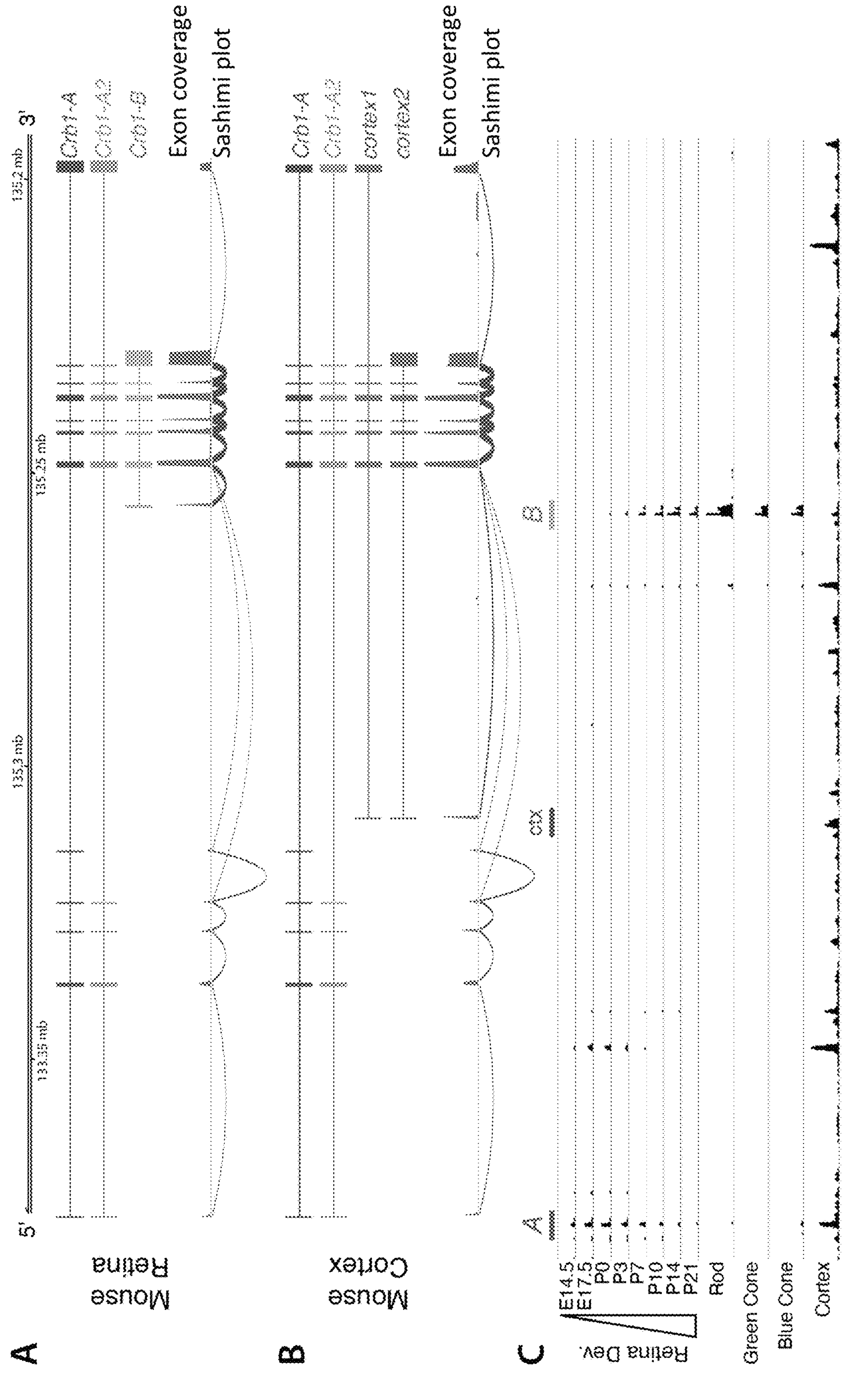
FIG. 5 demonstrates that Crb1-B is the most abundant Crb1 isoform in mouse and human retina. (A,B) Transcript maps of most abundant Crb1 isoforms from mouse retina (A) and cortex (B). A is the canonical isoform; A2 is a minor splice variant of A. These isoforms are shared between retina and cortex, whereas Cortex 1, Cortex 2, and Crb1-B are tissue-specific. Corresponding exon coverage and sashimi plots were generated from lrCaptureSeq dataset. Note prevalence of reads associated with Crb1-B isoform (A). (C) Assay for chromatin accessibility (ATAC-seq; GSE102092, GSE83312) identifies likely promoters of Crb1-A and -B isoforms. Bars indicate location of putative A and B promoters. Maps in A-C are aligned with each other. Crb1-A promoter is more open during development, but stays accessible in mature retina. Crb1-B promoter is open and presumed active in mature rods and both types of cones. DNase I hypersensitivity data from ENCODE project reveals distinct chromatin environment in frontal cortex, consistent with expression of A isoform, as well as shorter cortex isoforms (cortex 1 and 2; bar at top labeled "ctx"). (D) Retinal expression of top 3 Crb1 isoforms across mouse development, quantified from PacBio dataset. A isoforms predominate at P1 but Crb1-B becomes most abundant by P6. Data were normalized to total Crb1 read counts at each timepoint (P1=923 reads, P6=6,127 reads, P10=14,007 reads, Adult=10,975 reads). (E) Transcript maps of most abundant human retinal CRB1 isoforms, identified by lrCaptureSeq. A and B isoforms are highly homologous to mouse (A). CRB1-C encodes a putative secreted form of the protein; it was also identified in the mouse dataset but its relative abundance in mouse was much lower than A and B. Note that Crb1-A2 was not detected in the human dataset. Exon coverage and sashimi plots were generated from lrCaptureSeq data. (F) ATAC-seq (GSE99287) of human peripheral (per.) and macular (mac.) retina show open regulatory sites corresponding to putative promoters for CRB1-A (bar labeled "A") and CRB1-B (bar labeled "B"). Two biological replicates are shown. Maps in E,F are aligned with each other. (G) Expression of top 3 human CRB1 isoforms, quantified from adult human retina lrCaptureSeq dataset. (H,I) Quantification of top 3 mouse (H) or human (I) CRB1 isoforms using short-read RNA-seq data. Mouse dataset (GSE101986) confirms developmental regulation of each isoform observed in PacBio data (D). Human dataset (GSE94437) confirms CRB1-B is dominant isoform in adult retina. Lines (I) show measurements derived from same donor. Statistics (I): One-way ANOVA with Tukey's post-hoc comparison. **$P<1\times10^{-7}$. *$P=1.6\times10^{-6}$ (top); $P=6.6\times10^{-6}$ (bottom). Error bars, 95% confidence intervals (H) or S.D. (I).
Figure 5:
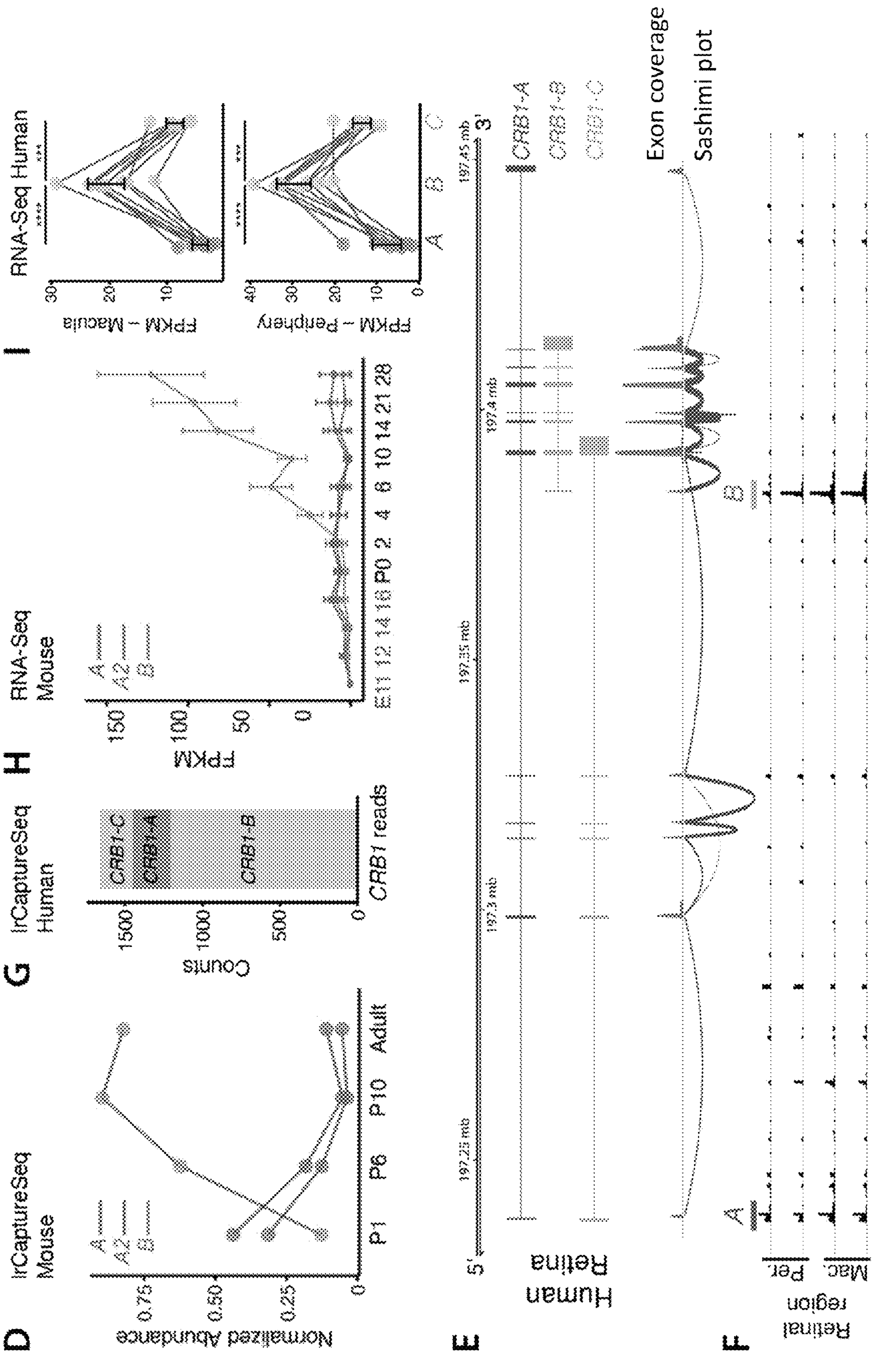
Figure 13:
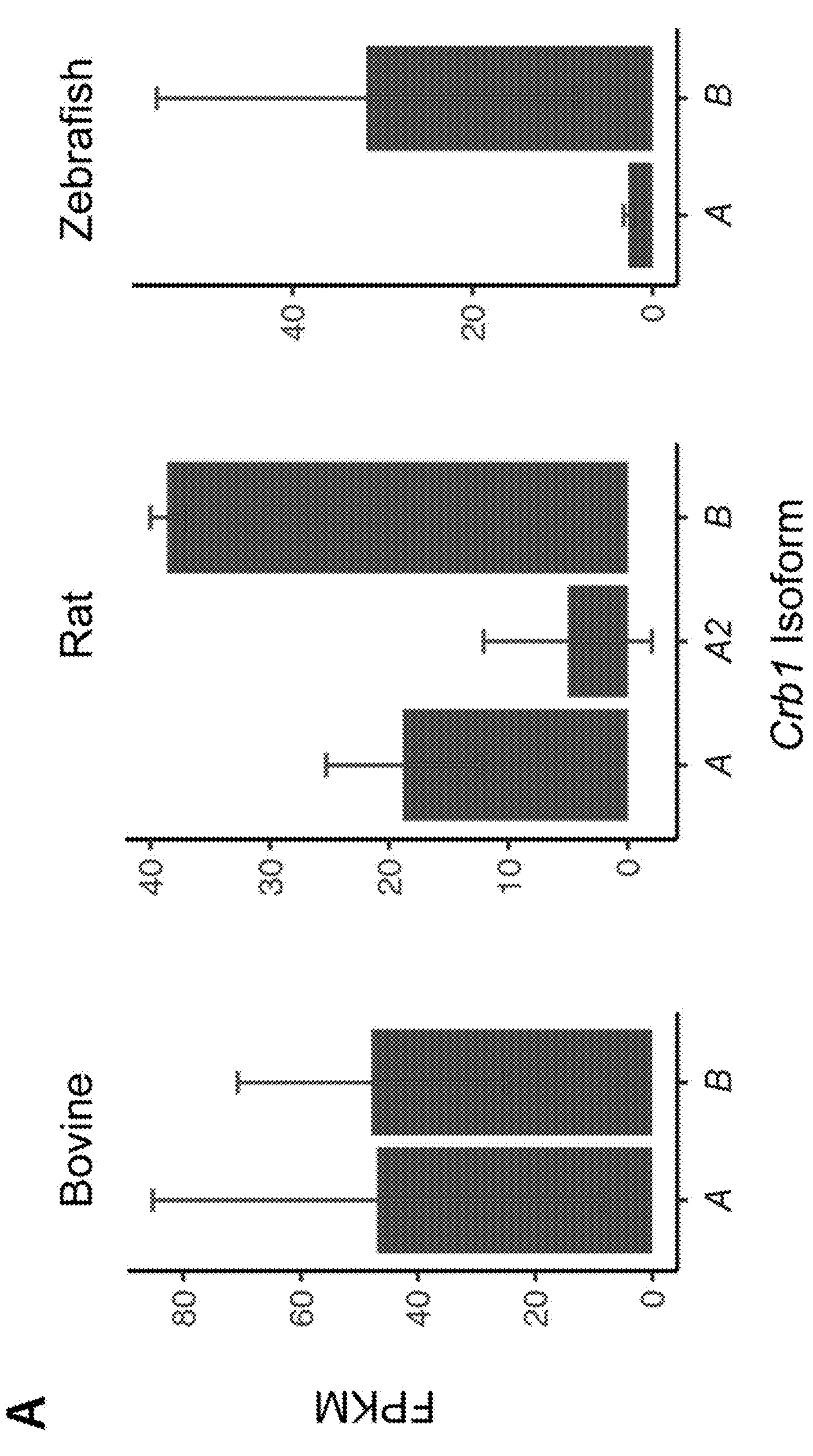
FIG. 13 demonstrates that the Crb1-B isoform is expressed across a variety of vertebrate species. (A) Quantification of Crb1 isoforms in bovine, rat, and zebrafish retina, based on publicly available RNA-seq data (bovine, GES59911; rat, GSE84932; zebrafish, GSE101544). Crb1-B is at least as abundant as Crb1-A in all species, and is more abundant in rat and zebrafish. Crb1-A2 was not detectable in bovine or zebrafish retina. Error bars represent 95% confidence intervals. (B) Quantitative (q) RT-PCR analysis of Crb1 isoforms in mouse retina confirm expression patterns identified using PacBio and short-read RNA-seq (FIG. 5). Crb1-A is most abundant at P1, while Crb1-B is most abundant in adulthood. PCR primers were designed to span splice junctions expressed by the indicated isoforms. Data were normalized to values obtained from pan-Crb1 primers. N=3 animals for each age. (C) RT-PCR on cDNA from mouse retina and cortex, using pan-Crb1 primers (pan), or primers targeting a Crb1-B splice junction (B). No Crb1-B band is detected in mouse cortex. Pan-Crb1 primers produce bands in both tissues. N=3 mice. L, ladder.
Figure 13:
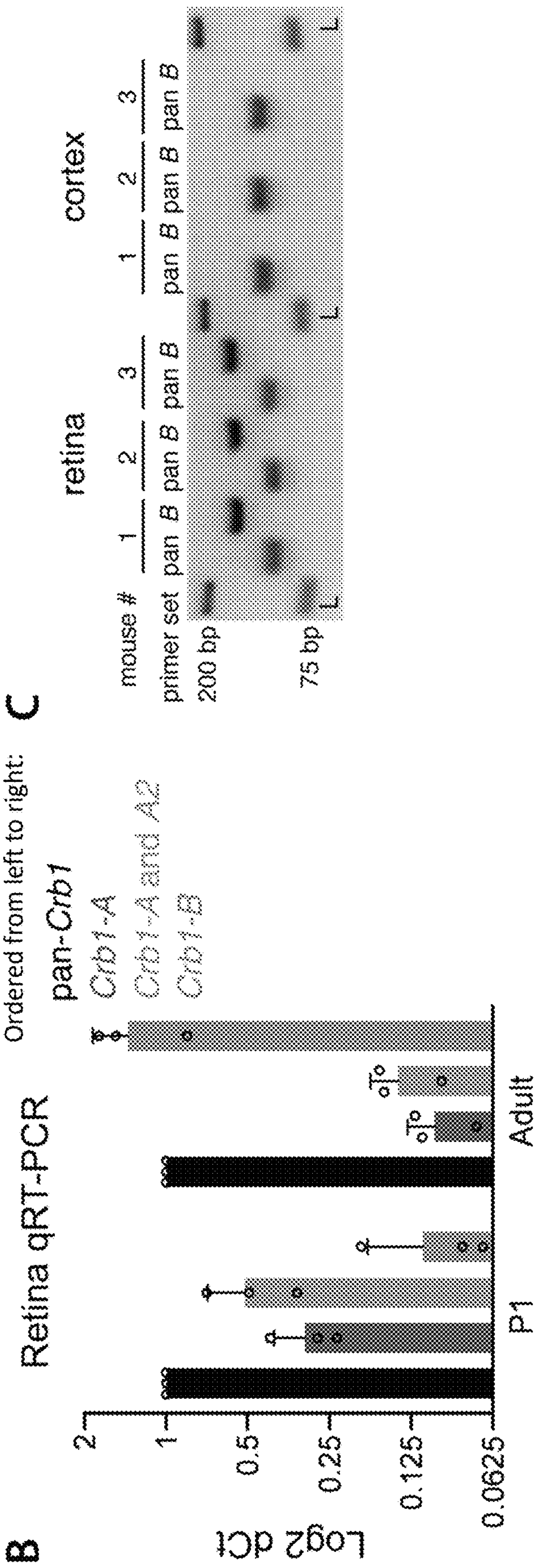
Figure 14:
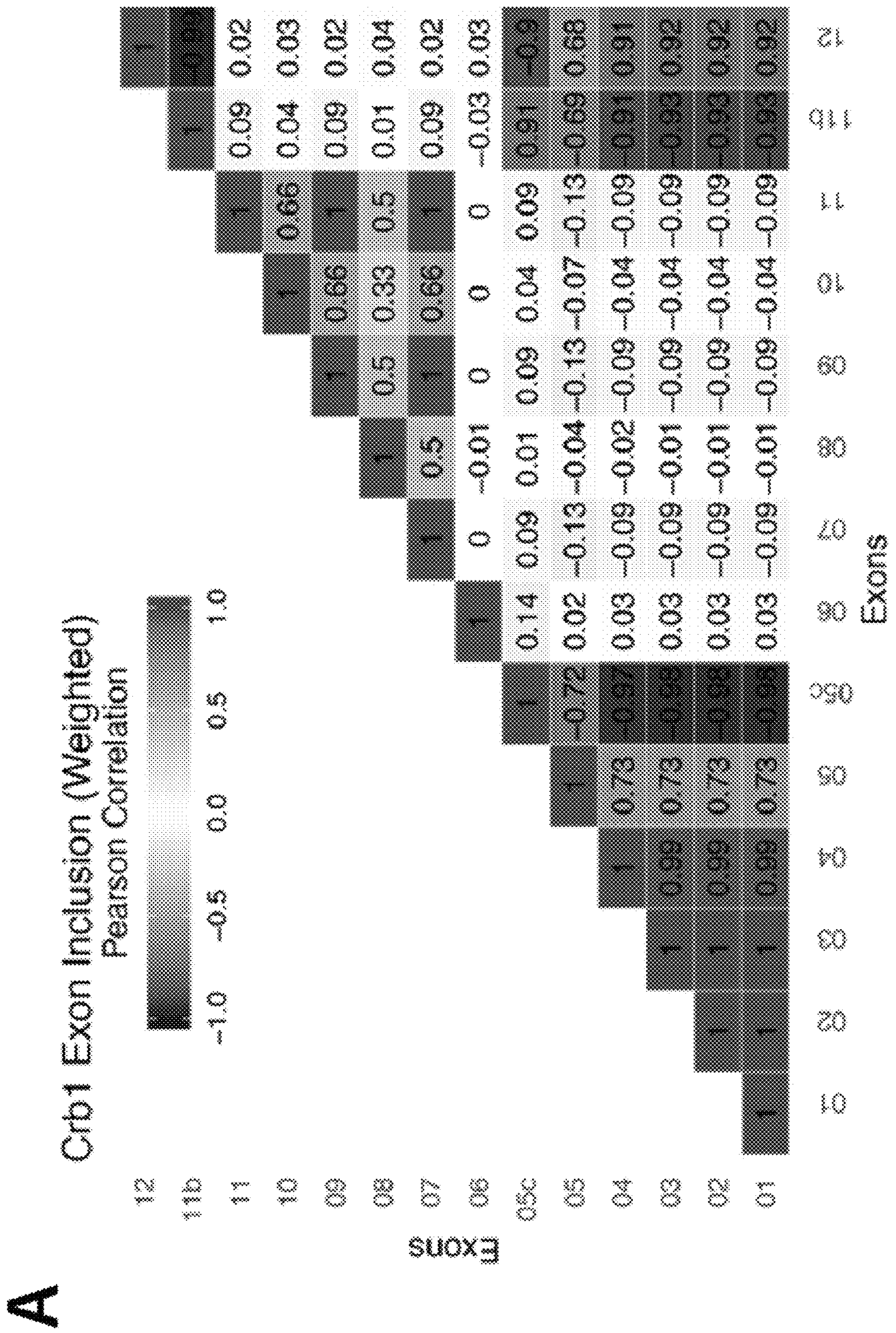
FIG. 14 shows the cell-type-specific expression of Crb1 isoforms. (A) Pearson correlation of Crb1 exons demonstrates that exons unique to Crb1-B (5c and 11b) are negatively correlated with exons unique to Crb1-A isoforms (1-5 and 12). The unique Crb1-B exons (5c and 11b) are strongly positively correlated suggesting that they are primarily used together. (B) Quantification of Crb1 isoforms from bulk RNA-seq of isolated cone (top) and rod (bottom) photoreceptors (dataset: GSE74660). Crb1-B is the only isoform expressed in photoreceptors. Error bars, 95% confidence intervals. (C) CRB1 isoforms expressed in K562 cells traffic to the plasma membrane. Images depict native fluorescence of CRB1-A and CRB1-B constructs tagged at C-terminus with YFP. (D) Mapping of Crb1 isoforms in single-cell RNA-seq data[31]. Jitter plot indicates relative transcript expression counts within individual cells. Each point represents one cell, shaded by the annotated cell type. Crb1-A is expressed by Müller glia whereas Crb1-B is expressed by rod and cone photoreceptors. Cell type-specific markers of Müller glia (Aqp4), rods (Gnat1), cones (Gnat2), and bipolar cells (Pcp2) are shown for comparison.
Figure 14:
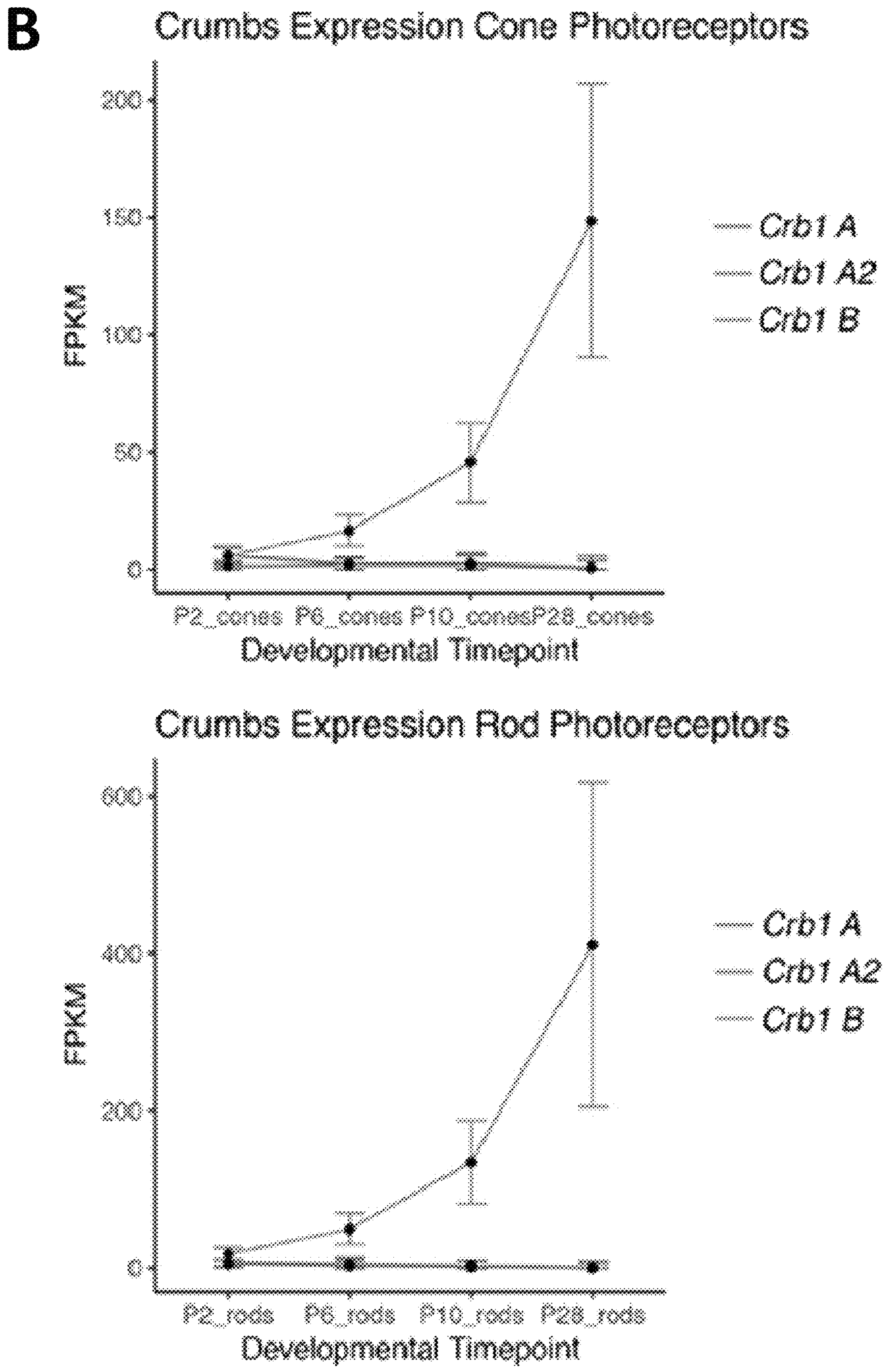
Figure 14:
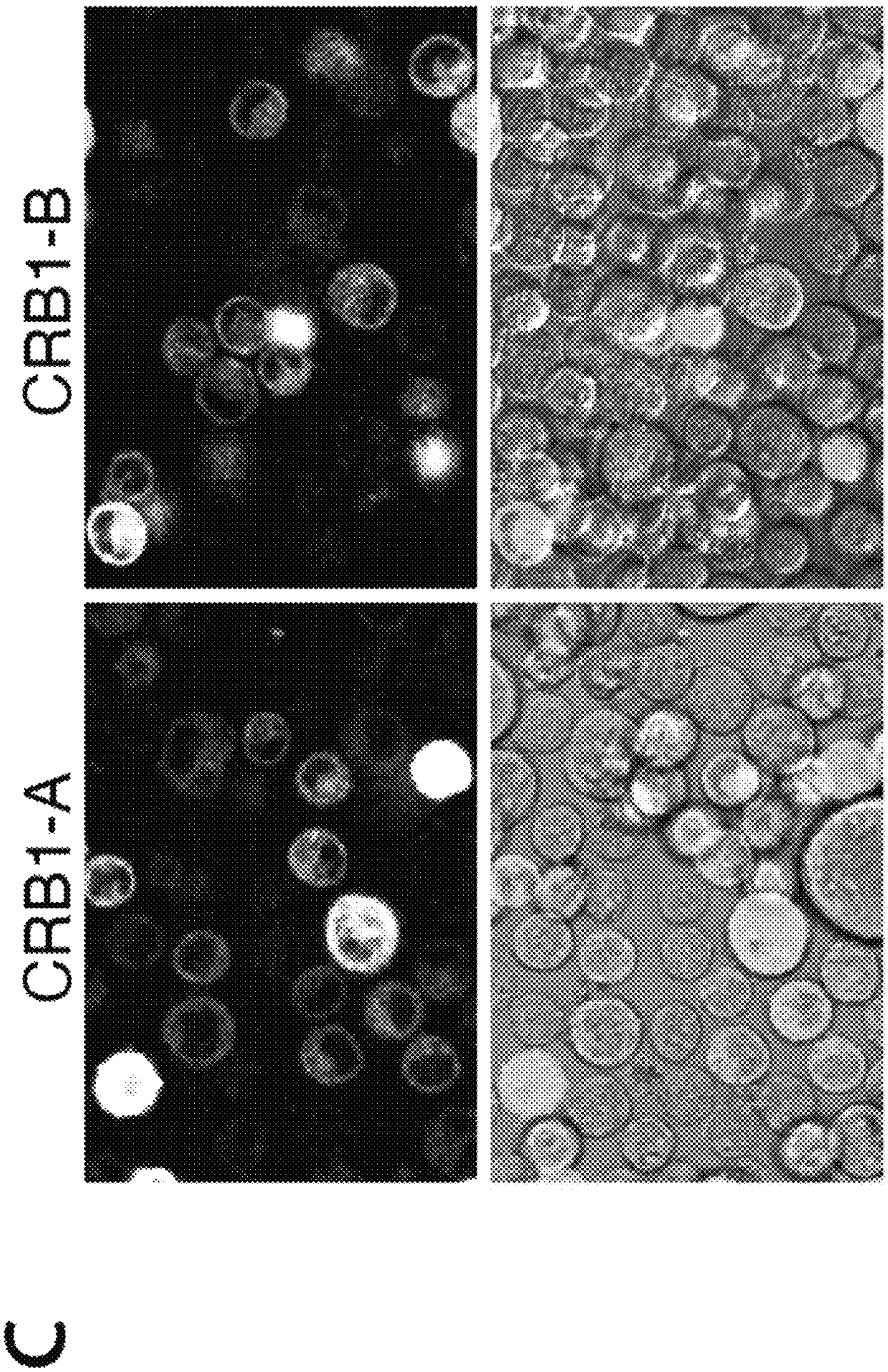
Figure 14:
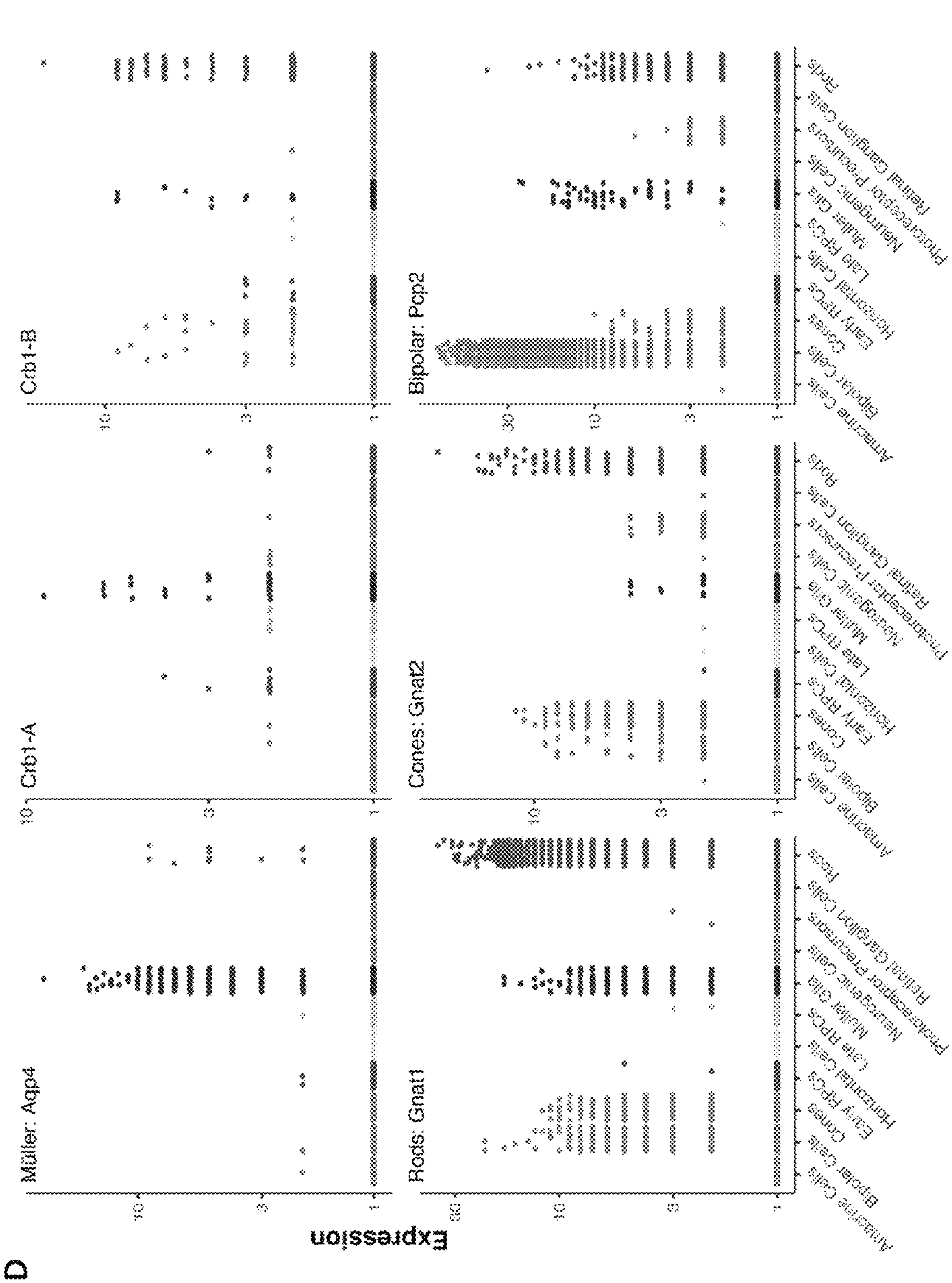

To investigate whether newly-discovered isoforms could provide insight into gene function, we focused on Crb1, a well-known retinal disease gene. Our Crb1 catalog contained 15 isoforms, several of which were tissue-specific and developmentally-regulated (FIG. 5A,B; FIG. 13B,C). In mature retina, Crb1 expression was dominated by a single isoform—but not the one that has been the subject of virtually all previous Crb1 studies. Instead, the dominant isoform was a retina-specific variant bearing unique 5' and 3' exons (FIG. 5A,D; FIG. 14A) and a unique promoter site just upstream of the novel 5' exon (FIG. 5C). We named this isoform Crb1-B, to distinguish it from the canonical Crb1-A isoform.

Even though Crb1-B was the most abundant of the 4,116 isoforms in our dataset (FIG. 2D), it was not annotated in the major genome databases (RefSeq, GENCODE, or, UCSC). Nor, to our knowledge, was it documented in the literature. CRB1-B is also the most abundant isoform in human retina, as shown by a lrCaptureSeq dataset generated from human retinal cDNA (FIG. 5E,G). A third variant, CRB1-C, was also expressed in human retina at moderate levels—much higher than in mouse—but it was still not as abundant as CRB1-B (FIG. 5E,G). As in mouse, ATAC-seq data revealed a putative B isoform promoter in human retina (FIG. 5C,F). Using short-read datasets, we corroborated the mouse and human findings and then extended them to several other vertebrate species (FIG. 5H,I; FIG. 13A). Together, these results demonstrate that the major retinal isoform of an important disease gene had previously been overlooked: Across a range of vertebrate species, CRB1-B is the predominant CRB1 isoform in the retina.

Figure 6:
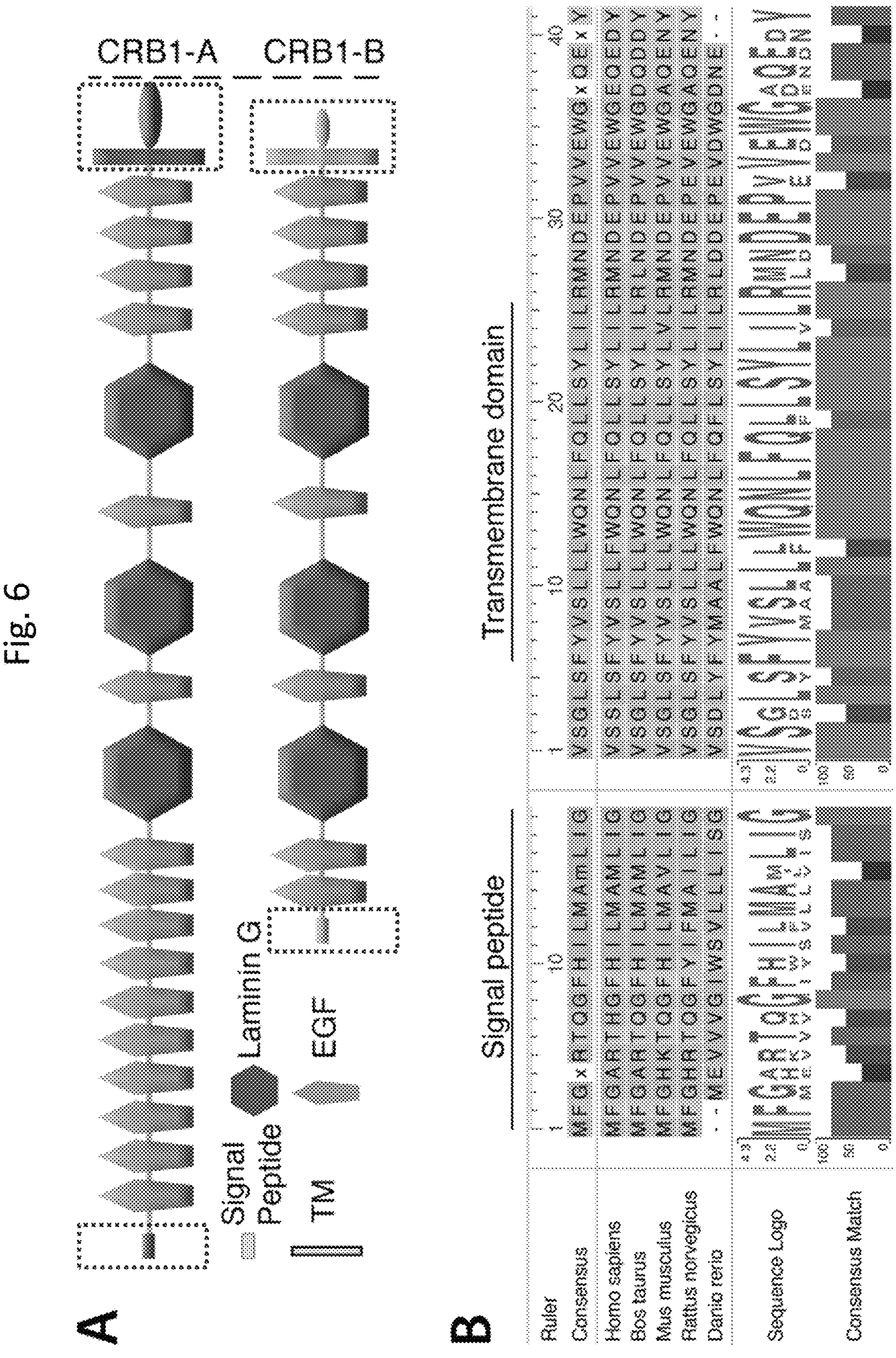
FIG. 6 demonstrates that CRB1-B is expressed by photoreceptors. (A) Domain structures of CRB1-A and CRB1-B protein isoforms. Isoform-specific regions are highlighted using dashed rectangles. Each isoform has unique sequences at N-termini, predicted to encode signal peptides, and at C-termini, predicted to encode transmembrane (TM) and intracellular domains. (B) ClustalW alignment of unique CRB1-B sequences. Both N- and C-terminal regions are highly conserved across vertebrate species. The N-terminal region comprises a signal peptide (left) and the C-terminal region comprises a transmembrane domain (right). The illustrated sequences are as follows: SEQ ID NO:87 is the consensus signal peptide, SEQ ID NO:88 is the consensus transmembrane domain, SEQ ID NO:89 is the *Homo sapiens* signal peptide, SEQ ID NO:3 is the *Homo sapiens* transmembrane domain, SEQ ID NO:90 is the *Bos taurus* signal peptide, SEQ ID NO:91 is the *Bos taurus* transmembrane domain, SEQ ID NO:92 is the *Mus musculus* signal peptide, SEQ ID NO:93 is the *Mus musculus* transmembrane domain, SEQ ID NO:94 is the *Rattus norvegicus* signal peptide, SEQ ID NO:95 is the *Rattus norvegicus* transmembrane domain, SEQ ID NO:96 is the *Danio rerio* signal peptide, and SEQ ID NO:97 is the *Danio rerio* transmembrane domain. (C) Western blot verifying CRB1-B protein expression in retinal lysates. CRB1-B antibodies were generated against unique CRB1-B C-terminus. Deletion of Crb1-B first exon in mutant mice ($Crb1^{deB}$ allele; see FIG. 7A) demonstrates antibody specificity and that unique first and last exons of Crb1-B are primarily used together, as predicted at transcript level (FIG. 5A). Photoreceptor protein ABCA4 is used as loading control. (D) Western blot on retinal lysates separated into soluble (S) and membrane-associated (M) protein fractions. CRB1-B is detected in the membrane fraction. Loading controls: Membrane fraction, ABCA4; soluble fraction, Phosducin. (E) Schematic showing anatomy of outer retinal region where CRB1 is expressed. Left, photomicrograph depicting photoreceptor nuclei; inner segment; and outer segment. The outer limiting membrane (OLM) separates nuclear layer from inner segment layer. Right, OLM anatomy schematic. OLM consists of junctions (dots) between photoreceptors and Müller cells. These junctions form selectively at particular subcellular domains of each cell type, i.e. glial apical membranes and photoreceptor inner segments. CRB1-A is expressed by Müller cells (F,G) where it localizes selectively to OLM junctions[49]. CRB1-B is expressed throughout the photoreceptor, including inner and outer segments (F-H). Also see FIG. 14. (F) Mapping of Crb1 isoforms in scRNA-seq data[48]. Heat map generated from gene profiles of >90,000 cells, showing normalized expression of Crb1 isoforms and retinal cell type marker genes. Unsupervised clustering was used to define genes co-expressed with Crb1 isoforms. Crb1-B clusters with known cone and rod photoreceptor genes, while Crb1-A clusters with known Müller glia genes. (G) BaseScope in situ hybridization of P20 mouse retinas using isoform-specific probes (red). Blue, Hoeschst nuclear counterstain. Crb1-A probe targeted exon 1-2 junction, which is also used by Crb1-A2 and Crb1-C (see FIG. 5A). Signal is primarily limited to central INL, where Müller cell bodies reside (left). Crb1-B probe targeted the junction between its unique 5' exon and exon 6 (FIG. 5A). Signal is limited to photoreceptors within ONL. Abbreviations: ONL=outer nuclear layer; INL=inner nuclear layer; GCL=ganglion cell layer. Scale bar, 100 μm. (H) Subcellular localization of CRB1-B within rod photoreceptors, assessed by Western blotting of serial 10 μm tangential sections through mouse outer retina. Each lane corresponds to photoreceptor cellular compartment denoted by cartoon at top. Rhodopsin (Rho, center) is an outer segment marker; GAPDH (bottom) is excluded from outer segment but is present throughout the rest of the cell. CRB1-B protein (top) is present in all compartments; expression is strongest in lanes corresponding to outer and inner segments.
Figure 6:
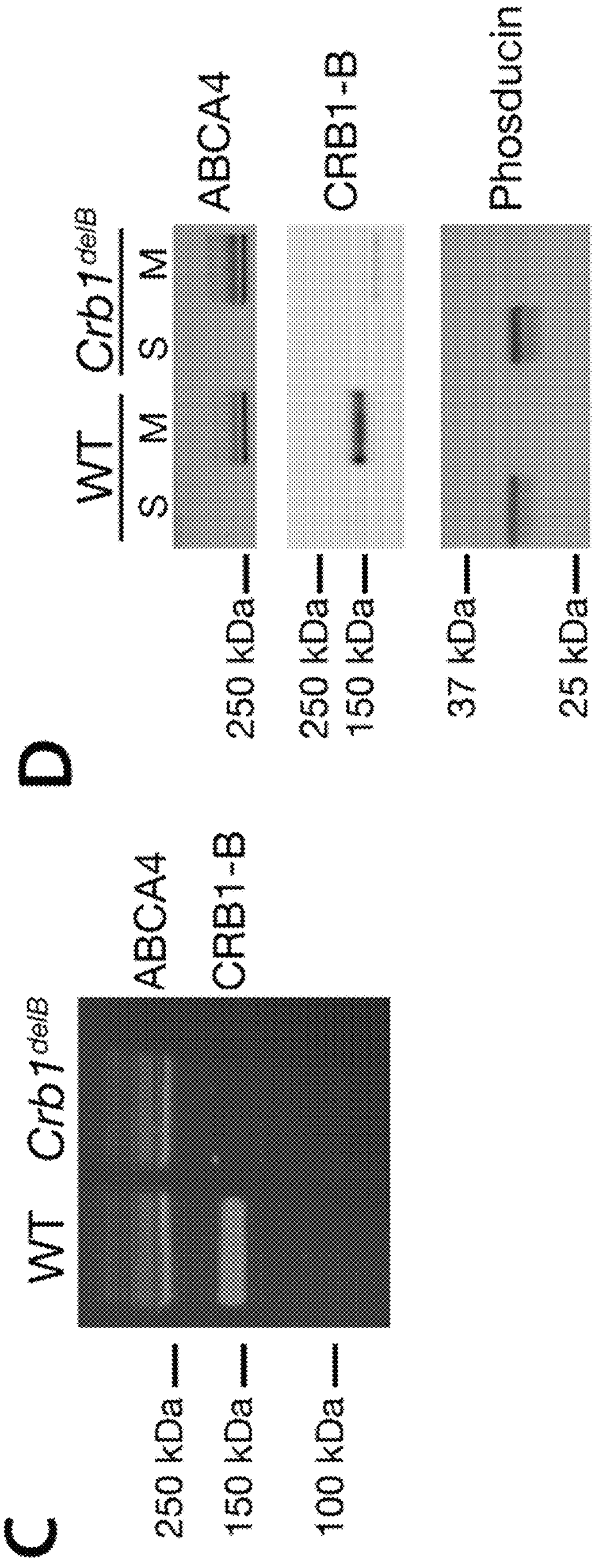
Figure 6:
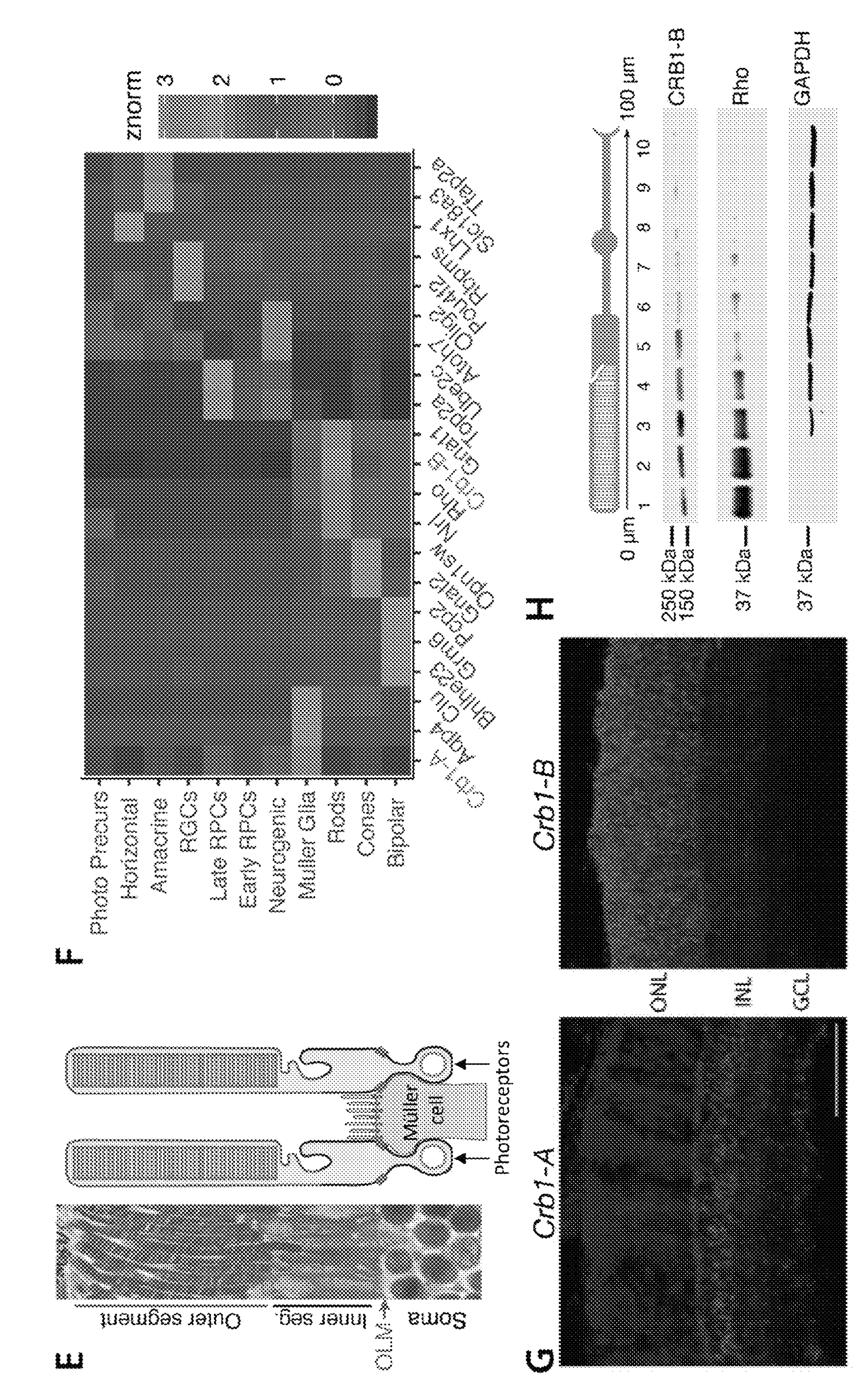
Figure 7:
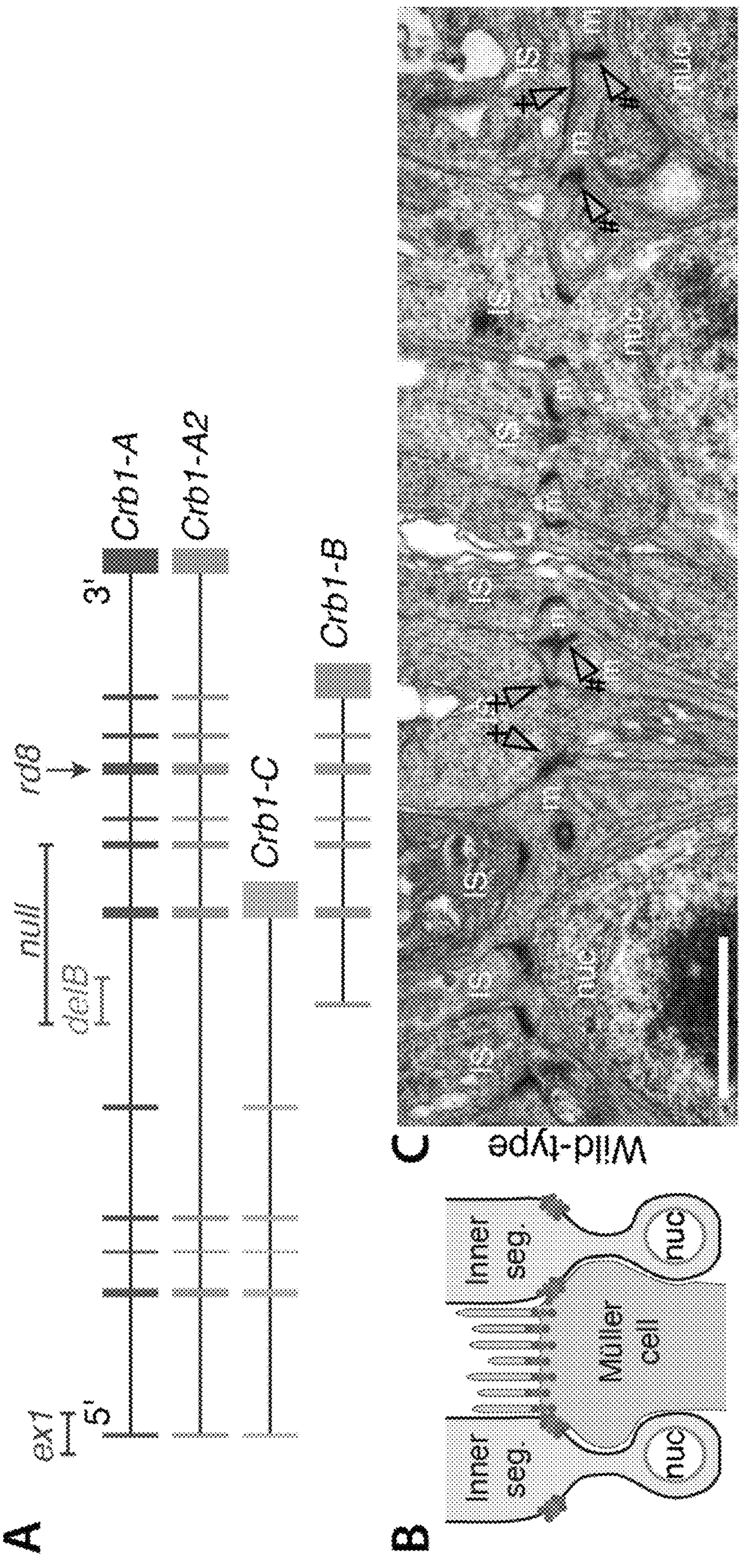
FIG. 7 demonstrates that Crb1 isoforms are required for outer limiting membrane integrity. (A) Schematic of Crb1 locus showing genetic lesions associated with mouse mutant alleles. Previously studied mutants: $Crb1^{ex1}$, a targeted deletion of exon 1 that does not impact the Crb1-B isoform; $Crb1^{rd8}$, a point mutation in exon 9. Mutant alleles generated for this study: $Crb1^{deB}$ a CRISPR-mediated deletion of the first Crb1-B exon and its promoter region, leaving the Crb1-A isoform intact; $Crb1^{null}$, a large CRISPR-mediated deletion of consecutive exons that are used in all Crb1 isoforms. Also see FIG. 15A for documentation of new alleles. (B,C) Assessment of OLM junctions by electron microscopy. B: schematic illustrating location of OLM junctions (dots) surrounding photoreceptor inner segments. C: Electron micrograph from wild-type mouse. All inner segments make OLM junctions with Müller cells. IS, inner segment. Arrowheads marked with plus sign (+), photoreceptor-glial junctions. Arrowheads marked with hash sign (#), glial-glial junctions. (D,E) OLM disruption phenotype in Crb1 mutants. D: electron micrograph from control (wild-type) mouse. OLM divides outer nuclear layer (ONL) from IS layer. In Crb1 mutants (E), gaps in OLM allow nuclei to penetrate into inner segment layer. Arrows demarcate region lacking OLM junctions. This image is from Crb1$^{delB/null}$ mutant, but is representative of OLM phenotypes observed in null, delB, and rd8 mutants (FIG. 15D-F). (F-I) Higher power views of OLM gaps in Crb1 mutants, showing inner segments that lack OLM junctions (asterisks). In each allelic combination, photoreceptors lacking Müller contacts were observed. Marked arrowheads as in C. (J) Quantification of OLM gap frequency. No gaps were observed in wild-type or Crb1$^{null/+}$ heterozygotes. The frequency of OLM disruption was similar in rd8, null, and delB/null mutants, the latter of which lack Crb1-B but still express Crb1-A. Statistics, one-way ANOVA with Tukey's post-hoc test. Null, rd8, and delB/null were all significantly different from wild-type and heterozygous controls (respective P-values: 0.014; 0.005; 0.019), but did not differ significantly from each other (rd8 vs. null P=0.991; rd8 vs. delB/null P=0.784; null vs. delB/null P=0.967). Also see FIG. 15F for quantification of gap sizes. Scale bars, 2 μm C, D (bar also applies to E); 1 μm G (bar also applies to F), H, I.
Figure 7:
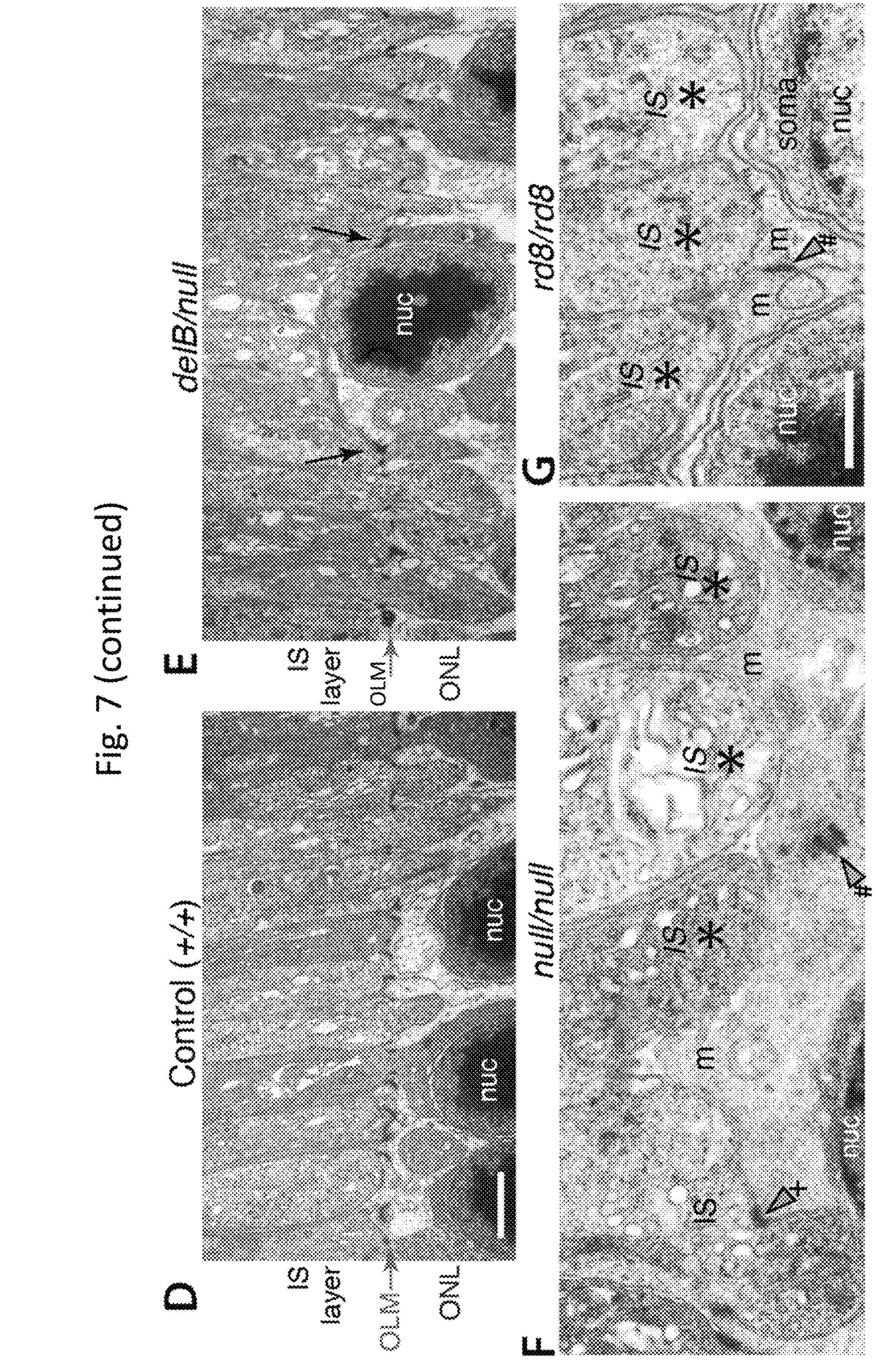
Figure 7:
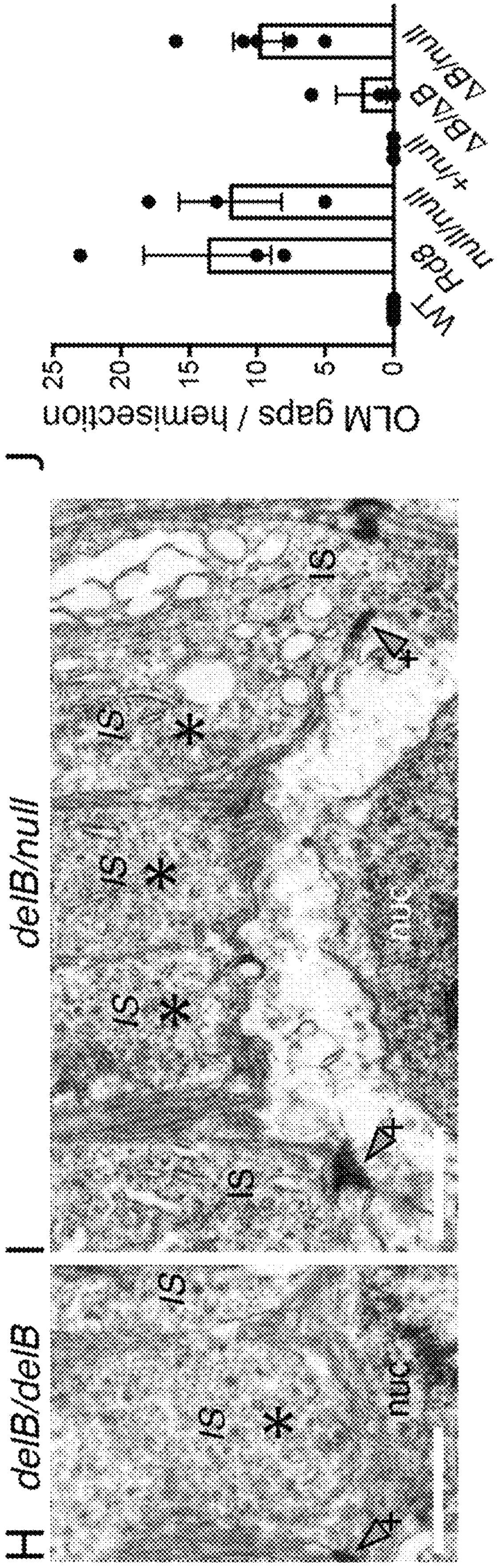
Figure 8:
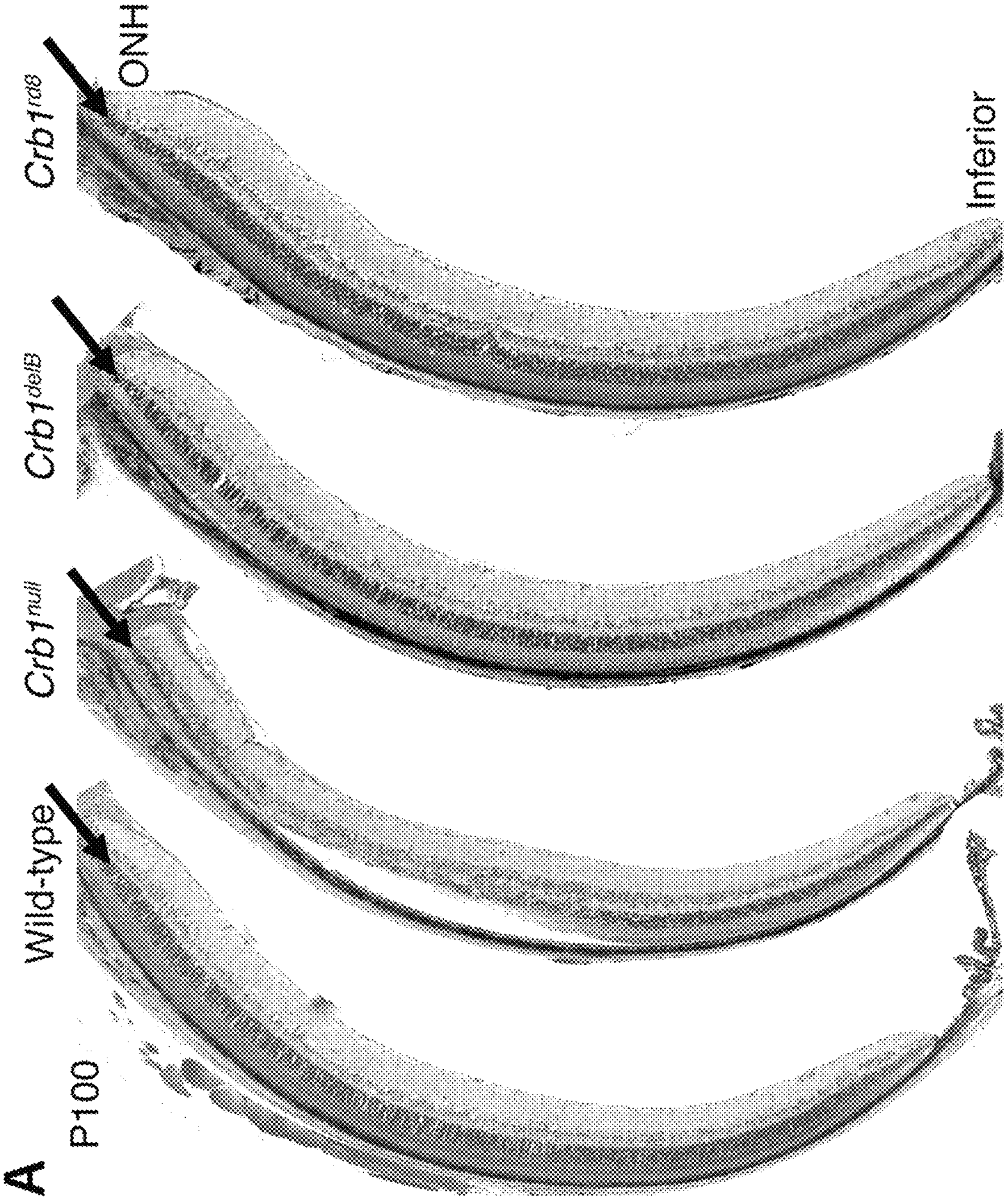
FIG. 8 demonstrates that ablation of all Crb1 isoforms causes retinal degeneration. (A) Retinal histology in Crb1 mutant mice at P100. Thin plastic sections through inferior hemisphere are shown for homozygous mutants of indicated genotype, and wild-type controls. Arrow, ONL layer containing photoreceptor nuclei. Large focal region of photoreceptor loss is evident in Crb1$^{null}$ retina, accompanied by retinal detachment. Areas outside the most aggressively degenerative patch show ONL thinning. Crb1$^{delB}$ and Crb1$^{rd8}$ mutants show no apparent loss of ONL cells. ONH, optic nerve head. (B) Higher magnification views of retinal histology, 450 μm inferior to ONH. Images from two different Crb1$^{null}$ animals are shown to highlight variability in focal degeneration. Even the mild null case has thinner ONL (light gray line) with fewer nuclei than age-matched Crb1$^{rd8}$. Outer segment length (dark gray line) is also diminished in null mutants. (C,D) Quantification of ONL cell number at P100. C: Spider plot showing counts of ONL nuclei in 100 μm bins distributed uniformly across retinal sections (e.g. B). Left, inferior side. For Crb1$^{delB}$ spider plot see FIG. 15. D: Total ONL nuclei counted in all 8 bins. Statistics (C): 2-way ANOVA with Sidak post-hoc test. P-values refer to WT vs. null comparison; rd8 was not significantly different from WT at any location. *P=0.015; P=0.007, P=0.004; P<1χ $10^{-7}$. Statistics (D): 1-way ANOVA with Tukey's post-hoc test. Crb1$^{null}$ was significantly different from all other groups. **P<1×$10^{-5}$ for all comparisons. None of the other Crb1 mutants differed from WT or each other. Sample sizes denoted by dots on graph (D).
Figure 8:
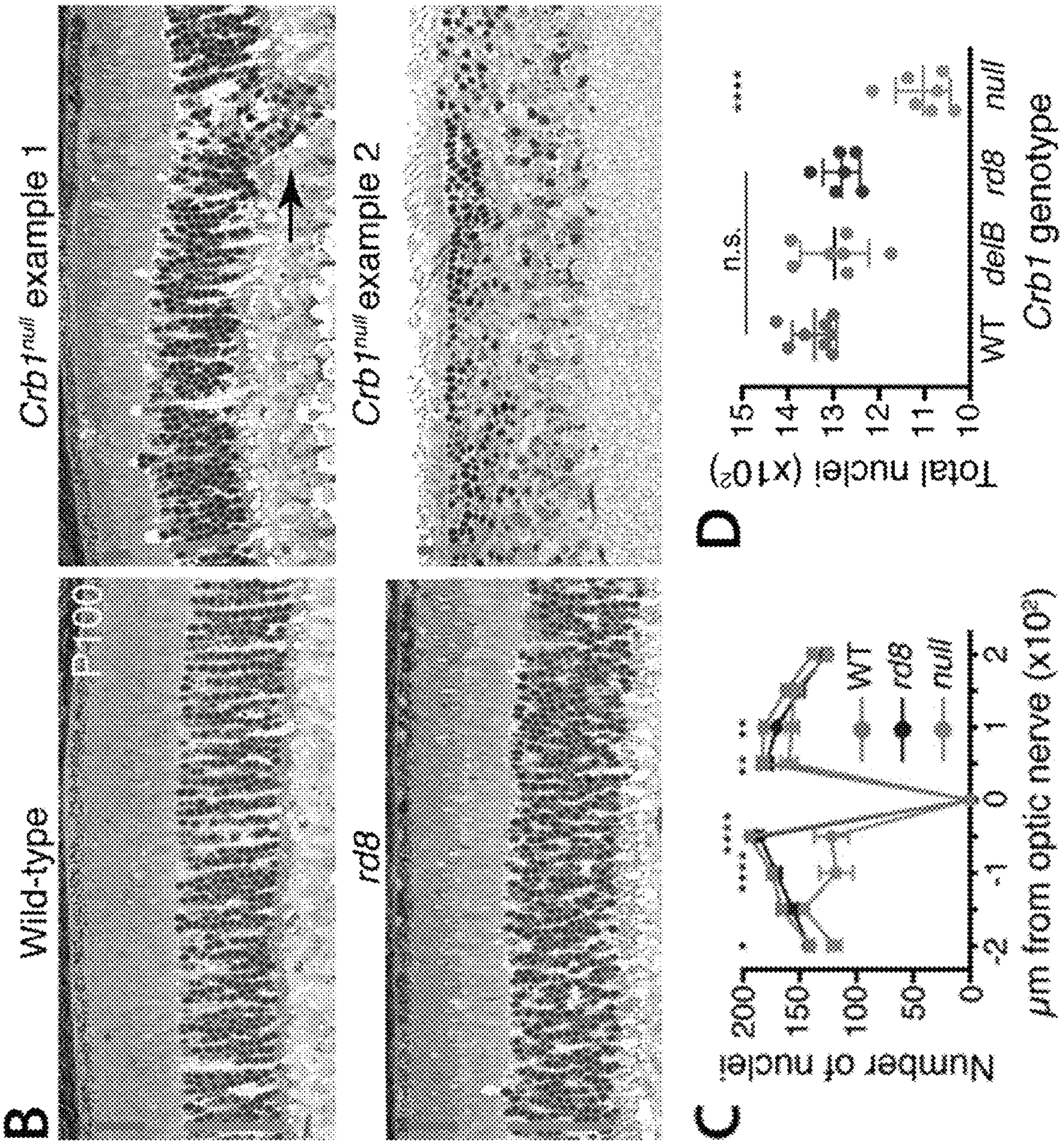

Crb1-A and Crb1-B Encode Cell-Surface Proteins Expressed in Different Cell Types Crb1-B is predicted to encode a transmembrane protein sharing significant extracellular domain overlap with CRB1-A, but an entirely different intracellular domain (FIG. 6A,B). We therefore asked whether this protein is expressed and, if so, where the protein is localized. Western blotting with an antibody raised against the CRB1-B intracellular domain demonstrated that the protein exists in vivo (FIG. 6C). Moreover, it exists in the configuration predicted by lrCaptureSeq (FIG. 6A), because intracellular domain expression was absent in mice engineered to lack the Crb1-B promoter and 5' exon (FIG. 6C; see FIG. 7A for mouse design). Consistent with the notion that CRB1-B is a transmembrane protein, it was detected in the membrane fraction but not the soluble fraction of retinal lysates (FIG. 6D). Further, when expressed in heterologous cells, CRB1-B trafficked to the plasma membrane in a manner strongly resembling CRB1-A (FIG. 14C). These data suggest that both major CRB1 isoforms localize at the cell surface.

To determine the expression patterns of Crb1-A and Crb1-B, we developed a strategy to evaluate expression of lrCaptureSeq isoforms within single cell (sc)-RNA-seq datasets. Applying this strategy to scRNA-seq data from developing mouse retina[48], we found distinct expression patterns for each isoform. Crb1-A was expressed largely by Müller glia (FIG. 6E,F; FIG. 14D), consistent with previous immunohistochemical studies[37,49]. Crb1-B, by contrast, was expressed by rod and cone photoreceptors (FIG. 6E,F; FIG. 14B,D). These cell-type-specific expression patterns were validated using two independent methods: First, ATAC-seq data from rods and cones showed that photoreceptors selectively use the Crb1-B promoter (FIG. 5C). Second, BaseScope staining confirmed mutually exclusive expression of the two isoforms, with Crb1-A localizing to Müller cells and Crb1-B to photoreceptors (FIG. 6G).

To examine CRB1-B protein localization, we initially attempted immunohistochemistry but found that our antibody was not suitable. Therefore, we turned to a technique that combines serial tangential cryosectioning of the retina with Western blotting[50,51]. Each tangential section contains a specific subset of cellular and subcellular structures that can be recognized by representative protein markers (FIG. 6H). This approach confirmed expression of CRB1-B in the photoreceptor layer, predominantly within the inner and outer segments. This localization is in marked contrast to CRB1-A which has been localized to the apical tips of Müller cells, within the OLM (FIG. 6E), using antibodies specific to this isoform[37,49].

CRB1-B is Required for Integrity of the Outer Limiting Membrane

Figure 15:
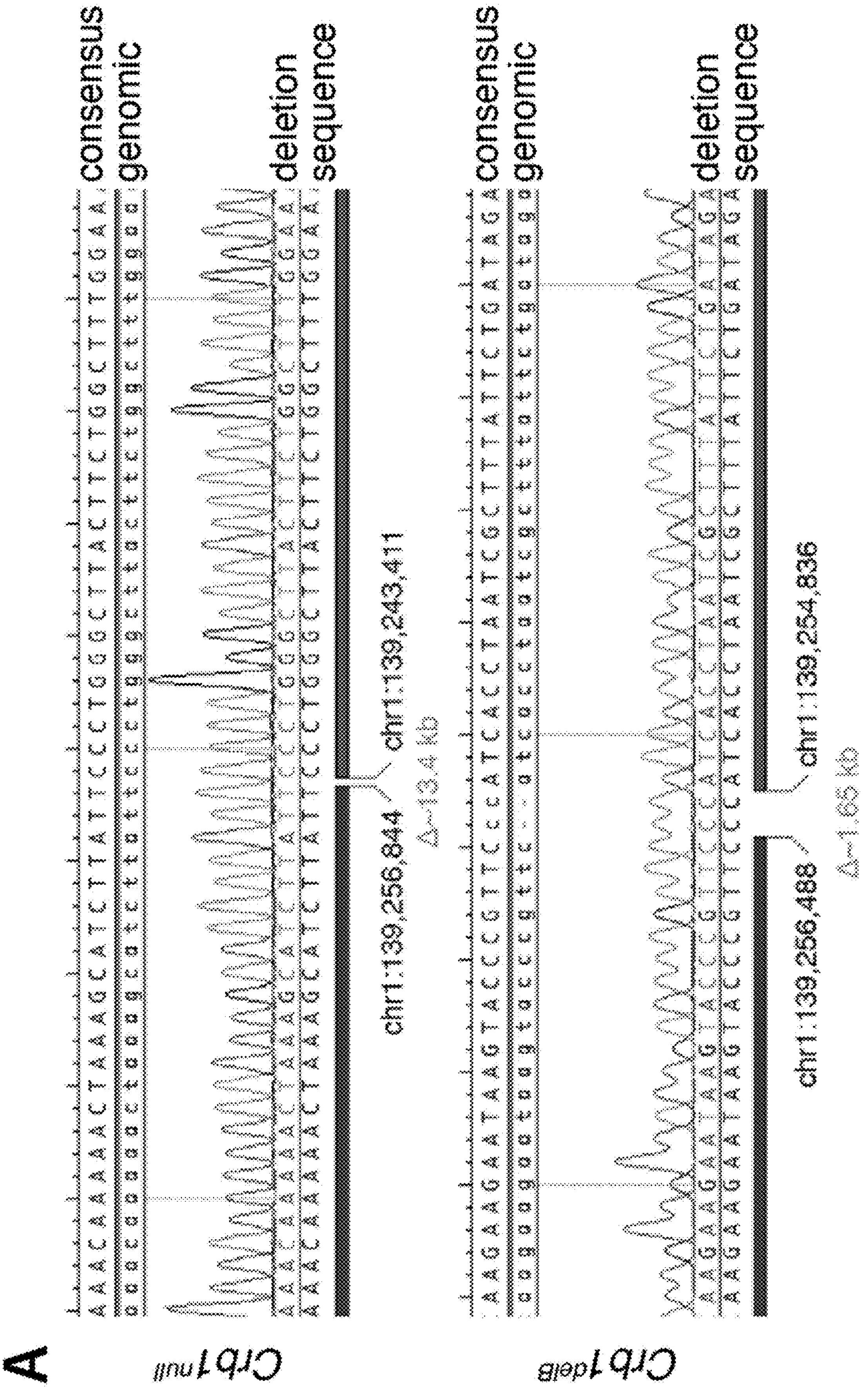
FIG. 15 depicts Crb1 mutant mice and OLM phenotypes. (A) Location of deletions within $Crb1^{null}$ and $Crb1^{delB}$ alleles, verified by Sanger sequencing. Delta symbol (A) indicates size of the deleted genomic fragment. The genomic region comprising the $Crb1^{null}$ allele is SEQ ID NO:98 (top four sequences), while genomic region comprising the $Crb1^{delB}$ allele is SEQ ID NO:99 (fifth, seventh, and eighth sequence). The sequence illustrating the $Crb1^{delB}$ deletion is SEQ ID NO:100 (sixth sequence). (B) Confirmation that CRB1-B protein is eliminated in $Crb1^{null}$ mutant mice. Western blots on retinal lysates were performed as in FIG. 6C. ABCA4, loading control. (C) Spider plot showing lack of photoreceptor loss in $Crb1^{delB/delB}$ mice at P100. Gray, wild-type controls. (D,E) Representative electron micrographs showing OLM disruptions in $Crb1^{null}$ and $Crb1^{rd8}$ mutants. Images are similar in scale to FIG. 7D,E. Arrows demarcate region lacking OLM junctions. Anatomical disturbances are similar to those previously reported for rd8[36], and to those observed in $Crb1^{delB/null}$ mice, which lack Crb1-B but still retain one copy of Crb1-A (FIG. 7). Scale bar, 5 μm. (F) OLM gap size in Crb1 mutants carrying various allele combinations. Size of OLM gaps was not significantly different across the various mutants. Statistics, one-way ANOVA (F=2.19; P=0.095).
Figure 15:
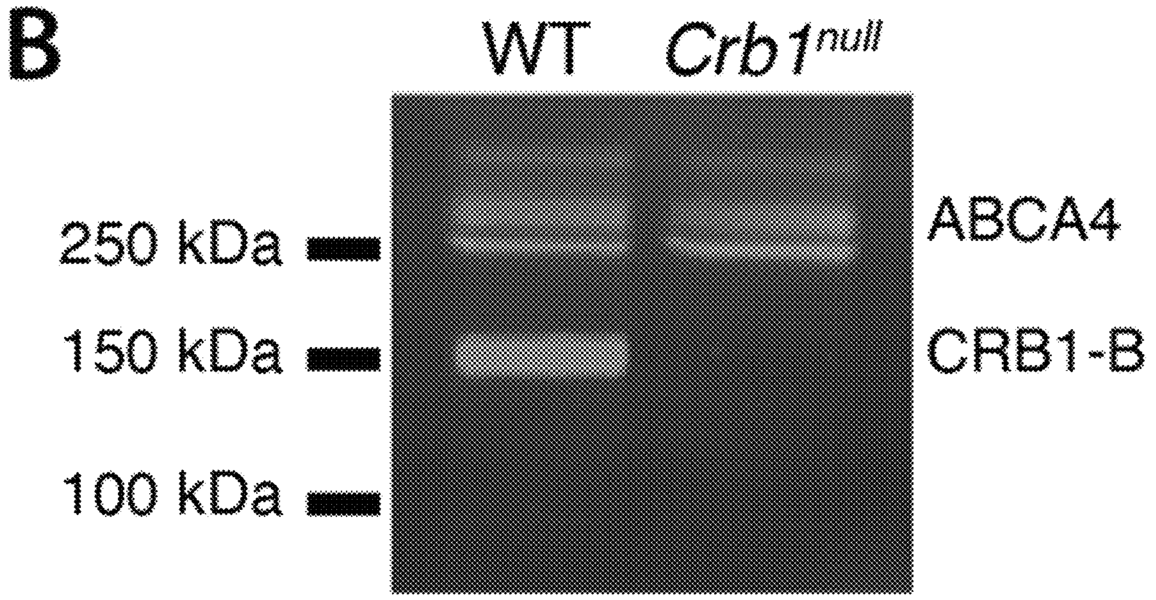
Figure 15:
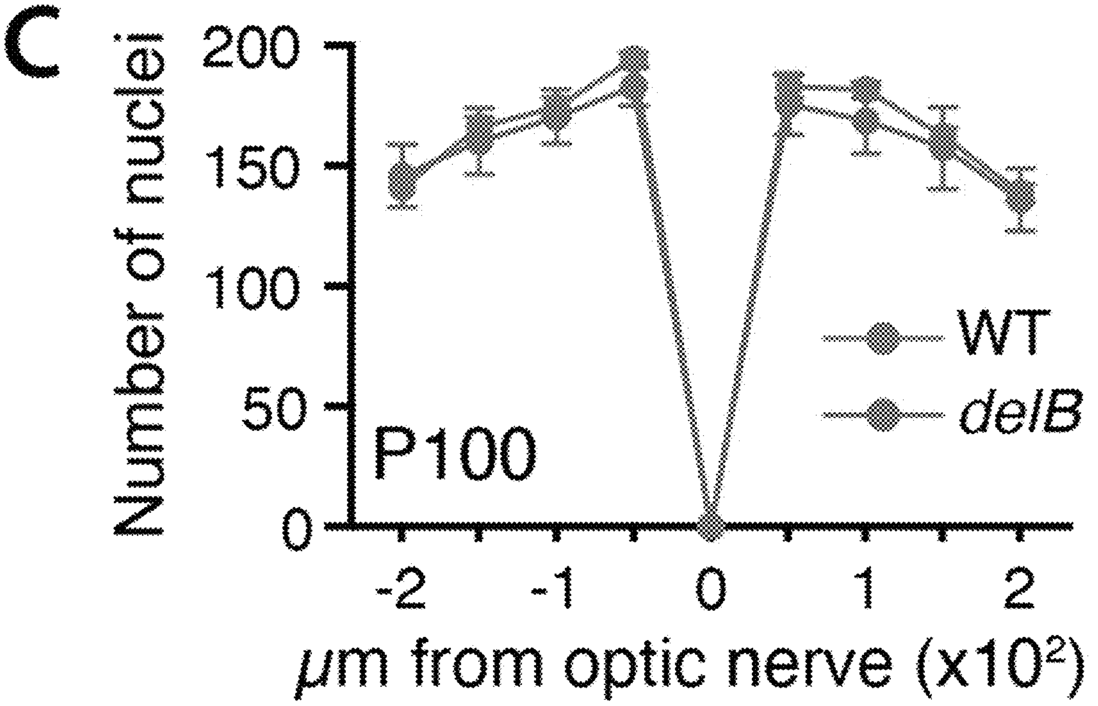
Figure 15:
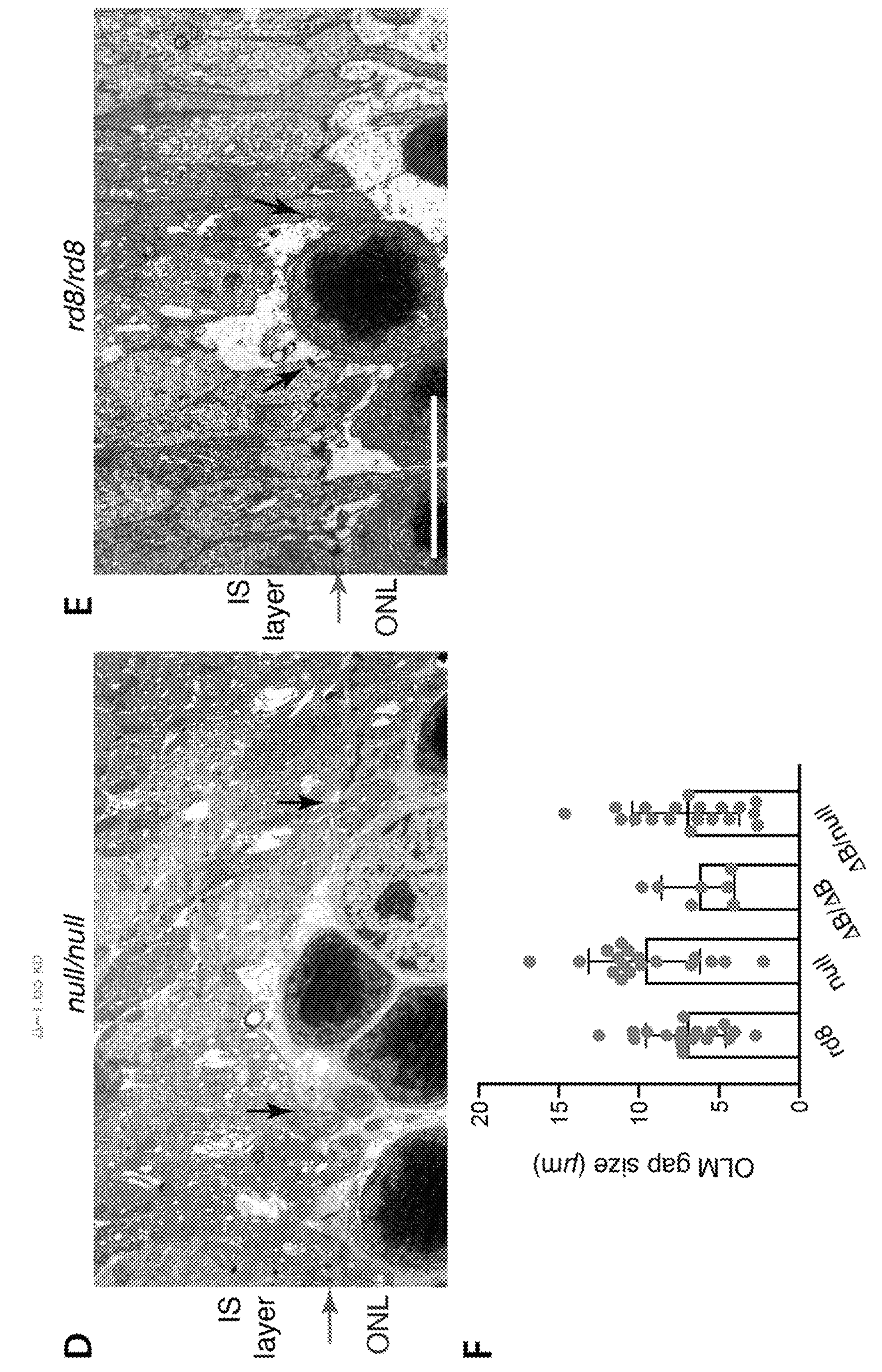

We next investigated the function of the CRB1-B isoform. Photoreceptors and Müller glia, the two cell types that express the major CRB1 isoforms (FIG. 6F,G), engage in specialized cell-cell junctions that form the OLM (FIG. 6E; FIG. 7B,C). It has been suggested that degenerative pathology in CRB1 disease may result from disruption of these junctions, but mouse studies have failed to clarify whether CRB1 is in fact required for OLM integrity. The two existing Crb1 mutant strains have conflicting OLM phenotypes: Mice bearing a Crb1 point mutation known as rd8 show sporadic OLM disruptions[36], whereas a Crb1 “knockout” allele, here denoted Crb1$^{ex1}$, fails to disturb OLM junctions[37]. Our lrCaptureSeq data revealed a key difference between these two alleles: rd8 affects both Crb1-A and Crb1-B isoforms, whereas the “knockout” ex1 allele leaves Crb1-B intact (FIG. 7A). Therefore, we hypothesized that Crb1-B has a key role in the integrity of photoreceptor-Müller junctions at the OLM. To test this hypothesis, we generated two new mutant alleles (FIG. 7A; FIG. 15A,B). The first, Crb1$^{delB}$, abolishes Crb1-B while preserving other isoforms including Crb1-A. The second, Crb1$^{null}$, is a large deletion designed to disrupt all Crb1 isoforms.

Using electron microscopy to evaluate OLM integrity, we found that Crb1$^{null}$ mutants exhibit disruptions at the OLM whereby photoreceptor nuclei invaded the inner segment layer, disturbing the structure of the outer retina (FIG. 7B-E; FIG. 15D). Within the disrupted regions, photoreceptor inner segments lacked their characteristic electron-dense junctions with apical Müller processes, indicating that OLM gaps arose due to disruption of photoreceptor-Müller contacts (FIG. 7F). A similar phenotype was also observed in Crb1$^{rd8}$ mutants, as previously reported[36] (FIG. 7F,G,J; FIG. 15D-F). To explore the contribution of each isoform to the OLM phenotype, we examined mice bearing various combinations of the Crb1$^{null}$ and Crb1$^{delB}$ alleles. In Crb1$^{delB/delB}$ mice, which lack Crb1-B but retain two copies of Crb1-A, the OLM phenotype was still evident but was weaker than in rd8 or null homozygotes (FIG. 7H,J). By contrast, the OLM phenotype was equivalent to rd8 and null mutants in Crb1$^{delB/null}$ mice, which lack Crb1-B but retain one copy of Crb1-A (FIG. 7E,J; FIG. 15F). These findings indicate that both Crb1 isoforms are needed for OLM junctional integrity, but the role of Crb1-B is particularly important, given that severe OLM disruptions can arise even when Crb1-A remains present.

Retinal Degeneration in Mice Lacking all Crb1 Isoforms

Finally, we asked whether insight into CRB1 isoforms could be used to improve animal models of CRB1 degenerative disease. Photoreceptor degeneration is absent or extremely slow in existing Crb1 loss-of-function mice, making them poor models of human degenerative phenotypes[36,37,52]. We hypothesized that previously unannotated Crb1 isoforms, such as Crb1-B, might help explain these mild phenotypes. Consistent with this possibility, we noted that neither of the existing Crb1 mutant alleles completely eliminates all Crb1 isoforms (FIG. 7A). To test the contribution of new Crb1 isoforms to photoreceptor degeneration, we took advantage of our newly-generated Crb1$^{delB}$ and Crb1$^{null}$ strains (FIG. 7A). Analysis of photoreceptor numbers in young adult mice (P100) revealed that both Crb1-A and Crb1-B isoforms are required for photoreceptor survival. Crb1$^{delB}$ mutants had normal photoreceptor numbers (FIG. 8A,D; FIG. 15C), similar to the previously-reported Crb1$^{ex1}$ mutant[37]. Therefore, removing either major isoform by itself has minimal degenerative effects. By contrast, deletion of all isoforms in Crb1$^{null}$ mice caused marked photoreceptor degeneration (FIG. 8A-D). Thus, significant cell loss requires compromise of both Crb1-A and Crb1-B. No degeneration was evident yet at P100 in Crb1$^{rd8}$ mutants (FIG. 8B-D), consistent with previous reports that significant degeneration takes ~2 years[36,52,53]. Together, these genetic experiments support the conclusion that multiple Crb1 isoforms contribute to photoreceptor survival—including the novel Crb1-B isoform. Thus, modeling of human disease can be achieved by rational design of mutant alleles guided by lrCaptureSeq isoform catalogs.

DISCUSSION

Despite recent advances in sequencing technology, the true diversity of the CNS transcriptome remains surprisingly murky[12]. For most genes, only a small subset of the full isoform portfolio has been documented. Here we show that lrCaptureSeq can unveil isoform diversity with an unprecedented level of detail. LrCaptureSeq is accurate and efficient, with sufficient depth to reveal the full-length sequence of even low-abundance isoforms. To facilitate interpretation of lrCaptureSeq data we provide a companion R software package for analyzing and visualizing isoform catalogs. Applying these new tools to the developing nervous system, we uncovered a vast diversity of isoforms encoding cell surface proteins, most of which were novel. Many were predicted to alter functional protein domains. Further, we found that the most abundant isoform in our entire dataset—a novel isoform of the Crb1 disease gene—has a distinct expression pattern and function from the canonical isoform, endowing it with disease-relevant functions. CRB1 therefore serves as a striking example of the value of comprehensive full-length isoform identification. We propose that lrCaptureSeq can be applied to generate full-length isoform catalogs for many different CNS regions and cell types, an approach that is likely to unlock many new insights into CNS gene function and dysfunction.

Isoform identification requires substantial sequencing depth. Even with short read RNA-seq, complete isoform portfolios are likely detectable only for the most abundant genes, given that the least abundant 44% of transcripts garner only 1% of the reads[31,54]. Targeted CaptureSeq approaches have been used to improve short-read detection of low-abundance transcripts[31,55]. Here, applying this strategy for long-read sequencing of protein-coding mRNAs, we obtained deep full-length coverage for a group of genes that would be poorly represented in existing PacBio transcriptomes, due to their cDNA size and expression levels. It is clear from the distribution of isoform abundances (FIG. 2C) that only the least abundant isoforms escaped detection. Some isoforms smaller than 4.5 kb may also have evaded detection, given the size selection step of our library preparation protocol (FIG. 1*i*). For these reasons we suspect that we have not detected every last isoform. However, even with our enrichment for long transcripts, we still obtained a large sample of shorter reads (FIG. 10E) and identified many smaller isoforms—including Crb1-B (3.0 kb). Thus, while the lrCaptureSeq catalogs may lack certain short and/or rare transcripts, we conclude that we have detected most of the isoforms expressed in our targeted tissues. We achieved this depth by targeting 30 genes for parallel sequencing, but higher-throughput PacBio instruments are now available; these should allow substantially more targeted genes to be sequenced in parallel without sacrificing isoform coverage.

Our results suggest many potential uses for lrCaptureSeq in transcriptome annotation. One particularly exciting use case is identification of cell-type-specific isoform expression patterns. We show that lrCaptureSeq data can be integrated with existing short-read RNA-seq datasets, including single-cell data, to reveal the time and place of isoform expression. As of now, this expression mapping works best for isoforms that differ at their 3' ends, due to 3' bias inherent in most single-cell library preparation methods. In the future, as scRNA-seq methods are refined to improve depth and coverage, we expect that other types of isoforms will be amenable to mapping in this way. With this methodology, it will not be necessary to generate lrCaptureSeq catalogs for each cell type in the nervous system; rather, cell-type-specific isoform expression can be determined bioinformatically by combining different types of sequencing data.

How many mRNA isoforms are produced by any given gene? For the 30 genes in our dataset the median number of RefSeq isoforms was 11.5, and no gene had more than 51. By contrast, the median number of isoforms in our lrCaptureSeq catalog was 50, while the most diverse gene, Nrxn3, had nearly 900. Overall, the number of lrCaptureSeq isoforms exceeded the number annotated in reference transcriptomes by nearly an order of magnitude (FIG. 2B). By contrast, a previous CaptureSeq study of long noncoding RNAs found only two-fold more isoforms[40]. Thus, even though it is widely recognized that most genes generate multiple isoforms, the scale of diversity we uncovered for cell-surface molecules was still surprising. Our 30 genes probably have more isoforms than the average gene, given that they were selected because they showed evidence of transcript diversity (FIG. 1A). Whether such diversity is typical of other gene classes and other tissues remains to be determined—perhaps through broader application of the lrCaptureSeq methodology.

It has long been suspected that extensive diversity of cell-surface proteins might be involved in formation of precise neuronal connections[5,8,56]. However, the need for numerous cell-surface cues has recently been called into question[57]. In this view, extensive diversity would be required only in certain select contexts, such as during the self vs. non-self recognition mediated by Dscam1 and clustered protocadherins[58,59]. Here we show that extensive isoform diversity is widespread across many cell-surface receptor genes, and that individual neurons most likely express numerous of isoforms of certain genes (e.g. Megf11; FIG. 4E). Thus, the molecular prerequisite for the "numerous cues" model is in place. Strikingly, the genes that have the most predicted protein diversity share a common function as trans-synaptic cell adhesion molecules (FIG. 3C). Many of these genes have known roles in synapse formation[19,60,61]. Therefore, these diverse molecular cues are likely positioned in exactly the right place to influence the precision of synaptic connections. It will be interesting to learn the extent to which isoforms described here function in synapse specificity.

A striking feature of Dscam1 isoform diversity is the modular deployment of Ig repeats to modify binding specificity. Other genes with equivalently high potential for modular swapping of extracellular domain motifs have not previously been identified. Here we show that Megf11, a recognition molecule that mediates homotypic cell-cell repulsion during retinal development[44], diversifies its extracellular domain through extensive modular use of EGF-like repeats. The phenomenon of modular EGF-repeat swapping through alternative splicing has been observed before, albeit at smaller scale, for Netrin-G proteins[62]. Therefore, it is possible that many EGF-repeat genes may generate large families of cell surface proteins using a similar modular strategy.

Our studies of CRB1 illustrate the value and importance of documenting the complete isoform output of individual genes. CRB1 is a major causal gene for inherited retinal degenerative diseases, including Leber's congenital amaurosis, retinitis pigmentosa, and macular dystrophy[63-65]. As such, both mouse Crb1 and human CRB1 have been studied intensively. Nevertheless, the major CRB1 isoform in mature human retina—CRB1-B—had evaded detection until now. CRB1-B may have been overlooked because its 5' and 3' exons are the only parts of the transcript that distinguish it from CRB1-A. With short-read sequencing it is difficult to tell that these two distant exons are typically used together in the same transcript. By contrast, lrCaptureSeq clearly showed that the most abundant retinal CRB1 isoform was a novel variant containing these unconventional 5' and 3' exons.

Due to their distinct 5' and 3' ends (FIG. 6A), Crb1-A and -B differ in crucial ways that likely endow them with distinct functions. Their 5' exons have different promoters that drive expression in different cell types—Crb1-A in Müller glia and Crb1-B in photoreceptors—while their 3' exons encode different intracellular domains. The CRB1-A intracellular domain, like other vertebrate homologs of *Drosophila* Crumbs, contains two highly-conserved motifs mediating interactions with polarity proteins known as the Crumbs complex[66]. These motifs localize Crumbs homologs to apical junctions, where they are required for maintaining epithelial structural integrity and apico-basal polarity[33]. CRB1-B lacks these conserved motifs, suggesting a model whereby CRB1-A and -B operate in different cell types through different intracellular interaction partners.

Our findings have implications for the prevailing model of CRB1 disease, which posits that CRB1 and the Crumbs complex are required for integrity of OLM junctions between Müller glia and photoreceptors[26]. A major challenge for this model has been the lack of OLM phenotypes or photoreceptor degeneration in $Crb1^{ex1}$ mutants[37], which lack CRB1-A (FIG. 7A). As this mutant mouse was thought to be a null allele, its weak phenotype suggested that CRB1 might be dispensable for photoreceptor survival in mice[26]. Here we show that CRB1 is indeed required for OLM integrity and photoreceptor survival, but the mechanism critically involves the photoreceptor-specific CRB1-B isoform. Moreover, we show a genetic interaction between the two isoforms, revealing OLM integrity and pro-survival functions for CRB1-A that were obscured in the $Crb1^{ex1}$ mutant strain. We propose that the concerted action of CRB1-A in glia and CRB1-B in photoreceptors controls OLM integrity and photoreceptor health, perhaps through the assembly or maintenance of the junctional protein complex in each respective cell type.

The notion of concerted Crb1-A and Crb1-B function is further supported by the fact that $Crb1^{rd8}$, a point mutation affecting both isoforms (FIG. 7A), exhibits more degeneration than $Crb1^{ex1}$ [36,37,53]. However, $Crb1^{rd8}$ is clearly less severe than $Crb1^{null}$ (FIG. 8), even though both A and B isoforms are affected in both mutants. One possible reason for this difference is that $Crb1^{rd8}$ may not be a mRNA or protein null[53]. Another possibility is that the Crb1-C isoform may play a compensatory role, as it is unaffected by $Crb1^{rd8}$ (FIG. 7A). Either way, our results show that the design of mouse disease models is significantly enhanced when a complete isoform catalog is available.

Overall, our work highlights the value of building complete and accurate full-length isoform catalogs. Lack of such information can cause key gene functions to be overlooked and can lead to misinterpretation of genetic experiments and disease phenotypes. We expect the transcriptomic "ground truth" provided by deep long-read capture sequencing will be an important addition to the transcriptome annotation toolbox, enabling discovery of specific mRNA isoforms that contribute to a wide range of normal and disease processes.

REFERENCES

1. Raj, B. & Blencowe, B. J. Alternative Splicing in the Mammalian Nervous System: Recent Insights into Mechanisms and Functional Roles. *Neuron* 87, 14-27 (2015).
2. Reyes, A. & Huber, W. Alternative start and termination sites of transcription drive most transcript isoform differences across human tissues. *Nucleic Acids Res.* 46, 582-592 (2018).

3. Taliaferro, J. M. et al. Distal Alternative Last Exons Localize mRNAs to Neural Projections. *Mol. Cell* 61, 821-33 (2016).
4. Tushev, G. et al. Alternative 3' UTRs Modify the Localization, Regulatory Potential, Stability, and Plasticity of mRNAs in Neuronal Compartments. *Neuron* 98, 495-511.e6 (2018).
5. Furlanis, E., Traunmüller, L., Fucile, G. & Scheiffele, P. Landscape of ribosome-engaged transcript isoforms reveals extensive neuronal-cell-class-specific alternative splicing programs. *Nat. Neurosci.* 22, 1709-1717 (2019).
6. Takahashi, H. & Craig, A. M. Protein tyrosine phosphatases PTPδ, PTPσ, and LAR: presynaptic hubs for synapse organization. *Trends Neurosci.* 36, 522-34 (2013).
7. Lipscombe, D. & Lopez Soto, E. J. Alternative splicing of neuronal genes: new mechanisms and new therapies. *Curr. Opin. Neurobiol.* 57, 26-31 (2019).
8. Zipursky, S. L. & Sanes, J. R. Chemoaffinity revisited: dscams, protocadherins, and neural circuit assembly. *Cell* 143, 343-53 (2010).
9. Gandal, M. J. et al. Transcriptome-wide isoform-level dysregulation in ASD, schizophrenia, and bipolar disorder. *Science* (80-.). 362, eaat8127 (2018).
10. Taylor, J. P., Brown, R. H. & Cleveland, D. W. Decoding ALS: from genes to mechanism. *Nature* 539, 197-206 (2016).
11. Li, Y. I. et al. *RNA splicing is a primary link between genetic variation and disease. Science* 352, 600-4 (2016).
12. Morillon, A. & Gautheret, D. Bridging the gap between reference and real transcriptomes. *Genome Biol.* 20, 112 (2019).
13. Schmucker, D. et al. *Drosophila* Dscam is an axon guidance receptor exhibiting extraordinary molecular diversity. *Cell* 101, 671-84 (2000).
14. Chen, W. V. & Maniatis, T. Clustered protocadherins. *Development* 140, 3297-3302 (2013).
15. Schreiner, D. et al. Targeted Combinatorial Alternative Splicing Generates Brain Region-Specific Repertoires of Neurexins. *Neuron* 1-13 (2014). doi:10.1016/j.neuron.2014.09.011
16. Treutlein, B., Gokce, O., Quake, S. R. & Südhof, T. C. Cartography of neurexin alternative splicing mapped by single-molecule long-read mRNA sequencing. *Proc. Natl. Acad. Sci. U.S.A* 111, E1291-9 (2014).
17. Rubinstein, R. et al. Molecular Logic of Neuronal Self-Recognition through Protocadherin Domain Interactions. *Cell* 163, 629-642 (2015).
18. Wojtowicz, W. M. et al. A vast repertoire of Dscam binding specificities arises from modular interactions of variable Ig domains. *Cell* 130, 1134-45 (2007).
19. Furlanis, E. & Scheiffele, P. Regulation of Neuronal Differentiation, Function, and Plasticity by Alternative Splicing. *Annu. Rev. Cell Dev. Biol.* 34, 451-469 (2018).
20. Südhof, T. C. Neuroligins and neurexins link synaptic function to cognitive disease. *Nature* 455, 903-11 (2008).
21. Mulley, J. C., Scheffer, I. E., Petrou, S. & Berkovic, S. F. Channelopathies as a genetic cause of epilepsy. *Curr. Opin. Neurol.* 16, 171-6 (2003).
22. Pederick, D. T. et al. Abnormal Cell Sorting Underlies the Unique X-Linked Inheritance of PCDH19 Epilepsy. *Neuron* 97, 59-66.e5 (2018).
23. Hammond, T. R., Marsh, S. E. & Stevens, B. Immune Signaling in Neurodegeneration. *Immunity* 50, 955-974 (2019).
24. Hollingworth, P. et al. Common variants at ABCA7, MS4A6A/MS4A4E, EPHA1, CD33 and CD2AP are associated with Alzheimer's disease. *Nat. Genet.* 43, 429-35 (2011).
25. Naj, A. C. et al. Common variants at MS4A4/MS4A6E, CD2AP, CD33 and EPHA1 are associated with late-onset Alzheimer's disease. *Nat. Genet.* 43, 436-441 (2011).
26. Quinn, P. M., Pellissier, L. P. & Wijnholds, J. The CRB1 Complex: Following the Trail of Crumbs to a Feasible Gene Therapy Strategy. *Front. Neurosci.* 11, 175 (2017).
27. Au, K. F. et al. Characterization of the human ESC transcriptome by hybrid sequencing. *Proc. Natl. Acad. Sci. U.S.A* 110, E4821-30 (2013).
28. Byrne, A. et al. Nanopore long-read RNAseq reveals widespread transcriptional variation among the surface receptors of individual B cells. *Nat. Commun.* 8, 16027 (2017).
29. Gupta, I. et al. Single-cell isoform RNA sequencing characterizes isoforms in thousands of cerebellar cells. *Nat. Biotechnol.* 36, (2018).
30. Karlsson, K. & Linnarsson, S. Single-cell mRNA isoform diversity in the mouse brain. *BMC Genomics* 18, 126 (2017).
31. Bussotti, G. et al. Improved definition of the mouse transcriptome via targeted RNA sequencing. *Genome Res.* 26, 705-716 (2016).
32. Mercer, T. R. et al. Targeted RNA sequencing reveals the deep complexity of the human transcriptome. *Nat. Biotechnol.* 30, 99-104 (2012).
33. Thompson, B. J., Pichaud, F. & Röper, K. Sticking together the Crumbs—an unexpected function for an old friend. *Nat. Rev. Mol. Cell Biol.* 14, 307-14 (2013).
34. Vecino, E., Rodriguez, F. D., Ruzafa, N., Pereiro, X. & Sharma, S. C. Glia-neuron interactions in the mammalian retina. *Prog. Retin. Eye Res.* 51, 1-40 (2016).
35. Ehrenberg, M., Pierce, E. A., Cox, G. F. & Fulton, A. B. CRB1: one gene, many phenotypes. *Semin. Ophthalmol.* 28, 397-405 (2013).
36. Mehalow, A. K. et al. CRB1 is essential for external limiting membrane integrity and photoreceptor morphogenesis in the mammalian retina. *Hum. Mol. Genet.* 12, 2179-89 (2003).
37. van de Pavert, S. a et al. Crumbs homologue 1 is required for maintenance of photoreceptor cell polarization and adhesion during light exposure. *J. Cell Sci.* 117, 4169-77 (2004).
38. Hoshino, A. et al. Molecular Anatomy of the Developing Human Retina. *Dev. Cell* 43, 763-779.e4 (2017).
39. Peng, J. et al. High-Throughput Sequencing and Co-Expression Network Analysis of lncRNAs and mRNAs in Early Brain Injury Following Experimental Subarachnoid Haemorrhage. *Sci. Rep.* 7, 46577 (2017).
40. Lagarde, J. et al. High-throughput annotation of full-length long noncoding RNAs with capture long-read sequencing. *Nat. Genet.* 49, 1731-1740 (2017).
41. Shiraki, T. et al. Cap analysis gene expression for high-throughput analysis of transcriptional starting point and identification of promoter usage. *Proc. Natl. Acad. Sci.* 100, 15776-15781(2003).
42. Yasuda, M. et al. Retinal transcriptome profiling at transcription start sites: a cap analysis of gene expression early after axonal injury. *BMC Genomics* 15, 982 (2014).
43. Magurran, A. *Measuring Biological Diversity*. (Wiley-Blackwell, 2004).

44. Kay, J. N., Chu, M. W. & Sanes, J. R. MEGF10 and MEGF11 mediate homotypic interactions required for mosaic spacing of retinal neurons. *Nature* 483, 465-9 (2012).
45. Logan, M. a et al. Negative regulation of glial engulfment activity by Draper terminates glial responses to axon injury. *Nat. Neurosci.* 15, 722-30 (2012).
46. Baker, A.-M. et al. Robust RNA-based in situ mutation detection delineates colorectal cancer subclonal evolution. *Nat. Commun.* 8, 1998 (2017).
47. Erben, L., He, M.-X., Laeremans, A., Park, E. & Buonanno, A. A Novel Ultrasensitive In Situ Hybridization Approach to Detect Short Sequences and Splice Variants with Cellular Resolution. *Mol. Neurobiol.* 55, 6169-6181 (2018).
48. Clark, B. S. et al. Single-Cell RNA-Seq Analysis of Retinal Development Identifies NFI Factors as Regulating Mitotic Exit and Late-Born Cell Specification. *Neuron* 102, 1111-1126.e5 (2019).
49. van Rossum, A. G. S. H. et al. Pals1/Mpp5 is required for correct localization of Crb1 at the subapical region in polarized Müller glia cells. *Hum. Mol. Genet.* 15, 2659-72 (2006).
50. Lobanova, E. S. et al. Transducin gamma-subunit sets expression levels of alpha- and beta-subunits and is crucial for rod viability. *J. Neurosci.* 28, 3510-20 (2008).
51. Sokolov, M. et al. Massive light-driven translocation of transducin between the two major compartments of rod cells: a novel mechanism of light adaptation. *Neuron* 34, 95-106 (2002).
52. Moore, B. A. et al. A Population Study of Common Ocular Abnormalities in C57BL/6N rd8 Mice. *Investig. Opthalmology Vis. Sci.* 59, 2252 (2018).
53. Luhmann, U. F. O. et al. The severity of retinal pathology in homozygous Crb1rd8/rd8 mice is dependent on additional genetic factors. *Hum. Mol. Genet.* 24, 128-141 (2015).
54. Jiang, L. et al. Synthetic spike-in standards for RNA-seq experiments. *Genome Res.* 21, 1543-51 (2011).
55. Clark, M. B. et al. Quantitative gene profiling of long noncoding RNAs with targeted RNA sequencing. *Nat. Methods* 12, 339-42 (2015).
56. Sperry, R. W. Chemoaffinity in the orderly growth of nerve fiber patterns and connections. *Proc. Natl. Acad. Sci. U.S.A* 50, 703-10 (1963).
57. Hassan, B. A. & Hiesinger, P. R. Beyond Molecular Codes: Simple Rules to Wire Complex Brains. *Cell* 163, 285-291 (2015).
58. Lefebvre, J. L., Sanes, J. R. & Kay, J. N. Development of dendritic form and function. *Annu. Rev. Cell Dev. Biol.* 31, 741-77 (2015).
59. Zipursky, S. L. & Grueber, W. B. The molecular basis of self-avoidance. *Annu. Rev. Neurosci.* 36, 547-68 (2013).
60. Li, Y. et al. Splicing-Dependent Trans-synaptic SALM3-LAR-RPTP Interactions Regulate Excitatory Synapse Development and Locomotion. *Cell Rep.* 12, 1618-1630 (2015).
61. Sando, R., Jiang, X. & Südhof, T. C. Latrophilin GPCRs direct synapse specificity by coincident binding of FLRTs and teneurins. *Science* 363, eaav7969 (2019).
62. Yin, Y., Miner, J. H. & Sanes, J. R. Laminets: laminin- and netrin-related genes expressed in distinct neuronal subsets. *Mol. Cell. Neurosci.* 19, 344-58 (2002).
63. den Hollander, A. I. et al. Mutations in a human homologue of *Drosophila* crumbs cause retinitis pigmentosa (RP12). *Nat. Genet.* 23, 217-21 (1999).
64. den Hollander, A. I. et al. Leber Congenital Amaurosis and Retinitis Pigmentosa with Coats-like Exudative Vasculopathy Are Associated with Mutations in the Crumbs Homologue 1 (CRB1) *Gene. Am. J. Hum. Genet.* 69, 198-203 (2001).
65. Khan, K. N. et al. A clinical and molecular characterisation of CRB1-associated maculopathy. *Eur. J. Hum. Genet.* 26, 687-694 (2018).
66. den Hollander, A. I. et al. CRB1 has a cytoplasmic domain that is functionally conserved between human and *Drosophila. Hum. Mol. Genet.* 10, 2767-2773 (2001).
67. Tardaguila, M. et al. SQANTI: extensive characterization of long-read transcript sequences for quality control in full-length transcriptome identification and quantification. *Genome Res.* 28, 396-411 (2018).
68. Aldiri, I. et al. The Dynamic Epigenetic Landscape of the Retina During Development, Reprogramming, and Tumorigenesis. *Neuron* 94, 550-568.e10 (2017).
69. Hughes, A. E. O., Enright, J. M., Myers, C. A., Shen, S. Q. & Corbo, J. C. Cell Type-Specific Epigenomic Analysis Reveals a Uniquely Closed Chromatin Architecture in Mouse Rod Photoreceptors. *Sci. Rep.* 7, 43184 (2017).
70. Wang, J. et al. ATAC-Seq analysis reveals a widespread decrease of chromatin accessibility in age-related macular degeneration. *Nat. Commun.* 9, 1364 (2018).
71. Davis, C. A. et al. The Encyclopedia of DNA elements (ENCODE): data portal update. *Nucleic Acids Res.* 46, D794-D801 (2018).
72. Qiu, X. et al. Single-cell mRNA quantification and differential analysis with Census. *Nat. Methods* 14, 309-315 (2017).
73. Trapnell, C. et al. The dynamics and regulators of cell fate decisions are revealed by pseudotemporal ordering of single cells. *Nat. Biotechnol.* 32, 381-386 (2014).
74. Puñal, V. M. et al. Large-scale death of retinal astrocytes during normal development mediated by microglia. *bioRxiv* 593731 (2019). doi:10.1101/593731
75. Schindelin, J. et al. Fiji: an open-source platform for biological-image analysis. *Nat. Methods* 9, 676-82 (2012).
76. Smolders, K., Lombaert, N., Valkenborg, D., Baggerman, G. & Arckens, L. An effective plasma membrane proteomics approach for small tissue samples. *Sci. Rep.* 5, 10917 (2015).

What is claimed:

1. An isolated polynucleotide comprising a polynucleotide sequence encoding a Crumbs 1-B (CRB1-B) isoform comprising SEQ ID NO:1 operably linked to a heterologous promoter capable of expressing the isoform in a retinal cell.

2. The isolated polynucleotide of claim 1, wherein the sequence encoding the CRB1-B isoform is SEQ ID NO:2.

3. The isolated polypeptide of claim 1, wherein the retinal cell is selected from the group consisting of a photoreceptor cell, a retinal pigmented epithelial cell, a bipolar cell, a horizontal cell, an amacrine cell, a Müller cell, and/or a ganglion cell.

4. The isolated polypeptide of claim 1, wherein the heterologous promoter is selected from the group consisting of a rhodopsin kinase (RK) promoter, an opsin promoter, a Cytomegalovirus (CMV) promoter, and a chicken β-actin (CBA promoter).

5. The isolated polynucleotide of claim 1, is in a viral vector.

6. The isolated polynucleotide of claim 5, wherein the viral vector is an AAV vector.

7. A pharmaceutical composition comprising the isolated polynucleotide of claim 1 and a pharmaceutically acceptable carrier.

8. The pharmaceutical composition of claim 7, further comprising a second vector encoding CRB1-A, CRB1-A2, CRB1-C, or combinations thereof.

9. A kit for treating an ocular disorder, reducing progression of an ocular disorder, reducing loss of vision, or maintaining vision function in a subject, the kit comprising the isolated polynucleotide of claim 1, a device for delivery of the isolated polynucleotide to the subject, and instructions for use.

10. The kit according to claim 9, in which the delivery comprises subretinal, intravitreal, or topical delivery.

* * * * *

SEQUENCE LISTING

<160> NUMBER OF SEQ ID NOS: 100

<210> SEQ ID NO 1
<211> LENGTH: 1003
<212> TYPE: PRT
<213> ORGANISM: Homo sapiens

<400> SEQUENCE: 1

```
Met Phe Gly Ala Arg Thr His Gly Phe His Ile Leu Met Ala Met Leu
1               5                   10                  15

Ile Gly Ile His Cys Glu Glu Asp Val Asn Glu Cys Ser Ser Asn Pro
            20                  25                  30

Cys Gln Asn Gly Gly Thr Cys Glu Asn Leu Pro Gly Asn Tyr Thr Cys
        35                  40                  45

His Cys Pro Phe Asp Asn Leu Ser Arg Thr Phe Tyr Gly Gly Arg Asp
    50                  55                  60

Cys Ser Asp Ile Leu Leu Gly Cys Thr His Gln Gln Cys Leu Asn Asn
65                  70                  75                  80

Gly Thr Cys Ile Pro His Phe Gln Asp Gly Gln His Gly Phe Ser Cys
                85                  90                  95

Leu Cys Pro Ser Gly Tyr Thr Gly Ser Leu Cys Glu Ile Ala Thr Thr
            100                 105                 110

Leu Ser Phe Glu Gly Asp Gly Phe Leu Trp Val Lys Ser Gly Ser Val
        115                 120                 125

Thr Thr Lys Gly Ser Val Cys Asn Ile Ala Leu Arg Phe Gln Thr Val
    130                 135                 140

Gln Pro Met Ala Leu Leu Leu Phe Arg Ser Asn Arg Asp Val Phe Val
145                 150                 155                 160

Lys Leu Glu Leu Leu Ser Gly Tyr Ile His Leu Ser Ile Gln Val Asn
                165                 170                 175

Asn Gln Ser Lys Val Leu Leu Phe Ile Ser His Asn Thr Ser Asp Gly
            180                 185                 190

Glu Trp His Phe Val Glu Val Ile Phe Ala Glu Ala Val Thr Leu Thr
        195                 200                 205

Leu Ile Asp Asp Ser Cys Lys Glu Lys Cys Ile Ala Lys Ala Pro Thr
    210                 215                 220

Pro Leu Glu Ser Asp Gln Ser Ile Cys Ala Phe Gln Asn Ser Phe Leu
225                 230                 235                 240

Gly Gly Leu Pro Val Gly Met Thr Ser Asn Gly Val Ala Leu Leu Asn
                245                 250                 255

Phe Tyr Asn Met Pro Ser Thr Pro Ser Phe Val Gly Cys Leu Gln Asp
            260                 265                 270

Ile Lys Ile Asp Trp Asn His Ile Thr Leu Glu Asn Ile Ser Ser Gly
        275                 280                 285

Ser Ser Leu Asn Val Lys Ala Gly Cys Val Arg Lys Asp Trp Cys Glu
    290                 295                 300

Ser Gln Pro Cys Gln Ser Arg Gly Arg Cys Ile Asn Leu Trp Leu Ser
305                 310                 315                 320

Tyr Gln Cys Asp Cys His Arg Pro Tyr Glu Gly Pro Asn Cys Leu Arg
                325                 330                 335

Glu Tyr Val Ala Gly Arg Phe Gly Gln Asp Asp Ser Thr Gly Tyr Val
            340                 345                 350

Ile Phe Thr Leu Asp Glu Ser Tyr Gly Asp Thr Ile Ser Leu Ser Met
        355                 360                 365

Phe Val Arg Thr Leu Gln Pro Ser Gly Leu Leu Leu Ala Leu Glu Asn
    370                 375                 380

Ser Thr Tyr Gln Tyr Ile Arg Val Trp Leu Glu Arg Gly Arg Leu Ala
385                 390                 395                 400

Met Leu Thr Pro Asn Ser Pro Lys Leu Val Val Lys Phe Val Leu Asn
                405                 410                 415
```

```
Asp Gly Asn Val His Leu Ile Ser Leu Lys Ile Lys Pro Tyr Lys Ile
            420                 425                 430

Glu Leu Tyr Gln Ser Ser Gln Asn Leu Gly Phe Ile Ser Ala Ser Thr
        435                 440                 445

Trp Lys Ile Glu Lys Gly Asp Val Ile Tyr Ile Gly Gly Leu Pro Asp
    450                 455                 460

Lys Gln Glu Thr Glu Leu Asn Gly Gly Phe Phe Lys Gly Cys Ile Gln
465                 470                 475                 480

Asp Val Arg Leu Asn Asn Gln Asn Leu Glu Phe Phe Pro Asn Pro Thr
                485                 490                 495

Asn Asn Ala Ser Leu Asn Pro Val Leu Val Asn Val Thr Gln Gly Cys
            500                 505                 510

Ala Gly Asp Asn Ser Cys Lys Ser Asn Pro Cys His Asn Gly Gly Val
        515                 520                 525

Cys His Ser Arg Trp Asp Asp Phe Ser Cys Ser Cys Pro Ala Leu Thr
    530                 535                 540

Ser Gly Lys Ala Cys Glu Glu Val Gln Trp Cys Gly Phe Ser Pro Cys
545                 550                 555                 560

Pro His Gly Ala Gln Cys Gln Pro Val Leu Gln Gly Phe Glu Cys Ile
                565                 570                 575

Ala Asn Ala Val Phe Asn Gly Gln Ser Gly Gln Ile Leu Phe Arg Ser
            580                 585                 590

Asn Gly Asn Ile Thr Arg Glu Leu Thr Asn Ile Thr Phe Gly Phe Arg
        595                 600                 605

Thr Arg Asp Ala Asn Val Ile Ile Leu His Ala Glu Lys Glu Pro Glu
    610                 615                 620

Phe Leu Asn Ile Ser Ile Gln Asp Ser Arg Leu Phe Phe Gln Leu Gln
625                 630                 635                 640

Ser Gly Asn Ser Phe Tyr Met Leu Ser Leu Thr Ser Leu Gln Ser Val
                645                 650                 655

Asn Asp Gly Thr Trp His Glu Val Thr Leu Ser Met Thr Asp Pro Leu
            660                 665                 670

Ser Gln Thr Ser Arg Trp Gln Met Glu Val Asp Asn Glu Thr Pro Phe
        675                 680                 685

Val Thr Ser Thr Ile Ala Thr Gly Ser Leu Asn Phe Leu Lys Asp Asn
    690                 695                 700

Thr Asp Ile Tyr Val Gly Asp Arg Ala Ile Asp Asn Ile Lys Gly Leu
705                 710                 715                 720

Gln Gly Cys Leu Ser Thr Ile Glu Ile Gly Gly Ile Tyr Leu Ser Tyr
                725                 730                 735

Phe Glu Asn Val His Gly Phe Ile Asn Lys Pro Gln Glu Glu Gln Phe
            740                 745                 750

Leu Lys Ile Ser Thr Asn Ser Val Val Thr Gly Cys Leu Gln Leu Asn
        755                 760                 765

Val Cys Asn Ser Asn Pro Cys Leu His Gly Gly Asn Cys Glu Asp Ile
    770                 775                 780

Tyr Ser Ser Tyr His Cys Ser Cys Pro Leu Gly Trp Ser Gly Lys His
785                 790                 795                 800

Cys Glu Leu Asn Ile Asp Glu Cys Phe Ser Asn Pro Cys Ile His Gly
                805                 810                 815

Asn Cys Ser Asp Arg Val Ala Ala Tyr His Cys Thr Cys Glu Pro Gly
            820                 825                 830

Tyr Thr Gly Val Asn Cys Glu Val Asp Ile Asp Asn Cys Gln Ser His
```

```
        835                 840                 845

Gln Cys Ala Asn Gly Ala Thr Cys Ile Ser His Thr Asn Gly Tyr Ser
    850                 855                 860

Cys Leu Cys Phe Gly Asn Phe Thr Gly Lys Phe Cys Arg Gln Ser Arg
865                 870                 875                 880

Leu Pro Ser Thr Val Cys Gly Asn Glu Lys Thr Asn Leu Thr Cys Tyr
                885                 890                 895

Asn Gly Gly Asn Cys Thr Glu Phe Gln Thr Glu Leu Lys Cys Met Cys
            900                 905                 910

Arg Pro Gly Phe Thr Gly Glu Trp Cys Glu Lys Asp Ile Asp Glu Cys
        915                 920                 925

Ala Ser Asp Pro Cys Val Asn Gly Gly Leu Cys Gln Asp Leu Leu Asn
    930                 935                 940

Lys Phe Gln Cys Leu Cys Asp Val Ala Phe Ala Gly Glu Arg Cys Glu
945                 950                 955                 960

Val Asp Val Ser Ser Leu Ser Phe Tyr Val Ser Leu Leu Phe Trp Gln
                965                 970                 975

Asn Leu Phe Gln Leu Leu Ser Tyr Leu Ile Leu Arg Met Asn Asp Glu
            980                 985                 990

Pro Val Val Glu Trp Gly Glu Gln  Glu Asp Tyr
        995                 1000
```

<210> SEQ ID NO 2
<211> LENGTH: 5621
<212> TYPE: DNA
<213> ORGANISM: Homo sapiens
<220> FEATURE:
<221> NAME/KEY: misc_feature
<222> LOCATION: (204)..(206)
<223> OTHER INFORMATION: Start codon

<400> SEQUENCE: 2

```
agcacaaatg agtcttacac taagccacac tgatccagct tggagggaaa tgagtcaaaa     60

ccaagtcccc atactctcta cctgcgagaa agaggtgaca ttgaagaaca agcccacact    120

tctggatatg gtccaaaatg atcagaaact cactctgtca acctagtagg tgtttggatg    180

gatacctctt ttttaacaga aagatgtttg gagccaggac acatggtttt cacattttaa    240

tggcaatgct cataggaatc cactgcgaag aagacgtcaa tgaatgttct tcaaaccctt    300

gccaaaatgg tggtacttgt gagaacttgc ctgggaatta tacttgccat tgcccatttg    360

ataacctttc tagaactttt tatggaggaa gggactgttc tgatattctc ctgggctgta    420

cccatcagca atgtctaaat aatggaacat gcatccctca cttccaagat ggccagcatg    480

gattcagctg cctatgtcca tctggctaca ccgggtccct gtgtgaaatc gcaaccacac    540

tttcatttga gggcgatggc ttcctgtggg tcaaaagtgg ctcagtgaca accaagggct    600

cagtttgtaa catagccctc aggtttcaga ctgttcagcc aatggctctt ctacttttcc    660

gaagcaacag ggatgtgttt gtgaagctgg agctgctaag tggctacatt cacttatcaa    720

ttcaggtcaa taatcagtca aaggtgcttc tgttcatttc ccacaacacc agcgatggag    780

agtggcattt cgtggaggta atatttgcag aggctgtgac ccttacctta atcgacgact    840

cctgtaagga gaaatgcatc gcgaaagctc ctactccact tgaaagtgat caatcaatat    900

gtgcttttca gaactccttt ttgggtggtt taccagtggg aatgaccagc aatggtgttg    960

ctctgcttaa cttctataat atgccatcca caccttcgtt tgtaggctgt ctccaagaca   1020

ttaaaattga ttggaatcac attaccctgg agaacatctc gtctggctca tcattaaatg   1080
```

-continued

```
tcaaggcagg ctgtgtgaga aaggattggt gtgaaagcca accttgtcaa agcagaggac   1140
gctgcatcaa cttgtggctg agttaccagt gtgactgcca caggccctat gaaggcccca   1200
actgtctgag agagtatgtg gcaggcagat ttggccagga tgactccact ggttatgtca   1260
tctttactct tgatgagagc tatggagaca ccatcagcct ctccatgttt gtccgaacgc   1320
ttcaaccatc aggcttactt ctagctttgg aaaacagcac ttatcaatat atccgtgtct   1380
ggctagagcg cggcagacta gcaatgctga ctccaaactc tcccaaatta gtagtaaaat   1440
ttgttcttaa tgatggaaat gtccacttga tatctttgaa aatcaagcca tataaaattg   1500
aactgtatca gtcttcacaa aacctaggat ttatttctgc ttctacgtgg aaaatcgaaa   1560
agggagatgt catctacatt ggtggcctac ctgacaagca agagactgaa cttaatggtg   1620
gattcttcaa aggctgtatc caagatgtaa gactaaacaa ccaaaatctg gaattctttc   1680
caaatccaac aaacaatgca tctctcaatc cagttcttgt caatgtaacc caaggctgtg   1740
ctggagacaa cagctgcaag tccaacccct gtcacaatgg aggtgtttgc cattcccggt   1800
gggatgactt ctcctgttcc tgtcctgccc tcacaagtgg gaaagcctgt gaggaggttc   1860
agtggtgtgg attcagcccg tgtcctcacg gagcccagtg ccagccggtg cttcaaggat   1920
ttgaatgtat tgcaaatgct gtttttaatg gacaaagcgg tcaaatatta ttcagaagca   1980
atgggaatat taccagagaa ctcaccaata tcacatttgg tttcagaaca agggatgcaa   2040
atgtaataat attgcatgca gaaaaagagc ctgaatttct taatattagc attcaagatt   2100
ccagattatt ctttcaattg caaagtggca acagctttta tatgctaagt ctgacaagtt   2160
tgcagtcagt gaatgatggc acatggcacg aagtgaccct ttccatgaca gacccactgt   2220
cccagacctc caggtggcaa atggaagtgg acaacgaaac accttttgtg accagcacaa   2280
ttgctactgg aagcctcaac tttttgaagg ataatacaga tatttatgtg ggagacagag   2340
ctattgacaa tataaagggc ctgcaagggt gtctaagtac aatagaaatc ggaggcattt   2400
atctctctta ctttgaaaat gttcatggtt tcattaataa acctcaggaa gagcaatttc   2460
tcaaaatctc taccaattca gtggtcactg gctgtttgca gttaaatgtc tgcaactcca   2520
acccctgttt gcatggagga aactgtgaag acatctatag ctcttatcat tgctcctgtc   2580
ccttgggatg gtcagggaaa cactgtgaac tcaacatcga tgaatgcttt tcaaacccct   2640
gtatccatgg caactgctct gacagagttg cagcctacca ctgcacatgt gagcctggat   2700
acactggtgt gaactgtgaa gtggatatag acaactgcca gagtcaccag tgtgcaaatg   2760
gagccacctg cattagtcat actaatggct attcttgcct ctgttttgga aattttacag   2820
gaaaattttg cagacagagc agattaccct caacagtctg tgggaatgag aagacaaatc   2880
tcacttgcta caatggaggc aactgcacag agttccagac tgaattaaaa tgtatgtgcc   2940
ggccaggttt tactggagaa tggtgtgaaa aggacattga tgagtgtgcc tctgatccgt   3000
gtgtcaatgg aggtctgtgc caggacttac tcaacaaatt ccagtgcctc tgtgatgttg   3060
cctttgctgg cgagcgctgc gaggtggacg taagcagcct ctccttttat gtctctctct   3120
tattctggca gaatcttttt cagcttcttt cttacctcat tttgcgtatg aatgacgagc   3180
cagttgttga gtggggtgaa caggaagatt attaacatac atttgaacat tcccaaatga   3240
aaaaaaaagc cattgaattt caagaaatgc cttgattcat tttagatctc tggggaagaa   3300
aaaggaaata aaaaccatct caataattaa ggtaaattca aggcttattt taaacatatc   3360
agaagcactt tgtctgtgta taaaatattt tcctattcta actttaaata tgaaaaaagt   3420
```

-continued

```
gttcttaata taactagaaa tatctcctta ttgtgtgtat ttagtacaaa catattatca   3480
ttctcaacac ttctatatgt gaatgaccac tgcaatttct tcccactcca tttctgggta   3540
ttttcacatt ttaagttgcc ctccatcact atgattctat tttcatttct gttctttcat   3600
tcttatctat tatttatgac acaaaaattg agaattacag gccaggtgtg gtggttcact   3660
cctataatcc cagcactatg ggaggctgaa gtgggcggaa cacctgaggc caggagtttg   3720
agaccagcct agccaacgtg gtgaaaacct gtctctacta aaaatacaaa agtaactggg   3780
agtggtggca catgcctgta atcccagcta ctcaggaggg tgaagcagga gacttgcttg   3840
aacccaggag gcggccgttg caatgagcca agattgtgcc actgcactcc agcctgggcg   3900
acaggtgaga ttctgtctaa aaaaaaaaaa aaaaaaagag agaattaccg attaaaatta   3960
ctgattatat tcatctatgt ttttacatga agctattcaa atgaattgtt acgttttctc   4020
tgatatatga ttaaatatat aaagagaaat caggaattta catcgagtcc ctaaattgta   4080
gaaaaacaat tatctagtat cagtactcaa attatacctc cctggtataa tttctgattc   4140
cataaaactg tctctctaac aaagttacaa ataatccttt ctctatttcc tttcctgcaa   4200
tactttccct tttcctaaca aatagaacaa tttttctgtt gtttctaaat ttatgagctc   4260
cttgactttt ctatcaaatg gactaatttc agttgctttt caatgaatat ttaataaaaa   4320
taagcactgt agtttataca taaatttaaa agtatatatt gtaaaacttg aattttctta   4380
gaagcatggt tttctaagat ttgcaagtaa atttattttc ttaagtatct ttcagaaaaa   4440
aatatgaaag catagtatac atcataacca aaatatattt gacattatga tttttttaaaa   4500
taaatgtata cctgaaataa tggatctata aagtatacta agatatgcaa aaattaatat   4560
attctttatt ataaatattt cagagattat aaaataataa tttaaaaaaa ctttcttaat   4620
gtttttattg tttccaccag tacgttatca tttatgctaa atatctttgt gtagatatac   4680
ccttccaaag aagacgttat ttgtgttcat ttaaaggaaa aatagtttga tcctatgaat   4740
taattcagaa agcaactaaa ataacaatgg cctgccaaat gtcattttgt aaatatacgt   4800
ctatgacttt aggagctgtc ctggtttgaa aacatgagga cagtttatcc attggatgcc   4860
atctatttag tcccaattaa gaaagttgtt tttttgtgag aatgaccaag gtaaatttaa   4920
atataccatt caaacaaaca aggacaaaat aatatccttg ttatagagta catgtagcat   4980
atagtatgaa gtaatatact acaaaagcaa agaaagtgta ttctatcttg caatagtaat   5040
agacaatttt tatatagcaa attcatatcc tttggagtag tgacaatcat ttcaaactgg   5100
gagcaactaa ttgtgaagat tttccttctt actcatccat tttcttcaca tccaaggctg   5160
aacgtgtgat gctgctgctt cagatgattt gttccaaagt taaattttgt gacaaaagac   5220
atggggaaaa ccttcccatc aatatttaca ttcacaagta tttgcaataa gcataaaata   5280
gattatagcc agaccatatg tatagttttc acatttactc ccttctagac atacctgtac   5340
ttatgtactt acaggctgtt ccaaatgtaa tatgttctct accaaatgtg gttaagaaat   5400
attcactcac aatttctttc tgtgtacaat tctgatgcct ctgttgtcac tgtaattgtc   5460
agttgctttt ctgttttcca aatgtcttct tgtcataagg tatctgactt taaaaaatgt   5520
tttccctttt ctttttattc ttctgtattt tccagctgca tgtgtgtgac tatggctttt   5580
acatatttgc acagaaaaat aaaacctttg tttctgtatc t                         5621
```

<210> SEQ ID NO 3
<211> LENGTH: 41
<212> TYPE: PRT
<213> ORGANISM: Homo sapiens

<400> SEQUENCE: 3

Val Ser Ser Leu Ser Phe Tyr Val Ser Leu Leu Phe Trp Gln Asn Leu
1 5 10 15

Phe Gln Leu Leu Ser Tyr Leu Ile Leu Arg Met Asn Asp Glu Pro Val
20 25 30

Val Glu Trp Gly Glu Gln Glu Asp Tyr
35 40

<210> SEQ ID NO 4
<211> LENGTH: 5619
<212> TYPE: DNA
<213> ORGANISM: Homo sapiens

<400> SEQUENCE: 4
acactattct aatgtaggcc cttttgagga ggcagcatga acagaagaaa actcgcagca 60
aaggcttgag gggggaatga atccaatcca gcctgaaaaa atctgcacca ggtttgaaaa 120
atcaccccat cctcccgtgt aagtgatgct aagaagcaca aactgcattt tgaatctaag 180
tccctgtatt ttctgtgaag gagctgtaag tagggtggga cagagatggc acctgggggt 240
tctgaggcac ccgctcctct ctgagacaga cagggatcag gagccggact gggaccagac 300
caccagcaac acaccagagg atgttctcta aataagacca tggcacttaa gaacattaac 360
taccttctca tcttctacct cagtttctca ctgcttatct acataaaaaa ttccttttgc 420
aataaaaaca acaccaggtg cctctcaaat tcttgccaaa acaattctac atgcaaagat 480
ttttcaaaag acaatgattg ttcttgttca gacacagcca ataatttgga caaagactgt 540
gacaacatga aagacccttg cttctccaat ccctgtcaag gaagtgccac ttgtgtgaac 600
accccaggag aaaggagctt tctgtgcaaa tgtcctcctg ggtacagtgg gacaatctgt 660
gaaactacca ttggttcctg tggcaagaac tcctgccaac atggaggtat ttgccatcag 720
gaccctattt atcctgtctg catctgccct gctggatatg ctggaagatt ctgtgagata 780
gatcacgatg agtgtgcttc cagcccttgc caaaatgggg ccgtgtgcca ggatggaatt 840
gatggttact cctgcttctg tgtcccagga tatcaaggca gacactgcga cttggaagtg 900
gatgaatgtg cttcagatcc ctgcaagaac gaggctacat gcctcaatga aataggaaga 960
tatacttgta tctgtcccca caattattct ggtgtaaact gtgaattgga aattgacgaa 1020
tgttggtccc agccttgttt aaatggtgca acttgtcagg atgctctggg ggcctatttc 1080
tgcgactgtg cccctggatt cctgggggat cactgtgaac tcaacactga tgagtgtgcc 1140
agtcaacctt gtctccatgg agggctgtgt gtggatggag aaaacagata tagctgtaac 1200
tgcacgggta gtggattcac agggacacac tgtgagacct tgatgcctct ttgttggtca 1260
aaaccttgtc acaataatgc tacatgtgag gacagtgttg acaattacac ttgtcactgc 1320
tggcctggat acacaggtgc ccagtgtgag atcgacctca atgaatgcaa tagtaacccc 1380
tgccagtcca atggggaatg tgtggagctg tcctcagaga aacaatatgg acgcatcact 1440
ggactgcctt cttctttcag ctaccatgaa gcctcaggtt atgtctgtat ctgtcagcct 1500
ggattcacag gaatccactg cgaagaagac gtcaatgaat gttcttcaaa cccttgccaa 1560
aatggtggta cttgtgagaa cttgcctggg aattatactt gccattgccc atttgataac 1620
ctttctagaa ctttttatgg aggaagggac tgttctgata ttctcctggg ctgtacccat 1680
cagcaatgtc taaataatgg aacatgcatc cctcacttcc aagatggcca gcatggattc 1740
agctgcctat gtccatctgg ctacaccggg tccctgtgtg aaatcgcaac cacactttca 1800

```
tttgagggcg atggcttcct gtgggtcaaa agtggctcag tgacaaccaa gggctcagtt   1860
tgtaacatag ccctcaggtt tcagactgtt cagccaatgg ctcttctact tttccgaagc   1920
aacagggatg tgtttgtgaa gctggagctg ctaagtggct acattcactt atcaattcag   1980
gtcaataatc agtcaaaggt gcttctgttc atttcccaca acaccagcga tggagagtgg   2040
catttcgtgg aggtaatatt tgcagaggct gtgaccctta ccttaatcga cgactcctgt   2100
aaggagaaat gcatcgcgaa agctcctact ccacttgaaa gtgatcaatc aatatgtgct   2160
tttcagaact cctttttggg tggtttacca gtgggaatga ccagcaatgg tgttgctctg   2220
cttaacttct ataatatgcc atccacacct tcgtttgtag gctgtctcca agacattaaa   2280
attgattgga atcacattac cctggagaac atctcgtctg gctcatcatt aaatgtcaag   2340
gcaggctgtg tgagaaagga ttggtgtgaa agccaacctt gtcaaagcag aggacgctgc   2400
atcaacttgt ggctgagtta ccagtgtgac tgccacaggc cctatgaagg ccccaactgt   2460
ctgagagagt atgtggcagg cagatttggc caggatgact ccactggtta tgtcatcttt   2520
actcttgatg agagctatgg agacaccatc agcctctcca tgtttgtccg aacgcttcaa   2580
ccatcaggct tacttctagc tttggaaaac agcacttatc aatatatccg tgtctggcta   2640
gagcgcggca gactagcaat gctgactcca aactctccca aattagtagt aaaatttgtt   2700
cttaatgatg gaaatgtcca cttgatatct ttgaaaatca agccatataa aattgaactg   2760
tatcagtctt cacaaaacct aggatttatt tctgcttcta cgtggaaaat cgaaaaggga   2820
gatgtcatct acattggtgg cctacctgac aagcaagaga ctgaacttaa tggtggattc   2880
ttcaaaggct gtatccaaga tgtaagacta aacaaccaaa atctggaatt ctttccaaat   2940
ccaacaaaca atgcatctct caatccagtt cttgtcaatg taacccaagg ctgtgctgga   3000
gacaacagct gcaagtccaa cccctgtcac aatggaggtg tttgccattc ccggtgggat   3060
gacttctcct gttcctgtcc tgccctcaca agtgggaaag cctgtgagga ggttcagtgg   3120
tgtggattca gcccgtgtcc tcacggagcc cagtgccagc cggtgcttca aggatttgaa   3180
tgtattgcaa atgctgtttt taatggacaa agcggtcaaa tattattcag aagcaatggg   3240
aatattacca gagaactcac caatatcaca tttggtttca gaacaaggga tgcaaatgta   3300
ataatattgc atgcagaaaa agagcctgaa tttcttaata ttagcattca agattccaga   3360
ttattctttc aattgcaaag tggcaacagc ttttatatgc taagtctgac aagtttgcag   3420
tcagtgaatg atggcacatg gcacgaagtg acccttttcca tgacagaccc actgtcccag   3480
acctccaggt ggcaaatgga agtggacaac gaaacacctt ttgtgaccag cacaattgct   3540
actggaagcc tcaacttttt gaaggataat acagatattt atgtgggaga cagagctatt   3600
gacaatataa agggcctgca agggtgtcta agtacaatag aaatcggagg catttatctc   3660
tcttactttg aaaatgttca tggtttcatt aataaacctc aggaagagca atttctcaaa   3720
atctctacca attcagtggt cactggctgt ttgcagttaa atgtctgcaa ctccaacccc   3780
tgtttgcatg gaggaaactg tgaagacatc tatagctctt atcattgctc ctgtcccttg   3840
ggatggtcag ggaaacactg tgaactcaac atcgatgaat gcttttcaaa cccctgtatc   3900
catggcaact gctctgacag agttgcagcc taccactgca catgtgagcc tggatacact   3960
ggtgtgaact gtgaagtgga tatagacaac tgccagagtc accagtgtgc aaatggagcc   4020
acctgcatta gtcatactaa tggctattct tgcctctgtt ttggaaattt tacaggaaaa   4080
ttttgcagac agagcagatt accctcaaca gtctgtggga atgagaagac aaatctcact   4140
```

```
tgctacaatg gaggcaactg cacagagttc cagactgaat taaaatgtat gtgccggcca   4200

ggttttactg gagaatggtg tgaaaaggac attgatgagt gtgcctctga tccgtgtgtc   4260

aatggaggtc tgtgccagga cttactcaac aaattccagt gcctctgtga tgttgccttt   4320

gctggcgagc gctgcgaggt ggacttggca gatgacttga tctccgacat tttcaccact   4380

attggctcag tgactgtcgc cttgttactg atcctcttgc tggccattgt tgcttctgtt   4440

gtcacctcca acaaaagggc aactcaggga acctacagcc ccagccgtca ggagaaggag   4500

ggctcccgag tggaaatgtg gaacttgatg ccaccccctg caatggagag actgatttag   4560

gagcattgtg tcccttcgag atggggatcc acacactgtg aatgtgatga ctgtacttca   4620

ggtatctctg acatacctga caatgttaat ctgcaactgg gattacactg gaactacagg   4680

aatgattcct ttgaccacct taaaaacttt cacagtggtt ccgctcgaca ccattgtttt   4740

attatattat atcagccaat tgcaaaaaaa gtctgtgcca gtaatttcag ccttataatt   4800

agcaaaaaca tcttccagag aataaagtct tctgtggctt tagtggctat cactgaaact   4860

ctttcctctt ttcaacctgg gaacaaattt tagttttcat tttaggtttc tgtactttct   4920

gtagtttctg tgtaaactgc catatgttta catggaaact acaggaaaaa attggctaca   4980

tttctcactt ctcctatcat gtggtcaaag ttattgttgt ataccagcga tgggatgtat   5040

acttttgtcc ttcattcatg gattcagaga aagctctggg aatgacttat ggtccaaaaa   5100

agtgacccaa tggcaacaaa taaaaattga aatgcagttg ttctcctttc tgagtacttt   5160

ttgcattttt gtgacattat gtgtgacaaa agtaacctct aggaacattt gaagaacctg   5220

cttatgaatt agacctttta cctaaatcat ttcaagttgg ttacattttc aaattattac   5280

tctttgtaaa gggttggtta aggcaaaacg cttcctagat agaaatcaaa acggggaaaa   5340

ctcagattct caagttcgaa aaatcgagtt cttttcttcc aactgctttt aggtaaatca   5400

gtgccaaaca gtgacattgt ttaaaggtaa gaactccaaa gttaaatgta tgcactttac   5460

ggagtatgtg ttttaagact atgggatatt tggagaaaat gctggggttt ctattcttat   5520

atttcttctt acaaagcatc tgattatatt tttatatgtg ctttgaaata tatgaaacat   5580

gctactgctg tagaatataa ataaaactta agaatagat                          5619
```

<210> SEQ ID NO 5
<211> LENGTH: 1406
<212> TYPE: PRT
<213> ORGANISM: Homo sapiens

<400> SEQUENCE: 5

```
Met Ala Leu Lys Asn Ile Asn Tyr Leu Leu Ile Phe Tyr Leu Ser Phe
1               5                   10                  15

Ser Leu Leu Ile Tyr Ile Lys Asn Ser Phe Cys Asn Lys Asn Asn Thr
            20                  25                  30

Arg Cys Leu Ser Asn Ser Cys Gln Asn Asn Ser Thr Cys Lys Asp Phe
        35                  40                  45

Ser Lys Asp Asn Asp Cys Ser Cys Ser Asp Thr Ala Asn Asn Leu Asp
    50                  55                  60

Lys Asp Cys Asp Asn Met Lys Asp Pro Cys Phe Ser Asn Pro Cys Gln
65                  70                  75                  80

Gly Ser Ala Thr Cys Val Asn Thr Pro Gly Glu Arg Ser Phe Leu Cys
                85                  90                  95

Lys Cys Pro Pro Gly Tyr Ser Gly Thr Ile Cys Glu Thr Thr Ile Gly
            100                 105                 110
```

```
Ser Cys Gly Lys Asn Ser Cys Gln His Gly Gly Ile Cys His Gln Asp
        115                 120                 125

Pro Ile Tyr Pro Val Cys Ile Cys Pro Ala Gly Tyr Ala Gly Arg Phe
    130                 135                 140

Cys Glu Ile Asp His Asp Glu Cys Ala Ser Ser Pro Cys Gln Asn Gly
145                 150                 155                 160

Ala Val Cys Gln Asp Gly Ile Asp Gly Tyr Ser Cys Phe Cys Val Pro
                165                 170                 175

Gly Tyr Gln Gly Arg His Cys Asp Leu Glu Val Asp Glu Cys Ala Ser
            180                 185                 190

Asp Pro Cys Lys Asn Glu Ala Thr Cys Leu Asn Glu Ile Gly Arg Tyr
        195                 200                 205

Thr Cys Ile Cys Pro His Asn Tyr Ser Gly Val Asn Cys Glu Leu Glu
    210                 215                 220

Ile Asp Glu Cys Trp Ser Gln Pro Cys Leu Asn Gly Ala Thr Cys Gln
225                 230                 235                 240

Asp Ala Leu Gly Ala Tyr Phe Cys Asp Cys Ala Pro Gly Phe Leu Gly
                245                 250                 255

Asp His Cys Glu Leu Asn Thr Asp Glu Cys Ala Ser Gln Pro Cys Leu
            260                 265                 270

His Gly Gly Leu Cys Val Asp Gly Glu Asn Arg Tyr Ser Cys Asn Cys
        275                 280                 285

Thr Gly Ser Gly Phe Thr Gly Thr His Cys Glu Thr Leu Met Pro Leu
    290                 295                 300

Cys Trp Ser Lys Pro Cys His Asn Asn Ala Thr Cys Glu Asp Ser Val
305                 310                 315                 320

Asp Asn Tyr Thr Cys His Cys Trp Pro Gly Tyr Thr Gly Ala Gln Cys
                325                 330                 335

Glu Ile Asp Leu Asn Glu Cys Asn Ser Asn Pro Cys Gln Ser Asn Gly
            340                 345                 350

Glu Cys Val Glu Leu Ser Ser Glu Lys Gln Tyr Gly Arg Ile Thr Gly
        355                 360                 365

Leu Pro Ser Ser Phe Ser Tyr His Glu Ala Ser Gly Tyr Val Cys Ile
    370                 375                 380

Cys Gln Pro Gly Phe Thr Gly Ile His Cys Glu Glu Asp Val Asn Glu
385                 390                 395                 400

Cys Ser Ser Asn Pro Cys Gln Asn Gly Gly Thr Cys Glu Asn Leu Pro
                405                 410                 415

Gly Asn Tyr Thr Cys His Cys Pro Phe Asp Asn Leu Ser Arg Thr Phe
            420                 425                 430

Tyr Gly Gly Arg Asp Cys Ser Asp Ile Leu Leu Gly Cys Thr His Gln
        435                 440                 445

Gln Cys Leu Asn Asn Gly Thr Cys Ile Pro His Phe Gln Asp Gly Gln
    450                 455                 460

His Gly Phe Ser Cys Leu Cys Pro Ser Gly Tyr Thr Gly Ser Leu Cys
465                 470                 475                 480

Glu Ile Ala Thr Thr Leu Ser Phe Glu Gly Asp Gly Phe Leu Trp Val
                485                 490                 495

Lys Ser Gly Ser Val Thr Thr Lys Gly Ser Val Cys Asn Ile Ala Leu
            500                 505                 510

Arg Phe Gln Thr Val Gln Pro Met Ala Leu Leu Leu Phe Arg Ser Asn
        515                 520                 525

Arg Asp Val Phe Val Lys Leu Glu Leu Leu Ser Gly Tyr Ile His Leu
```

```
    530                 535                 540

Ser Ile Gln Val Asn Asn Gln Ser Lys Val Leu Leu Phe Ile Ser His
545                 550                 555                 560

Asn Thr Ser Asp Gly Glu Trp His Phe Val Glu Val Ile Phe Ala Glu
                565                 570                 575

Ala Val Thr Leu Thr Leu Ile Asp Asp Ser Cys Lys Glu Lys Cys Ile
            580                 585                 590

Ala Lys Ala Pro Thr Pro Leu Glu Ser Asp Gln Ser Ile Cys Ala Phe
        595                 600                 605

Gln Asn Ser Phe Leu Gly Gly Leu Pro Val Gly Met Thr Ser Asn Gly
    610                 615                 620

Val Ala Leu Leu Asn Phe Tyr Asn Met Pro Ser Thr Pro Ser Phe Val
625                 630                 635                 640

Gly Cys Leu Gln Asp Ile Lys Ile Asp Trp Asn His Ile Thr Leu Glu
                645                 650                 655

Asn Ile Ser Ser Gly Ser Ser Leu Asn Val Lys Ala Gly Cys Val Arg
            660                 665                 670

Lys Asp Trp Cys Glu Ser Gln Pro Cys Gln Ser Arg Gly Arg Cys Ile
        675                 680                 685

Asn Leu Trp Leu Ser Tyr Gln Cys Asp Cys His Arg Pro Tyr Glu Gly
    690                 695                 700

Pro Asn Cys Leu Arg Glu Tyr Val Ala Gly Arg Phe Gly Gln Asp Asp
705                 710                 715                 720

Ser Thr Gly Tyr Val Ile Phe Thr Leu Asp Glu Ser Tyr Gly Asp Thr
                725                 730                 735

Ile Ser Leu Ser Met Phe Val Arg Thr Leu Gln Pro Ser Gly Leu Leu
            740                 745                 750

Leu Ala Leu Glu Asn Ser Thr Tyr Gln Tyr Ile Arg Val Trp Leu Glu
        755                 760                 765

Arg Gly Arg Leu Ala Met Leu Thr Pro Asn Ser Pro Lys Leu Val Val
    770                 775                 780

Lys Phe Val Leu Asn Asp Gly Asn Val His Leu Ile Ser Leu Lys Ile
785                 790                 795                 800

Lys Pro Tyr Lys Ile Glu Leu Tyr Gln Ser Ser Gln Asn Leu Gly Phe
                805                 810                 815

Ile Ser Ala Ser Thr Trp Lys Ile Glu Lys Gly Asp Val Ile Tyr Ile
            820                 825                 830

Gly Gly Leu Pro Asp Lys Gln Glu Thr Glu Leu Asn Gly Gly Phe Phe
        835                 840                 845

Lys Gly Cys Ile Gln Asp Val Arg Leu Asn Asn Gln Asn Leu Glu Phe
    850                 855                 860

Phe Pro Asn Pro Thr Asn Asn Ala Ser Leu Asn Pro Val Leu Val Asn
865                 870                 875                 880

Val Thr Gln Gly Cys Ala Gly Asp Asn Ser Cys Lys Ser Asn Pro Cys
                885                 890                 895

His Asn Gly Gly Val Cys His Ser Arg Trp Asp Asp Phe Ser Cys Ser
            900                 905                 910

Cys Pro Ala Leu Thr Ser Gly Lys Ala Cys Glu Glu Val Gln Trp Cys
        915                 920                 925

Gly Phe Ser Pro Cys Pro His Gly Ala Gln Cys Gln Pro Val Leu Gln
    930                 935                 940

Gly Phe Glu Cys Ile Ala Asn Ala Val Phe Asn Gly Gln Ser Gly Gln
945                 950                 955                 960
```

```
Ile Leu Phe Arg Ser Asn Gly Asn Ile Thr Arg Glu Leu Thr Asn Ile
                965                 970                 975

Thr Phe Gly Phe Arg Thr Arg Asp Ala Asn Val Ile Ile Leu His Ala
            980                 985                 990

Glu Lys Glu Pro Glu Phe Leu Asn  Ile Ser Ile Gln Asp  Ser Arg Leu
        995                 1000                 1005

Phe Phe  Gln Leu Gln Ser Gly  Asn Ser Phe Tyr Met  Leu Ser Leu
    1010                 1015                 1020

Thr Ser  Leu Gln Ser Val Asn  Asp Gly Thr Trp His  Glu Val Thr
    1025                 1030                 1035

Leu Ser  Met Thr Asp Pro Leu  Ser Gln Thr Ser Arg  Trp Gln Met
    1040                 1045                 1050

Glu Val  Asp Asn Glu Thr Pro  Phe Val Thr Ser Thr  Ile Ala Thr
    1055                 1060                 1065

Gly Ser  Leu Asn Phe Leu Lys  Asp Asn Thr Asp Ile  Tyr Val Gly
    1070                 1075                 1080

Asp Arg  Ala Ile Asp Asn Ile  Lys Gly Leu Gln Gly  Cys Leu Ser
    1085                 1090                 1095

Thr Ile  Glu Ile Gly Gly Ile  Tyr Leu Ser Tyr Phe  Glu Asn Val
    1100                 1105                 1110

His Gly  Phe Ile Asn Lys Pro  Gln Glu Glu Gln Phe  Leu Lys Ile
    1115                 1120                 1125

Ser Thr  Asn Ser Val Val Thr  Gly Cys Leu Gln Leu  Asn Val Cys
    1130                 1135                 1140

Asn Ser  Asn Pro Cys Leu His  Gly Gly Asn Cys Glu  Asp Ile Tyr
    1145                 1150                 1155

Ser Ser  Tyr His Cys Ser Cys  Pro Leu Gly Trp Ser  Gly Lys His
    1160                 1165                 1170

Cys Glu  Leu Asn Ile Asp Glu  Cys Phe Ser Asn Pro  Cys Ile His
    1175                 1180                 1185

Gly Asn  Cys Ser Asp Arg Val  Ala Ala Tyr His Cys  Thr Cys Glu
    1190                 1195                 1200

Pro Gly  Tyr Thr Gly Val Asn  Cys Glu Val Asp Ile  Asp Asn Cys
    1205                 1210                 1215

Gln Ser  His Gln Cys Ala Asn  Gly Ala Thr Cys Ile  Ser His Thr
    1220                 1225                 1230

Asn Gly  Tyr Ser Cys Leu Cys  Phe Gly Asn Phe Thr  Gly Lys Phe
    1235                 1240                 1245

Cys Arg  Gln Ser Arg Leu Pro  Ser Thr Val Cys Gly  Asn Glu Lys
    1250                 1255                 1260

Thr Asn  Leu Thr Cys Tyr Asn  Gly Gly Asn Cys Thr  Glu Phe Gln
    1265                 1270                 1275

Thr Glu  Leu Lys Cys Met Cys  Arg Pro Gly Phe Thr  Gly Glu Trp
    1280                 1285                 1290

Cys Glu  Lys Asp Ile Asp Glu  Cys Ala Ser Asp Pro  Cys Val Asn
    1295                 1300                 1305

Gly Gly  Leu Cys Gln Asp Leu  Leu Asn Lys Phe Gln  Cys Leu Cys
    1310                 1315                 1320

Asp Val  Ala Phe Ala Gly Glu  Arg Cys Glu Val Asp  Leu Ala Asp
    1325                 1330                 1335

Asp Leu  Ile Ser Asp Ile Phe  Thr Thr Ile Gly Ser  Val Thr Val
    1340                 1345                 1350
```

```
Ala Leu  Leu Leu Ile Leu Leu  Leu Ala Ile Val Ala  Ser Val Val
    1355                 1360                 1365

Thr Ser  Asn Lys Arg Ala Thr  Gln Gly Thr Tyr Ser  Pro Ser Arg
    1370                 1375                 1380

Gln Glu  Lys Glu Gly Ser Arg  Val Glu Met Trp Asn  Leu Met Pro
    1385                 1390                 1395

Pro Pro  Ala Met Glu Arg Leu  Ile
    1400                 1405
```

<210> SEQ ID NO 6
<211> LENGTH: 5541
<212> TYPE: DNA
<213> ORGANISM: Homo sapiens

<400> SEQUENCE: 6

```
gtcttggccc aacttacaaa cagcagaaat ctgagttgtg ggaatataat ttatgaacag     60

aaaagattac ttgtctgtga attattttct gaagatgaaa gtaaatatac aggaacatac    120

ggtattcctt taaaagttgc cagatcataa ttgtgtggca aggcagttat cagaaattaa    180

tccctctatt gagagcaatt gaagacacta ttctaatgta ggcccttttg aggaggcagc    240

atgaacagaa gaaaactcgc agcaaaggct tgaggggga atgaatccaa tccagcctga    300

aaaaatctgc accaggtttg aaaaatcacc ccatcctccc gtgtaagtga tgctaagaag    360

cacaaactgc attttgaatc taagtccctg tattttctgt gaaggagctg taagtagggt    420

gggacagaga tggcacctgg gggttctgag gcacccgctc ctctctgaga cagacaggga    480

tcaggagccg gactgggacc agaccaccag caacacacca gaggatgttc tctaaataag    540

accatggcac ttaagaacat taactacctt ctcatcttct acctcagttt ctcactgctt    600

atctacataa aaaattcctt ttgcaataaa aacaacacca ggtgcctctc aaattcttgc    660

caaaacaatt ctacatgcaa agatttttca aaagacaatg attgttcttg ttcagacaca    720

gccaataatt tggacaaaga ctgtgacaac atgaaagacc cttgcttctc caatccctgt    780

caaggaagtg ccacttgtgt gaacacccca ggagaaagga gctttctgtg caaatgtcct    840

cctgggtaca gtgggacaat ctgtgaaact accattggtt cctgtggcaa gaactcctgc    900

caacatggag gtatttgcca tcaggaccct atttatcctg tctgcatctg ccctgctgga    960

tatgctggaa gattctgtga gatagatcac gatgagtgtg cttccagccc ttgccaaaat   1020

ggggccgtgt gccaggatgg aattgatggt tactcctgct tctgtgtccc aggatatcaa   1080

ggcagacact gcgacttgga agtggatgaa tgtgcttcag atccctgcaa gaacgaggct   1140

acatgcctca atgaaatagg aagatatact tgtatctgtc cccacaatta ttctggtgta   1200

aactgtgaat tggaaattga cgaatgttgg tcccagcctt gtttaaatgg tgcaacttgt   1260

caggatgctc tgggggccta tttctgcgac tgtgcccctg gattcctggg ggatcactgt   1320

gaactcaaca ctgatgagtg tgccagtcaa ccttgtctcc atggagggct gtgtgtggat   1380

ggagaaaaca gatatagctg taactgcacg ggtagtggat tcacagggac acactgtgag   1440

accttgatgc ctctttgttg gtcaaaacct tgtcacaata atgctacatg tgaggacagt   1500

gttgacaatt acacttgtca ctgctggcct ggatacacag gtgcccagtg tgagatcgac   1560

ctcaatgaat gcaatagtaa cccctgccag tccaatgggg aatgtgtgga gctgtcctca   1620

gagaaacaat atggacgcat cactggactg ccttcttctt tcagctacca tgaagcctca   1680

ggttatgtct gtatctgtca gcctggattc acaggaatcc actgcgaaga agacgtcaat   1740

gaatgttctt caaacccttg ccaaaatggt ggtacttgtg agaacttgcc tgggaattat   1800
```

```
acttgccatt gcccatttga taacctttct agaacttttt atggaggaag ggactgttct   1860
gatattctcc tgggctgtac ccatcagcaa tgtctaaata atggaacatg catccctcac   1920
ttccaagatg gccagcatgg attcagctgc ctatgtccat ctggctacac cgggtccctg   1980
tgtgaaatcg caaccacact ttcatttgag ggcgatggct tcctgtgggt caaaagtggc   2040
tcagtgacaa ccaagggctc agtttgtaac atagccctca ggtttcagac tgttcagcca   2100
atggctcttc tacttttccg aagcaacagg gatgtgtttg tgaagctgga gctgctaagt   2160
ggctacattc acttatcaat tcaggtcaat aatcagtcaa aggtgcttct gttcatttcc   2220
cacaacacca gcgatggaga gtggcatttc gtggaggtaa tatttgcaga ggctgtgacc   2280
cttaccttaa tcgacgactc ctgtaaggag aaatgcatcg cgaaagctcc tactccactt   2340
gaaagtgatc aatcaatatg tgcttttcag aactcctttt tgggtggttt accagtggga   2400
atgaccagca atggtgttgc tctgcttaac ttctataata tgccatccac accttcgttt   2460
gtaggctgtc tccaagacat taaaattgat tggaatcaca ttaccctgga gaacatctcg   2520
tctggctcat cattaaatgt caaggcaggc tgtgtgagaa aggattggtg tgaaagccaa   2580
ccttgtcaaa gcagaggacg ctgcatcaac ttgtggctga gttaccagtg tgactgccac   2640
aggccctatg aaggccccaa ctgtctgaga ggtgagagaa agctgagtgc tatggctagg   2700
agtgccatgc ctcagagcag agcagaaaca gcaaaaacag ccagactgct tctgcctgct   2760
atgaaacata atgaccccac aagacttctg ctgctggttg cccactgatg agaaagaaaa   2820
gaagagggca gtgatgtgcg ttaattaatt ttgagtggat tcataggaca tcagtttcac   2880
tcatacagag aagtaaaaaa aataagcaga tagctctttt ccaaagaggt tttcatcttt   2940
gtgtttgcaa aatgctactg caattttacc attggtcaca tatcagaaat ttattgtaaa   3000
tcttatttga aagagaaata atcttttgaa aaaaaaaaac cttagacata aaatttgtca   3060
gtgccacata ctagcatgat atcttgtgca tagtaaattc tcggtaaata ttcatttcct   3120
tgctctcctt tccatgcaat tcacacttgc tccacaatca taattaagca tagcgttttt   3180
ataaaacgcc aattttattc aaaggtatct tttccaaggt tgccctggag aagacagata   3240
atatactagg tgtcttaaga aaaaaaaaaa agaaaaaaaa atgtggaaag taacaatagt   3300
agaacttggt agatgccata aactaattga tctaatttct ctagtaaacc acagtttgca   3360
aagtatttca aaatccttaa cttccaacat tgttctagag attgctgttg atagtgatca   3420
atatatacct gtttcttttt attattatta tcatacattg aaaaagtctg agaggtaatt   3480
gtaacggact gctttgaagt tcagctgtaa tttaccccaa gattttagag taacttgaag   3540
taggacaaca tctggtaagt agtcttctct gctttatatg aagtaaaatt aaaaccagtc   3600
ttagcctata ctctattcca tgttcaaatg tctaagaatt attagaaact actcaagggt   3660
ttcccccgac cacaatattc attacaaatc acggacctgt ttgacaatga agtatggtat   3720
ctactagctc tacgtaatat tttaagtaga atggcaagtt gttttgtgat tttttttaag   3780
gagaaaaagg gaaattatgc tgaggcaatg ttcacttttt gaagaaaaat ttaattgacc   3840
taaggcaata tttttactac atatacaaaa taacaaacag atgctgactc attttgactg   3900
gcttccagat gcagtgaccc atgaggttaa tactgaccat ggtgatgtta actgtcctag   3960
taaatagatt caagagatgc caatccactg ggttctggtt ttctttattt tatccaactt   4020
ggaaaaccat gaacttttca aaccaagttc ctgaattggt tacccttccc ccacttctcc   4080
cagtttcctt atactccaac attatttgaa actgcttaac cctcaagaaa atatttgact   4140
```

```
tcaaaagatc actttacaga cagagagagt tctgtgaaat cttttctttc tgaaaattct   4200

tggtataaat ttaaggaaaa ttatattttt catatcacct cttcattata aaattaaaat   4260

attctgtatt ttctgttatc ttgaaggaat gtttcctgga gagtttattc ccactaaaaa   4320

ctgcttttaa gtggtaatga gaacatggag tctttctgct actgtacata tacgtgcaag   4380

agggaggaga catactaaaa agcacaaagg caaacttcag cccattcatg acttgcactc   4440

atatttggct caatgttttc caaccatggt atacatttta atgaacaagg agactggata   4500

gaggattttg gtggctgact aaacacaaaa gacatagtga tttccaatgt atcaaggttg   4560

atctttttta aataatctaa tttctcaaca gaaagagtgc tgaaaaggat ttaactaagc   4620

ttaggtcaca gaagtgtcca taaggttctc tcagcatatc ttgtgttgac tgtttgtaag   4680

aacatgcagc attcaagata ctactactca gaataaatgg catcacctac ctcttgctct   4740

ctggtgaaca tttgacttac aaaagcaatt tacatatctc ttcttttcag ccatatacct   4800

agattttgag aattttattc tcttagaatt atagtttcct agatatagaa aaagattcat   4860

tctatgactg aatttttaac acaattgtac ctgccaaatg tagtggctca aatctctgct   4920

caaacacctt cacaaataga gagatcactc actccatctt gccaaaaatt gcccaaaagt   4980

tatttcctta tattgaaata gaataggatt tgcccgtagc tttccttcat tgaccttgtt   5040

gcatttctgg aacacatgca aataaaaatc tcaacttgcc tgctgcttga gaatacttaa   5100

tatctgaaga aaagtatctc gagccatcta aaccatcact tctattcagg ctaaacatcc   5160

tgtttcttct aatgtttgcc atatgacata gttttccgac acttcatcag ctgcttgcag   5220

gttttggaat atatttgctt ctttgtattc cttctaagat gtgatgtctg tatgtgctgg   5280

atgatacagt gacacacagg gccataacct cccttattct agataatgtg cttctgtttt   5340

tcagcttaat acaacattga ctttttggca gccacacttc gtgattgcgt cactttgtat   5400

cattgtcact catgatgcca catagtcctg tttctcccac tctaatctta taaacgcaca   5460

tttagatcga agtggctctt atttattctt gttaaatttc atcttgttgt attccatcaa   5520

tcattaaagc ttgccaaaat t                                             5541
```

<210> SEQ ID NO 7
<211> LENGTH: 754
<212> TYPE: PRT
<213> ORGANISM: Homo sapiens

<400> SEQUENCE: 7

```
Met Ala Leu Lys Asn Ile Asn Tyr Leu Leu Ile Phe Tyr Leu Ser Phe
1               5                   10                  15

Ser Leu Leu Ile Tyr Ile Lys Asn Ser Phe Cys Asn Lys Asn Asn Thr
            20                  25                  30

Arg Cys Leu Ser Asn Ser Cys Gln Asn Asn Ser Thr Cys Lys Asp Phe
        35                  40                  45

Ser Lys Asp Asn Asp Cys Ser Cys Ser Asp Thr Ala Asn Asn Leu Asp
    50                  55                  60

Lys Asp Cys Asp Asn Met Lys Asp Pro Cys Phe Ser Asn Pro Cys Gln
65                  70                  75                  80

Gly Ser Ala Thr Cys Val Asn Thr Pro Gly Glu Arg Ser Phe Leu Cys
                85                  90                  95

Lys Cys Pro Pro Gly Tyr Ser Gly Thr Ile Cys Glu Thr Thr Ile Gly
            100                 105                 110

Ser Cys Gly Lys Asn Ser Cys Gln His Gly Gly Ile Cys His Gln Asp
        115                 120                 125
```

```
Pro Ile Tyr Pro Val Cys Ile Cys Pro Ala Gly Tyr Ala Gly Arg Phe
    130                 135                 140

Cys Glu Ile Asp His Asp Glu Cys Ala Ser Ser Pro Cys Gln Asn Gly
145                 150                 155                 160

Ala Val Cys Gln Asp Gly Ile Asp Gly Tyr Ser Cys Phe Cys Val Pro
                165                 170                 175

Gly Tyr Gln Gly Arg His Cys Asp Leu Glu Val Asp Glu Cys Ala Ser
            180                 185                 190

Asp Pro Cys Lys Asn Glu Ala Thr Cys Leu Asn Glu Ile Gly Arg Tyr
        195                 200                 205

Thr Cys Ile Cys Pro His Asn Tyr Ser Gly Val Asn Cys Glu Leu Glu
    210                 215                 220

Ile Asp Glu Cys Trp Ser Gln Pro Cys Leu Asn Gly Ala Thr Cys Gln
225                 230                 235                 240

Asp Ala Leu Gly Ala Tyr Phe Cys Asp Cys Ala Pro Gly Phe Leu Gly
                245                 250                 255

Asp His Cys Glu Leu Asn Thr Asp Glu Cys Ala Ser Gln Pro Cys Leu
            260                 265                 270

His Gly Gly Leu Cys Val Asp Gly Glu Asn Arg Tyr Ser Cys Asn Cys
        275                 280                 285

Thr Gly Ser Gly Phe Thr Gly Thr His Cys Glu Thr Leu Met Pro Leu
    290                 295                 300

Cys Trp Ser Lys Pro Cys His Asn Asn Ala Thr Cys Glu Asp Ser Val
305                 310                 315                 320

Asp Asn Tyr Thr Cys His Cys Trp Pro Gly Tyr Thr Gly Ala Gln Cys
                325                 330                 335

Glu Ile Asp Leu Asn Glu Cys Asn Ser Asn Pro Cys Gln Ser Asn Gly
            340                 345                 350

Glu Cys Val Glu Leu Ser Ser Glu Lys Gln Tyr Gly Arg Ile Thr Gly
        355                 360                 365

Leu Pro Ser Ser Phe Ser Tyr His Glu Ala Ser Gly Tyr Val Cys Ile
    370                 375                 380

Cys Gln Pro Gly Phe Thr Gly Ile His Cys Glu Glu Asp Val Asn Glu
385                 390                 395                 400

Cys Ser Ser Asn Pro Cys Gln Asn Gly Gly Thr Cys Glu Asn Leu Pro
                405                 410                 415

Gly Asn Tyr Thr Cys His Cys Pro Phe Asp Asn Leu Ser Arg Thr Phe
            420                 425                 430

Tyr Gly Gly Arg Asp Cys Ser Asp Ile Leu Leu Gly Cys Thr His Gln
        435                 440                 445

Gln Cys Leu Asn Asn Gly Thr Cys Ile Pro His Phe Gln Asp Gly Gln
    450                 455                 460

His Gly Phe Ser Cys Leu Cys Pro Ser Gly Tyr Thr Gly Ser Leu Cys
465                 470                 475                 480

Glu Ile Ala Thr Thr Leu Ser Phe Glu Gly Asp Gly Phe Leu Trp Val
                485                 490                 495

Lys Ser Gly Ser Val Thr Thr Lys Gly Ser Val Cys Asn Ile Ala Leu
            500                 505                 510

Arg Phe Gln Thr Val Gln Pro Met Ala Leu Leu Leu Phe Arg Ser Asn
        515                 520                 525

Arg Asp Val Phe Val Lys Leu Glu Leu Leu Ser Gly Tyr Ile His Leu
    530                 535                 540
```

```
Ser Ile Gln Val Asn Asn Gln Ser Lys Val Leu Leu Phe Ile Ser His
545                 550                 555                 560

Asn Thr Ser Asp Gly Glu Trp His Phe Val Glu Val Ile Phe Ala Glu
                565                 570                 575

Ala Val Thr Leu Thr Leu Ile Asp Asp Ser Cys Lys Glu Lys Cys Ile
            580                 585                 590

Ala Lys Ala Pro Thr Pro Leu Glu Ser Asp Gln Ser Ile Cys Ala Phe
        595                 600                 605

Gln Asn Ser Phe Leu Gly Gly Leu Pro Val Gly Met Thr Ser Asn Gly
    610                 615                 620

Val Ala Leu Leu Asn Phe Tyr Asn Met Pro Ser Thr Pro Ser Phe Val
625                 630                 635                 640

Gly Cys Leu Gln Asp Ile Lys Ile Asp Trp Asn His Ile Thr Leu Glu
                645                 650                 655

Asn Ile Ser Ser Gly Ser Ser Leu Asn Val Lys Ala Gly Cys Val Arg
            660                 665                 670

Lys Asp Trp Cys Glu Ser Gln Pro Cys Gln Ser Arg Gly Arg Cys Ile
        675                 680                 685

Asn Leu Trp Leu Ser Tyr Gln Cys Asp Cys His Arg Pro Tyr Glu Gly
    690                 695                 700

Pro Asn Cys Leu Arg Gly Glu Arg Lys Leu Ser Ala Met Ala Arg Ser
705                 710                 715                 720

Ala Met Pro Gln Ser Arg Ala Glu Thr Ala Lys Thr Ala Arg Leu Leu
                725                 730                 735

Leu Pro Ala Met Lys His Asn Asp Pro Thr Arg Leu Leu Leu Leu Val
            740                 745                 750

Ala His
```

<210> SEQ ID NO 8
<211> LENGTH: 6170
<212> TYPE: DNA
<213> ORGANISM: Mus musculus

<400> SEQUENCE: 8

```
attgttcacg gaagcctgag ggggacacga atccaatcca ggctggaaaa atctgctcca     60

ggattgactg gttaccgtct tcctgtgcct gtaaggtgct gtgaaagaga agtgctttct    120

gattctctgt ctgtggagga gccctgggag gggtgggaca gagatggcat cctggctctc    180

tgaggcacct gctcttctct gaaccacaca ggagtcaaga gccaaacagg gatagcttca    240

gcagcacttc agagggtgtt ctctaagtaa gaacatgaag ctcaagagaa ctgcctacct    300

tctcttcctg tacctcagct cctcactgct catctgcata aagaattcat tttgcaataa    360

aaacaatacc aggtgccttt caggtccttg ccaaaacaat tctacgtgca agcattttcc    420

acaagacaac aattgttgct tagacacagc caataatttg gacaaagact gtgaagatct    480

gaaagaccct tgcttctcga gtccctgcca aggaattgcc acttgtgtga aaatcccagg    540

ggaagggaac ttcctgtgtc agtgtcctcc tgggtacagc gggctgaact gtgaaactgc    600

caccaattcc tgtggaggga acctctgcca acatggaggc acctgccgta aagaccctga    660

gcaccctgtc tgtatctgcc ctcctggata tgctggaagg ttctgtgaga ctgatcacaa    720

tgagtgtgct tctagccctt gccacaatgg ggctatgtgc caggatggaa tcaatggcta    780

ctcctgcttc tgtgtgcctg gataccaagg caggcattgt gacttggaag tggatgaatg    840

tgtttctgat ccctgcaaga atgaggctgt gtgcctcaat gagataggaa gatacacttg    900
```

```
tgtctgccct caagagtttt ctggcgtgaa ctgtgagttg gaaattgatg aatgcagatc    960
ccagccttgt ctccacggtg ccacatgtca ggacgctcca gggggctact cctgtgactg   1020
tgcacctgga ttccttggag agcactgtga actcagcgtt aatgaatgtg aaagtcagcc   1080
gtgtctccat ggaggtctat gtgtggatgg aagaaacagt taccactgtg actgcacagg   1140
tagtggattc acagggatgc actgtgagtc cttgattcct ctttgttggt caaagccttg   1200
tcacaacgac gcgacatgtg aagatactgt tgacagctat atttgtcact gccggcctgg   1260
atacacaggt gccctgtgtg agacagacat aaatgaatgc agtagcaacc cctgccaatt   1320
ttggggggaa tgtgtcgagc tgtcctcaga gggtctatat ggaaacactg ctggcctgcc   1380
ttcctccttc agctatgttg gagcctcggg ctatgtgtgt atctgtcagc ctggattcac   1440
aggaattcac tgtgaagaag acgttgatga atgtttactg cacccttgcc taaatggtgg   1500
tacttgtgag aacctgcctg ggaattatgc ctgtcactgt ccctttgatg acacttctag   1560
gacattttat ggaggagaaa actgctcaga aattctcctg ggctgcactc atcaccagtg   1620
tctgaacaat ggaaaatgta tccctcattt ccaaaatggc cagcatggat tcacttgcca   1680
gtgtctttct ggctatgcgg ggcccctgtg tgaaactgtc accacacttt catttgggag   1740
caatggcttc ctatgggtca caagtggctc ccatacaggc atagggccag aatgtaacat   1800
atccttgagg tttcacactg ttcaaccaaa cgcacttctc ctcatccgag gcaacaagga   1860
cgtgtctatg aagctggagt tgctgaatgg ttgtgttcac ttatcaattg aagtctggaa   1920
tcagttaaag gtgctcctgt ctatttctca caacaccagt gatggagaat ggcatttcgt   1980
ggaggtaaca atcgcagaaa ctctaaccct tgccctagtt ggcggctcct gcaaggagaa   2040
gtgcaccacc aagtcttctg ttccagttga gaatcatcaa tcaatatgtg ctttgcagga   2100
ctctttttg ggtggcttac caatggggac agccaacaac agtgtgtctg tgcttaacat   2160
ctataatgtg ccgtccacac cttcctttgt aggctgtctc caagacatta gatttgattt   2220
gaatcacatt actctggaga acgtttcatc tggcctgtca tcaaatgtta aagcaggctg   2280
cctgggaaag gactggtgtg aaagtcaacc ctgtcaaaac agaggacgct gcatcaactt   2340
gtggcagggt tatcagtgtg aatgtgacag gccctataca ggctccaact gcctgaaaga   2400
gtatgtagcg ggaagatttg gccaagatga ctccacagga tatgcggcct ttagtgttaa   2460
tgataattat ggacagaact tcagtctttc aatgtttgtc cgaacacgtc aacccctggg   2520
cttacttctg gctttggaaa atagtactta ccagtatgtc agtgtctggc tagagcacgg   2580
cagcctagca ctgcagactc caggctctcc caagttcatg gtaaactttt ttctcagtga   2640
tggaaatgtt cacttaatat ctttgagaat caaaccaaat gaaattgaac tgtatcagtc   2700
ttcacaaaac ctaggattca tttctgttcc tacatggaca attcgaagag gagacgtcat   2760
cttcattggt ggcttacctg acagagagaa gactgaagtt tatggtggct tcttcaaagg   2820
ctgtgttcaa gatgtcagat taaacagcca gactctggaa ttctttccca attcaacaaa   2880
caatgcatac gatgacccaa ttcttgtcaa tgtgactcaa ggctgtcccg gagacaacac   2940
atgtaagtcc aacccctgtc ataatggagg tgtctgccac tccctgtggg atgacttctc   3000
ctgctcctgc cctacaaaca cagcggggag agcctgcgag caagttcagt ggtgtcaact   3060
cagcccatgt cctcccactg cagagtgcca gctgctccct caagggtttg aatgtatcgc   3120
aaacgctgtt ttcagcggat taagcagaga aatactcttc agaagcaatg ggaacattac   3180
cagagaactc accaatatca catttgcttt cagaacacat gatacaaatg tgatgatatt   3240
gcatgcagaa aaagaaccag agtttcttaa tattagcatt caagatgcca gattattctt   3300
```

```
tcaattgcga agtggcaaca gcttttatac gctgcacctg atgggttccc aattggtgaa   3360
tgatggcaca tggcaccaag tgactttctc catgatagac ccagtggccc agacctcccg   3420
gtggcaaatg gaggtgaacg accagacacc ctttgtgata agtgaagttg ctactggaag   3480
cctgaacttt ttgaaggaca atacagacat ctatgtgggt gaccaatctg ttgacaatcc   3540
gaaaggcctg cagggctgtc tgagcacaat agagattgga ggcatatatc tttcttactt   3600
tgaaaatcta catggtttcc ctggtaagcc tcaggaagag caatttctca aagtttctac   3660
aaatatggta cttactggct gtttgccatc aaatgcctgc cactccagcc cctgtttgca   3720
tggaggaaac tgtgaagaca gctacagttc ttatcggtgt gcctgtctct cgggatggtc   3780
agggacacac tgtgaaatca acattgatga gtgcttttct agcccctgta tccatggcaa   3840
ctgctctgat ggagttgcag cctaccactg caggtgtgag cctggataca ccggtgtgaa   3900
ctgtgaggtg gatgtagaca attgcaagag tcatcagtgt gcaaatgggg ccacctgtgt   3960
tcctgaagct catggctact cttgtctctg ctttggaaat tttaccggga gattttgcag   4020
acacagcaga ttaccctcaa cagtctgtgg gaatgagaag agaaacttca cttgctacaa   4080
tggaggcagc tgctccatgt tccaggagga ctggcaatgt atgtgctggc caggtttcac   4140
tggagagtgg tgtgaagagg acatcaacga gtgtgcctcc gatccctgca tcaatggagg   4200
actgtgcagg gacttggtca acaggttcct atgcatctgt gatgtggcct tcgctggcga   4260
gcgctgtgag ctggacctgg ctgatgacag gctcctgggc attttcaccg ctgttggctc   4320
cggaactttg gccctgttct tcatcctctt gcttgctggg gttgcttctc ttattgcctc   4380
caacaaaagg gcgactcaag gaacctacag ccccagcggt caggagaagg ctggccctcg   4440
agtggaaatg tggatcagga tgccgccccc ggcactggaa aggctcatct aggagactgc   4500
tgctcttctc aggacagaga agaacatgat gagtaccggg tcgtgcctga gtgaagatgg   4560
ctttacatca ctagagatac atacagctgg gactgtggga aggaccttcc tgtggagtca   4620
ctgagtagtt atgtcatcca ttcacagaag agtgtccctg tgtttgcctg tcagcctcag   4680
aattagcaaa acatctagca gacagagaac acagtatttc agaagaactc cagaggctgc   4740
cccttaaact ctttactggt tgatccacat aaaatgctta gtagccaagt gccattaatt   4800
atacagagcc aagaagaaaa attagaatac aactttcact ttttattttg tagggaaggt   4860
tttatgtttt ggtttgttgt tgttgttgtg acagtgacag tgactcatta catagaccaa   4920
gctggcctca aaatcacatg gaccctcggg attacatgtg tccgaccatg ttcatcttat   4980
ttttgaatct tctgtcatat ggtaaaagat tccagtggga cctgaggagt gactagctag   5040
gtaaagcaag ggctgtgtaa gtgccagaac tggtgtttgt gtcctcatta tccacataag   5100
tgccaagtga gtgtggcccc tgcctgtcat cctaggcctc aggagatatc actgctcact   5160
ggagcaagcc ggttaaactg ttagggcagg taagttttga cttcaagtga gagaccctga   5220
ctcaatatga aaggcaatta gtgagtcaag atgaccctgt atgctaacct cttgcctata   5280
catgcatata cacacattta catatgtgcc caaacatgag gacacaagca cacgcgcgcg   5340
cgcacacaca cacacacaca cacacacaca cacacacaca cacacacacg agtctaattg   5400
tatatagtga taacagtaca ctttcctcct tctatttcgg atttagagaa agccatgaga   5460
agcgtgtatg gtttaaacca tgacccaagc ataacaaata aagttgaaat agttgttctc   5520
ctgtccaagc ttgtctttat tgttgtgcat tctgtaagct ggttgcttgg ttggctgatg   5580
gatggcttct gtttgtttgt tgttttttgt ttgtttgttt gtctgggata ttacatgtaa   5640
```

```
gaaaaataac tggtaagaac aatcaaagaa ctttgttatg aattaaatct tttgtctaag   5700

tcacttagag tcattattct ttatgtagat ttgcttccag tcaggacatt tcctagacag   5760

aatttaagac agtaagaaaa tgatttgtca cgtctgaaag aggttcttta ctttcaggga   5820

cttttgataa tgcccaacag agatggcatc gaaagaggag ctcatagcga gatgggcatt   5880

tgtgcatcct caaggagaaa atattgtacc ttctgtttgt atattgtcta ttctgtgatg   5940

gctgtatctt acatatgttt tgatgcatgt aacaatagta tcatatgaaa taaattatat   6000

atatatataa tatataatat atatcacaag ataaaaattg aaattacata aactttaaat   6060

ctaaaagaag aaacctatcc ttcccaagta ttatcagtgc agtcaccgag cttttttttgt   6120

tttttgtat tagccatttc ttcataatac aggaagttct ataacttcaa              6170
```

```
<210> SEQ ID NO 9
<211> LENGTH: 1405
<212> TYPE: PRT
<213> ORGANISM: Mus musculus

<400> SEQUENCE: 9

Met Lys Leu Lys Arg Thr Ala Tyr Leu Leu Phe Leu Tyr Leu Ser Ser
1               5                   10                  15

Ser Leu Leu Ile Cys Ile Lys Asn Ser Phe Cys Asn Lys Asn Asn Thr
            20                  25                  30

Arg Cys Leu Ser Gly Pro Cys Gln Asn Asn Ser Thr Cys Lys His Phe
        35                  40                  45

Pro Gln Asp Asn Asn Cys Cys Leu Asp Thr Ala Asn Asn Leu Asp Lys
    50                  55                  60

Asp Cys Glu Asp Leu Lys Asp Pro Cys Phe Ser Ser Pro Cys Gln Gly
65                  70                  75                  80

Ile Ala Thr Cys Val Lys Ile Pro Gly Glu Gly Asn Phe Leu Cys Gln
                85                  90                  95

Cys Pro Pro Gly Tyr Ser Gly Leu Asn Cys Glu Thr Ala Thr Asn Ser
            100                 105                 110

Cys Gly Gly Asn Leu Cys Gln His Gly Gly Thr Cys Arg Lys Asp Pro
        115                 120                 125

Glu His Pro Val Cys Ile Cys Pro Pro Gly Tyr Ala Gly Arg Phe Cys
    130                 135                 140

Glu Thr Asp His Asn Glu Cys Ala Ser Ser Pro Cys His Asn Gly Ala
145                 150                 155                 160

Met Cys Gln Asp Gly Ile Asn Gly Tyr Ser Cys Phe Cys Val Pro Gly
                165                 170                 175

Tyr Gln Gly Arg His Cys Asp Leu Glu Val Asp Glu Cys Val Ser Asp
            180                 185                 190

Pro Cys Lys Asn Glu Ala Val Cys Leu Asn Glu Ile Gly Arg Tyr Thr
        195                 200                 205

Cys Val Cys Pro Gln Glu Phe Ser Gly Val Asn Cys Glu Leu Glu Ile
    210                 215                 220

Asp Glu Cys Arg Ser Gln Pro Cys Leu His Gly Ala Thr Cys Gln Asp
225                 230                 235                 240

Ala Pro Gly Gly Tyr Ser Cys Asp Cys Ala Pro Gly Phe Leu Gly Glu
                245                 250                 255

His Cys Glu Leu Ser Val Asn Glu Cys Glu Ser Gln Pro Cys Leu His
            260                 265                 270

Gly Gly Leu Cys Val Asp Gly Arg Asn Ser Tyr His Cys Asp Cys Thr
        275                 280                 285
```

```
Gly Ser Gly Phe Thr Gly Met His Cys Glu Ser Leu Ile Pro Leu Cys
    290                 295                 300

Trp Ser Lys Pro Cys His Asn Asp Ala Thr Cys Glu Asp Thr Val Asp
305                 310                 315                 320

Ser Tyr Ile Cys His Cys Arg Pro Gly Tyr Thr Gly Ala Leu Cys Glu
                325                 330                 335

Thr Asp Ile Asn Glu Cys Ser Ser Asn Pro Cys Gln Phe Trp Gly Glu
            340                 345                 350

Cys Val Glu Leu Ser Ser Glu Gly Leu Tyr Gly Asn Thr Ala Gly Leu
        355                 360                 365

Pro Ser Ser Phe Ser Tyr Val Gly Ala Ser Gly Tyr Val Cys Ile Cys
    370                 375                 380

Gln Pro Gly Phe Thr Gly Ile His Cys Glu Glu Asp Val Asp Glu Cys
385                 390                 395                 400

Leu Leu His Pro Cys Leu Asn Gly Gly Thr Cys Glu Asn Leu Pro Gly
                405                 410                 415

Asn Tyr Ala Cys His Cys Pro Phe Asp Asp Thr Ser Arg Thr Phe Tyr
            420                 425                 430

Gly Gly Glu Asn Cys Ser Glu Ile Leu Leu Gly Cys Thr His His Gln
        435                 440                 445

Cys Leu Asn Asn Gly Lys Cys Ile Pro His Phe Gln Asn Gly Gln His
    450                 455                 460

Gly Phe Thr Cys Gln Cys Leu Ser Gly Tyr Ala Gly Pro Leu Cys Glu
465                 470                 475                 480

Thr Val Thr Thr Leu Ser Phe Gly Ser Asn Gly Phe Leu Trp Val Thr
                485                 490                 495

Ser Gly Ser His Thr Gly Ile Gly Pro Glu Cys Asn Ile Ser Leu Arg
            500                 505                 510

Phe His Thr Val Gln Pro Asn Ala Leu Leu Leu Ile Arg Gly Asn Lys
        515                 520                 525

Asp Val Ser Met Lys Leu Glu Leu Leu Asn Gly Cys Val His Leu Ser
    530                 535                 540

Ile Glu Val Trp Asn Gln Leu Lys Val Leu Leu Ser Ile Ser His Asn
545                 550                 555                 560

Thr Ser Asp Gly Glu Trp His Phe Val Glu Val Thr Ile Ala Glu Thr
                565                 570                 575

Leu Thr Leu Ala Leu Val Gly Gly Ser Cys Lys Glu Lys Cys Thr Thr
            580                 585                 590

Lys Ser Ser Val Pro Val Glu Asn His Gln Ser Ile Cys Ala Leu Gln
        595                 600                 605

Asp Ser Phe Leu Gly Gly Leu Pro Met Gly Thr Ala Asn Asn Ser Val
    610                 615                 620

Ser Val Leu Asn Ile Tyr Asn Val Pro Ser Thr Pro Ser Phe Val Gly
625                 630                 635                 640

Cys Leu Gln Asp Ile Arg Phe Asp Leu Asn His Ile Thr Leu Glu Asn
                645                 650                 655

Val Ser Ser Gly Leu Ser Ser Asn Val Lys Ala Gly Cys Leu Gly Lys
            660                 665                 670

Asp Trp Cys Glu Ser Gln Pro Cys Gln Asn Arg Gly Arg Cys Ile Asn
        675                 680                 685

Leu Trp Gln Gly Tyr Gln Cys Glu Cys Asp Arg Pro Tyr Thr Gly Ser
    690                 695                 700
```

```
Asn Cys Leu Lys Glu Tyr Val Ala Gly Arg Phe Gly Gln Asp Asp Ser
705                 710                 715                 720

Thr Gly Tyr Ala Ala Phe Ser Val Asn Asp Asn Tyr Gly Gln Asn Phe
                725                 730                 735

Ser Leu Ser Met Phe Val Arg Thr Arg Gln Pro Leu Gly Leu Leu Leu
            740                 745                 750

Ala Leu Glu Asn Ser Thr Tyr Gln Tyr Val Ser Val Trp Leu Glu His
        755                 760                 765

Gly Ser Leu Ala Leu Gln Thr Pro Gly Ser Pro Lys Phe Met Val Asn
    770                 775                 780

Phe Phe Leu Ser Asp Gly Asn Val His Leu Ile Ser Leu Arg Ile Lys
785                 790                 795                 800

Pro Asn Glu Ile Glu Leu Tyr Gln Ser Ser Gln Asn Leu Gly Phe Ile
                805                 810                 815

Ser Val Pro Thr Trp Thr Ile Arg Arg Gly Asp Val Ile Phe Ile Gly
            820                 825                 830

Gly Leu Pro Asp Arg Glu Lys Thr Glu Val Tyr Gly Gly Phe Phe Lys
        835                 840                 845

Gly Cys Val Gln Asp Val Arg Leu Asn Ser Gln Thr Leu Glu Phe Phe
    850                 855                 860

Pro Asn Ser Thr Asn Asn Ala Tyr Asp Asp Pro Ile Leu Val Asn Val
865                 870                 875                 880

Thr Gln Gly Cys Pro Gly Asp Asn Thr Cys Lys Ser Asn Pro Cys His
                885                 890                 895

Asn Gly Gly Val Cys His Ser Leu Trp Asp Asp Phe Ser Cys Ser Cys
            900                 905                 910

Pro Thr Asn Thr Ala Gly Arg Ala Cys Glu Gln Val Gln Trp Cys Gln
        915                 920                 925

Leu Ser Pro Cys Pro Pro Thr Ala Glu Cys Gln Leu Leu Pro Gln Gly
    930                 935                 940

Phe Glu Cys Ile Ala Asn Ala Val Phe Ser Gly Leu Ser Arg Glu Ile
945                 950                 955                 960

Leu Phe Arg Ser Asn Gly Asn Ile Thr Arg Glu Leu Thr Asn Ile Thr
                965                 970                 975

Phe Ala Phe Arg Thr His Asp Thr Asn Val Met Ile Leu His Ala Glu
            980                 985                 990

Lys Glu Pro Glu Phe Leu Asn Ile  Ser Ile Gln Asp Ala  Arg Leu Phe
        995                 1000                1005

Phe Gln  Leu Arg Ser Gly Asn  Ser Phe Tyr Thr Leu  His Leu Met
    1010                1015                1020

Gly Ser  Gln Leu Val Asn Asp  Gly Thr Trp His Gln  Val Thr Phe
    1025                1030                1035

Ser Met  Ile Asp Pro Val Ala  Gln Thr Ser Arg Trp  Gln Met Glu
    1040                1045                1050

Val Asn  Asp Gln Thr Pro Phe  Val Ile Ser Glu Val  Ala Thr Gly
    1055                1060                1065

Ser Leu  Asn Phe Leu Lys Asp  Asn Thr Asp Ile Tyr  Val Gly Asp
    1070                1075                1080

Gln Ser  Val Asp Asn Pro Lys  Gly Leu Gln Gly Cys  Leu Ser Thr
    1085                1090                1095

Ile Glu  Ile Gly Gly Ile Tyr  Leu Ser Tyr Phe Glu  Asn Leu His
    1100                1105                1110

Gly Phe  Pro Gly Lys Pro Gln  Glu Glu Gln Phe Leu  Lys Val Ser
```

1115 1120 1125

Thr Asn Met Val Leu Thr Gly Cys Leu Pro Ser Asn Ala Cys His
1130 1135 1140

Ser Ser Pro Cys Leu His Gly Gly Asn Cys Glu Asp Ser Tyr Ser
1145 1150 1155

Ser Tyr Arg Cys Ala Cys Leu Ser Gly Trp Ser Gly Thr His Cys
1160 1165 1170

Glu Ile Asn Ile Asp Glu Cys Phe Ser Ser Pro Cys Ile His Gly
1175 1180 1185

Asn Cys Ser Asp Gly Val Ala Ala Tyr His Cys Arg Cys Glu Pro
1190 1195 1200

Gly Tyr Thr Gly Val Asn Cys Glu Val Asp Val Asp Asn Cys Lys
1205 1210 1215

Ser His Gln Cys Ala Asn Gly Ala Thr Cys Val Pro Glu Ala His
1220 1225 1230

Gly Tyr Ser Cys Leu Cys Phe Gly Asn Phe Thr Gly Arg Phe Cys
1235 1240 1245

Arg His Ser Arg Leu Pro Ser Thr Val Cys Gly Asn Glu Lys Arg
1250 1255 1260

Asn Phe Thr Cys Tyr Asn Gly Gly Ser Cys Ser Met Phe Gln Glu
1265 1270 1275

Asp Trp Gln Cys Met Cys Trp Pro Gly Phe Thr Gly Glu Trp Cys
1280 1285 1290

Glu Glu Asp Ile Asn Glu Cys Ala Ser Asp Pro Cys Ile Asn Gly
1295 1300 1305

Gly Leu Cys Arg Asp Leu Val Asn Arg Phe Leu Cys Ile Cys Asp
1310 1315 1320

Val Ala Phe Ala Gly Glu Arg Cys Glu Leu Asp Leu Ala Asp Asp
1325 1330 1335

Arg Leu Leu Gly Ile Phe Thr Ala Val Gly Ser Gly Thr Leu Ala
1340 1345 1350

Leu Phe Phe Ile Leu Leu Leu Ala Gly Val Ala Ser Leu Ile Ala
1355 1360 1365

Ser Asn Lys Arg Ala Thr Gln Gly Thr Tyr Ser Pro Ser Gly Gln
1370 1375 1380

Glu Lys Ala Gly Pro Arg Val Glu Met Trp Ile Arg Met Pro Pro
1385 1390 1395

Pro Ala Leu Glu Arg Leu Ile
1400 1405

<210> SEQ ID NO 10
<211> LENGTH: 5764
<212> TYPE: DNA
<213> ORGANISM: Mus musculus

<400> SEQUENCE: 10
ttacagaagg gaggcaccgt gtctcctgcg gggtaggagc taagaatata gcaaagctgc 60
ttgggaagtg gcacagctga ctcttacatt aagccccact gatccagctt gaagaggagt 120
gaggcaaagc tgaaccctcc cactctcctt gacaagtgca agcccacact tttggaaaaa 180
agcacaaaga cgtcagaaac ggttcctgtc gacctactag gctttggatg gctaagtgtt 240
tttgctttgt atggaaatat gtttggacac aagacacaag gttttcacat tttaatggca 300
gtgctcatag gaattcactg tgaagaagac gttgatgaat gtttactgca cccttgccta 360

-continued aatggtggta cttgtgagaa cctgcctggg aattatgcct gtcactgtcc ctttgatgac 420
acttctagga cattttatgg aggagaaaac tgctcagaaa ttctcctggg ctgcactcat 480
caccagtgtc tgaacaatgg aaaatgtatc cctcatttcc aaaatggcca gcatggattc 540
acttgccagt gtctttctgg ctatgcgggg cccctgtgtg aaactgtcac cacactttca 600
tttgggagca atggcttcct atgggtcaca agtggctccc atacaggcat agggccagaa 660
tgtaacatat ccttgaggtt tcacactgtt caaccaaacg cacttctcct catccgaggc 720
aacaaggacg tgtctatgaa gctggagttg ctgaatggtt gtgttcactt atcaattgaa 780
gtctggaatc agttaaaggt gctcctgtct atttctcaca acaccagtga tggagaatgg 840
catttcgtgg aggtaacaat cgcagaaact ctaacccttg ccctagttgg cggctcctgc 900
aaggagaagt gcaccaccaa gtcttctgtt ccagttgaga atcatcaatc aatatgtgct 960
ttgcaggact ctttttgggg tggcttacca atggggacag ccaacaacag tgtgtctgtg 1020
cttaacatct ataatgtgcc gtccacacct tcctttgtag gctgtctcca agacattaga 1080
tttgatttga atcacattac tctggagaac gtttcatctg gcctgtcatc aaatgttaaa 1140
gcaggctgcc tgggaaagga ctggtgtgaa agtcaaccct gtcaaaacag aggacgctgc 1200
atcaacttgt ggcagggtta tcagtgtgaa tgtgacaggc cctatacagg ctccaactgc 1260
ctgaaagagt atgtagcggg aagatttggc caagatgact ccacaggata tgcggccttt 1320
agtgttaatg ataattatgg acagaacttc agtctttcaa tgtttgtccg aacacgtcaa 1380
cccctgggct tacttctggc tttggaaaat agtacttacc agtatgtcag tgtctggcta 1440
gagcacggca gcctagcact gcagactcca ggctctccca agttcatggt aaactttttt 1500
ctcagtgatg gaaatgttca cttaatatct ttgagaatca aaccaaatga aattgaactg 1560
tatcagtctt cacaaaacct aggattcatt tctgttccta catggacaat tcgaagagga 1620
gacgtcatct tcattggtgg cttacctgac agagagaaga ctgaagttta tggtggcttc 1680
ttcaaaggct gtgttcaaga tgtcagatta aacagccaga ctctggaatt ctttcccaat 1740
tcaacaaaca atgcatacga tgacccaatt cttgtcaatg tgactcaagg ctgtcccgga 1800
gacaacacat gtaagtccaa cccctgtcat aatggaggtg tctgccactc cctgtgggat 1860
gacttctcct gctcctgccc tacaaacaca gcggggagag cctgcgagca agttcagtgg 1920
tgtcaactca gcccatgtcc tcccactgca gagtgccagc tgctccctca agggtttgaa 1980
tgtatcgcaa acgctgtttt cagcggatta agcagagaaa tactcttcag aagcaatggg 2040
aacattacca gagaactcac caatatcaca tttgctttca gaacacatga tacaaatgtg 2100
atgatattgc atgcagaaaa agaaccagag tttcttaata ttagcattca agatgccaga 2160
ttattctttc aattgcgaag tggcaacagc ttttatacgc tgcacctgat gggttcccaa 2220
ttggtgaatg atggcacatg gcaccaagtg actttctcca tgatagaccc agtggcccag 2280
acctcccggt ggcaaatgga ggtgaacgac cagacaccct ttgtgataag tgaagttgct 2340
actggaagcc tgaacttttt gaaggacaat acagacatct atgtgggtga ccaatctgtt 2400
gacaatccga aaggcctgca gggctgtctg agcacaatag agattggagg catatatctt 2460
tcttactttg aaaatctaca tggtttccct ggtaagcctc aggaagagca atttctcaaa 2520
gtttctacaa atatggtact tactggctgt ttgccatcaa atgcctgcca ctccagcccc 2580
tgtttgcatg gaggaaactg tgaagacagc tacagttctt atcggtgtgc ctgtctctcg 2640
ggatggtcag ggacacactg tgaaatcaac attgatgagt gcttttctag cccctgtatc 2700
catggcaact gctctgatgg agttgcagcc taccactgca ggtgtgagcc tggatacacc 2760

```
ggtgtgaact gtgaggtgga tgtagacaat tgcaagagtc atcagtgtgc aaatggggcc   2820
acctgtgttc ctgaagctca tggctactct tgtctctgct ttggaaattt taccgggaga   2880
ttttgcagac acagcagatt accctcaaca gtctgtggga atgagaagag aaacttcact   2940
tgctacaatg gaggcagctg ctccatgttc caggaggact ggcaatgtat gtgctggcca   3000
ggtttcactg gagagtggtg tgaagaggac atcaacgagt gtgcctccga tccctgcatc   3060
aatggaggac tgtgcaggga cttggtcaac aggttcctat gcatctgtga tgtggccttc   3120
gctggcgagc gctgtgagct ggacgtaagc ggcctttcct tttatgtgtc cctcttacta   3180
tggcaaaacc tctttcagct cctgtcctac ctcgtactgc gcatgaatga tgagccagtt   3240
gtagagtggg gggcacagga aaattattaa tgtgcatggg agcattcaca agtgtaaaac   3300
attgacttgc aagaaacatc ttgtctcagt gtaggtttct aggaaagaca aagggaacat   3360
tagggaatag actccatcta gagcactggt tctcagtctt cctaatgctg caacccttta   3420
gtacagctct tcctgttgta gtgatcgcag ccataacatt attttcattg ccacttcata   3480
actgtaatcc ttctactgct gtgaatcaca atggaaatat ttatgttttc tgatggtctt   3540
aagcaacacc tctgaaaaag tcattgaccc ccccccaaa ggggctgtga tccacaggtt   3600
gagaaatgct catctggaag gtaaccatgc atttaagtgt acctctagta gtttgggtct   3660
atagaagata ttctcctatt ctaccttttt agacacgcca gaagagggca tctgattcca   3720
ttaaagatga ttgggagcca ccgtgtggtt cctgagaact gtactcgggc cctttggaag   3780
agcaatcagt gctctttcca gcccctaaga atatttttaa tacagccaga aaggtctcat   3840
tacccagtgt actgagccct aaggcacttt catcctcaat cgttccatgt tgaatggttt   3900
tcattacatt tggaaaatgt tttctctcca ctctaccttt acatgttcct attttcctat   3960
tgacaatttg ccccttcact gtaattctaa tttggtgtgg tccttcttct cataagttta   4020
tatgtgacat gaacatttaa aaatatctat gaatatttta tagtcatgta tgtctttctg   4080
caaagctatt caaatgaact atggacagtt cttttctaca cgaagaagag atgagtttaa   4140
tccccagtaa catgagaaaa agatgagtga gggacagtgc tcacagtatc cctcactagc   4200
atcatttgtg attccatggg ccattttttt ccaccagcaa atagcagaga gccctttccc   4260
tattcgtttc tcttacactt ccccttttct gttacaactg aacactttac attagttact   4320
cctttgtagg gggtttgact tttccaccgt tttctctggt tcactattta tgctaagtat   4380
ctgtgcaggg cgggtatatc agtccaacag aggtgtcatt agtgttcatt gaggaggaaa   4440
tactttgcat gaattcatga catcattgaa gtagcagtgg ccagaaagat acccttctgc   4500
gaatgtgtct gtgtattcag aagctgccct ggttagaaaa catgtgggtc acttttcctt   4560
tgcatgttac cagtgctcac tgggtcatga ttgttttaag acagagcttt tgctgtggca   4620
atgaccaagg tgaatccaga gatgcagatc agacaaagga caagacaatg tactatctga   4680
gtaaaaccct gccttgactt actcctcagt acttagagat tttacatagc aacctccacc   4740
ctgtggcaac ccgttcacac tagcagtgat gctgagattt gcccttcctt ctcatcatct   4800
tcctcacatc caaagcattt tgtgtccaca ctgctgtttc agataactgt ttctaaagtg   4860
ggattgttgt agccagaaag gtagggaaaa tgttccccaa aatatttgca ttcttaagta   4920
tgtgaagtaa gtagattata gtcagagaca atatgtaagg tttcaggttc actcccttct   4980
acacatatct tcaactgtgt atttgcagaa tattctgaat gtgacatact cccaacagaa   5040
tatatttaag gagtatttat ccacagtatt gttctctgta cagttctagt gcttctattg   5100
```

```
tcactgcaat tgtcaattgt ttttctgctt tccaactgtc ttattatcat ttaatagcat   5160

cttgctaaat gccctctttc tattctcctt atttctccat agttcatgtg tgtctgtgtg   5220

actaaggatt ctcctcattt ttgcagaaaa ataaaatctt ttcttcttta tgtcctgctt   5280

gtcattctct ggtgacacat gtctttgctt acttggactg agggttgtac agtaagtaca   5340

gaagcaggct cagtcacaca gacagagaca caccaccacc agcagcagca gcaccaccac   5400

caccaccacc accaccagaa aacagtatga gtactcatct cttgattaca tgtcatttca   5460

agtaagcacc atgacaccga gggccaggtt ccatggactt tctctgttag gcacgtgatt   5520

ctttagctga cctttgagaa cagactccaa caacctcact tatttttact gttgacttat   5580

atcatctctg acaacactgg acttcgtttg agctagtcaa gaggaaagac catgacacct   5640

aagggacaga aattcacaca ctcggttttt cataattcac acacattcct atgtatcaaa   5700

tctctgtaat agatgacatt tacttgaata aaaagtcatt tccctttgct gatgtttcat   5760

cttt                                                                5764


<210> SEQ ID NO 11
<211> LENGTH: 1003
<212> TYPE: PRT
<213> ORGANISM: Mus musculus

<400> SEQUENCE: 11

Met Phe Gly His Lys Thr Gln Gly Phe His Ile Leu Met Ala Val Leu
1               5                   10                  15

Ile Gly Ile His Cys Glu Glu Asp Val Asp Glu Cys Leu Leu His Pro
            20                  25                  30

Cys Leu Asn Gly Gly Thr Cys Glu Asn Leu Pro Gly Asn Tyr Ala Cys
        35                  40                  45

His Cys Pro Phe Asp Asp Thr Ser Arg Thr Phe Tyr Gly Gly Glu Asn
    50                  55                  60

Cys Ser Glu Ile Leu Leu Gly Cys Thr His His Gln Cys Leu Asn Asn
65                  70                  75                  80

Gly Lys Cys Ile Pro His Phe Gln Asn Gly Gln His Gly Phe Thr Cys
                85                  90                  95

Gln Cys Leu Ser Gly Tyr Ala Gly Pro Leu Cys Glu Thr Val Thr Thr
            100                 105                 110

Leu Ser Phe Gly Ser Asn Gly Phe Leu Trp Val Thr Ser Gly Ser His
        115                 120                 125

Thr Gly Ile Gly Pro Glu Cys Asn Ile Ser Leu Arg Phe His Thr Val
    130                 135                 140

Gln Pro Asn Ala Leu Leu Leu Ile Arg Gly Asn Lys Asp Val Ser Met
145                 150                 155                 160

Lys Leu Glu Leu Leu Asn Gly Cys Val His Leu Ser Ile Glu Val Trp
                165                 170                 175

Asn Gln Leu Lys Val Leu Leu Ser Ile Ser His Asn Thr Ser Asp Gly
            180                 185                 190

Glu Trp His Phe Val Glu Val Thr Ile Ala Glu Thr Leu Thr Leu Ala
        195                 200                 205

Leu Val Gly Gly Ser Cys Lys Glu Lys Cys Thr Thr Lys Ser Ser Val
    210                 215                 220

Pro Val Glu Asn His Gln Ser Ile Cys Ala Leu Gln Asp Ser Phe Leu
225                 230                 235                 240

Gly Gly Leu Pro Met Gly Thr Ala Asn Asn Ser Val Ser Val Leu Asn
                245                 250                 255
```

```
Ile Tyr Asn Val Pro Ser Thr Pro Ser Phe Val Gly Cys Leu Gln Asp
        260                 265                 270

Ile Arg Phe Asp Leu Asn His Ile Thr Leu Glu Asn Val Ser Ser Gly
    275                 280                 285

Leu Ser Ser Asn Val Lys Ala Gly Cys Leu Gly Lys Asp Trp Cys Glu
    290                 295                 300

Ser Gln Pro Cys Gln Asn Arg Gly Arg Cys Ile Asn Leu Trp Gln Gly
305                 310                 315                 320

Tyr Gln Cys Glu Cys Asp Arg Pro Tyr Thr Gly Ser Asn Cys Leu Lys
                325                 330                 335

Glu Tyr Val Ala Gly Arg Phe Gly Gln Asp Asp Ser Thr Gly Tyr Ala
            340                 345                 350

Ala Phe Ser Val Asn Asp Asn Tyr Gly Gln Asn Phe Ser Leu Ser Met
        355                 360                 365

Phe Val Arg Thr Arg Gln Pro Leu Gly Leu Leu Leu Ala Leu Glu Asn
    370                 375                 380

Ser Thr Tyr Gln Tyr Val Ser Val Trp Leu Glu His Gly Ser Leu Ala
385                 390                 395                 400

Leu Gln Thr Pro Gly Ser Pro Lys Phe Met Val Asn Phe Phe Leu Ser
                405                 410                 415

Asp Gly Asn Val His Leu Ile Ser Leu Arg Ile Lys Pro Asn Glu Ile
            420                 425                 430

Glu Leu Tyr Gln Ser Ser Gln Asn Leu Gly Phe Ile Ser Val Pro Thr
        435                 440                 445

Trp Thr Ile Arg Arg Gly Asp Val Ile Phe Ile Gly Gly Leu Pro Asp
    450                 455                 460

Arg Glu Lys Thr Glu Val Tyr Gly Gly Phe Phe Lys Gly Cys Val Gln
465                 470                 475                 480

Asp Val Arg Leu Asn Ser Gln Thr Leu Glu Phe Phe Pro Asn Ser Thr
                485                 490                 495

Asn Asn Ala Tyr Asp Asp Pro Ile Leu Val Asn Val Thr Gln Gly Cys
            500                 505                 510

Pro Gly Asp Asn Thr Cys Lys Ser Asn Pro Cys His Asn Gly Gly Val
        515                 520                 525

Cys His Ser Leu Trp Asp Asp Phe Ser Cys Ser Cys Pro Thr Asn Thr
    530                 535                 540

Ala Gly Arg Ala Cys Glu Gln Val Gln Trp Cys Gln Leu Ser Pro Cys
545                 550                 555                 560

Pro Pro Thr Ala Glu Cys Gln Leu Leu Pro Gln Gly Phe Glu Cys Ile
                565                 570                 575

Ala Asn Ala Val Phe Ser Gly Leu Ser Arg Glu Ile Leu Phe Arg Ser
            580                 585                 590

Asn Gly Asn Ile Thr Arg Glu Leu Thr Asn Ile Thr Phe Ala Phe Arg
        595                 600                 605

Thr His Asp Thr Asn Val Met Ile Leu His Ala Glu Lys Glu Pro Glu
    610                 615                 620

Phe Leu Asn Ile Ser Ile Gln Asp Ala Arg Leu Phe Phe Gln Leu Arg
625                 630                 635                 640

Ser Gly Asn Ser Phe Tyr Thr Leu His Leu Met Gly Ser Gln Leu Val
                645                 650                 655

Asn Asp Gly Thr Trp His Gln Val Thr Phe Ser Met Ile Asp Pro Val
            660                 665                 670
```

```
Ala Gln Thr Ser Arg Trp Gln Met Glu Val Asn Asp Gln Thr Pro Phe
        675                 680                 685

Val Ile Ser Glu Val Ala Thr Gly Ser Leu Asn Phe Leu Lys Asp Asn
    690                 695                 700

Thr Asp Ile Tyr Val Gly Asp Gln Ser Val Asp Asn Pro Lys Gly Leu
705                 710                 715                 720

Gln Gly Cys Leu Ser Thr Ile Glu Ile Gly Gly Ile Tyr Leu Ser Tyr
                725                 730                 735

Phe Glu Asn Leu His Gly Phe Pro Gly Lys Pro Gln Glu Glu Gln Phe
            740                 745                 750

Leu Lys Val Ser Thr Asn Met Val Leu Thr Gly Cys Leu Pro Ser Asn
        755                 760                 765

Ala Cys His Ser Ser Pro Cys Leu His Gly Gly Asn Cys Glu Asp Ser
    770                 775                 780

Tyr Ser Ser Tyr Arg Cys Ala Cys Leu Ser Gly Trp Ser Gly Thr His
785                 790                 795                 800

Cys Glu Ile Asn Ile Asp Glu Cys Phe Ser Ser Pro Cys Ile His Gly
                805                 810                 815

Asn Cys Ser Asp Gly Val Ala Ala Tyr His Cys Arg Cys Glu Pro Gly
            820                 825                 830

Tyr Thr Gly Val Asn Cys Glu Val Asp Val Asp Asn Cys Lys Ser His
        835                 840                 845

Gln Cys Ala Asn Gly Ala Thr Cys Val Pro Glu Ala His Gly Tyr Ser
    850                 855                 860

Cys Leu Cys Phe Gly Asn Phe Thr Gly Arg Phe Cys Arg His Ser Arg
865                 870                 875                 880

Leu Pro Ser Thr Val Cys Gly Asn Glu Lys Arg Asn Phe Thr Cys Tyr
                885                 890                 895

Asn Gly Gly Ser Cys Ser Met Phe Gln Glu Asp Trp Gln Cys Met Cys
            900                 905                 910

Trp Pro Gly Phe Thr Gly Glu Trp Cys Glu Glu Asp Ile Asn Glu Cys
        915                 920                 925

Ala Ser Asp Pro Cys Ile Asn Gly Gly Leu Cys Arg Asp Leu Val Asn
    930                 935                 940

Arg Phe Leu Cys Ile Cys Asp Val Ala Phe Ala Gly Glu Arg Cys Glu
945                 950                 955                 960

Leu Asp Val Ser Gly Leu Ser Phe Tyr Val Ser Leu Leu Leu Trp Gln
                965                 970                 975

Asn Leu Phe Gln Leu Leu Ser Tyr Leu Val Leu Arg Met Asn Asp Glu
            980                 985                 990

Pro Val Val Glu Trp Gly Ala Gln  Glu Asn Tyr
        995                 1000
```

<210> SEQ ID NO 12
<211> LENGTH: 5801
<212> TYPE: DNA
<213> ORGANISM: Mus musculus

<400> SEQUENCE: 12

```
tgttcacgga agcctgaggg ggacacgaat ccaatccagg ctggaaaaat ctgctccagg      60

attgactggt taccgtcttc ctgtgcctgt aaggtgctgt gaaagagaag tgctttctga     120

ttctctgtct gtggaggagc cctgggaggg gtgggacaga gatggcatcc tggctctctg     180

aggcacctgc tcttctctga accacacagg agtcaagagc caaacaggga tagcttcagc     240
```

-continued agcacttcag agggtgttct ctaagtaaga acatgaagct caagagaact gcctaccttc 300
tcttcctgta cctcagctcc tcactgctca tctgcataaa gaattcattt tgcaataaaa 360
acaataccag gtgcctttca ggtccttgcc aaaacaattc tacgtgcaag cattttccac 420
aagacaacaa ttgttgctta gacacagcca ataatttgga caaagactgt gaagatctga 480
aagacccttg cttctcgagt ccctgccaag gaattgccac ttgtgtgaaa atcccagggg 540
aagggaactt cctgtgtcag tgtcctcctg ggtacagcgg gctgaactgt gaaactgcca 600
ccaattcctg tggagggaac ctctgccaac atggaggcac ctgccgtaaa gaccctgagc 660
accctgtctg tatctgccct cctggatatg ctggaaggtt ctgtgagact gatcacaatg 720
agtgtgcttc tagcccttgc cacaatgggg ctatgtgcca ggatggaatc aatggctact 780
cctgcttctg tgtgcctgga taccaaggca ggcattgtga cttggaagtg gatgaatgtg 840
tttctgatcc ctgcaagaat gaggctgtgt gcctcaatga gataggaaga tacacttgtg 900
tctgccctca agagttttct ggcgtgaact gtgagttgga aattgatgaa tgcagatccc 960
agccttgtct ccacggtgcc acatgtcagg acgctccagg gggctactcc tgtgactgtg 1020
cacctggatt ccttggagag cactgtgaac tcagcgttaa tgaatgtgaa agtcagccgt 1080
gtctccatgg aggtctatgt gtggatggaa gaaacagtta ccactgtgac tgcacaggta 1140
gtggattcac agggatgcac tgtgagtcct tgattcctct ttgttggtca aagccttgtc 1200
acaacgacgc gacatgtgaa gatactgttg acagctatat ttgtcactgc cggcctggat 1260
acacaggtgc cctgtgtgag acagacataa atgaatgcag tagcaacccc tgccaatttt 1320
ggggggaatg tgtcgagctg tcctcagagg gtctatatgg aaacactgct ggcctgcctt 1380
cctccttcag ctatgttgga gcctcgggct atgtgtgtat ctgtcagcct ggattcacag 1440
gaattcactg tgaagaagac gttgatgaat gtttactgca cccttgccta aatggtggta 1500
cttgtgagaa cctgcctggg aattatgcct gtcactgtcc ctttgatgac acttctagga 1560
cattttatgg aggagaaaac tgctcagaaa ttctcctggg ctgcactcat caccagtgtc 1620
tgaacaatgg aaaatgtatc cctcatttcc aaaatggcca gcatggattc acttgccagt 1680
gtctttctgg ctatgcgggg cccctgtgtg aaactgtcac cacactttca tttgggagca 1740
atggcttcct atgggtcaca agtggctccc atacaggcat agggccagaa tgtaacatat 1800
ccttgaggtt tcacactgtt caaccaaacg cacttctcct catccgaggc aacaaggacg 1860
tgtctatgaa gctggagttg ctgaatggtt gtgttcactt atcaattgaa gtctggaatc 1920
agttaaaggt gctcctgtct atttctcaca acaccagtga tggagaatgg catttcgtgg 1980
aggtaacaat cgcagaaact ctaacccttg ccctagttgg cggctcctgc aaggagaagt 2040
gcaccaccaa gtcttctgtt ccagttgaga atcatcaatc aatatgtgct ttgcaggact 2100
ctttttttggg tggcttacca atggggacag ccaacaacag tgtgtctgtg cttaacatct 2160
ataatgtgcc gtccacacct tcctttgtag gctgtctcca agacattaga tttgatttga 2220
atcacattac tctggagaac gtttcatctg gcctgtcatc aaatgttaaa gcaggctgcc 2280
tgggaaagga ctggtgtgaa agtcaaccct gtcaaaacag aggacgctgc atcaacttgt 2340
ggcagggtta tcagtgtgaa tgtgacaggc cctatacagg ctccaactgc ctgaaaggtg 2400
agaggagtgg ggtgccccag agtgctgtgc ctctgagcag agccatctct aatcacccag 2460
ggtgccgtcc cctgttagga aacataagga cccctcagga cttatgctgg tatttgttca 2520
ctaatgagat aaaatggcat agtcatgata tgtattaatt atgagtgggt ttcataggat 2580
agctgagctt ttttgggctg aaaagtaaaa ttaataataa taacaataag caaataactc 2640
caattaatgt ggtgttttat ctagttagca aaatgctctt agcaatttgc cattcattgt 2700
gtatcagaaa tatatagaaa actttagttc tttgtacaag atgtcatctt ttagagaaag 2760
gggagttttg gacagaaaaa ctagttactg ccacgtacta ataccacacc ttgtgcttgc 2820
tagagtctca gtgaataaac cctttgctga tctctctgtg taactcatac ttccgtaaga 2880
atcgtggtta agattagcat gttgacaagc catcagttct agtcaagact gtctcctaaa 2940
aggccttgtt ttctaaagag gagagatgtc ttcagtcgga aaaagcaaga agacatgaac 3000
tgtattatca ggaaaacttg gtagttgtca cgcacagatc cgtgattcct ctagtgaatc 3060
agtttgaagt ggatttccaa tccctcactt ttgacatcac tctgaaggct gccatcaata 3120
gcgatcaata catacctgct cacttttatt attattatca tgtattgaga gggctgaaag 3180
ggaactctaa cagactgctt tgaagttcag ctgcaattta ctctagcatt ttagaatgag 3240
tccaagaaga acaacatatg gcaaataggc tacgctgttc cgtatgaagg aaaattaaaa 3300
ccagccgtag cctatactct actccatgtt caatggctaa gaattattag aaactattcg 3360
caggttttcc cctaaccaca atattcatta caatcatgga cctgcttgac aatgaggcat 3420
ggcatctgct gctccgcgca atattttaaa tggcgtggca agttgttttg tgattatttt 3480
taaaggtgaa attatgccga ggcaatggtt cacgttttga agaaaaatct aattgaccca 3540
aagcaatatt tttactacat atacaaaata acaaacagat gcggactaat tttgactggc 3600
ttccagatgc ggtgaccctt gaggttagca ctgacctggg aatgctgact gtcctaggaa 3660
atagattcga gagatgccaa gccagcaggt tctggttttc tttacatttt tttttccaac 3720
ttggaaaata atgaactttt gaaacaaaat tcctgatttg gttacacttt ccatattccc 3780
ccaaatagtg tgattacacc cctccactca caccgagtgt aactatatcc cctaccctta 3840
tacaaagtgt gattaaatct tctattttca cagtttgaaa ctgtttagct caacatttga 3900
tatcaaatga ttatagggca ggaatttcat aaaacccttc acttctgaaa atttaggagg 3960
agaattttaa aagaaagtta tatttttcat gtgaccctga gatcataaag ttaaagtatt 4020
ctttattgct gagatccata aggaaatatt ttctgtattt tattccttaa acacacacac 4080
acacacttaa gactccaaat gagactctat atacatatag agccattcta tatgcatatt 4140
caggatgagg cacactaaaa atcaagaggg gaagccatca aagtaacaat tttttaaaga 4200
tgtattttat tattctatgt gtgtgggtct gagtgtatgc ttctgcacca ggtgagtgga 4260
gattcccctg gaacaggagt taatgacagt tttgagctgc ctgatgtggg tattgggatc 4320
aaaccttggt cctctacaag gacagctcat acttttaacc actgagtcac ctctccagtt 4380
ctcaaacaat gattttggaa caatgcttgc cagtgttaaa cccaatgaaa gaagaaggca 4440
tgttgaataa agggtggagt tatctgaatg atacaaaatg tagatagaca ttgccaatat 4500
cttgaaactg atctcaagtc atttatgccc cccataaggt ttctgtaaca acctgaactg 4560
cctgcagtga taacattgta tgtcttgcat tatgtgttag aagaaggtct tctgggatat 4620
tggtctaaag cagttgttct caaccttcct aatgctgtga ccctttaata tagctccttg 4680
tgttttgctg acctcccaac catacagtta ttttgttgct acttcacaac tgtaactttt 4740
gctacttttg tgaattataa tataaatgtc tgtgttttcc aatggtctta gacaagccct 4800
gtgacagccc tgtgtcattc atctccaaag gcttacggcc cacaggtcct aagagaacat 4860
gtaacgtacc tctttctatg ttcggaaagt ctctaattta aaaaaaaaaa caatttatat 4920
atgcttgtct tcctttgtac gcccagactt ttagaatgct attatattag agtcagtgat 4980

```
agttaggttt gacagagcct catcagcagc tggatttctt atggaaccct ctgctttgaa   5040

cccacttcag gaatcgagaa gtcactatcc catctggccc caaattttga aacaattatt   5100

tctgatgacg atttaaccca gcttcccttt tcccacacag ttaccactgc ggatattctc   5160

acttagggct ttaacatccc ctcttgaaaa ttcctaaata tttgaagaaa aatattccat   5220

gcatagcatc cactcccagc atcctacaca cattccttac ctctagtatc tctggaaggc   5280

acgtcccagt gggacatcat tagctacctt acatgctcct ttgccataca tttgcctctt   5340

tctaacaggt ggtatctaaa tgtgcttgat gatgcactga catggaacca caacttccct   5400

ctttctatat aataggctct catttatcat gttagcacta catttaattt ttgggagagt   5460

ttacacactg tcttttgtca gtcattgtca ttgtgaagct agagagtcct cttctattgt   5520

atactgataa gtcacattta atatcaatgc ctcctattaa cctctcacta aacttcacct   5580

tatagtccat cagcattaaa atctctcaaa ttaaattttt ttctccatac atctttagaa   5640

catatccact acctgtatta gtatcaaatc ttccatgtgt agagttgggt ccttcctatg   5700

tggcttaccg tgtttctaaa atcaagtaac acatcacaca ctctgactac ctgcttgtga   5760

tttctgaaga ataggcttac tggagagtca agtttctaag g                       5801
```

<210> SEQ ID NO 13
<211> LENGTH: 761
<212> TYPE: PRT
<213> ORGANISM: Mus musculus

<400> SEQUENCE: 13

```
Met Lys Leu Lys Arg Thr Ala Tyr Leu Leu Phe Leu Tyr Leu Ser Ser
1               5                   10                  15

Ser Leu Leu Ile Cys Ile Lys Asn Ser Phe Cys Asn Lys Asn Asn Thr
            20                  25                  30

Arg Cys Leu Ser Gly Pro Cys Gln Asn Asn Ser Thr Cys Lys His Phe
        35                  40                  45

Pro Gln Asp Asn Asn Cys Cys Leu Asp Thr Ala Asn Asn Leu Asp Lys
    50                  55                  60

Asp Cys Glu Asp Leu Lys Asp Pro Cys Phe Ser Ser Pro Cys Gln Gly
65                  70                  75                  80

Ile Ala Thr Cys Val Lys Ile Pro Gly Glu Gly Asn Phe Leu Cys Gln
                85                  90                  95

Cys Pro Pro Gly Tyr Ser Gly Leu Asn Cys Glu Thr Ala Thr Asn Ser
            100                 105                 110

Cys Gly Gly Asn Leu Cys Gln His Gly Gly Thr Cys Arg Lys Asp Pro
        115                 120                 125

Glu His Pro Val Cys Ile Cys Pro Pro Gly Tyr Ala Gly Arg Phe Cys
    130                 135                 140

Glu Thr Asp His Asn Glu Cys Ala Ser Ser Pro Cys His Asn Gly Ala
145                 150                 155                 160

Met Cys Gln Asp Gly Ile Asn Gly Tyr Ser Cys Phe Cys Val Pro Gly
                165                 170                 175

Tyr Gln Gly Arg His Cys Asp Leu Glu Val Asp Glu Cys Val Ser Asp
            180                 185                 190

Pro Cys Lys Asn Glu Ala Val Cys Leu Asn Glu Ile Gly Arg Tyr Thr
        195                 200                 205

Cys Val Cys Pro Gln Glu Phe Ser Gly Val Asn Cys Glu Leu Glu Ile
    210                 215                 220

Asp Glu Cys Arg Ser Gln Pro Cys Leu His Gly Ala Thr Cys Gln Asp
```

```
225                 230                 235                 240

Ala Pro Gly Gly Tyr Ser Cys Asp Cys Ala Pro Gly Phe Leu Gly Glu
                245                 250                 255

His Cys Glu Leu Ser Val Asn Glu Cys Glu Ser Gln Pro Cys Leu His
            260                 265                 270

Gly Gly Leu Cys Val Asp Gly Arg Asn Ser Tyr His Cys Asp Cys Thr
        275                 280                 285

Gly Ser Gly Phe Thr Gly Met His Cys Glu Ser Leu Ile Pro Leu Cys
    290                 295                 300

Trp Ser Lys Pro Cys His Asn Asp Ala Thr Cys Glu Asp Thr Val Asp
305                 310                 315                 320

Ser Tyr Ile Cys His Cys Arg Pro Gly Tyr Thr Gly Ala Leu Cys Glu
                325                 330                 335

Thr Asp Ile Asn Glu Cys Ser Ser Asn Pro Cys Gln Phe Trp Gly Glu
            340                 345                 350

Cys Val Glu Leu Ser Ser Glu Gly Leu Tyr Gly Asn Thr Ala Gly Leu
        355                 360                 365

Pro Ser Ser Phe Ser Tyr Val Gly Ala Ser Gly Tyr Val Cys Ile Cys
    370                 375                 380

Gln Pro Gly Phe Thr Gly Ile His Cys Glu Glu Asp Val Asp Glu Cys
385                 390                 395                 400

Leu Leu His Pro Cys Leu Asn Gly Gly Thr Cys Glu Asn Leu Pro Gly
                405                 410                 415

Asn Tyr Ala Cys His Cys Pro Phe Asp Asp Thr Ser Arg Thr Phe Tyr
            420                 425                 430

Gly Gly Glu Asn Cys Ser Glu Ile Leu Leu Gly Cys Thr His His Gln
        435                 440                 445

Cys Leu Asn Asn Gly Lys Cys Ile Pro His Phe Gln Asn Gly Gln His
    450                 455                 460

Gly Phe Thr Cys Gln Cys Leu Ser Gly Tyr Ala Gly Pro Leu Cys Glu
465                 470                 475                 480

Thr Val Thr Thr Leu Ser Phe Gly Ser Asn Gly Phe Leu Trp Val Thr
                485                 490                 495

Ser Gly Ser His Thr Gly Ile Gly Pro Glu Cys Asn Ile Ser Leu Arg
            500                 505                 510

Phe His Thr Val Gln Pro Asn Ala Leu Leu Leu Ile Arg Gly Asn Lys
        515                 520                 525

Asp Val Ser Met Lys Leu Glu Leu Leu Asn Gly Cys Val His Leu Ser
    530                 535                 540

Ile Glu Val Trp Asn Gln Leu Lys Val Leu Leu Ser Ile Ser His Asn
545                 550                 555                 560

Thr Ser Asp Gly Glu Trp His Phe Val Glu Val Thr Ile Ala Glu Thr
                565                 570                 575

Leu Thr Leu Ala Leu Val Gly Gly Ser Cys Lys Glu Lys Cys Thr Thr
            580                 585                 590

Lys Ser Ser Val Pro Val Glu Asn His Gln Ser Ile Cys Ala Leu Gln
        595                 600                 605

Asp Ser Phe Leu Gly Gly Leu Pro Met Gly Thr Ala Asn Asn Ser Val
    610                 615                 620

Ser Val Leu Asn Ile Tyr Asn Val Pro Ser Thr Pro Ser Phe Val Gly
625                 630                 635                 640

Cys Leu Gln Asp Ile Arg Phe Asp Leu Asn His Ile Thr Leu Glu Asn
                645                 650                 655
```

Val Ser Ser Gly Leu Ser Ser Asn Val Lys Ala Gly Cys Leu Gly Lys
660 665 670

Asp Trp Cys Glu Ser Gln Pro Cys Gln Asn Arg Gly Arg Cys Ile Asn
675 680 685

Leu Trp Gln Gly Tyr Gln Cys Glu Cys Asp Arg Pro Tyr Thr Gly Ser
690 695 700

Asn Cys Leu Lys Gly Glu Arg Ser Gly Val Pro Gln Ser Ala Val Pro
705 710 715 720

Leu Ser Arg Ala Ile Ser Asn His Pro Gly Cys Arg Pro Leu Leu Gly
725 730 735

Asn Ile Arg Thr Pro Gln Asp Leu Cys Trp Tyr Leu Phe Thr Asn Glu
740 745 750

Ile Lys Trp His Ser His Asp Met Tyr
755 760

<210> SEQ ID NO 14
<211> LENGTH: 42
<212> TYPE: PRT
<213> ORGANISM: Homo sapiens

<400> SEQUENCE: 14

Asp Val Asn Glu Cys Ser Ser Asn Pro Cys Gln Asn Gly Gly Thr Cys
1 5 10 15

Glu Asn Leu Pro Gly Asn Tyr Thr Cys His Cys Pro Phe Asp Asn Leu
20 25 30

Ser Arg Thr Phe Tyr Gly Gly Arg Asp Cys
35 40

<210> SEQ ID NO 15
<211> LENGTH: 32
<212> TYPE: PRT
<213> ORGANISM: Homo sapiens

<400> SEQUENCE: 15

Cys Glu Ser Gln Pro Cys Gln Ser Arg Gly Arg Cys Ile Asn Leu Trp
1 5 10 15

Leu Ser Tyr Gln Cys Asp Cys His Arg Pro Tyr Glu Gly Pro Asn Cys
20 25 30

<210> SEQ ID NO 16
<211> LENGTH: 35
<212> TYPE: PRT
<213> ORGANISM: Homo sapiens

<400> SEQUENCE: 16

Asn Ser Cys Lys Ser Asn Pro Cys His Asn Gly Gly Val Cys His Ser
1 5 10 15

Arg Trp Asp Asp Phe Ser Cys Ser Cys Pro Ala Leu Thr Ser Gly Lys
20 25 30

Ala Cys Glu
35

<210> SEQ ID NO 17
<211> LENGTH: 30
<212> TYPE: PRT
<213> ORGANISM: Homo sapiens

<400> SEQUENCE: 17

Asn Pro Cys Leu His Gly Gly Asn Cys Glu Asp Ile Tyr Ser Ser Tyr 1 5 10 15

His Cys Ser Cys Pro Leu Gly Trp Ser Gly Lys His Cys Glu
20 25 30

<210> SEQ ID NO 18
<211> LENGTH: 29
<212> TYPE: PRT
<213> ORGANISM: Homo sapiens

<400> SEQUENCE: 18

Asn Pro Cys Ile His Gly Asn Cys Ser Asp Arg Val Ala Ala Tyr His
1 5 10 15

Cys Thr Cys Glu Pro Gly Tyr Thr Gly Val Asn Cys Glu
20 25

<210> SEQ ID NO 19
<211> LENGTH: 36
<212> TYPE: PRT
<213> ORGANISM: Homo sapiens

<400> SEQUENCE: 19

Asp Ile Asp Asn Cys Gln Ser His Gln Cys Ala Asn Gly Ala Thr Cys
1 5 10 15

Ile Ser His Thr Asn Gly Tyr Ser Cys Leu Cys Phe Gly Asn Phe Thr
20 25 30

Gly Lys Phe Cys
35

<210> SEQ ID NO 20
<211> LENGTH: 37
<212> TYPE: PRT
<213> ORGANISM: Homo sapiens

<400> SEQUENCE: 20

Asp Ile Asp Glu Cys Ala Ser Asp Pro Cys Val Asn Gly Gly Leu Cys
1 5 10 15

Gln Asp Leu Leu Asn Lys Phe Gln Cys Leu Cys Asp Val Ala Phe Ala
20 25 30

Gly Glu Arg Cys Glu
35

<210> SEQ ID NO 21
<211> LENGTH: 136
<212> TYPE: PRT
<213> ORGANISM: Homo sapiens

<400> SEQUENCE: 21

Phe Gln Thr Val Gln Pro Met Ala Leu Leu Leu Phe Arg Ser Asn Arg
1 5 10 15

Asp Val Phe Val Lys Leu Glu Leu Leu Ser Gly Tyr Ile His Leu Ser
20 25 30

Ile Gln Val Asn Asn Gln Ser Lys Val Leu Leu Phe Ile Ser His Asn
35 40 45

Thr Ser Asp Gly Glu Trp His Phe Val Glu Val Ile Phe Ala Glu Ala
50 55 60

Val Thr Leu Thr Leu Ile Asp Asp Ser Cys Lys Glu Lys Cys Ile Ala
65 70 75 80

Lys Ala Pro Thr Pro Leu Glu Ser Asp Gln Ser Ile Cys Ala Phe Gln
85 90 95

```
Asn Ser Phe Leu Gly Gly Leu Pro Val Gly Met Thr Ser Asn Gly Val
            100                 105                 110

Ala Leu Leu Asn Phe Tyr Asn Met Pro Ser Thr Pro Ser Phe Val Gly
        115                 120                 125

Cys Leu Gln Asp Ile Lys Ile Asp
    130                 135


<210> SEQ ID NO 22
<211> LENGTH: 118
<212> TYPE: PRT
<213> ORGANISM: Homo sapiens

<400> SEQUENCE: 22

Val Arg Thr Leu Gln Pro Ser Gly Leu Leu Leu Ala Leu Glu Asn Ser
1               5                   10                  15

Thr Tyr Gln Tyr Ile Arg Val Trp Leu Glu Arg Gly Arg Leu Ala Met
            20                  25                  30

Leu Thr Pro Asn Ser Pro Lys Leu Val Val Lys Phe Val Leu Asn Asp
        35                  40                  45

Gly Asn Val His Leu Ile Ser Leu Lys Ile Lys Pro Tyr Lys Ile Glu
    50                  55                  60

Leu Tyr Gln Ser Ser Gln Asn Leu Gly Phe Ile Ser Ala Ser Thr Trp
65                  70                  75                  80

Lys Ile Glu Lys Gly Asp Val Ile Tyr Ile Gly Gly Leu Pro Asp Lys
                85                  90                  95

Gln Glu Thr Glu Leu Asn Gly Gly Phe Phe Lys Gly Cys Ile Gln Asp
            100                 105                 110

Val Arg Leu Asn Asn Gln
        115


<210> SEQ ID NO 23
<211> LENGTH: 126
<212> TYPE: PRT
<213> ORGANISM: Homo sapiens

<400> SEQUENCE: 23

Phe Arg Thr Arg Asp Ala Asn Val Ile Ile Leu His Ala Glu Lys Glu
1               5                   10                  15

Pro Glu Phe Leu Asn Ile Ser Ile Gln Asp Ser Arg Leu Phe Phe Gln
            20                  25                  30

Leu Gln Ser Gly Asn Ser Phe Tyr Met Leu Ser Leu Thr Ser Leu Gln
        35                  40                  45

Ser Val Asn Asp Gly Thr Trp His Glu Val Thr Leu Ser Met Thr Asp
    50                  55                  60

Pro Leu Ser Gln Thr Ser Arg Trp Gln Met Glu Val Asp Asn Glu Thr
65                  70                  75                  80

Pro Phe Val Thr Ser Thr Ile Ala Thr Gly Ser Leu Asn Phe Leu Lys
                85                  90                  95

Asp Asn Thr Asp Ile Tyr Val Gly Asp Arg Ala Ile Asp Asn Ile Lys
            100                 105                 110

Gly Leu Gln Gly Cys Leu Ser Thr Ile Glu Ile Gly Gly Ile
        115                 120                 125


<210> SEQ ID NO 24
<211> LENGTH: 292
<212> TYPE: DNA
<213> ORGANISM: Homo sapiens
```

<400> SEQUENCE: 24

```
ctcaggggat tgtctttttc tagcaccttc ttgccactcc taagcgtcct ccgtgacccc     60

ggctgggatt tagcctggtg ctgtgtcagc cccgggctcc caggggcttc ccagtggtcc    120

ccaggaaccc tcgacagggc cagggcgtct ctctcgtcca gcaagggcag ggacgggcca    180

caggccaagg gcagcagtca ggcctgctct gtctgtgaac gctcccggct tggcctcggc    240

tgatgggccc tcacgcctga agcgggcagg aagctccggg atggatttcg gg            292
```

<210> SEQ ID NO 25
<211> LENGTH: 235
<212> TYPE: DNA
<213> ORGANISM: Mus musculus

<400> SEQUENCE: 25

```
caattaggcc ccggtggcag cagtgggatt agcgttagta tgatatctcg cggatgctga     60

atcagcctct ggcttaggga gagaaggtca ctttataagg gtctgggggg ggtcagtgcc    120

tggagttgcg ctgtgggagc cgtcagtggc tgagctcgcc aagcagcctt ggtctctgtc    180

tacgaagagc ccgtggggca gcctcgagag ccgcagccat gaacggcaca gaggg         235
```

<210> SEQ ID NO 26
<211> LENGTH: 508
<212> TYPE: DNA
<213> ORGANISM: cytomegalovirus

<400> SEQUENCE: 26

```
cgttacataa cttacggtaa atggcccgcc tggctgaccg cccaacgacc cccgcccatt     60

gacgtcaata atgacgtatg ttcccatagt aacgccaata gggactttcc attgacgtca    120

atgggtggag tatttacggt aaactgccca cttggcagta catcaagtgt atcatatgcc    180

aagtacgccc cctattgacg tcaatgacgg taaatggccc gcctggcatt atgcccagta    240

catgacctta tgggactttc ctacttggca gtacatctac gtattagtca tcgctattac    300

catggtgatg cggttttggc agtacatcaa tgggcgtgga tagcggtttg actcacgggg    360

atttccaagt ctccacccca ttgacgtcaa tgggagtttg ttttggcacc aaaatcaacg    420

ggactttcca aaatgtcgta acaactccgc cccattgacg caaatgggcg gtaggcgtgt    480

acggtgggag gtctatataa gcagagct                                       508
```

<210> SEQ ID NO 27
<211> LENGTH: 584
<212> TYPE: DNA
<213> ORGANISM: Artificial Sequence
<220> FEATURE:
<223> OTHER INFORMATION: Synthetic- chicken beta-actin (CBA promoter)

<400> SEQUENCE: 27

```
gcgttacata acttacggta aatggcccgc ctggctgacc gcccaacgac ccccgcccat     60

tgacgtcaat aatgacgtat gttcccatag taacgccaat agggactttc cattgacgtc    120

aatgggtgga gtatttacgg taaactgccc acttggcagt acatcaagtg tatcatatgc    180

caagtacgcc ccctattgac gtcaatgacg gtaaatggcc cgcctggcat tatgcccagt    240

acatgacctt atgggacttt cctacttggc agtacatcta cgtattagtc atcgctatta    300

ccatggtcga ggtgagcccc acgttctgct tcactctccc catctccccc ccctccccac    360

ccccaatttt gtatttattt atttttaat tattttgtgc agcgatgggg gcgggggggg    420

gggggggcg cgcgccaggc ggggcggggc ggggcgaggg gcggggcggg gcgaggcgga    480
```

gaggtgcggc ggcagccaat cagagcggcg cgctccgaaa gtttcctttt atggcgaggc 540
ggcggcggcg gcggccctat aaaaagcgaa gcgcgcggcg ggcg 584

<210> SEQ ID NO 28
<211> LENGTH: 20
<212> TYPE: DNA
<213> ORGANISM: Artificial Sequence
<220> FEATURE:
<223> OTHER INFORMATION: Synthetic- CRISPR gRNA primer for making Crb1 AB and B mouse

<400> SEQUENCE: 28
gaataagtac ccgttccttg 20

<210> SEQ ID NO 29
<211> LENGTH: 20
<212> TYPE: DNA
<213> ORGANISM: Artificial Sequence
<220> FEATURE:
<223> OTHER INFORMATION: Synthetic- CRISPR gRNA primer for making Crb1 B mouse

<400> SEQUENCE: 29
aaagcgatta ggtgatgccc 20

<210> SEQ ID NO 30
<211> LENGTH: 20
<212> TYPE: DNA
<213> ORGANISM: Artificial Sequence
<220> FEATURE:
<223> OTHER INFORMATION: Synthetic- CRISPR gRNA primer for making Crb1 AB mouse

<400> SEQUENCE: 30
tgtccgaaca cgtcaacccc 20

<210> SEQ ID NO 31
<211> LENGTH: 21
<212> TYPE: DNA
<213> ORGANISM: Artificial Sequence
<220> FEATURE:
<223> OTHER INFORMATION: Synthetic- RT-PCR primer

<400> SEQUENCE: 31
gcttgctcac tcgttctcag t 21

<210> SEQ ID NO 32
<211> LENGTH: 20
<212> TYPE: DNA
<213> ORGANISM: Artificial Sequence
<220> FEATURE:
<223> OTHER INFORMATION: Synthetic- RT-PCR primer

<400> SEQUENCE: 32
agctctctcc ttccaaaccc 20

<210> SEQ ID NO 33
<211> LENGTH: 20
<212> TYPE: DNA
<213> ORGANISM: Artificial Sequence
<220> FEATURE:
<223> OTHER INFORMATION: Synthetic- RT-PCR primer

<400> SEQUENCE: 33
acccacaagc gtttgctaag 20

<210> SEQ ID NO 34
<211> LENGTH: 20
<212> TYPE: DNA
<213> ORGANISM: Artificial Sequence
<220> FEATURE:
<223> OTHER INFORMATION: Synthetic- genotyping primer

<400> SEQUENCE: 34
cagtatccca ggagcattcc 20

<210> SEQ ID NO 35
<211> LENGTH: 21
<212> TYPE: DNA
<213> ORGANISM: Artificial Sequence
<220> FEATURE:
<223> OTHER INFORMATION: Synthetic- genotyping primer

<400> SEQUENCE: 35
tttttcagtg tgccaggaag t 21

<210> SEQ ID NO 36
<211> LENGTH: 20
<212> TYPE: DNA
<213> ORGANISM: Artificial Sequence
<220> FEATURE:
<223> OTHER INFORMATION: Synthetic- genotyping primer

<400> SEQUENCE: 36
aagactttcc gaagccatga 20

<210> SEQ ID NO 37
<211> LENGTH: 20
<212> TYPE: DNA
<213> ORGANISM: Artificial Sequence
<220> FEATURE:
<223> OTHER INFORMATION: Synthetic- genotyping primer

<400> SEQUENCE: 37
caagacaccc aggaccaagt 20

<210> SEQ ID NO 38
<211> LENGTH: 20
<212> TYPE: DNA
<213> ORGANISM: Artificial Sequence
<220> FEATURE:
<223> OTHER INFORMATION: Synthetic- genotyping primer

<400> SEQUENCE: 38
cttccctctt tggacattgc 20

<210> SEQ ID NO 39
<211> LENGTH: 20
<212> TYPE: DNA
<213> ORGANISM: Artificial Sequence
<220> FEATURE:
<223> OTHER INFORMATION: Synthetic- genotyping primer

<400> SEQUENCE: 39
aacttgggag agcctggagt 20

<210> SEQ ID NO 40
<211> LENGTH: 20
<212> TYPE: DNA
<213> ORGANISM: Artificial Sequence
<220> FEATURE:

<223> OTHER INFORMATION: Synthetic- qPCR primer

<400> SEQUENCE: 40
gcctcgggct atgtgtgtat 20

<210> SEQ ID NO 41
<211> LENGTH: 20
<212> TYPE: DNA
<213> ORGANISM: Artificial Sequence
<220> FEATURE:
<223> OTHER INFORMATION: Synthetic- qPCR primer

<400> SEQUENCE: 41
aaacggttcc tgtcgaccta 20

<210> SEQ ID NO 42
<211> LENGTH: 20
<212> TYPE: DNA
<213> ORGANISM: Artificial Sequence
<220> FEATURE:
<223> OTHER INFORMATION: Synthetic- qPCR primer

<400> SEQUENCE: 42
ggcaagggtg cagtaaacat 20

<210> SEQ ID NO 43
<211> LENGTH: 20
<212> TYPE: DNA
<213> ORGANISM: Artificial Sequence
<220> FEATURE:
<223> OTHER INFORMATION: Synthetic- qPCR primer

<400> SEQUENCE: 43
tgcatcaatg gaggactgtg 20

<210> SEQ ID NO 44
<211> LENGTH: 20
<212> TYPE: DNA
<213> ORGANISM: Artificial Sequence
<220> FEATURE:
<223> OTHER INFORMATION: Synthetic- qPCR primer

<400> SEQUENCE: 44
tcatgcgcag tacgaggtag 20

<210> SEQ ID NO 45
<211> LENGTH: 20
<212> TYPE: DNA
<213> ORGANISM: Artificial Sequence
<220> FEATURE:
<223> OTHER INFORMATION: Synthetic- qPCR primer

<400> SEQUENCE: 45
tgaagaacag ggccaaagtt 20

<210> SEQ ID NO 46
<211> LENGTH: 20
<212> TYPE: DNA
<213> ORGANISM: Artificial Sequence
<220> FEATURE:
<223> OTHER INFORMATION: Synthetic- qPCR primer

<400> SEQUENCE: 46
agaggacgct gcatcaactt 20

<210> SEQ ID NO 47
<211> LENGTH: 20
<212> TYPE: DNA
<213> ORGANISM: Artificial Sequence
<220> FEATURE:
<223> OTHER INFORMATION: Synthetic- qPCR primer

<400> SEQUENCE: 47
tcatcttggc caaatcttcc 20

<210> SEQ ID NO 48
<211> LENGTH: 20
<212> TYPE: DNA
<213> ORGANISM: Artificial Sequence
<220> FEATURE:
<223> OTHER INFORMATION: Synthetic- qPCR primer

<400> SEQUENCE: 48
gctccctcaa gggtttgaat 20

<210> SEQ ID NO 49
<211> LENGTH: 20
<212> TYPE: DNA
<213> ORGANISM: Artificial Sequence
<220> FEATURE:
<223> OTHER INFORMATION: Synthetic- qPCR primer

<400> SEQUENCE: 49
ccatcaggtg cagcgtataa 20

<210> SEQ ID NO 50
<211> LENGTH: 48
<212> TYPE: DNA
<213> ORGANISM: Artificial Sequence
<220> FEATURE:
<223> OTHER INFORMATION: Synthetic- BaseScope probe

<400> SEQUENCE: 50
cacaaggttt tcacatttta atggcagtgc tcataggaat tcactgtg 48

<210> SEQ ID NO 51
<211> LENGTH: 45
<212> TYPE: DNA
<213> ORGANISM: Artificial Sequence
<220> FEATURE:
<223> OTHER INFORMATION: Synthetic- BaseScope probe

<400> SEQUENCE: 51
acctcagctc ctcactgctc atctgcataa agaattcatt ttgca 45

<210> SEQ ID NO 52
<211> LENGTH: 42
<212> TYPE: PRT
<213> ORGANISM: Homo sapiens

<400> SEQUENCE: 52

Ile Leu Leu Gly Cys Thr His Gln Gln Cys Leu Asn Asn Gly Thr Cys
1 5 10 15

Ile Pro His Phe Gln Asp Gly Gln His Gly Phe Ser Cys Leu Cys Pro
20 25 30

Ser Gly Tyr Thr Gly Ser Leu Cys Glu Ile
35 40

<210> SEQ ID NO 53
<211> LENGTH: 16

<212> TYPE: PRT
<213> ORGANISM: Mus musculus

<400> SEQUENCE: 53

Arg Met Asn Asp Glu Pro Val Val Glu Trp Gly Ala Gln Glu Asn Tyr
1 5 10 15

<210> SEQ ID NO 54
<211> LENGTH: 17
<212> TYPE: DNA
<213> ORGANISM: Artificial Sequence
<220> FEATURE:
<223> OTHER INFORMATION: Megf11-specific primer

<400> SEQUENCE: 54
ggctccgggg tatagga 17

<210> SEQ ID NO 55
<211> LENGTH: 18
<212> TYPE: DNA
<213> ORGANISM: Artificial Sequence
<220> FEATURE:
<223> OTHER INFORMATION: Megf11-specific primer

<400> SEQUENCE: 55
ctggctgcat tgcattgg 18

<210> SEQ ID NO 56
<211> LENGTH: 16
<212> TYPE: DNA
<213> ORGANISM: Artificial Sequence
<220> FEATURE:
<223> OTHER INFORMATION: Megf11-specific primer

<400> SEQUENCE: 56
ggtgtccaat aaagtc 16

<210> SEQ ID NO 57
<211> LENGTH: 5764
<212> TYPE: DNA
<213> ORGANISM: Mus musculus

<400> SEQUENCE: 57
ttacagaagg gaggcaccgt gtctcctgcg gggtaggagc taagaatata gcaaagctgc 60
ttgggaagtg gcacagctga ctcttacatt aagccccact gatccagctt gaagaggagt 120
gaggcaaagc tgaaccctcc cactctcctt gacaagtgca agcccacact tttggaaaaa 180
agcacaaaga cgtcagaaac ggttcctgtc gacctactag gctttggatg gctaagtgtt 240
tttgctttgt atggaaatat gtttggacac aagacacaag gttttcacat tttaatggca 300
gtgctcatag gaattcactg tgaagaagac gttgatgaat gtttactgca cccttgccta 360
aatggtggta cttgtgagaa cctgcctggg aattatgcct gtcactgtcc ctttgatgac 420
acttctagga cattttatgg aggagaaaac tgctcagaaa ttctcctggg ctgcactcat 480
caccagtgtc tgaacaatgg aaaatgtatc cctcatttcc aaaatggcca gcatggattc 540
acttgccagt gtctttctgg ctatgcgggg cccctgtgtg aaactgtcac cacactttca 600
tttgggagca atggcttcct atgggtcaca agtggctccc atacaggcat agggccagaa 660
tgtaacatat ccttgaggtt tcacactgtt caaccaaacg cacttctcct catccgaggc 720
aacaaggacg tgtctatgaa gctggagttg ctgaatggtt gtgttcactt atcaattgaa 780
gtctggaatc agttaaaggt gctcctgtct atttctcaca acaccagtga tggagaatgg 840

```
catttcgtgg aggtaacaat cgcagaaact ctaacccttg ccctagttgg cggctcctgc    900
aaggagaagt gcaccaccaa gtcttctgtt ccagttgaga atcatcaatc aatatgtgct    960
ttgcaggact ctttttttggg tggcttacca atggggacag ccaacaacag tgtgtctgtg   1020
cttaacatct ataatgtgcc gtccacacct tcctttgtag gctgtctcca agacattaga   1080
tttgatttga atcacattac tctggagaac gtttcatctg gcctgtcatc aaatgttaaa   1140
gcaggctgcc tgggaaagga ctggtgtgaa agtcaaccct gtcaaaacag aggacgctgc   1200
atcaacttgt ggcagggtta tcagtgtgaa tgtgacaggc cctatacagg ctccaactgc   1260
ctgaaagagt atgtagcggg aagatttggc caagatgact ccacaggata tgcggccttt   1320
agtgttaatg ataattatgg acagaacttc agtctttcaa tgtttgtccg aacacgtcaa   1380
cccctgggct tacttctggc tttggaaaat agtacttacc agtatgtcag tgtctggcta   1440
gagcacggca gcctagcact gcagactcca ggctctccca agttcatggt aaactttttt   1500
ctcagtgatg gaaatgttca cttaatatct ttgagaatca aaccaaatga aattgaactg   1560
tatcagtctt cacaaaacct aggattcatt tctgttccta catggacaat tcgaagagga   1620
gacgtcatct tcattggtgg cttacctgac agagagaaga ctgaagttta tggtggcttc   1680
ttcaaaggct gtgttcaaga tgtcagatta aacagccaga ctctggaatt ctttcccaat   1740
tcaacaaaca atgcatacga tgacccaatt cttgtcaatg tgactcaagg ctgtcccgga   1800
gacaacacat gtaagtccaa cccctgtcat aatggaggtg tctgccactc cctgtgggat   1860
gacttctcct gctcctgccc tacaaacaca gcggggagag cctgcgagca agttcagtgg   1920
tgtcaactca gcccatgtcc tcccactgca gagtgccagc tgctccctca agggtttgaa   1980
tgtatcgcaa acgctgtttt cagcggatta agcagagaaa tactcttcag aagcaatggg   2040
aacattacca gagaactcac caatatcaca tttgctttca gaacacatga tacaaatgtg   2100
atgatattgc atgcagaaaa agaaccagag tttcttaata ttagcattca agatgccaga   2160
ttattctttc aattgcgaag tggcaacagc ttttatacgc tgcacctgat gggttcccaa   2220
ttggtgaatg atggcacatg gcaccaagtg actttctcca tgatagaccc agtggcccag   2280
acctcccggt ggcaaatgga ggtgaacgac cagacaccct ttgtgataag tgaagttgct   2340
actggaagcc tgaacttttt gaaggacaat acagacatct atgtgggtga ccaatctgtt   2400
gacaatccga aaggcctgca gggctgtctg agcacaatag agattggagg catatatctt   2460
tcttactttg aaaatctaca tggtttccct ggtaagcctc aggaagagca atttctcaaa   2520
gtttctacaa atatggtact tactggctgt ttgccatcaa atgcctgcca ctccagcccc   2580
tgtttgcatg gaggaaactg tgaagacagc tacagttctt atcggtgtgc ctgtctctcg   2640
ggatggtcag ggacacactg tgaaatcaac attgatgagt gcttttctag cccctgtatc   2700
catggcaact gctctgatgg agttgcagcc taccactgca ggtgtgagcc tggatacacc   2760
ggtgtgaact gtgaggtgga tgtagacaat tgcaagagtc atcagtgtgc aaatggggcc   2820
acctgtgttc ctgaagctca tggctactct tgtctctgct ttggaaattt taccgggaga   2880
ttttgcagac acagcagatt accctcaaca gtctgtggga atgagaagag aaacttcact   2940
tgctacaatg gaggcagctg ctccatgttc caggaggact ggcaatgtat gtgctggcca   3000
ggtttcactg gagagtggtg tgaagaggac atcaacgagt gtgcctccga tccctgcatc   3060
aatggaggac tgtgcaggga cttggtcaac aggttcctat gcatctgtga tgtggccttc   3120
gctggcgagc gctgtgagct ggacgtaagc ggcctttcct tttatgtgtc cctcttacta   3180
```

-continued

```
tggcaaaacc tctttcagct cctgtcctac ctcgtactgc gcatgaatga tgagccagtt   3240
gtagagtggg gggcacagga aaattattaa tgtgcatggg agcattcaca agtgtaaaac   3300
attgacttgc aagaaacatc ttgtctcagt gtaggtttct aggaaagaca aagggaacat   3360
tagggaatag actccatcta gagcactggt tctcagtctt cctaatgctg caacccttta   3420
gtacagctct tcctgttgta gtgatcgcag ccataacatt attttcattg ccacttcata   3480
actgtaatcc ttctactgct gtgaatcaca atggaaatat ttatgttttc tgatggtctt   3540
aagcaacacc tctgaaaaag tcattgaccc cccccccaaa ggggctgtga tccacaggtt   3600
gagaaatgct catctggaag gtaaccatgc atttaagtgt acctctagta gtttgggtct   3660
atagaagata ttctcctatt ctaccttttt agacacgcca gaagagggca tctgattcca   3720
ttaaagatga ttgggagcca ccgtgtggtt cctgagaact gtactcgggc cctttggaag   3780
agcaatcagt gctctttcca gcccctaaga atatttttaa tacagccaga aaggtctcat   3840
tacccagtgt actgagccct aaggcacttt catcctcaat cgttccatgt tgaatggttt   3900
tcattacatt tggaaaatgt tttctctcca ctctaccttt acatgttcct attttcctat   3960
tgacaatttg ccccttcact gtaattctaa tttggtgtgg tccttcttct cataagttta   4020
tatgtgacat gaacatttaa aaatatctat gaatatttta tagtcatgta tgtctttctg   4080
caaagctatt caaatgaact atggacagtt cttttctaca cgaagaagag atgagtttaa   4140
tccccagtaa catgagaaaa agatgagtga gggacagtgc tcacagtatc cctcactagc   4200
atcatttgtg attccatggg ccattttttt ccaccagcaa atagcagaga gccctttccc   4260
tattcgtttc tcttacactt cccctttctt gttacaactg aacactttac attagttact   4320
cctttgtagg gggtttgact tttccaccgt tttctctggt tcactattta tgctaagtat   4380
ctgtgcaggg cgggtatatc agtccaacag aggtgtcatt agtgttcatt gaggaggaaa   4440
tactttgcat gaattcatga catcattgaa gtagcagtgg ccagaaagat acccttctgc   4500
gaatgtgtct gtgtattcag aagctgccct ggttagaaaa catgtgggtc acttttcctt   4560
tgcatgttac cagtgctcac tgggtcatga ttgttttaag acagagcttt tgctgtggca   4620
atgaccaagg tgaatccaga gatgcagatc agacaaagga caagacaatg tactatctga   4680
gtaaaaccct gccttgactt actcctcagt acttagagat tttacatagc aacctccacc   4740
ctgtggcaac ccgttcacac tagcagtgat gctgagattt gcccttcctt ctcatcatct   4800
tcctcacatc caaagcattt tgtgtccaca ctgctgtttc agataactgt ttctaaagtg   4860
ggattgttgt agccagaaag gtagggaaaa tgttccccaa aatatttgca ttcttaagta   4920
tgtgaagtaa gtagattata gtcagagaca atatgtaagg tttcaggttc actcccttct   4980
acacatatct tcaactgtgt atttgcagaa tattctgaat gtgacatact cccaacagaa   5040
tatatttaag gagtatttat ccacagtatt gttctctgta cagttctagt gcttctattg   5100
tcactgcaat tgtcaattgt ttttctgctt tccaactgtc ttattatcat ttaatagcat   5160
cttgctaaat gccctctttc tattctcctt atttctccat agttcatgtg tgtctgtgtg   5220
actaaggatt ctcctcattt ttgcagaaaa ataaaatctt ttcttcttta tgtcctgctt   5280
gtcattctct ggtgacacat gtctttgctt acttggactg agggttgtac agtaagtaca   5340
gaagcaggct cagtcacaca gacagagaca caccaccacc agcagcagca gcaccaccac   5400
caccaccacc accaccagaa aacagtatga gtactcatct cttgattaca tgtcatttca   5460
agtaagcacc atgacaccga gggccaggtt ccatggactt tctctgttag gcacgtgatt   5520
ctttagctga cctttgagaa cagactccaa caacctcact tatttttact gttgacttat   5580
```

atcatctctg acaacactgg acttcgtttg agctagtcaa gaggaaagac catgacacct 5640
aagggacaga aattcacaca ctcggttttt cataattcac acacattcct atgtatcaaa 5700
tctctgtaat agatgacatt tacttgaata aaaagtcatt tccctttgct gatgtttcat 5760
cttt 5764

<210> SEQ ID NO 58
<211> LENGTH: 1003
<212> TYPE: PRT
<213> ORGANISM: Mus musculus

<400> SEQUENCE: 58

Met Phe Gly His Lys Thr Gln Gly Phe His Ile Leu Met Ala Val Leu
1 5 10 15

Ile Gly Ile His Cys Glu Glu Asp Val Asp Glu Cys Leu Leu His Pro
20 25 30

Cys Leu Asn Gly Gly Thr Cys Glu Asn Leu Pro Gly Asn Tyr Ala Cys
35 40 45

His Cys Pro Phe Asp Asp Thr Ser Arg Thr Phe Tyr Gly Gly Glu Asn
50 55 60

Cys Ser Glu Ile Leu Leu Gly Cys Thr His His Gln Cys Leu Asn Asn
65 70 75 80

Gly Lys Cys Ile Pro His Phe Gln Asn Gly Gln His Gly Phe Thr Cys
85 90 95

Gln Cys Leu Ser Gly Tyr Ala Gly Pro Leu Cys Glu Thr Val Thr Thr
100 105 110

Leu Ser Phe Gly Ser Asn Gly Phe Leu Trp Val Thr Ser Gly Ser His
115 120 125

Thr Gly Ile Gly Pro Glu Cys Asn Ile Ser Leu Arg Phe His Thr Val
130 135 140

Gln Pro Asn Ala Leu Leu Leu Ile Arg Gly Asn Lys Asp Val Ser Met
145 150 155 160

Lys Leu Glu Leu Leu Asn Gly Cys Val His Leu Ser Ile Glu Val Trp
165 170 175

Asn Gln Leu Lys Val Leu Leu Ser Ile Ser His Asn Thr Ser Asp Gly
180 185 190

Glu Trp His Phe Val Glu Val Thr Ile Ala Glu Thr Leu Thr Leu Ala
195 200 205

Leu Val Gly Gly Ser Cys Lys Glu Lys Cys Thr Thr Lys Ser Ser Val
210 215 220

Pro Val Glu Asn His Gln Ser Ile Cys Ala Leu Gln Asp Ser Phe Leu
225 230 235 240

Gly Gly Leu Pro Met Gly Thr Ala Asn Asn Ser Val Ser Val Leu Asn
245 250 255

Ile Tyr Asn Val Pro Ser Thr Pro Ser Phe Val Gly Cys Leu Gln Asp
260 265 270

Ile Arg Phe Asp Leu Asn His Ile Thr Leu Glu Asn Val Ser Ser Gly
275 280 285

Leu Ser Ser Asn Val Lys Ala Gly Cys Leu Gly Lys Asp Trp Cys Glu
290 295 300

Ser Gln Pro Cys Gln Asn Arg Gly Arg Cys Ile Asn Leu Trp Gln Gly
305 310 315 320

Tyr Gln Cys Glu Cys Asp Arg Pro Tyr Thr Gly Ser Asn Cys Leu Lys
325 330 335

```
Glu Tyr Val Ala Gly Arg Phe Gly Gln Asp Asp Ser Thr Gly Tyr Ala
            340                 345                 350

Ala Phe Ser Val Asn Asp Asn Tyr Gly Gln Asn Phe Ser Leu Ser Met
        355                 360                 365

Phe Val Arg Thr Arg Gln Pro Leu Gly Leu Leu Leu Ala Leu Glu Asn
    370                 375                 380

Ser Thr Tyr Gln Tyr Val Ser Val Trp Leu Glu His Gly Ser Leu Ala
385                 390                 395                 400

Leu Gln Thr Pro Gly Ser Pro Lys Phe Met Val Asn Phe Phe Leu Ser
                405                 410                 415

Asp Gly Asn Val His Leu Ile Ser Leu Arg Ile Lys Pro Asn Glu Ile
            420                 425                 430

Glu Leu Tyr Gln Ser Ser Gln Asn Leu Gly Phe Ile Ser Val Pro Thr
        435                 440                 445

Trp Thr Ile Arg Arg Gly Asp Val Ile Phe Ile Gly Gly Leu Pro Asp
    450                 455                 460

Arg Glu Lys Thr Glu Val Tyr Gly Gly Phe Phe Lys Gly Cys Val Gln
465                 470                 475                 480

Asp Val Arg Leu Asn Ser Gln Thr Leu Glu Phe Phe Pro Asn Ser Thr
                485                 490                 495

Asn Asn Ala Tyr Asp Asp Pro Ile Leu Val Asn Val Thr Gln Gly Cys
            500                 505                 510

Pro Gly Asp Asn Thr Cys Lys Ser Asn Pro Cys His Asn Gly Gly Val
        515                 520                 525

Cys His Ser Leu Trp Asp Asp Phe Ser Cys Ser Cys Pro Thr Asn Thr
    530                 535                 540

Ala Gly Arg Ala Cys Glu Gln Val Gln Trp Cys Gln Leu Ser Pro Cys
545                 550                 555                 560

Pro Pro Thr Ala Glu Cys Gln Leu Leu Pro Gln Gly Phe Glu Cys Ile
                565                 570                 575

Ala Asn Ala Val Phe Ser Gly Leu Ser Arg Glu Ile Leu Phe Arg Ser
            580                 585                 590

Asn Gly Asn Ile Thr Arg Glu Leu Thr Asn Ile Thr Phe Ala Phe Arg
        595                 600                 605

Thr His Asp Thr Asn Val Met Ile Leu His Ala Glu Lys Glu Pro Glu
    610                 615                 620

Phe Leu Asn Ile Ser Ile Gln Asp Ala Arg Leu Phe Phe Gln Leu Arg
625                 630                 635                 640

Ser Gly Asn Ser Phe Tyr Thr Leu His Leu Met Gly Ser Gln Leu Val
                645                 650                 655

Asn Asp Gly Thr Trp His Gln Val Thr Phe Ser Met Ile Asp Pro Val
            660                 665                 670

Ala Gln Thr Ser Arg Trp Gln Met Glu Val Asn Asp Gln Thr Pro Phe
        675                 680                 685

Val Ile Ser Glu Val Ala Thr Gly Ser Leu Asn Phe Leu Lys Asp Asn
    690                 695                 700

Thr Asp Ile Tyr Val Gly Asp Gln Ser Val Asp Asn Pro Lys Gly Leu
705                 710                 715                 720

Gln Gly Cys Leu Ser Thr Ile Glu Ile Gly Gly Ile Tyr Leu Ser Tyr
                725                 730                 735

Phe Glu Asn Leu His Gly Phe Pro Gly Lys Pro Gln Glu Glu Gln Phe
            740                 745                 750
```

```
Leu Lys Val Ser Thr Asn Met Val Leu Thr Gly Cys Leu Pro Ser Asn
        755                 760                 765

Ala Cys His Ser Ser Pro Cys Leu His Gly Gly Asn Cys Glu Asp Ser
    770                 775                 780

Tyr Ser Ser Tyr Arg Cys Ala Cys Leu Ser Gly Trp Ser Gly Thr His
785                 790                 795                 800

Cys Glu Ile Asn Ile Asp Glu Cys Phe Ser Ser Pro Cys Ile His Gly
                805                 810                 815

Asn Cys Ser Asp Gly Val Ala Ala Tyr His Cys Arg Cys Glu Pro Gly
            820                 825                 830

Tyr Thr Gly Val Asn Cys Glu Val Asp Val Asp Asn Cys Lys Ser His
        835                 840                 845

Gln Cys Ala Asn Gly Ala Thr Cys Val Pro Glu Ala His Gly Tyr Ser
    850                 855                 860

Cys Leu Cys Phe Gly Asn Phe Thr Gly Arg Phe Cys Arg His Ser Arg
865                 870                 875                 880

Leu Pro Ser Thr Val Cys Gly Asn Glu Lys Arg Asn Phe Thr Cys Tyr
                885                 890                 895

Asn Gly Gly Ser Cys Ser Met Phe Gln Glu Asp Trp Gln Cys Met Cys
            900                 905                 910

Trp Pro Gly Phe Thr Gly Glu Trp Cys Glu Glu Asp Ile Asn Glu Cys
        915                 920                 925

Ala Ser Asp Pro Cys Ile Asn Gly Gly Leu Cys Arg Asp Leu Val Asn
    930                 935                 940

Arg Phe Leu Cys Ile Cys Asp Val Ala Phe Ala Gly Glu Arg Cys Glu
945                 950                 955                 960

Leu Asp Val Ser Gly Leu Ser Phe Tyr Val Ser Leu Leu Leu Trp Gln
                965                 970                 975

Asn Leu Phe Gln Leu Leu Ser Tyr Leu Val Leu Arg Met Asn Asp Glu
            980                 985                 990

Pro Val Val Glu Trp Gly Ala Gln  Glu Asn Tyr
        995                 1000
```

<210> SEQ ID NO 59
<211> LENGTH: 6170
<212> TYPE: DNA
<213> ORGANISM: Mus musculus

<400> SEQUENCE: 59

```
attgttcacg gaagcctgag ggggacacga atccaatcca ggctggaaaa atctgctcca      60

ggattgactg gttaccgtct tcctgtgcct gtaaggtgct gtgaaagaga agtgctttct     120

gattctctgt ctgtggagga gccctgggag gggtgggaca gagatggcat cctggctctc     180

tgaggcacct gctcttctct gaaccacaca ggagtcaaga gccaaacagg gatagcttca     240

gcagcacttc agagggtgtt ctctaagtaa gaacatgaag ctcaagagaa ctgcctacct     300

tctcttcctg tacctcagct cctcactgct catctgcata aagaattcat tttgcaataa     360

aaacaatacc aggtgccttt caggtccttg ccaaaacaat tctacgtgca agcattttcc     420

acaagacaac aattgttgct tagacacagc caataatttg gacaaagact gtgaagatct     480

gaaagaccct tgcttctcga gtccctgcca aggaattgcc acttgtgtga aaatcccagg     540

ggaagggaac ttcctgtgtc agtgtcctcc tgggtacagc gggctgaact gtgaaactgc     600

caccaattcc tgtggaggga acctctgcca acatggaggc acctgccgta aagaccctga     660

gcaccctgtc tgtatctgcc ctcctggata tgctggaagg ttctgtgaga ctgatcacaa     720
```

-continued

```
tgagtgtgct tctagccctt gccacaatgg ggctatgtgc caggatggaa tcaatggcta    780
ctcctgcttc tgtgtgcctg gataccaagg caggcattgt gacttggaag tggatgaatg    840
tgtttctgat ccctgcaaga atgaggctgt gtgcctcaat gagataggaa gatacacttg    900
tgtctgccct caagagtttt ctggcgtgaa ctgtgagttg gaaattgatg aatgcagatc    960
ccagccttgt ctccacggtg ccacatgtca ggacgctcca gggggctact cctgtgactg   1020
tgcacctgga ttccttggag agcactgtga actcagcgtt aatgaatgtg aaagtcagcc   1080
gtgtctccat ggaggtctat gtgtggatgg aagaaacagt taccactgtg actgcacagg   1140
tagtggattc acagggatgc actgtgagtc cttgattcct ctttgttggt caaagccttg   1200
tcacaacgac gcgacatgtg aagatactgt tgacagctat atttgtcact gccggcctgg   1260
atacacaggt gccctgtgtg agacagacat aaatgaatgc agtagcaacc cctgccaatt   1320
ttggggggaa tgtgtcgagc tgtcctcaga gggtctatat ggaaacactg ctggcctgcc   1380
ttcctccttc agctatgttg gagcctcggg ctatgtgtgt atctgtcagc ctggattcac   1440
aggaattcac tgtgaagaag acgttgatga atgtttactg caccccttgcc taaatggtgg  1500
tacttgtgag aacctgcctg ggaattatgc ctgtcactgt ccctttgatg acacttctag   1560
gacattttat ggaggagaaa actgctcaga aattctcctg ggctgcactc atcaccagtg   1620
tctgaacaat ggaaaatgta tccctcattt ccaaaatggc cagcatggat tcacttgcca   1680
gtgtctttct ggctatgcgg ggcccctgtg tgaaactgtc accacacttt catttgggag   1740
caatggcttc ctatgggtca caagtggctc ccatacaggc atagggccag aatgtaacat   1800
atccttgagg tttcacactg ttcaaccaaa cgcacttctc ctcatccgag gcaacaagga   1860
cgtgtctatg aagctggagt tgctgaatgg ttgtgttcac ttatcaattg aagtctggaa   1920
tcagttaaag gtgctcctgt ctatttctca caacaccagt gatggagaat ggcatttcgt   1980
ggaggtaaca atcgcagaaa ctctaaccct tgccctagtt ggcggctcct gcaaggagaa   2040
gtgcaccacc aagtcttctg ttccagttga gaatcatcaa tcaatatgtg ctttgcagga   2100
ctctttttg ggtggcttac caatggggac agccaacaac agtgtgtctg tgcttaacat   2160
ctataatgtg ccgtccacac cttcctttgt aggctgtctc caagacatta gatttgattt   2220
gaatcacatt actctggaga acgtttcatc tggcctgtca tcaaatgtta aagcaggctg   2280
cctgggaaag gactggtgtg aaagtcaacc ctgtcaaaac agaggacgct gcatcaactt   2340
gtggcagggt tatcagtgtg aatgtgacag gccctataca ggctccaact gcctgaaaga   2400
gtatgtagcg ggaagatttg gccaagatga ctccacagga tatgcggcct ttagtgttaa   2460
tgataattat ggacagaact tcagtctttc aatgtttgtc cgaacacgtc aacccctggg   2520
cttacttctg gctttggaaa atagtactta ccagtatgtc agtgtctggc tagagcacgg   2580
cagcctagca ctgcagactc caggctctcc caagttcatg gtaaactttt ttctcagtga   2640
tggaaatgtt cacttaatat ctttgagaat caaaccaaat gaaattgaac tgtatcagtc   2700
ttcacaaaac ctaggattca tttctgttcc tacatggaca attcgaagag gagacgtcat   2760
cttcattggt ggcttacctg acagagagaa gactgaagtt tatggtggct tcttcaaagg   2820
ctgtgttcaa gatgtcagat taaacagcca gactctggaa ttctttccca attcaacaaa   2880
caatgcatac gatgacccaa ttcttgtcaa tgtgactcaa ggctgtcccg gagacaacac   2940
atgtaagtcc aacccctgtc ataatggagg tgtctgccac tccctgtggg atgacttctc   3000
ctgctcctgc cctacaaaca cagcggggag agcctgcgag caagttcagt ggtgtcaact   3060
```

cagcccatgt cctcccactg cagagtgcca gctgctccct caagggtttg aatgtatcgc 3120
aaacgctgtt ttcagcggat taagcagaga aatactcttc agaagcaatg ggaacattac 3180
cagagaactc accaatatca catttgcttt cagaacacat gatacaaatg tgatgatatt 3240
gcatgcagaa aaagaaccag agtttcttaa tattagcatt caagatgcca gattattctt 3300
tcaattgcga agtggcaaca gcttttatac gctgcacctg atgggttccc aattggtgaa 3360
tgatggcaca tggcaccaag tgactttctc catgatagac ccagtggccc agacctcccg 3420
gtggcaaatg gaggtgaacg accagacacc ctttgtgata agtgaagttg ctactggaag 3480
cctgaacttt ttgaaggaca atacagacat ctatgtgggt gaccaatctg ttgacaatcc 3540
gaaaggcctg cagggctgtc tgagcacaat agagattgga ggcatatatc tttcttactt 3600
tgaaaatcta catggtttcc ctggtaagcc tcaggaagag caatttctca aagtttctac 3660
aaatatggta cttactggct gtttgccatc aaatgcctgc cactccagcc cctgtttgca 3720
tggaggaaac tgtgaagaca gctacagttc ttatcggtgt gcctgtctct cgggatggtc 3780
agggacacac tgtgaaatca acattgatga gtgcttttct agcccctgta tccatggcaa 3840
ctgctctgat ggagttgcag cctaccactg caggtgtgag cctggataca ccggtgtgaa 3900
ctgtgaggtg gatgtagaca attgcaagag tcatcagtgt gcaaatgggg ccacctgtgt 3960
tcctgaagct catggctact cttgtctctg ctttggaaat tttaccggga gattttgcag 4020
acacagcaga ttaccctcaa cagtctgtgg gaatgagaag agaaacttca cttgctacaa 4080
tggaggcagc tgctccatgt tccaggagga ctggcaatgt atgtgctggc caggtttcac 4140
tggagagtgg tgtgaagagg acatcaacga gtgtgcctcc gatccctgca tcaatggagg 4200
actgtgcagg gacttggtca acaggttcct atgcatctgt gatgtggcct tcgctggcga 4260
gcgctgtgag ctggacctgg ctgatgacag gctcctgggc attttcaccg ctgttggctc 4320
cggaactttg gccctgttct tcatcctctt gcttgctggg gttgcttctc ttattgcctc 4380
caacaaaagg gcgactcaag gaacctacag ccccagcggt caggagaagg ctggccctcg 4440
agtggaaatg tggatcagga tgccgccccc ggcactggaa aggctcatct aggagactgc 4500
tgctcttctc aggacagaga agaacatgat gagtaccggg tcgtgcctga gtgaagatgg 4560
ctttacatca ctagagatac atacagctgg gactgtggga aggaccttcc tgtggagtca 4620
ctgagtagtt atgtcatcca ttcacagaag agtgtccctg tgtttgcctg tcagcctcag 4680
aattagcaaa acatctagca gacagagaac acagtatttc agaagaactc cagaggctgc 4740
cccttaaact ctttactggt tgatccacat aaaatgctta gtagccaagt gccattaatt 4800
atacagagcc aagaagaaaa attagaatac aactttcact tttttatttg tagggaaggt 4860
tttatgtttt ggtttgttgt tgttgttgtg acagtgacag tgactcatta catagaccaa 4920
gctggcctca aaatcacatg gaccctcggg attacatgtg tccgaccatg ttcatcttat 4980
ttttgaatct tctgtcatat ggtaaaagat tccagtggga cctgaggagt gactagctag 5040
gtaaagcaag ggctgtgtaa gtgccagaac tggtgtttgt gtcctcatta tccacataag 5100
tgccaagtga gtgtggcccc tgcctgtcat cctaggcctc aggagatatc actgctcact 5160
ggagcaagcc ggttaaactg ttagggcagg taagttttga cttcaagtga gagaccctga 5220
ctcaatatga aaggcaatta gtgagtcaag atgaccctgt atgctaacct cttgcctata 5280
catgcatata cacacattta catatgtgcc caaacatgag gacacaagca cacgcgcgcg 5340
cgcacacaca cacacacaca cacacacaca cacacacaca cacacacacg agtctaattg 5400
tatatagtga taacagtaca ctttcctcct tctatttcgg atttagagaa agccatgaga 5460

```
agcgtgtatg gtttaaacca tgacccaagc ataacaaata aagttgaaat agttgttctc   5520

ctgtccaagc ttgtctttat tgttgtgcat tctgtaagct ggttgcttgg ttggctgatg   5580

gatggcttct gtttgtttgt tgttttttgt ttgtttgttt gtctgggata ttacatgtaa   5640

gaaaaataac tggtaagaac aatcaaagaa ctttgttatg aattaaatct tttgtctaag   5700

tcacttagag tcattattct ttatgtagat ttgcttccag tcaggacatt tcctagacag   5760

aatttaagac agtaagaaaa tgatttgtca cgtctgaaag aggttcttta ctttcaggga   5820

cttttgataa tgcccaacag agatggcatc gaaagaggag ctcatagcga gatgggcatt   5880

tgtgcatcct caaggagaaa atattgtacc ttctgtttgt atattgtcta ttctgtgatg   5940

gctgtatctt acatatgttt tgatgcatgt aacaatagta tcatatgaaa taaattatat   6000

atatatataa tatataatat atatcacaag ataaaaattg aaattacata aactttaaat   6060

ctaaaagaag aaacctatcc ttcccaagta ttatcagtgc agtcaccgag ctttttttgt   6120

tttttgtat tagccatttc ttcataatac aggaagttct ataacttcaa              6170
```

<210> SEQ ID NO 60
<211> LENGTH: 1405
<212> TYPE: PRT
<213> ORGANISM: Mus musculus

<400> SEQUENCE: 60

```
Met Lys Leu Lys Arg Thr Ala Tyr Leu Leu Phe Leu Tyr Leu Ser Ser
1               5                   10                  15

Ser Leu Leu Ile Cys Ile Lys Asn Ser Phe Cys Asn Lys Asn Asn Thr
            20                  25                  30

Arg Cys Leu Ser Gly Pro Cys Gln Asn Asn Ser Thr Cys Lys His Phe
        35                  40                  45

Pro Gln Asp Asn Asn Cys Cys Leu Asp Thr Ala Asn Asn Leu Asp Lys
    50                  55                  60

Asp Cys Glu Asp Leu Lys Asp Pro Cys Phe Ser Ser Pro Cys Gln Gly
65                  70                  75                  80

Ile Ala Thr Cys Val Lys Ile Pro Gly Glu Gly Asn Phe Leu Cys Gln
                85                  90                  95

Cys Pro Pro Gly Tyr Ser Gly Leu Asn Cys Glu Thr Ala Thr Asn Ser
            100                 105                 110

Cys Gly Gly Asn Leu Cys Gln His Gly Gly Thr Cys Arg Lys Asp Pro
        115                 120                 125

Glu His Pro Val Cys Ile Cys Pro Pro Gly Tyr Ala Gly Arg Phe Cys
    130                 135                 140

Glu Thr Asp His Asn Glu Cys Ala Ser Ser Pro Cys His Asn Gly Ala
145                 150                 155                 160

Met Cys Gln Asp Gly Ile Asn Gly Tyr Ser Cys Phe Cys Val Pro Gly
                165                 170                 175

Tyr Gln Gly Arg His Cys Asp Leu Glu Val Asp Glu Cys Val Ser Asp
            180                 185                 190

Pro Cys Lys Asn Glu Ala Val Cys Leu Asn Glu Ile Gly Arg Tyr Thr
        195                 200                 205

Cys Val Cys Pro Gln Glu Phe Ser Gly Val Asn Cys Glu Leu Glu Ile
    210                 215                 220

Asp Glu Cys Arg Ser Gln Pro Cys Leu His Gly Ala Thr Cys Gln Asp
225                 230                 235                 240

Ala Pro Gly Gly Tyr Ser Cys Asp Cys Ala Pro Gly Phe Leu Gly Glu
```

```
                245                 250                 255

His Cys Glu Leu Ser Val Asn Glu Cys Glu Ser Gln Pro Cys Leu His
            260                 265                 270

Gly Gly Leu Cys Val Asp Gly Arg Asn Ser Tyr His Cys Asp Cys Thr
        275                 280                 285

Gly Ser Gly Phe Thr Gly Met His Cys Glu Ser Leu Ile Pro Leu Cys
    290                 295                 300

Trp Ser Lys Pro Cys His Asn Asp Ala Thr Cys Glu Asp Thr Val Asp
305                 310                 315                 320

Ser Tyr Ile Cys His Cys Arg Pro Gly Tyr Thr Gly Ala Leu Cys Glu
                325                 330                 335

Thr Asp Ile Asn Glu Cys Ser Ser Asn Pro Cys Gln Phe Trp Gly Glu
            340                 345                 350

Cys Val Glu Leu Ser Ser Glu Gly Leu Tyr Gly Asn Thr Ala Gly Leu
        355                 360                 365

Pro Ser Ser Phe Ser Tyr Val Gly Ala Ser Gly Tyr Val Cys Ile Cys
    370                 375                 380

Gln Pro Gly Phe Thr Gly Ile His Cys Glu Glu Asp Val Asp Glu Cys
385                 390                 395                 400

Leu Leu His Pro Cys Leu Asn Gly Gly Thr Cys Glu Asn Leu Pro Gly
                405                 410                 415

Asn Tyr Ala Cys His Cys Pro Phe Asp Asp Thr Ser Arg Thr Phe Tyr
            420                 425                 430

Gly Gly Glu Asn Cys Ser Glu Ile Leu Leu Gly Cys Thr His His Gln
        435                 440                 445

Cys Leu Asn Asn Gly Lys Cys Ile Pro His Phe Gln Asn Gly Gln His
    450                 455                 460

Gly Phe Thr Cys Gln Cys Leu Ser Gly Tyr Ala Gly Pro Leu Cys Glu
465                 470                 475                 480

Thr Val Thr Thr Leu Ser Phe Gly Ser Asn Gly Phe Leu Trp Val Thr
                485                 490                 495

Ser Gly Ser His Thr Gly Ile Gly Pro Glu Cys Asn Ile Ser Leu Arg
            500                 505                 510

Phe His Thr Val Gln Pro Asn Ala Leu Leu Leu Ile Arg Gly Asn Lys
        515                 520                 525

Asp Val Ser Met Lys Leu Glu Leu Leu Asn Gly Cys Val His Leu Ser
    530                 535                 540

Ile Glu Val Trp Asn Gln Leu Lys Val Leu Leu Ser Ile Ser His Asn
545                 550                 555                 560

Thr Ser Asp Gly Glu Trp His Phe Val Glu Val Thr Ile Ala Glu Thr
                565                 570                 575

Leu Thr Leu Ala Leu Val Gly Gly Ser Cys Lys Glu Lys Cys Thr Thr
            580                 585                 590

Lys Ser Ser Val Pro Val Glu Asn His Gln Ser Ile Cys Ala Leu Gln
        595                 600                 605

Asp Ser Phe Leu Gly Gly Leu Pro Met Gly Thr Ala Asn Asn Ser Val
    610                 615                 620

Ser Val Leu Asn Ile Tyr Asn Val Pro Ser Thr Pro Ser Phe Val Gly
625                 630                 635                 640

Cys Leu Gln Asp Ile Arg Phe Asp Leu Asn His Ile Thr Leu Glu Asn
                645                 650                 655

Val Ser Ser Gly Leu Ser Ser Asn Val Lys Ala Gly Cys Leu Gly Lys
            660                 665                 670
```

```
Asp Trp Cys Glu Ser Gln Pro Cys Gln Asn Arg Gly Arg Cys Ile Asn
        675                 680                 685

Leu Trp Gln Gly Tyr Gln Cys Glu Cys Asp Arg Pro Tyr Thr Gly Ser
    690                 695                 700

Asn Cys Leu Lys Glu Tyr Val Ala Gly Arg Phe Gly Gln Asp Asp Ser
705                 710                 715                 720

Thr Gly Tyr Ala Ala Phe Ser Val Asn Asp Asn Tyr Gly Gln Asn Phe
                725                 730                 735

Ser Leu Ser Met Phe Val Arg Thr Arg Gln Pro Leu Gly Leu Leu Leu
            740                 745                 750

Ala Leu Glu Asn Ser Thr Tyr Gln Tyr Val Ser Val Trp Leu Glu His
        755                 760                 765

Gly Ser Leu Ala Leu Gln Thr Pro Gly Ser Pro Lys Phe Met Val Asn
    770                 775                 780

Phe Phe Leu Ser Asp Gly Asn Val His Leu Ile Ser Leu Arg Ile Lys
785                 790                 795                 800

Pro Asn Glu Ile Glu Leu Tyr Gln Ser Ser Gln Asn Leu Gly Phe Ile
                805                 810                 815

Ser Val Pro Thr Trp Thr Ile Arg Arg Gly Asp Val Ile Phe Ile Gly
            820                 825                 830

Gly Leu Pro Asp Arg Glu Lys Thr Glu Val Tyr Gly Gly Phe Phe Lys
        835                 840                 845

Gly Cys Val Gln Asp Val Arg Leu Asn Ser Gln Thr Leu Glu Phe Phe
    850                 855                 860

Pro Asn Ser Thr Asn Asn Ala Tyr Asp Asp Pro Ile Leu Val Asn Val
865                 870                 875                 880

Thr Gln Gly Cys Pro Gly Asp Asn Thr Cys Lys Ser Asn Pro Cys His
                885                 890                 895

Asn Gly Gly Val Cys His Ser Leu Trp Asp Asp Phe Ser Cys Ser Cys
            900                 905                 910

Pro Thr Asn Thr Ala Gly Arg Ala Cys Glu Gln Val Gln Trp Cys Gln
        915                 920                 925

Leu Ser Pro Cys Pro Pro Thr Ala Glu Cys Gln Leu Leu Pro Gln Gly
    930                 935                 940

Phe Glu Cys Ile Ala Asn Ala Val Phe Ser Gly Leu Ser Arg Glu Ile
945                 950                 955                 960

Leu Phe Arg Ser Asn Gly Asn Ile Thr Arg Glu Leu Thr Asn Ile Thr
                965                 970                 975

Phe Ala Phe Arg Thr His Asp Thr Asn Val Met Ile Leu His Ala Glu
            980                 985                 990

Lys Glu Pro Glu Phe Leu Asn Ile  Ser Ile Gln Asp Ala  Arg Leu Phe
        995                 1000                 1005

Phe Gln  Leu Arg Ser Gly Asn  Ser Phe Tyr Thr Leu  His Leu Met
    1010                 1015                 1020

Gly Ser  Gln Leu Val Asn Asp  Gly Thr Trp His Gln  Val Thr Phe
    1025                 1030                 1035

Ser Met  Ile Asp Pro Val Ala  Gln Thr Ser Arg Trp  Gln Met Glu
    1040                 1045                 1050

Val Asn  Asp Gln Thr Pro Phe  Val Ile Ser Glu Val  Ala Thr Gly
    1055                 1060                 1065

Ser Leu  Asn Phe Leu Lys Asp  Asn Thr Asp Ile Tyr  Val Gly Asp
    1070                 1075                 1080
```

Gln Ser Val Asp Asn Pro Lys Gly Leu Gln Gly Cys Leu Ser Thr
1085 1090 1095

Ile Glu Ile Gly Gly Ile Tyr Leu Ser Tyr Phe Glu Asn Leu His
1100 1105 1110

Gly Phe Pro Gly Lys Pro Gln Glu Glu Gln Phe Leu Lys Val Ser
1115 1120 1125

Thr Asn Met Val Leu Thr Gly Cys Leu Pro Ser Asn Ala Cys His
1130 1135 1140

Ser Ser Pro Cys Leu His Gly Gly Asn Cys Glu Asp Ser Tyr Ser
1145 1150 1155

Ser Tyr Arg Cys Ala Cys Leu Ser Gly Trp Ser Gly Thr His Cys
1160 1165 1170

Glu Ile Asn Ile Asp Glu Cys Phe Ser Ser Pro Cys Ile His Gly
1175 1180 1185

Asn Cys Ser Asp Gly Val Ala Ala Tyr His Cys Arg Cys Glu Pro
1190 1195 1200

Gly Tyr Thr Gly Val Asn Cys Glu Val Asp Val Asp Asn Cys Lys
1205 1210 1215

Ser His Gln Cys Ala Asn Gly Ala Thr Cys Val Pro Glu Ala His
1220 1225 1230

Gly Tyr Ser Cys Leu Cys Phe Gly Asn Phe Thr Gly Arg Phe Cys
1235 1240 1245

Arg His Ser Arg Leu Pro Ser Thr Val Cys Gly Asn Glu Lys Arg
1250 1255 1260

Asn Phe Thr Cys Tyr Asn Gly Gly Ser Cys Ser Met Phe Gln Glu
1265 1270 1275

Asp Trp Gln Cys Met Cys Trp Pro Gly Phe Thr Gly Glu Trp Cys
1280 1285 1290

Glu Glu Asp Ile Asn Glu Cys Ala Ser Asp Pro Cys Ile Asn Gly
1295 1300 1305

Gly Leu Cys Arg Asp Leu Val Asn Arg Phe Leu Cys Ile Cys Asp
1310 1315 1320

Val Ala Phe Ala Gly Glu Arg Cys Glu Leu Asp Leu Ala Asp Asp
1325 1330 1335

Arg Leu Leu Gly Ile Phe Thr Ala Val Gly Ser Gly Thr Leu Ala
1340 1345 1350

Leu Phe Phe Ile Leu Leu Leu Ala Gly Val Ala Ser Leu Ile Ala
1355 1360 1365

Ser Asn Lys Arg Ala Thr Gln Gly Thr Tyr Ser Pro Ser Gly Gln
1370 1375 1380

Glu Lys Ala Gly Pro Arg Val Glu Met Trp Ile Arg Met Pro Pro
1385 1390 1395

Pro Ala Leu Glu Arg Leu Ile
1400 1405

<210> SEQ ID NO 61
<211> LENGTH: 5894
<212> TYPE: DNA
<213> ORGANISM: Mus musculus

<400> SEQUENCE: 61
gcctttccag gaggcattgt tcacggaagc ctgaggggga cacgaatcca atccaggctg 60
gaaaaatctg ctccaggatt gactggttac cgtcttcctg tgcctgtaag gtgctgtgaa 120
agagaagtgc tttctgattc tctgtctgtg gaggagccct gggaggggtg ggacagagat 180

```
ggcatcctgg ctctctgagg cacctgctct tctctgaacc acacaggagt caagagccaa    240
acagggatag cttcagcagc acttcagagg gtgttctcta agtaagaaca tgaagctcaa    300
gagaactgcc taccttctct tcctgtacct cagctcctca ctgctcatct gcataaagaa    360
ttcattttgc aataaaaaca ataccaggtg cctttcaggt ccttgccaaa acaattctac    420
gtgcaagcat tttccacaag acaacaattg ttgcttagac acagccaata atttggacaa    480
agactgtgaa gatctgaaag acccttgctt ctcgagtccc tgccaaggaa ttgccacttg    540
tgtgaaaatc ccaggggaag ggaacttcct gtgtcagtgt cctcctgggt acagcgggct    600
gaactgtgaa actgccacca attcctgtgg agggaacctc tgccaacatg gaggcacctg    660
ccgtaaagac cctgagcacc ctgtctgtat ctgccctcct ggatatgctg gaaggttctg    720
tgagactgat cacaatgagt gtgcttctag cccttgccac aatggggcta tgtgccagga    780
tggaatcaat ggctactcct gcttctgtgt gcctggatac caaggcaggc attgtgactt    840
ggaagtggat gaatgtgttt ctgatccctg caagaatgag gctgtgtgcc tcaatgagat    900
aggaagatac acttgtgtct gccctcaaga gttttctggc gtgaactgtg agttggaaat    960
tgatgaatgc agatcccagc cttgtctcca cggtgccaca tgtcaggacg ctccaggggg   1020
ctactcctgt gactgtgcac ctggattcct tggagagcac tgtgaactca gcgttaatga   1080
atgtgaaagt cagccgtgtc tccatggagg tctatgtgtg gatggaagaa acagttacca   1140
ctgtgactgc acaggtagtg gattcacagg gatgcactgt gagtccttga ttcctctttg   1200
ttggtcaaag ccttgtcaca acgacgcgac atgtgaagat actgttgaca gctatatttg   1260
tcactgccgg cctggaattc actgtgaaga agacgttgat gaatgtttac tgcacccttg   1320
cctaaatggt ggtacttgtg agaacctgcc tgggaattat gcctgtcact gtccctttga   1380
tgacacttct aggacatttt atggaggaga aaactgctca gaaattctcc tgggctgcac   1440
tcatcaccag tgtctgaaca atggaaaatg tatccctcat ttccaaaatg gccagcatgg   1500
attcacttgc cagtgtcttt ctggctatgc ggggcccctg tgtgaaactg tcaccacact   1560
ttcatttggg agcaatggct tcctatgggt cacaagtggc tcccatacag gcatagggcc   1620
agaatgtaac atatccttga ggtttcacac tgttcaacca aacgcacttc tcctcatccg   1680
aggcaacaag gacgtgtcta tgaagctgga gttgctgaat ggttgtgttc acttatcaat   1740
tgaagtctgg aatcagttaa aggtgctcct gtctatttct cacaacacca gtgatggaga   1800
atggcatttc gtggaggtaa caatcgcaga aactctaacc cttgccctag ttggcggctc   1860
ctgcaaggag aagtgcacca ccaagtcttc tgttccagtt gagaatcatc aatcaatatg   1920
tgctttgcag gactcttttt tgggtggctt accaatgggg acagccaaca acagtgtgtc   1980
tgtgcttaac atctataatg tgccgtccac accttccttt gtaggctgtc tccaagacat   2040
tagatttgat ttgaatcaca ttactctgga gaacgtttca tctggcctgt catcaaatgt   2100
taaagcaggc tgcctgggaa aggactggtg tgaaagtcaa ccctgtcaaa acagaggacg   2160
ctgcatcaac ttgtggcagg gttatcagtg tgaatgtgac aggccctata caggctccaa   2220
ctgcctgaaa gagtatgtag cgggaagatt tggccaagat gactccacag gatatgcggc   2280
ctttagtgtt aatgataatt atggacagaa cttcagtctt tcaatgtttg tccgaacacg   2340
tcaacccctg ggcttacttc tggctttgga aaatagtact taccagtatg tcagtgtctg   2400
gctagagcac ggcagcctag cactgcagac tccaggctct cccaagttca tggtaaactt   2460
ttttctcagt gatggaaatg ttcacttaat atctttgaga atcaaaccaa atgaaattga   2520
```

actgtatcag tcttcacaaa acctaggatt catttctgtt cctacatgga caattcgaag 2580
aggagacgtc atcttcattg gtggcttacc tgacagagag aagactgaag tttatggtgg 2640
cttcttcaaa ggctgtgttc aagatgtcag attaaacagc cagactctgg aattctttcc 2700
caattcaaca aacaatgcat acgatgaccc aattcttgtc aatgtgactc aaggctgtcc 2760
cggagacaac acatgtaagt ccaacccctg tcataatgga ggtgtctgcc actccctgtg 2820
ggatgacttc tcctgctcct gccctacaaa cacagcgggg agagcctgcg agcaagttca 2880
gtggtgtcaa ctcagcccat gtcctcccac tgcagagtgc cagctgctcc ctcaagggtt 2940
tgaatgtatc gcaaacgctg ttttcagcgg attaagcaga gaaatactct tcagaagcaa 3000
tgggaacatt accagagaac tcaccaatat cacatttgct ttcagaacac atgatacaaa 3060
tgtgatgata ttgcatgcag aaaaagaacc agagtttctt aatattagca ttcaagatgc 3120
cagattattc tttcaattgc gaagtggcaa cagcttttat acgctgcacc tgatgggttc 3180
ccaattggtg aatgatggca catggcacca agtgactttc tccatgatag acccagtggc 3240
ccagacctcc cggtggcaaa tggaggtgaa cgaccagaca ccctttgtga taagtgaagt 3300
tgctactgga agcctgaact tttgaagga caatacagac atctatgtgg gtgaccaatc 3360
tgttgacaat ccgaaaggcc tgcagggctg tctgagcaca atagagattg gaggcatata 3420
tctttcttac tttgaaaatc tacatggttt ccctggtaag cctcaggaag agcaatttct 3480
caaagtttct acaaatatgg tacttactgg ctgtttgcca tcaaatgcct gccactccag 3540
cccctgtttg catggaggaa actgtgaaga cagctacagt tcttatcggt gtgcctgtct 3600
ctcgggatgg tcagggacac actgtgaaat caacattgat gagtgctttt ctagcccctg 3660
tatccatggc aactgctctg atggagttgc agcctaccac tgcaggtgtg agcctggata 3720
caccggtgtg aactgtgagg tggatgtaga caattgcaag agtcatcagt gtgcaaatgg 3780
ggccacctgt gttcctgaag ctcatggcta ctcttgtctc tgctttggaa attttaccgg 3840
gagattttgc agacacagca gattaccctc aacagtctgt gggaatgaga agagaaactt 3900
cacttgctac aatggaggca gctgctccat gttccaggag gactggcaat gtatgtgctg 3960
gccaggtttc actggagagt ggtgtgaaga ggacatcaac gagtgtgcct ccgatccctg 4020
catcaatgga ggactgtgca gggacttggt caacaggttc ctatgcatct gtgatgtggc 4080
cttcgctggc gagcgctgtg agctggacct ggctgatgac aggctcctgg gcattttcac 4140
cgctgttggc tccggaactt tggccctgtt cttcatcctc ttgcttgctg ggttgcttc 4200
tcttattgcc tccaacaaaa gggcgactca aggaacctac agccccagcg gtcaggagaa 4260
ggctggccct cgagtggaaa tgtggatcag gatgccgccc ccggcactgg aaaggctcat 4320
ctaggagact gctgctcttc tcaggacaga gaagaacatg atgagtaccg ggtcgtgcct 4380
gagtgaagat ggctttacat cactagagat acatacagct gggactgtgg gaaggacctt 4440
cctgtggagt cactgagtag ttatgtcatc cattcacaga agagtgtccc tgtgtttgcc 4500
tgtcagcctc agaattagca aaacatctag cagacagaga acacagtatt tcagaagaac 4560
tccagaggct gccccttaaa ctctttactg gttgatccac ataaaatgct tagtagccaa 4620
gtgccattaa ttatacagag ccaagaagaa aaattagaat acaactttca ctttttattt 4680
tgtagggaag gttttatgtt ttggtttgtt gttgttgttg tgacagtgac agtgactcat 4740
tacatagacc aagctggcct caaaatcaca tggaccctcg ggattacatg tgtccgacca 4800
tgttcatctt atttttgaat cttctgtcat atggtaaaag attccagtgg gacctgagga 4860
gtgactagct aggtaaagca agggctgtgt aagtgccaga actggtgttt gtgtcctcat 4920

```
tatccacata agtgccaagt gagtgtggcc cctgcctgtc atcctaggcc tcaggagata   4980

tcactgctca ctggagcaag ccggttaaac tgttagggca ggtaagtttt gacttcaagt   5040

gagagaccct gactcaatat gaaaggcaat tagtgagtca agatgaccct gtatgctaac   5100

ctcttgccta tacatgcata tacacacatt tacatatgtg cccaaacatg aggacacaag   5160

cacacgcgcg cgcgcacaca cacacacaca cacacacaca cacacacaca cacacacaca   5220

cgagtctaat tgtatatagt gataacagta cactttcctc cttctatttc ggatttagag   5280

aaagccatga gaagcgtgta tggtttaaac catgacccaa gcataacaaa taaagttgaa   5340

atagttgttc tcctgtccaa gcttgtcttt attgttgtgc attctgtaag ctggttgctt   5400

ggttggctga tggatggctt ctgtttgttt gttgtttttt gtttgtttgt ttgtctggga   5460

tattacatgt aagaaaaata actggtaaga acaatcaaag aactttgtta tgaattaaat   5520

cttttgtcta agtcacttag agtcattatt ctttatgtag atttgcttcc agtcaggaca   5580

tttcctagac agaatttaag acagtaagaa aatgatttgt cacgtctgaa agaggttctt   5640

tactttcagg gacttttgat aatgcccaac agagatggca tcgaaagagg agctcatagc   5700

gagatgggca tttgtgcatc ctcaaggaga aaatattgta ccttctgttt gtatattgtc   5760

tattctgtga tggctgtatc ttacatatgt tttgatgcat gtaacaatag tatcatatga   5820

aataaattat atatatatat aatatataat atatatcaca agataaaaat tgaaattaca   5880

taaactttaa atct                                                     5894
```

<210> SEQ ID NO 62
<211> LENGTH: 1344
<212> TYPE: PRT
<213> ORGANISM: Mus musculus

<400> SEQUENCE: 62

```
Met Lys Leu Lys Arg Thr Ala Tyr Leu Leu Phe Leu Tyr Leu Ser Ser
1               5                   10                  15

Ser Leu Leu Ile Cys Ile Lys Asn Ser Phe Cys Asn Lys Asn Asn Thr
            20                  25                  30

Arg Cys Leu Ser Gly Pro Cys Gln Asn Asn Ser Thr Cys Lys His Phe
        35                  40                  45

Pro Gln Asp Asn Asn Cys Cys Leu Asp Thr Ala Asn Asn Leu Asp Lys
    50                  55                  60

Asp Cys Glu Asp Leu Lys Asp Pro Cys Phe Ser Ser Pro Cys Gln Gly
65                  70                  75                  80

Ile Ala Thr Cys Val Lys Ile Pro Gly Glu Gly Asn Phe Leu Cys Gln
                85                  90                  95

Cys Pro Pro Gly Tyr Ser Gly Leu Asn Cys Glu Thr Ala Thr Asn Ser
            100                 105                 110

Cys Gly Gly Asn Leu Cys Gln His Gly Gly Thr Cys Arg Lys Asp Pro
        115                 120                 125

Glu His Pro Val Cys Ile Cys Pro Pro Gly Tyr Ala Gly Arg Phe Cys
    130                 135                 140

Glu Thr Asp His Asn Glu Cys Ala Ser Ser Pro Cys His Asn Gly Ala
145                 150                 155                 160

Met Cys Gln Asp Gly Ile Asn Gly Tyr Ser Cys Phe Cys Val Pro Gly
                165                 170                 175

Tyr Gln Gly Arg His Cys Asp Leu Glu Val Asp Glu Cys Val Ser Asp
            180                 185                 190
```

```
Pro Cys Lys Asn Glu Ala Val Cys Leu Asn Glu Ile Gly Arg Tyr Thr
        195                 200                 205

Cys Val Cys Pro Gln Glu Phe Ser Gly Val Asn Cys Glu Leu Glu Ile
    210                 215                 220

Asp Glu Cys Arg Ser Gln Pro Cys Leu His Gly Ala Thr Cys Gln Asp
225                 230                 235                 240

Ala Pro Gly Gly Tyr Ser Cys Asp Cys Ala Pro Gly Phe Leu Gly Glu
                245                 250                 255

His Cys Glu Leu Ser Val Asn Glu Cys Glu Ser Gln Pro Cys Leu His
            260                 265                 270

Gly Gly Leu Cys Val Asp Gly Arg Asn Ser Tyr His Cys Asp Cys Thr
        275                 280                 285

Gly Ser Gly Phe Thr Gly Met His Cys Glu Ser Leu Ile Pro Leu Cys
    290                 295                 300

Trp Ser Lys Pro Cys His Asn Asp Ala Thr Cys Glu Asp Thr Val Asp
305                 310                 315                 320

Ser Tyr Ile Cys His Cys Arg Pro Gly Ile His Cys Glu Glu Asp Val
                325                 330                 335

Asp Glu Cys Leu Leu His Pro Cys Leu Asn Gly Gly Thr Cys Glu Asn
            340                 345                 350

Leu Pro Gly Asn Tyr Ala Cys His Cys Pro Phe Asp Asp Thr Ser Arg
        355                 360                 365

Thr Phe Tyr Gly Gly Glu Asn Cys Ser Glu Ile Leu Leu Gly Cys Thr
    370                 375                 380

His His Gln Cys Leu Asn Asn Gly Lys Cys Ile Pro His Phe Gln Asn
385                 390                 395                 400

Gly Gln His Gly Phe Thr Cys Gln Cys Leu Ser Gly Tyr Ala Gly Pro
                405                 410                 415

Leu Cys Glu Thr Val Thr Thr Leu Ser Phe Gly Ser Asn Gly Phe Leu
            420                 425                 430

Trp Val Thr Ser Gly Ser His Thr Gly Ile Gly Pro Glu Cys Asn Ile
        435                 440                 445

Ser Leu Arg Phe His Thr Val Gln Pro Asn Ala Leu Leu Leu Ile Arg
    450                 455                 460

Gly Asn Lys Asp Val Ser Met Lys Leu Glu Leu Leu Asn Gly Cys Val
465                 470                 475                 480

His Leu Ser Ile Glu Val Trp Asn Gln Leu Lys Val Leu Leu Ser Ile
                485                 490                 495

Ser His Asn Thr Ser Asp Gly Glu Trp His Phe Val Glu Val Thr Ile
            500                 505                 510

Ala Glu Thr Leu Thr Leu Ala Leu Val Gly Gly Ser Cys Lys Glu Lys
        515                 520                 525

Cys Thr Thr Lys Ser Ser Val Pro Val Glu Asn His Gln Ser Ile Cys
    530                 535                 540

Ala Leu Gln Asp Ser Phe Leu Gly Gly Leu Pro Met Gly Thr Ala Asn
545                 550                 555                 560

Asn Ser Val Ser Val Leu Asn Ile Tyr Asn Val Pro Ser Thr Pro Ser
                565                 570                 575

Phe Val Gly Cys Leu Gln Asp Ile Arg Phe Asp Leu Asn His Ile Thr
            580                 585                 590

Leu Glu Asn Val Ser Ser Gly Leu Ser Ser Asn Val Lys Ala Gly Cys
        595                 600                 605

Leu Gly Lys Asp Trp Cys Glu Ser Gln Pro Cys Gln Asn Arg Gly Arg
```

-continued

```
    610                 615                 620

Cys Ile Asn Leu Trp Gln Gly Tyr Gln Cys Glu Cys Asp Arg Pro Tyr
625                 630                 635                 640

Thr Gly Ser Asn Cys Leu Lys Glu Tyr Val Ala Gly Arg Phe Gly Gln
                645                 650                 655

Asp Asp Ser Thr Gly Tyr Ala Ala Phe Ser Val Asn Asp Asn Tyr Gly
            660                 665                 670

Gln Asn Phe Ser Leu Ser Met Phe Val Arg Thr Arg Gln Pro Leu Gly
        675                 680                 685

Leu Leu Leu Ala Leu Glu Asn Ser Thr Tyr Gln Tyr Val Ser Val Trp
    690                 695                 700

Leu Glu His Gly Ser Leu Ala Leu Gln Thr Pro Gly Ser Pro Lys Phe
705                 710                 715                 720

Met Val Asn Phe Phe Leu Ser Asp Gly Asn Val His Leu Ile Ser Leu
                725                 730                 735

Arg Ile Lys Pro Asn Glu Ile Glu Leu Tyr Gln Ser Ser Gln Asn Leu
            740                 745                 750

Gly Phe Ile Ser Val Pro Thr Trp Thr Ile Arg Arg Gly Asp Val Ile
        755                 760                 765

Phe Ile Gly Gly Leu Pro Asp Arg Glu Lys Thr Glu Val Tyr Gly Gly
    770                 775                 780

Phe Phe Lys Gly Cys Val Gln Asp Val Arg Leu Asn Ser Gln Thr Leu
785                 790                 795                 800

Glu Phe Phe Pro Asn Ser Thr Asn Asn Ala Tyr Asp Asp Pro Ile Leu
                805                 810                 815

Val Asn Val Thr Gln Gly Cys Pro Gly Asp Asn Thr Cys Lys Ser Asn
            820                 825                 830

Pro Cys His Asn Gly Gly Val Cys His Ser Leu Trp Asp Asp Phe Ser
        835                 840                 845

Cys Ser Cys Pro Thr Asn Thr Ala Gly Arg Ala Cys Glu Gln Val Gln
    850                 855                 860

Trp Cys Gln Leu Ser Pro Cys Pro Pro Thr Ala Glu Cys Gln Leu Leu
865                 870                 875                 880

Pro Gln Gly Phe Glu Cys Ile Ala Asn Ala Val Phe Ser Gly Leu Ser
                885                 890                 895

Arg Glu Ile Leu Phe Arg Ser Asn Gly Asn Ile Thr Arg Glu Leu Thr
            900                 905                 910

Asn Ile Thr Phe Ala Phe Arg Thr His Asp Thr Asn Val Met Ile Leu
        915                 920                 925

His Ala Glu Lys Glu Pro Glu Phe Leu Asn Ile Ser Ile Gln Asp Ala
    930                 935                 940

Arg Leu Phe Phe Gln Leu Arg Ser Gly Asn Ser Phe Tyr Thr Leu His
945                 950                 955                 960

Leu Met Gly Ser Gln Leu Val Asn Asp Gly Thr Trp His Gln Val Thr
                965                 970                 975

Phe Ser Met Ile Asp Pro Val Ala Gln Thr Ser Arg Trp Gln Met Glu
            980                 985                 990

Val Asn Asp Gln Thr Pro Phe Val  Ile Ser Glu Val Ala  Thr Gly Ser
        995                 1000                1005

Leu Asn  Phe Leu Lys Asp Asn  Thr Asp Ile Tyr Val  Gly Asp Gln
    1010                1015                1020

Ser Val  Asp Asn Pro Lys Gly  Leu Gln Gly Cys Leu  Ser Thr Ile
    1025                1030                1035
```

```
Glu Ile  Gly Gly Ile Tyr Leu  Ser Tyr Phe Glu Asn  Leu His Gly
    1040                 1045                 1050

Phe Pro  Gly Lys Pro Gln Glu  Glu Gln Phe Leu Lys  Val Ser Thr
    1055                 1060                 1065

Asn Met  Val Leu Thr Gly Cys  Leu Pro Ser Asn Ala  Cys His Ser
    1070                 1075                 1080

Ser Pro  Cys Leu His Gly Gly  Asn Cys Glu Asp Ser  Tyr Ser Ser
    1085                 1090                 1095

Tyr Arg  Cys Ala Cys Leu Ser  Gly Trp Ser Gly Thr  His Cys Glu
    1100                 1105                 1110

Ile Asn  Ile Asp Glu Cys Phe  Ser Ser Pro Cys Ile  His Gly Asn
    1115                 1120                 1125

Cys Ser  Asp Gly Val Ala Ala  Tyr His Cys Arg Cys  Glu Pro Gly
    1130                 1135                 1140

Tyr Thr  Gly Val Asn Cys Glu  Val Asp Val Asp Asn  Cys Lys Ser
    1145                 1150                 1155

His Gln  Cys Ala Asn Gly Ala  Thr Cys Val Pro Glu  Ala His Gly
    1160                 1165                 1170

Tyr Ser  Cys Leu Cys Phe Gly  Asn Phe Thr Gly Arg  Phe Cys Arg
    1175                 1180                 1185

His Ser  Arg Leu Pro Ser Thr  Val Cys Gly Asn Glu  Lys Arg Asn
    1190                 1195                 1200

Phe Thr  Cys Tyr Asn Gly Gly  Ser Cys Ser Met Phe  Gln Glu Asp
    1205                 1210                 1215

Trp Gln  Cys Met Cys Trp Pro  Gly Phe Thr Gly Glu  Trp Cys Glu
    1220                 1225                 1230

Glu Asp  Ile Asn Glu Cys Ala  Ser Asp Pro Cys Ile  Asn Gly Gly
    1235                 1240                 1245

Leu Cys  Arg Asp Leu Val Asn  Arg Phe Leu Cys Ile  Cys Asp Val
    1250                 1255                 1260

Ala Phe  Ala Gly Glu Arg Cys  Glu Leu Asp Leu Ala  Asp Asp Arg
    1265                 1270                 1275

Leu Leu  Gly Ile Phe Thr Ala  Val Gly Ser Gly Thr  Leu Ala Leu
    1280                 1285                 1290

Phe Phe  Ile Leu Leu Leu Ala  Gly Val Ala Ser Leu  Ile Ala Ser
    1295                 1300                 1305

Asn Lys  Arg Ala Thr Gln Gly  Thr Tyr Ser Pro Ser  Gly Gln Glu
    1310                 1315                 1320

Lys Ala  Gly Pro Arg Val Glu  Met Trp Ile Arg Met  Pro Pro Pro
    1325                 1330                 1335

Ala Leu  Glu Arg Leu Ile
    1340
```

<210> SEQ ID NO 63
<211> LENGTH: 5554
<212> TYPE: DNA
<213> ORGANISM: Mus musculus

<400> SEQUENCE: 63

```
cccactgatc cagcttgaag aggagtgagg caaagctgaa ccctccccact ctccttgaca     60

agtgcaagcc cacacttttg gaaaaaagca caaagacgtc agaaacggtt cctgtcgacc    120

tactaggctt tggatggcta agtgtttttg ctttgtatgg aaatatgttt ggacacaaga    180

cacaaggttt tcacatttta atggcagtgc tcataggaat tcactgtgaa gaagacgttg    240
```

```
atgaatgttt actgcaccct tgcctaaatg gtggtacttg tgagaacctg cctgggaatt    300
atgcctgtca ctgtcccttt gatgacactt ctaggacatt ttatggagga gaaaactgct    360
cagaaattct cctgggctgc actcatcacc agtgtctgaa caatggaaaa tgtatccctc    420
atttccaaaa tggccagcat ggattcactt gccagtgtct ttctggctat gcggggcccc    480
tgtgtgaaac tgtcaccaca ctttcatttg ggagcaatgg cttcctatgg gtcacaagtg    540
gctcccatac aggcataggg ccagaatgta acatatcctt gaggtttcac actgttcaac    600
caaacgcact tctcctcatc cgaggcaaca aggacgtgtc tatgaagctg gagttgctga    660
atggttgtgt tcacttatca attgaagtct ggaatcagtt aaaggtgctc ctgtctattt    720
ctcacaacac cagtgatgga gaatggcatt tcgtggaggt aacaatcgca gaaactctaa    780
cccttgccct agttggcggc tcctgcaagg agaagtgcac caccaagtct tctgttccag    840
ttgagaatca tcaatcaata tgtgctttgc aggactcttt tttgggtggc ttaccaatgg    900
ggacagccaa caacagtgtg tctgtgctta acatctataa tgtgccgtcc acaccttcct    960
ttgtaggctg tctccaagac attagatttg atttgaatca cattactctg gagaacgttt   1020
catctggcct gtcatcaaat gttaaagcag gctgcctggg aaaggactgg tgtgaaagtc   1080
aaccctgtca aaacagagga cgctgcatca acttgtggca gggttatcag tgtgaatgtg   1140
acaggcccta tacaggctcc aactgcctga aagagtatgt agcgggaaga tttggccaag   1200
atgactccac aggatatgcg gcctttagtg ttaatgataa ttatggacag aacttcagtc   1260
tttcaatgtt tgtccgaaca cgtcaacccc tgggcttact tctggctttg gaaaatagta   1320
cttaccagta tgtcagtgtc tggctagagc acggcagcct agcactgcag actccaggct   1380
ctcccaagtt catggtaaac tttttctca gtgatggaaa tgttcactta atatctttga   1440
gaatcaaacc aaatgaaatt gaactgtatc agtcttcaca aaacctagga ttcatttctg   1500
ttcctacatg gacaattcga agaggagacg tcatcttcat tggtggctta cctgacagag   1560
agaagactga agtttatggt ggcttcttca aaggctgtgt tcaagatgtc agattaaaca   1620
gccagactct ggaattcttt cccaattcaa caaacaatgc atacgatgac ccaattcttg   1680
tcaatgtgac tcaaggctgt cccggagaca acacatgtaa gtccaacccc tgtcataatg   1740
gaggtgtctg ccactccctg tgggatgact tctcctgctc ctgccctaca aacacagcgg   1800
ggagagcctg cgagcaagtt cagtggtgtc aactcagccc atgtcctccc actgcagagt   1860
gccagctgct ccctcaaggg tttgaataac acatgataca aatgtgatga tattgcatgc   1920
agaaaaagaa ccagagtttc ttaatattag cattcaagat gccagattat tctttcaatt   1980
gcgaagtggc aacagctttt atacgctgca cctgatgggt tcccaattgg tgaatgatgg   2040
cacatggcac caagtgactt tctccatgat agacccagtg gcccagacct cccggtggca   2100
aatggaggtg aacgaccaga caccctttgt gataagtgaa gttgctactg gaagcctgaa   2160
ctttttgaag gacaatacag acatctatgt gggtgaccaa tctgttgaca atccgaaagg   2220
cctgcagggc tgtctgagca caatagagat tggaggcata tatctttctt actttgaaaa   2280
tctacatggt ttccctggta agcctcagga agagcaattt ctcaaagttt ctacaaatat   2340
ggtacttact ggctgtttgc catcaaatgc ctgccactcc agcccctgtt tgcatggagg   2400
aaactgtgaa gacagctaca gttcttatcg gtgtgcctgt ctctcgggat ggtcagggac   2460
acactgtgaa atcaacattg atgagtgctt ttctagcccc tgtatccatg gcaactgctc   2520
tgatggagtt gcagcctacc actgcaggtg tgagcctgga tacaccggtg tgaactgtga   2580
```

ggtggatgta gacaattgca agagtcatca gtgtgcaaat ggggccacct gtgttcctga 2640
agctcatggc tactcttgtc tctgctttgg aaattttacc gggagatttt gcagacacag 2700
cagattaccc tcaacagtct gtgggaatga gaagagaaac ttcacttgct acaatggagg 2760
cagctgctcc atgttccagg aggactggca atgtatgtgc tggccaggtt tcactggaga 2820
gtggtgtgaa gaggacatca acgagtgtgc ctccgatccc tgcatcaatg gaggactgtg 2880
cagggacttg gtcaacaggt tcctatgcat ctgtgatgtg gccttcgctg gcgagcgctg 2940
tgagctggac gtaagcggcc tttcctttta tgtgtccctc ttactatggc aaaacctctt 3000
tcagctcctg tcctacctcg tactgcgcat gaatgatgag ccagttgtag agtgggggc 3060
acaggaaaat tattaatgtg catgggagca ttcacaagtg taaaacattg acttgcaaga 3120
aacatcttgt ctcagtgtag gtttctagga aagacaaagg gaacattagg gaatagactc 3180
catctagagc actggttctc agtcttccta atgctgcaac cctttagtac agctcttcct 3240
gttgtagtga tcgcagccat aacattattt tcattgccac ttcataactg taatccttct 3300
actgctgtga atcacaatgg aaatatttat gttttctgat ggtcttaagc aacacctctg 3360
aaaaagtcat tgaccccccc cccaaagggg ctgtgatcca caggttgaga aatgctcatc 3420
tggaaggtaa ccatgcattt aagtgtacct ctagtagttt gggtctatag aagatattct 3480
cctattctac ctttttagac acgccagaag agggcatctg attccattaa agatgattgg 3540
gagccaccgt gtggttcctg agaactgtac tcgggccctt tggaagagca atcagtgctc 3600
tttccagccc ctaagaatat ttttaataca gccagaaagg tctcattacc cagtgtactg 3660
agccctaagg cactttcatc ctcaatcgtt ccatgttgaa tggttttcat tacatttgga 3720
aaatgttttc tctccactct acctttacat gttcctattt tcctattgac aatttgcccc 3780
ttcactgtaa ttctaatttg gtgtggtcct tcttctcata agtttatatg tgacatgaac 3840
atttaaaaat atctatgaat attttatagt catgtatgtc tttctgcaaa gctattcaaa 3900
tgaactatgg acagttcttt tctacacgaa gaagagatga gtttaatccc cagtaacatg 3960
agaaaaagat gagtgaggga cagtgctcac agtatccctc actagcatca tttgtgattc 4020
catgggccat ttttttccac cagcaaatag cagagagccc tttccctatt cgtttctctt 4080
acacttcccc ttttctgtta caactgaaca ctttacatta gttactcctt tgtagggggt 4140
ttgactttc caccgtttc tctggttcac tatttatgct aagtatctgt gcagggcggg 4200
tatatcagtc caacagaggt gtcattagtg ttcattgagg aggaaatact ttgcatgaat 4260
tcatgacatc attgaagtag cagtggccag aaagataccc ttctgcgaat gtgtctgtgt 4320
attcagaagc tgccctggtt agaaaacatg tgggtcactt ttcctttgca tgttaccagt 4380
gctcactggg tcatgattgt tttaagacag agcttttgct gtggcaatga ccaaggtgaa 4440
tccagagatg cagatcagac aaaggacaag acaatgtact atctgagtaa aaccctgcct 4500
tgacttactc ctcagtactt agagatttta catagcaacc tccaccctgt ggcaacccgt 4560
tcacactagc agtgatgctg agatttgccc ttccttctca tcatcttcct cacatccaaa 4620
gcattttgtg tccacactgc tgtttcagat aactgtttct aaagtgggat tgttgtagcc 4680
agaaaggtag ggaaaatgtt ccccaaaata tttgcattct taagtatgtg aagtaagtag 4740
attatagtca gagacaatat gtaaggtttc aggttcactc ccttctacac atatcttcaa 4800
ctgtgtattt gcagaatatt ctgaatgtga catactccca acagaatata tttaaggagt 4860
atttatccac agtattgttc tctgtacagt tctagtgctt ctattgtcac tgcaattgtc 4920
aattgttttt ctgctttcca actgtcttat tatcatttaa tagcatcttg ctaaatgccc 4980

```
tctttctatt ctccttattt ctccatagtt catgtgtgtc tgtgtgacta aggattctcc   5040

tcatttttgc agaaaaataa aatcttttct tctttatgtc ctgcttgtca ttctctggtg   5100

acacatgtct ttgcttactt ggactgaggg ttgtacagta agtacagaag caggctcagt   5160

cacacagaca gagacacacc accaccagca gcagcagcac caccaccacc accaccacca   5220

ccagaaaaca gtatgagtac tcatctcttg attacatgtc atttcaagta agcaccatga   5280

caccgagggc caggttccat ggactttctc tgttaggcac gtgattcttt agctgacctt   5340

tgagaacaga ctccaacaac ctcacttatt tttactgttg acttatatca tctctgacaa   5400

cactggactt cgtttgagct agtcaagagg aaagaccatg acacctaagg gacagaaatt   5460

cacacactcg gtttttcata attcacacac attcctatgt atcaaatctc tgtaatagat   5520

gacatttact tgaataaaaa gtcatttccc tttg                               5554
```

<210> SEQ ID NO 64
<211> LENGTH: 574
<212> TYPE: PRT
<213> ORGANISM: Mus musculus

<400> SEQUENCE: 64

```
Met Phe Gly His Lys Thr Gln Gly Phe His Ile Leu Met Ala Val Leu
1               5                   10                  15

Ile Gly Ile His Cys Glu Glu Asp Val Asp Glu Cys Leu Leu His Pro
            20                  25                  30

Cys Leu Asn Gly Gly Thr Cys Glu Asn Leu Pro Gly Asn Tyr Ala Cys
        35                  40                  45

His Cys Pro Phe Asp Asp Thr Ser Arg Thr Phe Tyr Gly Gly Glu Asn
    50                  55                  60

Cys Ser Glu Ile Leu Leu Gly Cys Thr His His Gln Cys Leu Asn Asn
65                  70                  75                  80

Gly Lys Cys Ile Pro His Phe Gln Asn Gly Gln His Gly Phe Thr Cys
                85                  90                  95

Gln Cys Leu Ser Gly Tyr Ala Gly Pro Leu Cys Glu Thr Val Thr Thr
            100                 105                 110

Leu Ser Phe Gly Ser Asn Gly Phe Leu Trp Val Thr Ser Gly Ser His
        115                 120                 125

Thr Gly Ile Gly Pro Glu Cys Asn Ile Ser Leu Arg Phe His Thr Val
    130                 135                 140

Gln Pro Asn Ala Leu Leu Leu Ile Arg Gly Asn Lys Asp Val Ser Met
145                 150                 155                 160

Lys Leu Glu Leu Leu Asn Gly Cys Val His Leu Ser Ile Glu Val Trp
                165                 170                 175

Asn Gln Leu Lys Val Leu Leu Ser Ile Ser His Asn Thr Ser Asp Gly
            180                 185                 190

Glu Trp His Phe Val Glu Val Thr Ile Ala Glu Thr Leu Thr Leu Ala
        195                 200                 205

Leu Val Gly Gly Ser Cys Lys Glu Lys Cys Thr Thr Lys Ser Ser Val
    210                 215                 220

Pro Val Glu Asn His Gln Ser Ile Cys Ala Leu Gln Asp Ser Phe Leu
225                 230                 235                 240

Gly Gly Leu Pro Met Gly Thr Ala Asn Asn Ser Val Ser Val Leu Asn
                245                 250                 255

Ile Tyr Asn Val Pro Ser Thr Pro Ser Phe Val Gly Cys Leu Gln Asp
            260                 265                 270
```

Ile Arg Phe Asp Leu Asn His Ile Thr Leu Glu Asn Val Ser Ser Gly
275 280 285

Leu Ser Ser Asn Val Lys Ala Gly Cys Leu Gly Lys Asp Trp Cys Glu
290 295 300

Ser Gln Pro Cys Gln Asn Arg Gly Arg Cys Ile Asn Leu Trp Gln Gly
305 310 315 320

Tyr Gln Cys Glu Cys Asp Arg Pro Tyr Thr Gly Ser Asn Cys Leu Lys
325 330 335

Glu Tyr Val Ala Gly Arg Phe Gly Gln Asp Asp Ser Thr Gly Tyr Ala
340 345 350

Ala Phe Ser Val Asn Asp Asn Tyr Gly Gln Asn Phe Ser Leu Ser Met
355 360 365

Phe Val Arg Thr Arg Gln Pro Leu Gly Leu Leu Leu Ala Leu Glu Asn
370 375 380

Ser Thr Tyr Gln Tyr Val Ser Val Trp Leu Glu His Gly Ser Leu Ala
385 390 395 400

Leu Gln Thr Pro Gly Ser Pro Lys Phe Met Val Asn Phe Phe Leu Ser
405 410 415

Asp Gly Asn Val His Leu Ile Ser Leu Arg Ile Lys Pro Asn Glu Ile
420 425 430

Glu Leu Tyr Gln Ser Ser Gln Asn Leu Gly Phe Ile Ser Val Pro Thr
435 440 445

Trp Thr Ile Arg Arg Gly Asp Val Ile Phe Ile Gly Gly Leu Pro Asp
450 455 460

Arg Glu Lys Thr Glu Val Tyr Gly Gly Phe Phe Lys Gly Cys Val Gln
465 470 475 480

Asp Val Arg Leu Asn Ser Gln Thr Leu Glu Phe Phe Pro Asn Ser Thr
485 490 495

Asn Asn Ala Tyr Asp Asp Pro Ile Leu Val Asn Val Thr Gln Gly Cys
500 505 510

Pro Gly Asp Asn Thr Cys Lys Ser Asn Pro Cys His Asn Gly Gly Val
515 520 525

Cys His Ser Leu Trp Asp Asp Phe Ser Cys Ser Cys Pro Thr Asn Thr
530 535 540

Ala Gly Arg Ala Cys Glu Gln Val Gln Trp Cys Gln Leu Ser Pro Cys
545 550 555 560

Pro Pro Thr Ala Glu Cys Gln Leu Leu Pro Gln Gly Phe Glu
565 570

<210> SEQ ID NO 65
<211> LENGTH: 4783
<212> TYPE: DNA
<213> ORGANISM: Mus musculus

<400> SEQUENCE: 65
gatccagctt gaagaggagt gaggcaaagc tgaaccctcc cactctcctt gacaagtgca 60
agcccacact tttggaaaaa agcacaaaga cgtcagaaac ggttcctgtc gacctactag 120
gctttggatg gctaagtgtt tttgctttgt atggaaatat gtttggacac aagacacaag 180
gttttcacat tttaatggca gtgctcatag gaattcactg tgaagaagac gttgatgaat 240
gtttactgca cccttgccta aatggtggta cttgtgagaa cctgcctggg aattatgcct 300
gtcactgtcc ctttgatgac acttctagga cattttatgg aggagaaaac tgctcagaaa 360
ttctcctggg ctgcactcat caccagtgtc tgaacaatgg aaaatgtatc cctcatttcc 420

```
aaaatggcca gcatggattc acttgccagt gtctttctgg ctatgcgggg cccctgtgtg    480
aaactgtcac cacactttca tttgggagca atggcttcct atgggtcaca agtggctccc    540
atacaggcat agggccagaa tgtaacatat ccttgaggtt tcacactgtt caaccaaacg    600
cacttctcct catccgaggc aacaaggacg tgtctatgaa gctggagttg ctgaatggtt    660
gtgttcactt atcaattgaa gtctggaatc agttaaaggt gctcctgtct atttctcaca    720
acaccagtga tggagaatgg catttcgtgg aggtaacaat cgcagaaact ctaacccttg    780
ccctagttgg cggctcctgc aaggagaagt gcaccaccaa gtcttctgtt ccagttgaga    840
atcatcaatc aatatgtgct ttgcaggact ctttttttggg tggcttacca atggggacag    900
ccaacaacag tgtgtctgtg cttaacatct ataatgtgcc gtccacacct tcctttgtag    960
gctgtctcca agacattaga tttgatttga atcacattac tctggagaac gtttcatctg   1020
gcctgtcatc aaatgttaaa gcaggctgcc tgggaaagga ctggtgtgaa agtcaaccct   1080
gtcaaaacag aggacgctgc atcaacttgt ggcagggtta tcagtgtgaa tgtgacaggc   1140
cctatacagg ctccaactgc ctgaaagagt atgtagcggg aagatttggc caagatgact   1200
ccacaggata tgcggccttt agtgttaatg ataattatgg acagaacttc agtctttcaa   1260
tgtttgtccg aacacgtcaa cccctgggct tacttctggc tttggaaaat agtacttacc   1320
agtatgtcag tgtctggcta gagcacggca gcctagcact gcagactcca ggctctccca   1380
agttcatggt aaactttttt ctcagtgatg gaaatgttca cttaatatct ttgagaatca   1440
aaccaaatga aattgaactg tatcagtctt cacaaaacct aggattcatt tctgttccta   1500
catggacaat tcgaagagga gacgtcatct tcattggtgg cttacctgac agagagaaga   1560
ctgaagttta tggtggcttc ttcaaaggct gtgttcaaga tgtcagatta aacagccaga   1620
ctctggaatt ctttcccaat tcaacaaaca atgcatacga tgacccaatt cttgtcaatg   1680
tgactcaagg ctgtcccgga gacaacacat gtaagtccaa cccctgtcat aatggaggtg   1740
tctgccactc cctgtgggat gacttctcct gctcctgccc tacaaacaca gcggggagag   1800
cctgcgagca agttcagtgg tgtcaactca gcccatgtcc tcccactgca gagtgccagc   1860
tgctccctca agggtttgaa tgtatcgcaa acgctgtttt cagcggatta agcagagaaa   1920
tactcttcag aagcaatggg aacattacca gagaactcac caatatcaca tttgctttca   1980
gaacacatga tacaaatgtg atgatattgc atgcagaaaa agaaccagag tttcttaata   2040
ttagcattca agatgccaga ttattctttc aattgcgaag tggcaacagc ttttatacgc   2100
tgcacctgat gggttcccaa ttggtgaatg atggcacatg gcaccaagtg actttctcca   2160
tgatagaccc agtggcccag acctcccggt ggcaaatgga ggtgaacgac cagacaccct   2220
ttgtgataag tgaagttgct actggaagcc tgaacttttt gaaggacaat acagacatct   2280
atgtgggtga ccaatctgtt gacaatccga aaggcctgca gggctgtctg agcacaatag   2340
agattggagg catatatctt tcttactttg aaaatctaca tggtttccct ggtaagcctc   2400
aggaagagca atttctcaaa gtttctacaa atatggtact tactggctgt ttgccatcaa   2460
atgcctgcca ctccagcccc tgtttgcatg gaggaaactg tgaagacagc tacagttctt   2520
atcggtgtgc ctgtctctcg ggatggtcag ggacacactg tgaaatcaac attgatgagt   2580
gcttttctag cccctgtatc catggcaact gctctgatgg agttgcagcc taccactgca   2640
ggtgtgagcc tggatacacc ggtgtgaact gtgaggtgga tgtagacaat tgcaagagtc   2700
atcagtgtgc aaatggggcc acctgtgttc ctgaagctca tggctactct tgtctctgct   2760
```

```
ttggaaattt taccgggaga ttttgcagac acagcagatt accctcaaca gtctgtggga   2820
atgagaagag aaacttcact tgctacaatg gaggcagctg ctccatgttc caggaggact   2880
ggcaatgtat gtgctggcca ggtttcactg gagagtggtg tgaagaggac atcaacgagt   2940
gtgcctccga tccctgcatc aatggaggac tgtgcaggga cttggtcaac aggttcctat   3000
gcatctgtga tgtggccttc gctggcgagc gctgtgagct ggacctggct gatgacaggc   3060
tcctgggcat tttcaccgct gttggctccg gaactttggc cctgttcttc atcctcttgc   3120
ttgctggggt tgcttctctt attgcctcca acaaaagggc gactcaagga acctacagcc   3180
ccagcggtca ggagaaggct ggccctcgag tggaaatgtg gatcaggatg ccgccccccgg  3240
cactggaaag gctcatctag gagactgctg ctcttctcag gacagagaag aacatgatga   3300
gtaccgggtc gtgcctgagt gaagatggct ttacatcact agagatacat acagctggga   3360
ctgtgggaag gaccttcctg tggagtcact gagtagttat gtcatccatt cacagaagag   3420
tgtccctgtg tttgcctgtc agcctcagaa ttagcaaaac atctagcaga cagagaacac   3480
agtatttcag aagaactcca gaggctgccc cttaaactct ttactggttg atccacataa   3540
aatgcttagt agccaagtgc cattaattat acagagccaa gaagaaaaat tagaatacaa   3600
ctttcacttt ttattttgta gggaaggttt tatgttttgg tttgttgttg ttgttgtgac   3660
agtgacagtg actcattaca tagaccaagc tggcctcaaa atcacatgga ccctcgggat   3720
tacatgtgtc cgaccatgtt catcttattt ttgaatcttc tgtcatatgg taaaagattc   3780
cagtgggacc tgaggagtga ctagctaggt aaagcaaggg ctgtgtaagt gccagaactg   3840
gtgtttgtgt cctcattatc cacataagtg ccaagtgagt gtggcccctg cctgtcatcc   3900
taggcctcag gagatatcac tgctcactgg agcaagccgg ttaaactgtt agggcaggta   3960
agttttgact tcaagtgaga gaccctgact caatatgaaa ggcaattagt gagtcaagat   4020
gaccctgtat gctaacctct tgcctataca tgcatataca cacatttaca tatgtgccca   4080
aacatgagga cacaagcaca cgcgcgcgcg cacacacaca cacacacaca cacacacaca   4140
cacacacaca cacacacgag tctaattgta tatagtgata acagtacact ttcctccttc   4200
tatttcggat ttagagaaag ccatgagaag cgtgtatggt ttaaaccatg acccaagcat   4260
aacaaataaa gttgaaatag ttgttctcct gtccaagctt gtctttattg ttgtgcattc   4320
tgtaagctgg ttgcttggtt ggctgatgga tggcttctgt ttgtttgttg ttttttgttt   4380
gtttgtttgt ctgggatatt acatgtaaga aaaataactg gtaagaacaa tcaaagaact   4440
ttgttatgaa ttaaatcttt tgtctaagtc acttagagtc attattcttt atgtagattt   4500
gcttccagtc aggacatttc ctagacagaa tttaagacag taagaaaatg atttgtcacg   4560
tctgaaagag gttctttact ttcagggact tttgataatg cccaacagag atggcatcga   4620
aagaggagct catagcgaga tgggcatttg tgcatcctca aggagaaaat attgtacctt   4680
ctgtttgtat attgtctatt ctgtgatggc tgtatcttac atatgttttg atgcatgtaa   4740
caatagtatc atatgaaata aattatatat atatataata tat                      4783
```

```
<210> SEQ ID NO 66
<211> LENGTH: 1033
<212> TYPE: PRT
<213> ORGANISM: Mus musculus

<400> SEQUENCE: 66

Met Phe Gly His Lys Thr Gln Gly Phe His Ile Leu Met Ala Val Leu
1               5                   10                  15
```

```
Ile Gly Ile His Cys Glu Glu Asp Val Asp Glu Cys Leu Leu His Pro
            20                  25                  30

Cys Leu Asn Gly Gly Thr Cys Glu Asn Leu Pro Gly Asn Tyr Ala Cys
        35                  40                  45

His Cys Pro Phe Asp Asp Thr Ser Arg Thr Phe Tyr Gly Gly Glu Asn
    50                  55                  60

Cys Ser Glu Ile Leu Leu Gly Cys Thr His His Gln Cys Leu Asn Asn
65                  70                  75                  80

Gly Lys Cys Ile Pro His Phe Gln Asn Gly Gln His Gly Phe Thr Cys
                85                  90                  95

Gln Cys Leu Ser Gly Tyr Ala Gly Pro Leu Cys Glu Thr Val Thr Thr
            100                 105                 110

Leu Ser Phe Gly Ser Asn Gly Phe Leu Trp Val Thr Ser Gly Ser His
        115                 120                 125

Thr Gly Ile Gly Pro Glu Cys Asn Ile Ser Leu Arg Phe His Thr Val
    130                 135                 140

Gln Pro Asn Ala Leu Leu Leu Ile Arg Gly Asn Lys Asp Val Ser Met
145                 150                 155                 160

Lys Leu Glu Leu Leu Asn Gly Cys Val His Leu Ser Ile Glu Val Trp
                165                 170                 175

Asn Gln Leu Lys Val Leu Leu Ser Ile Ser His Asn Thr Ser Asp Gly
            180                 185                 190

Glu Trp His Phe Val Glu Val Thr Ile Ala Glu Thr Leu Thr Leu Ala
        195                 200                 205

Leu Val Gly Gly Ser Cys Lys Glu Lys Cys Thr Thr Lys Ser Ser Val
    210                 215                 220

Pro Val Glu Asn His Gln Ser Ile Cys Ala Leu Gln Asp Ser Phe Leu
225                 230                 235                 240

Gly Gly Leu Pro Met Gly Thr Ala Asn Asn Ser Val Ser Val Leu Asn
                245                 250                 255

Ile Tyr Asn Val Pro Ser Thr Pro Ser Phe Val Gly Cys Leu Gln Asp
            260                 265                 270

Ile Arg Phe Asp Leu Asn His Ile Thr Leu Glu Asn Val Ser Ser Gly
        275                 280                 285

Leu Ser Ser Asn Val Lys Ala Gly Cys Leu Gly Lys Asp Trp Cys Glu
    290                 295                 300

Ser Gln Pro Cys Gln Asn Arg Gly Arg Cys Ile Asn Leu Trp Gln Gly
305                 310                 315                 320

Tyr Gln Cys Glu Cys Asp Arg Pro Tyr Thr Gly Ser Asn Cys Leu Lys
                325                 330                 335

Glu Tyr Val Ala Gly Arg Phe Gly Gln Asp Asp Ser Thr Gly Tyr Ala
            340                 345                 350

Ala Phe Ser Val Asn Asp Asn Tyr Gly Gln Asn Phe Ser Leu Ser Met
        355                 360                 365

Phe Val Arg Thr Arg Gln Pro Leu Gly Leu Leu Leu Ala Leu Glu Asn
    370                 375                 380

Ser Thr Tyr Gln Tyr Val Ser Val Trp Leu Glu His Gly Ser Leu Ala
385                 390                 395                 400

Leu Gln Thr Pro Gly Ser Pro Lys Phe Met Val Asn Phe Phe Leu Ser
                405                 410                 415

Asp Gly Asn Val His Leu Ile Ser Leu Arg Ile Lys Pro Asn Glu Ile
            420                 425                 430

Glu Leu Tyr Gln Ser Ser Gln Asn Leu Gly Phe Ile Ser Val Pro Thr
```

```
        435                 440                 445

Trp Thr Ile Arg Arg Gly Asp Val Ile Phe Ile Gly Gly Leu Pro Asp
    450                 455                 460

Arg Glu Lys Thr Glu Val Tyr Gly Gly Phe Phe Lys Gly Cys Val Gln
465                 470                 475                 480

Asp Val Arg Leu Asn Ser Gln Thr Leu Glu Phe Phe Pro Asn Ser Thr
                485                 490                 495

Asn Asn Ala Tyr Asp Asp Pro Ile Leu Val Asn Val Thr Gln Gly Cys
            500                 505                 510

Pro Gly Asp Asn Thr Cys Lys Ser Asn Pro Cys His Asn Gly Gly Val
        515                 520                 525

Cys His Ser Leu Trp Asp Asp Phe Ser Cys Ser Cys Pro Thr Asn Thr
    530                 535                 540

Ala Gly Arg Ala Cys Glu Gln Val Gln Trp Cys Gln Leu Ser Pro Cys
545                 550                 555                 560

Pro Pro Thr Ala Glu Cys Gln Leu Leu Pro Gln Gly Phe Glu Cys Ile
                565                 570                 575

Ala Asn Ala Val Phe Ser Gly Leu Ser Arg Glu Ile Leu Phe Arg Ser
            580                 585                 590

Asn Gly Asn Ile Thr Arg Glu Leu Thr Asn Ile Thr Phe Ala Phe Arg
        595                 600                 605

Thr His Asp Thr Asn Val Met Ile Leu His Ala Glu Lys Glu Pro Glu
    610                 615                 620

Phe Leu Asn Ile Ser Ile Gln Asp Ala Arg Leu Phe Phe Gln Leu Arg
625                 630                 635                 640

Ser Gly Asn Ser Phe Tyr Thr Leu His Leu Met Gly Ser Gln Leu Val
                645                 650                 655

Asn Asp Gly Thr Trp His Gln Val Thr Phe Ser Met Ile Asp Pro Val
            660                 665                 670

Ala Gln Thr Ser Arg Trp Gln Met Glu Val Asn Asp Gln Thr Pro Phe
        675                 680                 685

Val Ile Ser Glu Val Ala Thr Gly Ser Leu Asn Phe Leu Lys Asp Asn
    690                 695                 700

Thr Asp Ile Tyr Val Gly Asp Gln Ser Val Asp Asn Pro Lys Gly Leu
705                 710                 715                 720

Gln Gly Cys Leu Ser Thr Ile Glu Ile Gly Gly Ile Tyr Leu Ser Tyr
                725                 730                 735

Phe Glu Asn Leu His Gly Phe Pro Gly Lys Pro Gln Glu Glu Gln Phe
            740                 745                 750

Leu Lys Val Ser Thr Asn Met Val Leu Thr Gly Cys Leu Pro Ser Asn
        755                 760                 765

Ala Cys His Ser Ser Pro Cys Leu His Gly Gly Asn Cys Glu Asp Ser
    770                 775                 780

Tyr Ser Ser Tyr Arg Cys Ala Cys Leu Ser Gly Trp Ser Gly Thr His
785                 790                 795                 800

Cys Glu Ile Asn Ile Asp Glu Cys Phe Ser Ser Pro Cys Ile His Gly
                805                 810                 815

Asn Cys Ser Asp Gly Val Ala Ala Tyr His Cys Arg Cys Glu Pro Gly
            820                 825                 830

Tyr Thr Gly Val Asn Cys Glu Val Asp Val Asp Asn Cys Lys Ser His
        835                 840                 845

Gln Cys Ala Asn Gly Ala Thr Cys Val Pro Glu Ala His Gly Tyr Ser
    850                 855                 860
```

```
Cys Leu Cys Phe Gly Asn Phe Thr Gly Arg Phe Cys Arg His Ser Arg
865                 870                 875                 880

Leu Pro Ser Thr Val Cys Gly Asn Glu Lys Arg Asn Phe Thr Cys Tyr
                885                 890                 895

Asn Gly Gly Ser Cys Ser Met Phe Gln Glu Asp Trp Gln Cys Met Cys
            900                 905                 910

Trp Pro Gly Phe Thr Gly Glu Trp Cys Glu Glu Asp Ile Asn Glu Cys
        915                 920                 925

Ala Ser Asp Pro Cys Ile Asn Gly Gly Leu Cys Arg Asp Leu Val Asn
    930                 935                 940

Arg Phe Leu Cys Ile Cys Asp Val Ala Phe Ala Gly Glu Arg Cys Glu
945                 950                 955                 960

Leu Asp Leu Ala Asp Asp Arg Leu Leu Gly Ile Phe Thr Ala Val Gly
                965                 970                 975

Ser Gly Thr Leu Ala Leu Phe Phe Ile Leu Leu Leu Ala Gly Val Ala
            980                 985                 990

Ser Leu Ile Ala Ser Asn Lys Arg  Ala Thr Gln Gly Thr  Tyr Ser Pro
        995                 1000                1005

Ser Gly  Gln Glu Lys Ala Gly  Pro Arg Val Glu Met  Trp Ile Arg
    1010                1015                1020

Met Pro  Pro Pro Ala Leu Glu  Arg Leu Ile
    1025                1030
```

<210> SEQ ID NO 67
<211> LENGTH: 6739
<212> TYPE: DNA
<213> ORGANISM: Mus musculus

<400> SEQUENCE: 67

```
gcaatcaagg accctatcct aaaacaaagc ctttccagga ggcattgttc acggaagcct     60

gagggggaca cgaatccaat ccaggctgga aaaatctgct ccaggattga ctggttaccg    120

tcttcctgtg cctgtaaggt gctgtgaaag agaagtgctt tctgattctc tgtctgtgga    180

ggagccctgg gaggggtggg acagagatgg catcctggct ctctgaggca cctgctcttc    240

tctgaaccac acaggagtca agagccaaac agggatagct tcagcagcac ttcagagggt    300

gttctctaag taagaacatg aagctcaaga gaactgccta ccttctcttc ctgtacctca    360

gctcctcact gctcatctgc ataaagaatt cattttgcaa taaaaacaat accaggtgcc    420

tttcaggtcc ttgccaaaac aattctacgt gcaagcattt tccacaagac aacaattgtt    480

gcttagacac agccaataat ttggacaaag actgtgaaga tctgaaagac ccttgcttct    540

cgagtccctg ccaaggaatt gccacttgtg tgaaaatccc aggggaaggg aacttcctgt    600

gtcagtgtcc tcctgggtac agcgggctga actgtgaaac tgccaccaat tcctgtggag    660

ggaacctctg ccaacatgga ggcacctgcc gtaaagaccc tgagcaccct gtctgtatct    720

gccctcctgg atatgctgga aggttctgtg agactgatca caatgagtgt gcttctagcc    780

cttgccacaa tggggctatg tgccaggatg gaatcaatgg ctactcctgc ttctgtgtgc    840

ctggatacca aggcaggcat tgtgacttgg aagtggatga atgtgtttct gatccctgca    900

agaatgaggc tgtgtgcctc aatgagatag gaagatacac ttgtgtctgc cctcaagagt    960

tttctggcgt gaactgtgag ttggaaattg atgaatgcag atcccagcct tgtctccacg   1020

gtgccacatg tcaggacgct ccagggggct actcctgtga ctgtgcacct ggattccttg   1080

gagagcactg tgaactcagc gttaatgaat gtgaaagtca gccgtgtctc catggaggtc   1140
```

```
tatgtgtgga tggaagaaac agttaccact gtgactgcac aggtagtgga ttcacaggga   1200
tgcactgtga gtccttgatt cctctttgtt ggtcaaagcc ttgtcacaac gacgcgacat   1260
gtgaagatac tgttgacagc tatatttgtc actgccggcc tggaattcac tgtgaagaag   1320
acgttgatga atgtttactg cacccttgcc taaatggtgg tacttgtgag aacctgcctg   1380
ggaattatgc ctgtcactgt ccctttgatg acacttctag gacattttat ggaggagaaa   1440
actgctcaga aattctcctg ggctgcactc atcaccagtg tctgaacaat ggaaaatgta   1500
tccctcattt ccaaaatggc cagcatggat tcacttgcca gtgtctttct ggctatgcgg   1560
ggcccctgtg tgaaactgtc accacacttt catttgggag caatggcttc ctatgggtca   1620
caagtggctc ccatacaggc atagggccag aatgtaacat atccttgagg tttcacactg   1680
ttcaaccaaa cgcacttctc ctcatccgag gcaacaagga cgtgtctatg aagctggagt   1740
tgctgaatgg ttgtgttcac ttatcaattg aagtctggaa tcagttaaag gtgctcctgt   1800
ctatttctca caacaccagt gatggagaat ggcatttcgt ggaggtaaca atcgcagaaa   1860
ctctaaccct tgccctagtt ggcggctcct gcaaggagaa gtgcaccacc aagtcttctg   1920
ttccagttga gaatcatcaa tcaatatgtg ctttgcagga ctctttttg ggtggcttac   1980
caatggggac agccaacaac agtgtgtctg tgcttaacat ctataatgtg ccgtccacac   2040
cttcctttgt aggctgtctc caagacatta gatttgattt gaatcacatt actctggaga   2100
acgtttcatc tggcctgtca tcaaatgtta aagcaggctg cctgggaaag gactggtgtg   2160
aaagtcaacc ctgtcaaaac agaggacgct gcatcaactt gtggcagggt tatcagtgtg   2220
aatgtgacag gccctataca ggctccaact gcctgaaaga gtatgtagcg ggaagatttg   2280
gccaagatga ctccacagga tatgcggcct ttagtgttaa tgataattat ggacagaact   2340
tcagtctttc aatgtttgtc cgaacacgtc aacccctggg cttacttctg gctttggaaa   2400
atagtactta ccagtatgtc agtgtctggc tagagcacgg cagcctagca ctgcagactc   2460
caggctctcc caagttcatg gtaaactttt ttctcagtga tggaaatgtt cacttaatat   2520
ctttgagaat caaaccaaat gaaattgaac tgtatcagtc ttcacaaaac ctaggattca   2580
tttctgttcc tacatggaca attcgaagag gagacgtcat cttcattggt ggcttacctg   2640
acagagagaa gactgaagtt tatggtggct tcttcaaagg ctgtgttcaa gatgtcagat   2700
taaacagcca gactctggaa ttctttccca attcaacaaa caatgcatac gatgacccaa   2760
ttcttgtcaa tgtgactcaa ggctgtcccg gagacaacac atgtaagtcc aacccctgtc   2820
ataatggagg tgtctgccac tccctgtggg atgacttctc ctgctcctgc cctacaaaca   2880
cagcggggag agcctgcgag caagttcagt ggtgtcaact cagcccatgt cctcccactg   2940
cagagtgcca gctgctccct caagggtttg aatgtatcgc aaacgctgtt ttcagcggat   3000
taagcagaga aatactcttc agaagcaatg ggaacattac cagagaactc accaatatca   3060
catttgcttt cagaacacat gatacaaatg tgatgatatt gcatgcagaa aaagaaccag   3120
agtttcttaa tattagcatt caagatgcca gattattctt tcaattgcga agtggcaaca   3180
gcttttatac gctgcacctg atgggttccc aattggtgaa tgatggcaca tggcaccaag   3240
tgactttctc catgatagac ccagtggccc agacctcccg gtggcaaatg gaggtgaacg   3300
accagacacc ctttgtgata agtgaagttg ctactggaag cctgaacttt ttgaaggaca   3360
atacagacat ctatgtgggt gaccaatctg ttgacaatcc gaaaggcctg cagggctgtc   3420
tgagcacaat agagattgga ggcatatatc tttcttactt tgaaaatcta catggtttcc   3480
```

```
ctggtaagcc tcaggaagag caatttctca aagtttctac aaatatggta cttactggct   3540
gtttgccatc aaatgcctgc cactccagcc cctgtttgca tggaggaaac tgtgaagaca   3600
gctacagttc ttatcggtgt gcctgtctct cgggatggtc agggacacac tgtgaaatca   3660
acattgatga gtgcttttct agcccctgta tccatggcaa ctgctctgat ggagttgcag   3720
cctaccactg caggtgtgag cctggataca ccggtgtgaa ctgtgaggtg gatgtagaca   3780
attgcaagag tcatcagtgt gcaaatgggg ccacctgtgt tcctgaagct catggctact   3840
cttgtctctg ctttggaaat tttaccggga gattttgcag acacagcaga ttaccctcaa   3900
cagtctgtgg gaatgagaag agaaacttca cttgctacaa tggaggcagc tgctccatgt   3960
tccaggagga ctggcaatgt atgtgctggc caggtttcac tggagagtgg tgtgaagagg   4020
acatcaacga gtgtgcctcc gatccctgca tcaatggagg actgtgcagg gacttggtca   4080
acaggttcct atgcatctgt gatgtggcct tcgctggcga gcgctgtgag ctggacgtaa   4140
gcggcctttc cttttatgtg tccctcttac tatggcaaaa cctctttcag ctcctgtcct   4200
acctcgtact gcgcatgaat gatgagccag ttgtagagtg gggggcacag gaaaattatt   4260
aatgtgcatg ggagcattca caagtgtaaa acattgactt gcaagaaaca tcttgtctca   4320
gtgtaggttt ctaggaaaga caaagggaac attagggaat agactccatc tagagcactg   4380
gttctcagtc ttcctaatgc tgcaaccctt tagtacagct cttcctgttg tagtgatcgc   4440
agccataaca ttattttcat tgccacttca taactgtaat ccttctactg ctgtgaatca   4500
caatggaaat atttatgttt tctgatggtc ttaagcaaca cctctgaaaa agtcattgac   4560
ccccccccca aaggggctgt gatccacagg ttgagaaatg ctcatctgga aggtaaccat   4620
gcatttaagt gtacctctag tagtttgggt ctatagaaga tattctccta ttctaccttt   4680
ttagacacgc cagaagaggg catctgattc cattaaagat gattgggagc caccgtgtgg   4740
ttcctgagaa ctgtactcgg gccctttgga agagcaatca gtgctctttc cagcccctaa   4800
gaatattttt aatacagcca gaaaggtctc attacccagt gtactgagcc ctaaggcact   4860
ttcatcctca atcgttccat gttgaatggt tttcattaca tttggaaaat gttttctctc   4920
cactctacct ttacatgttc ctattttcct attgacaatt tgccccttca ctgtaattct   4980
aatttggtgt ggtccttctt ctcataagtt tatatgtgac atgaacattt aaaaatatct   5040
atgaatattt tatagtcatg tatgtctttc tgcaaagcta ttcaaatgaa ctatggacag   5100
ttcttttcta cacgaagaag agatgagttt aatccccagt aacatgagaa aaagatgagt   5160
gagggacagt gctcacagta tccctcacta gcatcatttg tgattccatg ggccattttt   5220
ttccaccagc aaatagcaga gagccctttc cctattcgtt tctcttacac ttccccttttt   5280
ctgttacaac tgaacacttt acattagtta ctcctttgta gggggtttga cttttccacc   5340
gttttctctg gttcactatt tatgctaagt atctgtgcag ggcgggtata tcagtccaac   5400
agaggtgtca ttagtgttca ttgaggagga aatactttgc atgaattcat gacatcattg   5460
aagtagcagt ggccagaaag atacccttct gcgaatgtgt ctgtgtattc agaagctgcc   5520
ctggttagaa aacatgtggg tcacttttcc tttgcatgtt accagtgctc actgggtcat   5580
gattgtttta agacagagct tttgctgtgg caatgaccaa ggtgaatcca gagatgcaga   5640
tcagacaaag gacaagacaa tgtactatct gagtaaaacc ctgccttgac ttactcctca   5700
gtacttagag attttacata gcaacctcca ccctgtggca acccgttcac actagcagtg   5760
atgctgagat ttgcccttcc ttctcatcat cttcctcaca tccaaagcat tttgtgtcca   5820
cactgctgtt tcagataact gtttctaaag tgggattgtt gtagccagaa aggtagggaa   5880
```

```
aatgttcccc aaaatatttg cattcttaag tatgtgaagt aagtagatta tagtcagaga   5940

caatatgtaa ggtttcaggt tcactccctt ctacacatat cttcaactgt gtatttgcag   6000

aatattctga atgtgacata ctcccaacag aatatattta aggagtattt atccacagta   6060

ttgttctctg tacagttcta gtgcttctat tgtcactgca attgtcaatt gtttttctgc   6120

tttccaactg tcttattatc atttaatagc atcttgctaa atgccctctt tctattctcc   6180

ttatttctcc atagttcatg tgtgtctgtg tgactaagga ttctcctcat ttttgcagaa   6240

aaataaaatc ttttcttctt tatgtcctgc ttgtcattct ctggtgacac atgtctttgc   6300

ttacttggac tgagggttgt acagtaagta cagaagcagg ctcagtcaca cagacagaga   6360

cacaccacca ccagcagcag cagcaccacc accaccacca ccaccaccag aaaacagtat   6420

gagtactcat ctcttgatta catgtcattt caagtaagca ccatgacacc gagggccagg   6480

ttccatggac tttctctgtt aggcacgtga ttctttagct gacctttgag aacagactcc   6540

aacaacctca cttattttta ctgttgactt atatcatctc tgacaacact ggacttcgtt   6600

tgagctagtc aagaggaaag accatgacac ctaagggaca gaaattcaca cactcggttt   6660

ttcataattc acacacattc ctatgtatca aatctctgta atagatgaca tttacttgaa   6720

taaaaagtca tttccctttt                                                6739
```

<210> SEQ ID NO 68
<211> LENGTH: 1314
<212> TYPE: PRT
<213> ORGANISM: Mus musculus

<400> SEQUENCE: 68

```
Met Lys Leu Lys Arg Thr Ala Tyr Leu Leu Phe Leu Tyr Leu Ser Ser
1               5                   10                  15

Ser Leu Leu Ile Cys Ile Lys Asn Ser Phe Cys Asn Lys Asn Asn Thr
            20                  25                  30

Arg Cys Leu Ser Gly Pro Cys Gln Asn Asn Ser Thr Cys Lys His Phe
        35                  40                  45

Pro Gln Asp Asn Asn Cys Cys Leu Asp Thr Ala Asn Asn Leu Asp Lys
    50                  55                  60

Asp Cys Glu Asp Leu Lys Asp Pro Cys Phe Ser Ser Pro Cys Gln Gly
65                  70                  75                  80

Ile Ala Thr Cys Val Lys Ile Pro Gly Glu Gly Asn Phe Leu Cys Gln
                85                  90                  95

Cys Pro Pro Gly Tyr Ser Gly Leu Asn Cys Glu Thr Ala Thr Asn Ser
            100                 105                 110

Cys Gly Gly Asn Leu Cys Gln His Gly Gly Thr Cys Arg Lys Asp Pro
        115                 120                 125

Glu His Pro Val Cys Ile Cys Pro Pro Gly Tyr Ala Gly Arg Phe Cys
    130                 135                 140

Glu Thr Asp His Asn Glu Cys Ala Ser Ser Pro Cys His Asn Gly Ala
145                 150                 155                 160

Met Cys Gln Asp Gly Ile Asn Gly Tyr Ser Cys Phe Cys Val Pro Gly
                165                 170                 175

Tyr Gln Gly Arg His Cys Asp Leu Glu Val Asp Glu Cys Val Ser Asp
            180                 185                 190

Pro Cys Lys Asn Glu Ala Val Cys Leu Asn Glu Ile Gly Arg Tyr Thr
        195                 200                 205

Cys Val Cys Pro Gln Glu Phe Ser Gly Val Asn Cys Glu Leu Glu Ile
```

```
    210                 215                 220

Asp Glu Cys Arg Ser Gln Pro Cys Leu His Gly Ala Thr Cys Gln Asp
225                 230                 235                 240

Ala Pro Gly Gly Tyr Ser Cys Asp Cys Ala Pro Gly Phe Leu Gly Glu
                245                 250                 255

His Cys Glu Leu Ser Val Asn Glu Cys Glu Ser Gln Pro Cys Leu His
            260                 265                 270

Gly Gly Leu Cys Val Asp Gly Arg Asn Ser Tyr His Cys Asp Cys Thr
        275                 280                 285

Gly Ser Gly Phe Thr Gly Met His Cys Glu Ser Leu Ile Pro Leu Cys
    290                 295                 300

Trp Ser Lys Pro Cys His Asn Asp Ala Thr Cys Glu Asp Thr Val Asp
305                 310                 315                 320

Ser Tyr Ile Cys His Cys Arg Pro Gly Ile His Cys Glu Glu Asp Val
                325                 330                 335

Asp Glu Cys Leu Leu His Pro Cys Leu Asn Gly Gly Thr Cys Glu Asn
            340                 345                 350

Leu Pro Gly Asn Tyr Ala Cys His Cys Pro Phe Asp Asp Thr Ser Arg
        355                 360                 365

Thr Phe Tyr Gly Gly Glu Asn Cys Ser Glu Ile Leu Leu Gly Cys Thr
    370                 375                 380

His His Gln Cys Leu Asn Asn Gly Lys Cys Ile Pro His Phe Gln Asn
385                 390                 395                 400

Gly Gln His Gly Phe Thr Cys Gln Cys Leu Ser Gly Tyr Ala Gly Pro
                405                 410                 415

Leu Cys Glu Thr Val Thr Thr Leu Ser Phe Gly Ser Asn Gly Phe Leu
            420                 425                 430

Trp Val Thr Ser Gly Ser His Thr Gly Ile Gly Pro Glu Cys Asn Ile
        435                 440                 445

Ser Leu Arg Phe His Thr Val Gln Pro Asn Ala Leu Leu Leu Ile Arg
    450                 455                 460

Gly Asn Lys Asp Val Ser Met Lys Leu Glu Leu Leu Asn Gly Cys Val
465                 470                 475                 480

His Leu Ser Ile Glu Val Trp Asn Gln Leu Lys Val Leu Leu Ser Ile
                485                 490                 495

Ser His Asn Thr Ser Asp Gly Glu Trp His Phe Val Glu Val Thr Ile
            500                 505                 510

Ala Glu Thr Leu Thr Leu Ala Leu Val Gly Gly Ser Cys Lys Glu Lys
        515                 520                 525

Cys Thr Thr Lys Ser Ser Val Pro Val Glu Asn His Gln Ser Ile Cys
    530                 535                 540

Ala Leu Gln Asp Ser Phe Leu Gly Gly Leu Pro Met Gly Thr Ala Asn
545                 550                 555                 560

Asn Ser Val Ser Val Leu Asn Ile Tyr Asn Val Pro Ser Thr Pro Ser
                565                 570                 575

Phe Val Gly Cys Leu Gln Asp Ile Arg Phe Asp Leu Asn His Ile Thr
            580                 585                 590

Leu Glu Asn Val Ser Ser Gly Leu Ser Ser Asn Val Lys Ala Gly Cys
        595                 600                 605

Leu Gly Lys Asp Trp Cys Glu Ser Gln Pro Cys Gln Asn Arg Gly Arg
    610                 615                 620

Cys Ile Asn Leu Trp Gln Gly Tyr Gln Cys Glu Cys Asp Arg Pro Tyr
625                 630                 635                 640
```

```
Thr Gly Ser Asn Cys Leu Lys Glu Tyr Val Ala Gly Arg Phe Gly Gln
                645                 650                 655

Asp Asp Ser Thr Gly Tyr Ala Ala Phe Ser Val Asn Asp Asn Tyr Gly
            660                 665                 670

Gln Asn Phe Ser Leu Ser Met Phe Val Arg Thr Arg Gln Pro Leu Gly
        675                 680                 685

Leu Leu Leu Ala Leu Glu Asn Ser Thr Tyr Gln Tyr Val Ser Val Trp
    690                 695                 700

Leu Glu His Gly Ser Leu Ala Leu Gln Thr Pro Gly Ser Pro Lys Phe
705                 710                 715                 720

Met Val Asn Phe Phe Leu Ser Asp Gly Asn Val His Leu Ile Ser Leu
                725                 730                 735

Arg Ile Lys Pro Asn Glu Ile Glu Leu Tyr Gln Ser Ser Gln Asn Leu
            740                 745                 750

Gly Phe Ile Ser Val Pro Thr Trp Thr Ile Arg Arg Gly Asp Val Ile
        755                 760                 765

Phe Ile Gly Gly Leu Pro Asp Arg Glu Lys Thr Glu Val Tyr Gly Gly
    770                 775                 780

Phe Phe Lys Gly Cys Val Gln Asp Val Arg Leu Asn Ser Gln Thr Leu
785                 790                 795                 800

Glu Phe Phe Pro Asn Ser Thr Asn Asn Ala Tyr Asp Asp Pro Ile Leu
                805                 810                 815

Val Asn Val Thr Gln Gly Cys Pro Gly Asp Asn Thr Cys Lys Ser Asn
            820                 825                 830

Pro Cys His Asn Gly Gly Val Cys His Ser Leu Trp Asp Asp Phe Ser
        835                 840                 845

Cys Ser Cys Pro Thr Asn Thr Ala Gly Arg Ala Cys Glu Gln Val Gln
    850                 855                 860

Trp Cys Gln Leu Ser Pro Cys Pro Pro Thr Ala Glu Cys Gln Leu Leu
865                 870                 875                 880

Pro Gln Gly Phe Glu Cys Ile Ala Asn Ala Val Phe Ser Gly Leu Ser
                885                 890                 895

Arg Glu Ile Leu Phe Arg Ser Asn Gly Asn Ile Thr Arg Glu Leu Thr
            900                 905                 910

Asn Ile Thr Phe Ala Phe Arg Thr His Asp Thr Asn Val Met Ile Leu
        915                 920                 925

His Ala Glu Lys Glu Pro Glu Phe Leu Asn Ile Ser Ile Gln Asp Ala
    930                 935                 940

Arg Leu Phe Phe Gln Leu Arg Ser Gly Asn Ser Phe Tyr Thr Leu His
945                 950                 955                 960

Leu Met Gly Ser Gln Leu Val Asn Asp Gly Thr Trp His Gln Val Thr
                965                 970                 975

Phe Ser Met Ile Asp Pro Val Ala Gln Thr Ser Arg Trp Gln Met Glu
            980                 985                 990

Val Asn Asp Gln Thr Pro Phe Val  Ile Ser Glu Val Ala  Thr Gly Ser
        995                 1000                 1005

Leu Asn  Phe Leu Lys Asp Asn  Thr Asp Ile Tyr Val  Gly Asp Gln
    1010                 1015                 1020

Ser Val  Asp Asn Pro Lys Gly  Leu Gln Gly Cys Leu  Ser Thr Ile
    1025                 1030                 1035

Glu Ile  Gly Gly Ile Tyr Leu  Ser Tyr Phe Glu Asn  Leu His Gly
    1040                 1045                 1050
```

```
Phe Pro  Gly Lys Pro Gln Glu  Glu Gln Phe Leu Lys  Val Ser Thr
    1055                 1060                 1065

Asn Met  Val Leu Thr Gly Cys  Leu Pro Ser Asn Ala  Cys His Ser
    1070                 1075                 1080

Ser Pro  Cys Leu His Gly Gly  Asn Cys Glu Asp Ser  Tyr Ser Ser
    1085                 1090                 1095

Tyr Arg  Cys Ala Cys Leu Ser  Gly Trp Ser Gly Thr  His Cys Glu
    1100                 1105                 1110

Ile Asn  Ile Asp Glu Cys Phe  Ser Ser Pro Cys Ile  His Gly Asn
    1115                 1120                 1125

Cys Ser  Asp Gly Val Ala Ala  Tyr His Cys Arg Cys  Glu Pro Gly
    1130                 1135                 1140

Tyr Thr  Gly Val Asn Cys Glu  Val Asp Val Asp Asn  Cys Lys Ser
    1145                 1150                 1155

His Gln  Cys Ala Asn Gly Ala  Thr Cys Val Pro Glu  Ala His Gly
    1160                 1165                 1170

Tyr Ser  Cys Leu Cys Phe Gly  Asn Phe Thr Gly Arg  Phe Cys Arg
    1175                 1180                 1185

His Ser  Arg Leu Pro Ser Thr  Val Cys Gly Asn Glu  Lys Arg Asn
    1190                 1195                 1200

Phe Thr  Cys Tyr Asn Gly Gly  Ser Cys Ser Met Phe  Gln Glu Asp
    1205                 1210                 1215

Trp Gln  Cys Met Cys Trp Pro  Gly Phe Thr Gly Glu  Trp Cys Glu
    1220                 1225                 1230

Glu Asp  Ile Asn Glu Cys Ala  Ser Asp Pro Cys Ile  Asn Gly Gly
    1235                 1240                 1245

Leu Cys  Arg Asp Leu Val Asn  Arg Phe Leu Cys Ile  Cys Asp Val
    1250                 1255                 1260

Ala Phe  Ala Gly Glu Arg Cys  Glu Leu Asp Val Ser  Gly Leu Ser
    1265                 1270                 1275

Phe Tyr  Val Ser Leu Leu Leu  Trp Gln Asn Leu Phe  Gln Leu Leu
    1280                 1285                 1290

Ser Tyr  Leu Val Leu Arg Met  Asn Asp Glu Pro Val  Val Glu Trp
    1295                 1300                 1305

Gly Ala  Gln Glu Asn Tyr
    1310
```

<210> SEQ ID NO 69
<211> LENGTH: 5481
<212> TYPE: DNA
<213> ORGANISM: Mus musculus

<400> SEQUENCE: 69

```
gatccagctt gaagaggagt gaggcaaagc tgaaccctcc cactctcctt gacaagtgca     60

agcccacact tttggaaaaa agcacaaaga cgtcagaaac ggttcctgtc gacctactag    120

gctttggatg gctaagtgtt tttgctttgt atggaaatat gtttggacac aagacacaag    180

gttttcacat tttaatggca gtgctcatag gaattcactg tgaagaagac gttgatgaat    240

gtttactgca cccttgccta aatggtggta cttgtgagaa cctgcctggg aattatgcct    300

gtcactgtcc ctttgatgac acttctagga cattttatgg aggagaaaac tgctcagaaa    360

ttctcctggg ctgcactcat caccagtgtc tgaacaatgg aaaatgtatc cctcatttcc    420

aaaatggcca gcatggattc acttgccagt gtctttctgg ctatgcgggg cccctgtgtg    480

aaactgtcac cacactttca tttgggagca atggcttcct atgggtcaca agtggctccc    540
```

```
atacaggcat agggccagaa tgtaacatat ccttgaggtt tcacactgtt caaccaaacg    600
cacttctcct catccgaggc aacaaggacg tgtctatgaa gctggagttg ctgaatggtt    660
gtgttcactt atcaattgaa gtctggaatc agttaaaggt gctcctgtct atttctcaca    720
acaccagtga tggagaatgg catttcgtgg aggtaacaat cgcagaaact ctaacccttg    780
ccctagttgg cggctcctgc aaggagaagt gcaccaccaa gtcttctgtt ccagttgaga    840
atcatcaatc aatatgtgct ttgcaggact ctttttttggg tggcttacca atggggacag    900
ccaacaacag tgtgtctgtg cttaacatct ataatgtgcc gtccacacct tcctttgtag    960
gctgtctcca agacattaga tttgatttga atcacattac tctggagaac gtttcatctg   1020
gcctgtcatc aaatgttaaa gcaggctgcc tgggaaagga ctggtgtgaa agtcaaccct   1080
gtcaaaacag aggacgctgc atcaacttgt ggcagggtta tcagtgtgaa tgtgacaggc   1140
cctatacagg ctccaactgc ctgaaagagt atgtagcggg aagatttggc caagatgact   1200
ccacaggata tgcggccttt agtgttaatg ataattatgg acagaacttc agtctttcaa   1260
tgtttgtccg aacacgtcaa cccctgggct tacttctggc tttggaaaat agtacttacc   1320
agtatgtcag tgtctggcta gagcacggca gcctagcact gcagactcca ggctctccca   1380
agttcatggt aaactttttt ctcagtgatg gaaatgttca cttaatatct ttgagaatca   1440
aaccaaatga aattgaactg tatcagtctt cacaaaacct aggattcatt tctgttccta   1500
catggacaat tcgaagagga gacgtcatct tcattggtgg cttacctgac agagagaaga   1560
ctgaagttta tggtggcttc ttcaaaggct gtgttcaaga tgtcagatta aacagccaga   1620
ctctggaatt ctttcccaat tcaacaaaca atgcatacga tgacccaatt cttgtcaatg   1680
tgactcaagg ctgtcccgga gacaacacat gtaaggtatc gcaaacgctg ttttcagcgg   1740
attaagcaga gaaatactct tcagaagcaa tgggaacatt accagagaac tcaccaatat   1800
cacatttgct ttcagaacac atgatacaaa tgtgatgata ttgcatgcag aaaaagaacc   1860
agagtttctt aatattagca ttcaagatgc cagattattc tttcaattgc gaagtggcaa   1920
cagcttttat acgctgcacc tgatgggttc ccaattggtg aatgatggca catggcacca   1980
agtgactttc tccatgatag acccagtggc ccagacctcc cggtggcaaa tggaggtgaa   2040
cgaccagaca ccctttgtga taagtgaagt tgctactgga agcctgaact tttgaagga    2100
caatacagac atctatgtgg gtgaccaatc tgttgacaat ccgaaaggcc tgcagggctg   2160
tctgagcaca atagagattg gaggcatata tctttcttac tttgaaaatc tacatggttt   2220
ccctggtaag cctcaggaag agcaatttct caaagtttct acaaatatgg tacttactgg   2280
ctgtttgcca tcaaatgcct gccactccag cccctgtttg catggaggaa actgtgaaga   2340
cagctacagt tcttatcggt gtgcctgtct ctcgggatgg tcagggacac actgtgaaat   2400
caacattgat gagtgctttt ctagcccctg tatccatggc aactgctctg atggagttgc   2460
agcctaccac tgcaggtgtg agcctggata caccggtgtg aactgtgagg tggatgtaga   2520
caattgcaag agtcatcagt gtgcaaatgg ggccacctgt gttcctgaag ctcatggcta   2580
ctcttgtctc tgctttggaa attttaccgg gagattttgc agacacagca gattaccctc   2640
aacagtctgt gggaatgaga agagaaactt cacttgctac aatggaggca gctgctccat   2700
gttccaggag gactggcaat gtatgtgctg gccaggtttc actggagagt ggtgtgaaga   2760
ggacatcaac gagtgtgcct ccgatccctg catcaatgga ggactgtgca gggacttggt   2820
caacaggttc ctatgcatct gtgatgtggc cttcgctggc gagcgctgtg agctggacgt   2880
```

aagcggcctt tccttttatg tgtccctctt actatggcaa aacctctttc agctcctgtc 2940
ctacctcgta ctgcgcatga atgatgagcc agttgtagag tggggggcac aggaaaatta 3000
ttaatgtgca tgggagcatt cacaagtgta aaacattgac ttgcaagaaa catcttgtct 3060
cagtgtaggt ttctaggaaa gacaaaggga acattaggga atagactcca tctagagcac 3120
tggttctcag tcttcctaat gctgcaaccc tttagtacag ctcttcctgt tgtagtgatc 3180
gcagccataa cattattttc attgccactt cataactgta atccttctac tgctgtgaat 3240
cacaatggaa atatttatgt tttctgatgg tcttaagcaa cacctctgaa aaagtcattg 3300
accccccccc caaaggggct gtgatccaca ggttgagaaa tgctcatctg gaaggtaacc 3360
atgcatttaa gtgtacctct agtagtttgg gtctatagaa gatattctcc tattctacct 3420
ttttagacac gccagaagag ggcatctgat tccattaaag atgattggga gccaccgtgt 3480
ggttcctgag aactgtactc gggccctttg gaagagcaat cagtgctctt tccagcccct 3540
aagaatattt ttaatacagc cagaaaggtc tcattaccca gtgtactgag ccctaaggca 3600
ctttcatcct caatcgttcc atgttgaatg gttttcatta catttggaaa atgttttctc 3660
tccactctac ctttacatgt tcctattttc ctattgacaa tttgcccctt cactgtaatt 3720
ctaatttggt gtggtccttc ttctcataag tttatatgtg acatgaacat ttaaaaatat 3780
ctatgaatat tttatagtca tgtatgtctt tctgcaaagc tattcaaatg aactatggac 3840
agttcttttc tacacgaaga agagatgagt ttaatcccca gtaacatgag aaaaagatga 3900
gtgagggaca gtgctcacag tatccctcac tagcatcatt tgtgattcca tgggccattt 3960
ttttccacca gcaaatagca gagagccctt tccctattcg tttctcttac acttcccctt 4020
ttctgttaca actgaacact ttacattagt tactcctttg taggggggttt gacttttcca 4080 ccgttttctc tggttcacta tttatgctaa gtatctgtgc agggcgggta tatcagtcca 4140
acagaggtgt cattagtgtt cattgaggag gaaatacttt gcatgaattc atgacatcat 4200
tgaagtagca gtggccagaa agataccctt ctgcgaatgt gtctgtgtat tcagaagctg 4260
ccctggttag aaaacatgtg ggtcactttt cctttgcatg ttaccagtgc tcactgggtc 4320
atgattgttt taagacagag cttttgctgt ggcaatgacc aaggtgaatc cagagatgca 4380
gatcagacaa aggacaagac aatgtactat ctgagtaaaa ccctgccttg acttactcct 4440
cagtacttag agattttaca tagcaacctc caccctgtgg caacccgttc acactagcag 4500
tgatgctgag atttgccctt ccttctcatc atcttcctca catccaaagc attttgtgtc 4560
cacactgctg tttcagataa ctgtttctaa agtgggattg ttgtagccag aaaggtaggg 4620
aaaatgttcc ccaaaatatt tgcattctta agtatgtgaa gtaagtagat tatagtcaga 4680
gacaatatgt aaggtttcag gttcactccc ttctacacat atcttcaact gtgtatttgc 4740
agaatattct gaatgtgaca tactcccaac agaatatatt taaggagtat ttatccacag 4800
tattgttctc tgtacagttc tagtgcttct attgtcactg caattgtcaa ttgtttttct 4860
gctttccaac tgtcttatta tcatttaata gcatcttgct aaatgccctc tttctattct 4920
ccttatttct ccatagttca tgtgtgtctg tgtgactaag gattctcctc atttttgcag 4980
aaaaataaaa tcttttcttc tttatgtcct gcttgtcatt ctctggtgac acatgtcttt 5040
gcttacttgg actgagggtt gtacagtaag tacagaagca ggctcagtca cacagacaga 5100
gacacaccac caccagcagc agcagcacca ccaccaccac caccaccacc agaaaacagt 5160
atgagtactc atctcttgat tacatgtcat ttcaagtaag caccatgaca ccgagggcca 5220
ggttccatgg actttctctg ttaggcacgt gattctttag ctgacctttg agaacagact 5280

```
ccaacaacct cacttatttt tactgttgac ttatatcatc tctgacaaca ctggacttcg   5340

tttgagctag tcaagaggaa agaccatgac acctaaggga cagaaattca cacactcggt   5400

ttttcataat tcacacacat tcctatgtat caaatctctg taatagatga catttacttg   5460

aataaaaagt catttccctt t                                             5481


<210> SEQ ID NO 70
<211> LENGTH: 528
<212> TYPE: PRT
<213> ORGANISM: Mus musculus

<400> SEQUENCE: 70

Met Phe Gly His Lys Thr Gln Gly Phe His Ile Leu Met Ala Val Leu
1               5                   10                  15

Ile Gly Ile His Cys Glu Glu Asp Val Asp Glu Cys Leu Leu His Pro
            20                  25                  30

Cys Leu Asn Gly Gly Thr Cys Glu Asn Leu Pro Gly Asn Tyr Ala Cys
        35                  40                  45

His Cys Pro Phe Asp Asp Thr Ser Arg Thr Phe Tyr Gly Gly Glu Asn
    50                  55                  60

Cys Ser Glu Ile Leu Leu Gly Cys Thr His His Gln Cys Leu Asn Asn
65                  70                  75                  80

Gly Lys Cys Ile Pro His Phe Gln Asn Gly Gln His Gly Phe Thr Cys
                85                  90                  95

Gln Cys Leu Ser Gly Tyr Ala Gly Pro Leu Cys Glu Thr Val Thr Thr
            100                 105                 110

Leu Ser Phe Gly Ser Asn Gly Phe Leu Trp Val Thr Ser Gly Ser His
        115                 120                 125

Thr Gly Ile Gly Pro Glu Cys Asn Ile Ser Leu Arg Phe His Thr Val
    130                 135                 140

Gln Pro Asn Ala Leu Leu Leu Ile Arg Gly Asn Lys Asp Val Ser Met
145                 150                 155                 160

Lys Leu Glu Leu Leu Asn Gly Cys Val His Leu Ser Ile Glu Val Trp
                165                 170                 175

Asn Gln Leu Lys Val Leu Leu Ser Ile Ser His Asn Thr Ser Asp Gly
            180                 185                 190

Glu Trp His Phe Val Glu Val Thr Ile Ala Glu Thr Leu Thr Leu Ala
        195                 200                 205

Leu Val Gly Gly Ser Cys Lys Glu Lys Cys Thr Thr Lys Ser Ser Val
    210                 215                 220

Pro Val Glu Asn His Gln Ser Ile Cys Ala Leu Gln Asp Ser Phe Leu
225                 230                 235                 240

Gly Gly Leu Pro Met Gly Thr Ala Asn Asn Ser Val Ser Val Leu Asn
                245                 250                 255

Ile Tyr Asn Val Pro Ser Thr Pro Ser Phe Val Gly Cys Leu Gln Asp
            260                 265                 270

Ile Arg Phe Asp Leu Asn His Ile Thr Leu Glu Asn Val Ser Ser Gly
        275                 280                 285

Leu Ser Ser Asn Val Lys Ala Gly Cys Leu Gly Lys Asp Trp Cys Glu
    290                 295                 300

Ser Gln Pro Cys Gln Asn Arg Gly Arg Cys Ile Asn Leu Trp Gln Gly
305                 310                 315                 320

Tyr Gln Cys Glu Cys Asp Arg Pro Tyr Thr Gly Ser Asn Cys Leu Lys
                325                 330                 335
```

```
Glu Tyr Val Ala Gly Arg Phe Gly Gln Asp Asp Ser Thr Gly Tyr Ala
            340                 345                 350

Ala Phe Ser Val Asn Asp Asn Tyr Gly Gln Asn Phe Ser Leu Ser Met
        355                 360                 365

Phe Val Arg Thr Arg Gln Pro Leu Gly Leu Leu Leu Ala Leu Glu Asn
    370                 375                 380

Ser Thr Tyr Gln Tyr Val Ser Val Trp Leu Glu His Gly Ser Leu Ala
385                 390                 395                 400

Leu Gln Thr Pro Gly Ser Pro Lys Phe Met Val Asn Phe Phe Leu Ser
                405                 410                 415

Asp Gly Asn Val His Leu Ile Ser Leu Arg Ile Lys Pro Asn Glu Ile
            420                 425                 430

Glu Leu Tyr Gln Ser Ser Gln Asn Leu Gly Phe Ile Ser Val Pro Thr
        435                 440                 445

Trp Thr Ile Arg Arg Gly Asp Val Ile Phe Ile Gly Gly Leu Pro Asp
    450                 455                 460

Arg Glu Lys Thr Glu Val Tyr Gly Gly Phe Phe Lys Gly Cys Val Gln
465                 470                 475                 480

Asp Val Arg Leu Asn Ser Gln Thr Leu Glu Phe Phe Pro Asn Ser Thr
                485                 490                 495

Asn Asn Ala Tyr Asp Asp Pro Ile Leu Val Asn Val Thr Gln Gly Cys
            500                 505                 510

Pro Gly Asp Asn Thr Cys Lys Val Ser Gln Thr Leu Phe Ser Ala Asp
        515                 520                 525


<210> SEQ ID NO 71
<211> LENGTH: 6950
<212> TYPE: DNA
<213> ORGANISM: Mus musculus

<400> SEQUENCE: 71

gtcagaagaa attaatttct ctattaggag caatcaagga ccctatccta aaacaaagcc     60

tttccaggag gcattgttca cggaagcctg agggggacac gaatccaatc caggctggaa    120

aaatctgctc caggattgac tggttaccgt cttcctgtgc ctgtaaggtg ctgtgaaaga    180

gaagtgcttt ctgattctct gtctgtggag gagccctggg aggggtggga cagagatggc    240

atcctggctc tctgaggcac ctgctcttct ctgaaccaca caggagtcaa gagccaaaca    300

gggatagctt cagcagcact tcagagggtg ttctctaagt aagaacatga agctcaagag    360

aactgcctac cttctcttcc tgtacctcag ctcctcactg ctcatctgca taaagaattc    420

attttgcaat aaaaacaata ccaggtgcct ttcaggtcct tgccaaaaca attctacgtg    480

caagcatttt ccacaagaca acaattgttg cttagacaca gccaataatt tggacaaaga    540

ctgtgaagat ctgaaagacc cttgcttctc gagtccctgc caaggaattg ccacttgtgt    600

gaaaatccca ggggaaggga acttcctgtg tcagtgtcct cctgggtaca gcgggctgaa    660

ctgtgaaact gccaccaatt cctgtggagg gaacctctgc caacatggag gcacctgccg    720

taaagaccct gagcaccctg tctgtatctg ccctcctgga tatgctggaa ggttctgtga    780

gactgatcac aatgagtgtg cttctagccc ttgccacaat ggggctatgt gccaggatgg    840

aatcaatggc tactcctgct tctgtgtgcc tggataccaa ggcaggcatt gtgacttgga    900

agtggatgaa tgtgtttctg atccctgcaa gaatgaggct gtgtgcctca atgagatagg    960

aagatacact tgtgtctgcc ctcaagagtt ttctggcgtg aactgtgagt tggaaattga   1020
```

-continued

```
tgaatgcaga tcccagcctt gtctccacgg tgccacatgt caggacgctc caggggggcta   1080
ctcctgtgac tgtgcacctg gattccttgg agagcactgt gaactcagcg ttaatgaatg   1140
tgaaagtcag ccgtgtctcc atggaggtct atgtgtggat ggaagaaaca gttaccactg   1200
tgactgcaca ggtagtggat tcacagggat gcactgtgag tccttgattc ctctttgttg   1260
gtcaaagcct tgtcacaacg acgcgacatg tgaagatact gttgacagct atatttgtca   1320
ctgccggcct ggatacacag gtgccctgtg tgagacagac ataaatgaat gcagtagcaa   1380
cccctgccaa ttttgggggg aatgtgtcga gctgtcctca gagggtctat atggaaacac   1440
tgctggcctg ccttcctcct tcagctatgt tggagcctcg ggctatgtgt gtatctgtca   1500
gcctggattc acaggaattc actgtgaaga agacgttgat gaatgtttac tgcacccttg   1560
cctaaatggt ggtacttgtg agaacctgcc tgggaattat gcctgtcact gtccctttga   1620
tgacacttct aggacatttt atggaggaga aaactgctca gaaattctcc tgggctgcac   1680
tcatcaccag tgtctgaaca atggaaaatg tatccctcat ttccaaaatg gccagcatgg   1740
attcacttgc cagtgtcttt ctggctatgc ggggcccctg tgtgaaactg tcaccacact   1800
ttcatttggg agcaatggct tcctatgggt cacaagtggc tcccatacag gcatagggcc   1860
agaatgtaac atatccttga ggtttcacac tgttcaacca aacgcacttc tcctcatccg   1920
aggcaacaag gacgtgtcta tgaagctgga gttgctgaat ggttgtgttc acttatcaat   1980
tgaagtctgg aatcagttaa aggtgctcct gtctatttct cacaacacca gtgatggaga   2040
atggcatttc gtggaggtaa caatcgcaga aactctaacc cttgccctag ttggcggctc   2100
ctgcaaggag aagtgcacca ccaagtcttc tgttccagtt gagaatcatc aatcaatatg   2160
tgctttgcag gactcttttt tgggtggctt accaatgggg acagccaaca acagtgtgtc   2220
tgtgcttaac atctataatg tgccgtccac accttccttt gtaggctgtc tccaagacat   2280
tagatttgat ttgaatcaca ttactctgga gaacgtttca tctggcctgt catcaaatgt   2340
taaagcaggc tgcctgggaa aggactggtg tgaaagtcaa ccctgtcaaa acagaggacg   2400
ctgcatcaac ttgtggcagg gttatcagtg tgaatgtgac aggccctata caggctccaa   2460
ctgcctgaaa gagtatgtag cgggaagatt tggccaagat gactccacag gatatgcggc   2520
ctttagtgtt aatgataatt atggacagaa cttcagtctt tcaatgtttg tccgaacacg   2580
tcaacccctg ggcttacttc tggctttgga aaatagtact taccagtatg tcagtgtctg   2640
gctagagcac ggcagcctag cactgcagac tccaggctct cccaagttca tggtaaactt   2700
ttttctcagt gatggaaatg ttcacttaat atctttgaga atcaaaccaa atgaaattga   2760
actgtatcag tcttcacaaa acctaggatt catttctgtt cctacatgga caattcgaag   2820
aggagacgtc atcttcattg gtggcttacc tgacagagag aagactgaag tttatggtgg   2880
cttcttcaaa ggctgtgttc aagatgtcag attaaacagc cagactctgg aattctttcc   2940
caattcaaca aacaatgcat acgatgaccc aattcttgtc aatgtgactc aaggctgtcc   3000
cggagacaac acatgtaagt ccaacccctg tcataatgga ggtgtctgcc actccctgtg   3060
ggatgacttc tcctgctcct gccctacaaa cacagcgggg agagcctgcg agcaagttca   3120
gtggtgtcaa ctcagcccat gtcctcccac tgcagagtgc cagctgctcc ctcaagggtt   3180
tgaatgtatc gcaaacgctg ttttcagcgg attaagcaga gaaatactct tcagaagcaa   3240
tgggaacatt accagagaac tcaccaatat cacatttgct ttcagaacac atgatacaaa   3300
tgtgatgata ttgcatgcag aaaaagaacc agagtttctt aatattagca ttcaagatgc   3360
cagattattc tttcaattgc gaagtggcaa cagcttttat acgctgcacc tgatgggttc   3420
```

ccaattggtg aatgatggca catggcacca agtgactttc tccatgatag acccagtggc 3480
ccagacctcc cggtggcaaa tggaggtgaa cgaccagaca ccctttgtga taagtgaagt 3540
tgctactgga agcctgaact ttttgaagga caatacagac atctatgtgg gtgaccaatc 3600
tgttgacaat ccgaaaggcc tgcagggctg tctgagcaca atagagattg gaggcatata 3660
tctttcttac tttgaaaatc tacatggttt ccctggtaag cctcaggaag agcaatttct 3720
caaagtttct acaaatatgg tacttactgg ctgtttgcca tcaaatgcct gccactccag 3780
cccctgtttg catggaggaa actgtgaaga cagctacagt tcttatcggt gtgcctgtct 3840
ctcgggatgg tcagggacac actgtgaaat caacattgat gagtgctttt ctagcccctg 3900
tatccatggc aactgctctg atggagttgc agcctaccac tgcaggtgtg agcctggata 3960
caccggtgtg aactgtgagg tggatgtaga caattgcaag agtcatcagt gtgcaaatgg 4020
ggccacctgt gttcctgaag ctcatggcta ctcttgtctc tgctttggaa attttaccgg 4080
gagattttgc agacacagca gattaccctc aacagtctgt gggaatgaga agagaaactt 4140
cacttgctac aatggaggca gctgctccat gttccaggag gactggcaat gtatgtgctg 4200
gccaggtttc actggagagt ggtgtgaaga ggacatcaac gagtgtgcct ccgatccctg 4260
catcaatgga ggactgtgca gggacttggt caacaggttc ctatgcatct gtgatgtggc 4320
cttcgctggc gagcgctgtg agctggacgt aagcggcctt tccttttatg tgtccctctt 4380
actatggcaa aacctctttc agctcctgtc ctacctcgta ctgcgcatga atgatgagcc 4440
agttgtagag tggggggcac aggaaaatta ttaatgtgca tgggagcatt cacaagtgta 4500
aaacattgac ttgcaagaaa catcttgtct cagtgtaggt ttctaggaaa gacaaaggga 4560
acattaggga atagactcca tctagagcac tggttctcag tcttcctaat gctgcaaccc 4620
tttagtacag ctcttcctgt tgtagtgatc gcagccataa cattattttc attgccactt 4680
cataactgta atccttctac tgctgtgaat cacaatggaa atatttatgt tttctgatgg 4740
tcttaagcaa cacctctgaa aaagtcattg accccccccc caaaggggct gtgatccaca 4800
ggttgagaaa tgctcatctg gaaggtaacc atgcatttaa gtgtacctct agtagtttgg 4860
gtctatagaa gatattctcc tattctacct ttttagacac gccagaagag ggcatctgat 4920
tccattaaag atgattggga gccaccgtgt ggttcctgag aactgtactc gggccctttg 4980
gaagagcaat cagtgctctt tccagcccct aagaatattt ttaatacagc cagaaaggtc 5040
tcattaccca gtgtactgag ccctaaggca ctttcatcct caatcgttcc atgttgaatg 5100
gttttcatta catttggaaa atgttttctc tccactctac ctttacatgt tcctattttc 5160
ctattgacaa tttgcccctt cactgtaatt ctaatttggt gtggtccttc ttctcataag 5220
tttatatgtg acatgaacat ttaaaaatat ctatgaatat tttatagtca tgtatgtctt 5280
tctgcaaagc tattcaaatg aactatggac agttcttttc tacacgaaga agagatgagt 5340
ttaatcccca gtaacatgag aaaaagatga gtgagggaca gtgctcacag tatccctcac 5400
tagcatcatt tgtgattcca tgggccattt ttttccacca gcaaatagca gagagccctt 5460
tccctattcg tttctcttac acttcccctt ttctgttaca actgaacact ttacattagt 5520
tactcctttg tagggggttt gacttttcca ccgttttctc tggttcacta tttatgctaa 5580
gtatctgtgc agggcgggta tatcagtcca acagaggtgt cattagtgtt cattgaggag 5640
gaaatacttt gcatgaattc atgacatcat tgaagtagca gtggccagaa agataccctt 5700
ctgcgaatgt gtctgtgtat tcagaagctg ccctggttag aaaacatgtg ggtcactttt 5760

```
cctttgcatg ttaccagtgc tcactgggtc atgattgttt taagacagag cttttgctgt   5820

ggcaatgacc aaggtgaatc cagagatgca gatcagacaa aggacaagac aatgtactat   5880

ctgagtaaaa ccctgccttg acttactcct cagtacttag agattttaca tagcaacctc   5940

caccctgtgg caacccgttc acactagcag tgatgctgag atttgccctt ccttctcatc   6000

atcttcctca catccaaagc attttgtgtc cacactgctg tttcagataa ctgtttctaa   6060

agtgggattg ttgtagccag aaaggtaggg aaaatgttcc ccaaaatatt tgcattctta   6120

agtatgtgaa gtaagtagat tatagtcaga gacaatatgt aaggtttcag gttcactccc   6180

ttctacacat atcttcaact gtgtatttgc agaatattct gaatgtgaca tactcccaac   6240

agaatatatt taaggagtat ttatccacag tattgttctc tgtacagttc tagtgcttct   6300

attgtcactg caattgtcaa ttgtttttct gctttccaac tgtcttatta tcatttaata   6360

gcatcttgct aaatgccctc tttctattct ccttatttct ccatagttca tgtgtgtctg   6420

tgtgactaag gattctcctc atttttgcag aaaaataaaa tcttttcttc tttatgtcct   6480

gcttgtcatt ctctggtgac acatgtcttt gcttacttgg actgagggtt gtacagtaag   6540

tacagaagca ggctcagtca cacagacaga gacacaccac caccagcagc agcagcacca   6600

ccaccaccac caccaccacc agaaaacagt atgagtactc atctcttgat tacatgtcat   6660

ttcaagtaag caccatgaca ccgagggcca ggttccatgg actttctctg ttaggcacgt   6720

gattctttag ctgacctttg agaacagact ccaacaacct cacttatttt tactgttgac   6780

ttatatcatc tctgacaaca ctggacttcg tttgagctag tcaagaggaa agaccatgac   6840

acctaaggga cagaaattca cacactcggt tttcataat tcacacacat tcctatgtat    6900

caaatctctg taatagatga catttacttg aataaaaagt catttccctt              6950
```

<210> SEQ ID NO 72
<211> LENGTH: 1375
<212> TYPE: PRT
<213> ORGANISM: Mus musculus

<400> SEQUENCE: 72

```
Met Lys Leu Lys Arg Thr Ala Tyr Leu Leu Phe Leu Tyr Leu Ser Ser
1               5                   10                  15

Ser Leu Leu Ile Cys Ile Lys Asn Ser Phe Cys Asn Lys Asn Asn Thr
            20                  25                  30

Arg Cys Leu Ser Gly Pro Cys Gln Asn Asn Ser Thr Cys Lys His Phe
        35                  40                  45

Pro Gln Asp Asn Asn Cys Cys Leu Asp Thr Ala Asn Asn Leu Asp Lys
    50                  55                  60

Asp Cys Glu Asp Leu Lys Asp Pro Cys Phe Ser Ser Pro Cys Gln Gly
65                  70                  75                  80

Ile Ala Thr Cys Val Lys Ile Pro Gly Glu Gly Asn Phe Leu Cys Gln
                85                  90                  95

Cys Pro Pro Gly Tyr Ser Gly Leu Asn Cys Glu Thr Ala Thr Asn Ser
            100                 105                 110

Cys Gly Gly Asn Leu Cys Gln His Gly Gly Thr Cys Arg Lys Asp Pro
        115                 120                 125

Glu His Pro Val Cys Ile Cys Pro Pro Gly Tyr Ala Gly Arg Phe Cys
    130                 135                 140

Glu Thr Asp His Asn Glu Cys Ala Ser Ser Pro Cys His Asn Gly Ala
145                 150                 155                 160

Met Cys Gln Asp Gly Ile Asn Gly Tyr Ser Cys Phe Cys Val Pro Gly
```

```
                165                 170                 175

Tyr Gln Gly Arg His Cys Asp Leu Glu Val Asp Glu Cys Val Ser Asp
            180                 185                 190

Pro Cys Lys Asn Glu Ala Val Cys Leu Asn Glu Ile Gly Arg Tyr Thr
        195                 200                 205

Cys Val Cys Pro Gln Glu Phe Ser Gly Val Asn Cys Glu Leu Glu Ile
    210                 215                 220

Asp Glu Cys Arg Ser Gln Pro Cys Leu His Gly Ala Thr Cys Gln Asp
225                 230                 235                 240

Ala Pro Gly Gly Tyr Ser Cys Asp Cys Ala Pro Gly Phe Leu Gly Glu
                245                 250                 255

His Cys Glu Leu Ser Val Asn Glu Cys Glu Ser Gln Pro Cys Leu His
            260                 265                 270

Gly Gly Leu Cys Val Asp Gly Arg Asn Ser Tyr His Cys Asp Cys Thr
        275                 280                 285

Gly Ser Gly Phe Thr Gly Met His Cys Glu Ser Leu Ile Pro Leu Cys
    290                 295                 300

Trp Ser Lys Pro Cys His Asn Asp Ala Thr Cys Glu Asp Thr Val Asp
305                 310                 315                 320

Ser Tyr Ile Cys His Cys Arg Pro Gly Tyr Thr Gly Ala Leu Cys Glu
                325                 330                 335

Thr Asp Ile Asn Glu Cys Ser Ser Asn Pro Cys Gln Phe Trp Gly Glu
            340                 345                 350

Cys Val Glu Leu Ser Ser Glu Gly Leu Tyr Gly Asn Thr Ala Gly Leu
        355                 360                 365

Pro Ser Ser Phe Ser Tyr Val Gly Ala Ser Gly Tyr Val Cys Ile Cys
    370                 375                 380

Gln Pro Gly Phe Thr Gly Ile His Cys Glu Glu Asp Val Asp Glu Cys
385                 390                 395                 400

Leu Leu His Pro Cys Leu Asn Gly Gly Thr Cys Glu Asn Leu Pro Gly
                405                 410                 415

Asn Tyr Ala Cys His Cys Pro Phe Asp Asp Thr Ser Arg Thr Phe Tyr
            420                 425                 430

Gly Gly Glu Asn Cys Ser Glu Ile Leu Leu Gly Cys Thr His His Gln
        435                 440                 445

Cys Leu Asn Asn Gly Lys Cys Ile Pro His Phe Gln Asn Gly Gln His
    450                 455                 460

Gly Phe Thr Cys Gln Cys Leu Ser Gly Tyr Ala Gly Pro Leu Cys Glu
465                 470                 475                 480

Thr Val Thr Thr Leu Ser Phe Gly Ser Asn Gly Phe Leu Trp Val Thr
                485                 490                 495

Ser Gly Ser His Thr Gly Ile Gly Pro Glu Cys Asn Ile Ser Leu Arg
            500                 505                 510

Phe His Thr Val Gln Pro Asn Ala Leu Leu Leu Ile Arg Gly Asn Lys
        515                 520                 525

Asp Val Ser Met Lys Leu Glu Leu Leu Asn Gly Cys Val His Leu Ser
    530                 535                 540

Ile Glu Val Trp Asn Gln Leu Lys Val Leu Leu Ser Ile Ser His Asn
545                 550                 555                 560

Thr Ser Asp Gly Glu Trp His Phe Val Glu Val Thr Ile Ala Glu Thr
                565                 570                 575

Leu Thr Leu Ala Leu Val Gly Gly Ser Cys Lys Glu Lys Cys Thr Thr
            580                 585                 590
```

```
Lys Ser Ser Val Pro Val Glu Asn His Gln Ser Ile Cys Ala Leu Gln
        595                 600                 605

Asp Ser Phe Leu Gly Gly Leu Pro Met Gly Thr Ala Asn Asn Ser Val
    610                 615                 620

Ser Val Leu Asn Ile Tyr Asn Val Pro Ser Thr Pro Ser Phe Val Gly
625                 630                 635                 640

Cys Leu Gln Asp Ile Arg Phe Asp Leu Asn His Ile Thr Leu Glu Asn
                645                 650                 655

Val Ser Ser Gly Leu Ser Ser Asn Val Lys Ala Gly Cys Leu Gly Lys
            660                 665                 670

Asp Trp Cys Glu Ser Gln Pro Cys Gln Asn Arg Gly Arg Cys Ile Asn
        675                 680                 685

Leu Trp Gln Gly Tyr Gln Cys Glu Cys Asp Arg Pro Tyr Thr Gly Ser
    690                 695                 700

Asn Cys Leu Lys Glu Tyr Val Ala Gly Arg Phe Gly Gln Asp Asp Ser
705                 710                 715                 720

Thr Gly Tyr Ala Ala Phe Ser Val Asn Asp Asn Tyr Gly Gln Asn Phe
                725                 730                 735

Ser Leu Ser Met Phe Val Arg Thr Arg Gln Pro Leu Gly Leu Leu Leu
            740                 745                 750

Ala Leu Glu Asn Ser Thr Tyr Gln Tyr Val Ser Val Trp Leu Glu His
        755                 760                 765

Gly Ser Leu Ala Leu Gln Thr Pro Gly Ser Pro Lys Phe Met Val Asn
    770                 775                 780

Phe Phe Leu Ser Asp Gly Asn Val His Leu Ile Ser Leu Arg Ile Lys
785                 790                 795                 800

Pro Asn Glu Ile Glu Leu Tyr Gln Ser Ser Gln Asn Leu Gly Phe Ile
                805                 810                 815

Ser Val Pro Thr Trp Thr Ile Arg Arg Gly Asp Val Ile Phe Ile Gly
            820                 825                 830

Gly Leu Pro Asp Arg Glu Lys Thr Glu Val Tyr Gly Gly Phe Phe Lys
        835                 840                 845

Gly Cys Val Gln Asp Val Arg Leu Asn Ser Gln Thr Leu Glu Phe Phe
    850                 855                 860

Pro Asn Ser Thr Asn Asn Ala Tyr Asp Asp Pro Ile Leu Val Asn Val
865                 870                 875                 880

Thr Gln Gly Cys Pro Gly Asp Asn Thr Cys Lys Ser Asn Pro Cys His
                885                 890                 895

Asn Gly Gly Val Cys His Ser Leu Trp Asp Asp Phe Ser Cys Ser Cys
            900                 905                 910

Pro Thr Asn Thr Ala Gly Arg Ala Cys Glu Gln Val Gln Trp Cys Gln
        915                 920                 925

Leu Ser Pro Cys Pro Pro Thr Ala Glu Cys Gln Leu Leu Pro Gln Gly
    930                 935                 940

Phe Glu Cys Ile Ala Asn Ala Val Phe Ser Gly Leu Ser Arg Glu Ile
945                 950                 955                 960

Leu Phe Arg Ser Asn Gly Asn Ile Thr Arg Glu Leu Thr Asn Ile Thr
                965                 970                 975

Phe Ala Phe Arg Thr His Asp Thr Asn Val Met Ile Leu His Ala Glu
            980                 985                 990

Lys Glu Pro Glu Phe Leu Asn Ile  Ser Ile Gln Asp Ala  Arg Leu Phe
        995                 1000                 1005
```

```
Phe Gln  Leu Arg Ser Gly Asn  Ser Phe Tyr Thr Leu  His Leu Met
    1010                 1015                 1020

Gly Ser  Gln Leu Val Asn Asp  Gly Thr Trp His Gln  Val Thr Phe
    1025                 1030                 1035

Ser Met  Ile Asp Pro Val Ala  Gln Thr Ser Arg Trp  Gln Met Glu
    1040                 1045                 1050

Val Asn  Asp Gln Thr Pro Phe  Val Ile Ser Glu Val  Ala Thr Gly
    1055                 1060                 1065

Ser Leu  Asn Phe Leu Lys Asp  Asn Thr Asp Ile Tyr  Val Gly Asp
    1070                 1075                 1080

Gln Ser  Val Asp Asn Pro Lys  Gly Leu Gln Gly Cys  Leu Ser Thr
    1085                 1090                 1095

Ile Glu  Ile Gly Gly Ile Tyr  Leu Ser Tyr Phe Glu  Asn Leu His
    1100                 1105                 1110

Gly Phe  Pro Gly Lys Pro Gln  Glu Glu Gln Phe Leu  Lys Val Ser
    1115                 1120                 1125

Thr Asn  Met Val Leu Thr Gly  Cys Leu Pro Ser Asn  Ala Cys His
    1130                 1135                 1140

Ser Ser  Pro Cys Leu His Gly  Gly Asn Cys Glu Asp  Ser Tyr Ser
    1145                 1150                 1155

Ser Tyr  Arg Cys Ala Cys Leu  Ser Gly Trp Ser Gly  Thr His Cys
    1160                 1165                 1170

Glu Ile  Asn Ile Asp Glu Cys  Phe Ser Ser Pro Cys  Ile His Gly
    1175                 1180                 1185

Asn Cys  Ser Asp Gly Val Ala  Ala Tyr His Cys Arg  Cys Glu Pro
    1190                 1195                 1200

Gly Tyr  Thr Gly Val Asn Cys  Glu Val Asp Val Asp  Asn Cys Lys
    1205                 1210                 1215

Ser His  Gln Cys Ala Asn Gly  Ala Thr Cys Val Pro  Glu Ala His
    1220                 1225                 1230

Gly Tyr  Ser Cys Leu Cys Phe  Gly Asn Phe Thr Gly  Arg Phe Cys
    1235                 1240                 1245

Arg His  Ser Arg Leu Pro Ser  Thr Val Cys Gly Asn  Glu Lys Arg
    1250                 1255                 1260

Asn Phe  Thr Cys Tyr Asn Gly  Gly Ser Cys Ser Met  Phe Gln Glu
    1265                 1270                 1275

Asp Trp  Gln Cys Met Cys Trp  Pro Gly Phe Thr Gly  Glu Trp Cys
    1280                 1285                 1290

Glu Glu  Asp Ile Asn Glu Cys  Ala Ser Asp Pro Cys  Ile Asn Gly
    1295                 1300                 1305

Gly Leu  Cys Arg Asp Leu Val  Asn Arg Phe Leu Cys  Ile Cys Asp
    1310                 1315                 1320

Val Ala  Phe Ala Gly Glu Arg  Cys Glu Leu Asp Val  Ser Gly Leu
    1325                 1330                 1335

Ser Phe  Tyr Val Ser Leu Leu  Leu Trp Gln Asn Leu  Phe Gln Leu
    1340                 1345                 1350

Leu Ser  Tyr Leu Val Leu Arg  Met Asn Asp Glu Pro  Val Val Glu
    1355                 1360                 1365

Trp Gly  Ala Gln Glu Asn Tyr
    1370                 1375
```

<210> SEQ ID NO 73
<211> LENGTH: 5434
<212> TYPE: DNA

<213> ORGANISM: Mus musculus

<400> SEQUENCE: 73
tcactgtgaa gaagacgttg atgaatgttt actgcaccct tgcctaaatg gtggtacttg 60
tgagaacctg cctgggaatt atgcctgtca ctgtcccttt gatgacactt ctaggacatt 120
ttatggagga gaaaactgct cagaaattct cctgggctgc actcatcacc agtgtctgaa 180
caatggaaaa tgtatccctc atttccaaaa tggccagcat ggattcactt gccagtgtct 240
ttctggctat gcggggcccc tgtgtgaaac tgtcaccaca ctttcatttg ggagcaatgg 300
cttcctatgg gtcacaagtg gctcccatac aggcataggg ccagaatgta acatatcctt 360
gaggtttcac actgttcaac caaacgcact tctcctcatc cgaggcaaca aggacgtgtc 420
tatgaagctg gagttgctga atggttgtgt tcacttatca attgaagtct ggaatcagtt 480
aaaggtgctc ctgtctattt ctcacaacac cagtgatgga gaatggcatt tcgtggaggt 540
aacaatcgca gaaactctaa cccttgccct agttggcggc tcctgcaagg agaagtgcac 600
caccaagtct tctgttccag ttgagaatca tcaatcaata tgtgctttgc aggactcttt 660
tttgggtggc ttaccaatgg ggacagccaa caacagtgtg tctgtgctta acatctataa 720
tgtgccgtcc acaccttcct ttgtaggctg tctccaagac attagatttg atttgaatca 780
cattactctg gagaacgttt catctggcct gtcatcaaat gttaaagcag gctgcctggg 840
aaaggactgg tgtgaaagtc aaccctgtca aaacagagga cgctgcatca acttgtggca 900
gggttatcag tgtgaatgtg acaggcccta tacaggctcc aactgcctga aagagtatgt 960
agcgggaaga tttggccaag atgactccac aggatatgcg gcctttagtg ttaatgataa 1020
ttatggacag aacttcagtc tttcaatgtt tgtccgaaca cgtcaacccc tgggcttact 1080
tctggctttg gaaaatagta cttaccagta tgtcagtgtc tggctagagc acggcagcct 1140
agcactgcag actccaggct ctcccaagtt catggtaaac tttttctca gtgatggaaa 1200
tgttcactta atatctttga gaatcaaacc aaatgaaatt gaactgtatc agtcttcaca 1260
aaacctagga ttcatttctg ttcctacatg gacaattcga agaggagacg tcatcttcat 1320
tggtggctta cctgacagag agaagactga agtttatggt ggcttcttca aaggctgtgt 1380
tcaagatgtc agattaaaca gccagactct ggaattcttt cccaattcaa caaacaatgc 1440
atacgatgac ccaattcttg tcaatgtgac tcaaggctgt cccggagaca acacatgtaa 1500
gtccaacccc tgtcataatg gaggtgtctg ccactccctg tgggatgact tctcctgctc 1560
ctgccctaca aacacagcgg ggagagcctg cgagcaagtt cagtggtgtc aactcagccc 1620
atgtcctccc actgcagagt gccagctgct ccctcaaggg tttgaatgta tcgcaaacgc 1680
tgttttcagc ggattaagca gagaaatact cttcagaagc aatgggaaca ttaccagaga 1740
actcaccaat atcacatttg ctttcagaac acatgataca aatgtgatga tattgcatgc 1800
agaaaaagaa ccagagtttc ttaatattag cattcaagat gccagattat tctttcaatt 1860
gcgaagtggc aacagctttt atacgctgca cctgatgggt tcccaattgg tgaatgatgg 1920
cacatggcac caagtgactt tctccatgat agacccagtg gcccagacct cccggtggca 1980
aatggaggtg aacgaccaga caccctttgt gataagtgaa gttgctactg gaagcctgaa 2040
ctttttgaag gacaatacag acatctatgt gggtgaccaa tctgttgaca atccgaaagg 2100
cctgcagggc tgtctgagca caatagagat tggaggcata tatctttctt actttgaaaa 2160
tctacatggt ttccctggta agcctcagga agagcaattt ctcaaagttt ctacaaatat 2220
ggtacttact ggctgtttgc catcaaatgc ctgccactcc agcccctgtt tgcatggagg 2280
aaactgtgaa gacagctaca gttcttatcg gtgtgcctgt ctctcgggat ggtcagggac 2340
acactgtgaa atcaacattg atgagtgctt ttctagcccc tgtatccatg gcaactgctc 2400
tgatggagtt gcagcctacc actgcaggtg tgagcctgga tacaccggtg tgaactgtga 2460
ggtggatgta gacaattgca agagtcatca gtgtgcaaat ggggccacct gtgttcctga 2520
agctcatggc tactcttgtc tctgctttgg aaattttacc gggagatttt gcagacacag 2580
cagattaccc tcaacagtct gtgggaatga gaagagaaac ttcacttgct acaatggagg 2640
cagctgctcc atgttccagg aggactggca atgtatgtgc tggccaggtt tcactggaga 2700
gtggtgtgaa gaggacatca acgagtgtgc ctccgatccc tgcatcaatg gaggactgtg 2760
cagggacttg gtcaacaggt tcctatgcat ctgtgatgtg gccttcgctg gcgagcgctg 2820
tgagctggac gtaagcggcc tttcctttta tgtgtccctc ttactatggc aaaacctctt 2880
tcagctcctg tcctacctcg tactgcgcat gaatgatgag ccagttgtag agtgggggc 2940 acaggaaaat tattaatgtg catgggagca ttcacaagtg taaaacattg acttgcaaga 3000
aacatcttgt ctcagtgtag gtttctagga aagacaaagg gaacattagg gaatagactc 3060
catctagagc actggttctc agtcttccta atgctgcaac cctttagtac agctcttcct 3120
gttgtagtga tcgcagccat aacattattt tcattgccac ttcataactg taatccttct 3180
actgctgtga atcacaatgg aaatatttat gttttctgat ggtcttaagc aacacctctg 3240
aaaaagtcat tgacccccc cccaaagggg ctgtgatcca caggttgaga aatgctcatc 3300
tggaaggtaa ccatgcattt aagtgtacct ctagtagttt gggtctatag aagatattct 3360
cctattctac ctttttagac acgccagaag agggcatctg attccattaa agatgattgg 3420
gagccaccgt gtggttcctg agaactgtac tcgggccctt tggaagagca atcagtgctc 3480
tttccagccc ctaagaatat ttttaataca gccagaaagg tctcattacc cagtgtactg 3540
agccctaagg cactttcatc ctcaatcgtt ccatgttgaa tggttttcat tacatttgga 3600 aaatgtttc tctccactct acctttacat gttcctattt tcctattgac aatttgcccc 3660
ttcactgtaa ttctaatttg gtgtggtcct tcttctcata agtttatatg tgacatgaac 3720
atttaaaaat atctatgaat attttatagt catgtatgtc tttctgcaaa gctattcaaa 3780
tgaactatgg acagttcttt tctacacgaa gaagagatga gtttaatccc cagtaacatg 3840
agaaaaagat gagtgaggga cagtgctcac agtatccctc actagcatca tttgtgattc 3900
catgggccat ttttttccac cagcaaatag cagagagccc tttccctatt cgtttctctt 3960
acacttcccc ttttctgtta caactgaaca ctttacatta gttactcctt tgtagggggt 4020
ttgacttttc caccgttttc tctggttcac tatttatgct aagtatctgt gcagggcggg 4080
tatatcagtc caacagaggt gtcattagtg ttcattgagg aggaaatact ttgcatgaat 4140
tcatgacatc attgaagtag cagtggccag aaagataccc ttctgcgaat gtgtctgtgt 4200
attcagaagc tgccctggtt agaaaacatg tgggtcactt ttcctttgca tgttaccagt 4260
gctcactggg tcatgattgt tttaagacag agcttttgct gtggcaatga ccaaggtgaa 4320
tccagagatg cagatcagac aaaggacaag acaatgtact atctgagtaa aaccctgcct 4380
tgacttactc ctcagtactt agagatttta catagcaacc tccaccctgt ggcaacccgt 4440
tcacactagc agtgatgctg agatttgccc ttccttctca tcatcttcct cacatccaaa 4500
gcattttgtg tccacactgc tgtttcagat aactgtttct aaagtgggat tgttgtagcc 4560
agaaaggtag ggaaaatgtt ccccaaaata tttgcattct taagtatgtg aagtaagtag 4620

```
attatagtca gagacaatat gtaaggtttc aggttcactc ccttctacac atatcttcaa   4680

ctgtgtattt gcagaatatt ctgaatgtga catactccca acagaatata tttaaggagt   4740

atttatccac agtattgttc tctgtacagt tctagtgctt ctattgtcac tgcaattgtc   4800

aattgttttt ctgctttcca actgtcttat tatcatttaa tagcatcttg ctaaatgccc   4860

tctttctatt ctccttattt ctccatagtt catgtgtgtc tgtgtgacta aggattctcc   4920

tcatttttgc agaaaaataa aatcttttct tctttatgtc ctgcttgtca ttctctggtg   4980

acacatgtct ttgcttactt ggactgaggg ttgtacagta agtacagaag caggctcagt   5040

cacacagaca gagacacacc accaccagca gcagcagcac caccaccacc accaccacca   5100

ccagaaaaca gtatgagtac tcatctcttg attacatgtc atttcaagta agcaccatga   5160

caccgagggc caggttccat ggactttctc tgttaggcac gtgattcttt agctgacctt   5220

tgagaacaga ctccaacaac ctcacttatt tttactgttg acttatatca tctctgacaa   5280

cactggactt cgtttgagct agtcaagagg aaagaccatg acacctaagg gacagaaatt   5340

cacacactcg gtttttcata attcacacac attcctatgt atcaaatctc tgtaatagat   5400

gacatttact tgaataaaaa gtcatttccc tttg                               5434
```

<210> SEQ ID NO 74
<211> LENGTH: 844
<212> TYPE: PRT
<213> ORGANISM: Mus musculus

<400> SEQUENCE: 74

```
Met Lys Leu Glu Leu Leu Asn Gly Cys Val His Leu Ser Ile Glu Val
1               5                   10                  15

Trp Asn Gln Leu Lys Val Leu Leu Ser Ile Ser His Asn Thr Ser Asp
            20                  25                  30

Gly Glu Trp His Phe Val Glu Val Thr Ile Ala Glu Thr Leu Thr Leu
        35                  40                  45

Ala Leu Val Gly Gly Ser Cys Lys Glu Lys Cys Thr Thr Lys Ser Ser
    50                  55                  60

Val Pro Val Glu Asn His Gln Ser Ile Cys Ala Leu Gln Asp Ser Phe
65                  70                  75                  80

Leu Gly Gly Leu Pro Met Gly Thr Ala Asn Asn Ser Val Ser Val Leu
                85                  90                  95

Asn Ile Tyr Asn Val Pro Ser Thr Pro Ser Phe Val Gly Cys Leu Gln
            100                 105                 110

Asp Ile Arg Phe Asp Leu Asn His Ile Thr Leu Glu Asn Val Ser Ser
        115                 120                 125

Gly Leu Ser Ser Asn Val Lys Ala Gly Cys Leu Gly Lys Asp Trp Cys
    130                 135                 140

Glu Ser Gln Pro Cys Gln Asn Arg Gly Arg Cys Ile Asn Leu Trp Gln
145                 150                 155                 160

Gly Tyr Gln Cys Glu Cys Asp Arg Pro Tyr Thr Gly Ser Asn Cys Leu
                165                 170                 175

Lys Glu Tyr Val Ala Gly Arg Phe Gly Gln Asp Asp Ser Thr Gly Tyr
            180                 185                 190

Ala Ala Phe Ser Val Asn Asp Asn Tyr Gly Gln Asn Phe Ser Leu Ser
        195                 200                 205

Met Phe Val Arg Thr Arg Gln Pro Leu Gly Leu Leu Leu Ala Leu Glu
    210                 215                 220

Asn Ser Thr Tyr Gln Tyr Val Ser Val Trp Leu Glu His Gly Ser Leu
```

-continued

```
225                 230                 235                 240

Ala Leu Gln Thr Pro Gly Ser Pro Lys Phe Met Val Asn Phe Phe Leu
                245                 250                 255

Ser Asp Gly Asn Val His Leu Ile Ser Leu Arg Ile Lys Pro Asn Glu
            260                 265                 270

Ile Glu Leu Tyr Gln Ser Ser Gln Asn Leu Gly Phe Ile Ser Val Pro
        275                 280                 285

Thr Trp Thr Ile Arg Arg Gly Asp Val Ile Phe Ile Gly Gly Leu Pro
    290                 295                 300

Asp Arg Glu Lys Thr Glu Val Tyr Gly Gly Phe Phe Lys Gly Cys Val
305                 310                 315                 320

Gln Asp Val Arg Leu Asn Ser Gln Thr Leu Glu Phe Phe Pro Asn Ser
                325                 330                 335

Thr Asn Asn Ala Tyr Asp Asp Pro Ile Leu Val Asn Val Thr Gln Gly
            340                 345                 350

Cys Pro Gly Asp Asn Thr Cys Lys Ser Asn Pro Cys His Asn Gly Gly
        355                 360                 365

Val Cys His Ser Leu Trp Asp Asp Phe Ser Cys Ser Cys Pro Thr Asn
    370                 375                 380

Thr Ala Gly Arg Ala Cys Glu Gln Val Gln Trp Cys Gln Leu Ser Pro
385                 390                 395                 400

Cys Pro Pro Thr Ala Glu Cys Gln Leu Leu Pro Gln Gly Phe Glu Cys
                405                 410                 415

Ile Ala Asn Ala Val Phe Ser Gly Leu Ser Arg Glu Ile Leu Phe Arg
            420                 425                 430

Ser Asn Gly Asn Ile Thr Arg Glu Leu Thr Asn Ile Thr Phe Ala Phe
        435                 440                 445

Arg Thr His Asp Thr Asn Val Met Ile Leu His Ala Glu Lys Glu Pro
    450                 455                 460

Glu Phe Leu Asn Ile Ser Ile Gln Asp Ala Arg Leu Phe Phe Gln Leu
465                 470                 475                 480

Arg Ser Gly Asn Ser Phe Tyr Thr Leu His Leu Met Gly Ser Gln Leu
                485                 490                 495

Val Asn Asp Gly Thr Trp His Gln Val Thr Phe Ser Met Ile Asp Pro
            500                 505                 510

Val Ala Gln Thr Ser Arg Trp Gln Met Glu Val Asn Asp Gln Thr Pro
        515                 520                 525

Phe Val Ile Ser Glu Val Ala Thr Gly Ser Leu Asn Phe Leu Lys Asp
    530                 535                 540

Asn Thr Asp Ile Tyr Val Gly Asp Gln Ser Val Asp Asn Pro Lys Gly
545                 550                 555                 560

Leu Gln Gly Cys Leu Ser Thr Ile Glu Ile Gly Gly Ile Tyr Leu Ser
                565                 570                 575

Tyr Phe Glu Asn Leu His Gly Phe Pro Gly Lys Pro Gln Glu Glu Gln
            580                 585                 590

Phe Leu Lys Val Ser Thr Asn Met Val Leu Thr Gly Cys Leu Pro Ser
        595                 600                 605

Asn Ala Cys His Ser Ser Pro Cys Leu His Gly Gly Asn Cys Glu Asp
    610                 615                 620

Ser Tyr Ser Ser Tyr Arg Cys Ala Cys Leu Ser Gly Trp Ser Gly Thr
625                 630                 635                 640

His Cys Glu Ile Asn Ile Asp Glu Cys Phe Ser Ser Pro Cys Ile His
                645                 650                 655
```

```
Gly Asn Cys Ser Asp Gly Val Ala Ala Tyr His Cys Arg Cys Glu Pro
            660                 665                 670

Gly Tyr Thr Gly Val Asn Cys Glu Val Asp Val Asp Asn Cys Lys Ser
        675                 680                 685

His Gln Cys Ala Asn Gly Ala Thr Cys Val Pro Glu Ala His Gly Tyr
    690                 695                 700

Ser Cys Leu Cys Phe Gly Asn Phe Thr Gly Arg Phe Cys Arg His Ser
705                 710                 715                 720

Arg Leu Pro Ser Thr Val Cys Gly Asn Glu Lys Arg Asn Phe Thr Cys
                725                 730                 735

Tyr Asn Gly Gly Ser Cys Ser Met Phe Gln Glu Asp Trp Gln Cys Met
            740                 745                 750

Cys Trp Pro Gly Phe Thr Gly Glu Trp Cys Glu Glu Asp Ile Asn Glu
        755                 760                 765

Cys Ala Ser Asp Pro Cys Ile Asn Gly Gly Leu Cys Arg Asp Leu Val
    770                 775                 780

Asn Arg Phe Leu Cys Ile Cys Asp Val Ala Phe Ala Gly Glu Arg Cys
785                 790                 795                 800

Glu Leu Asp Val Ser Gly Leu Ser Phe Tyr Val Ser Leu Leu Leu Trp
                805                 810                 815

Gln Asn Leu Phe Gln Leu Leu Ser Tyr Leu Val Leu Arg Met Asn Asp
            820                 825                 830

Glu Pro Val Val Glu Trp Gly Ala Gln Glu Asn Tyr
        835                 840
```

<210> SEQ ID NO 75
<211> LENGTH: 5678
<212> TYPE: DNA
<213> ORGANISM: Mus musculus

<400> SEQUENCE: 75

```
acgaatccaa tccaggctgg aaaaatctgc tccaggattg actggttacc gtcttcctgt     60

gcctgtaagg tgctgtgaaa gagaagtgct ttctgattct ctgtctgtgg aggagccctg    120

ggaggggtgg gacagagatg gcatcctggc tctctgaggc acctgctctt ctctgaacca    180

cacaggagtc aagagccaaa cagggatagc ttcagcagca cttcagaggg tgttctctaa    240

gtaagaacat gaagctcaag agaactgcct accttctctt cctgtacctc agctcctcac    300

tgctcatctg cataaagaat tcattttgca ataaaaacaa taccaggtgc ctttcaggtc    360

cttgccaaaa caattctacg tgcaagcatt ttccacaaga caacaattgt tgcttagaca    420

cagccaataa tttggacaaa gactgtgaag atctgaaaga cccttgcttc tcgagtccct    480

gccaaggaat tgccacttgt gtgaaaatcc caggggaagg gaacttcctg tgtcagtgtc    540

ctcctgggta cagcgggctg aactgtgaaa ctgccaccaa ttcctgtgga gggaacctct    600

gccaacatgg aggcacctgc cgtaaagacc ctgagcaccc tgtctgtatc tgccctcctg    660

gatatgctgg aaggttctgt gagactgatc acaatgagtg tgcttctagc ccttgccaca    720

atggggctat gtgccaggat ggaatcaatg gctactcctg cttctgtgtg cctggatacc    780

aaggcaggca ttgtgacttg gaagtggatg aatgtgtttc tgatccctgc aagaatgagg    840

ctgtgtgcct caatgagata ggaagataca cttgtgtctg ccctcaagag ttttctggcg    900

tgaactgtga gttggaaatt gatgaatgca gatcccagcc ttgtctccac ggtgccacat    960

gtcaggacgc tccagggggc tactcctgtg actgtgcacc tggattcctt ggagagcact   1020
```

-continued

```
gtgaactcag cgttaatgaa tgtgaaagtc agccgtgtct ccatggaggt ctatgtgtgg   1080
atggaagaaa caggaattca ctgtgaagaa gacgttgatg aatgtttact gcacccttgc   1140
ctaaatggtg gtacttgtga gaacctgcct gggaattatg cctgtcactg tccctttgat   1200
gacacttcta ggacatttta tggaggagaa aactgctcag aaattctcct gggctgcact   1260
catcaccagt gtctgaacaa tggaaaatgt atccctcatt tccaaaatgg ccagcatgga   1320
ttcacttgcc agtgtctttc tggctatgcg ggcccctgt gtgaaactgt caccacactt   1380
tcatttggga gcaatggctt cctatgggtc acaagtggct cccatacagg catagggcca   1440
gaatgtaaca tatccttgag gtttcacact gttcaaccaa acgcacttct cctcatccga   1500
ggcaacaagg acgtgtctat gaagctggag ttgctgaatg gttgtgttca cttatcaatt   1560
gaagtctgga atcagttaaa ggtgctcctg tctatttctc acaacaccag tgatggagaa   1620
tggcatttcg tggaggtaac aatcgcagaa actctaaccc ttgccctagt tggcggctcc   1680
tgcaaggaga agtgcaccac caagtcttct gttccagttg agaatcatca atcaatatgt   1740
gctttgcagg actctttttt gggtggctta ccaatgggga cagccaacaa cagtgtgtct   1800
gtgcttaaca tctataatgt gccgtccaca ccttcctttg taggctgtct ccaagacatt   1860
agatttgatt tgaatcacat tactctggag aacgtttcat ctggcctgtc atcaaatgtt   1920
aaagcaggct gcctgggaaa ggactggtgt gaaagtcaac cctgtcaaaa cagaggacgc   1980
tgcatcaact tgtggcaggg ttatcagtgt gaatgtgaca ggccctatac aggctccaac   2040
tgcctgaaag agtatgtagc gggaagattt ggccaagatg actccacagg atatgcggcc   2100
tttagtgtta atgataatta tggacagaac ttcagtcttt caatgtttgt ccgaacacgt   2160
caacccctgg gcttacttct ggctttggaa aatagtactt accagtatgt cagtgtctgg   2220
ctagagcacg gcagcctagc actgcagact ccaggctctc ccaagttcat ggtaaacttt   2280
tttctcagtg atggaaatgt tcacttaata tctttgagaa tcaaaccaaa tgaaattgaa   2340
ctgtatcagt cttcacaaaa cctaggattc atttctgttc ctacatggac aattcgaaga   2400
ggagacgtca tcttcattgg tggcttacct gacagagaga agactgaagt ttatggtggc   2460
ttcttcaaag gctgtgttca agatgtcaga ttaaacagcc agactctgga attctttccc   2520
aattcaacaa acaatgcata cgatgaccca attcttgtca atgtgactca aggctgtccc   2580
ggagacaaca catgtaagtc caacccctgt cataatggag gtgtctgcca ctccctgtgg   2640
gatgacttct cctgctcctg ccctacaaac acagcgggga gagcctgcga gcaagttcag   2700
tggtgtcaac tcagcccatg tcctcccact gcagagtgcc agctgctccc tcaagggttt   2760
gaatgtatcg caaacgctgt tttcagcgga ttaagcagag aaatactctt cagaagcaat   2820
gggaacatta ccagagaact caccaatatc acatttgctt tcagaacaca tgatacaaat   2880
gtgatgatat tgcatgcaga aaaagaacca gagtttctta atattagcat tcaagatgcc   2940
agattattct ttcaattgcg aagtggcaac agcttttata cgctgcacct gatgggttcc   3000
caattggtga atgatggcac atggcaccaa gtgactttct ccatgataga cccagtggcc   3060
cagacctccc ggtggcaaat ggaggtgaac gaccagacac cctttgtgat aagtgaagtt   3120
gctactggaa gcctgaactt tttgaaggac aatacagaca tctatgtggg tgaccaatct   3180
gttgacaatc cgaaaggcct gcagggctgt ctgagcacaa tagagattgg aggcatatat   3240
ctttcttact ttgaaaatct acatggtttc cctggtaagc ctcaggaaga gcaatttctc   3300
aaagtttcta caaatatggt acttactggc tgtttgccat caaatgcctg ccactccagc   3360
ccctgtttgc atggaggaaa ctgtgaagac agctacagtt cttatcggtg tgcctgtctc   3420
```

```
tcgggatggt cagggacaca ctgtgaaatc aacattgatg agtgcttttc tagcccctgt   3480
atccatggca actgctctga tggagttgca gcctaccact gcaggtgtga gcctggatac   3540
accggtgtga actgtgaggt ggatgtagac aattgcaaga gtcatcagtg tgcaaatggg   3600
gccacctgtg ttcctgaagc tcatggctac tcttgtctct gctttggaaa ttttaccggg   3660
agattttgca gacacagcag attaccctca acagtctgtg ggaatgagaa gagaaacttc   3720
acttgctaca atggaggcag ctgctccatg ttccaggagg actggcaatg tatgtgctgg   3780
ccaggtttca ctggagagtg gtgtgaagag gacatcaacg agtgtgcctc cgatccctgc   3840
atcaatggag gactgtgcag ggacttggtc aacaggttcc tatgcatctg tgatgtggcc   3900
ttcgctggcg agcgctgtga gctggacctg gctgatgaca ggctcctggg cattttcacc   3960
gctgttggct ccggaacttt ggccctgttc ttcatcctct tgcttgctgg ggttgcttct   4020
cttattgcct ccaacaaaag ggcgactcaa ggaacctaca gccccagcgg tcaggagaag   4080
gctggccctc gagtggaaat gtggatcagg atgccgcccc cggcactgga aaggctcatc   4140
taggagactg ctgctcttct caggacagag aagaacatga tgagtaccgg gtcgtgcctg   4200
agtgaagatg gctttacatc actagagata catacagctg ggactgtggg aaggaccttc   4260
ctgtggagtc actgagtagt tatgtcatcc attcacagaa gagtgtccct gtgtttgcct   4320
gtcagcctca gaattagcaa aacatctagc agacagagaa cacagtattt cagaagaact   4380
ccagaggctg ccccttaaac tctttactgg ttgatccaca taaaatgctt agtagccaag   4440
tgccattaat tatacagagc caagaagaaa aattagaata caactttcac tttttatttt   4500
gtagggaagg ttttatgttt tggtttgttg ttgttgttgt gacagtgaca gtgactcatt   4560
acatagacca agctggcctc aaaatcacat ggaccctcgg gattacatgt gtccgaccat   4620
gttcatctta tttttgaatc ttctgtcata tggtaaaaga ttccagtggg acctgaggag   4680
tgactagcta ggtaaagcaa gggctgtgta agtgccagaa ctggtgtttg tgtcctcatt   4740
atccacataa gtgccaagtg agtgtggccc ctgcctgtca tcctaggcct caggagatat   4800
cactgctcac tggagcaagc cggttaaact gttagggcag gtaagttttg acttcaagtg   4860
agagaccctg actcaatatg aaaggcaatt agtgagtcaa gatgaccctg tatgctaacc   4920
tcttgcctat acatgcatat acacacattt acatatgtgc ccaaacatga ggacacaagc   4980
acacgcgcgc gcgcacacac acacacacac acacacacac acacacacac acacacacac   5040
gagtctaatt gtatatagtg ataacagtac actttcctcc ttctatttcg gatttagaga   5100
aagccatgag aagcgtgtat ggtttaaacc atgacccaag cataacaaat aaagttgaaa   5160
tagttgttct cctgtccaag cttgtcttta ttgttgtgca ttctgtaagc tggttgcttg   5220
gttggctgat ggatggcttc tgtttgtttg ttgtttttttg tttgtttgtt tgtctgggat   5280
attacatgta agaaaaataa ctggtaagaa caatcaaaga actttgttat gaattaaatc   5340
ttttgtctaa gtcacttaga gtcattattc tttatgtaga tttgcttcca gtcaggacat   5400
ttcctagaca gaatttaaga cagtaagaaa atgatttgtc acgtctgaaa gaggttcttt   5460
actttcaggg acttttgata atgcccaaca gagatggcat cgaaagagga gctcatagcg   5520
agatgggcat ttgtgcatcc tcaaggagaa aatattgtac cttctgtttg tatattgtct   5580
attctgtgat ggctgtatct tacatatgtt ttgatgcatg taacaatagt atcatatgaa   5640
ataaattata tatatatata atatataata tatatcac                           5678
```

<210> SEQ ID NO 76

<211> LENGTH: 874
<212> TYPE: PRT
<213> ORGANISM: Mus musculus

<400> SEQUENCE: 76

Met Lys Leu Glu Leu Leu Asn Gly Cys Val His Leu Ser Ile Glu Val
1               5                   10                  15

Trp Asn Gln Leu Lys Val Leu Leu Ser Ile Ser His Asn Thr Ser Asp
            20                  25                  30

Gly Glu Trp His Phe Val Glu Val Thr Ile Ala Glu Thr Leu Thr Leu
        35                  40                  45

Ala Leu Val Gly Gly Ser Cys Lys Glu Lys Cys Thr Thr Lys Ser Ser
    50                  55                  60

Val Pro Val Glu Asn His Gln Ser Ile Cys Ala Leu Gln Asp Ser Phe
65                  70                  75                  80

Leu Gly Gly Leu Pro Met Gly Thr Ala Asn Asn Ser Val Ser Val Leu
                85                  90                  95

Asn Ile Tyr Asn Val Pro Ser Thr Pro Ser Phe Val Gly Cys Leu Gln
            100                 105                 110

Asp Ile Arg Phe Asp Leu Asn His Ile Thr Leu Glu Asn Val Ser Ser
        115                 120                 125

Gly Leu Ser Ser Asn Val Lys Ala Gly Cys Leu Gly Lys Asp Trp Cys
    130                 135                 140

Glu Ser Gln Pro Cys Gln Asn Arg Gly Arg Cys Ile Asn Leu Trp Gln
145                 150                 155                 160

Gly Tyr Gln Cys Glu Cys Asp Arg Pro Tyr Thr Gly Ser Asn Cys Leu
                165                 170                 175

Lys Glu Tyr Val Ala Gly Arg Phe Gly Gln Asp Asp Ser Thr Gly Tyr
            180                 185                 190

Ala Ala Phe Ser Val Asn Asp Asn Tyr Gly Gln Asn Phe Ser Leu Ser
        195                 200                 205

Met Phe Val Arg Thr Arg Gln Pro Leu Gly Leu Leu Leu Ala Leu Glu
    210                 215                 220

Asn Ser Thr Tyr Gln Tyr Val Ser Val Trp Leu Glu His Gly Ser Leu
225                 230                 235                 240

Ala Leu Gln Thr Pro Gly Ser Pro Lys Phe Met Val Asn Phe Phe Leu
                245                 250                 255

Ser Asp Gly Asn Val His Leu Ile Ser Leu Arg Ile Lys Pro Asn Glu
            260                 265                 270

Ile Glu Leu Tyr Gln Ser Ser Gln Asn Leu Gly Phe Ile Ser Val Pro
        275                 280                 285

Thr Trp Thr Ile Arg Arg Gly Asp Val Ile Phe Ile Gly Gly Leu Pro
    290                 295                 300

Asp Arg Glu Lys Thr Glu Val Tyr Gly Gly Phe Phe Lys Gly Cys Val
305                 310                 315                 320

Gln Asp Val Arg Leu Asn Ser Gln Thr Leu Glu Phe Phe Pro Asn Ser
                325                 330                 335

Thr Asn Asn Ala Tyr Asp Asp Pro Ile Leu Val Asn Val Thr Gln Gly
            340                 345                 350

Cys Pro Gly Asp Asn Thr Cys Lys Ser Asn Pro Cys His Asn Gly Gly
        355                 360                 365

Val Cys His Ser Leu Trp Asp Asp Phe Ser Cys Ser Cys Pro Thr Asn
    370                 375                 380

Thr Ala Gly Arg Ala Cys Glu Gln Val Gln Trp Cys Gln Leu Ser Pro

```
385                 390                 395                 400

Cys Pro Pro Thr Ala Glu Cys Gln Leu Leu Pro Gln Gly Phe Glu Cys
                405                 410                 415

Ile Ala Asn Ala Val Phe Ser Gly Leu Ser Arg Glu Ile Leu Phe Arg
            420                 425                 430

Ser Asn Gly Asn Ile Thr Arg Glu Leu Thr Asn Ile Thr Phe Ala Phe
        435                 440                 445

Arg Thr His Asp Thr Asn Val Met Ile Leu His Ala Glu Lys Glu Pro
    450                 455                 460

Glu Phe Leu Asn Ile Ser Ile Gln Asp Ala Arg Leu Phe Phe Gln Leu
465                 470                 475                 480

Arg Ser Gly Asn Ser Phe Tyr Thr Leu His Leu Met Gly Ser Gln Leu
                485                 490                 495

Val Asn Asp Gly Thr Trp His Gln Val Thr Phe Ser Met Ile Asp Pro
            500                 505                 510

Val Ala Gln Thr Ser Arg Trp Gln Met Glu Val Asn Asp Gln Thr Pro
        515                 520                 525

Phe Val Ile Ser Glu Val Ala Thr Gly Ser Leu Asn Phe Leu Lys Asp
    530                 535                 540

Asn Thr Asp Ile Tyr Val Gly Asp Gln Ser Val Asp Asn Pro Lys Gly
545                 550                 555                 560

Leu Gln Gly Cys Leu Ser Thr Ile Glu Ile Gly Gly Ile Tyr Leu Ser
                565                 570                 575

Tyr Phe Glu Asn Leu His Gly Phe Pro Gly Lys Pro Gln Glu Glu Gln
            580                 585                 590

Phe Leu Lys Val Ser Thr Asn Met Val Leu Thr Gly Cys Leu Pro Ser
        595                 600                 605

Asn Ala Cys His Ser Ser Pro Cys Leu His Gly Gly Asn Cys Glu Asp
    610                 615                 620

Ser Tyr Ser Ser Tyr Arg Cys Ala Cys Leu Ser Gly Trp Ser Gly Thr
625                 630                 635                 640

His Cys Glu Ile Asn Ile Asp Glu Cys Phe Ser Ser Pro Cys Ile His
                645                 650                 655

Gly Asn Cys Ser Asp Gly Val Ala Ala Tyr His Cys Arg Cys Glu Pro
            660                 665                 670

Gly Tyr Thr Gly Val Asn Cys Glu Val Asp Val Asp Asn Cys Lys Ser
        675                 680                 685

His Gln Cys Ala Asn Gly Ala Thr Cys Val Pro Glu Ala His Gly Tyr
    690                 695                 700

Ser Cys Leu Cys Phe Gly Asn Phe Thr Gly Arg Phe Cys Arg His Ser
705                 710                 715                 720

Arg Leu Pro Ser Thr Val Cys Gly Asn Glu Lys Arg Asn Phe Thr Cys
                725                 730                 735

Tyr Asn Gly Gly Ser Cys Ser Met Phe Gln Glu Asp Trp Gln Cys Met
            740                 745                 750

Cys Trp Pro Gly Phe Thr Gly Glu Trp Cys Glu Glu Asp Ile Asn Glu
        755                 760                 765

Cys Ala Ser Asp Pro Cys Ile Asn Gly Gly Leu Cys Arg Asp Leu Val
    770                 775                 780

Asn Arg Phe Leu Cys Ile Cys Asp Val Ala Phe Ala Gly Glu Arg Cys
785                 790                 795                 800

Glu Leu Asp Leu Ala Asp Asp Arg Leu Leu Gly Ile Phe Thr Ala Val
                805                 810                 815
```

```
Gly Ser Gly Thr Leu Ala Leu Phe Phe Ile Leu Leu Leu Ala Gly Val
            820                 825                 830

Ala Ser Leu Ile Ala Ser Asn Lys Arg Ala Thr Gln Gly Thr Tyr Ser
        835                 840                 845

Pro Ser Gly Gln Glu Lys Ala Gly Pro Arg Val Glu Met Trp Ile Arg
    850                 855                 860

Met Pro Pro Pro Ala Leu Glu Arg Leu Ile
865                 870


<210> SEQ ID NO 77
<211> LENGTH: 5277
<212> TYPE: DNA
<213> ORGANISM: Mus musculus

<400> SEQUENCE: 77

gccccactga tccagcttga agaggagtga ggcaaagctg aaccctccca ctctccttga      60

caagtgcaag cccacacttt tggaaaaaag cacaaagacg tcagaaacgg ttcctgtcga     120

cctactaggc tttggatggc taagtgtttt tgctttgtat ggaaatatgt ttggacacaa     180

gacacaaggt tttcacattt taatggcagt gctcatagga attcactgtg aagaagacgt     240

tgatgaatgt ttactgcacc cttgcctaaa tggtggtact tgtgagaacc tgcctgggaa     300

ttatgcctgt cactgtccct ttgatgacac ttctaggaca ttttatggag gagaaaactg     360

ctcagaaatt ctcctgggct gcactcatca ccagtgtctg aacaatggaa aatgtatccc     420

tcatttccaa aatggccagc atggattcac ttgccagtgt ctttctggct atgcggggcc     480

cctgtgtgaa actgtcacca cactttcatt tgggagcaat ggcttcctat gggtcacaag     540

tggctcccat acaggcatag ggccagaatg taacatatcc ttgaggtttc acactgttca     600

accaaacgca cttctcctca tccgaggcaa caaggacgtg tctatgaagc tggagttgct     660

gaatggttgt gttcacttat caattgaagt ctggaatcag ttaaaggtgc tcctgtctat     720

ttctcacaac accagtgatg gagaatggca tttcgtggag gtaacaatcg cagaaactct     780

aacccttgcc ctagttggcg gctcctgcaa ggagaagtgc accaccaagt cttctgttcc     840

agttgagaat catcaatcaa tatgtgcttt gcaggactct tttttgggtg gcttaccaat     900

ggggacagcc aacaacagtg tgtctgtgct taacatctat aatgtgccgt ccacaccttc     960

ctttgtaggc tgtctccaag acattagatt tgatttgaat cacattactc tggagaacgt    1020

ttcatctggc ctgtcatcaa atgttaaagc aggctgcctg ggaaaggact ggtgtgaaag    1080

tcaaccctgt caaaacagag gacgctgcat caacttgtgg cagggttatc agtgtgaatg    1140

tgacaggccc tatacaggct ccaactgcct gaaagagtat gtagcgggaa gatttggcca    1200

agatgactcc acaggatatg cggcctttag tgttaatgat aattatggac agaacttcag    1260

tctttcaatg tttgtccgaa cacgtcaacc cctgggctta cttctggctt tggaaaatag    1320

tacttaccag tatgtcagtg tctggctaga gcacggcagc ctagcactgc agactccagg    1380

ctctcccaag ttcatggtaa actttttct cagtgatgga aatgttcact taatatcttt    1440

gagaatcaaa ccaaatgaaa ttgaactgta tcagtcttca caaaacctag gattcatttc    1500

tgttcctaca tggacaattc gaagaggaga cgtcatcttc attggtggct tacctgacag    1560

agagaagact gaagtttatg gtggcttctt caaaggctgt gttcaagatg tcagattaaa    1620

cagccagact ctggaattct ttcccaattc aacaaacaat gcatacgatg acccaattct    1680

tgtcaatgtg actcaaggct gtcccggaga caacacatgt aagctttaaa catgcgggat    1740
```

gattatctct ttatgagctt ttgaagaatg agaagaaaca tcactggcat gacttgaaca 1800
tctatgagcc ccaataatta cttccaaccc ctgtcataat ggaggtgtct gccactccct 1860
gtgggatgac ttctcctgct cctgccctac aaacacagcg gggagagcct gcgagcaagt 1920
tcagtggtgt caactcagcc catgtcctcc cactgcagag tgccagctgc tccctcaagg 1980
gtttgaatgt atcgcaaacg ctgttttcag cggattaagc agagaaatac tcttcagaag 2040
caatgggaac attaccagag aactcaccaa tatcacattt gctttcagaa cacatgatac 2100
aaatgtgatg atattgcatg cagaaaaaga accagagttt cttaatatta gcattcaaga 2160
tgccagatta ttctttcaat tgcgaagtgg caacagcttt tatacgctgc acctgatggg 2220
ttcccaattg gtgaatgatg gcacatggca ccaagtgact ttctccatga tagacccagt 2280
ggcccagacc tcccggtggc aaatggaggt gaacgaccag acaccctttg tgataagtga 2340
agttgctact ggaagcctga actttttgaa ggacaataca gacatctatg tgggtgacca 2400
atctgttgac aatccgaaag gcctgcaggg ctgtctgagc acaatagaga ttggaggcat 2460
atatctttct tactttgaaa atctacatgg tttccctggt aagcctcagg aagagcaatt 2520
tctcaaagtt tctacaaata tggtacttac tggctgtttg ccatcaaatg cctgccactc 2580
cagcccctgt ttgcatggag gaaactgtga agacagctac agttcttatc ggtgtgcctg 2640
tctctcggga tggtcaggga cacactgtga aatcaacatt gatgagtgct tttctagccc 2700
ctgtatccat ggcaactgct ctgatggagt tgcagcctac cactgcaggt gtgagcctgg 2760
atacaccggt gtgaactgtg aggtggatgt agacaattgc aagagtcatc agtgtgcaaa 2820
tggggccacc tgtgttcctg aagctcatgg ctactcttgt ctctgctttg gaaattttac 2880
cgggagattt tgcagacaca gcagattacc ctcaacagtc tgtgggaatg agaagagaaa 2940
cttcacttgc tacaatggag gcagctgctc catgttccag gaggactggc aatgtatgtg 3000
ctggccaggt ttcactggag agtggtgtga agaggacatc aacgagtgtg cctccgatcc 3060
ctgcatcaat ggaggactgt gcagggactt ggtcaacagg ttcctatgca tctgtgatgt 3120
ggccttcgct ggcgagcgct gtgagctgga cgtaagcggc ctttcctttt atgtgtccct 3180
cttactatgg caaaacctct ttcagctcct gtcctacctc gtactgcgca tgaatgatga 3240
gccagttgta gagtgggggg cacaggaaaa ttattaatgt gcatgggagc attcacaagt 3300
gtaaaacatt gacttgcaag aaacatcttg tctcagtgta ggtttctagg aaagacaaag 3360
ggaacattag ggaatagact ccatctagag cactggttct cagtcttcct aatgctgcaa 3420
ccctttagta cagctcttcc tgttgtagtg atcgcagcca taacattatt ttcattgcca 3480
cttcataact gtaatccttc tactgctgtg aatcacaatg gaaatattta tgttttctga 3540
tggtcttaag caacacctct gaaaaagtca ttgacccccc ccccaaaggg gctgtgatcc 3600
acaggttgag aaatgctcat ctggaaggta accatgcatt taagtgtacc tctagtagtt 3660
tgggtctata gaagatattc tcctattcta cctttttaga cacgccagaa gagggcatct 3720
gattccatta aagatgattg ggagccaccg tgtggttcct gagaactgta ctcgggccct 3780
ttggaagagc aatcagtgct ctttccagcc cctaagaata tttttaatac agccagaaag 3840
gtctcattac ccagtgtact gagccctaag gcactttcat cctcaatcgt tccatgttga 3900
atggttttca ttacatttgg aaaatgtttt ctctccactc tacctttaca tgttcctatt 3960
ttcctattga caatttgccc cttcactgta attctaattt ggtgtggtcc ttcttctcat 4020
aagtttatat gtgacatgaa catttaaaaa tatctatgaa tattttatag tcatgtatgt 4080
ctttctgcaa agctattcaa atgaactatg gacagttctt ttctacacga agaagagatg 4140
agtttaatcc ccagtaacat gagaaaaaga tgagtgaggg acagtgctca cagtatccct 4200
cactagcatc atttgtgatt ccatgggcca ttttttttcca ccagcaaata gcagagagcc 4260
ctttccctat tcgtttctct tacacttccc cttttctgtt acaactgaac actttacatt 4320
agttactcct ttgtaggggg tttgactttt ccaccgtttt ctctggttca ctatttatgc 4380
taagtatctg tgcagggcgg gtatatcagt ccaacagagg tgtcattagt gttcattgag 4440
gaggaaatac tttgcatgaa ttcatgacat cattgaagta gcagtggcca gaaagatacc 4500
cttctgcgaa tgtgtctgtg tattcagaag ctgccctggt tagaaaacat gtgggtcact 4560
tttcctttgc atgttaccag tgctcactgg gtcatgattg ttttaagaca gagcttttgc 4620
tgtggcaatg accaaggtga atccagagat gcagatcaga caaaggacaa gacaatgtac 4680
tatctgagta aaaccctgcc ttgacttact cctcagtact tagagatttt acatagcaac 4740
ctccaccctg tggcaacccg ttcacactag cagtgatgct gagatttgcc cttccttctc 4800
atcatcttcc tcacatccaa agcattttgt gtccacactg ctgtttcaga taactgtttc 4860
taaagtggga ttgttgtagc cagaaaggta gggaaaatgt tccccaaaat atttgcattc 4920
ttaagtatgt gaagtaagta gattatagtc agagacaata tgtaaggttt caggttcact 4980
cccttctaca catatcttca actgtgtatt tgcagaatat tctgaatgtg acatactccc 5040
aacagaatat atttaaggag tatttatcca cagtattgtt ctctgtacag ttctagtgct 5100
tctattgtca ctgcaattgt caattgtttt tctgctttcc aactgtctta ttatcattta 5160
atagcatctt gctaaatgcc ctctttctat tctccttatt tctccatagt tcatgtgtgt 5220
ctgtgtgact aaggattctc ctcatttttg cagaaaaata aaatcttttc ttcttta 5277

<210> SEQ ID NO 78
<211> LENGTH: 520
<212> TYPE: PRT
<213> ORGANISM: Mus musculus

<400> SEQUENCE: 78

Met Phe Gly His Lys Thr Gln Gly Phe His Ile Leu Met Ala Val Leu
1               5                   10                  15

Ile Gly Ile His Cys Glu Glu Asp Val Asp Glu Cys Leu Leu His Pro
            20                  25                  30

Cys Leu Asn Gly Gly Thr Cys Glu Asn Leu Pro Gly Asn Tyr Ala Cys
        35                  40                  45

His Cys Pro Phe Asp Asp Thr Ser Arg Thr Phe Tyr Gly Gly Glu Asn
    50                  55                  60

Cys Ser Glu Ile Leu Leu Gly Cys Thr His His Gln Cys Leu Asn Asn
65                  70                  75                  80

Gly Lys Cys Ile Pro His Phe Gln Asn Gly Gln His Gly Phe Thr Cys
                85                  90                  95

Gln Cys Leu Ser Gly Tyr Ala Gly Pro Leu Cys Glu Thr Val Thr Thr
            100                 105                 110

Leu Ser Phe Gly Ser Asn Gly Phe Leu Trp Val Thr Ser Gly Ser His
        115                 120                 125

Thr Gly Ile Gly Pro Glu Cys Asn Ile Ser Leu Arg Phe His Thr Val
    130                 135                 140

Gln Pro Asn Ala Leu Leu Leu Ile Arg Gly Asn Lys Asp Val Ser Met
145                 150                 155                 160

Lys Leu Glu Leu Leu Asn Gly Cys Val His Leu Ser Ile Glu Val Trp
                165                 170                 175

Asn Gln Leu Lys Val Leu Leu Ser Ile Ser His Asn Thr Ser Asp Gly
180 185 190

Glu Trp His Phe Val Glu Val Thr Ile Ala Glu Thr Leu Thr Leu Ala
195 200 205

Leu Val Gly Gly Ser Cys Lys Glu Lys Cys Thr Thr Lys Ser Ser Val
210 215 220

Pro Val Glu Asn His Gln Ser Ile Cys Ala Leu Gln Asp Ser Phe Leu
225 230 235 240

Gly Gly Leu Pro Met Gly Thr Ala Asn Asn Ser Val Ser Val Leu Asn
245 250 255

Ile Tyr Asn Val Pro Ser Thr Pro Ser Phe Val Gly Cys Leu Gln Asp
260 265 270

Ile Arg Phe Asp Leu Asn His Ile Thr Leu Glu Asn Val Ser Ser Gly
275 280 285

Leu Ser Ser Asn Val Lys Ala Gly Cys Leu Gly Lys Asp Trp Cys Glu
290 295 300

Ser Gln Pro Cys Gln Asn Arg Gly Arg Cys Ile Asn Leu Trp Gln Gly
305 310 315 320

Tyr Gln Cys Glu Cys Asp Arg Pro Tyr Thr Gly Ser Asn Cys Leu Lys
325 330 335

Glu Tyr Val Ala Gly Arg Phe Gly Gln Asp Asp Ser Thr Gly Tyr Ala
340 345 350

Ala Phe Ser Val Asn Asp Asn Tyr Gly Gln Asn Phe Ser Leu Ser Met
355 360 365

Phe Val Arg Thr Arg Gln Pro Leu Gly Leu Leu Leu Ala Leu Glu Asn
370 375 380

Ser Thr Tyr Gln Tyr Val Ser Val Trp Leu Glu His Gly Ser Leu Ala
385 390 395 400

Leu Gln Thr Pro Gly Ser Pro Lys Phe Met Val Asn Phe Phe Leu Ser
405 410 415

Asp Gly Asn Val His Leu Ile Ser Leu Arg Ile Lys Pro Asn Glu Ile
420 425 430

Glu Leu Tyr Gln Ser Ser Gln Asn Leu Gly Phe Ile Ser Val Pro Thr
435 440 445

Trp Thr Ile Arg Arg Gly Asp Val Ile Phe Ile Gly Gly Leu Pro Asp
450 455 460

Arg Glu Lys Thr Glu Val Tyr Gly Gly Phe Phe Lys Gly Cys Val Gln
465 470 475 480

Asp Val Arg Leu Asn Ser Gln Thr Leu Glu Phe Phe Pro Asn Ser Thr
485 490 495

Asn Asn Ala Tyr Asp Asp Pro Ile Leu Val Asn Val Thr Gln Gly Cys
500 505 510

Pro Gly Asp Asn Thr Cys Lys Leu
515 520

<210> SEQ ID NO 79
<211> LENGTH: 5530
<212> TYPE: DNA
<213> ORGANISM: Mus musculus

<400> SEQUENCE: 79
agccccactg atccagcttg aagaggagtg aggcaaagct gaaccctccc actctccttg 60
acaagtgcaa gcccacactt ttggaaaaaa gcacaaagac gtcagaaacg gttcctgtcg 120

```
acctactagg ctttggatgg ctaagtgttt ttgctttgta tggaaatatg tttggacaca    180
agacacaagg ttttcacatt ttaatggcag tgctcatagg aattcactgt gaagaagacg    240
ttgatgaatg tttactgcac ccttgcctaa atggtggtac ttgtgagaac ctgcctggga    300
attatgcctg tcactgtccc tttgatgaca cttctaggac attttatgga ggagaaaact    360
gctcagaaat tctcctgggc tgcactcatc accagtgtct gaacaatgga aaatgtatcc    420
ctcatttcca aaatggccag catggattca cttgccagtg tctttctggc tatgcggggc    480
ccctgtgtga aactgtcacc acactttcat ttgggagcaa tggcttccta tgggtcacaa    540
gtggctccca tacaggcata gggccagaat gtaacatatc cttgaggttt cacactgttc    600
aaccaaacgc acttctcctc atccgaggca acaaggacgt gtctatgaag ctggagttgc    660
tgaatggttg tgttcactta tcaattgaag tctggaatca gttaaaggtg ctcctgtcta    720
tttctcacaa caccagtgat ggagaatggc atttcgtgga ggtaacaatc gcagaaactc    780
taacccttgc cctagttggc ggctcctgca aggagaagtg caccaccaag tcttctgttc    840
cagttgagaa tcatcaatca atatgtgctt tgcaggactc tttttgggt ggcttaccaa     900
tggggacagc caacaacagt gtgtctgtgc ttaacatcta taatgtgccg tccacacctt    960
cctttgtagg ctgtctccaa gacattagat ttgatttgaa tcacattact ctggagaacg   1020
tttcatctgg cctgtcatca aatgttaaag caggctgcct gggaaaggac tggtgtgaaa   1080
gtcaaccctg tcaaaacaga ggacgctgca tcaacttgtg gcagggttat cagtgtgaat   1140
gtgacaggcc ctatacaggc tccaactgcc tgaaagagta tgtagcggga agatttggcc   1200
aagatgactc cacaggatat gcggccttta gtgttaatga taattatgga cagaacttca   1260
gtctttcaat gtttgtccga acacgtcaac ccctgggctt acttctggct ttggaaaata   1320
gtacttacca gtatgtcagt gtctggctag agcacggcag cctagcactg cagactccag   1380
gctctcccaa gttcatggta aacttttttc tcagtgatgg aaatgttcac ttaatatctt   1440
tgagaatcaa accaaatgaa attgaactgt atcagtcttc acaaaaccta ggattcattt   1500
ctgttcctac atggacaatt cgaagaggag acgtcatctt cattggtggc ttacctgaca   1560
gagagaagac tgaagtttat ggtggcttct tcaaaggctg tgttcaagat gtcagattaa   1620
acagccagac tctggaattc tttcccaatt caacaaacaa tgcatacgat gacccaattc   1680
ttgtcaatgt gactcaaggc tgtcccggag acaacacatg taagtccaac ccctgtcata   1740
atggaggtgt ctgccactcc ctgtgggatg acttctcctg ctcctgccct acaaacacag   1800
cggggagagc ctgcgagcaa gttcagtggt gtcaactcag cccatgtcct cccactgcag   1860
agtgccagct gctccctcaa gggtttgaat gtatcgcaaa cgctgttttc agcggattaa   1920
gcagagaaat actcttcaga agcaatggga acattaccag agaactcacc aatatcacat   1980
ttgctttcag aacacatgat acaaatgtga tgatattgca tgcagaaaaa gaaccagagt   2040
ttcttaatat tagcattcaa gatgccagat tattctttca attgcgaagt ggcaacagct   2100
tttatacgct gcacctgatg ggttcccaat tggtgaatga tggcacatgg caccaagtga   2160
ctttctccat gatagaccca gtggcccaga cctcccggtg gcaaatggag gtgaacgacc   2220
agacaccctt tgtgataagt gaagttgcta ctggaagcct gaactttttg aaggacaata   2280
cagacatcta tgtgggtgac caatctgttg acaatccgaa aggcctgcag ggctgtctga   2340
gcacaataga gattggaggc atatatcttt cttactttga aaatctacat ggtttccctg   2400
gtaagcctca ggaagagcaa tttctcaaag tttctacaaa tatggtactt actggctgtt   2460
tgccatcaaa tgcctgccac tccagcccct gtttgcatgg aggaaactgt gaagacagct   2520
```

acagttctta tcggtgtgcc tgtctctcgg gatggtcagg gacacactgt gaaatcaaca 2580
ttgatgagtg cttttctagc ccctgtatcc atggcaactg ctctgatgga gttgcagcct 2640
accactgcag gtgtgagcct ggatacaccg gtgtgaactg tgaggtggat gtagacaatt 2700
gcaagagtca tcagtgtgca aatggggcca cctgtgttcc tgaagctcat ggctactctt 2760
gtctctgctt tggaaatttt accgggagat tttgcaggtg tgaagaggac atcaacgagt 2820
gtgcctccga tccctgcatc aatggaggac tgtgcaggga cttggtcaac aggttcctat 2880
gcatctgtga tgtggccttc gctggcgagc gctgtgagct ggacgtaagc ggcctttcct 2940
tttatgtgtc cctcttacta tggcaaaacc tctttcagct cctgtcctac ctcgtactgc 3000
gcatgaatga tgagccagtt gtagagtggg gggcacagga aaattattaa tgtgcatggg 3060
agcattcaca agtgtaaaac attgacttgc aagaaacatc ttgtctcagt gtaggtttct 3120
aggaaagaca aagggaacat tagggaatag actccatcta gagcactggt tctcagtctt 3180
cctaatgctg caaccccttta gtacagctct tcctgttgta gtgatcgcag ccataacatt 3240
attttcattg ccacttcata actgtaatcc ttctactgct gtgaatcaca atggaaatat 3300
ttatgttttc tgatggtctt aagcaacacc tctgaaaaag tcattgaccc cccccccaaa 3360
ggggctgtga tccacaggtt gagaaatgct catctggaag gtaaccatgc atttaagtgt 3420
acctctagta gtttgggtct atagaagata ttctcctatt ctaccttttt agacacgcca 3480
gaagagggca tctgattcca ttaaagatga ttgggagcca ccgtgtggtt cctgagaact 3540
gtactcgggc cctttggaag agcaatcagt gctctttcca gcccctaaga atatttttaa 3600
tacagccaga aaggtctcat tacccagtgt actgagccct aaggcacttt catcctcaat 3660
cgttccatgt tgaatggttt tcattacatt tggaaaatgt tttctctcca ctctaccttt 3720
acatgttcct attttcctat tgacaatttg ccccttcact gtaattctaa tttggtgtgg 3780
tccttcttct cataagttta tatgtgacat gaacatttaa aaatatctat gaatatttta 3840
tagtcatgta tgtctttctg caaagctatt caaatgaact atggacagtt cttttctaca 3900
cgaagaagag atgagtttaa tccccagtaa catgagaaaa agatgagtga gggacagtgc 3960
tcacagtatc cctcactagc atcatttgtg attccatggg ccattttttt ccaccagcaa 4020
atagcagaga gccctttccc tattcgtttc tcttacactt ccccttttct gttacaactg 4080
aacactttac attagttact cctttgtagg gggtttgact tttccaccgt tttctctggt 4140
tcactattta tgctaagtat ctgtgcaggg cgggtatatc agtccaacag aggtgtcatt 4200
agtgttcatt gaggaggaaa tactttgcat gaattcatga catcattgaa gtagcagtgg 4260
ccagaaagat acccttctgc gaatgtgtct gtgtattcag aagctgccct ggttagaaaa 4320
catgtgggtc actttttcctt tgcatgttac cagtgctcac tgggtcatga ttgttttaag 4380
acagagcttt tgctgtggca atgaccaagg tgaatccaga gatgcagatc agacaaagga 4440
caagacaatg tactatctga gtaaaaccct gccttgactt actcctcagt acttagagat 4500
tttacatagc aacctccacc ctgtggcaac ccgttcacac tagcagtgat gctgagattt 4560
gcccttcctt ctcatcatct tcctcacatc caaagcattt tgtgtccaca ctgctgtttc 4620
agataactgt ttctaaagtg ggattgttgt agccagaaag gtagggaaaa tgttccccaa 4680
aatatttgca ttcttaagta tgtgaagtaa gtagattata gtcagagaca atatgtaagg 4740
tttcaggttc actcccttct acacatatct tcaactgtgt atttgcagaa tattctgaat 4800
gtgacatact cccaacagaa tatatttaag gagtatttat ccacagtatt gttctctgta 4860
cagttctagt gcttctattg tcactgcaat tgtcaattgt ttttctgctt tccaactgtc 4920
ttattatcat ttaatagcat cttgctaaat gccctctttc tattctcctt atttctccat 4980
agttcatgtg tgtctgtgtg actaaggatt ctcctcattt ttgcagaaaa ataaaatctt 5040
ttcttcttta tgtcctgctt gtcattctct ggtgacacat gtctttgctt acttggactg 5100
agggttgtac agtaagtaca gaagcaggct cagtcacaca gacagagaca caccaccacc 5160
agcagcagca gcaccaccac caccaccacc accaccagaa aacagtatga gtactcatct 5220
cttgattaca tgtcatttca agtaagcacc atgacaccga gggccaggtt ccatggactt 5280
tctctgttag gcacgtgatt ctttagctga cctttgagaa cagactccaa caacctcact 5340
tatttttact gttgacttat atcatctctg acaacactgg acttcgtttg agctagtcaa 5400
gaggaaagac catgacacct aagggacaga aattcacaca ctcggttttt cataattcac 5460
acacattcct atgtatcaaa tctctgtaat agatgacatt tacttgaata aaaagtcatt 5520
tccctttgct 5530

<210> SEQ ID NO 80
<211> LENGTH: 960
<212> TYPE: PRT
<213> ORGANISM: Mus musculus

<400> SEQUENCE: 80

Met Phe Gly His Lys Thr Gln Gly Phe His Ile Leu Met Ala Val Leu
1 5 10 15

Ile Gly Ile His Cys Glu Glu Asp Val Asp Glu Cys Leu Leu His Pro
20 25 30

Cys Leu Asn Gly Gly Thr Cys Glu Asn Leu Pro Gly Asn Tyr Ala Cys
35 40 45

His Cys Pro Phe Asp Asp Thr Ser Arg Thr Phe Tyr Gly Gly Glu Asn
50 55 60

Cys Ser Glu Ile Leu Leu Gly Cys Thr His His Gln Cys Leu Asn Asn
65 70 75 80

Gly Lys Cys Ile Pro His Phe Gln Asn Gly Gln His Gly Phe Thr Cys
85 90 95

Gln Cys Leu Ser Gly Tyr Ala Gly Pro Leu Cys Glu Thr Val Thr Thr
100 105 110

Leu Ser Phe Gly Ser Asn Gly Phe Leu Trp Val Thr Ser Gly Ser His
115 120 125

Thr Gly Ile Gly Pro Glu Cys Asn Ile Ser Leu Arg Phe His Thr Val
130 135 140

Gln Pro Asn Ala Leu Leu Leu Ile Arg Gly Asn Lys Asp Val Ser Met
145 150 155 160

Lys Leu Glu Leu Leu Asn Gly Cys Val His Leu Ser Ile Glu Val Trp
165 170 175

Asn Gln Leu Lys Val Leu Leu Ser Ile Ser His Asn Thr Ser Asp Gly
180 185 190

Glu Trp His Phe Val Glu Val Thr Ile Ala Glu Thr Leu Thr Leu Ala
195 200 205

Leu Val Gly Gly Ser Cys Lys Glu Lys Cys Thr Thr Lys Ser Ser Val
210 215 220

Pro Val Glu Asn His Gln Ser Ile Cys Ala Leu Gln Asp Ser Phe Leu
225 230 235 240

Gly Gly Leu Pro Met Gly Thr Ala Asn Asn Ser Val Ser Val Leu Asn
245 250 255

```
Ile Tyr Asn Val Pro Ser Thr Pro Ser Phe Val Gly Cys Leu Gln Asp
            260                 265                 270

Ile Arg Phe Asp Leu Asn His Ile Thr Leu Glu Asn Val Ser Ser Gly
        275                 280                 285

Leu Ser Ser Asn Val Lys Ala Gly Cys Leu Gly Lys Asp Trp Cys Glu
    290                 295                 300

Ser Gln Pro Cys Gln Asn Arg Gly Arg Cys Ile Asn Leu Trp Gln Gly
305                 310                 315                 320

Tyr Gln Cys Glu Cys Asp Arg Pro Tyr Thr Gly Ser Asn Cys Leu Lys
                325                 330                 335

Glu Tyr Val Ala Gly Arg Phe Gly Gln Asp Asp Ser Thr Gly Tyr Ala
            340                 345                 350

Ala Phe Ser Val Asn Asp Asn Tyr Gly Gln Asn Phe Ser Leu Ser Met
        355                 360                 365

Phe Val Arg Thr Arg Gln Pro Leu Gly Leu Leu Leu Ala Leu Glu Asn
    370                 375                 380

Ser Thr Tyr Gln Tyr Val Ser Val Trp Leu Glu His Gly Ser Leu Ala
385                 390                 395                 400

Leu Gln Thr Pro Gly Ser Pro Lys Phe Met Val Asn Phe Phe Leu Ser
                405                 410                 415

Asp Gly Asn Val His Leu Ile Ser Leu Arg Ile Lys Pro Asn Glu Ile
            420                 425                 430

Glu Leu Tyr Gln Ser Ser Gln Asn Leu Gly Phe Ile Ser Val Pro Thr
        435                 440                 445

Trp Thr Ile Arg Arg Gly Asp Val Ile Phe Ile Gly Gly Leu Pro Asp
    450                 455                 460

Arg Glu Lys Thr Glu Val Tyr Gly Gly Phe Phe Lys Gly Cys Val Gln
465                 470                 475                 480

Asp Val Arg Leu Asn Ser Gln Thr Leu Glu Phe Phe Pro Asn Ser Thr
                485                 490                 495

Asn Asn Ala Tyr Asp Asp Pro Ile Leu Val Asn Val Thr Gln Gly Cys
            500                 505                 510

Pro Gly Asp Asn Thr Cys Lys Ser Asn Pro Cys His Asn Gly Gly Val
        515                 520                 525

Cys His Ser Leu Trp Asp Asp Phe Ser Cys Ser Cys Pro Thr Asn Thr
    530                 535                 540

Ala Gly Arg Ala Cys Glu Gln Val Gln Trp Cys Gln Leu Ser Pro Cys
545                 550                 555                 560

Pro Pro Thr Ala Glu Cys Gln Leu Leu Pro Gln Gly Phe Glu Cys Ile
                565                 570                 575

Ala Asn Ala Val Phe Ser Gly Leu Ser Arg Glu Ile Leu Phe Arg Ser
            580                 585                 590

Asn Gly Asn Ile Thr Arg Glu Leu Thr Asn Ile Thr Phe Ala Phe Arg
        595                 600                 605

Thr His Asp Thr Asn Val Met Ile Leu His Ala Glu Lys Glu Pro Glu
    610                 615                 620

Phe Leu Asn Ile Ser Ile Gln Asp Ala Arg Leu Phe Phe Gln Leu Arg
625                 630                 635                 640

Ser Gly Asn Ser Phe Tyr Thr Leu His Leu Met Gly Ser Gln Leu Val
                645                 650                 655

Asn Asp Gly Thr Trp His Gln Val Thr Phe Ser Met Ile Asp Pro Val
            660                 665                 670
```

```
Ala Gln Thr Ser Arg Trp Gln Met Glu Val Asn Asp Gln Thr Pro Phe
        675                 680                 685

Val Ile Ser Glu Val Ala Thr Gly Ser Leu Asn Phe Leu Lys Asp Asn
    690                 695                 700

Thr Asp Ile Tyr Val Gly Asp Gln Ser Val Asp Asn Pro Lys Gly Leu
705                 710                 715                 720

Gln Gly Cys Leu Ser Thr Ile Glu Ile Gly Gly Ile Tyr Leu Ser Tyr
                725                 730                 735

Phe Glu Asn Leu His Gly Phe Pro Gly Lys Pro Gln Glu Glu Gln Phe
            740                 745                 750

Leu Lys Val Ser Thr Asn Met Val Leu Thr Gly Cys Leu Pro Ser Asn
        755                 760                 765

Ala Cys His Ser Ser Pro Cys Leu His Gly Gly Asn Cys Glu Asp Ser
    770                 775                 780

Tyr Ser Ser Tyr Arg Cys Ala Cys Leu Ser Gly Trp Ser Gly Thr His
785                 790                 795                 800

Cys Glu Ile Asn Ile Asp Glu Cys Phe Ser Ser Pro Cys Ile His Gly
                805                 810                 815

Asn Cys Ser Asp Gly Val Ala Ala Tyr His Cys Arg Cys Glu Pro Gly
            820                 825                 830

Tyr Thr Gly Val Asn Cys Glu Val Asp Val Asp Asn Cys Lys Ser His
        835                 840                 845

Gln Cys Ala Asn Gly Ala Thr Cys Val Pro Glu Ala His Gly Tyr Ser
    850                 855                 860

Cys Leu Cys Phe Gly Asn Phe Thr Gly Arg Phe Cys Arg Cys Glu Glu
865                 870                 875                 880

Asp Ile Asn Glu Cys Ala Ser Asp Pro Cys Ile Asn Gly Gly Leu Cys
                885                 890                 895

Arg Asp Leu Val Asn Arg Phe Leu Cys Ile Cys Asp Val Ala Phe Ala
            900                 905                 910

Gly Glu Arg Cys Glu Leu Asp Val Ser Gly Leu Ser Phe Tyr Val Ser
        915                 920                 925

Leu Leu Leu Trp Gln Asn Leu Phe Gln Leu Leu Ser Tyr Leu Val Leu
    930                 935                 940

Arg Met Asn Asp Glu Pro Val Val Glu Trp Gly Ala Gln Glu Asn Tyr
945                 950                 955                 960
```

<210> SEQ ID NO 81
<211> LENGTH: 5692
<212> TYPE: DNA
<213> ORGANISM: Mus musculus

<400> SEQUENCE: 81

```
attaagcccc actgatccag cttgaagagg agtgaggcaa agctgaaccc tcccactctc      60

cttgacaagt gcaagcccac acttttggaa aaaagcacaa agacgtcaga aacggttcct     120

gtcgacctac taggctttgg atggctaagt gtttttgctt tgtatggaaa tatgtttgga     180

cacaagacac aaggttttca cattttaatg gcagtgctca taggaattca ctgtgaagaa     240

gacgttgatg aatgtttact gcacccttgc ctaaatggtg gtacttgtga gaacctgcct     300

gggaattatg cctgtcactg tccctttgat gacacttcta ggacatttta tggaggagaa     360

aactgctcag aaattctcct gggctgcact catcaccagt gtctgaacaa tggaaaatgt     420

atccctcatt tccaaaatgg ccagcatgga ttcacttgcc agtgtctttc tggctatgcg     480

gggcccctgt gtgaaactgt caccacactt tcatttggga gcaatggctt cctatgggtc     540
```

acaagtggct cccatacagg catagggcca gaatgtaaca tatccttgag gtttcacact 600
gttcaaccaa acgcacttct cctcatccga ggcaacaagg acgtgtctat gaagctggag 660
ttgctgaatg gttgtgttca cttatcaatt gaagtctgga atcagttaaa ggtgctcctg 720
tctatttctc acaacaccag tgatggagaa tggcatttcg tggaggtaac aatcgcagaa 780
actctaaccc ttgccctagt tggcggctcc tgcaaggaga agtgcaccac caagtcttct 840
gttccagttg agaatcatca atcaatatgt gctttgcagg actctttttt gggtggctta 900
ccaatgggga cagccaacaa cagtgtgtct gtgcttaaca tctataatgt gccgtccaca 960
ccttcctttg taggctgtct ccaagacatt agatttgatt tgaatcacat tactctggag 1020
aacgtttcat ctggcctgtc atcaaatgtt aaagcaggct gcctgggaaa ggactggtgt 1080
gaaagtcaac cctgtcaaaa cagaggacgc tgcatcaact tgtggcaggg ttatcagtgt 1140
gaatgtgaca ggccctatac aggctccaac tgcctgaaag agtatgtagc gggaagattt 1200
ggccaagatg actccacagg atatgcggcc tttagtgtta atgataatta tggacagaac 1260
ttcagtcttt caatgtttgt ccgaacacgt caacccctgg gcttacttct ggctttggaa 1320
aatagtactt accagtatgt cagtgtctgg ctagagcacg gcagcctagc actgcagact 1380
ccaggctctc ccaagttcat ggtaaacttt tttctcagtg atggaaatgt tcacttaata 1440
tctttgagaa tcaaaccaaa tgaaattgaa ctgtatcagt cttcacaaaa cctaggattc 1500
atttctgttc ctacatggac aattcgaaga ggagacgtca tcttcattgg tggcttacct 1560
gacagagaga agactgaagt ttatggtggc ttcttcaaag gctgtgttca agatgtcaga 1620
ttaaacagcc agactctgga attctttccc aattcaacaa acaatgcata cgatgaccca 1680
attcttgtca atgtgactca aggctgtccc ggagacaaca catgtaagtc caacccctgt 1740
cataatggag gtgtctgcca ctccctgtgg gatgacttct cctgctcctg ccctacaaac 1800
acagcgggga gagcctgcga gcaagttcag tggtgtcaac tcagcccatg tcctcccact 1860
gcagagtgcc agctgctccc tcaagggttt gaatgtaggt agcattcaaa gctgtcatcc 1920
atccaggtat cgcaaacgct gttttcagcg gattaagcag agaaatactc ttcagaagca 1980
atgggaacat taccagagaa ctcaccaata tcacatttgc tttcagaaca catgatacaa 2040
atgtgatgat attgcatgca gaaaaagaac cagagtttct taatattagc attcaagatg 2100
ccagattatt ctttcaattg cgaagtggca acagctttta tacgctgcac ctgatgggtt 2160
cccaattggt gaatgatggc acatggcacc aagtgacttt ctccatgata gacccagtgg 2220
cccagacctc ccggtggcaa atggaggtga acgaccagac accctttgtg ataagtgaag 2280
ttgctactgg aagcctgaac tttttgaagg acaatacaga catctatgtg ggtgaccaat 2340
ctgttgacaa tccgaaaggc ctgcagggct gtctgagcac aatagagatt ggaggcatat 2400
atctttctta ctttgaaaat ctacatggtt tccctggtaa gcctcaggaa gagcaatttc 2460
tcaaagtttc tacaaatatg gtacttactg gctgtttgcc atcaaatgcc tgccactcca 2520
gcccctgttt gcatggagga aactgtgaag acagctacag ttcttatcgg tgtgcctgtc 2580
tctcgggatg gtcagggaca cactgtgaaa tcaacattga tgagtgcttt tctagcccct 2640
gtatccatgg caactgctct gatggagttg cagcctacca ctgcaggtgt gagcctggat 2700
acaccggtgt gaactgtgag gtggatgtag acaattgcaa gagtcatcag tgtgcaaatg 2760
gggccacctg tgttcctgaa gctcatggct actcttgtct ctgctttgga aattttaccg 2820
ggagattttg cagacacagc agattaccct caacagtctg tgggaatgag aagagaaact 2880
tcacttgcta caatggaggc agctgctcca tgttccagga ggactggcaa tgtatgtgct 2940
ggccaggttt cactggagag tggtgtgaag aggacatcaa cgagtgtgcc tccgatccct 3000
gcatcaatgg aggactgtgc agggacttgg tcaacaggtt cctatgcatc tgtgatgtgg 3060
ccttcgctgg cgagcgctgt gagctggacg taagcggcct ttccttttat gtgtccctct 3120
tactatggca aaacctcttt cagctcctgt cctacctcgt actgcgcatg aatgatgagc 3180
cagttgtaga gtgggggca caggaaaatt attaatgtgc atgggagcat tcacaagtgt 3240
aaaacattga cttgcaagaa acatcttgtc tcagtgtagg tttctaggaa agacaaaggg 3300
aacattaggg aatagactcc atctagagca ctggttctca gtcttcctaa tgctgcaacc 3360
ctttagtaca gctcttcctg ttgtagtgat cgcagccata acattatttt cattgccact 3420
tcataactgt aatccttcta ctgctgtgaa tcacaatgga aatatttatg ttttctgatg 3480
gtcttaagca acacctctga aaaagtcatt gacccccccc ccaaaggggc tgtgatccac 3540
aggttgagaa atgctcatct ggaaggtaac catgcattta agtgtacctc tagtagtttg 3600
ggtctataga agatattctc ctattctacc tttttagaca cgccagaaga gggcatctga 3660
ttccattaaa gatgattggg agccaccgtg tggttcctga gaactgtact cgggcccttt 3720
ggaagagcaa tcagtgctct ttccagcccc taagaatatt tttaatacag ccagaaaggt 3780
ctcattaccc agtgtactga gccctaaggc actttcatcc tcaatcgttc catgttgaat 3840
ggttttcatt acatttggaa aatgttttct ctccactcta cctttacatg ttcctatttt 3900
cctattgaca atttgcccct tcactgtaat tctaatttgg tgtggtcctt cttctcataa 3960
gtttatatgt gacatgaaca tttaaaaata tctatgaata ttttatagtc atgtatgtct 4020
ttctgcaaag ctattcaaat gaactatgga cagttctttt ctacacgaag aagagatgag 4080
tttaatcccc agtaacatga gaaaaagatg agtgagggac agtgctcaca gtatccctca 4140
ctagcatcat ttgtgattcc atgggccatt tttttccacc agcaaatagc agagagccct 4200
ttccctattc gtttctctta cacttcccct tttctgttac aactgaacac tttacattag 4260
ttactccttt gtagggggtt tgacttttcc accgttttct ctggttcact atttatgcta 4320
agtatctgtg cagggcgggt atatcagtcc aacagaggtg tcattagtgt tcattgagga 4380
ggaaatactt tgcatgaatt catgacatca ttgaagtagc agtggccaga aagataccct 4440
tctgcgaatg tgtctgtgta ttcagaagct gccctggtta gaaaacatgt gggtcacttt 4500
tcctttgcat gttaccagtg ctcactgggt catgattgtt ttaagacaga gcttttgctg 4560
tggcaatgac caaggtgaat ccagagatgc agatcagaca aaggacaaga caatgtacta 4620
tctgagtaaa accctgcctt gacttactcc tcagtactta gagattttac atagcaacct 4680
ccaccctgtg gcaacccgtt cacactagca gtgatgctga gatttgccct tccttctcat 4740
catcttcctc acatccaaag cattttgtgt ccacactgct gtttcagata actgtttcta 4800
aagtgggatt gttgtagcca gaaaggtagg gaaaatgttc cccaaaatat ttgcattctt 4860
aagtatgtga agtaagtaga ttatagtcag agacaatatg taaggtttca ggttcactcc 4920
cttctacaca tatcttcaac tgtgtatttg cagaatattc tgaatgtgac atactcccaa 4980
cagaatatat ttaaggagta tttatccaca gtattgttct ctgtacagtt ctagtgcttc 5040
tattgtcact gcaattgtca attgtttttc tgctttccaa ctgtcttatt atcatttaat 5100
agcatcttgc taaatgccct ctttctattc tccttatttc tccatagttc atgtgtgtct 5160
gtgtgactaa ggattctcct catttttgca gaaaaataaa atcttttctt ctttatgtcc 5220
tgcttgtcat tctctggtga cacatgtctt tgcttacttg gactgagggt tgtacagtaa 5280

```
gtacagaagc aggctcagtc acacagacag agacacacca ccaccagcag cagcagcacc   5340

accaccacca ccaccaccac cagaaaacag tatgagtact catctcttga ttacatgtca   5400

tttcaagtaa gcaccatgac accgagggcc aggttccatg gactttctct gttaggcacg   5460

tgattcttta gctgaccttt gagaacagac tccaacaacc tcacttattt ttactgttga   5520

cttatatcat ctctgacaac actggacttc gtttgagcta gtcaagagga aagaccatga   5580

cacctaaggg acagaaattc acacactcgg tttttcataa ttcacacaca ttcctatgta   5640

tcaaatctct gtaatagatg acatttactt gaataaaaag tcatttccct tt           5692
```

<210> SEQ ID NO 82
<211> LENGTH: 576
<212> TYPE: PRT
<213> ORGANISM: Mus musculus

<400> SEQUENCE: 82

```
Met Phe Gly His Lys Thr Gln Gly Phe His Ile Leu Met Ala Val Leu
1               5                   10                  15

Ile Gly Ile His Cys Glu Glu Asp Val Asp Glu Cys Leu Leu His Pro
            20                  25                  30

Cys Leu Asn Gly Gly Thr Cys Glu Asn Leu Pro Gly Asn Tyr Ala Cys
        35                  40                  45

His Cys Pro Phe Asp Asp Thr Ser Arg Thr Phe Tyr Gly Gly Glu Asn
    50                  55                  60

Cys Ser Glu Ile Leu Leu Gly Cys Thr His His Gln Cys Leu Asn Asn
65                  70                  75                  80

Gly Lys Cys Ile Pro His Phe Gln Asn Gly Gln His Gly Phe Thr Cys
                85                  90                  95

Gln Cys Leu Ser Gly Tyr Ala Gly Pro Leu Cys Glu Thr Val Thr Thr
            100                 105                 110

Leu Ser Phe Gly Ser Asn Gly Phe Leu Trp Val Thr Ser Gly Ser His
        115                 120                 125

Thr Gly Ile Gly Pro Glu Cys Asn Ile Ser Leu Arg Phe His Thr Val
    130                 135                 140

Gln Pro Asn Ala Leu Leu Leu Ile Arg Gly Asn Lys Asp Val Ser Met
145                 150                 155                 160

Lys Leu Glu Leu Leu Asn Gly Cys Val His Leu Ser Ile Glu Val Trp
                165                 170                 175

Asn Gln Leu Lys Val Leu Leu Ser Ile Ser His Asn Thr Ser Asp Gly
            180                 185                 190

Glu Trp His Phe Val Glu Val Thr Ile Ala Glu Thr Leu Thr Leu Ala
        195                 200                 205

Leu Val Gly Gly Ser Cys Lys Glu Lys Cys Thr Thr Lys Ser Ser Val
    210                 215                 220

Pro Val Glu Asn His Gln Ser Ile Cys Ala Leu Gln Asp Ser Phe Leu
225                 230                 235                 240

Gly Gly Leu Pro Met Gly Thr Ala Asn Asn Ser Val Ser Val Leu Asn
                245                 250                 255

Ile Tyr Asn Val Pro Ser Thr Pro Ser Phe Val Gly Cys Leu Gln Asp
            260                 265                 270

Ile Arg Phe Asp Leu Asn His Ile Thr Leu Glu Asn Val Ser Ser Gly
        275                 280                 285

Leu Ser Ser Asn Val Lys Ala Gly Cys Leu Gly Lys Asp Trp Cys Glu
    290                 295                 300
```

```
Ser Gln Pro Cys Gln Asn Arg Gly Arg Cys Ile Asn Leu Trp Gln Gly
305                 310                 315                 320

Tyr Gln Cys Glu Cys Asp Arg Pro Tyr Thr Gly Ser Asn Cys Leu Lys
                325                 330                 335

Glu Tyr Val Ala Gly Arg Phe Gly Gln Asp Asp Ser Thr Gly Tyr Ala
            340                 345                 350

Ala Phe Ser Val Asn Asp Asn Tyr Gly Gln Asn Phe Ser Leu Ser Met
        355                 360                 365

Phe Val Arg Thr Arg Gln Pro Leu Gly Leu Leu Leu Ala Leu Glu Asn
    370                 375                 380

Ser Thr Tyr Gln Tyr Val Ser Val Trp Leu Glu His Gly Ser Leu Ala
385                 390                 395                 400

Leu Gln Thr Pro Gly Ser Pro Lys Phe Met Val Asn Phe Phe Leu Ser
                405                 410                 415

Asp Gly Asn Val His Leu Ile Ser Leu Arg Ile Lys Pro Asn Glu Ile
            420                 425                 430

Glu Leu Tyr Gln Ser Ser Gln Asn Leu Gly Phe Ile Ser Val Pro Thr
        435                 440                 445

Trp Thr Ile Arg Arg Gly Asp Val Ile Phe Ile Gly Gly Leu Pro Asp
    450                 455                 460

Arg Glu Lys Thr Glu Val Tyr Gly Gly Phe Phe Lys Gly Cys Val Gln
465                 470                 475                 480

Asp Val Arg Leu Asn Ser Gln Thr Leu Glu Phe Phe Pro Asn Ser Thr
                485                 490                 495

Asn Asn Ala Tyr Asp Asp Pro Ile Leu Val Asn Val Thr Gln Gly Cys
            500                 505                 510

Pro Gly Asp Asn Thr Cys Lys Ser Asn Pro Cys His Asn Gly Gly Val
        515                 520                 525

Cys His Ser Leu Trp Asp Asp Phe Ser Cys Ser Cys Pro Thr Asn Thr
    530                 535                 540

Ala Gly Arg Ala Cys Glu Gln Val Gln Trp Cys Gln Leu Ser Pro Cys
545                 550                 555                 560

Pro Pro Thr Ala Glu Cys Gln Leu Leu Pro Gln Gly Phe Glu Cys Arg
                565                 570                 575
```

<210> SEQ ID NO 83
<211> LENGTH: 5801
<212> TYPE: DNA
<213> ORGANISM: Mus musculus

<400> SEQUENCE: 83

```
tgttcacgga agcctgaggg ggacacgaat ccaatccagg ctggaaaaat ctgctccagg      60

attgactggt taccgtcttc ctgtgcctgt aaggtgctgt gaaagagaag tgctttctga     120

ttctctgtct gtggaggagc cctgggaggg gtgggacaga gatggcatcc tggctctctg     180

aggcacctgc tcttctctga accacacagg agtcaagagc caaacaggga tagcttcagc     240

agcacttcag agggtgttct ctaagtaaga acatgaagct caagagaact gcctaccttc     300

tcttcctgta cctcagctcc tcactgctca tctgcataaa gaattcattt tgcaataaaa     360

acaataccag gtgccttca ggtccttgcc aaaacaattc tacgtgcaag cattttccac     420

aagacaacaa ttgttgctta gacacagcca ataatttgga caaagactgt gaagatctga     480

aagacccttg cttctcgagt ccctgccaag gaattgccac ttgtgtgaaa atcccagggg     540

aagggaactt cctgtgtcag tgtcctcctg ggtacagcgg gctgaactgt gaaactgcca     600
```

```
ccaattcctg tggagggaac ctctgccaac atggaggcac ctgccgtaaa gaccctgagc    660
accctgtctg tatctgccct cctggatatg ctggaaggtt ctgtgagact gatcacaatg    720
agtgtgcttc tagcccttgc cacaatgggg ctatgtgcca ggatggaatc aatggctact    780
cctgcttctg tgtgcctgga taccaaggca ggcattgtga cttggaagtg gatgaatgtg    840
tttctgatcc ctgcaagaat gaggctgtgt gcctcaatga gataggaaga tacacttgtg    900
tctgccctca agagttttct ggcgtgaact gtgagttgga aattgatgaa tgcagatccc    960
agccttgtct ccacggtgcc acatgtcagg acgctccagg gggctactcc tgtgactgtg   1020
cacctggatt ccttggagag cactgtgaac tcagcgttaa tgaatgtgaa agtcagccgt   1080
gtctccatgg aggtctatgt gtggatggaa gaaacagtta ccactgtgac tgcacaggta   1140
gtggattcac agggatgcac tgtgagtcct tgattcctct ttgttggtca aagccttgtc   1200
acaacgacgc gacatgtgaa gatactgttg acagctatat ttgtcactgc cggcctggat   1260
acacaggtgc cctgtgtgag acagacataa atgaatgcag tagcaacccc tgccaatttt   1320
gggggaaatg tgtcgagctg tcctcagagg gtctatatgg aaacactgct ggcctgcctt   1380
cctccttcag ctatgttgga gcctcgggct atgtgtgtat ctgtcagcct ggattcacag   1440
gaattcactg tgaagaagac gttgatgaat gtttactgca cccttgccta aatggtggta   1500
cttgtgagaa cctgcctggg aattatgcct gtcactgtcc ctttgatgac acttctagga   1560
cattttatgg aggagaaaac tgctcagaaa ttctcctggg ctgcactcat caccagtgtc   1620
tgaacaatgg aaaatgtatc cctcatttcc aaaatggcca gcatggattc acttgccagt   1680
gtctttctgg ctatgcgggg cccctgtgtg aaactgtcac cacactttca tttgggagca   1740
atggcttcct atgggtcaca agtggctccc atacaggcat agggccagaa tgtaacatat   1800
ccttgaggtt tcacactgtt caaccaaacg cacttctcct catccgaggc aacaaggacg   1860
tgtctatgaa gctggagttg ctgaatggtt gtgttcactt atcaattgaa gtctggaatc   1920
agttaaaggt gctcctgtct atttctcaca acaccagtga tggagaatgg catttcgtgg   1980
aggtaacaat cgcagaaact ctaacccttg ccctagttgg cggctcctgc aaggagaagt   2040
gcaccaccaa gtcttctgtt ccagttgaga atcatcaatc aatatgtgct ttgcaggact   2100
ctttttttggg tggcttacca atggggacag ccaacaacag tgtgtctgtg cttaacatct   2160
ataatgtgcc gtccacacct tcctttgtag gctgtctcca agacattaga tttgatttga   2220
atcacattac tctggagaac gtttcatctg gcctgtcatc aaatgttaaa gcaggctgcc   2280
tgggaaagga ctggtgtgaa agtcaaccct gtcaaaacag aggacgctgc atcaacttgt   2340
ggcagggtta tcagtgtgaa tgtgacaggc cctatacagg ctccaactgc ctgaaaggtg   2400
agaggagtgg ggtgccccag agtgctgtgc ctctgagcag agccatctct aatcacccag   2460
ggtgccgtcc cctgttagga aacataagga cccctcagga cttatgctgg tatttgttca   2520
ctaatgagat aaaatggcat agtcatgata tgtattaatt atgagtgggt ttcataggat   2580
agctgagctt ttttgggctg aaaagtaaaa ttaataataa taacaataag caaataactc   2640
caattaatgt ggtgttttat ctagttagca aaatgctctt agcaatttgc cattcattgt   2700
gtatcagaaa tatatagaaa actttagttc tttgtacaag atgtcatctt ttagagaaag   2760
gggagttttg gacagaaaaa ctagttactg ccacgtacta ataccacacc ttgtgcttgc   2820
tagagtctca gtgaataaac cctttgctga tctctctgtg taactcatac ttccgtaaga   2880
atcgtggtta agattagcat gttgacaagc catcagttct agtcaagact gtctcctaaa   2940
```

aggccttgtt ttctaaagag gagagatgtc ttcagtcgga aaaagcaaga agacatgaac 3000
tgtattatca ggaaaacttg gtagttgtca cgcacagatc cgtgattcct ctagtgaatc 3060
agtttgaagt ggatttccaa tccctcactt ttgacatcac tctgaaggct gccatcaata 3120
gcgatcaata catacctgct cacttttatt attattatca tgtattgaga gggctgaaag 3180
ggaactctaa cagactgctt tgaagttcag ctgcaattta ctctagcatt ttagaatgag 3240
tccaagaaga acaacatatg gcaaataggc tacgctgttc cgtatgaagg aaaattaaaa 3300
ccagccgtag cctatactct actccatgtt caatggctaa gaattattag aaactattcg 3360
caggttttcc cctaaccaca atattcatta caatcatgga cctgcttgac aatgaggcat 3420
ggcatctgct gctccgcgca atattttaaa tggcgtggca agttgttttg tgattatttt 3480
taaaggtgaa attatgccga ggcaatggtt cacgttttga agaaaaatct aattgaccca 3540
aagcaatatt tttactacat atacaaaata acaaacagat gcggactaat tttgactggc 3600
ttccagatgc ggtgaccctt gaggttagca ctgacctggg aatgctgact gtcctaggaa 3660
atagattcga gagatgccaa gccagcaggt tctggttttc tttacatttt tttttccaac 3720
ttggaaaata atgaactttt gaaacaaaat tcctgatttg gttacacttt ccatattccc 3780
ccaaatagtg tgattacacc cctccactca caccgagtgt aactatatcc cctaccctta 3840
tacaaagtgt gattaaatct tctattttca cagtttgaaa ctgtttagct caacatttga 3900
tatcaaatga ttatagggca ggaatttcat aaaacccttc acttctgaaa atttaggagg 3960
agaattttaa aagaaagtta tatttttcat gtgaccctga gatcataaag ttaaagtatt 4020
ctttattgct gagatccata aggaaatatt ttctgtattt tattccttaa acacacacac 4080
acacacttaa gactccaaat gagactctat atacatatag agccattcta tatgcatatt 4140
caggatgagg cacactaaaa atcaagaggg gaagccatca aagtaacaat tttttaaaga 4200
tgtattttat tattctatgt gtgtgggtct gagtgtatgc ttctgcacca ggtgagtgga 4260
gattcccctg gaacaggagt taatgacagt tttgagctgc ctgatgtggg tattgggatc 4320
aaaccttggt cctctacaag gacagctcat acttttaacc actgagtcac ctctccagtt 4380
ctcaaacaat gattttggaa caatgcttgc cagtgttaaa cccaatgaaa gaagaaggca 4440
tgttgaataa agggtggagt tatctgaatg atacaaaatg tagatagaca ttgccaatat 4500
cttgaaactg atctcaagtc atttatgccc cccataaggt ttctgtaaca acctgaactg 4560
cctgcagtga taacattgta tgtcttgcat tatgtgttag aagaaggtct tctgggatat 4620
tggtctaaag cagttgttct caaccttcct aatgctgtga ccctttaata tagctccttg 4680
tgttttgctg acctcccaac catacagtta ttttgttgct acttcacaac tgtaactttt 4740
gctacttttg tgaattataa tataaatgtc tgtgttttcc aatggtctta gacaagccct 4800
gtgacagccc tgtgtcattc atctccaaag gcttacggcc cacaggtcct aagagaacat 4860
gtaacgtacc tctttctatg ttcggaaagt ctctaattta aaaaaaaaaa caatttatat 4920
atgcttgtct tcctttgtac gcccagactt ttagaatgct attatattag agtcagtgat 4980
agttaggttt gacagagcct catcagcagc tggatttctt atggaaccct ctgctttgaa 5040
cccacttcag gaatcgagaa gtcactatcc catctggccc caaattttga aacaattatt 5100
tctgatgacg atttaaccca gcttcccttt tcccacacag ttaccactgc ggatattctc 5160
acttagggct ttaacatccc ctcttgaaaa ttcctaaata tttgaagaaa aatattccat 5220
gcatagcatc cactcccagc atcctacaca cattccttac ctctagtatc tctggaaggc 5280
acgtcccagt gggacatcat tagctacctt acatgctcct ttgccataca tttgcctctt 5340

```
tctaacaggt ggtatctaaa tgtgcttgat gatgcactga catggaacca caacttccct   5400

ctttctatat aataggctct catttatcat gttagcacta catttaattt ttgggagagt   5460

ttacacactg tcttttgtca gtcattgtca ttgtgaagct agagagtcct cttctattgt   5520

atactgataa gtcacattta atatcaatgc ctcctattaa cctctcacta aacttcacct   5580

tatagtccat cagcattaaa atctctcaaa ttaaattttt ttctccatac atctttagaa   5640

catatccact acctgtatta gtatcaaatc ttccatgtgt agagttgggt ccttcctatg   5700

tggcttaccg tgtttctaaa atcaagtaac acatcacaca ctctgactac ctgcttgtga   5760

tttctgaaga ataggcttac tggagagtca agtttctaag g                       5801

<210> SEQ ID NO 84
<211> LENGTH: 761
<212> TYPE: PRT
<213> ORGANISM: Mus musculus

<400> SEQUENCE: 84

Met Lys Leu Lys Arg Thr Ala Tyr Leu Leu Phe Leu Tyr Leu Ser Ser
1               5                   10                  15

Ser Leu Leu Ile Cys Ile Lys Asn Ser Phe Cys Asn Lys Asn Asn Thr
            20                  25                  30

Arg Cys Leu Ser Gly Pro Cys Gln Asn Asn Ser Thr Cys Lys His Phe
        35                  40                  45

Pro Gln Asp Asn Asn Cys Cys Leu Asp Thr Ala Asn Asn Leu Asp Lys
    50                  55                  60

Asp Cys Glu Asp Leu Lys Asp Pro Cys Phe Ser Ser Pro Cys Gln Gly
65                  70                  75                  80

Ile Ala Thr Cys Val Lys Ile Pro Gly Glu Gly Asn Phe Leu Cys Gln
                85                  90                  95

Cys Pro Pro Gly Tyr Ser Gly Leu Asn Cys Glu Thr Ala Thr Asn Ser
            100                 105                 110

Cys Gly Gly Asn Leu Cys Gln His Gly Gly Thr Cys Arg Lys Asp Pro
        115                 120                 125

Glu His Pro Val Cys Ile Cys Pro Pro Gly Tyr Ala Gly Arg Phe Cys
    130                 135                 140

Glu Thr Asp His Asn Glu Cys Ala Ser Ser Pro Cys His Asn Gly Ala
145                 150                 155                 160

Met Cys Gln Asp Gly Ile Asn Gly Tyr Ser Cys Phe Cys Val Pro Gly
                165                 170                 175

Tyr Gln Gly Arg His Cys Asp Leu Glu Val Asp Glu Cys Val Ser Asp
            180                 185                 190

Pro Cys Lys Asn Glu Ala Val Cys Leu Asn Glu Ile Gly Arg Tyr Thr
        195                 200                 205

Cys Val Cys Pro Gln Glu Phe Ser Gly Val Asn Cys Glu Leu Glu Ile
    210                 215                 220

Asp Glu Cys Arg Ser Gln Pro Cys Leu His Gly Ala Thr Cys Gln Asp
225                 230                 235                 240

Ala Pro Gly Gly Tyr Ser Cys Asp Cys Ala Pro Gly Phe Leu Gly Glu
                245                 250                 255

His Cys Glu Leu Ser Val Asn Glu Cys Glu Ser Gln Pro Cys Leu His
            260                 265                 270

Gly Gly Leu Cys Val Asp Gly Arg Asn Ser Tyr His Cys Asp Cys Thr
        275                 280                 285
```

```
Gly Ser Gly Phe Thr Gly Met His Cys Glu Ser Leu Ile Pro Leu Cys
    290                 295                 300

Trp Ser Lys Pro Cys His Asn Asp Ala Thr Cys Glu Asp Thr Val Asp
305                 310                 315                 320

Ser Tyr Ile Cys His Cys Arg Pro Gly Tyr Thr Gly Ala Leu Cys Glu
                325                 330                 335

Thr Asp Ile Asn Glu Cys Ser Ser Asn Pro Cys Gln Phe Trp Gly Glu
            340                 345                 350

Cys Val Glu Leu Ser Ser Glu Gly Leu Tyr Gly Asn Thr Ala Gly Leu
        355                 360                 365

Pro Ser Ser Phe Ser Tyr Val Gly Ala Ser Gly Tyr Val Cys Ile Cys
    370                 375                 380

Gln Pro Gly Phe Thr Gly Ile His Cys Glu Glu Asp Val Asp Glu Cys
385                 390                 395                 400

Leu Leu His Pro Cys Leu Asn Gly Gly Thr Cys Glu Asn Leu Pro Gly
                405                 410                 415

Asn Tyr Ala Cys His Cys Pro Phe Asp Asp Thr Ser Arg Thr Phe Tyr
            420                 425                 430

Gly Gly Glu Asn Cys Ser Glu Ile Leu Leu Gly Cys Thr His His Gln
        435                 440                 445

Cys Leu Asn Asn Gly Lys Cys Ile Pro His Phe Gln Asn Gly Gln His
    450                 455                 460

Gly Phe Thr Cys Gln Cys Leu Ser Gly Tyr Ala Gly Pro Leu Cys Glu
465                 470                 475                 480

Thr Val Thr Thr Leu Ser Phe Gly Ser Asn Gly Phe Leu Trp Val Thr
                485                 490                 495

Ser Gly Ser His Thr Gly Ile Gly Pro Glu Cys Asn Ile Ser Leu Arg
            500                 505                 510

Phe His Thr Val Gln Pro Asn Ala Leu Leu Leu Ile Arg Gly Asn Lys
        515                 520                 525

Asp Val Ser Met Lys Leu Glu Leu Leu Asn Gly Cys Val His Leu Ser
    530                 535                 540

Ile Glu Val Trp Asn Gln Leu Lys Val Leu Leu Ser Ile Ser His Asn
545                 550                 555                 560

Thr Ser Asp Gly Glu Trp His Phe Val Glu Val Thr Ile Ala Glu Thr
                565                 570                 575

Leu Thr Leu Ala Leu Val Gly Gly Ser Cys Lys Glu Lys Cys Thr Thr
            580                 585                 590

Lys Ser Ser Val Pro Val Glu Asn His Gln Ser Ile Cys Ala Leu Gln
        595                 600                 605

Asp Ser Phe Leu Gly Gly Leu Pro Met Gly Thr Ala Asn Asn Ser Val
    610                 615                 620

Ser Val Leu Asn Ile Tyr Asn Val Pro Ser Thr Pro Ser Phe Val Gly
625                 630                 635                 640

Cys Leu Gln Asp Ile Arg Phe Asp Leu Asn His Ile Thr Leu Glu Asn
                645                 650                 655

Val Ser Ser Gly Leu Ser Ser Asn Val Lys Ala Gly Cys Leu Gly Lys
            660                 665                 670

Asp Trp Cys Glu Ser Gln Pro Cys Gln Asn Arg Gly Arg Cys Ile Asn
        675                 680                 685

Leu Trp Gln Gly Tyr Gln Cys Glu Cys Asp Arg Pro Tyr Thr Gly Ser
    690                 695                 700

Asn Cys Leu Lys Gly Glu Arg Ser Gly Val Pro Gln Ser Ala Val Pro
```

```
705                 710                 715                 720

Leu Ser Arg Ala Ile Ser Asn His Pro Gly Cys Arg Pro Leu Leu Gly
                725                 730                 735

Asn Ile Arg Thr Pro Gln Asp Leu Cys Trp Tyr Leu Phe Thr Asn Glu
            740                 745                 750

Ile Lys Trp His Ser His Asp Met Tyr
        755                 760


<210> SEQ ID NO 85
<211> LENGTH: 5547
<212> TYPE: DNA
<213> ORGANISM: Mus musculus

<400> SEQUENCE: 85

acagctgact cttacattaa gccccactga tccagcttga agaggagtga ggcaaagctg     60

aaccctccca ctctccttga caagtgcaag cccacacttt tggaaaaaag cacaaagacg    120

tcagaaacgg ttcctgtcga cctactaggc tttggatggc taagtgtttt tgctttgtat    180

ggaaatatgt ttggacacaa gacacaaggt tttcacattt taatggcagt gctcatagga    240

attcactgtg aagaagacgt tgatgaatgt ttactgcacc cttgcctaaa tggtggtact    300

tgtgagaacc tgcctgggaa ttatgcctgt cactgtccct ttgatgacac ttctaggaca    360

ttttatggag gagaaaactg ctcagaaatt ctcctgggct gcactcatca ccagtgtctg    420

aacaatggaa aatgtatccc tcatttccaa aatggccagc atggattcac ttgccagtgt    480

ctttctggct atgcggggcc cctgtgtgaa actgtcacca cactttcatt tgggagcaat    540

ggcttcctat gggtcacaag tggctcccat acaggcatag ggccagaatg taacatatcc    600

ttgaggtttc acactgttca accaaacgca cttctcctca tccgaggcaa caaggacgtg    660

tctatgaagc tggagttgct gaatggttgt gttcacttat caattgaagt ctggaatcag    720

ttaaaggtgc tcctgtctat ttctcacaac accagtgatg gagaatggca tttcgtggag    780

gtaacaatcg cagaaactct aacccttgcc ctagttggcg gctcctgcaa ggagaagtgc    840

accaccaagt cttctgttcc agttgagaat catcaatcaa tatgtgcttt gcaggactct    900

tttttgggtg gcttaccaat ggggacagcc aacaacagtg tgtctgtgct taacatctat    960

aatgtgccgt ccacaccttc ctttgtaggc tgtctccaag acattagatt tgatttgaat   1020

cacattactc tggagaacgt ttcatctggc ctgtcatcaa atgttaaagc aggctgcctg   1080

ggaaaggact ggtgtgaaag tcaaccctgt caaaacagag gacgctgcat caacttgtgg   1140

cagggttatc agtgtgaatg tgacaggccc tatacaggct ccaactgcct gaaagagtat   1200

gtagcgggaa gatttggcca agatgactcc acaggatatg cggcctttag tgttaatgat   1260

aattatggac agaacttcag tctttcaatg tttgtccgaa cacgtcaacc cctgggctta   1320

cttctggctt tggaaaatag tacttaccag tatgtcagtg tctggctaga gcacggcagc   1380

ctagcactgc agactccagg ctctcccaag ttcatgagga gacgtcatct tcattggtgg   1440

cttacctgac agagagaaga ctgaagttta tggtggcttc ttcaaaggct gtgttcaaga   1500

tgtcagatta aacagccaga ctctggaatt ctttcccaat tcaacaaaca atgcatacga   1560

tgacccaatt cttgtcaatg tgactcaagg ctgtcccgga gacaacacat gtaagtccaa   1620

cccctgtcat aatggaggtg tctgccactc cctgtgggat gacttctcct gctcctgccc   1680

tacaaacaca gcggggagag cctgcgagca agttcagtgg tgtcaactca gcccatgtcc   1740

tcccactgca gagtgccagc tgctccctca agggtttgaa tgtatcgcaa acgctgtttt   1800
```

-continued

```
cagcggatta agcagagaaa tactcttcag aagcaatggg aacattacca gagaactcac   1860
caatatcaca tttgctttca gaacacatga tacaaatgtg atgatattgc atgcagaaaa   1920
agaaccagag tttcttaata ttagcattca agatgccaga ttattctttc aattgcgaag   1980
tggcaacagc ttttatacgc tgcacctgat gggttcccaa ttggtgaatg atggcacatg   2040
gcaccaagtg actttctcca tgatagaccc agtggcccag acctcccggt ggcaaatgga   2100
ggtgaacgac cagacaccct ttgtgataag tgaagttgct actggaagcc tgaacttttt   2160
gaaggacaat acagacatct atgtgggtga ccaatctgtt gacaatccga aaggcctgca   2220
gggctgtctg agcacaatag agattggagg catatatctt tcttactttg aaaatctaca   2280
tggtttccct ggtaagcctc aggaagagca atttctcaaa gtttctacaa atatggtact   2340
tactggctgt ttgccatcaa atgcctgcca ctccagcccc tgtttgcatg gaggaaactg   2400
tgaagacagc tacagttctt atcggtgtgc ctgtctctcg ggatggtcag ggacacactg   2460
tgaaatcaac attgatgagt gcttttctag cccctgtatc catggcaact gctctgatgg   2520
agttgcagcc taccactgca ggtgtgagcc tggatacacc ggtgtgaact gtgaggtgga   2580
tgtagacaat tgcaagagtc atcagtgtgc aaatggggcc acctgtgttc ctgaagctca   2640
tggctactct tgtctctgct ttggaaattt taccgggaga ttttgcagac acagcagatt   2700
accctcaaca gtctgtggga atgagaagag aaacttcact tgctacaatg gaggcagctg   2760
ctccatgttc caggaggact ggcaatgtat gtgctggcca ggtttcactg gagagtggtg   2820
tgaagaggac atcaacgagt gtgcctccga tccctgcatc aatggaggac tgtgcaggga   2880
cttggtcaac aggttcctat gcatctgtga tgtggccttc gctggcgagc gctgtgagct   2940
ggacgtaagc ggcctttcct tttatgtgtc cctcttacta tggcaaaacc tctttcagct   3000
cctgtcctac ctcgtactgc gcatgaatga tgagccagtt gtagagtggg gggcacagga   3060
aaattattaa tgtgcatggg agcattcaca agtgtaaaac attgacttgc aagaaacatc   3120
ttgtctcagt gtaggtttct aggaaagaca aagggaacat tagggaatag actccatcta   3180
gagcactggt tctcagtctt cctaatgctg caacccttta gtacagctct tcctgttgta   3240
gtgatcgcag ccataacatt attttcattg ccacttcata actgtaatcc ttctactgct   3300
gtgaatcaca atggaaatat ttatgttttc tgatggtctt aagcaacacc tctgaaaaag   3360
tcattgaccc cccccccaaa ggggctgtga tccacaggtt gagaaatgct catctggaag   3420
gtaaccatgc atttaagtgt acctctagta gtttgggtct atagaagata ttctcctatt   3480
ctaccttttt agacacgcca gaagagggca tctgattcca ttaaagatga ttgggagcca   3540
ccgtgtggtt cctgagaact gtactcgggc cctttggaag agcaatcagt gctctttcca   3600
gcccctaaga atatttttaa tacagccaga aaggtctcat tacccagtgt actgagccct   3660
aaggcacttt catcctcaat cgttccatgt tgaatggttt tcattacatt tggaaaatgt   3720
tttctctcca ctctaccttt acatgttcct attttcctat tgacaatttg ccccttcact   3780
gtaattctaa tttggtgtgg tccttcttct cataagttta tatgtgacat gaacatttaa   3840
aaatatctat gaatatttta tagtcatgta tgtctttctg caaagctatt caaatgaact   3900
atggacagtt cttttctaca cgaagaagag atgagtttaa tccccagtaa catgagaaaa   3960
agatgagtga gggacagtgc tcacagtatc cctcactagc atcatttgtg attccatggg   4020
ccattttttt ccaccagcaa atagcagaga gccctttccc tattcgtttc tcttacactt   4080
cccctttttct gttacaactg aacactttac attagttact cctttgtagg gggtttgact   4140
tttccaccgt tttctctggt tcactattta tgctaagtat ctgtgcaggg cgggtatatc   4200
```

```
agtccaacag aggtgtcatt agtgttcatt gaggaggaaa tactttgcat gaattcatga   4260

catcattgaa gtagcagtgg ccagaaagat acccttctgc gaatgtgtct gtgtattcag   4320

aagctgccct ggttagaaaa catgtgggtc acttttcctt tgcatgttac cagtgctcac   4380

tgggtcatga ttgttttaag acagagcttt tgctgtggca atgaccaagg tgaatccaga   4440

gatgcagatc agacaaagga caagacaatg tactatctga gtaaaaccct gccttgactt   4500

actcctcagt acttagagat tttacatagc aacctccacc ctgtggcaac ccgttcacac   4560

tagcagtgat gctgagattt gcccttcctt ctcatcatct tcctcacatc caaagcattt   4620

tgtgtccaca ctgctgtttc agataactgt ttctaaagtg ggattgttgt agccagaaag   4680

gtagggaaaa tgttccccaa aatatttgca ttcttaagta tgtgaagtaa gtagattata   4740

gtcagagaca atatgtaagg tttcaggttc actcccttct acacatatct tcaactgtgt   4800

atttgcagaa tattctgaat gtgacatact cccaacagaa tatatttaag gagtatttat   4860

ccacagtatt gttctctgta cagttctagt gcttctattg tcactgcaat tgtcaattgt   4920

ttttctgctt tccaactgtc ttattatcat ttaatagcat cttgctaaat gccctctttc   4980

tattctcctt atttctccat agttcatgtg tgtctgtgtg actaaggatt ctcctcattt   5040

ttgcagaaaa ataaaatctt ttcttcttta tgtcctgctt gtcattctct ggtgacacat   5100

gtctttgctt acttggactg agggttgtac agtaagtaca gaagcaggct cagtcacaca   5160

gacagagaca caccaccacc agcagcagca gcaccaccac caccaccacc accaccagaa   5220

aacagtatga gtactcatct cttgattaca tgtcatttca agtaagcacc atgacaccga   5280

gggccaggtt ccatggactt tctctgttag gcacgtgatt ctttagctga cctttgagaa   5340

cagactccaa caacctcact tatttttact gttgacttat atcatctctg acaacactgg   5400

acttcgtttg agctagtcaa gaggaaagac catgacacct aagggacaga aattcacaca   5460

ctcggttttt cataattcac acacattcct atgtatcaaa tctctgtaat agatgacatt   5520

tacttgaata aaaagtcatt tcccttt                                     5547
```

<210> SEQ ID NO 86
<211> LENGTH: 420
<212> TYPE: PRT
<213> ORGANISM: Mus musculus

<400> SEQUENCE: 86

```
Met Phe Gly His Lys Thr Gln Gly Phe His Ile Leu Met Ala Val Leu
1               5                   10                  15

Ile Gly Ile His Cys Glu Glu Asp Val Asp Glu Cys Leu Leu His Pro
            20                  25                  30

Cys Leu Asn Gly Gly Thr Cys Glu Asn Leu Pro Gly Asn Tyr Ala Cys
        35                  40                  45

His Cys Pro Phe Asp Asp Thr Ser Arg Thr Phe Tyr Gly Gly Glu Asn
    50                  55                  60

Cys Ser Glu Ile Leu Leu Gly Cys Thr His His Gln Cys Leu Asn Asn
65                  70                  75                  80

Gly Lys Cys Ile Pro His Phe Gln Asn Gly Gln His Gly Phe Thr Cys
                85                  90                  95

Gln Cys Leu Ser Gly Tyr Ala Gly Pro Leu Cys Glu Thr Val Thr Thr
            100                 105                 110

Leu Ser Phe Gly Ser Asn Gly Phe Leu Trp Val Thr Ser Gly Ser His
        115                 120                 125
```

```
Thr Gly Ile Gly Pro Glu Cys Asn Ile Ser Leu Arg Phe His Thr Val
    130                 135                 140

Gln Pro Asn Ala Leu Leu Leu Ile Arg Gly Asn Lys Asp Val Ser Met
145                 150                 155                 160

Lys Leu Glu Leu Leu Asn Gly Cys Val His Leu Ser Ile Glu Val Trp
                165                 170                 175

Asn Gln Leu Lys Val Leu Leu Ser Ile Ser His Asn Thr Ser Asp Gly
            180                 185                 190

Glu Trp His Phe Val Glu Val Thr Ile Ala Glu Thr Leu Thr Leu Ala
        195                 200                 205

Leu Val Gly Gly Ser Cys Lys Glu Lys Cys Thr Thr Lys Ser Ser Val
    210                 215                 220

Pro Val Glu Asn His Gln Ser Ile Cys Ala Leu Gln Asp Ser Phe Leu
225                 230                 235                 240

Gly Gly Leu Pro Met Gly Thr Ala Asn Asn Ser Val Ser Val Leu Asn
                245                 250                 255

Ile Tyr Asn Val Pro Ser Thr Pro Ser Phe Val Gly Cys Leu Gln Asp
            260                 265                 270

Ile Arg Phe Asp Leu Asn His Ile Thr Leu Glu Asn Val Ser Ser Gly
        275                 280                 285

Leu Ser Ser Asn Val Lys Ala Gly Cys Leu Gly Lys Asp Trp Cys Glu
    290                 295                 300

Ser Gln Pro Cys Gln Asn Arg Gly Arg Cys Ile Asn Leu Trp Gln Gly
305                 310                 315                 320

Tyr Gln Cys Glu Cys Asp Arg Pro Tyr Thr Gly Ser Asn Cys Leu Lys
                325                 330                 335

Glu Tyr Val Ala Gly Arg Phe Gly Gln Asp Asp Ser Thr Gly Tyr Ala
            340                 345                 350

Ala Phe Ser Val Asn Asp Asn Tyr Gly Gln Asn Phe Ser Leu Ser Met
        355                 360                 365

Phe Val Arg Thr Arg Gln Pro Leu Gly Leu Leu Leu Ala Leu Glu Asn
    370                 375                 380

Ser Thr Tyr Gln Tyr Val Ser Val Trp Leu Glu His Gly Ser Leu Ala
385                 390                 395                 400

Leu Gln Thr Pro Gly Ser Pro Lys Phe Met Arg Arg Arg His Leu His
                405                 410                 415

Trp Trp Leu Thr
            420
```

<210> SEQ ID NO 87
<211> LENGTH: 18
<212> TYPE: PRT
<213> ORGANISM: Artificial Sequence
<220> FEATURE:
<223> OTHER INFORMATION: Consensus signal peptide generated in silico
<220> FEATURE:
<221> NAME/KEY: misc_feature
<222> LOCATION: (4)..(4)
<223> OTHER INFORMATION: Xaa can be any naturally occurring amino acid

<400> SEQUENCE: 87

```
Met Phe Gly Xaa Arg Thr Gln Gly Phe His Ile Leu Met Ala Met Leu
1               5                   10                  15

Ile Gly
```

<210> SEQ ID NO 88
<211> LENGTH: 41

<212> TYPE: PRT
<213> ORGANISM: Artificial Sequence
<220> FEATURE:
<223> OTHER INFORMATION: Consensus transmembrane domain generated in silico
<220> FEATURE:
<221> NAME/KEY: misc_feature
<222> LOCATION: (37)..(37)
<223> OTHER INFORMATION: Xaa can be any naturally occurring amino acid
<220> FEATURE:
<221> NAME/KEY: misc_feature
<222> LOCATION: (40)..(40)
<223> OTHER INFORMATION: Xaa can be any naturally occurring amino acid

<400> SEQUENCE: 88

```
Val Ser Gly Leu Ser Phe Tyr Val Ser Leu Leu Leu Trp Gln Asn Leu
1               5                   10                  15

Phe Gln Leu Leu Ser Tyr Leu Ile Leu Arg Met Asn Asp Glu Pro Val
            20                  25                  30

Val Glu Trp Gly Xaa Gln Glu Xaa Tyr
        35                  40
```

<210> SEQ ID NO 89
<211> LENGTH: 18
<212> TYPE: PRT
<213> ORGANISM: Homo sapiens

<400> SEQUENCE: 89

```
Met Phe Gly Ala Arg Thr His Gly Phe His Ile Leu Met Ala Met Leu
1               5                   10                  15

Ile Gly
```

<210> SEQ ID NO 90
<211> LENGTH: 18
<212> TYPE: PRT
<213> ORGANISM: Bos taurus

<400> SEQUENCE: 90

```
Met Phe Gly Ala Arg Thr Gln Gly Phe His Ile Leu Met Ala Met Leu
1               5                   10                  15

Ile Gly
```

<210> SEQ ID NO 91
<211> LENGTH: 41
<212> TYPE: PRT
<213> ORGANISM: Bos taurus

<400> SEQUENCE: 91

```
Val Ser Gly Leu Ser Phe Tyr Val Ser Leu Leu Leu Trp Gln Asn Leu
1               5                   10                  15

Phe Gln Leu Leu Ser Tyr Leu Ile Leu Arg Leu Asn Asp Glu Pro Val
            20                  25                  30

Val Glu Trp Gly Asp Gln Asp Asp Tyr
        35                  40
```

<210> SEQ ID NO 92
<211> LENGTH: 18
<212> TYPE: PRT
<213> ORGANISM: Mus musculus

<400> SEQUENCE: 92

```
Met Phe Gly His Lys Thr Gln Gly Phe His Ile Leu Met Ala Val Leu
1               5                   10                  15
```

Ile Gly

<210> SEQ ID NO 93
<211> LENGTH: 41
<212> TYPE: PRT
<213> ORGANISM: Mus musculus

<400> SEQUENCE: 93

Val Ser Gly Leu Ser Phe Tyr Val Ser Leu Leu Leu Trp Gln Asn Leu
1               5                   10                  15

Phe Gln Leu Leu Ser Tyr Leu Val Leu Arg Met Asn Asp Glu Pro Val
            20                  25                  30

Val Glu Trp Gly Ala Gln Glu Asn Tyr
        35                  40

<210> SEQ ID NO 94
<211> LENGTH: 18
<212> TYPE: PRT
<213> ORGANISM: Rattus norvegicus

<400> SEQUENCE: 94

Met Phe Gly His Arg Thr Gln Gly Phe Tyr Ile Phe Met Ala Ile Leu
1               5                   10                  15

Ile Gly

<210> SEQ ID NO 95
<211> LENGTH: 41
<212> TYPE: PRT
<213> ORGANISM: Rattus norvegicus

<400> SEQUENCE: 95

Val Ser Gly Leu Ser Phe Tyr Val Ser Leu Leu Leu Trp Gln Asn Leu
1               5                   10                  15

Phe Gln Leu Leu Ser Tyr Leu Ile Leu Arg Met Asn Asp Glu Pro Glu
            20                  25                  30

Val Glu Trp Gly Ala Gln Glu Asn Tyr
        35                  40

<210> SEQ ID NO 96
<211> LENGTH: 16
<212> TYPE: PRT
<213> ORGANISM: Danio rerio

<400> SEQUENCE: 96

Met Glu Val Val Val Gly Ile Trp Ser Val Leu Leu Leu Ile Ser Gly
1               5                   10                  15

<210> SEQ ID NO 97
<211> LENGTH: 39
<212> TYPE: PRT
<213> ORGANISM: Danio rerio

<400> SEQUENCE: 97

Val Ser Asp Leu Tyr Phe Tyr Met Ala Ala Leu Phe Trp Gln Asn Leu
1               5                   10                  15

Phe Gln Phe Leu Ser Tyr Leu Ile Leu Arg Leu Asp Asp Glu Pro Glu
            20                  25                  30

Val Asp Trp Gly Asp Asn Glu
        35

<210> SEQ ID NO 98

-continued

```
<211> LENGTH: 50
<212> TYPE: DNA
<213> ORGANISM: Mus musculus

<400> SEQUENCE: 98

aaacaaaaac taaagcatct tattccctgg gcttacttct ggctttggaa            50


<210> SEQ ID NO 99
<211> LENGTH: 50
<212> TYPE: DNA
<213> ORGANISM: Mus musculus

<400> SEQUENCE: 99

aagaagaata agtacccgtt cccatcacct aatcgcttta ttctgataga            50


<210> SEQ ID NO 100
<211> LENGTH: 48
<212> TYPE: DNA
<213> ORGANISM: Artificial Sequence
<220> FEATURE:
<223> OTHER INFORMATION: Crb1 delB allele

<400> SEQUENCE: 100

aagaagaata agtacccgtt catcacctaa tcgctttatt ctgataga              48
```